US012359208B2

(12) United States Patent
Abedi et al.

(10) Patent No.: US 12,359,208 B2
(45) Date of Patent: Jul. 15, 2025

(54) THERMAL CONTROL OF T-CELL IMMUNOTHERAPY THROUGH MOLECULAR AND PHYSICAL ACTUATION

(71) Applicant: California Institute of Technology, Pasadena, CA (US)

(72) Inventors: Mohamad H. Abedi, Pasadena, CA (US); Mikhail Shapiro, Pasadena, CA (US); Dan I. Piraner, Pasadena, CA (US); Justin Lee, Pasadena, CA (US)

(73) Assignee: California Institute of Technology, Pasadena, CA (US)

(*) Notice: Subject to any disclaimer, the term of this patent is extended or adjusted under 35 U.S.C. 154(b) by 1087 days.

(21) Appl. No.: 17/230,998

(22) Filed: Apr. 15, 2021

(65) Prior Publication Data

US 2021/0324389 A1 Oct. 21, 2021

Related U.S. Application Data

(60) Provisional application No. 63/010,525, filed on Apr. 15, 2020.

(51) Int. Cl.

| | |
|---|---|
| ***C12N 15/82*** | (2006.01) |
| ***C07K 14/725*** | (2006.01) |
| ***C12N 15/63*** | (2006.01) |

(52) U.S. Cl.

CPC ........ *C12N 15/635* (2013.01); *C07K 14/7051* (2013.01); *C07K 2319/03* (2013.01); *C12N 2830/008* (2013.01)

(58) Field of Classification Search

CPC .... C07K 14/7051; C12N 15/635; C12N 9/22; C12N 15/63; C12N 15/8217; A61K 39/4631

USPC ........................................................ 435/69.1

See application file for complete search history.

(56) References Cited

U.S. PATENT DOCUMENTS

| | | | |
|---|---|---|---|
| 5,260,291 | A | 11/1993 | Lunt et al. |
| 5,747,498 | A | 5/1998 | Schnur et al. |
| 5,827,642 | A | 10/1998 | Riddell et al. |
| 6,040,177 | A | 3/2000 | Riddell et al. |
| 6,326,193 | B1 | 12/2001 | Liu et al. |
| 6,703,199 | B1 | 3/2004 | Koide |
| 6,797,514 | B2 | 9/2004 | Berenson et al. |
| 6,867,041 | B2 | 3/2005 | Berenson et al. |
| 6,905,874 | B2 | 6/2005 | Berenson et al. |
| 2002/0165191 | A1 | 11/2002 | Moonen |
| 2008/0139587 | A1 | 6/2008 | Huang et al. |
| 2013/0287748 | A1 | 10/2013 | June et al. |
| 2019/0055297 | A1 | 2/2019 | Zhao et al. |
| 2020/0299686 | A1 | 9/2020 | Kwong et al. |

FOREIGN PATENT DOCUMENTS

| | | |
|---|---|---|
| EP | 0564409 | 3/1993 |
| EP | 0566226 | 11/1995 |
| EP | 0520722 | 12/1996 |
| EP | 0787722 | 8/1997 |
| EP | 0837063 | 4/1998 |
| WO | WO1996033980 | 10/1996 |
| WO | WO1997002266 | 1/1997 |
| WO | WO1997030034 | 8/1997 |
| WO | WO1997038983 | 10/1997 |
| WO | WO1997049688 | 12/1997 |
| WO | WO1998/006864 | 2/1998 |
| WO | WO1998010767 | 3/1998 |
| WO | WO1999003854 | 1/1999 |
| WO | WO2001029058 | 4/2001 |
| WO | WO2001096584 | 12/2001 |
| WO | WO2002022577 | 3/2002 |
| WO | WO2003013541 | 2/2003 |
| WO | WO2012079000 | 6/2012 |
| WO | WO2012129514 | 9/2012 |
| WO | WO2018/050225 | 3/2018 |
| WO | WO2019070704 | 4/2019 |
| WO | WO2020146260 | 7/2020 |

OTHER PUBLICATIONS

Kisselev L., (Structure, 2002, vol. 10: 8-9.*

Witkowski et al., (Biochemistry 38:11643-11650, 1999.*

Whisstock et al., (Quarterly Reviews of Biophysics 2003, vol. 36 (3): 307-340.*

Devos et al., (Proteins: Structure, Function and Genetics, 2000, vol. 41: 98-107.*

Aandahl et al., "Inhibition of Antigen-Specific T Cell Proliferation and Cytokine Production by Protein Kinase A Type I," J Immunol 2002, 169, 802-808.

Abedi et al., "Thermal Control of Engineered T-cells," ACS Synth. Biol. 2020, in 27 pages.

Aggen et al., "Single-Chain VαVβ T Cell Receptors Function Without Mispairing With Endogenous TCR Chains," Gene Therapy 2012, 19(4), 365-374.

Bird et al., "Single-Chain Antigen-Binding Proteins," Science 1988, 242(4877), 423-426.

Brentjens, "Safety and persistence of adoptively transferred autologous CD19-targeted T cells in patients with relapsed or chemotherapy refractory B-cell leukemias," Blood 2011, 118(18), 4817-4828.

(Continued)

*Primary Examiner* — Robert B Mondesi
*Assistant Examiner* — Mohammad Y Meah
(74) *Attorney, Agent, or Firm* — Dickinson Wright PLLC

(57) ABSTRACT

Disclosed herein include methods, compositions, and kits suitable for use in spatiotemporal regulation of therapeutic T-cells through a combination of molecular and physical actuation. There are provided, in some embodiments, thermal bioswitches that allow T-cells to sense small changes in temperature and use them as inputs for the actuation of genetic circuits. Also disclosed herein are T cell activity sensors. Genetic circuits capable of inducing expression of a payload upon thermal stimulation and/or immune cell stimulation are provided. There are provided, in some embodiments, thermally actuated immune cells and methods of using are provided. Oscillator circuits and methods of preventing T cell exhaustion are also disclosed.

18 Claims, 29 Drawing Sheets

Specification includes a Sequence Listing.

(56) References Cited

OTHER PUBLICATIONS

Dao et al., "Targeting the Intracellular WT1 Oncogene Product with a Therapeutic Human Antibody," Sci Transl Med 2013, 5(176), in 22 pages.
Davila & Brentjens, "CD19-Targeted T Cells Rapidly Induce Molecular Remissions in Adults with Chemotherapy-Refractory Acute Lymphoblastic Leukemia," Science Translational Medicine 2013, 5, 177ra38.
Day et al., "PD-1 expression on HIV-specific T cells is associated with T-cell exhaustion and disease progression," Nature 2006, 443, 350-354.
Deckers et al., "Image-guided, noninvasive, spatiotemporal control of gene expression," PNAS 2009, 106(4), 1175-1180.
Di Stasi et al., "Inducible Apoptosis as a Safety Switch for Adoptive Cell Therapy," N Engl J Med 2011, 365(18), 1673-1683.
Ellebrecht et al., "Reengineering chimeric antigen receptor T cells for targeted therapy of autoimmune disease," Science 2016, 353(6295), 179-184.
Ferreira et al., "Reengineering chimeric antigen receptor T cells for targeted therapy of autoimmune disease," PNAS 2013, 110(28), 11284-11289.
Ferreira et al., "Tuning gene expression with synthetic upstream open reading frames," PNAS 2013, 110(28), 11284-11289.
Gossen & Bujard, "Tight control of gene expression in mammalian cells by tetracycline-responsive promoters," PNAS 1992, 89, 5547-5551.
Guilhon et al., "Spatial and temporal control of transgene expression in vivo using a heat-sensitive promoter and MRI-guided focused ultrasound," The Journal of Gene Medicine 2003, 5, 333-342.
Haar & Coussios, "High intensity focused ultrasound: Physical principles and devices," Int. J. Hyperthermia 2007, 23(2), 89-104.
Hildebrandt et al., "The cellular and molecular basis of hyperthermia," Critical Reviews in Oncology/Hematology 2002, 43, 33-56.
Hinrichs et al., "Structure of the Tet Repressor-Tetracycline Complex and Regulation of Antibiotic Resistance," Science 1994, 264(5157), 418-420.
Hollinger & Hudson, "Engineered antibody fragments and the rise of single domains," Nature Biotechnology 2005, 23(9), 1126-1136.
Huang et al., "Cancer Cell Imaging and Photothermal Therapy in the Near-Infrared Region by Using Gold Nanorods," Journal of the American Chemical Society 2006, 128, 2115-2120.
Huston et al., "Protein engineering of antibody binding sites: Recovery of specific activity in an anti-digoxin single-chain Fv analogue produced in *Escherichia coli*," PNAS 1988, 85, 5879-5883.
International Search Report and Written Opinion dated Jul. 22, 2021 in PCT Application No. PCT/US2021/027376.
Kay, "Efficient Transcription of a *Caenorhabditis elegans* Heat Shock Gene Pair in Mouse Fibroblasts Is Dependent on Multiple Promoter Elements Which Can Function Bidirectionally," Molecular and Cellular Biology 1986, 6(9), 3134-3143.
Kochenderfer et al., "Eradication of B-lineage cells and regression of lymphoma in a patient treated with autologous T cells genetically engineered to recognize CD19," Blood 2010, 116(20), 4099-4102.
Kregel, "Heat shock proteins: modifying factors in physiological stress responses and acquired thermotolerance," J Appl Physiol 2002, 92, 2177-2186.
Kregel, "Molecular Biology of Thermoregulation Invited Review: Heat shock proteins: modifying factors in physiological stress responses and acquired thermotolerance," J Appl Physiol 2002, 92, 2177-2186.
Kruse et al., "Short-duration-focused ultrasound stimulation of Hsp70 expression in vivo," Phys. Med. Biol. 2008, 53(6639), 3641-3660.
Maetzig et al., "Gammaretroviral Vectors: Biology, Technology and Application," Viruses 2011, 3(6), 677-713.
Miller et al., "Remote Control of Mammalian Cells with Heat-Triggered Gene Switches and Photothermal Pulse Trains," ACS Synth Biol 2018, 7(4), 1167-1173.
Milone et al., "Chimeric Receptors Containing CD137 Signal Transduction Domains Mediate Enhanced Survival of T Cells and Increased Antileukemic Efficacy In Vivo," Molecular Therapy 2009, 17(8), 1453-1464.
Morgan et al., "Cancer regression and neurologic toxicity following anti-MAGE-A3 TCR gene therapy," J Immunother. 2013, 36(2), 133-151.
Morgan et al., "Case Report of a Serious Adverse Event Following the Administration of T Cells Transduced With a Chimeric Antigen Receptor Recognizing ERBB2," Molecular Therapy 2010, 18(4) 843-851.
Morimoto, "Regulation of the heat shock transcriptional response: cross talk between a family of heat shock factors, molecular chaperones, and negative regulators," Genes and Development 1998, 12, 3788-3796.
Nishikawa & Huang, "Nonviral Vectors in the New Millennium: Delivery Barriers in Gene Transfer," Human Gene Therapy 2001, 12, 861-870.
Paley et al., " Progenitor and Terminal Subsets of CD8+ T Cells Cooperate to Contain Chronic Viral Infection," Science 2012, 338, 1220-1225.
Piraner et al., "Going Deeper: Biomolecular Tools for Acoustic and Magnetic Imaging and Control of Cellular Function," Biochemistry 2017, 56(39), 5202-5209.
Piraner et al., "Tunable thermal bioswitches for in vivo control of microbial therapeutics," Nature Chemical Biology 2017, 13, 75-80.
Piraner et al., "Modular Thermal Control of Protein Dimerization," ACS Synth Biol 2019, 8, 2256-2262.
Rome et al., "Spatial and temporal control of expression of therapeutic genes using heat shock protein promoters," Methods 2005, 35, 188-198.
Roybal et al., "Precision Tumor Recognition by T Cells With Combinatorial Antigen Sensing Circuits," Cell 2016, 164(4), 770-779.
Sastry et al., "Targeting Hepatitis B Virus-Infected Cells with a T-Cell Receptor-Like Antibody," Journal of Virology 2011, 85(5), 1935-1942.
Sergeeva et al., "An anti-PR1/HLA-A2 T-cell receptor-like antibody mediates complement-dependent cytotoxicity against acute myeloid leukemia progenitor cells," Immunobiology 2011, 117(16), 4262-4272.
Singh et al., "Reprogramming CD19-specific T cells with IL-21 signaling can improve adoptive immunotherapy of B-lineage malignancies," Cancer Research 2011, 71(10), 3516-3527.
Søndergaard & Skak, "IL-21: roles in immunopathology and cancer therapy," Tissue Antigens 2009, 74, 467-479.
Tassev et al., "Retargeting NK92 cells using an HLA-A2-restricted, EBNA3C-specific chimeric antigen receptor," Cancer Gene Therapy 2012, 19, 84-100.
Teixeira et al., "Engineering mammalian cells for disease diagnosis and treatment," Current Opinion in Biotechnology 2019, 55, 87-94.
Tey et al., "Inducible Caspase 9 Suicide Gene to Improve the Safety of Allodepleted T Cells after Haploidentical Stem Cell Transplantation," Biology of Blood and Marrow Transplantation 2007, 13, 913-924.
Thiesen & Jordan, "Clinical applications of magnetic nanoparticles for hyperthermia." Int. J. Hyperthermia 2008, 24(6), 467-474.
Trautmann et al., "Upregulation of PD-1 expression on HIV-specific CD8+ T cells leads to reversible immune dysfunction," Nature 2006, 12(10), 1198-1202.
Traversari et al., "The potential immunogenicity of the TK suicide gene does not prevent full clinical benefit associated with the use of TK-transduced donor lymphocytes in HSCT for hematologic malignancies," Blood 2007, 109(11), 4708-4715.
Turtle et al., "CD19 CAR-T cells of defined CD4+:CD8+ composition in adult B cell ALL patients," The Journal of Clinical Investigation 2016, 126(6), 2123-2138.
Uchibori, "Functional Analysis of an Inducible Promoter Driven by Activation Signals from a Chimeric Antigen Receptor," Molecular Therapy: Oncolytic 2018, 12, 16-29.

(56) References Cited

OTHER PUBLICATIONS

Urbani et al., "PD-1 Expression in Acute Hepatitis C Virus (HCV) Infection Is Associated with HCV-Specific CD8 Exhaustion," Journal of Virology 2006, 80(22), 11398-11403.
Verma et al., "TCR Mimic Monoclonal Antibody Targets a Specific Peptide/HLA Class I Complex and Significantly Impedes Tumor Growth In Vivo Using Breast Cancer Models," J Immunol 2010, 184(4), 2156-2165.
Wada et al., "Highly Sensitive Detection of Cytotoxicity Using a Modified HSP70B' Promoter," Biotechnology and Bioengineering 2006, 97(4), 871-876.
Wang et al., "Heat Inducible Chimeric Antigen Receptor (CAR) T Cell for Prostate Cancer Therapy," University of California at San Diego, The Degree of Master of Science 2019, in 33 pages.
Wherry & Ahmed, "Memory CD8 T-Cell Differentiation during Viral Infection," Journal of Virology 2004, 78(11) 5535-5545.
Willemsen et al., "A phage display selected Fab fragment with MHC class I-restricted specificity for MAGE-A1 allows for retargeting of primary human T lymphocytes," Gene Therapy 2001, 8, 1601-1608.
Willemsen et al., "Grafting primary human T lymphocytes with cancer-specific chimeric single chain and two chain TCR," Gene Therapy 2000, 7, 1369-1377.
Xu et al., "Optogenetic control of chemokine receptor signal and T-cell migration," PNAS 2014, 111(17), 6371-6376.
Yamaguchi et al., "Heat-inducible transgene expression system incorporating a positive feedback loop of transcriptional amplification for hyperthermia-induced gene therapy," Journal of Bioscience and Bioengineering 2012, 114(4), 460-465.
Yi et al., "T-cell exhaustion: characteristics, causes and conversion," Immunology 2010, 129, 474-481.
Zah et al., "T cells expressing CD19/CD20 bi-specific chimeric antigen receptors prevent antigen escape by malignant B cells," Cancer Immunol Res. 2016, 4(6), 498-508.
Zhang & Ertl, "Starved and Asphyxiated: How Can CD8+ T Cells within a Tumor Microenvironment Prevent Tumor Progression," Frontiers in Immunology 2016, 7(32), 1-7.
Zhang et al., "Transgenic TCR expression: comparison of single chain with full-length receptor constructs for T-cell function," Cancer Gene Therapy 2004, 11, 487-496.
Extended European Search Report dated Aug. 14, 2024 in European Patent Application No. 21788583.9.
Gamboa et al., "Heat-triggered remote control of CRISPR-dCas9 for tunable transcriptional modulation," ACS chemical biology 2020, 15(2), 533-542.
Gamboa et al., "Synthetic immunity by remote control," Theranostics 2020, 10(8), 3652.
Ortner et al., "Magnetic field-controlled gene expression in encapsulated cells," Journal of controlled release 2012, 158(3), 424-432.
Partial supplementary European Search Report dated May 24, 2024 in European Patent Application No. 21788583.9.

* cited by examiner

SEQUENCE LISTING

<160> NUMBER OF SEQ ID NOS: 44

<210> SEQ ID NO 1
<211> LENGTH: 483
<212> TYPE: DNA
<213> ORGANISM: Artificial Sequence
<220> FEATURE:
<223> OTHER INFORMATION: HSPB

<400> SEQUENCE: 1
aattagcttg aggatcctcc acagccccgg ggagaccttg cctctaaagt tgctgctttt 60
gcagctctgc cacaaccgcg cgtcctcaga gccagccggg aggagctaga accttccccg 120
cgtttctttc agcagccctg agtcagaggc gggctggcct tgcaagtagc cgcccagcct 180
tcttcggtct cacggaccga tccgcccgaa ccttctcccg gggtcagcgc cgcgctgcgc 240
cgcccggctg actcagcccg ggcgggcggg cgggaggctc tcgactgggc gggaaggtgc 300
gggaaggttc gcggcggcgg ggtcggggag gtgcaaaagg atgaaaagcc cgtggacgga 360
gctgagcaga tccggccggg ctggcggcag agaaaccgca gggagagcct cactgctgag 420
cgcccctcga cgcgggcggc agcagcctcc gtggcctcca gcatccgaca agaagcttca 480
gcc 483

<210> SEQ ID NO 2
<211> LENGTH: 538
<212> TYPE: DNA
<213> ORGANISM: Artificial Sequence
<220> FEATURE:
<223> OTHER INFORMATION: HSPB'1

<400> SEQUENCE: 2
aattagcttg agcctctaaa gttgctgctt ttgcagcctc tgccacaacc gcgcgtcctc 60
agagccagcc cggaggagct agaaccttcc ccgcatttct ttcagcagcc tgagtcagag 120
gcgggctggc ctggcgtagc cgcccagcct cgcggctcat gccccgatct gcccgaacct 180
tctcccgggg tcagcgccgc gccgcgccac ccggctgagt cagcccgggc gggcgagagg 240
ctctcaactg ggcgggaagg tgcgggaagg tgcggaaagg ttcgcgaaag ttcgcggcgg 300
cgggggtcgg gtgaggcgca aaaggataaa aagccggtgg aagcggagct gagcagatcc 360
gagccgggct ggctgcagag aaaccgcagg gagagcctca ctgctgagcg cccctcgacg 420
gcggagcggc agcagcctcc gtggcctcca gcatccgaca agaagcttga attcgagctc 480
gccggggatc ctctagtcag ctgacgcgtg ctagcgcggc cgcaccacta gtgccacc 538

<210> SEQ ID NO 3
<211> LENGTH: 526
<212> TYPE: DNA
<213> ORGANISM: Artificial Sequence
<220> FEATURE:
<223> OTHER INFORMATION: HSPB'2

<400> SEQUENCE: 3
aattagcttg agcctctaaa gttgctgctt ttgcagcctc tgccacaacc gcgcgtcctc 60
agagccagcc cggaggagct agaaccttcc ccgcatttct ttcagcagcc tgagtcagag 120
gcgggctggc ctggcgtagc cgcccagcct cgcggctcat gccccgatct gcccgaacct 180
tctcccgggg tcagcgccgc gccgcgccac ccggctgagt cagcccgggc gggcgagagg 240
ctctcaactg ggcgggaagg tgcgggaagg tgcggaaagg ttcgcgaaag ttcgcggcgg 300
cgggggtcgg gtgaggcgca aaaggataaa aagccggtgg aagcggagct gagcagatcc 360
gagccgggct ggctgcagag aaaccgcagg gagagcctca ctgctgagcg cccctcgacg 420
gcggagcggc agcagcctcc gtggcctcca gcatccgaca agaagcttga attcgagctc 480
gccggggatc ctctagtcag ctgacgcgtg ctagcgcggc gccacc 526

<210> SEQ ID NO 4
<211> LENGTH: 473
<212> TYPE: DNA
<213> ORGANISM: Artificial Sequence
<220> FEATURE:
<223> OTHER INFORMATION: HSPB'3

<400> SEQUENCE: 4
aattagcttg agcctctaaa gttgctgctt ttgcagcctc tgccacaacc gcgcgtcctc 60
agagccagcc cggaggagct agaaccttcc ccgcatttct ttcagcagcc tgagtcagag 120
gcgggctggc ctggcgtagc cgcccagcct cgcggctcat gccccgatct gcccgaacct 180
tctcccgggg tcagcgccgc gccgcgccac ccggctgagt cagcccgggc gggcgagagg 240
ctctcaactg ggcgggaagg tgcgggaagg tgcggaaagg ttcgcgaaag ttcgcggcgg 300

```
cgggggtcgg gtgaggcgca aaaggataaa aagccggtgg aagcggagct gagcagatcc    360

gagccgggct ggctgcagag aaaccgcagg gagagcctca ctgctgagcg cccctcgacg    420

gcggagcggc agcagcctcc gtggcctcca gcatccgaca agaagcttca gcc           473


<210> SEQ ID NO 5
<211> LENGTH: 323
<212> TYPE: DNA
<213> ORGANISM: Artificial Sequence
<220> FEATURE:
<223> OTHER INFORMATION: SynHSPB'1

<400> SEQUENCE: 5

aattagcttg accccgatct gcccgaacct tctcccgggg tcagcgccgc gccgcgccac     60

ccggctgagt cagcccgggc gggcgagagg ctctcaactg ggcgggaagg tgcgggaagg    120

tgcggaaagg ttcgcgaaag ttcgcggcgg cgggggtcgg gtgaggcgca aaaggataaa    180

aagccggtgg aagcggagct gagcagatcc gagccgggct ggctgcagag aaaccgcagg    240

gagagcctca ctgctgagcg cccctcgacg gcggagcggc agcagcctcc gtggcctcca    300

gcatccgaca agaagcttca gcc                                            323


<210> SEQ ID NO 6
<211> LENGTH: 323
<212> TYPE: DNA
<213> ORGANISM: Artificial Sequence
<220> FEATURE:
<223> OTHER INFORMATION: SynHSPB'2

<400> SEQUENCE: 6

aattagcttg accccgatct gcccgaacct tctcccgggg tcagcgccgc gccgcgccac     60

ccggctgcag cagcccgggc gggcgagagg ctctcaactg ggcgggaagg tgcgggaagg    120

tgcggaaagg ttcgcgaaag ttcgcggcgg cgggggtcgg gtgaggcgca aaaggataaa    180

aagccggtgg aagcggagct gagcagatcc gagccgggct ggctgcagag aaaccgcagg    240

gagagcctca ctgctgagcg cccctcgacg gcggagcggc agcagcctcc gtggcctcca    300

gcatccgaca agaagcttca gcc                                            323


<210> SEQ ID NO 7
<211> LENGTH: 628
<212> TYPE: DNA
<213> ORGANISM: Artificial Sequence
<220> FEATURE:
<223> OTHER INFORMATION: SynHSPB'3

<400> SEQUENCE: 7

aattagcttg accccgatct gcccgaacct tctcccgggg tcagcgccgc gccgcgccac     60

ccggctgcag cagcccgggc gggcgagagg ctctcaactg ggcgggaagg tgcgggaagg    120

tgcggaaagg ttcgcgaaag ttcgcggccg gactagagtg gcgagatccc ccgatctgcc    180

cgaaccttct cccggggtca gcgccgcgcc gcgccacccg gctgcagcag cccgggcggg    240

cgagaggctc tcaactgggc gggaaggtgc gggaaggtgc ggaaaggttc gcgaaagttc    300

gcggcaatta gcttgacccc gatctgcccg aaccttctcc cggggtcagc gccgcgccgc    360

gccacccggc tgcagcagcc cgggcgggcg agaggctctc aactgggcgg gaaggtgcgg    420

gaaggtgcgg aaaggttcgc gaaagttcgc ggcggcgggg gtcgggtgag gcgcaaaagg    480

ataaaaagcc ggtggaagcg gagctgagca gatccgagcc gggctggctg cagagaaacc    540
```

```
gcagggagag cctcactgct gagcgcccct cgacggcgga gcggcagcag cctccgtggc    600

ctccagcatc cgacaagaag cttcagcc                                       628


<210> SEQ ID NO 8
<211> LENGTH: 476
<212> TYPE: DNA
<213> ORGANISM: Artificial Sequence
<220> FEATURE:
<223> OTHER INFORMATION: HSPA/A

<400> SEQUENCE: 8

aattagcttg agccgcccac tccccctcc tctcagggtc cctgtcccct ccagtgaatc      60

ccagaagact ctggagagtt ctgagcaggg ggcggcactc tggcctctga ttggtccaag    120

gaaggctggg gggcaggacg ggaggcgaaa accctggaat attcccgacc tggcagcctc    180

atcgagctcg gtgattggct cagaagggaa aaggcgggtc tccgtgacga cttataaaag    240

cccaggggca agcggtccgg ataacggcta gcctgaggag ctgctgcgac agtccactac    300

ctttttcgag agtgactccc gttgtcccaa ggcttcccag agcgaacctg tgcggctgca    360

ggcaccggcg cgtcgagttt ccggcgtccg gaaggaccga gctcttctcg cggatccagt    420

gttccgtttc cagcccccaa tctcagagcg gagccgacag agagcaggga accgcc        476


<210> SEQ ID NO 9
<211> LENGTH: 774
<212> TYPE: DNA
<213> ORGANISM: Artificial Sequence
<220> FEATURE:
<223> OTHER INFORMATION: HSPA/B

<400> SEQUENCE: 9

aattagcttg actccttccc attaagacgg aaaaaacatc cgggagagcc ggtccgtttc     60

tcaggcagac taggccatta ggtgcctcgg agaaaggacc caaggctgct ccgtccttca    120

cagacacagt ccaatcagag tttcccaggc acatcgatgc accgcctcct tcgagaaaca    180

aggtaacttt cgggttctgg ttgtctccaa agtcatccga ccaatctcgc accgcccaga    240

gcgggccctt cctgtcaatt acctactgaa gggcaggcgg ccagcatcgc catggagacc    300

aacacccttc ccaccaccac tccccctttc tctcagggcc cctgtcccct ccagtgaatc    360

ccagaagact ctggagagtt ctgagcagag ggcggcaccc tgccctctga ttggtccaag    420

gaaggctggg gggcaggacg ggaggcgaaa cccctggaat attcccgacc tggcagcctc    480

atcgagcttg gtgattggct cagaagggga aaggcgggtc tccacgacga cttataaaag    540

ccgaggggcg cgcggtccgg aaaacggcca gcctgaggag ctgctgcgag ggtccgcttc    600

gtctttcgag agtgactccc gcggtcccaa ggctttccag agcgaacctg tgcggctgca    660

ggcaccggcg tgttgagttt ccggcgttcc gaaggactga gctcttgtcg cggatcccgt    720

ccgccgtttc cagcccccag tctcagagcg gagcccacag agcagggcac cggc          774


<210> SEQ ID NO 10
<211> LENGTH: 1060
<212> TYPE: DNA
<213> ORGANISM: Artificial Sequence
<220> FEATURE:
<223> OTHER INFORMATION: HSPm1

<400> SEQUENCE: 10

aattagcttg aaaatcagtc aaacctaaga aaattctcaa ccgcatcaaa ccgaggacca     60

actgggacac agagcttctg ccccactcca atcagagcct tcccagctca cctgggatct    120
```

-continued ctacgccttc gatccagttt ggaaaatttc aagtcgctga gcccctacga gaggagctcc 180
aggaacatac caaactgagg cagccggggt cccccccacc ccccaccccg cccctcccgg 240
caactttgag cctgtgctgg gacagagcct ctagttccta aattagtcca tgaggtcaga 300
ggcagcactg ccattgtaac cgcgattgga gaggatcacg tcaccggaca cgccccaggc 360
atctccctgg gtctcctaaa cttggccggg gagaagtttt agcccttaag gttttagcct 420
ttaaccccca tattcagaac tgtgcgagtt ggcgaaaccc cacaaatcac aacaaactgt 480
acacaacacc gaggctagag gtgatctttc ttgtccattc cacacaggcc ttagtaattg 540
cgtcgccata gcaacagtgt cactagtagc accagcacgt tccccacacc ctccccctca 600
ggaatccgta ctctccagtg aaccccagaa acctctggag agttctggac aagggcggaa 660
cccacaactc cgattactca agggaggcgg ggaagctcca ccagacgcga aactgctgga 720
agattcctgg ccccaaggcc tcctccggct cgctgattgg cccagcggag agtgggcggg 780
gccggtgaag actccttaaa ggcgcagggc ggcgagcacg gtcaccagac gctgacagct 840
actcagaacc aaatctggtt ccatccagag acaagcgaag acaagagaag cagagcagag 900
cggcgcgttc ccgatcctcg gccaggacca gccttcccca gagcatccct gccgcgggac 960
gcaaccttcc caggagcatc cctgccgcgg agcaactttc cccggagcat ccagcccgga 1020
cgcagccttc cagaagcacg agcccaccac tagtgccacc 1060

<210> SEQ ID NO 11
<211> LENGTH: 1064
<212> TYPE: DNA
<213> ORGANISM: Artificial Sequence
<220> FEATURE:
<223> OTHER INFORMATION: HSPm2

<400> SEQUENCE: 11
aattagcttg acctgcagcc tgaggcaaag ggagtggcta cagcctggca cggtcgatta 60
agccctgctc tccgggtcct gggacacttt ccttttttcct cttttgagtc acaggtcctc 120
ctaacatgag aatcaagtat tttcacgctg atttccttat aaaattgtga gaactccata 180
ggcgatgtac cgcctactcc taccttaacc gtgatgtaaa gacagcaaaa caaatgaact 240
atactgcaag atctcttcta tttccctatt caaacctaaa atgaagaggg agggggagac 300
atggacaagc aagcattcca caggcgcccc tgcccaacgc tgtcactcaa accaggaccc 360
aatcacagac tttttagcca agccttatcc cgcctctctt gagaaacttt ctgcgtccgc 420
catcctgtag gaaggatttg tacactttaa actccctccc tggtctgagt cccacactct 480
caccacccag caccttcagg agctgaccct taacagcttc acccacaggg accccgaagt 540
tgcgtcgcct ccgcaacagt gtcaatagca gcaccagcac ttccccacac cctccccctc 600
aggaatccgt actctctagc gaaccccaga aacctctgga gagttctgga caagggcgga 660
acccacaact ccgattactc aagggaggcg gggaagctcc accagacgcg aaactgctgg 720
aagattcctg gccccaaggc ctcctccggc tcgctgattg gcccagcgga gagtgggcgg 780
ggccggtgaa gactccttaa aggcgcaggg cggcgagcag ggcaccagac gctgacagct 840
actcagaatc aaatctggtt ccatccagag acaagcgaag acaagagaag cagagcgagc 900
ggcgcgttcc cgatcctcgg ccaggaccag ccttccccag agcatccacg ccgcggagcg 960
caaccttccc aggagcatcc ctgccgcgga gcgcaacttt ccccggagca tccacgccgc 1020
ggagcgcagc cttccagaag cagagcgcca ccactagtgc cacc 1064

-continued

<210> SEQ ID NO 12
<211> LENGTH: 231
<212> TYPE: DNA
<213> ORGANISM: Artificial Sequence
<220> FEATURE:
<223> OTHER INFORMATION: HSPm3

<400> SEQUENCE: 12
accagacgct gacagctact cagaaccaaa tctggttcca tccagagaca agcgaagaca 60
agagaagcag agcgagcggc gcgttcccga tcctcggcca ggaccagcct tccccagagc 120
atccctgccg cggagcgcaa ccttcccagg agcatccctg ccgcggagcg caactttccc 180
cggagcatcc acgccgcgga gcgcagcctt ccagaagcag agcgcggcgc c 231

<210> SEQ ID NO 13
<211> LENGTH: 228
<212> TYPE: DNA
<213> ORGANISM: Artificial Sequence
<220> FEATURE:
<223> OTHER INFORMATION: HSP16F

<400> SEQUENCE: 13
gattgtagtt tgaagatttc acaattagag tgaatgttgt ttggttcggt tttgtcactg 60
tatttatact catttccacc tttttctaga aggtcctaga tgcatctagg accttctaga 120
acattctaaa cggctgcagg atacgggtat ataagccaat cgtgttcaga ggaaaccaat 180
acactttgtt caagtgctta ctgttcattc tctaaacttc aagacacc 228

<210> SEQ ID NO 14
<211> LENGTH: 217
<212> TYPE: DNA
<213> ORGANISM: Artificial Sequence
<220> FEATURE:
<223> OTHER INFORMATION: HSPmin

<400> SEQUENCE: 14
acatttcctg tacaagtgcc ctaggagctc ggatccagga ggcctaactg gccggtacct 60
gagctcctgg aagattctag aacgttctgg aagattctag aacgttcctc gaggatatca 120
agatctggcc tcggcggcca agcttagaca ctagagggta tataatggaa gctcgacttc 180
cagcttggca atccggtact gttggtaaag cgccacc 217

<210> SEQ ID NO 15
<211> LENGTH: 18
<212> TYPE: DNA
<213> ORGANISM: Artificial Sequence
<220> FEATURE:
<223> OTHER INFORMATION: kozak

<400> SEQUENCE: 15
accatgggtt gagccatg 18

<210> SEQ ID NO 16
<211> LENGTH: 9872
<212> TYPE: DNA
<213> ORGANISM: Artificial Sequence
<220> FEATURE:
<223> OTHER INFORMATION: pTLL-phHsp70A1A

<400> SEQUENCE: 16
ccggagctga atgaagccat accaaacgac gagcgtgaca ccacgatgcc tgtagcaatg 60
gcaacaacgt tgcgcaaact attaactggc gaactactta ctctagcttc ccggcaacaa 120

```
ttaatagact ggatggaggc ggataaagtt gcaggaccac ttctgcgctc ggcccttccg    180
gctggctggt ttattgctga taaatctgga gccggtgagc gtgggtctcg cggtatcatt    240
gcagcactgg ggccagatgg taagccctcc cgtatcgtag ttatctacac gacggggagt    300
caggcaacta tggatgaacg aaatagacag atcgctgaga taggtgcctc actgattaag    360
cattggtaac tgtcagacca agtttactca tatatacttt agattgattt aaaacttcat    420
ttttaattta aaaggatcta ggtgaagatc ctttttgata atctcatgac caaaatccct    480
taacgtgagt tttcgttcca ctgagcgtca gaccccgtag aaaagatcaa aggatcttct    540
tgagatcctt tttttctgcg cgtaatctgc tgcttgcaaa caaaaaaacc accgctacca    600
gcggtggttt gtttgccgga tcaagagcta ccaactcttt ttccgaaggt aactggcttc    660
agcagagcgc agataccaaa tactgtcctt ctagtgtagc cgtagttagg ccaccacttc    720
aagaactctg tagcaccgcc tacatacctc gctctgctaa tcctgttacc agtggctgct    780
gccagtggcg ataagtcgtg tcttaccggg ttggactcaa gacgatagtt accggataag    840
gcgcagcggt cgggctgaac ggggggttcg tgcacacagc ccagcttgga gcgaacgacc    900
tacaccgaac tgagatacct acagcgtgag ctatgagaaa gcgccacgct tcccgaaggg    960
agaaaggcgg acaggtatcc ggtaagcggc agggtcggaa caggagagcg cacgagggag   1020
cttccagggg gaaacgcctg gtatctttat agtcctgtcg ggtttcgcca cctctgactt   1080
gagcgtcgat ttttgtgatg ctcgtcaggg gggcggagcc tatggaaaaa cgccagcaac   1140
gcggcctttt tacggttcct ggccttttgc tggccttttg ctcacatgtt ctttcctgcg   1200
ttatcccctg attctgtgga taaccgtatt accgcctttg agtgagctga taccgctcgc   1260
cgcagccgaa cgaccgagcg cagcgagtca gtgagcgagg aagcggaaga gcgcccaata   1320
cgcaaaccgc ctctccccgc gcgttggccg attcattaat gcagctggca cgacaggttt   1380
cccgactgga aagcgggcag tgagcgcaac gcaattaatg tgagttagct cactcattag   1440
gcaccccagg ctttacactt tatgcttccg gctcgtatgt tgtgtggaat tgtgagcgga   1500
taacaatttc acacaggaaa cagctatgac catgattacg ccaagcgcgc aattaaccct   1560
cactaaaggg aacaaaagct ggagctgcaa gcttggccat tgcatacgtt gtatccatat   1620
cataatatgt acatttatat tggctcatgt ccaacattac cgccatgttg acattgatta   1680
ttgactagtt attaatagta atcaattacg gggtcattag ttcatagccc atatatggag   1740
ttccgcgtta cataacttac ggtaaatggc ccgcctggct gaccgcccaa cgacccccgc   1800
ccattgacgt caataatgac gtatgttccc atagtaacgc caatagggac tttccattga   1860
cgtcaatggg tggagtattt acggtaaact gcccacttgg cagtacatca agtgtatcat   1920
atgccaagta cgccccctat tgacgtcaat gacggtaaat ggcccgcctg gcattatgcc   1980
cagtacatga ccttatggga ctttcctact tggcagtaca tctacgtatt agtcatcgct   2040
attaccatgg tgatgcggtt ttggcagtac atcaatgggc gtggatagcg gtttgactca   2100
cggggatttc caagtctcca ccccattgac gtcaatggga gtttgttttg gcaccaaaat   2160
caacgggact ttccaaaatg tcgtaacaac tccgccccat tgacgcaaat gggcggtagg   2220
cgtgtacggt gggaggtcta tataagcaga gctcgtttag tgaaccgggg tctctctggt   2280
tagaccagat ctgagcctgg gagctctctg gctaactagg gaacccactg cttaagcctc   2340
aataaagctt gccttgagtg cttcaagtag tgtgtgcccg tctgttgtgt gactctggta   2400
actagagatc cctcagaccc ttttagtcag tgtggaaaat ctctagcagt ggcgcccgaa   2460
```

-continued

```
cagggacctg aaagcgaaag ggaaaccaga ggagctctct cgacgcagga ctcggcttgc   2520
tgaagcgcgc acggcaagag gcgaggggcg gcgactggtg agtacgccaa aaattttgac   2580
tagcggaggc tagaaggaga gagatgggtg cgagagcgtc agtattaagc gggggagaat   2640
tagatcgcga tgggaaaaaa ttcggttaag gccaggggga aagaaaaaat ataaattaaa   2700
acatatagta tgggcaagca gggagctaga acgattcgca gttaatcctg gcctgttaga   2760
aacatcagaa ggctgtagac aaatactggg acagctacaa ccatcccttc agacaggatc   2820
agaagaactt agatcattat ataatacagt agcaaccctc tattgtgtgc atcaaaggat   2880
agagataaaa gacaccaagg aagctttaga caagatagag gaagagcaaa acaaaagtaa   2940
gaccaccgca cagcaagcgg ccgctgatct tcagacctgg aggaggagat atgagggaca   3000
attggagaag tgaattatat aaatataaag tagtaaaaat tgaaccatta ggagtagcac   3060
ccaccaaggc aaagagaaga gtggtgcaga gagaaaaaag agcagtggga ataggagctt   3120
tgttccttgg gttcttggga gcagcaggaa gcactatggg cgcagcctca atgacgctga   3180
cggtacaggc cagacaatta ttgtctggta tagtgcagca gcagaacaat ttgctgaggg   3240
ctattgaggc gcaacagcat ctgttgcaac tcacagtctg gggcatcaag cagctccagg   3300
caagaatcct ggctgtggaa agatacctaa aggatcaaca gctcctgggg atttggggtt   3360
gctctggaaa actcatttgc accactgctg tgccttggaa tgctagttgg agtaataaat   3420
ctctggaaca gattggaatc acacgacctg gatggagtgg gacagagaaa ttaacaatta   3480
cacaagctta atacactcct taattgaaga atcgcaaaac cagcaagaaa agaatgaaca   3540
agaattattg gaattagata aatgggcaag tttgtggaat tggtttaaca taacaaattg   3600
gctgtggtat ataaaattat tcataatgat agtaggaggc ttggtaggtt taagaatagt   3660
ttttgctgta ctttctatag tgaatagagt taggcaggga tattcaccat tatcgtttca   3720
gacccacctc ccaaccccga ggggacccga caggcccgaa ggaatagaag aagaaggtgg   3780
agagagagac agagacagat ccattcgatt agtgaacgga tctcgacggt atcgatctcg   3840
acacaaatgg cagtattcat ccacaatttt aaaagaaaag gggggattgg ggggtacagt   3900
gcaggggaaa gaatagtaga cataatagca acagacatac aaactaaaga attacaaaaa   3960
caaattacaa aaattcaaaa ttttcgggtt tattacaggg acagcagaga tccagtttgg   4020
gaattagctt gagccgccca ctcccccttc ctctcagggt ccctgtcccc tccagtgaat   4080
cccagaagac tctggagagt tctgagcagg gggcggcact ctggcctctg attggtccaa   4140
ggaaggctgg ggggcaggac gggaggcgaa aaccctggaa tattcccgac ctggcagcct   4200
catcgagctc ggtgattggc tcagaaggga aaaggcgggt ctccgtgacg acttataaaa   4260
gcccaggggc aagcggtccg gataacggct agcctgagga gctgctgcga cagtccacta   4320
cctttttcga gagtgactcc cgttgtccca aggcttccca gagcgaacct gtgcggctgc   4380
aggcaccggc gcgtcgagtt tccggcgtcc ggaaggaccg agctcttctc gcggatccag   4440
tgttccgttt ccagccccca atctcagagc ggagccgaca gagagcaggg aaccgccatg   4500
gtgagcaagg gagaggagga taacatggcc tctctcccag ctacacatga gcttcacatc   4560
tttggatcca tcaacggtgt ggactttgac atggtgggtc agggaaccgg aaatccaaat   4620
gatggatatg aggagcttaa ccttaagtcc accaagggtg acctccagtt ctccccatgg   4680
attcttgtcc ctcatatcgg atatggattc catcagtacc ttccttaccc tgacggtatg   4740
tctcctttcc aggccgccat ggttgatgga tccggatacc aagtccatag aacaatgcag   4800
tttgaagatg gtgcctccct tactgttaac tacagataca cctacgaggg aagccacatc   4860
```

aaaggagagg cccaggtgaa gggaactggt ttccctgctg acggtcctgt gatgaccaac 4920
tctcttaccg ctgctgactg gtgcaggtct aagaaaactt accctaacga caaaaccatc 4980
atcagtacct ttaagtggag ttacaccact ggaaatggta agagatacag aagcactgct 5040
agaaccacct acacctttgc caagccaatg gctgctaact atcttaagaa ccagcctatg 5100
tacgtgttcc gtaagactga gctcaagcac tccaagaccg agctcaactt caaggagtgg 5160
caaaaggcct ttaccgatgt gatgggaatg gacgagcttt acaagtaatg tacaacacgt 5220
gctacgagat ttcgattccg agctcgaatt gacggatcgg gagatctact agaagctttg 5280
caaagatgga taaagtttta aacagagagg aatctttgca gctaatggac cttctaggtc 5340
ttgaaaggag tgggaattgg ctccggtgcc cgtcagtggg cagagcgcac atcgcccaca 5400
gtccccgaga agttgggggg aggggtcggc aattgaaccg gtgcctagag aaggtggcgc 5460
ggggtaaact gggaaagtga tgtcgtgtac tggctccgcc tttttcccga gggtggggga 5520
gaaccgtata taagtgcagt agtcgccgtg aacgttcttt ttcgcaacgg gtttgccgcc 5580
agaacacagg taagtgccgt gtgtggttcc cgcgggcctg gcctctttac gggttatggc 5640
ccttgcgtgc cttgaattac ttccactggc tgcagtacgt gattcttgat cccgagcttc 5700
gggttggaag tgggtgggag agttcgaggc cttgcgctta aggagcccct tcgcctcgtg 5760
cttgagttga ggcctggcct gggcgctggg gccgccgcgt gcgaatctgg tggcaccttc 5820
gcgcctgtct cgctgctttc gataagtctc tagccattta aaatttttga tgacctgctg 5880
cgacgctttt tttctggcaa gatagtcttg taaatgcggg ccaagatctg cacactggta 5940
tttcggtttt tggggccgcg ggcggcgacg gggcccgtgc gtcccagcgc acatgttcgg 6000
cgaggcgggg cctgcgagcg cggccaccga gaatcggacg ggggtagtct caagctggcc 6060
ggcctgctct ggtgcctggc ctcgcgccgc cgtgtatcgc cccgccctgg gcggcaaggc 6120
tggcccggtc ggcaccagtt gcgtgagcgg aaagatggcc gcttcccggc cctgctgcag 6180
ggagctcaaa atggaggacg cggcgctcgg gagagcgggc gggtgagtca cccacacaaa 6240
ggaaaagggc ctttccgtcc tcagccgtcg cttcatgtga ctccacggag taccgggcgc 6300
cgtccaggca cctcgattag ttctcgagct tttggagtac gtcgtcttta ggttgggggg 6360
aggggtttta tgcgatggag tttccccaca ctgagtgggt ggagactgaa gttaggccag 6420
cttggcactt gatgtaattc tccttggaat ttgccctttt tgagtttgga tcttggttca 6480
ttctcaagcc tcagacagtg gttcaaagtt tttttcttcc atttcaggtg tcgtgaccgg 6540
tcgccaccat ggtgtctaag ggcgaagagc tgattaagga gaacatgcac atgaagctgt 6600
acatggaggg caccgtggac aaccatcact tcaagtgcac atccgagggc gaaggcaagc 6660
cctacgaggg cacccagacc atgagaatca aggtggtcga gggcggccct ctccccttcg 6720
ccttcgacat cctggctact agcttcctct acggcagcaa gaccttcatc aaccacaccc 6780
agggcatccc cgacttcttc aagcagtcct tccctgaggg cttcacatgg gagagagtca 6840
ccacatacga agacgggggc gtgctgaccg ctacccagga caccagcctc caggacggct 6900
gcctcatcta caacgtcaag atcagagggg tgaacttcac atccaacggc cctgtgatgc 6960
agaagaaaac actcggctgg gaggccttca ccgagacgct gtaccccgct gacggcggcc 7020
tggaaggcag aaacgacatg gccctgaagc tcgtgggcgg gagccatctg atcgcaaacg 7080
ccaagaccac atatagatcc aagaaacccg ctaagaacct caagatgcct ggcgtctact 7140
atgtggacta cagactggaa agaatcaagg aggccaacaa cgagacctac gtcgagcagc 7200

-continued acgaggtggc agtggccaga tactgcgacc tccctagcaa actggggcac aagcttaatt 7260
aatgtacaaa tcaacctctg gattacaaaa tttgtgaaag attgactggt attcttaact 7320
atgttgctcc ttttacgcta tgtggatacg ctgctttaat gcctttgtat catgctattg 7380
cttcccgtat ggctttcatt ttctcctcct tgtataaatc ctggttgctg tctctttatg 7440
aggagttgtg gcccgttgtc aggcaacgtg gcgtggtgtg cactgtgttt gctgacgcaa 7500
cccccactgg ttggggcatt gccaccacct gtcagctcct ttccgggact ttcgctttcc 7560
ccctccctat tgccacggcg gaactcatcg ccgcctgcct tgcccgctgc tggacagggg 7620
ctcggctgtt gggcactgac aattccgtgg tgttgtcggg gaaatcatcg tcctttcctt 7680
ggctgctcgc ctatgttgcc acctggattc tgcgcgggac gtccttctgc tacgtccctt 7740
cggccctcaa tccagcggac cttccttccc gcggcctgct gccggctctg cggcctcttc 7800
cgcgtcttcg ccttcgccct cagacgagtc ggatctccct ttgggccgcc tccccgctac 7860
aaggcagctg tagatccctt tcatagaagg cggcggtggt acctttaaga ccaatgactt 7920
acaaggcagc tgtagatctt agccactttt taaaagaaaa ggggggactg gaagggctaa 7980
ttcactccca acgaagacaa gatctgcttt ttgcttgtac tgggtctctc tggttagacc 8040
agatctgagc ctgggagctc tctggctaac tagggaaccc actgcttaag cctcaataaa 8100
gcttgccttg agtgcttcaa gtagtgtgtg cccgtctgtt gtgtgactct ggtaactaga 8160
gatccctcag acccttttag tcagtgtgga aaatctctag cagtagtagt tcatgtcatc 8220
ttattattca gtatttataa cttgcaaaga aatgaatatc agagagtgag aggaacttgt 8280
ttattgcagc ttataatggt tacaaataaa gcaatagcat cacaaatttc acaaataaag 8340
catttttttc actgcattct agttgtggtt tgtccaaact catcaatgta tcttatcatg 8400
tctggctcta gctatcccgc ccctaactcc gcccatcccg cccctaactc cgcccagttc 8460
cgcccattct ccgccccatg gctgactaat tttttttatt tatgcagagg ccgaggccgc 8520
ctcggcctct gagctattcc agaagtagtg aggaggcttt tttggaggcc taggcttttg 8580
cgtcgagacg tacccaattc gccctatagt gagtcgtatt acgcgcgctc actggccgtc 8640
gttttacaac gtcgtgactg ggaaaaccct ggcgttaccc aacttaatcg ccttgcagca 8700
catccccctt tcgccagctg gcgtaatagc gaagaggccc gcaccgatcg cccttcccaa 8760
cagttgcgca gcctgaatgg cgaatggcgc gacgcgccct gtagcggcgc attaagcgcg 8820
gcgggtgtgg tggttacgcg cagcgtgacc gctacacttg ccagcgccct agcgcccgct 8880
cctttcgctt tcttcccttc ctttctcgcc acgttcgccg gctttccccg tcaagctcta 8940
aatcgggggc tccctttagg gttccgattt agtgctttac ggcacctcga ccccaaaaaa 9000
cttgattagg gtgatggttc acgtagtggg ccatcgccct gatagacggt ttttcgccct 9060
ttgacgttgg agtccacgtt ctttaatagt ggactcttgt tccaaactgg aacaacactc 9120
aaccctatct cggtctattc ttttgattta taagggattt tgccgatttc ggcctattgg 9180
ttaaaaaatg agctgattta acaaaaattt aacgcgaatt ttaacaaaat attaacgttt 9240
acaatttccc aggtggcact tttcggggaa atgtgcgcgg aacccctatt tgtttatttt 9300
tctaaataca ttcaaatatg tatccgctca tgagacaata accctgataa atgcttcaat 9360
aatattgaaa aaggaagagt atgagtattc aacatttccg tgtcgccctt attccctttt 9420
ttgcggcatt ttgccttcct gtttttgctc acccagaaac gctggtgaaa gtaaaagatg 9480
ctgaagatca gttgggtgca cgagtgggtt acatcgaact ggatctcaac agcggtaaga 9540
tccttgagag ttttcgcccc gaagaacgtt ttccaatgat gagcactttt aaagttctgc 9600
tatgtggcgc ggtattatcc cgtattgacg ccgggcaaga gcaactcggt cgccgcatac 9660
actattctca gaatgacttg gttgagtact caccagtcac agaaaagcat cttacggatg 9720
gcatgacagt aagagaatta tgcagtgctg ccataaccat gagtgataac actgcggcca 9780
acttacttct gacaacgatc ggaggaccga aggagctaac cgcttttttg cacaacatgg 9840
gggatcatgt aactcgcctt gatcgttggg aa 9872

<210> SEQ ID NO 17
<211> LENGTH: 10170
<212> TYPE: DNA
<213> ORGANISM: Artificial Sequence
<220> FEATURE:
<223> OTHER INFORMATION: pTLL-phHsp70A1B

<400> SEQUENCE: 17
ccggagctga atgaagccat accaaacgac gagcgtgaca ccacgatgcc tgtagcaatg 60
gcaacaacgt tgcgcaaact attaactggc gaactactta ctctagcttc ccggcaacaa 120
ttaatagact ggatggaggc ggataaagtt gcaggaccac ttctgcgctc ggcccttccg 180
gctggctggt ttattgctga taaatctgga gccggtgagc gtgggtctcg cggtatcatt 240
gcagcactgg ggccagatgg taagccctcc cgtatcgtag ttatctacac gacggggagt 300
caggcaacta tggatgaacg aaatagacag atcgctgaga taggtgcctc actgattaag 360
cattggtaac tgtcagacca agtttactca tatatacttt agattgattt aaaacttcat 420
ttttaattta aaaggatcta ggtgaagatc ctttttgata atctcatgac caaaatccct 480
taacgtgagt tttcgttcca ctgagcgtca gaccccgtag aaaagatcaa aggatcttct 540
tgagatcctt tttttctgcg cgtaatctgc tgcttgcaaa caaaaaaacc accgctacca 600
gcggtggttt gtttgccgga tcaagagcta ccaactcttt ttccgaaggt aactggcttc 660
agcagagcgc agataccaaa tactgtcctt ctagtgtagc cgtagttagg ccaccacttc 720
aagaactctg tagcaccgcc tacatacctc gctctgctaa tcctgttacc agtggctgct 780
gccagtggcg ataagtcgtg tcttaccggg ttggactcaa gacgatagtt accggataag 840
gcgcagcggt cgggctgaac ggggggttcg tgcacacagc ccagcttgga gcgaacgacc 900
tacaccgaac tgagatacct acagcgtgag ctatgagaaa gcgccacgct tcccgaaggg 960
agaaaggcgg acaggtatcc ggtaagcggc agggtcggaa caggagagcg cacgagggag 1020
cttccagggg gaaacgcctg gtatctttat agtcctgtcg ggtttcgcca cctctgactt 1080
gagcgtcgat ttttgtgatg ctcgtcaggg gggcggagcc tatggaaaaa cgccagcaac 1140
gcggcctttt tacggttcct ggccttttgc tggccttttg ctcacatgtt ctttcctgcg 1200
ttatcccctg attctgtgga taaccgtatt accgcctttg agtgagctga taccgctcgc 1260
cgcagccgaa cgaccgagcg cagcgagtca gtgagcgagg aagcggaaga gcgcccaata 1320
cgcaaaccgc ctctccccgc gcgttggccg attcattaat gcagctggca cgacaggttt 1380
cccgactgga aagcgggcag tgagcgcaac gcaattaatg tgagttagct cactcattag 1440
gcaccccagg ctttacactt tatgcttccg gctcgtatgt tgtgtggaat tgtgagcgga 1500
taacaatttc acacaggaaa cagctatgac catgattacg ccaagcgcgc aattaaccct 1560
cactaaaggg aacaaaagct ggagctgcaa gcttggccat tgcatacgtt gtatccatat 1620
cataatatgt acatttatat tggctcatgt ccaacattac cgccatgttg acattgatta 1680
ttgactagtt attaatagta atcaattacg gggtcattag ttcatagccc atatatggag 1740

-continued

```
ttccgcgtta cataacttac ggtaaatggc ccgcctggct gaccgcccaa cgacccccgc   1800
ccattgacgt caataatgac gtatgttccc atagtaacgc caatagggac tttccattga   1860
cgtcaatggg tggagtattt acggtaaact gcccacttgg cagtacatca agtgtatcat   1920
atgccaagta cgccccctat tgacgtcaat gacggtaaat ggcccgcctg gcattatgcc   1980
cagtacatga ccttatggga ctttcctact tggcagtaca tctacgtatt agtcatcgct   2040
attaccatgg tgatgcggtt ttggcagtac atcaatgggc gtggatagcg gtttgactca   2100
cggggatttc caagtctcca ccccattgac gtcaatggga gtttgttttg gcaccaaaat   2160
caacgggact ttccaaaatg tcgtaacaac tccgccccat tgacgcaaat gggcggtagg   2220
cgtgtacggt gggaggtcta tataagcaga gctcgtttag tgaaccgggg tctctctggt   2280
tagaccagat ctgagcctgg gagctctctg gctaactagg gaacccactg cttaagcctc   2340
aataaagctt gccttgagtg cttcaagtag tgtgtgcccg tctgttgtgt gactctggta   2400
actagagatc cctcagaccc ttttagtcag tgtggaaaat ctctagcagt ggcgcccgaa   2460
cagggacctg aaagcgaaag ggaaaccaga ggagctctct cgacgcagga ctcggcttgc   2520
tgaagcgcgc acggcaagag gcgaggggcg gcgactggtg agtacgccaa aaattttgac   2580
tagcggaggc tagaaggaga gagatgggtg cgagagcgtc agtattaagc gggggagaat   2640
tagatcgcga tgggaaaaaa ttcggttaag gccaggggga aagaaaaaat ataaattaaa   2700
acatatagta tgggcaagca gggagctaga acgattcgca gttaatcctg gcctgttaga   2760
aacatcagaa ggctgtagac aaatactggg acagctacaa ccatcccttc agacaggatc   2820
agaagaactt agatcattat ataatacagt agcaaccctc tattgtgtgc atcaaaggat   2880
agagataaaa gacaccaagg aagctttaga caagatagag gaagagcaaa acaaaagtaa   2940
gaccaccgca cagcaagcgg ccgctgatct tcagacctgg aggaggagat atgagggaca   3000
attggagaag tgaattatat aaatataaag tagtaaaaat tgaaccatta ggagtagcac   3060
ccaccaaggc aaagagaaga gtggtgcaga gagaaaaaag agcagtggga ataggagctt   3120
tgttccttgg gttcttggga gcagcaggaa gcactatggg cgcagcctca atgacgctga   3180
cggtacaggc cagacaatta ttgtctggta tagtgcagca gcagaacaat ttgctgaggg   3240
ctattgaggc gcaacagcat ctgttgcaac tcacagtctg gggcatcaag cagctccagg   3300
caagaatcct ggctgtggaa agatacctaa aggatcaaca gctcctgggg atttggggtt   3360
gctctggaaa actcatttgc accactgctg tgccttggaa tgctagttgg agtaataaat   3420
ctctggaaca gattggaatc acacgacctg gatggagtgg gacagagaaa ttaacaatta   3480
cacaagctta atacactcct taattgaaga atcgcaaaac cagcaagaaa agaatgaaca   3540
agaattattg gaattagata aatgggcaag tttgtggaat tggtttaaca taacaaattg   3600
gctgtggtat ataaaattat tcataatgat agtaggaggc ttggtaggtt taagaatagt   3660
tttgctgta ctttctatag tgaatagagt taggcaggga tattcaccat tatcgtttca   3720
gacccacctc ccaaccccga ggggacccga caggcccgaa ggaatagaag aagaaggtgg   3780
agagagagac agagacagat ccattcgatt agtgaacgga tctcgacggt atcgatctcg   3840
acacaaatgg cagtattcat ccacaatttt aaaagaaaag gggggattgg ggggtacagt   3900
gcaggggaaa gaatagtaga cataatagca acagacatac aaactaaaga attacaaaaa   3960
caaattacaa aaattcaaaa ttttcgggtt tattacaggg acagcagaga tccagtttgg   4020
gaattagctt gactccttcc cattaagacg gaaaaaacat ccgggagagc cggtccgttt   4080
ctcaggcaga ctaggccatt aggtgcctcg gagaaaggac ccaaggctgc tccgtccttc   4140
```

-continued

```
acagacacag tccaatcaga gtttcccagg cacatcgatg caccgcctcc ttcgagaaac   4200
aaggtaactt tcgggttctg gttgtctcca aagtcatccg accaatctcg caccgcccag   4260
agcgggccct tcctgtcaat tacctactga agggcaggcg gccagcatcg ccatggagac   4320
caacaccctt cccaccacca ctcccccttt ctctcagggc ccctgtcccc tccagtgaat   4380
cccagaagac tctggagagt tctgagcaga gggcggcacc ctgccctctg attggtccaa   4440
ggaaggctgg ggggcaggac gggaggcgaa acccctggaa tattcccgac ctggcagcct   4500
catcgagctt ggtgattggc tcagaagggg aaaggcgggt ctccacgacg acttataaaa   4560
gccgaggggc gcgcggtccg gaaaacggcc agcctgagga gctgctgcga gggtccgctt   4620
cgtctttcga gagtgactcc cgcggtccca aggctttcca gagcgaacct gtgcggctgc   4680
aggcaccggc gtgttgagtt tccggcgttc cgaaggactg agctcttgtc gcggatcccg   4740
tccgccgttt ccagccccca gtctcagagc ggagcccaca gagcagggca ccggcatggt   4800
gagcaaggga gaggaggata acatggcctc tctcccagct acacatgagc ttcacatctt   4860
tggatccatc aacggtgtgg actttgacat ggtgggtcag ggaaccggaa atccaaatga   4920
tggatatgag gagcttaacc ttaagtccac caagggtgac ctccagttct ccccatggat   4980
tcttgtccct catatcggat atggattcca tcagtacctt ccttaccctg acggtatgtc   5040
tcctttccag gccgccatgg ttgatggatc cggataccaa gtccatagaa caatgcagtt   5100
tgaagatggt gcctccctta ctgttaacta cagatacacc tacgagggaa gccacatcaa   5160
aggagaggcc caggtgaagg gaactggttt ccctgctgac ggtcctgtga tgaccaactc   5220
tcttaccgct gctgactggt gcaggtctaa gaaaacttac cctaacgaca aaaccatcat   5280
cagtaccttt aagtggagtt acaccactgg aaatggtaag agatacagaa gcactgctag   5340
aaccacctac acctttgcca agccaatggc tgctaactat cttaagaacc agcctatgta   5400
cgtgttccgt aagactgagc tcaagcactc caagaccgag ctcaacttca aggagtggca   5460
aaaggccttt accgatgtga tgggaatgga cgagctttac aagtaatgta caacacgtgc   5520
tacgagattt cgattccgag ctcgaattga cggatcggga gatctactag aagctttgca   5580
aagatggata aagttttaaa cagagaggaa tctttgcagc taatggacct tctaggtctt   5640
gaaaggagtg ggaattggct ccggtgcccg tcagtgggca gagcgcacat cgcccacagt   5700
ccccgagaag ttgggggggag gggtcggcaa ttgaaccggt gcctagagaa ggtggcgcgg   5760
ggtaaactgg gaaagtgatg tcgtgtactg gctccgcctt tttcccgagg gtgggggaga   5820
accgtatata agtgcagtag tcgccgtgaa cgttcttttt cgcaacgggt ttgccgccag   5880
aacacaggta agtgccgtgt gtggttcccg cgggcctggc ctctttacgg gttatggccc   5940
ttgcgtgcct tgaattactt ccactggctg cagtacgtga ttcttgatcc cgagcttcgg   6000
gttggaagtg ggtgggagag ttcgaggcct tgcgcttaag gagccccttc gcctcgtgct   6060
tgagttgagg cctggcctgg gcgctggggc cgccgcgtgc gaatctggtg gcaccttcgc   6120
gcctgtctcg ctgctttcga taagtctcta gccatttaaa atttttgatg acctgctgcg   6180
acgctttttt tctggcaaga tagtcttgta aatgcgggcc aagatctgca cactggtatt   6240
tcggtttttg gggccgcggg cggcgacggg gcccgtgcgt cccagcgcac atgttcggcg   6300
aggcggggcc tgcgagcgcg gccaccgaga atcggacggg ggtagtctca agctggccgg   6360
cctgctctgg tgcctggcct cgcgccgccg tgtatcgccc cgccctgggc ggcaaggctg   6420
gcccggtcgg caccagttgc gtgagcggaa agatggccgc ttcccggccc tgctgcaggg   6480
```

-continued

```
agctcaaaat ggaggacgcg gcgctcggga gagcgggcgg gtgagtcacc cacacaaagg   6540
aaaagggcct ttccgtcctc agccgtcgct tcatgtgact ccacggagta ccgggcgccg   6600
tccaggcacc tcgattagtt ctcgagcttt tggagtacgt cgtctttagg ttgggggggag  6660
gggttttatg cgatggagtt tccccacact gagtgggtgg agactgaagt taggccagct   6720
tggcacttga tgtaattctc cttggaattt gcccttttttg agtttggatc ttggttcatt  6780
ctcaagcctc agacagtggt tcaaagtttt tttcttccat ttcaggtgtc gtgaccggtc   6840
gccaccatgg tgtctaaggg cgaagagctg attaaggaga acatgcacat gaagctgtac   6900
atggagggca ccgtggacaa ccatcacttc aagtgcacat ccgagggcga aggcaagccc   6960
tacgagggca cccagaccat gagaatcaag gtggtcgagg gcggccctct ccccttcgcc   7020
ttcgacatcc tggctactag cttcctctac ggcagcaaga ccttcatcaa ccacacccag   7080
ggcatccccg acttcttcaa gcagtccttc cctgagggct tcacatggga gagagtcacc   7140
acatacgaag acgggggcgt gctgaccgct acccaggaca ccagcctcca ggacggctgc   7200
ctcatctaca acgtcaagat cagaggggtg aacttcacat ccaacggccc tgtgatgcag   7260
aagaaaacac tcggctggga ggccttcacc gagacgctgt accccgctga cggcggcctg   7320
gaaggcagaa acgacatggc cctgaagctc gtgggcggga gccatctgat cgcaaacgcc   7380
aagaccacat atagatccaa gaaacccgct aagaacctca agatgcctgg cgtctactat   7440
gtggactaca gactggaaag aatcaaggag gccaacaacg agacctacgt cgagcagcac   7500
gaggtggcag tggccagata ctgcgacctc cctagcaaac tggggcacaa gcttaattaa   7560
tgtacaaatc aacctctgga ttacaaaatt tgtgaaagat tgactggtat tcttaactat   7620
gttgctcctt ttacgctatg tggatacgct gctttaatgc ctttgtatca tgctattgct   7680
tcccgtatgg ctttcatttt ctcctccttg tataaatcct ggttgctgtc tctttatgag   7740
gagttgtggc ccgttgtcag gcaacgtggc gtggtgtgca ctgtgtttgc tgacgcaacc   7800
cccactggtt ggggcattgc caccacctgt cagctccttt ccgggacttt cgctttcccc   7860
ctccctattg ccacggcgga actcatcgcc gcctgccttg cccgctgctg gacaggggct   7920
cggctgttgg gcactgacaa ttccgtggtg ttgtcgggga aatcatcgtc ctttccttgg   7980
ctgctcgcct atgttgccac ctggattctg cgcgggacgt ccttctgcta cgtcccttcg   8040
gccctcaatc cagcggacct tccttcccgc ggcctgctgc cggctctgcg gcctcttccg   8100
cgtcttcgcc ttcgccctca gacgagtcgg atctcccttt gggccgcctc cccgctacaa   8160
ggcagctgta gatccctttc atagaaggcg gcggtggtac ctttaagacc aatgacttac   8220
aaggcagctg tagatcttag ccactttttta aaagaaaagg ggggactgga agggctaatt  8280
cactcccaac gaagacaaga tctgcttttt gcttgtactg ggtctctctg gttagaccag   8340
atctgagcct gggagctctc tggctaacta gggaacccac tgcttaagcc tcaataaagc   8400
ttgccttgag tgcttcaagt agtgtgtgcc cgtctgttgt gtgactctgg taactagaga   8460
tccctcagac ccttttagtc agtgtggaaa atctctagca gtagtagttc atgtcatctt   8520
attattcagt atttataact tgcaaagaaa tgaatatcag agagtgagag gaacttgttt   8580
attgcagctt ataatggtta caaataaagc aatagcatca caaatttcac aaataaagca   8640
ttttttcac tgcattctag ttgtggtttg tccaaactca tcaatgtatc ttatcatgtc    8700
tggctctagc tatcccgccc ctaactccgc ccatcccgcc cctaactccg cccagttccg   8760
cccattctcc gccccatggc tgactaattt ttttatttta tgcagaggcc gaggccgcct   8820
cggcctctga gctattccag aagtagtgag gaggcttttt tggaggccta ggcttttgcg   8880
```

tcgagacgta cccaattcgc cctatagtga gtcgtattac gcgcgctcac tggccgtcgt 8940
tttacaacgt cgtgactggg aaaaccctgg cgttacccaa cttaatcgcc ttgcagcaca 9000
tccccctttc gccagctggc gtaatagcga agaggcccgc accgatcgcc cttcccaaca 9060
gttgcgcagc ctgaatggcg aatggcgcga cgcgccctgt agcggcgcat taagcgcggc 9120
gggtgtggtg gttacgcgca gcgtgaccgc tacacttgcc agcgccctag cgcccgctcc 9180
tttcgctttc ttcccttcct ttctcgccac gttcgccggc tttccccgtc aagctctaaa 9240
tcgggggctc cctttagggt tccgatttag tgctttacgg cacctcgacc ccaaaaaact 9300
tgattagggt gatggttcac gtagtgggcc atcgccctga tagacggttt ttcgcccttt 9360
gacgttggag tccacgttct ttaatagtgg actcttgttc caaactggaa caacactcaa 9420
ccctatctcg gtctattctt ttgatttata agggattttg ccgatttcgg cctattggtt 9480
aaaaaatgag ctgatttaac aaaaatttaa cgcgaatttt aacaaaatat taacgtttac 9540
aatttcccag gtggcacttt tcggggaaat gtgcgcggaa cccctatttg tttatttttc 9600
taaatacatt caaatatgta tccgctcatg agacaataac cctgataaat gcttcaataa 9660
tattgaaaaa ggaagagtat gagtattcaa catttccgtg tcgcccttat tccctttttt 9720
gcggcatttt gccttcctgt ttttgctcac ccagaaacgc tggtgaaagt aaaagatgct 9780
gaagatcagt tgggtgcacg agtgggttac atcgaactgg atctcaacag cggtaagatc 9840
cttgagagtt ttcgccccga agaacgtttt ccaatgatga gcacttttaa agttctgcta 9900
tgtggcgcgg tattatcccg tattgacgcc gggcaagagc aactcggtcg ccgcatacac 9960
tattctcaga atgacttggt tgagtactca ccagtcacag aaaagcatct tacggatggc 10020
atgacagtaa gagaattatg cagtgctgcc ataaccatga gtgataacac tgcggccaac 10080
ttacttctga caacgatcgg aggaccgaag gagctaaccg cttttttgca caacatgggg 10140
gatcatgtaa ctcgccttga tcgttgggaa 10170

<210> SEQ ID NO 18
<211> LENGTH: 9879
<212> TYPE: DNA
<213> ORGANISM: Artificial Sequence
<220> FEATURE:
<223> OTHER INFORMATION: pTLL-phHsp70B

<400> SEQUENCE: 18
ccggagctga atgaagccat accaaacgac gagcgtgaca ccacgatgcc tgtagcaatg 60
gcaacaacgt tgcgcaaact attaactggc gaactactta ctctagcttc ccggcaacaa 120
ttaatagact ggatggaggc ggataaagtt gcaggaccac ttctgcgctc ggcccttccg 180
gctggctggt ttattgctga taaatctgga gccggtgagc gtgggtctcg cggtatcatt 240
gcagcactgg ggccagatgg taagccctcc cgtatcgtag ttatctacac gacggggagt 300
caggcaacta tggatgaacg aaatagacag atcgctgaga taggtgcctc actgattaag 360
cattggtaac tgtcagacca agtttactca tatatacttt agattgattt aaaacttcat 420
ttttaattta aaaggatcta ggtgaagatc ctttttgata atctcatgac caaaatccct 480
taacgtgagt tttcgttcca ctgagcgtca gaccccgtag aaaagatcaa aggatcttct 540
tgagatcctt tttttctgcg cgtaatctgc tgcttgcaaa caaaaaaacc accgctacca 600
gcggtggttt gtttgccgga tcaagagcta ccaactcttt ttccgaaggt aactggcttc 660
agcagagcgc agataccaaa tactgtcctt ctagtgtagc cgtagttagg ccaccacttc 720

-continued

```
aagaactctg tagcaccgcc tacatacctc gctctgctaa tcctgttacc agtggctgct    780
gccagtggcg ataagtcgtg tcttaccggg ttggactcaa gacgatagtt accggataag    840
gcgcagcggt cgggctgaac ggggggttcg tgcacacagc ccagcttgga gcgaacgacc    900
tacaccgaac tgagatacct acagcgtgag ctatgagaaa gcgccacgct tcccgaaggg    960
agaaaggcgg acaggtatcc ggtaagcggc agggtcggaa caggagagcg cacgagggag   1020
cttccagggg gaaacgcctg gtatctttat agtcctgtcg ggtttcgcca cctctgactt   1080
gagcgtcgat ttttgtgatg ctcgtcaggg gggcggagcc tatggaaaaa cgccagcaac   1140
gcggcctttt tacggttcct ggccttttgc tggccttttg ctcacatgtt ctttcctgcg   1200
ttatcccctg attctgtgga taaccgtatt accgcctttg agtgagctga taccgctcgc   1260
cgcagccgaa cgaccgagcg cagcgagtca gtgagcgagg aagcggaaga gcgcccaata   1320
cgcaaaccgc ctctccccgc gcgttggccg attcattaat gcagctggca cgacaggttt   1380
cccgactgga aagcgggcag tgagcgcaac gcaattaatg tgagttagct cactcattag   1440
gcaccccagg ctttacactt tatgcttccg gctcgtatgt tgtgtggaat tgtgagcgga   1500
taacaatttc acacaggaaa cagctatgac catgattacg ccaagcgcgc aattaaccct   1560
cactaaaggg aacaaaagct ggagctgcaa gcttggccat tgcatacgtt gtatccatat   1620
cataatatgt acatttatat tggctcatgt ccaacattac cgccatgttg acattgatta   1680
ttgactagtt attaatagta atcaattacg gggtcattag ttcatagccc atatatggag   1740
ttccgcgtta cataacttac ggtaaatggc ccgcctggct gaccgcccaa cgacccccgc   1800
ccattgacgt caataatgac gtatgttccc atagtaacgc caatagggac tttccattga   1860
cgtcaatggg tggagtattt acggtaaact gcccacttgg cagtacatca agtgtatcat   1920
atgccaagta cgccccctat tgacgtcaat gacggtaaat ggcccgcctg gcattatgcc   1980
cagtacatga ccttatggga ctttcctact tggcagtaca tctacgtatt agtcatcgct   2040
attaccatgg tgatgcggtt ttggcagtac atcaatgggc gtggatagcg gtttgactca   2100
cggggatttc caagtctcca ccccattgac gtcaatggga gtttgttttg gcaccaaaat   2160
caacgggact ttccaaaatg tcgtaacaac tccgccccat tgacgcaaat gggcggtagg   2220
cgtgtacggt gggaggtcta tataagcaga gctcgtttag tgaaccgggg tctctctggt   2280
tagaccagat ctgagcctgg gagctctctg gctaactagg gaacccactg cttaagcctc   2340
aataaagctt gccttgagtg cttcaagtag tgtgtgcccg tctgttgtgt gactctggta   2400
actagagatc cctcagaccc ttttagtcag tgtggaaaat ctctagcagt ggcgcccgaa   2460
cagggacctg aaagcgaaag ggaaaccaga ggagctctct cgacgcagga ctcggcttgc   2520
tgaagcgcgc acggcaagag gcgagggcgg gcgactggtg agtacgccaa aaattttgac   2580
tagcggaggc tagaaggaga gagatgggtg cgagagcgtc agtattaagc gggggagaat   2640
tagatcgcga tgggaaaaaa ttcggttaag gccaggggga aagaaaaaat ataaattaaa   2700
acatatagta tgggcaagca gggagctaga acgattcgca gttaatcctg gcctgttaga   2760
aacatcagaa ggctgtagac aaatactggg acagctacaa ccatcccttc agacaggatc   2820
agaagaactt agatcattat ataatacagt agcaaccctc tattgtgtgc atcaaaggat   2880
agagataaaa gacaccaagg aagctttaga caagatagag gaagagcaaa acaaaagtaa   2940
gaccaccgca cagcaagcgg ccgctgatct tcagacctgg aggaggagat atgagggaca   3000
attggagaag tgaattatat aaatataaag tagtaaaaat tgaaccatta ggagtagcac   3060
ccaccaaggc aaagagaaga gtggtgcaga gagaaaaaag agcagtggga ataggagctt   3120
```

-continued

```
tgttccttgg gttcttggga gcagcaggaa gcactatggg cgcagcctca atgacgctga   3180
cggtacaggc cagacaatta ttgtctggta tagtgcagca gcagaacaat ttgctgaggg   3240
ctattgaggc gcaacagcat ctgttgcaac tcacagtctg gggcatcaag cagctccagg   3300
caagaatcct ggctgtggaa agatacctaa aggatcaaca gctcctgggg atttggggtt   3360
gctctggaaa actcatttgc accactgctg tgccttggaa tgctagttgg agtaataaat   3420
ctctggaaca gattggaatc acacgacctg gatggagtgg gacagagaaa ttaacaatta   3480
cacaagctta atacactcct taattgaaga atcgcaaaac cagcaagaaa agaatgaaca   3540
agaattattg gaattagata aatgggcaag tttgtggaat tggtttaaca taacaaattg   3600
gctgtggtat ataaaattat tcataatgat agtaggaggc ttggtaggtt taagaatagt   3660
tttgctgtta ctttctatag tgaatagagt taggcaggga tattcaccat tatcgtttca   3720
gacccacctc ccaaccccga ggggacccga caggcccgaa ggaatagaag aagaaggtgg   3780
agagagagac agagacagat ccattcgatt agtgaacgga tctcgacggt atcgatctcg   3840
acacaaatgg cagtattcat ccacaatttt aaaagaaaag gggggattgg ggggtacagt   3900
gcaggggaaa gaatagtaga cataatagca acagacatac aaactaaaga attacaaaaa   3960
caaattacaa aaattcaaaa ttttcgggtt tattacaggg acagcagaga tccagtttgg   4020
gaattagctt gaggatcctc cacagccccg gggagacctt gcctctaaag ttgctgcttt   4080
tgcagctctg ccacaaccgc gcgtcctcag agccagccgg gaggagctag aaccttcccc   4140
gcgtttcttt cagcagccct gagtcagagg cgggctggcc ttgcaagtag ccgcccagcc   4200
ttcttcggtc tcacggaccg atccgcccga accttctccc ggggtcagcg ccgcgctgcg   4260
ccgcccggct gactcagccc gggcgggcgg gcgggaggct ctcgactggg cgggaaggtg   4320
cgggaaggtt cgcggcggcg gggtcgggga ggtgcaaaag gatgaaaagc ccgtggacgg   4380
agctgagcag atccggccgg gctggcggca gagaaaccgc agggagagcc tcactgctga   4440
gcgcccctcg acgcgggcgg cagcagcctc cgtggcctcc agcatccgac aagaagcttc   4500
agccatggtg agcaagggag aggaggataa catggcctct ctcccagcta cacatgagct   4560
tcacatcttt ggatccatca acggtgtgga ctttgacatg gtgggtcagg gaaccggaaa   4620
tccaaatgat ggatatgagg agcttaacct taagtccacc aagggtgacc tccagttctc   4680
cccatggatt cttgtccctc atatcggata tggattccat cagtaccttc cttaccctga   4740
cggtatgtct cctttccagg ccgccatggt tgatggatcc ggataccaag tccatagaac   4800
aatgcagttt gaagatggtg cctcccttac tgttaactac agatacacct acgagggaag   4860
ccacatcaaa ggagaggccc aggtgaaggg aactggtttc cctgctgacg gtcctgtgat   4920
gaccaactct cttaccgctg ctgactggtg caggtctaag aaaacttacc ctaacgacaa   4980
aaccatcatc agtaccttta agtggagtta caccactgga aatggtaaga gatacagaag   5040
cactgctaga accacctaca cctttgccaa gccaatggct gctaactatc ttaagaacca   5100
gcctatgtac gtgttccgta agactgagct caagcactcc aagaccgagc tcaacttcaa   5160
ggagtggcaa aaggccttta ccgatgtgat gggaatggac gagctttaca agtaatgtac   5220
aacacgtgct acgagatttc gattccgagc tcgaattgac ggatcgggag atctactaga   5280
agctttgcaa agatggataa agttttaaac agagaggaat ctttgcagct aatggacctt   5340
ctaggtcttg aaaggagtgg gaattggctc cggtgcccgt cagtgggcag agcgcacatc   5400
gcccacagtc cccgagaagt tggggggagg ggtcggcaat tgaaccggtg cctagagaag   5460
```

-continued

```
gtggcgcggg gtaaactggg aaagtgatgt cgtgtactgg ctccgccttt ttcccgaggg   5520
tgggggagaa ccgtatataa gtgcagtagt cgccgtgaac gttctttttc gcaacgggtt   5580
tgccgccaga acacaggtaa gtgccgtgtg tggttcccgc gggcctggcc tctttacggg   5640
ttatggccct tgcgtgcctt gaattacttc cactggctgc agtacgtgat tcttgatccc   5700
gagcttcggg ttggaagtgg gtgggagagt tcgaggcctt gcgcttaagg agccccttcg   5760
cctcgtgctt gagttgaggc ctggcctggg cgctggggcc gccgcgtgcg aatctggtgg   5820
caccttcgcg cctgtctcgc tgctttcgat aagtctctag ccatttaaaa tttttgatga   5880
cctgctgcga cgcttttttt ctggcaagat agtcttgtaa atgcgggcca agatctgcac   5940
actggtattt cggtttttgg ggccgcgggc ggcgacgggg cccgtgcgtc ccagcgcaca   6000
tgttcggcga ggcggggcct gcgagcgcgg ccaccgagaa tcggacgggg gtagtctcaa   6060
gctggccggc ctgctctggt gcctggcctc gcgccgccgt gtatcgcccc gccctgggcg   6120
gcaaggctgg cccggtcggc accagttgcg tgagcggaaa gatggccgct tcccggccct   6180
gctgcaggga gctcaaaatg gaggacgcgg cgctcgggag agcgggcggg tgagtcaccc   6240
acacaaagga aaagggcctt tccgtcctca gccgtcgctt catgtgactc cacggagtac   6300
cgggcgccgt ccaggcacct cgattagttc tcgagctttt ggagtacgtc gtctttaggt   6360
tggggggagg ggttttatgc gatggagttt ccccacactg agtgggtgga gactgaagtt   6420
aggccagctt ggcacttgat gtaattctcc ttggaatttg ccctttttga gtttggatct   6480
tggttcattc tcaagcctca gacagtggtt caaagttttt ttcttccatt tcaggtgtcg   6540
tgaccggtcg ccaccatggt gtctaagggc gaagagctga ttaaggagaa catgcacatg   6600
aagctgtaca tggagggcac cgtggacaac catcacttca agtgcacatc cgagggcgaa   6660
ggcaagccct acgagggcac ccagaccatg agaatcaagg tggtcgaggg cggccctctc   6720
cccttcgcct tcgacatcct ggctactagc ttcctctacg gcagcaagac cttcatcaac   6780
cacacccagg gcatccccga cttcttcaag cagtccttcc ctgagggctt cacatgggag   6840
agagtcacca catacgaaga cgggggcgtg ctgaccgcta cccaggacac cagcctccag   6900
gacggctgcc tcatctacaa cgtcaagatc agaggggtga acttcacatc caacggccct   6960
gtgatgcaga agaaaacact cggctgggag gccttcaccg agacgctgta ccccgctgac   7020
ggcggcctgg aaggcagaaa cgacatggcc ctgaagctcg tgggcgggag ccatctgatc   7080
gcaaacgcca agaccacata tagatccaag aaacccgcta agaacctcaa gatgcctggc   7140
gtctactatg tggactacag actggaaaga atcaaggagg ccaacaacga gacctacgtc   7200
gagcagcacg aggtggcagt ggccagatac tgcgacctcc ctagcaaact ggggcacaag   7260
cttaattaat gtacaaatca acctctggat tacaaaattt gtgaaagatt gactggtatt   7320
cttaactatg ttgctccttt tacgctatgt ggatacgctg ctttaatgcc tttgtatcat   7380
gctattgctt cccgtatggc tttcattttc tcctccttgt ataaatcctg gttgctgtct   7440
ctttatgagg agttgtggcc cgttgtcagg caacgtggcg tggtgtgcac tgtgtttgct   7500
gacgcaaccc ccactggttg gggcattgcc accacctgtc agctcctttc cgggactttc   7560
gctttccccc tccctattgc cacggcggaa ctcatcgccg cctgccttgc ccgctgctgg   7620
acaggggctc ggctgttggg cactgacaat tccgtggtgt tgtcggggaa atcatcgtcc   7680
tttccttggc tgctcgccta tgttgccacc tggattctgc gcgggacgtc cttctgctac   7740
gtcccttcgg ccctcaatcc agcggacctt ccttcccgcg gcctgctgcc ggctctgcgg   7800
cctcttccgc gtcttcgcct tcgccctcag acgagtcgga tctccctttg ggccgcctcc   7860
```

```
ccgctacaag gcagctgtag atccctttca tagaaggcgg cggtggtacc tttaagacca   7920
atgacttaca aggcagctgt agatcttagc cactttttaa aagaaaaggg gggactggaa   7980
gggctaattc actcccaacg aagacaagat ctgctttttg cttgtactgg gtctctctgg   8040
ttagaccaga tctgagcctg ggagctctct ggctaactag ggaacccact gcttaagcct   8100
caataaagct tgccttgagt gcttcaagta gtgtgtgccc gtctgttgtg tgactctggt   8160
aactagagat ccctcagacc cttttagtca gtgtggaaaa tctctagcag tagtagttca   8220
tgtcatctta ttattcagta tttataactt gcaaagaaat gaatatcaga gagtgagagg   8280
aacttgttta ttgcagctta taatggttac aaataaagca atagcatcac aaatttcaca   8340
aataaagcat ttttttcact gcattctagt tgtggtttgt ccaaactcat caatgtatct   8400
tatcatgtct ggctctagct atcccgcccc taactccgcc catcccgccc ctaactccgc   8460
ccagttccgc ccattctccg ccccatggct gactaatttt ttttatttat gcagaggccg   8520
aggccgcctc ggcctctgag ctattccaga agtagtgagg aggctttttt ggaggcctag   8580
gcttttgcgt cgagacgtac ccaattcgcc ctatagtgag tcgtattacg cgcgctcact   8640
ggccgtcgtt ttacaacgtc gtgactggga aaaccctggc gttacccaac ttaatcgcct   8700
tgcagcacat ccccctttcg ccagctggcg taatagcgaa gaggcccgca ccgatcgccc   8760
ttcccaacag ttgcgcagcc tgaatggcga atggcgcgac gcgccctgta gcggcgcatt   8820
aagcgcggcg ggtgtggtgg ttacgcgcag cgtgaccgct acacttgcca gcgccctagc   8880
gcccgctcct ttcgctttct tcccttcctt tctcgccacg ttcgccggct ttccccgtca   8940
agctctaaat cgggggctcc ctttagggtt ccgatttagt gctttacggc acctcgaccc   9000
caaaaaactt gattagggtg atggttcacg tagtgggcca tcgccctgat agacggtttt   9060
tcgccctttg acgttggagt ccacgttctt taatagtgga ctcttgttcc aaactggaac   9120
aacactcaac cctatctcgg tctattcttt tgatttataa gggattttgc cgatttcggc   9180
ctattggtta aaaaatgagc tgatttaaca aaaatttaac gcgaatttta acaaaatatt   9240
aacgtttaca atttcccagg tggcactttt cggggaaatg tgcgcggaac ccctatttgt   9300
ttatttttct aaatacattc aaatatgtat ccgctcatga gacaataacc ctgataaatg   9360
cttcaataat attgaaaaag gaagagtatg agtattcaac atttccgtgt cgcccttatt   9420
cccttttttg cggcattttg ccttcctgtt tttgctcacc cagaaacgct ggtgaaagta   9480
aaagatgctg aagatcagtt gggtgcacga gtgggttaca tcgaactgga tctcaacagc   9540
ggtaagatcc ttgagagttt tcgccccgaa gaacgttttc caatgatgag cacttttaaa   9600
gttctgctat gtggcgcggt attatcccgt attgacgccg ggcaagagca actcggtcgc   9660
cgcatacact attctcagaa tgacttggtt gagtactcac cagtcacaga aaagcatctt   9720
acggatggca tgacagtaag agaattatgc agtgctgcca taaccatgag tgataacact   9780
gcggccaact tacttctgac aacgatcgga ggaccgaagg agctaaccgc ttttttgcac   9840
aacatggggg atcatgtaac tcgccttgat cgttgggaa                          9879
```

<210> SEQ ID NO 19
<211> LENGTH: 9644
<212> TYPE: DNA
<213> ORGANISM: Artificial Sequence
<220> FEATURE:
<223> OTHER INFORMATION: pTLL-pHsp16-F-mWasabi

<400> SEQUENCE: 19

-continued

```
ggctccggtg cccgtcagtg ggcagagcgc acatcgccca cagtccccga gaagttgggg     60
ggaggggtcg gcaattgaac cggtgcctag agaaggtggc gcggggtaaa ctgggaaagt    120
gatgtcgtgt actggctccg cctttttccc gagggtgggg gagaaccgta tataagtgca    180
gtagtcgccg tgaacgttct ttttcgcaac gggtttgccg ccagaacaca ggtaagtgcc    240
gtgtgtggtt cccgcgggcc tggcctcttt acgggttatg gcccttgcgt gccttgaatt    300
acttccactg gctgcagtac gtgattcttg atcccgagct tcgggttgga agtgggtggg    360
agagttcgag gccttgcgct taaggagccc cttcgcctcg tgcttgagtt gaggcctggc    420
ctgggcgctg gggccgccgc gtgcgaatct ggtggcacct tcgcgcctgt ctcgctgctt    480
tcgataagtc tctagccatt taaaattttt gatgacctgc tgcgacgctt tttttctggc    540
aagatagtct tgtaaatgcg ggccaagatc tgcacactgg tatttcggtt tttggggccg    600
cgggcggcga cggggcccgt gcgtcccagc gcacatgttc ggcgaggcgg ggcctgcgag    660
cgcggccacc gagaatcgga cgggggtagt ctcaagctgg ccggcctgct ctggtgcctg    720
gcctcgcgcc gccgtgtatc gccccgccct gggcggcaag gctggcccgg tcggcaccag    780
ttgcgtgagc ggaaagatgg ccgcttcccg gccctgctgc agggagctca aaatggagga    840
cgcggcgctc gggagagcgg gcgggtgagt cacccacaca aaggaaaagg gcctttccgt    900
cctcagccgt cgcttcatgt gactccacgg agtaccgggc gccgtccagg cacctcgatt    960
agttctcgag cttttggagt acgtcgtctt taggttgggg ggaggggttt tatgcgatgg   1020
agtttcccca cactgagtgg gtggagactg aagttaggcc agcttggcac ttgatgtaat   1080
tctccttgga atttgccctt tttgagtttg gatcttggtt cattctcaag cctcagacag   1140
tggttcaaag tttttttctt ccatttcagg tgtcgtgacc ggtcgccacc atggtgtcta   1200
agggcgaaga gctgattaag gagaacatgc acatgaagct gtacatggag ggcaccgtgg   1260
acaaccatca cttcaagtgc acatccgagg gcgaaggcaa gccctacgag ggcacccaga   1320
ccatgagaat caaggtggtc gagggcggcc ctctcccctt cgccttcgac atcctggcta   1380
ctagcttcct ctacggcagc aagaccttca tcaaccacac ccagggcatc cccgacttct   1440
tcaagcagtc cttccctgag ggcttcacat gggagagagt caccacatac gaagacgggg   1500
gcgtgctgac cgctacccag gacaccagcc tccaggacgg ctgcctcatc tacaacgtca   1560
agatcagagg ggtgaacttc acatccaacg gccctgtgat gcagaagaaa acactcggct   1620
gggaggcctt caccgagacg ctgtaccccg ctgacggcgg cctggaaggc agaaacgaca   1680
tggccctgaa gctcgtgggc gggagccatc tgatcgcaaa cgccaagacc acatatagat   1740
ccaagaaacc cgctaagaac ctcaagatgc ctggcgtcta ctatgtggac tacagactgg   1800
aaagaatcaa ggaggccaac aacgagacct acgtcgagca gcacgaggtg gcagtggcca   1860
gatactgcga cctccctagc aaactggggc acaagcttaa ttaatgtaca aatcaacctc   1920
tggattacaa aatttgtgaa agattgactg gtattcttaa ctatgttgct ccttttacgc   1980
tatgtggata cgctgcttta atgcctttgt atcatgctat tgcttcccgt atggctttca   2040
ttttctcctc cttgtataaa tcctggttgc tgtctcttta tgaggagttg tggcccgttg   2100
tcaggcaacg tggcgtggtg tgcactgtgt ttgctgacgc aacccccact ggttggggca   2160
ttgccaccac ctgtcagctc ctttccggga ctttcgcttt ccccctccct attgccacgg   2220
cggaactcat cgccgcctgc cttgcccgct gctggacagg ggctcggctg ttgggcactg   2280
acaattccgt ggtgttgtcg gggaaatcat cgtcctttcc ttggctgctc gcctatgttg   2340
ccacctggat tctgcgcggg acgtccttct gctacgtccc ttcggccctc aatccagcgg   2400
```

-continued

```
acctt ccttc ccgcggcctg ctgccggctc tgcggcctct tccgcgtctt cgccttcgcc   2460
ctcagacgag tcggatctcc ctttgggccg cctccccgct acaaggcagc tgtagatccc   2520
tttcatagaa ggcggcggtg gtacctttaa gaccaatgac ttacaaggca gctgtagatc   2580
ttagccactt tttaaaagaa aaggggggac tggaagggct aattcactcc caacgaagac   2640
aagatctgct ttttgcttgt actgggtctc tctggttaga ccagatctga gcctgggagc   2700
tctctggcta actagggaac ccactgctta agcctcaata aagcttgcct tgagtgcttc   2760
aagtagtgtg tgcccgtctg ttgtgtgact ctggtaacta gagatccctc agaccctttt   2820
agtcagtgtg gaaaatctct agcagtagta gttcatgtca tcttattatt cagtatttat   2880
aacttgcaaa gaaatgaata tcagagagtg agaggaactt gtttattgca gcttataatg   2940
gttacaaata aagcaatagc atcacaaatt tcacaaataa agcatttttt tcactgcatt   3000
ctagttgtgg tttgtccaaa ctcatcaatg tatcttatca tgtctggctc tagctatccc   3060
gcccctaact ccgcccatcc cgcccctaac tccgcccagt tccgcccatt ctccgcccca   3120
tggctgacta attttttta tttatgcaga ggccgaggcc gcctcggcct ctgagctatt   3180
ccagaagtag tgaggaggct tttttggagg cctaggcttt tgcgtcgaga cgtacccaat   3240
tcgccctata gtgagtcgta ttacgcgcgc tcactggccg tcgttttaca acgtcgtgac   3300
tgggaaaacc ctggcgttac ccaacttaat cgccttgcag cacatccccc tttcgccagc   3360
tggcgtaata gcgaagaggc ccgcaccgat cgcccttccc aacagttgcg cagcctgaat   3420
ggcgaatggc gcgacgcgcc ctgtagcggc gcattaagcg cggcgggtgt ggtggttacg   3480
cgcagcgtga ccgctacact tgccagcgcc ctagcgcccg ctcctttcgc tttcttccct   3540
tcctttctcg ccacgttcgc cggctttccc cgtcaagctc taaatcgggg gctcccttta   3600
gggttccgat ttagtgcttt acggcacctc gaccccaaaa aacttgatta gggtgatggt   3660
tcacgtagtg ggccatcgcc ctgatagacg gtttttcgcc ctttgacgtt ggagtccacg   3720
ttctttaata gtggactctt gttccaaact ggaacaacac tcaaccctat ctcggtctat   3780
tcttttgatt tataagggat tttgccgatt tcggcctatt ggttaaaaaa tgagctgatt   3840
taacaaaaat ttaacgcgaa ttttaacaaa atattaacgt ttacaatttc ccaggtggca   3900
cttttcgggg aaatgtgcgc ggaaccccta tttgtttatt tttctaaata cattcaaata   3960
tgtatccgct catgagacaa taaccctgat aaatgcttca ataatattga aaaaggaaga   4020
gtatgagtat tcaacatttc cgtgtcgccc ttattccctt ttttgcggca ttttgccttc   4080
ctgtttttgc tcacccagaa acgctggtga aagtaaaaga tgctgaagat cagttgggtg   4140
cacgagtggg ttacatcgaa ctggatctca acagcggtaa gatccttgag agttttcgcc   4200
ccgaagaacg ttttccaatg atgagcactt ttaaagttct gctatgtggc gcggtattat   4260
cccgtattga cgccgggcaa gagcaactcg gtcgccgcat acactattct cagaatgact   4320
tggttgagta ctcaccagtc acagaaaagc atcttacgga tggcatgaca gtaagagaat   4380
tatgcagtgc tgccataacc atgagtgata acactgcggc caacttactt ctgacaacga   4440
tcggaggacc gaaggagcta accgcttttt tgcacaacat gggggatcat gtaactcgcc   4500
ttgatcgttg ggaaccggag ctgaatgaag ccataccaaa cgacgagcgt gacaccacga   4560
tgcctgtagc aatggcaaca acgttgcgca aactattaac tggcgaacta cttactctag   4620
cttcccggca acaattaata gactggatgg aggcggataa agttgcagga ccacttctgc   4680
gctcggccct tccggctggc tggtttattg ctgataaatc tggagccggt gagcgtgggt   4740
```

-continued

```
ctcgcggtat cattgcagca ctggggccag atggtaagcc ctcccgtatc gtagttatct   4800
acacgacggg gagtcaggca actatggatg aacgaaatag acagatcgct gagataggtg   4860
cctcactgat taagcattgg taactgtcag accaagttta ctcatatata ctttagattg   4920
atttaaaact tcatttttaa tttaaaagga tctaggtgaa gatccttttt gataatctca   4980
tgaccaaaat cccttaacgt gagttttcgt tccactgagc gtcagacccc gtagaaaaga   5040
tcaaaggatc ttcttgagat cctttttttc tgcgcgtaat ctgctgcttg caaacaaaaa   5100
aaccaccgct accagcggtg gtttgtttgc cggatcaaga gctaccaact ctttttccga   5160
aggtaactgg cttcagcaga gcgcagatac caaatactgt ccttctagtg tagccgtagt   5220
taggccacca cttcaagaac tctgtagcac cgcctacata cctcgctctg ctaatcctgt   5280
taccagtggc tgctgccagt ggcgataagt cgtgtcttac cgggttggac tcaagacgat   5340
agttaccgga taaggcgcag cggtcgggct gaacgggggg ttcgtgcaca cagcccagct   5400
tggagcgaac gacctacacc gaactgagat acctacagcg tgagctatga gaaagcgcca   5460
cgcttcccga agggagaaag gcggacaggt atccggtaag cggcagggtc ggaacaggag   5520
agcgcacgag ggagcttcca gggggaaacg cctggtatct ttatagtcct gtcgggtttc   5580
gccacctctg acttgagcgt cgatttttgt gatgctcgtc aggggggcgg agcctatgga   5640
aaaacgccag caacgcggcc tttttacggt tcctggcctt ttgctggcct tttgctcaca   5700
tgttctttcc tgcgttatcc cctgattctg tggataaccg tattaccgcc tttgagtgag   5760
ctgataccgc tcgccgcagc cgaacgaccg agcgcagcga gtcagtgagc gaggaagcgg   5820
aagagcgccc aatacgcaaa ccgcctctcc ccgcgcgttg gccgattcat taatgcagct   5880
ggcacgacag gtttcccgac tggaaagcgg gcagtgagcg caacgcaatt aatgtgagtt   5940
agctcactca ttaggcaccc caggctttac actttatgct tccggctcgt atgttgtgtg   6000
gaattgtgag cggataacaa tttcacacag gaaacagcta tgaccatgat tacgccaagc   6060
gcgcaattaa ccctcactaa agggaacaaa agctggagct gcaagcttgg ccattgcata   6120
cgttgtatcc atatcataat atgtacattt atattggctc atgtccaaca ttaccgccat   6180
gttgacattg attattgact agttattaat agtaatcaat tacggggtca ttagttcata   6240
gcccatatat ggagttccgc gttacataac ttacggtaaa tggcccgcct ggctgaccgc   6300
ccaacgaccc ccgcccattg acgtcaataa tgacgtatgt tcccatagta acgccaatag   6360
ggactttcca ttgacgtcaa tgggtggagt atttacggta aactgcccac ttggcagtac   6420
atcaagtgta tcatatgcca agtacgcccc ctattgacgt caatgacggt aaatggcccg   6480
cctggcatta tgcccagtac atgaccttat gggactttcc tacttggcag tacatctacg   6540
tattagtcat cgctattacc atggtgatgc ggttttggca gtacatcaat gggcgtggat   6600
agcggtttga ctcacgggga tttccaagtc tccaccccat tgacgtcaat gggagtttgt   6660
tttggcacca aaatcaacgg gactttccaa aatgtcgtaa caactccgcc ccattgacgc   6720
aaatgggcgg taggcgtgta cggtgggagg tctatataag cagagctcgt ttagtgaacc   6780
ggggtctctc tggttagacc agatctgagc ctgggagctc tctggctaac tagggaaccc   6840
actgcttaag cctcaataaa gcttgccttg agtgcttcaa gtagtgtgtg cccgtctgtt   6900
gtgtgactct ggtaactaga gatccctcag acccttttag tcagtgtgga aaatctctag   6960
cagtggcgcc cgaacaggga cctgaaagcg aaagggaaac cagaggagct ctctcgacgc   7020
aggactcggc ttgctgaagc gcgcacggca agaggcgagg ggcggcgact ggtgagtacg   7080
ccaaaaattt tgactagcgg aggctagaag gagagagatg ggtgcgagag cgtcagtatt   7140
```

-continued

```
aagcggggga gaattagatc gcgatgggaa aaaattcggt taaggccagg gggaaagaaa   7200
aaatataaat taaaacatat agtatgggca agcagggagc tagaacgatt cgcagttaat   7260
cctggcctgt tagaaacatc agaaggctgt agacaaatac tgggacagct acaaccatcc   7320
cttcagacag gatcagaaga acttagatca ttatataata cagtagcaac cctctattgt   7380
gtgcatcaaa ggatagagat aaaagacacc aaggaagctt tagacaagat agaggaagag   7440
caaaacaaaa gtaagaccac cgcacagcaa gcggccgctg atcttcagac ctggaggagg   7500
agatatgagg gacaattgga gaagtgaatt atataaatat aaagtagtaa aaattgaacc   7560
attaggagta gcacccacca aggcaaagag aagagtggtg cagagagaaa aaagagcagt   7620
gggaatagga gctttgttcc ttgggttctt gggagcagca ggaagcacta tgggcgcagc   7680
ctcaatgacg ctgacggtac aggccagaca attattgtct ggtatagtgc agcagcagaa   7740
caatttgctg agggctattg aggcgcaaca gcatctgttg caactcacag tctggggcat   7800
caagcagctc caggcaagaa tcctggctgt ggaaagatac ctaaaggatc aacagctcct   7860
ggggatttgg ggttgctctg gaaaactcat ttgcaccact gctgtgcctt ggaatgctag   7920
ttggagtaat aaatctctgg aacagattgg aatcacacga cctggatgga gtgggacaga   7980
gaaattaaca attacacaag cttaatacac tccttaattg aagaatcgca aaaccagcaa   8040
gaaaagaatg aacaagaatt attggaatta gataaatggg caagtttgtg gaattggttt   8100
aacataacaa attggctgtg gtatataaaa ttattcataa tgatagtagg aggcttggta   8160
ggtttaagaa tagtttttgc tgtactttct atagtgaata gagttaggca gggatattca   8220
ccattatcgt ttcagaccca cctcccaacc ccgaggggac ccgacaggcc cgaaggaata   8280
gaagaagaag gtggagagag agacagagac agatccattc gattagtgaa cggatctcga   8340
cggtatcgat ctcgacacaa atggcagtat tcatccacaa ttttaaaaga aaaggggga    8400
ttgggggta cagtgcaggg gaaagaatag tagacataat agcaacagac atacaaacta   8460
aagaattaca aaaacaaatt acaaaaattc aaaattttcg ggtttattac agggacagcc   8520
ttgatcactg cctcgccctt gctcaccatg gtggcgattg tagtttgaag atttcacaat   8580
tagagtgaat gttgtttggt tcggttttgt cactgtattt atactcattt ccaccttttt   8640
ctagaaggtc ctagatgcat ctaggacctt ctagaacatt ctaaacggct gcaggatacg   8700
ggtatataag ccaatcgtgt tcagaggaaa ccaatacact ttgttcaagt gcttactgtt   8760
cattctctaa acttcaagac accatggtga gcaagggaga ggaggataac atggcctctc   8820
tcccagctac acatgagctt cacatctttg gatccatcaa cggtgtggac tttgacatgg   8880
tgggtcaggg aaccggaaat ccaaatgatg gatatgagga gcttaacctt aagtccacca   8940
agggtgacct ccagttctcc ccatggattc ttgtccctca tatcggatat ggattccatc   9000
agtaccttcc ttaccctgac ggtatgtctc ctttccaggc cgccatggtt gatggatccg   9060
gataccaagt ccatagaaca atgcagtttg aagatggtgc ctcccttact gttaactaca   9120
gatacaccta cgagggaagc cacatcaaag gagaggccca ggtgaaggga actggtttcc   9180
ctgctgacgg tcctgtgatg accaactctc ttaccgctgc tgactggtgc aggtctaaga   9240
aaacttaccc taacgacaaa accatcatca gtacctttaa gtggagttac accactggaa   9300
atggtaagag atacagaagc actgctagaa ccacctacac ctttgccaag ccaatggctg   9360
ctaactatct taagaaccag cctatgtacg tgttccgtaa gactgagctc aagcactcca   9420
agaccgagct caacttcaag gagtggcaaa aggcctttac cgatgtgatg ggaatggacg   9480
```

agctttacaa gtaatgtaca acacgtgcta cgagatttcg attccgagct cgaattgacg 9540
gatcgggaga tctactagaa gctttgcaaa gatggataaa gttttaaaca gagaggaatc 9600
tttgcagcta atggaccttc taggtcttga aaggagtggg aatt 9644

<210> SEQ ID NO 20
<211> LENGTH: 9934
<212> TYPE: DNA
<213> ORGANISM: Artificial Sequence
<220> FEATURE:
<223> OTHER INFORMATION: pTLL-pHsp70B'1(a6)

<400> SEQUENCE: 20
taccaaacga cgagcgtgac accacgatgc ctgtagcaat ggcaacaacg ttgcgcaaac 60
tattaactgg cgaactactt actctagctt cccggcaaca attaatagac tggatggagg 120
cggataaagt tgcaggacca cttctgcgct cggcccttcc ggctggctgg tttattgctg 180
ataaatctgg agccggtgag cgtgggtctc gcggtatcat tgcagcactg gggccagatg 240
gtaagccctc ccgtatcgta gttatctaca cgacggggag tcaggcaact atggatgaac 300
gaaatagaca gatcgctgag ataggtgcct cactgattaa gcattggtaa ctgtcagacc 360
aagtttactc atatatactt tagattgatt taaaacttca tttttaattt aaaaggatct 420
aggtgaagat cctttttgat aatctcatga ccaaaatccc ttaacgtgag ttttcgttcc 480
actgagcgtc agaccccgta gaaaagatca aaggatcttc ttgagatcct ttttttctgc 540
gcgtaatctg ctgcttgcaa acaaaaaaac caccgctacc agcggtggtt tgtttgccgg 600
atcaagagct accaactctt tttccgaagg taactggctt cagcagagcg cagataccaa 660
atactgtcct tctagtgtag ccgtagttag gccaccactt caagaactct gtagcaccgc 720
ctacatacct cgctctgcta atcctgttac cagtggctgc tgccagtggc gataagtcgt 780
gtcttaccgg gttggactca agacgatagt taccggataa ggcgcagcgg tcgggctgaa 840
cggggggttc gtgcacacag cccagcttgg agcgaacgac ctacaccgaa ctgagatacc 900
tacagcgtga gctatgagaa agcgccacgc ttcccgaagg gagaaaggcg gacaggtatc 960
cggtaagcgg cagggtcgga acaggagagc gcacgaggga gcttccaggg ggaaacgcct 1020
ggtatcttta tagtcctgtc gggtttcgcc acctctgact tgagcgtcga tttttgtgat 1080
gctcgtcagg ggggcggagc ctatggaaaa acgccagcaa cgcggccttt ttacggttcc 1140
tggccttttg ctggcctttt gctcacatgt tctttcctgc gttatcccct gattctgtgg 1200
ataaccgtat taccgccttt gagtgagctg ataccgctcg ccgcagccga acgaccgagc 1260
gcagcgagtc agtgagcgag gaagcggaag agcgcccaat acgcaaaccg cctctccccg 1320
cgcgttggcc gattcattaa tgcagctggc acgacaggtt tcccgactgg aaagcgggca 1380
gtgagcgcaa cgcaattaat gtgagttagc tcactcatta ggcaccccag gctttacact 1440
ttatgcttcc ggctcgtatg ttgtgtggaa ttgtgagcgg ataacaattt cacacaggaa 1500
acagctatga ccatgattac gccaagcgcg caattaaccc tcactaaagg gaacaaaagc 1560
tggagctgca agcttggcca ttgcatacgt tgtatccata tcataatatg tacatttata 1620
ttggctcatg tccaacatta ccgccatgtt gacattgatt attgactagt tattaatagt 1680
aatcaattac ggggtcatta gttcatagcc catatatgga gttccgcgtt acataactta 1740
cggtaaatgg cccgcctggc tgaccgccca acgacccccg cccattgacg tcaataatga 1800
cgtatgttcc catagtaacg ccaataggga ctttccattg acgtcaatgg gtggagtatt 1860
tacggtaaac tgcccacttg gcagtacatc aagtgtatca tatgccaagt acgcccccta 1920
ttgacgtcaa tgacggtaaa tggcccgcct ggcattatgc ccagtacatg accttatggg 1980
actttcctac ttggcagtac atctacgtat tagtcatcgc tattaccatg gtgatgcggt 2040
tttggcagta catcaatggg cgtggatagc ggtttgactc acggggattt ccaagtctcc 2100
accccattga cgtcaatggg agtttgtttt ggcaccaaaa tcaacgggac tttccaaaat 2160
gtcgtaacaa ctccgcccca ttgacgcaaa tgggcggtag gcgtgtacgg tgggaggtct 2220
atataagcag agctcgttta gtgaaccggg gtctctctgg ttagaccaga tctgagcctg 2280
ggagctctct ggctaactag ggaacccact gcttaagcct caataaagct tgccttgagt 2340
gcttcaagta gtgtgtgccc gtctgttgtg tgactctggt aactagagat ccctcagacc 2400
cttttagtca gtgtggaaaa tctctagcag tggcgcccga acagggacct gaaagcgaaa 2460
gggaaaccag aggagctctc tcgacgcagg actcggcttg ctgaagcgcg cacggcaaga 2520
ggcgaggggc ggcgactggt gagtacgcca aaaattttga ctagcggagg ctagaaggag 2580
agagatgggt gcgagagcgt cagtattaag cgggggagaa ttagatcgcg atgggaaaaa 2640
attcggttaa ggccaggggg aaagaaaaaa tataaattaa aacatatagt atgggcaagc 2700
agggagctag aacgattcgc agttaatcct ggcctgttag aaacatcaga aggctgtaga 2760
caaatactgg gacagctaca accatccctt cagacaggat cagaagaact tagatcatta 2820
tataatacag tagcaaccct ctattgtgtg catcaaagga tagagataaa agacaccaag 2880
gaagctttag acaagataga ggaagagcaa aacaaaagta agaccaccgc acagcaagcg 2940
gccgctgatc ttcagacctg gaggaggaga tatgagggac aattggagaa gtgaattata 3000
taaatataaa gtagtaaaaa ttgaaccatt aggagtagca cccaccaagg caaagagaag 3060
agtggtgcag agagaaaaaa gagcagtggg aataggagct ttgttccttg ggttcttggg 3120
agcagcagga agcactatgg gcgcagcctc aatgacgctg acggtacagg ccagacaatt 3180
attgtctggt atagtgcagc agcagaacaa tttgctgagg gctattgagg cgcaacagca 3240
tctgttgcaa ctcacagtct ggggcatcaa gcagctccag gcaagaatcc tggctgtgga 3300
aagataccta aaggatcaac agctcctggg gatttggggt tgctctggaa aactcatttg 3360
caccactgct gtgccttgga atgctagttg gagtaataaa tctctggaac agattggaat 3420
cacacgacct ggatggagtg ggacagagaa attaacaatt acacaagctt aatacactcc 3480
ttaattgaag aatcgcaaaa ccagcaagaa aagaatgaac aagaattatt ggaattagat 3540
aaatgggcaa gtttgtggaa ttggtttaac ataacaaatt ggctgtggta tataaaatta 3600
ttcataatga tagtaggagg cttggtaggt ttaagaatag tttttgctgt actttctata 3660
gtgaatagag ttaggcaggg atattcacca ttatcgtttc agacccacct cccaaccccg 3720
aggggacccg acaggcccga aggaatagaa gaagaaggtg gagagagaga cagagacaga 3780
tccattcgat tagtgaacgg atctcgacgg tatcgatctc gacacaaatg gcagtattca 3840
tccacaattt taaaagaaaa ggggggattg gggggtacag tgcaggggaa agaatagtag 3900
acataatagc aacagacata caaactaaag aattacaaaa acaaattaca aaaattcaaa 3960
attttcgggt ttattacagg gacagcagag atccagtttg ggaattagct tgagcctcta 4020
aagttgctgc ttttgcagcc tctgccacaa ccgcgcgtcc tcagagccag cccggaggag 4080
ctagaacctt ccccgcattt ctttcagcag cctgagtcag aggcgggctg gcctggcgta 4140
gccgcccagc ctcgcggctc atgccccgat ctgcccgaac cttctcccgg ggtcagcgcc 4200
gcgccgcgcc acccggctga gtcagcccgg gcgggcgaga ggctctcaac tgggcgggaa 4260

-continued

```
ggtgcgggaa ggtgcggaaa ggttcgcgaa agttcgcggc ggcgggggtc gggtgaggcg   4320
caaaaggata aaaagccggt ggaagcggag ctgagcagat ccgagccggg ctggctgcag   4380
agaaaccgca gggagagcct cactgctgag cgcccctcga cggcggagcg gcagcagcct   4440
ccgtggcctc cagcatccga caagaagctt gaattcgagc tcgccgggga tcctctagtc   4500
agctgacgcg tgctagcgcg gccgcaccac tagtgccacc atggtgagca agggagagga   4560
ggataacatg gcctctctcc cagctacaca tgagcttcac atctttggat ccatcaacgg   4620
tgtggacttt gacatggtgg gtcagggaac cggaaatcca aatgatggat atgaggagct   4680
taaccttaag tccaccaagg gtgacctcca gttctcccca tggattcttg tccctcatat   4740
cggatatgga ttccatcagt accttcctta ccctgacggt atgtctcctt tccaggccgc   4800
catggttgat ggatccggat accaagtcca tagaacaatg cagtttgaag atggtgcctc   4860
ccttactgtt aactacagat acacctacga gggaagccac atcaaaggag aggcccaggt   4920
gaagggaact ggtttccctg ctgacggtcc tgtgatgacc aactctctta ccgctgctga   4980
ctggtgcagg tctaagaaaa cttaccctaa cgacaaaacc atcatcagta cctttaagtg   5040
gagttacacc actggaaatg gtaagagata cagaagcact gctagaacca cctacacctt   5100
tgccaagcca atggctgcta actatcttaa gaaccagcct atgtacgtgt tccgtaagac   5160
tgagctcaag cactccaaga ccgagctcaa cttcaaggag tggcaaaagg cctttaccga   5220
tgtgatggga atggacgagc tttacaagta atgtacaaca cgtgctacga gatttcgatt   5280
ccgagctcga attgacggat cgggagatct actagaagct ttgcaaagat ggataaagtt   5340
ttaaacagag aggaatcttt gcagctaatg gaccttctag gtcttgaaag gagtgggaat   5400
tggctccggt gcccgtcagt gggcagagcg cacatcgccc acagtccccg agaagttggg   5460
gggaggggtc ggcaattgaa ccggtgccta gagaaggtgg cgcggggtaa actgggaaag   5520
tgatgtcgtg tactggctcc gcctttttcc cgagggtggg ggagaaccgt atataagtgc   5580
agtagtcgcc gtgaacgttc tttttcgcaa cgggtttgcc gccagaacac aggtaagtgc   5640
cgtgtgtggt tcccgcgggc ctggcctctt tacgggttat ggcccttgcg tgccttgaat   5700
tacttccact ggctgcagta cgtgattctt gatcccgagc ttcgggttgg aagtgggtgg   5760
gagagttcga ggccttgcgc ttaaggagcc ccttcgcctc gtgcttgagt tgaggcctgg   5820
cctgggcgct ggggccgccg cgtgcgaatc tggtggcacc ttcgcgcctg tctcgctgct   5880
ttcgataagt ctctagccat ttaaaatttt tgatgacctg ctgcgacgct ttttttctgg   5940
caagatagtc ttgtaaatgc gggccaagat ctgcacactg gtatttcggt ttttggggcc   6000
gcgggcggcg acggggcccg tgcgtcccag cgcacatgtt cggcgaggcg gggcctgcga   6060
gcgcggccac cgagaatcgg acgggggtag tctcaagctg gccggcctgc tctggtgcct   6120
ggcctcgcgc cgccgtgtat cgccccgccc tgggcggcaa ggctggcccg gtcggcacca   6180
gttgcgtgag cggaaagatg gccgcttccc ggccctgctg cagggagctc aaaatggagg   6240
acgcggcgct cgggagagcg ggcgggtgag tcacccacac aaaggaaaag ggcctttccg   6300
tcctcagccg tcgcttcatg tgactccacg gagtaccggg cgccgtccag gcacctcgat   6360
tagttctcga gcttttggag tacgtcgtct ttaggttggg gggaggggtt ttatgcgatg   6420
gagtttcccc acactgagtg ggtggagact gaagttaggc cagcttggca cttgatgtaa   6480
ttctccttgg aatttgccct ttttgagttt ggatcttggt tcattctcaa gcctcagaca   6540
gtggttcaaa gtttttttct tccatttcag gtgtcgtgac cggtcgccac catggtgtct   6600
aagggcgaag agctgattaa ggagaacatg cacatgaagc tgtacatgga gggcaccgtg   6660
```

-continued

```
gacaaccatc acttcaagtg cacatccgag ggcgaaggca agccctacga gggcacccag   6720
accatgagaa tcaaggtggt cgagggcggc cctctcccct tcgccttcga catcctggct   6780
actagcttcc tctacggcag caagaccttc atcaaccaca cccagggcat ccccgacttc   6840
ttcaagcagt ccttccctga gggcttcaca tgggagagag tcaccacata cgaagacggg   6900
ggcgtgctga ccgctaccca ggacaccagc ctccaggacg gctgcctcat ctacaacgtc   6960
aagatcagag ggtgaactt cacatccaac ggccctgtga tgcagaagaa aacactcggc   7020
tgggaggcct tcaccgagac gctgtacccc gctgacggcg gcctggaagg cagaaacgac   7080
atggccctga agctcgtggg cgggagccat ctgatcgcaa acgccaagac cacatataga   7140
tccaagaaac ccgctaagaa cctcaagatg cctggcgtct actatgtgga ctacagactg   7200
gaaagaatca aggaggccaa caacgagacc tacgtcgagc agcacgaggt ggcagtggcc   7260
agatactgcg acctccctag caaactgggg cacaagctta attaatgtac aaatcaacct   7320
ctggattaca aaatttgtga aagattgact ggtattctta actatgttgc tccttttacg   7380
ctatgtggat acgctgcttt aatgcctttg tatcatgcta ttgcttcccg tatggctttc   7440
attttctcct ccttgtataa atcctggttg ctgtctcttt atgaggagtt gtggcccgtt   7500
gtcaggcaac gtggcgtggt gtgcactgtg tttgctgacg caacccccac tggttggggc   7560
attgccacca cctgtcagct cctttccggg actttcgctt tccccctccc tattgccacg   7620
gcggaactca tcgccgcctg ccttgcccgc tgctggacag gggctcggct gttgggcact   7680
gacaattccg tggtgttgtc ggggaaatca tcgtcctttc cttggctgct cgcctatgtt   7740
gccacctgga ttctgcgcgg gacgtccttc tgctacgtcc cttcggccct caatccagcg   7800
gaccttcctt cccgcggcct gctgccggct ctgcggcctc ttccgcgtct tcgccttcgc   7860
cctcagacga gtcggatctc cctttgggcc gcctccccgc tacaaggcag ctgtagatcc   7920
ctttcataga aggcggcggt ggtaccttta agaccaatga cttacaaggc agctgtagat   7980
cttagccact ttttaaaaga aaagggggga ctggaagggc taattcactc ccaacgaaga   8040
caagatctgc tttttgcttg tactgggtct ctctggttag accagatctg agcctgggag   8100
ctctctggct aactagggaa cccactgctt aagcctcaat aaagcttgcc ttgagtgctt   8160
caagtagtgt gtgcccgtct gttgtgtgac tctggtaact agagatccct cagacccttt   8220
tagtcagtgt ggaaaatctc tagcagtagt agttcatgtc atcttattat tcagtattta   8280
taacttgcaa agaaatgaat atcagagagt gagaggaact tgtttattgc agcttataat   8340
ggttacaaat aaagcaatag catcacaaat ttcacaaata aagcattttt ttcactgcat   8400
tctagttgtg gtttgtccaa actcatcaat gtatcttatc atgtctggct ctagctatcc   8460
cgcccctaac tccgcccatc ccgcccctaa ctccgcccag ttccgcccat tctccgcccc   8520
atggctgact aattttttt atttatgcag aggccgaggc cgcctcggcc tctgagctat   8580
tccagaagta gtgaggaggc ttttttggag gcctaggctt ttgcgtcgag acgtacccaa   8640
ttcgccctat agtgagtcgt attacgcgcg ctcactggcc gtcgttttac aacgtcgtga   8700
ctgggaaaac cctggcgtta cccaacttaa tcgccttgca gcacatcccc ctttcgccag   8760
ctggcgtaat agcgaagagg cccgcaccga tcgcccttcc caacagttgc gcagcctgaa   8820
tggcgaatgg cgcgacgcgc cctgtagcgg cgcattaagc gcggcgggtg tggtggttac   8880
gcgcagcgtg accgctacac ttgccagcgc cctagcgccc gctcctttcg ctttcttccc   8940
ttcctttctc gccacgttcg ccggctttcc ccgtcaagct ctaaatcggg ggctcccttt   9000
```

agggttccga tttagtgctt tacggcacct cgaccccaaa aaacttgatt agggtgatgg 9060
ttcacgtagt gggccatcgc cctgatagac ggtttttcgc cctttgacgt tggagtccac 9120
gttctttaat agtggactct tgttccaaac tggaacaaca ctcaacccta tctcggtcta 9180
ttcttttgat ttataaggga ttttgccgat ttcggcctat tggttaaaaa atgagctgat 9240
ttaacaaaaa tttaacgcga attttaacaa aatattaacg tttacaattt cccaggtggc 9300
acttttcggg gaaatgtgcg cggaacccct atttgtttat ttttctaaat acattcaaat 9360
atgtatccgc tcatgagaca ataaccctga taaatgcttc aataatattg aaaaaggaag 9420
agtatgagta ttcaacattt ccgtgtcgcc cttattccct tttttgcggc attttgcctt 9480
cctgtttttg ctcacccaga aacgctggtg aaagtaaaag atgctgaaga tcagttgggt 9540
gcacgagtgg gttacatcga actggatctc aacagcggta agatccttga gagttttcgc 9600
cccgaagaac gttttccaat gatgagcact tttaaagttc tgctatgtgg cgcggtatta 9660
tcccgtattg acgccgggca agagcaactc ggtcgccgca tacactattc tcagaatgac 9720
ttggttgagt actcaccagt cacagaaaag catcttacgg atggcatgac agtaagagaa 9780
ttatgcagtg ctgccataac catgagtgat aacactgcgg ccaacttact tctgacaacg 9840
atcggaggac cgaaggagct aaccgctttt ttgcacaaca tgggggatca tgtaactcgc 9900
cttgatcgtt gggaaccgga gctgaatgaa gcca 9934

<210> SEQ ID NO 21
<211> LENGTH: 9922
<212> TYPE: DNA
<213> ORGANISM: Artificial Sequence
<220> FEATURE:
<223> OTHER INFORMATION: pTLL-pHsp70B'2(a6)

<400> SEQUENCE: 21
ccggagctga atgaagccat accaaacgac gagcgtgaca ccacgatgcc tgtagcaatg 60
gcaacaacgt tgcgcaaact attaactggc gaactactta ctctagcttc ccggcaacaa 120
ttaatagact ggatggaggc ggataaagtt gcaggaccac ttctgcgctc ggcccttccg 180
gctggctggt ttattgctga taaatctgga gccggtgagc gtgggtctcg cggtatcatt 240
gcagcactgg ggccagatgg taagccctcc cgtatcgtag ttatctacac gacggggagt 300
caggcaacta tggatgaacg aaatagacag atcgctgaga taggtgcctc actgattaag 360
cattggtaac tgtcagacca agtttactca tatatacttt agattgattt aaaacttcat 420
ttttaattta aaaggatcta ggtgaagatc ctttttgata atctcatgac caaaatccct 480
taacgtgagt tttcgttcca ctgagcgtca gaccccgtag aaaagatcaa aggatcttct 540
tgagatcctt tttttctgcg cgtaatctgc tgcttgcaaa caaaaaaacc accgctacca 600
gcggtggttt gtttgccgga tcaagagcta ccaactcttt ttccgaaggt aactggcttc 660
agcagagcgc agataccaaa tactgtcctt ctagtgtagc cgtagttagg ccaccacttc 720
aagaactctg tagcaccgcc tacatacctc gctctgctaa tcctgttacc agtggctgct 780
gccagtggcg ataagtcgtg tcttaccggg ttggactcaa gacgatagtt accggataag 840
gcgcagcggt cgggctgaac ggggggttcg tgcacacagc ccagcttgga gcgaacgacc 900
tacaccgaac tgagatacct acagcgtgag ctatgagaaa gcgccacgct tcccgaaggg 960
agaaaggcgg acaggtatcc ggtaagcggc agggtcggaa caggagagcg cacgagggag 1020
cttccagggg gaaacgcctg gtatctttat agtcctgtcg ggtttcgcca cctctgactt 1080
gagcgtcgat ttttgtgatg ctcgtcaggg gggcggagcc tatggaaaaa cgccagcaac 1140

-continued

```
gcggcctttt tacggttcct ggccttttgc tggccttttg ctcacatgtt ctttcctgcg   1200
ttatcccctg attctgtgga taaccgtatt accgcctttg agtgagctga taccgctcgc   1260
cgcagccgaa cgaccgagcg cagcgagtca gtgagcgagg aagcggaaga gcgcccaata   1320
cgcaaaccgc ctctccccgc gcgttggccg attcattaat gcagctggca cgacaggttt   1380
cccgactgga aagcgggcag tgagcgcaac gcaattaatg tgagttagct cactcattag   1440
gcaccccagg ctttacactt tatgcttccg gctcgtatgt tgtgtggaat tgtgagcgga   1500
taacaatttc acacaggaaa cagctatgac catgattacg ccaagcgcgc aattaaccct   1560
cactaaaggg aacaaaagct ggagctgcaa gcttggccat tgcatacgtt gtatccatat   1620
cataatatgt acatttatat tggctcatgt ccaacattac cgccatgttg acattgatta   1680
ttgactagtt attaatagta atcaattacg gggtcattag ttcatagccc atatatggag   1740
ttccgcgtta cataacttac ggtaaatggc ccgcctggct gaccgcccaa cgacccccgc   1800
ccattgacgt caataatgac gtatgttccc atagtaacgc caatagggac tttccattga   1860
cgtcaatggg tggagtattt acggtaaact gcccacttgg cagtacatca agtgtatcat   1920
atgccaagta cgccccctat tgacgtcaat gacggtaaat ggcccgcctg gcattatgcc   1980
cagtacatga ccttatggga ctttcctact tggcagtaca tctacgtatt agtcatcgct   2040
attaccatgg tgatgcggtt ttggcagtac atcaatgggc gtggatagcg gtttgactca   2100
cggggatttc caagtctcca ccccattgac gtcaatggga gtttgttttg gcaccaaaat   2160
caacgggact ttccaaaatg tcgtaacaac tccgccccat tgacgcaaat gggcggtagg   2220
cgtgtacggt gggaggtcta tataagcaga gctcgtttag tgaaccgggg tctctctggt   2280
tagaccagat ctgagcctgg gagctctctg gctaactagg gaacccactg cttaagcctc   2340
aataaagctt gccttgagtg cttcaagtag tgtgtgcccg tctgttgtgt gactctggta   2400
actagagatc cctcagaccc ttttagtcag tgtggaaaat ctctagcagt ggcgcccgaa   2460
cagggacttg aaagcgaaag ggaaaccaga ggagctctct cgacgcagga ctcggcttgc   2520
tgaagcgcgc acggcaagag gcgaggggcg gcgactggtg agtacgccaa aaattttgac   2580
tagcggaggc tagaaggaga gagatgggtg cgagagcgtc agtattaagc gggggagaat   2640
tagatcgcga tgggaaaaaa ttcggttaag gccaggggga aagaaaaaat ataaattaaa   2700
acatatagta tgggcaagca gggagctaga acgattcgca gttaatcctg gcctgttaga   2760
aacatcagaa ggctgtagac aaatactggg acagctacaa ccatcccttc agacaggatc   2820
agaagaactt agatcattat ataatacagt agcaaccctc tattgtgtgc atcaaaggat   2880
agagataaaa gacaccaagg aagctttaga caagatagag gaagagcaaa acaaaagtaa   2940
gaccaccgca cagcaagcgg ccgctgatct tcagacctgg aggaggagat atgagggaca   3000
attggagaag tgaattatat aaatataaag tagtaaaaat tgaaccatta ggagtagcac   3060
ccaccaaggc aaagagaaga gtggtgcaga gagaaaaaag agcagtggga ataggagctt   3120
tgttccttgg gttcttggga gcagcaggaa gcactatggg cgcagcctca atgacgctga   3180
cggtacaggc cagacaatta ttgtctggta tagtgcagca gcagaacaat ttgctgaggg   3240
ctattgaggc gcaacagcat ctgttgcaac tcacagtctg gggcatcaag cagctccagg   3300
caagaatcct ggctgtggaa agatacctaa aggatcaaca gctcctgggg atttggggtt   3360
gctctggaaa actcatttgc accactgctg tgccttggaa tgctagttgg agtaataaat   3420
ctctggaaca gattggaatc acacgacctg gatggagtgg gacagagaaa ttaacaatta   3480
```

-continued

```
cacaagctta atacactcct taattgaaga atcgcaaaac cagcaagaaa agaatgaaca   3540
agaattattg gaattagata aatgggcaag tttgtggaat tggtttaaca taacaaattg   3600
gctgtggtat ataaaattat tcataatgat agtaggaggc ttggtaggtt taagaatagt   3660
ttttgctgta ctttctatag tgaatagagt taggcaggga tattcaccat tatcgtttca   3720
gacccacctc ccaaccccga ggggacccga caggcccgaa ggaatagaag aagaaggtgg   3780
agagagagac agagacagat ccattcgatt agtgaacgga tctcgacggt atcgatctcg   3840
acacaaatgg cagtattcat ccacaatttt aaaagaaaag gggggattgg ggggtacagt   3900
gcaggggaaa gaatagtaga cataatagca acagacatac aaactaaaga attacaaaaa   3960
caaattacaa aaattcaaaa ttttcgggtt tattacaggg acagcagaga tccagtttgg   4020
gaattagctt gagcctctaa agttgctgct tttgcagcct ctgccacaac cgcgcgtcct   4080
cagagccagc ccggaggagc tagaaccttc cccgcatttc tttcagcagc ctgagtcaga   4140
ggcgggctgg cctggcgtag ccgcccagcc tcgcggctca tgccccgatc tgcccgaacc   4200
ttctcccggg gtcagcgccg cgccgcgcca cccggctgag tcagcccggg cgggcgagag   4260
gctctcaact gggcgggaag gtgcgggaag gtgcggaaag gttcgcgaaa gttcgcggcg   4320
gcgggggtcg ggtgaggcgc aaaaggataa aaagccggtg gaagcggagc tgagcagatc   4380
cgagccgggc tggctgcaga gaaaccgcag ggagagcctc actgctgagc gcccctcgac   4440
ggcggagcgg cagcagcctc cgtggcctcc agcatccgac aagaagcttg aattcgagct   4500
cgccggggat cctctagtca gctgacgcgt gctagcgcgg cgccaccatg gtgagcaagg   4560
gagaggagga taacatggcc tctctcccag ctacacatga gcttcacatc tttggatcca   4620
tcaacggtgt ggactttgac atggtgggtc agggaaccgg aaatccaaat gatggatatg   4680
aggagcttaa ccttaagtcc accaagggtg acctccagtt ctccccatgg attcttgtcc   4740
ctcatatcgg atatggattc catcagtacc ttccttaccc tgacggtatg tctcctttcc   4800
aggccgccat ggttgatgga tccggatacc aagtccatag aacaatgcag tttgaagatg   4860
gtgcctccct tactgttaac tacagataca cctacgaggg aagccacatc aaaggagagg   4920
cccaggtgaa gggaactggt ttccctgctg acggtcctgt gatgaccaac tctcttaccg   4980
ctgctgactg gtgcaggtct aagaaaactt accctaacga caaaaccatc atcagtacct   5040
ttaagtggag ttacaccact ggaaatggta agagatacag aagcactgct agaaccacct   5100
acacctttgc caagccaatg gctgctaact atcttaagaa ccagcctatg tacgtgttcc   5160
gtaagactga gctcaagcac tccaagaccg agctcaactt caaggagtgg caaaaggcct   5220
ttaccgatgt gatgggaatg gacgagcttt acaagtaatg tacaacacgt gctacgagat   5280
ttcgattccg agctcgaatt gacggatcgg gagatctact agaagctttg caaagatgga   5340
taaagtttta aacagagagg aatctttgca gctaatggac cttctaggtc ttgaaaggag   5400
tgggaattgg ctccggtgcc cgtcagtggg cagagcgcac atcgcccaca gtccccgaga   5460
agttgggggg aggggtcggc aattgaaccg gtgcctagag aaggtggcgc ggggtaaact   5520
gggaaagtga tgtcgtgtac tggctccgcc tttttcccga gggtggggga gaaccgtata   5580
taagtgcagt agtcgccgtg aacgttcttt ttcgcaacgg gtttgccgcc agaacacagg   5640
taagtgccgt gtgtggttcc cgcgggcctg gcctctttac gggttatggc ccttgcgtgc   5700
cttgaattac ttccactggc tgcagtacgt gattcttgat cccgagcttc gggttggaag   5760
tgggtgggag agttcgaggc cttgcgctta aggagcccct tcgcctcgtg cttgagttga   5820
ggcctggcct gggcgctggg gccgccgcgt gcgaatctgg tggcaccttc gcgcctgtct   5880
```

-continued

```
cgctgctttc gataagtctc tagccattta aaatttttga tgacctgctg cgacgctttt   5940
tttctggcaa gatagtcttg taaatgcggg ccaagatctg cacactggta tttcggtttt   6000
tggggccgcg ggcggcgacg gggcccgtgc gtcccagcgc acatgttcgg cgaggcgggg   6060
cctgcgagcg cggccaccga gaatcggacg ggggtagtct caagctggcc ggcctgctct   6120
ggtgcctggc ctcgcgccgc cgtgtatcgc cccgccctgg gcggcaaggc tggcccggtc   6180
ggcaccagtt gcgtgagcgg aaagatggcc gcttcccggc cctgctgcag ggagctcaaa   6240
atggaggacg cggcgctcgg gagagcgggc gggtgagtca cccacacaaa ggaaaagggc   6300
ctttccgtcc tcagccgtcg cttcatgtga ctccacggag taccgggcgc cgtccaggca   6360
cctcgattag ttctcgagct tttggagtac gtcgtcttta ggttgggggg aggggtttta   6420
tgcgatggag tttccccaca ctgagtgggt ggagactgaa gttaggccag cttggcactt   6480
gatgtaattc tccttggaat ttgccctttt tgagtttgga tcttggttca ttctcaagcc   6540
tcagacagtg gttcaaagtt tttttcttcc atttcaggtg tcgtgaccgg tcgccaccat   6600
ggtgtctaag ggcgaagagc tgattaagga gaacatgcac atgaagctgt acatggaggg   6660
caccgtggac aaccatcact tcaagtgcac atccgagggc gaaggcaagc cctacgaggg   6720
cacccagacc atgagaatca aggtggtcga gggcggccct ctccccttcg ccttcgacat   6780
cctggctact agcttcctct acggcagcaa gaccttcatc aaccacaccc agggcatccc   6840
cgacttcttc aagcagtcct tccctgaggg cttcacatgg gagagagtca ccacatacga   6900
agacgggggc gtgctgaccg ctacccagga caccagcctc caggacggct gcctcatcta   6960
caacgtcaag atcagagggg tgaacttcac atccaacggc cctgtgatgc agaagaaaac   7020
actcggctgg gaggccttca ccgagacgct gtaccccgct gacggcggcc tggaaggcag   7080
aaacgacatg gccctgaagc tcgtgggcgg gagccatctg atcgcaaacg ccaagaccac   7140
atatagatcc aagaaacccg ctaagaacct caagatgcct ggcgtctact atgtggacta   7200
cagactggaa agaatcaagg aggccaacaa cgagacctac gtcgagcagc acgaggtggc   7260
agtggccaga tactgcgacc tccctagcaa actggggcac aagcttaatt aatgtacaaa   7320
tcaacctctg gattacaaaa tttgtgaaag attgactggt attcttaact atgttgctcc   7380
ttttacgcta tgtggatacg ctgctttaat gcctttgtat catgctattg cttcccgtat   7440
ggctttcatt ttctcctcct tgtataaatc ctggttgctg tctctttatg aggagttgtg   7500
gcccgttgtc aggcaacgtg gcgtggtgtg cactgtgttt gctgacgcaa cccccactgg   7560
ttggggcatt gccaccacct gtcagctcct ttccgggact ttcgctttcc ccctccctat   7620
tgccacggcg gaactcatcg ccgcctgcct tgcccgctgc tggacagggg ctcggctgtt   7680
gggcactgac aattccgtgg tgttgtcggg gaaatcatcg tcctttcctt ggctgctcgc   7740
ctatgttgcc acctggattc tgcgcgggac gtccttctgc tacgtccctt cggccctcaa   7800
tccagcggac cttccttccc gcggcctgct gccggctctg cggcctcttc cgcgtcttcg   7860
ccttcgccct cagacgagtc ggatctccct ttgggccgcc tccccgctac aaggcagctg   7920
tagatccctt tcatagaagg cggcggtggt acctttaaga ccaatgactt acaaggcagc   7980
tgtagatctt agccactttt taaaagaaaa ggggggactg gaagggctaa ttcactccca   8040
acgaagacaa gatctgcttt ttgcttgtac tgggtctctc tggttagacc agatctgagc   8100
ctgggagctc tctggctaac tagggaaccc actgcttaag cctcaataaa gcttgccttg   8160
agtgcttcaa gtagtgtgtg cccgtctgtt gtgtgactct ggtaactaga gatccctcag   8220
```

acccttttag tcagtgtgga aaatctctag cagtagtagt tcatgtcatc ttattattca 8280
gtatttataa cttgcaaaga aatgaatatc agagagtgag aggaacttgt ttattgcagc 8340
ttataatggt tacaaataaa gcaatagcat cacaaatttc acaaataaag catttttttc 8400
actgcattct agttgtggtt tgtccaaact catcaatgta tcttatcatg tctggctcta 8460
gctatcccgc ccctaactcc gcccatcccg cccctaactc cgcccagttc cgcccattct 8520
ccgccccatg gctgactaat tttttttatt tatgcagagg ccgaggccgc ctcggcctct 8580
gagctattcc agaagtagtg aggaggcttt tttggaggcc taggcttttg cgtcgagacg 8640
tacccaattc gccctatagt gagtcgtatt acgcgcgctc actggccgtc gttttacaac 8700
gtcgtgactg ggaaaaccct ggcgttaccc aacttaatcg ccttgcagca catccccctt 8760
tcgccagctg gcgtaatagc gaagaggccc gcaccgatcg cccttcccaa cagttgcgca 8820
gcctgaatgg cgaatggcgc gacgcgccct gtagcggcgc attaagcgcg gcgggtgtgg 8880
tggttacgcg cagcgtgacc gctacacttg ccagcgccct agcgcccgct cctttcgctt 8940
tcttcccttc ctttctcgcc acgttcgccg gctttccccg tcaagctcta aatcgggggc 9000
tccctttagg gttccgattt agtgctttac ggcacctcga ccccaaaaaa cttgattagg 9060
gtgatggttc acgtagtggg ccatcgccct gatagacggt ttttcgccct ttgacgttgg 9120
agtccacgtt ctttaatagt ggactcttgt tccaaactgg aacaacactc aaccctatct 9180
cggtctattc ttttgattta taagggattt tgccgatttc ggcctattgg ttaaaaaatg 9240
agctgattta acaaaaattt aacgcgaatt ttaacaaaat attaacgttt acaatttccc 9300
aggtggcact tttcggggaa atgtgcgcgg aacccctatt tgtttatttt tctaaataca 9360
ttcaaatatg tatccgctca tgagacaata accctgataa atgcttcaat aatattgaaa 9420
aaggaagagt atgagtattc aacatttccg tgtcgccctt attccctttt ttgcggcatt 9480
ttgccttcct gtttttgctc acccagaaac gctggtgaaa gtaaaagatg ctgaagatca 9540
gttgggtgca cgagtgggtt acatcgaact ggatctcaac agcggtaaga tccttgagag 9600
ttttcgcccc gaagaacgtt ttccaatgat gagcactttt aaagttctgc tatgtggcgc 9660
ggtattatcc cgtattgacg ccgggcaaga gcaactcggt cgccgcatac actattctca 9720
gaatgacttg gttgagtact caccagtcac agaaaagcat cttacggatg gcatgacagt 9780
aagagaatta tgcagtgctg ccataaccat gagtgataac actgcggcca acttacttct 9840
gacaacgatc ggaggaccga aggagctaac cgcttttttg cacaacatgg gggatcatgt 9900
aactcgcctt gatcgttggg aa 9922

<210> SEQ ID NO 22
<211> LENGTH: 9869
<212> TYPE: DNA
<213> ORGANISM: Artificial Sequence
<220> FEATURE:
<223> OTHER INFORMATION: pTLL-pHsp70B'3(a6 native)

<400> SEQUENCE: 22
ccggagctga atgaagccat accaaacgac gagcgtgaca ccacgatgcc tgtagcaatg 60
gcaacaacgt tgcgcaaact attaactggc gaactactta ctctagcttc ccggcaacaa 120
ttaatagact ggatggaggc ggataaagtt gcaggaccac ttctgcgctc ggcccttccg 180
gctggctggt ttattgctga taaatctgga gccggtgagc gtgggtctcg cggtatcatt 240
gcagcactgg ggccagatgg taagccctcc cgtatcgtag ttatctacac gacggggagt 300
caggcaacta tggatgaacg aaatagacag atcgctgaga taggtgcctc actgattaag 360

-continued

```
cattggtaac tgtcagacca agtttactca tatatacttt agattgattt aaaacttcat    420
ttttaattta aaaggatcta ggtgaagatc ctttttgata atctcatgac caaaatccct    480
taacgtgagt tttcgttcca ctgagcgtca gaccccgtag aaaagatcaa aggatcttct    540
tgagatcctt tttttctgcg cgtaatctgc tgcttgcaaa caaaaaaacc accgctacca    600
gcggtggttt gtttgccgga tcaagagcta ccaactcttt ttccgaaggt aactggcttc    660
agcagagcgc agataccaaa tactgtcctt ctagtgtagc cgtagttagg ccaccacttc    720
aagaactctg tagcaccgcc tacatacctc gctctgctaa tcctgttacc agtggctgct    780
gccagtggcg ataagtcgtg tcttaccggg ttggactcaa gacgatagtt accggataag    840
gcgcagcggt cgggctgaac ggggggttcg tgcacacagc ccagcttgga gcgaacgacc    900
tacaccgaac tgagatacct acagcgtgag ctatgagaaa gcgccacgct tcccgaaggg    960
agaaaggcgg acaggtatcc ggtaagcggc agggtcggaa caggagagcg cacgagggag   1020
cttccagggg gaaacgcctg gtatctttat agtcctgtcg ggtttcgcca cctctgactt   1080
gagcgtcgat ttttgtgatg ctcgtcaggg gggcggagcc tatggaaaaa cgccagcaac   1140
gcggcctttt tacggttcct ggccttttgc tggccttttg ctcacatgtt ctttcctgcg   1200
ttatcccctg attctgtgga taaccgtatt accgcctttg agtgagctga taccgctcgc   1260
cgcagccgaa cgaccgagcg cagcgagtca gtgagcgagg aagcggaaga gcgcccaata   1320
cgcaaaccgc ctctccccgc gcgttggccg attcattaat gcagctggca cgacaggttt   1380
cccgactgga aagcgggcag tgagcgcaac gcaattaatg tgagttagct cactcattag   1440
gcaccccagg ctttacactt tatgcttccg gctcgtatgt tgtgtggaat tgtgagcgga   1500
taacaatttc acacaggaaa cagctatgac catgattacg ccaagcgcgc aattaaccct   1560
cactaaaggg aacaaaagct ggagctgcaa gcttggccat tgcatacgtt gtatccatat   1620
cataatatgt acatttatat tggctcatgt ccaacattac cgccatgttg acattgatta   1680
ttgactagtt attaatagta atcaattacg gggtcattag ttcatagccc atatatggag   1740
ttccgcgtta cataacttac ggtaaatggc ccgcctggct gaccgcccaa cgacccccgc   1800
ccattgacgt caataatgac gtatgttccc atagtaacgc caatagggac tttccattga   1860
cgtcaatggg tggagtattt acggtaaact gcccacttgg cagtacatca agtgtatcat   1920
atgccaagta cgccccctat tgacgtcaat gacggtaaat ggcccgcctg gcattatgcc   1980
cagtacatga ccttatggga ctttcctact tggcagtaca tctacgtatt agtcatcgct   2040
attaccatgg tgatgcggtt ttggcagtac atcaatgggc gtggatagcg gtttgactca   2100
cggggatttc caagtctcca ccccattgac gtcaatggga gtttgttttg gcaccaaaat   2160
caacgggact ttccaaaatg tcgtaacaac tccgccccat tgacgcaaat gggcggtagg   2220
cgtgtacggt gggaggtcta tataagcaga gctcgtttag tgaaccgggg tctctctggt   2280
tagaccagat ctgagcctgg gagctctctg gctaactagg gaacccactg cttaagcctc   2340
aataaagctt gccttgagtg cttcaagtag tgtgtgcccg tctgttgtgt gactctggta   2400
actagagatc cctcagaccc ttttagtcag tgtggaaaat ctctagcagt ggcgcccgaa   2460
cagggacttg aaagcgaaag ggaaaccaga ggagctctct cgacgcagga ctcggcttgc   2520
tgaagcgcgc acggcaagag gcgaggggcg gcgactggtg agtacgccaa aaattttgac   2580
tagcggaggc tagaaggaga gagatgggtg cgagagcgtc agtattaagc gggggagaat   2640
tagatcgcga tgggaaaaaa ttcggttaag gccaggggga aagaaaaaat ataaattaaa   2700
```

-continued acatatagta tgggcaagca gggagctaga acgattcgca gttaatcctg gcctgttaga 2760
aacatcagaa ggctgtagac aaatactggg acagctacaa ccatcccttc agacaggatc 2820
agaagaactt agatcattat ataatacagt agcaaccctc tattgtgtgc atcaaaggat 2880
agagataaaa gacaccaagg aagctttaga caagatagag gaagagcaaa acaaaagtaa 2940
gaccaccgca cagcaagcgg ccgctgatct tcagacctgg aggaggagat atgagggaca 3000
attggagaag tgaattatat aaatataaag tagtaaaaat tgaaccatta ggagtagcac 3060
ccaccaaggc aaagagaaga gtggtgcaga gagaaaaaag agcagtggga ataggagctt 3120
tgttccttgg gttcttggga gcagcaggaa gcactatggg cgcagcctca atgacgctga 3180
cggtacaggc cagacaatta ttgtctggta tagtgcagca gcagaacaat ttgctgaggg 3240
ctattgaggc gcaacagcat ctgttgcaac tcacagtctg gggcatcaag cagctccagg 3300
caagaatcct ggctgtggaa agatacctaa aggatcaaca gctcctgggg atttggggtt 3360
gctctggaaa actcatttgc accactgctg tgccttggaa tgctagttgg agtaataaat 3420
ctctggaaca gattggaatc acacgacctg gatggagtgg gacagagaaa ttaacaatta 3480
cacaagctta atacactcct taattgaaga atcgcaaaac cagcaagaaa agaatgaaca 3540
agaattattg gaattagata aatgggcaag tttgtggaat tggtttaaca taacaaattg 3600
gctgtggtat ataaaattat tcataatgat agtaggaggc ttggtaggtt taagaatagt 3660
ttttgctgta ctttctatag tgaatagagt taggcaggga tattcaccat tatcgtttca 3720
gacccacctc ccaaccccga ggggacccga caggcccgaa ggaatagaag aagaaggtgg 3780
agagagagac agagacagat ccattcgatt agtgaacgga tctcgacggt atcgatctcg 3840
acacaaatgg cagtattcat ccacaatttt aaaagaaaag gggggattgg ggggtacagt 3900
gcaggggaaa gaatagtaga cataatagca acagacatac aaactaaaga attacaaaaa 3960
caaattacaa aaattcaaaa ttttcgggtt tattacaggg acagcagaga tccagtttgg 4020
gaattagctt gagcctctaa agttgctgct tttgcagcct ctgccacaac cgcgcgtcct 4080
cagagccagc ccggaggagc tagaaccttc cccgcatttc tttcagcagc ctgagtcaga 4140
ggcgggctgg cctggcgtag ccgcccagcc tcgcggctca tgccccgatc tgcccgaacc 4200
ttctcccggg gtcagcgccg cgccgcgcca cccggctgag tcagcccggg cgggcgagag 4260
gctctcaact gggcgggaag gtgcgggaag gtgcggaaag gttcgcgaaa gttcgcggcg 4320
gcgggggtcg ggtgaggcgc aaaaggataa aaagccggtg gaagcggagc tgagcagatc 4380
cgagccgggc tggctgcaga gaaaccgcag ggagagcctc actgctgagc gcccctcgac 4440
ggcggagcgg cagcagcctc cgtggcctcc agcatccgac aagaagcttc agccatggtg 4500
agcaagggag aggaggataa catggcctct ctcccagcta cacatgagct tcacatcttt 4560
ggatccatca acggtgtgga ctttgacatg gtgggtcagg gaaccggaaa tccaaatgat 4620
ggatatgagg agcttaacct taagtccacc aagggtgacc tccagttctc cccatggatt 4680
cttgtccctc atatcggata tggattccat cagtaccttc cttaccctga cggtatgtct 4740
cctttccagg ccgccatggt tgatggatcc ggataccaag tccatagaac aatgcagttt 4800
gaagatggtg cctcccttac tgttaactac agatacacct acgagggaag ccacatcaaa 4860
ggagaggccc aggtgaaggg aactggtttc cctgctgacg gtcctgtgat gaccaactct 4920
cttaccgctg ctgactggtg caggtctaag aaaacttacc ctaacgacaa aaccatcatc 4980
agtaccttta agtggagtta caccactgga aatggtaaga gatacagaag cactgctaga 5040
accacctaca cctttgccaa gccaatggct gctaactatc ttaagaacca gcctatgtac 5100

-continued

```
gtgttccgta agactgagct caagcactcc aagaccgagc tcaacttcaa ggagtggcaa   5160
aaggccttta ccgatgtgat gggaatggac gagctttaca agtaatgtac aacacgtgct   5220
acgagatttc gattccgagc tcgaattgac ggatcgggag atctactaga agctttgcaa   5280
agatggataa agttttaaac agagaggaat ctttgcagct aatggacctt ctaggtcttg   5340
aaaggagtgg gaattggctc cggtgcccgt cagtgggcag agcgcacatc gcccacagtc   5400
cccgagaagt tggggggagg ggtcggcaat tgaaccggtg cctagagaag gtggcgcggg   5460
gtaaactggg aaagtgatgt cgtgtactgg ctccgccttt ttcccgaggg tgggggagaa   5520
ccgtatataa gtgcagtagt cgccgtgaac gttctttttc gcaacgggtt tgccgccaga   5580
acacaggtaa gtgccgtgtg tggttcccgc gggcctggcc tctttacggg ttatggccct   5640
tgcgtgcctt gaattacttc cactggctgc agtacgtgat tcttgatccc gagcttcggg   5700
ttggaagtgg gtgggagagt tcgaggcctt gcgcttaagg agccccttcg cctcgtgctt   5760
gagttgaggc ctggcctggg cgctggggcc gccgcgtgcg aatctggtgg caccttcgcg   5820
cctgtctcgc tgctttcgat aagtctctag ccatttaaaa tttttgatga cctgctgcga   5880
cgcttttttt ctggcaagat agtcttgtaa atgcgggcca agatctgcac actggtattt   5940
cggtttttgg ggccgcgggc ggcgacgggg cccgtgcgtc ccagcgcaca tgttcggcga   6000
ggcggggcct gcgagcgcgg ccaccgagaa tcggacgggg gtagtctcaa gctggccggc   6060
ctgctctggt gcctggcctc gcgccgccgt gtatcgcccc gccctgggcg gcaaggctgg   6120
cccggtcggc accagttgcg tgagcggaaa gatggccgct tcccggccct gctgcaggga   6180
gctcaaaatg gaggacgcgg cgctcgggag agcgggcggg tgagtcaccc acacaaagga   6240
aaagggcctt tccgtcctca gccgtcgctt catgtgactc cacggagtac cgggcgccgt   6300
ccaggcacct cgattagttc tcgagctttt ggagtacgtc gtctttaggt tggggggagg   6360
ggttttatgc gatggagttt ccccacactg agtgggtgga gactgaagtt aggccagctt   6420
ggcacttgat gtaattctcc ttggaatttg cccttttga gtttggatct tggttcattc   6480
tcaagcctca gacagtggtt caaagttttt ttcttccatt tcaggtgtcg tgaccggtcg   6540
ccaccatggt gtctaagggc gaagagctga ttaaggagaa catgcacatg aagctgtaca   6600
tggagggcac cgtggacaac catcacttca agtgcacatc cgagggcgaa ggcaagccct   6660
acgagggcac ccagaccatg agaatcaagg tggtcgaggg cggccctctc cccttcgcct   6720
tcgacatcct ggctactagc ttcctctacg gcagcaagac cttcatcaac cacacccagg   6780
gcatccccga cttcttcaag cagtccttcc ctgagggctt cacatgggag agagtcacca   6840
catacgaaga cgggggcgtg ctgaccgcta cccaggacac cagcctccag gacggctgcc   6900
tcatctacaa cgtcaagatc agaggggtga acttcacatc caacggccct gtgatgcaga   6960
agaaaacact cggctgggag gccttcaccg agacgctgta ccccgctgac ggcggcctgg   7020
aaggcagaaa cgacatggcc ctgaagctcg tgggcgggag ccatctgatc gcaaacgcca   7080
agaccacata tagatccaag aaacccgcta agaacctcaa gatgcctggc gtctactatg   7140
tggactacag actggaaaga atcaaggagg ccaacaacga gacctacgtc gagcagcacg   7200
aggtggcagt ggccagatac tgcgacctcc ctagcaaact ggggcacaag cttaattaat   7260
gtacaaatca acctctggat tacaaaattt gtgaaagatt gactggtatt cttaactatg   7320
ttgctccttt tacgctatgt ggatacgctg ctttaatgcc tttgtatcat gctattgctt   7380
cccgtatggc tttcattttc tcctccttgt ataaatcctg gttgctgtct ctttatgagg   7440
```

-continued

```
agttgtggcc cgttgtcagg caacgtggcg tggtgtgcac tgtgtttgct gacgcaaccc   7500
ccactggttg gggcattgcc accacctgtc agctcctttc cgggactttc gctttccccc   7560
tccctattgc cacggcggaa ctcatcgccg cctgccttgc ccgctgctgg acaggggctc   7620
ggctgttggg cactgacaat tccgtggtgt tgtcggggaa atcatcgtcc tttccttggc   7680
tgctcgccta tgttgccacc tggattctgc gcgggacgtc cttctgctac gtcccttcgg   7740
ccctcaatcc agcggacctt ccttcccgcg gcctgctgcc ggctctgcgg cctcttccgc   7800
gtcttcgcct tcgccctcag acgagtcgga tctccctttg ggccgcctcc ccgctacaag   7860
gcagctgtag atccctttca tagaaggcgg cggtggtacc tttaagacca atgacttaca   7920
aggcagctgt agatcttagc cactttttaa aagaaaaggg gggactggaa gggctaattc   7980
actcccaacg aagacaagat ctgctttttg cttgtactgg gtctctctgg ttagaccaga   8040
tctgagcctg ggagctctct ggctaactag ggaacccact gcttaagcct caataaagct   8100
tgccttgagt gcttcaagta gtgtgtgccc gtctgttgtg tgactctggt aactagagat   8160
ccctcagacc cttttagtca gtgtggaaaa tctctagcag tagtagttca tgtcatctta   8220
ttattcagta tttataactt gcaaagaaat gaatatcaga gagtgagagg aacttgttta   8280
ttgcagctta taatggttac aaataaagca atagcatcac aaatttcaca aataaagcat   8340
tttttcact gcattctagt tgtggtttgt ccaaactcat caatgtatct tatcatgtct   8400
ggctctagct atcccgcccc taactccgcc catcccgccc ctaactccgc ccagttccgc   8460
ccattctccg ccccatggct gactaatttt ttttatttat gcagaggccg aggccgcctc   8520
ggcctctgag ctattccaga agtagtgagg aggctttttt ggaggcctag gcttttgcgt   8580
cgagacgtac ccaattcgcc ctatagtgag tcgtattacg cgcgctcact ggccgtcgtt   8640
ttacaacgtc gtgactggga aaaccctggc gttacccaac ttaatcgcct tgcagcacat   8700
ccccctttcg ccagctggcg taatagcgaa gaggcccgca ccgatcgccc ttcccaacag   8760
ttgcgcagcc tgaatggcga atggcgcgac gcgccctgta gcggcgcatt aagcgcggcg   8820
ggtgtggtgg ttacgcgcag cgtgaccgct acacttgcca gcgccctagc gcccgctcct   8880
ttcgctttct tcccttcctt tctcgccacg ttcgccggct ttccccgtca agctctaaat   8940
cgggggctcc ctttagggtt ccgatttagt gctttacggc acctcgaccc caaaaaactt   9000
gattagggtg atggttcacg tagtgggcca tcgccctgat agacggtttt tcgccctttg   9060
acgttggagt ccacgttctt taatagtgga ctcttgttcc aaactggaac aacactcaac   9120
cctatctcgg tctattcttt tgatttataa gggattttgc cgatttcggc ctattggtta   9180
aaaaatgagc tgatttaaca aaaatttaac gcgaatttta acaaaatatt aacgtttaca   9240
atttcccagg tggcactttt cggggaaatg tgcgcggaac ccctatttgt ttatttttct   9300
aaatacattc aaatatgtat ccgctcatga gacaataacc ctgataaatg cttcaataat   9360
attgaaaaag gaagagtatg agtattcaac atttccgtgt cgcccttatt cccttttttg   9420
cggcattttg ccttcctgtt tttgctcacc cagaaacgct ggtgaaagta aaagatgctg   9480
aagatcagtt gggtgcacga gtgggttaca tcgaactgga tctcaacagc ggtaagatcc   9540
ttgagagttt tcgccccgaa gaacgttttc caatgatgag cacttttaaa gttctgctat   9600
gtggcgcggt attatcccgt attgacgccg ggcaagagca actcggtcgc cgcatacact   9660
attctcagaa tgacttggtt gagtactcac cagtcacaga aaagcatctt acggatggca   9720
tgacagtaag agaattatgc agtgctgcca taaccatgag tgataacact gcggccaact   9780
tacttctgac aacgatcgga ggaccgaagg agctaaccgc ttttttgcac aacatggggg   9840
```

atcatgtaac tcgccttgat cgttgggaa 9869

<210> SEQ ID NO 23
<211> LENGTH: 10460
<212> TYPE: DNA
<213> ORGANISM: Artificial Sequence
<220> FEATURE:
<223> OTHER INFORMATION: pTLL-pm1Hsp70A1 Fixed

<400> SEQUENCE: 23
ccggagctga atgaagccat accaaacgac gagcgtgaca ccacgatgcc tgtagcaatg 60
gcaacaacgt tgcgcaaact attaactggc gaactactta ctctagcttc ccggcaacaa 120
ttaatagact ggatggaggc ggataaagtt gcaggaccac ttctgcgctc ggcccttccg 180
gctggctggt ttattgctga taaatctgga gccggtgagc gtgggtctcg cggtatcatt 240
gcagcactgg ggccagatgg taagccctcc cgtatcgtag ttatctacac gacggggagt 300
caggcaacta tggatgaacg aaatagacag atcgctgaga taggtgcctc actgattaag 360
cattggtaac tgtcagacca agtttactca tatatacttt agattgattt aaaacttcat 420
ttttaattta aaaggatcta ggtgaagatc ctttttgata atctcatgac caaaatccct 480
taacgtgagt tttcgttcca ctgagcgtca gaccccgtag aaaagatcaa aggatcttct 540
tgagatcctt tttttctgcg cgtaatctgc tgcttgcaaa caaaaaaacc accgctacca 600
gcggtggttt gtttgccgga tcaagagcta ccaactcttt ttccgaaggt aactggcttc 660
agcagagcgc agataccaaa tactgtcctt ctagtgtagc cgtagttagg ccaccacttc 720
aagaactctg tagcaccgcc tacatacctc gctctgctaa tcctgttacc agtggctgct 780
gccagtggcg ataagtcgtg tcttaccggg ttggactcaa gacgatagtt accggataag 840
gcgcagcggt cgggctgaac ggggggttcg tgcacacagc ccagcttgga gcgaacgacc 900
tacaccgaac tgagatacct acagcgtgag ctatgagaaa gcgccacgct tcccgaaggg 960
agaaaggcgg acaggtatcc ggtaagcggc agggtcggaa caggagagcg cacgagggag 1020
cttccagggg gaaacgcctg gtatctttat agtcctgtcg ggtttcgcca cctctgactt 1080
gagcgtcgat ttttgtgatg ctcgtcaggg gggcggagcc tatggaaaaa cgccagcaac 1140
gcggcctttt tacggttcct ggccttttgc tggccttttg ctcacatgtt ctttcctgcg 1200
ttatcccctg attctgtgga taaccgtatt accgcctttg agtgagctga taccgctcgc 1260
cgcagccgaa cgaccgagcg cagcgagtca gtgagcgagg aagcggaaga gcgcccaata 1320
cgcaaaccgc ctctccccgc gcgttggccg attcattaat gcagctggca cgacaggttt 1380
cccgactgga aagcgggcag tgagcgcaac gcaattaatg tgagttagct cactcattag 1440
gcaccccagg ctttacactt tatgcttccg gctcgtatgt tgtgtggaat tgtgagcgga 1500
taacaatttc acacaggaaa cagctatgac catgattacg ccaagcgcgc aattaaccct 1560
cactaaaggg aacaaaagct ggagctgcaa gcttggccat tgcatacgtt gtatccatat 1620
cataatatgt acatttatat tggctcatgt ccaacattac cgccatgttg acattgatta 1680
ttgactagtt attaatagta atcaattacg gggtcattag ttcatagccc atatatggag 1740
ttccgcgtta cataacttac ggtaaatggc ccgcctggct gaccgcccaa cgacccccgc 1800
ccattgacgt caataatgac gtatgttccc atagtaacgc caatagggac tttccattga 1860
cgtcaatggg tggagtattt acggtaaact gcccacttgg cagtacatca agtgtatcat 1920
atgccaagta cgccccctat tgacgtcaat gacggtaaat ggcccgcctg gcattatgcc 1980

-continued

```
cagtacatga ccttatggga ctttcctact tggcagtaca tctacgtatt agtcatcgct   2040
attaccatgg tgatgcggtt ttggcagtac atcaatgggc gtggatagcg gtttgactca   2100
cggggatttc caagtctcca ccccattgac gtcaatggga gtttgttttg gcaccaaaat   2160
caacgggact ttccaaaatg tcgtaacaac tccgccccat tgacgcaaat gggcggtagg   2220
cgtgtacggt gggaggtcta tataagcaga gctcgtttag tgaaccgggg tctctctggt   2280
tagaccagat ctgagcctgg gagctctctg gctaactagg gaacccactg cttaagcctc   2340
aataaagctt gccttgagtg cttcaagtag tgtgtgcccg tctgttgtgt gactctggta   2400
actagagatc cctcagaccc ttttagtcag tgtggaaaat ctctagcagt ggcgcccgaa   2460
cagggacctg aaagcgaaag ggaaaccaga ggagctctct cgacgcagga ctcggcttgc   2520
tgaagcgcgc acggcaagag gcgaggggcg gcgactggtg agtacgccaa aaattttgac   2580
tagcggaggc tagaaggaga gagatgggtg cgagagcgtc agtattaagc gggggagaat   2640
tagatcgcga tgggaaaaaa ttcggttaag gccaggggga aagaaaaaat ataaattaaa   2700
acatatagta tgggcaagca gggagctaga acgattcgca gttaatcctg gcctgttaga   2760
aacatcagaa ggctgtagac aaatactggg acagctacaa ccatcccttc agacaggatc   2820
agaagaactt agatcattat ataatacagt agcaaccctc tattgtgtgc atcaaaggat   2880
agagataaaa gacaccaagg aagctttaga caagatagag gaagagcaaa acaaaagtaa   2940
gaccaccgca cagcaagcgg ccgctgatct tcagacctgg aggaggagat atgagggaca   3000
attggagaag tgaattatat aaatataaag tagtaaaaat tgaaccatta ggagtagcac   3060
ccaccaaggc aaagagaaga gtggtgcaga gagaaaaaag agcagtggga ataggagctt   3120
tgttccttgg gttcttggga gcagcaggaa gcactatggg cgcagcctca atgacgctga   3180
cggtacaggc cagacaatta ttgtctggta tagtgcagca gcagaacaat ttgctgaggg   3240
ctattgaggc gcaacagcat ctgttgcaac tcacagtctg gggcatcaag cagctccagg   3300
caagaatcct ggctgtggaa agatacctaa aggatcaaca gctcctgggg atttggggtt   3360
gctctggaaa actcatttgc accactgctg tgccttggaa tgctagttgg agtaataaat   3420
ctctggaaca gattggaatc acacgacctg gatggagtgg gacagagaaa ttaacaatta   3480
cacaagctta atacactcct taattgaaga atcgcaaaac cagcaagaaa agaatgaaca   3540
agaattattg gaattagata aatgggcaag tttgtggaat tggtttaaca taacaaattg   3600
gctgtggtat ataaaattat tcataatgat agtaggaggc ttggtaggtt taagaatagt   3660
ttttgctgta ctttctatag tgaatagagt taggcaggga tattcaccat tatcgtttca   3720
gacccacctc ccaaccccga ggggacccga caggcccgaa ggaatagaag aagaaggtgg   3780
agagagagac agagacagat ccattcgatt agtgaacgga tctcgacggt atcgataagc   3840
taattcacaa atggcagtat tcatccacaa ttttaaaaga aaagggggga ttggggggta   3900
cagtgcaggg gaaagaatag tagacataat agcaacagac atacaaacta aagaattaca   3960
aaaacaaatt acaaaaattc aaaattttcg ggtttattac agggacagca gagatccagt   4020
ttgggaatta gcttgaaaat cagtcaaacc taagaaaatt ctcaaccgca tcaaaccgag   4080
gaccaactgg gacacagagc ttctgcccca ctccaatcag agccttccca gctcacctgg   4140
gatctctacg ccttcgatcc agtttggaaa atttcaagtc gctgagcccc tacgagagga   4200
gctccaggaa cataccaaac tgaggcagcc ggggtccccc ccacccccca ccccgcccct   4260
cccggcaact ttgagcctgt gctgggacag agcctctagt tcctaaatta gtccatgagg   4320
tcagaggcag cactgccatt gtaaccgcga ttggagagga tcacgtcacc ggacacgccc   4380
```

caggcatctc cctgggtctc ctaaacttgg ccggggagaa gttttagccc ttaaggtttt 4440
agcctttaac cccatattc agaactgtgc gagttggcga aaccccacaa atcacaacaa 4500
actgtacaca acaccgaggc tagaggtgat ctttcttgtc cattccacac aggccttagt 4560
aattgcgtcg ccatagcaac agtgtcacta gtagcaccag cacgttcccc acaccctccc 4620
cctcaggaat ccgtactctc cagtgaaccc cagaaacctc tggagagttc tggacaaggg 4680
cggaacccac aactccgatt actcaaggga ggcggggaag ctccaccaga cgcgaaactg 4740
ctggaagatt cctggcccca aggcctcctc cggctcgctg attggcccag cggagagtgg 4800
gcggggccgg tgaagactcc ttaaaggcgc agggcggcga gcacggtcac cagacgctga 4860
cagctactca gaaccaaatc tggttccatc cagagacaag cgaagacaag agaagcagag 4920
cagagcggcg cgttcccgat cctcggccag gaccagcctt ccccagagca tccctgccgc 4980
gggacgcaac cttcccagga gcatccctgc cgcggagcaa ctttccccgg agcatccagc 5040
ccggacgcag ccttccagaa gcacgagccc accactagtg ccaccatggt gagcaaggga 5100
gaggaggata acatggcctc tctcccagct acacatgagc ttcacatctt tggatccatc 5160
aacggtgtgg actttgacat ggtgggtcag ggaaccggaa atccaaatga tggatatgag 5220
gagcttaacc ttaagtccac caagggtgac ctccagttct ccccatggat tcttgtccct 5280
catatcggat atggattcca tcagtacctt ccttaccctg acggtatgtc tcctttccag 5340
gccgccatgg ttgatggatc cggataccaa gtccatagaa caatgcagtt tgaagatggt 5400
gcctccctta ctgttaacta cagatacacc tacgagggaa gccacatcaa aggagaggcc 5460
caggtgaagg gaactggttt ccctgctgac ggtcctgtga tgaccaactc tcttaccgct 5520
gctgactggt gcaggtctaa gaaaacttac cctaacgaca aaaccatcat cagtaccttt 5580
aagtggagtt acaccactgg aaatggtaag agatacagaa gcactgctag aaccacctac 5640
acctttgcca agccaatggc tgctaactat cttaagaacc agcctatgta cgtgttccgt 5700
aagactgagc tcaagcactc caagaccgag ctcaacttca aggagtggca aaaggccttt 5760
accgatgtga tgggaatgga cgagctttac aagtaatgta caacacgtgc tacgagattt 5820
cgattccgag ctcgaattga cggatcggga gatctactag aagctttgca aagatggata 5880
aagttttaaa cagagaggaa tctttgcagc taatggacct tctaggtctt gaaaggagtg 5940
ggaattggct ccggtgcccg tcagtgggca gagcgcacat cgcccacagt ccccgagaag 6000
ttggggggag gggtcggcaa ttgaaccggt gcctagagaa ggtggcgcgg ggtaaactgg 6060
gaaagtgatg tcgtgtactg gctccgcctt tttcccgagg gtgggggaga accgtatata 6120
agtgcagtag tcgccgtgaa cgttcttttt cgcaacgggt ttgccgccag aacacaggta 6180
agtgccgtgt gtggttcccg cgggcctggc ctctttacgg gttatggccc ttgcgtgcct 6240
tgaattactt ccactggctg cagtacgtga ttcttgatcc cgagcttcgg gttggaagtg 6300
ggtgggagag ttcgaggcct tgcgcttaag gagccccttc gcctcgtgct tgagttgagg 6360
cctggcctgg gcgctggggc cgccgcgtgc gaatctggtg gcaccttcgc gcctgtctcg 6420
ctgctttcga taagtctcta gccatttaaa atttttgatg acctgctgcg acgctttttt 6480
tctggcaaga tagtcttgta aatgcgggcc aagatctgca cactggtatt tcggtttttg 6540
gggccgcggg cggcgacggg gcccgtgcgt cccagcgcac atgttcggcg aggcggggcc 6600
tgcgagcgcg gccaccgaga atcggacggg ggtagtctca agctggccgg cctgctctgg 6660
tgcctggcct cgcgccgccg tgtatcgccc cgccctgggc ggcaaggctg gcccggtcgg 6720

-continued

```
caccagttgc gtgagcggaa agatggccgc ttcccggccc tgctgcaggg agctcaaaat   6780
ggaggacgcg gcgctcggga gagcgggcgg gtgagtcacc cacacaaagg aaaagggcct   6840
ttccgtcctc agccgtcgct tcatgtgact ccacggagta ccgggcgccg tccaggcacc   6900
tcgattagtt ctcgagcttt tggagtacgt cgtctttagg ttggggggag gggttttatg   6960
cgatggagtt tccccacact gagtgggtgg agactgaagt taggccagct tggcacttga   7020
tgtaattctc cttggaattt gccctttttg agtttggatc ttggttcatt ctcaagcctc   7080
agacagtggt tcaaagtttt tttcttccat ttcaggtgtc gtgaccggtc gccaccatgg   7140
tgtctaaggg cgaagagctg attaaggaga acatgcacat gaagctgtac atggagggca   7200
ccgtggacaa ccatcacttc aagtgcacat ccgagggcga aggcaagccc tacgagggca   7260
cccagaccat gagaatcaag gtggtcgagg gcggccctct ccccttcgcc ttcgacatcc   7320
tggctactag cttcctctac ggcagcaaga ccttcatcaa ccacacccag ggcatccccg   7380
acttcttcaa gcagtccttc cctgagggct tcacatggga gagagtcacc acatacgaag   7440
acgggggcgt gctgaccgct acccaggaca ccagcctcca ggacggctgc ctcatctaca   7500
acgtcaagat cagaggggtg aacttcacat ccaacggccc tgtgatgcag aagaaaacac   7560
tcggctggga ggccttcacc gagacgctgt accccgctga cggcggcctg gaaggcagaa   7620
acgacatggc cctgaagctc gtgggcggga gccatctgat cgcaaacgcc aagaccacat   7680
atagatccaa gaaacccgct aagaacctca agatgcctgg cgtctactat gtggactaca   7740
gactggaaag aatcaaggag gccaacaacg agacctacgt cgagcagcac gaggtggcag   7800
tggccagata ctgcgacctc cctagcaaac tggggcacaa gcttaattaa tgtacaaatc   7860
aacctctgga ttacaaaatt tgtgaaagat tgactggtat tcttaactat gttgctcctt   7920
ttacgctatg tggatacgct gctttaatgc ctttgtatca tgctattgct tcccgtatgg   7980
ctttcatttt ctcctccttg tataaatcct ggttgctgtc tctttatgag gagttgtggc   8040
ccgttgtcag gcaacgtggc gtggtgtgca ctgtgtttgc tgacgcaacc cccactggtt   8100
ggggcattgc caccacctgt cagctccttt ccgggacttt cgctttcccc ctccctattg   8160
ccacggcgga actcatcgcc gcctgccttg cccgctgctg gacaggggct cggctgttgg   8220
gcactgacaa ttccgtggtg ttgtcgggga aatcatcgtc ctttccttgg ctgctcgcct   8280
atgttgccac ctggattctg cgcgggacgt ccttctgcta cgtcccttcg gccctcaatc   8340
cagcggacct tccttcccgc ggcctgctgc cggctctgcg gcctcttccg cgtcttcgcc   8400
ttcgccctca gacgagtcgg atctcccttt gggccgcctc cccgctacaa ggcagctgta   8460
gatccctttc atagaaggcg gcggtggtac ctttaagacc aatgacttac aaggcagctg   8520
tagatcttag ccactttta aaagaaaagg ggggactgga agggctaatt cactcccaac   8580
gaagacaaga tctgcttttt gcttgtactg ggtctctctg gttagaccag atctgagcct   8640
gggagctctc tggctaacta gggaacccac tgcttaagcc tcaataaagc ttgccttgag   8700
tgcttcaagt agtgtgtgcc cgtctgttgt gtgactctgg taactagaga tccctcagac   8760
ccttttagtc agtgtggaaa atctctagca gtagtagttc atgtcatctt attattcagt   8820
atttataact tgcaaagaaa tgaatatcag agagtgagag gaacttgttt attgcagctt   8880
ataatggtta caaataaagc aatagcatca caaatttcac aaataaagca tttttttcac   8940
tgcattctag ttgtggtttg tccaaactca tcaatgtatc ttatcatgtc tggctctagc   9000
tatcccgccc ctaactccgc ccatcccgcc cctaactccg cccagttccg cccattctcc   9060
gccccatggc tgactaattt ttttattta tgcagaggcc gaggccgcct cggcctctga   9120
```

```
gctattccag aagtagtgag gaggcttttt tggaggccta ggcttttgcg tcgagacgta   9180
cccaattcgc cctatagtga gtcgtattac gcgcgctcac tggccgtcgt tttacaacgt   9240
cgtgactggg aaaaccctgg cgttacccaa cttaatcgcc ttgcagcaca tccccctttc   9300
gccagctggc gtaatagcga agaggcccgc accgatcgcc cttcccaaca gttgcgcagc   9360
ctgaatggcg aatggcgcga cgcgccctgt agcggcgcat taagcgcggc gggtgtggtg   9420
gttacgcgca gcgtgaccgc tacacttgcc agcgccctag cgcccgctcc tttcgctttc   9480
ttcccttcct ttctcgccac gttcgccggc tttccccgtc aagctctaaa tcgggggctc   9540
cctttagggt tccgatttag tgctttacgg cacctcgacc ccaaaaaact tgattagggt   9600
gatggttcac gtagtgggcc atcgccctga tagacggttt ttcgcccttt gacgttggag   9660
tccacgttct ttaatagtgg actcttgttc caaactggaa caacactcaa ccctatctcg   9720
gtctattctt ttgatttata agggattttg ccgatttcgg cctattggtt aaaaaatgag   9780
ctgatttaac aaaaatttaa cgcgaatttt aacaaaatat taacgtttac aatttcccag   9840
gtggcacttt tcggggaaat gtgcgcggaa cccctatttg tttatttttc taaatacatt   9900
caaatatgta tccgctcatg agacaataac cctgataaat gcttcaataa tattgaaaaa   9960
ggaagagtat gagtattcaa catttccgtg tcgcccttat tccctttttt gcggcatttt  10020
gccttcctgt ttttgctcac ccagaaacgc tggtgaaagt aaaagatgct gaagatcagt  10080
tgggtgcacg agtgggttac atcgaactgg atctcaacag cggtaagatc cttgagagtt  10140
ttcgccccga agaacgtttt ccaatgatga gcacttttaa agttctgcta tgtggcgcgg  10200
tattatcccg tattgacgcc gggcaagagc aactcggtcg ccgcatacac tattctcaga  10260
atgacttggt tgagtactca ccagtcacag aaaagcatct tacggatggc atgacagtaa  10320
gagaattatg cagtgctgcc ataaccatga gtgataacac tgcggccaac ttacttctga  10380
caacgatcgg aggaccgaag gagctaaccg cttttttgca caacatgggg gatcatgtaa  10440
ctcgccttga tcgttgggaa                                              10460
```

```
<210> SEQ ID NO 24
<211> LENGTH: 10464
<212> TYPE: DNA
<213> ORGANISM: Artificial Sequence
<220> FEATURE:
<223> OTHER INFORMATION: pTLL-pm2Hsp70A2(a1b)

<400> SEQUENCE: 24

actgttaact acagatacac ctacgaggga agccacatca aaggagaggc ccaggtgaag     60
ggaactggtt tccctgctga cggtcctgtg atgaccaact ctcttaccgc tgctgactgg    120
tgcaggtcta agaaaactta ccctaacgac aaaaccatca tcagtacctt taagtggagt    180
tacaccactg gaaatggtaa gagatacaga agcactgcta gaaccaccta cacctttgcc    240
aagccaatgg ctgctaacta tcttaagaac cagcctatgt acgtgttccg taagactgag    300
ctcaagcact ccaagaccga gctcaacttc aaggagtggc aaaaggcctt taccgatgtg    360
atgggaatgg acgagcttta caagtaatgt acaacacgtg ctacgagatt tcgattccga    420
gctcgaattg acggatcggg agatctacta gaagctttgc aaagatggat aaagttttaa    480
acagagagga atctttgcag ctaatggacc ttctaggtct tgaaaggagt gggaattggc    540
tccggtgccc gtcagtgggc agagcgcaca tcgcccacag tccccgagaa gttgggggga    600
ggggtcggca attgaaccgg tgcctagaga aggtggcgcg gggtaaactg ggaaagtgat    660
```

-continued

```
gtcgtgtact ggctccgcct ttttcccgag ggtgggggag aaccgtatat aagtgcagta    720
gtcgccgtga acgttctttt tcgcaacggg tttgccgcca gaacacaggt aagtgccgtg    780
tgtggttccc gcgggcctgg cctctttacg ggttatggcc cttgcgtgcc ttgaattact    840
tccactggct gcagtacgtg attcttgatc ccgagcttcg ggttggaagt gggtgggaga    900
gttcgaggcc ttgcgcttaa ggagcccctt cgcctcgtgc ttgagttgag gcctggcctg    960
ggcgctgggg ccgccgcgtg cgaatctggt ggcaccttcg cgcctgtctc gctgctttcg   1020
ataagtctct agccatttaa aatttttgat gacctgctgc gacgcttttt ttctggcaag   1080
atagtcttgt aaatgcgggc caagatctgc acactggtat ttcggttttt ggggccgcgg   1140
gcggcgacgg ggcccgtgcg tcccagcgca catgttcggc gaggcggggc ctgcgagcgc   1200
ggccaccgag aatcggacgg gggtagtctc aagctggccg gcctgctctg gtgcctggcc   1260
tcgcgccgcc gtgtatcgcc ccgccctggg cggcaaggct ggcccggtcg gcaccagttg   1320
cgtgagcgga aagatggccg cttcccggcc ctgctgcagg gagctcaaaa tggaggacgc   1380
ggcgctcggg agagcgggcg ggtgagtcac ccacacaaag gaaaagggcc tttccgtcct   1440
cagccgtcgc ttcatgtgac tccacggagt accgggcgcc gtccaggcac ctcgattagt   1500
tctcgagctt ttggagtacg tcgtctttag gttgggggga ggggttttat gcgatggagt   1560
ttccccacac tgagtgggtg gagactgaag ttaggccagc ttggcacttg atgtaattct   1620
ccttggaatt tgcccttttt gagtttggat cttggttcat tctcaagcct cagacagtgg   1680
ttcaaagttt ttttcttcca tttcaggtgt cgtgaccggt cgccaccatg gtgtctaagg   1740
gcgaagagct gattaaggag aacatgcaca tgaagctgta catggagggc accgtggaca   1800
accatcactt caagtgcaca tccgagggcg aaggcaagcc ctacgagggc acccagacca   1860
tgagaatcaa ggtggtcgag ggcggccctc tccccttcgc cttcgacatc ctggctacta   1920
gcttcctcta cggcagcaag accttcatca accacaccca gggcatcccc gacttcttca   1980
agcagtcctt ccctgagggc ttcacatggg agagagtcac cacatacgaa gacgggggcg   2040
tgctgaccgc tacccaggac accagcctcc aggacggctg cctcatctac aacgtcaaga   2100
tcagaggggt gaacttcaca tccaacggcc ctgtgatgca gaagaaaaca ctcggctggg   2160
aggccttcac cgagacgctg taccccgctg acggcggcct ggaaggcaga aacgacatgg   2220
ccctgaagct cgtgggcggg agccatctga tcgcaaacgc caagaccaca tatagatcca   2280
agaaacccgc taagaacctc aagatgcctg gcgtctacta tgtggactac agactggaaa   2340
gaatcaagga ggccaacaac gagacctacg tcgagcagca cgaggtggca gtggccagat   2400
actgcgacct ccctagcaaa ctggggcaca agcttaatta atgtacaaat caacctctgg   2460
attacaaaat ttgtgaaaga ttgactggta ttcttaacta tgttgctcct tttacgctat   2520
gtggatacgc tgctttaatg cctttgtatc atgctattgc ttcccgtatg gctttcattt   2580
tctcctcctt gtataaatcc tggttgctgt ctctttatga ggagttgtgg cccgttgtca   2640
ggcaacgtgg cgtggtgtgc actgtgtttg ctgacgcaac ccccactggt tggggcattg   2700
ccaccacctg tcagctcctt tccgggactt tcgctttccc cctccctatt gccacggcgg   2760
aactcatcgc cgcctgcctt gcccgctgct ggacaggggc tcggctgttg ggcactgaca   2820
attccgtggt gttgtcgggg aaatcatcgt cctttccttg gctgctcgcc tatgttgcca   2880
cctggattct gcgcgggacg tccttctgct acgtcccttc ggccctcaat ccagcggacc   2940
ttccttcccg cggcctgctg ccggctctgc ggcctcttcc gcgtcttcgc cttcgccctc   3000
agacgagtcg gatctccctt tgggccgcct ccccgctaca aggcagctgt agatcccttt   3060
```

catagaaggc ggcggtggta cctttaagac caatgactta caaggcagct gtagatctta 3120
gccacttttt aaaagaaaag gggggactgg aagggctaat tcactcccaa cgaagacaag 3180
atctgctttt tgcttgtact gggtctctct ggttagacca gatctgagcc tgggagctct 3240
ctggctaact agggaaccca ctgcttaagc ctcaataaag cttgccttga gtgcttcaag 3300
tagtgtgtgc ccgtctgttg tgtgactctg gtaactagag atccctcaga cccttttagt 3360
cagtgtggaa aatctctagc agtagtagtt catgtcatct tattattcag tatttataac 3420
ttgcaaagaa atgaatatca gagagtgaga ggaacttgtt tattgcagct tataatggtt 3480
acaaataaag caatagcatc acaaatttca caaataaagc atttttttca ctgcattcta 3540
gttgtggttt gtccaaactc atcaatgtat cttatcatgt ctggctctag ctatcccgcc 3600
cctaactccg cccatcccgc ccctaactcc gcccagttcc gcccattctc cgccccatgg 3660
ctgactaatt ttttttattt atgcagaggc cgaggccgcc tcggcctctg agctattcca 3720
gaagtagtga ggaggctttt ttggaggcct aggcttttgc gtcgagacgt acccaattcg 3780
ccctatagtg agtcgtatta cgcgcgctca ctggccgtcg ttttacaacg tcgtgactgg 3840
gaaaaccctg gcgttaccca acttaatcgc cttgcagcac atcccccttt cgccagctgg 3900
cgtaatagcg aagaggcccg caccgatcgc ccttcccaac agttgcgcag cctgaatggc 3960
gaatggcgcg acgcgccctg tagcggcgca ttaagcgcgg cgggtgtggt ggttacgcgc 4020
agcgtgaccg ctacacttgc cagcgcccta gcgcccgctc ctttcgcttt cttcccttcc 4080
tttctcgcca cgttcgccgg ctttccccgt caagctctaa atcgggggct ccctttaggg 4140
ttccgattta gtgctttacg gcacctcgac cccaaaaaac ttgattaggg tgatggttca 4200
cgtagtgggc catcgccctg atagacggtt tttcgccctt tgacgttgga gtccacgttc 4260
tttaatagtg gactcttgtt ccaaactgga acaacactca accctatctc ggtctattct 4320
tttgatttat aagggatttt gccgatttcg gcctattggt taaaaaatga gctgatttaa 4380
caaaaattta acgcgaattt taacaaaata ttaacgttta caatttccca ggtggcactt 4440
ttcggggaaa tgtgcgcgga acccctattt gtttattttt ctaaatacat tcaaatatgt 4500
atccgctcat gagacaataa ccctgataaa tgcttcaata atattgaaaa aggaagagta 4560
tgagtattca acatttccgt gtcgccctta ttcccttttt tgcggcattt tgccttcctg 4620
tttttgctca cccagaaacg ctggtgaaag taaaagatgc tgaagatcag ttgggtgcac 4680
gagtgggtta catcgaactg gatctcaaca gcggtaagat ccttgagagt tttcgccccg 4740
aagaacgttt tccaatgatg agcactttta aagttctgct atgtggcgcg gtattatccc 4800
gtattgacgc cgggcaagag caactcggtc gccgcataca ctattctcag aatgacttgg 4860
ttgagtactc accagtcaca gaaaagcatc ttacggatgg catgacagta agagaattat 4920
gcagtgctgc cataaccatg agtgataaca ctgcggccaa cttacttctg acaacgatcg 4980
gaggaccgaa ggagctaacc gcttttttgc acaacatggg ggatcatgta actcgccttg 5040
atcgttggga accggagctg aatgaagcca taccaaacga cgagcgtgac accacgatgc 5100
ctgtagcaat ggcaacaacg ttgcgcaaac tattaactgg cgaactactt actctagctt 5160
cccggcaaca attaatagac tggatggagg cggataaagt tgcaggacca cttctgcgct 5220
cggcccttcc ggctggctgg tttattgctg ataaatctgg agccggtgag cgtgggtctc 5280
gcggtatcat tgcagcactg gggccagatg gtaagccctc ccgtatcgta gttatctaca 5340
cgacggggag tcaggcaact atggatgaac gaaatagaca gatcgctgag ataggtgcct 5400

-continued

```
cactgattaa gcattggtaa ctgtcagacc aagtttactc atatatactt tagattgatt   5460
taaaacttca tttttaattt aaaaggatct aggtgaagat cctttttgat aatctcatga   5520
ccaaaatccc ttaacgtgag ttttcgttcc actgagcgtc agaccccgta gaaaagatca   5580
aaggatcttc ttgagatcct ttttttctgc gcgtaatctg ctgcttgcaa acaaaaaaac   5640
caccgctacc agcggtggtt tgtttgccgg atcaagagct accaactctt tttccgaagg   5700
taactggctt cagcagagcg cagataccaa atactgtcct tctagtgtag ccgtagttag   5760
gccaccactt caagaactct gtagcaccgc ctacatacct cgctctgcta atcctgttac   5820
cagtggctgc tgccagtggc gataagtcgt gtcttaccgg gttggactca agacgatagt   5880
taccggataa ggcgcagcgg tcgggctgaa cggggggttc gtgcacacag cccagcttgg   5940
agcgaacgac ctacaccgaa ctgagatacc tacagcgtga gctatgagaa agcgccacgc   6000
ttcccgaagg gagaaaggcg gacaggtatc cggtaagcgg cagggtcgga acaggagagc   6060
gcacgaggga gcttccaggg ggaaacgcct ggtatcttta tagtcctgtc gggtttcgcc   6120
acctctgact tgagcgtcga tttttgtgat gctcgtcagg ggggcggagc ctatggaaaa   6180
acgccagcaa cgcggccttt ttacggttcc tggccttttg ctggcctttt gctcacatgt   6240
tctttcctgc gttatcccct gattctgtgg ataaccgtat taccgccttt gagtgagctg   6300
ataccgctcg ccgcagccga acgaccgagc gcagcgagtc agtgagcgag gaagcggaag   6360
agcgcccaat acgcaaaccg cctctccccg cgcgttggcc gattcattaa tgcagctggc   6420
acgacaggtt tcccgactgg aaagcgggca gtgagcgcaa cgcaattaat gtgagttagc   6480
tcactcatta ggcaccccag gctttacact ttatgcttcc ggctcgtatg ttgtgtggaa   6540
ttgtgagcgg ataacaattt cacacaggaa acagctatga ccatgattac gccaagcgcg   6600
caattaaccc tcactaaagg gaacaaaagc tggagctgca agcttggcca ttgcatacgt   6660
tgtatccata tcataatatg tacatttata ttggctcatg tccaacatta ccgccatgtt   6720
gacattgatt attgactagt tattaatagt aatcaattac ggggtcatta gttcatagcc   6780
catatatgga gttccgcgtt acataactta cggtaaatgg cccgcctggc tgaccgccca   6840
acgacccccg cccattgacg tcaataatga cgtatgttcc catagtaacg ccaataggga   6900
ctttccattg acgtcaatgg gtggagtatt tacggtaaac tgcccacttg gcagtacatc   6960
aagtgtatca tatgccaagt acgcccccta ttgacgtcaa tgacggtaaa tggcccgcct   7020
ggcattatgc ccagtacatg accttatggg actttcctac ttggcagtac atctacgtat   7080
tagtcatcgc tattaccatg gtgatgcggt tttggcagta catcaatggg cgtggatagc   7140
ggtttgactc acggggattt ccaagtctcc accccattga cgtcaatggg agtttgtttt   7200
ggcaccaaaa tcaacgggac tttccaaaat gtcgtaacaa ctccgcccca ttgacgcaaa   7260
tgggcggtag gcgtgtacgg tgggaggtct atataagcag agctcgttta gtgaaccggg   7320
gtctctctgg ttagaccaga tctgagcctg ggagctctct ggctaactag ggaacccact   7380
gcttaagcct caataaagct tgccttgagt gcttcaagta gtgtgtgccc gtctgttgtg   7440
tgactctggt aactagagat ccctcagacc cttttagtca gtgtggaaaa tctctagcag   7500
tggcgcccga acagggacct gaaagcgaaa gggaaaccag aggagctctc tcgacgcagg   7560
actcggcttg ctgaagcgcg cacggcaaga ggcgaggggc ggcgactggt gagtacgcca   7620
aaaattttga ctagcggagg ctagaaggag agagatgggt gcgagagcgt cagtattaag   7680
cgggggagaa ttagatcgcg atgggaaaaa attcggttaa ggccaggggg aaagaaaaaa   7740
tataaattaa aacatatagt atgggcaagc agggagctag aacgattcgc agttaatcct   7800
```

-continued

```
ggcctgttag aaacatcaga aggctgtaga caaatactgg gacagctaca accatccctt   7860
cagacaggat cagaagaact tagatcatta tataatacag tagcaaccct ctattgtgtg   7920
catcaaagga tagagataaa agacaccaag gaagctttag acaagataga ggaagagcaa   7980
aacaaaagta agaccaccgc acagcaagcg gccgctgatc ttcagacctg gaggaggaga   8040
tatgagggac aattggagaa gtgaattata taaatataaa gtagtaaaaa ttgaaccatt   8100
aggagtagca cccaccaagg caaagagaag agtggtgcag agagaaaaaa gagcagtggg   8160
aataggagct ttgttccttg ggttcttggg agcagcagga agcactatgg gcgcagcctc   8220
aatgacgctg acggtacagg ccagacaatt attgtctggt atagtgcagc agcagaacaa   8280
tttgctgagg gctattgagg cgcaacagca tctgttgcaa ctcacagtct ggggcatcaa   8340
gcagctccag gcaagaatcc tggctgtgga aagataccta aaggatcaac agctcctggg   8400
gatttggggt tgctctggaa aactcatttg caccactgct gtgccttgga atgctagttg   8460
gagtaataaa tctctggaac agattggaat cacacgacct ggatggagtg ggacagagaa   8520
attaacaatt acacaagctt aatacactcc ttaattgaag aatcgcaaaa ccagcaagaa   8580
aagaatgaac aagaattatt ggaattagat aaatgggcaa gtttgtggaa ttggtttaac   8640
ataacaaatt ggctgtggta tataaaatta ttcataatga tagtaggagg cttggtaggt   8700
ttaagaatag tttttgctgt actttctata gtgaatagag ttaggcaggg atattcacca   8760
ttatcgtttc agacccacct cccaaccccg aggggacccg acaggcccga aggaatagaa   8820
gaagaaggtg gagagagaga cagagacaga tccattcgat tagtgaacgg atctcgacgg   8880
tatcgataag ctaattcaca aatggcagta ttcatccaca attttaaaag aaaagggggg   8940
attggggggt acagtgcagg ggaaagaata gtagacataa tagcaacaga catacaaact   9000
aaagaattac aaaaacaaat tacaaaaatt caaaattttc gggtttatta cagggacagc   9060
agagatccag tttgggaatt agcttgacct gcagcctgag gcaaagggag tggctacagc   9120
ctggcacggt cgattaagcc ctgctctccg ggtcctggga cactttcctt tttcctcttt   9180
tgagtcacag gtcctcctaa catgagaatc aagtattttc acgctgattt ccttataaaa   9240
ttgtgagaac tccataggcg atgtaccgcc tactcctacc ttaaccgtga tgtaaagaca   9300
gcaaaacaaa tgaactatac tgcaagatct cttctatttc cctattcaaa cctaaaatga   9360
agagggaggg ggagacatgg acaagcaagc attccacagg cgcccctgcc caacgctgtc   9420
actcaaacca ggacccaatc acagactttt tagccaagcc ttatcccgcc tctcttgaga   9480
aactttctgc gtccgccatc ctgtaggaag gatttgtaca ctttaaactc cctccctggt   9540
ctgagtccca cactctcacc acccagcacc ttcaggagct gacccttaac agcttcaccc   9600
acagggaccc cgaagttgcg tcgcctccgc aacagtgtca atagcagcac cagcacttcc   9660
ccacaccctc cccctcagga atccgtactc tctagcgaac cccagaaacc tctggagagt   9720
tctggacaag ggcggaaccc acaactccga ttactcaagg gaggcgggga agctccacca   9780
gacgcgaaac tgctggaaga ttcctggccc caaggcctcc tccggctcgc tgattggccc   9840
agcggagagt gggcggggcc ggtgaagact ccttaaaggc gcagggcggc gagcagggca   9900
ccagacgctg acagctactc agaatcaaat ctggttccat ccagagacaa gcgaagacaa   9960
gagaagcaga gcgagcggcg cgttcccgat cctcggccag gaccagcctt ccccagagca  10020
tccacgccgc ggagcgcaac cttcccagga gcatccctgc cgcggagcgc aactttcccc  10080
ggagcatcca cgccgcggag cgcagccttc cagaagcaga gcgccaccac tagtgccacc  10140
```

-continued

```
atggtgagca agggagagga ggataacatg gcctctctcc cagctacaca tgagcttcac  10200

atctttggat ccatcaacgg tgtggacttt gacatggtgg gtcagggaac cggaaatcca  10260

aatgatggat atgaggagct taaccttaag tccaccaagg gtgacctcca gttctcccca  10320

tggattcttg tccctcatat cggatatgga ttccatcagt accttcctta ccctgacggt  10380

atgtctcctt tccaggccgc catggttgat ggatccggat accaagtcca tagaacaatg  10440

cagtttgaag atggtgcctc cctt                                         10464
```

<210> SEQ ID NO 25
<211> LENGTH: 10193
<212> TYPE: DNA
<213> ORGANISM: Artificial Sequence
<220> FEATURE:
<223> OTHER INFORMATION: pTLL-pm3Hsp70(a1a)

<400> SEQUENCE: 25

```
gagctgaatg aagccatacc aaacgacgag cgtgacacca cgatgcctgt agcaatggca     60

acaacgttgc gcaaactatt aactggcgaa ctacttactc tagcttcccg gcaacaatta    120

atagactgga tggaggcgga taaagttgca ggaccacttc tgcgctcggc ccttccggct    180

ggctggttta ttgctgataa atctggagcc ggtgagcgtg ggtctcgcgg tatcattgca    240

gcactggggc cagatggtaa gccctcccgt atcgtagtta tctacacgac ggggagtcag    300

gcaactatgg atgaacgaaa tagacagatc gctgagatag gtgcctcact gattaagcat    360

tggtaactgt cagaccaagt ttactcatat atactttaga ttgatttaaa acttcatttt    420

taatttaaaa ggatctaggt gaagatcctt tttgataatc tcatgaccaa aatcccttaa    480

cgtgagtttt cgttccactg agcgtcagac cccgtagaaa agatcaaagg atcttcttga    540

gatccttttt ttctgcgcgt aatctgctgc ttgcaaacaa aaaaaccacc gctaccagcg    600

gtggtttgtt tgccggatca agagctacca actctttttc cgaaggtaac tggcttcagc    660

agagcgcaga taccaaatac tgtccttcta gtgtagccgt agttaggcca ccacttcaag    720

aactctgtag caccgcctac atacctcgct ctgctaatcc tgttaccagt ggctgctgcc    780

agtggcgata agtcgtgtct taccgggttg gactcaagac gatagttacc ggataaggcg    840

cagcggtcgg gctgaacggg gggttcgtgc acacagccca gcttggagcg aacgacctac    900

accgaactga gatacctaca gcgtgagcta tgagaaagcg ccacgcttcc cgaagggaga    960

aaggcggaca ggtatccggt aagcggcagg gtcggaacag gagagcgcac gagggagctt   1020

ccagggggaa acgcctggta tctttatagt cctgtcgggt ttcgccacct ctgacttgag   1080

cgtcgatttt tgtgatgctc gtcagggggg cggagcctat ggaaaaacgc cagcaacgcg   1140

gcctttttac ggttcctggc cttttgctgg ccttttgctc acatgttctt tcctgcgtta   1200

tcccctgatt ctgtggataa ccgtattacc gcctttgagt gagctgatac cgctcgccgc   1260

agccgaacga ccgagcgcag cgagtcagtg agcgaggaag cggaagagcg cccaatacgc   1320

aaaccgcctc tccccgcgcg ttggccgatt cattaatgca gctggcacga caggtttccc   1380

gactggaaag cgggcagtga gcgcaacgca attaatgtga gttagctcac tcattaggca   1440

ccccaggctt tacactttat gcttccggct cgtatgttgt gtggaattgt gagcggataa   1500

caatttcaca caggaaacag ctatgaccat gattacgcca agcgcgcaat taaccctcac   1560

taaagggaac aaaagctgga gctgcaagct tggccattgc atacgttgta tccatatcat   1620

aatatgtaca tttatattgg ctcatgtcca acattaccgc catgttgaca ttgattattg   1680

actagttatt aatagtaatc aattacgggg tcattagttc atagcccata tatggagttc   1740
```

-continued

```
cgcgttacat aacttacggt aaatggcccg cctggctgac cgcccaacga cccccgccca   1800
ttgacgtcaa taatgacgta tgttcccata gtaacgccaa tagggacttt ccattgacgt   1860
caatgggtgg agtatttacg gtaaactgcc cacttggcag tacatcaagt gtatcatatg   1920
ccaagtacgc cccctattga cgtcaatgac ggtaaatggc ccgcctggca ttatgcccag   1980
tacatgacct tatgggactt tcctacttgg cagtacatct acgtattagt catcgctatt   2040
accatggtga tgcggttttg gcagtacatc aatgggcgtg gatagcggtt tgactcacgg   2100
ggatttccaa gtctccaccc cattgacgtc aatgggagtt tgttttggca ccaaaatcaa   2160
cgggactttc caaaatgtcg taacaactcc gccccattga cgcaaatggg cggtaggcgt   2220
gtacggtggg aggtctatat aagcagagct cgtttagtga accggggtct ctctggttag   2280
accagatctg agcctgggag ctctctggct aactagggaa cccactgctt aagcctcaat   2340
aaagcttgcc ttgagtgctt caagtagtgt gtgcccgtct gttgtgtgac tctggtaact   2400
agagatccct cagacccttt tagtcagtgt ggaaaatctc tagcagtggc gcccgaacag   2460
ggacctgaaa gcgaaaggga aaccagagga gctctctcga cgcaggactc ggcttgctga   2520
agcgcgcacg gcaagaggcg aggggcggcg actggtgagt acgccaaaaa ttttgactag   2580
cggaggctag aaggagagag atgggtgcga gagcgtcagt attaagcggg ggagaattag   2640
atcgcgatgg gaaaaaattc ggttaaggcc agggggaaag aaaaaatata aattaaaaca   2700
tatagtatgg gcaagcaggg agctagaacg attcgcagtt aatcctggcc tgttagaaac   2760
atcagaaggc tgtagacaaa tactgggaca gctacaacca tcccttcaga caggatcaga   2820
agaacttaga tcattatata atacagtagc aaccctctat tgtgtgcatc aaaggataga   2880
gataaaagac accaaggaag ctttagacaa gatagaggaa gagcaaaaca aaagtaagac   2940
caccgcacag caagcggccg ctgatcttca gacctggagg aggagatatg agggacaatt   3000
ggagaagtga attatataaa tataaagtag taaaaattga accattagga gtagcaccca   3060
ccaaggcaaa gagaagagtg gtgcagagag aaaaaagagc agtgggaata ggagctttgt   3120
tccttgggtt cttgggagca gcaggaagca ctatgggcgc agcctcaatg acgctgacgg   3180
tacaggccag acaattattg tctggtatag tgcagcagca gaacaatttg ctgagggcta   3240
ttgaggcgca acagcatctg ttgcaactca cagtctgggg catcaagcag ctccaggcaa   3300
gaatcctggc tgtggaaaga tacctaaagg atcaacagct cctggggatt tggggttgct   3360
ctggaaaact catttgcacc actgctgtgc cttggaatgc tagttggagt aataaatctc   3420
tggaacagat tggaatcaca cgacctggat ggagtgggac agagaaatta acaattacac   3480
aagcttaata cactccttaa ttgaagaatc gcaaaaccag caagaaaaga atgaacaaga   3540
attattggaa ttagataaat gggcaagttt gtggaattgg tttaacataa caaattggct   3600
gtggtatata aaattattca taatgatagt aggaggcttg gtaggtttaa gaatagtttt   3660
tgctgtactt tctatagtga atagagttag gcagggatat tcaccattat cgtttcagac   3720
ccacctccca accccgaggg gacccgacag gcccgaagga atagaagaag aaggtggaga   3780
gagagacaga gacagatcca ttcgattagt gaacggatct cgacggtatc gatctcgaca   3840
caaatggcag tattcatcca caattttaaa agaaaagggg ggattggggg gtacagtgca   3900
ggggaaagaa tagtagacat aatagcaaca gacatacaaa ctaaagaatt acaaaaacaa   3960
attacaaaaa ttcaaaattt tcgggtttat tacagggaca gcagagatcc agtttgggaa   4020
ttagcttgag gatcctccaa gttcctaaat tagtccatga ggtcagaggc agcactgcca   4080
```

-continued

```
ttgtaacgcg attggagagg atcacgtcac cggacacgcc cccaggcatc tccctgggtc   4140
tcctaaactt ggcggggaga agttttagcc cttaagtttt agcctttaac cccatattc    4200
agaactgtgc gagttggcga aaccccacaa atcacaacaa actgtacaca acaccgagct   4260
agaggtgatc tttcttgtcc attccacaca ggccttagta atgcgtcgcc atagcaacag   4320
tgtcactagt agcaccagca cttccccaca ccctccccct caggaatccg tactctccag   4380
tgaaccccag aaacctctgg agagttctgg acaagggcgg aacccacaac tccgattact   4440
caagggaggc ggggaagctc caccagacgc gaaactgctg gaagattcct ggccccaagg   4500
cctcctccgg ctcgctgatt ggcccagcgg agagtgggcg gggccggtga agactcctta   4560
aaggcgcagg gcggcgagca ggtcaccaga cgctgacagc tactcagaac caaatctggt   4620
tccatccaga gacaagcgaa gacaagagaa gcagagcgag cggcgcgttc ccgatcctcg   4680
gccaggacca gccttcccca gagcatccct gccgcggagc gcaaccttcc caggagcatc   4740
cctgccgcgg agcgcaactt tccccggagc atccacgccg cggagcgcag ccttccagaa   4800
gcagagcgcg gcgccatggt gagcaaggga gaggaggata acatggcctc tctcccagct   4860
acacatgagc ttcacatctt tggatccatc aacggtgtgg actttgacat ggtgggtcag   4920
ggaaccggaa atccaaatga tggatatgag gagcttaacc ttaagtccac caagggtgac   4980
ctccagttct ccccatggat tcttgtccct catatcggat atggattcca tcagtacctt   5040
ccttaccctg acggtatgtc tcctttccag gccgccatgg ttgatggatc cggataccaa   5100
gtccatagaa caatgcagtt tgaagatggt gcctccctta ctgttaacta cagatacacc   5160
tacgagggaa gccacatcaa aggagaggcc caggtgaagg gaactggttt ccctgctgac   5220
ggtcctgtga tgaccaactc tcttaccgct gctgactggt gcaggtctaa gaaaacttac   5280
cctaacgaca aaaccatcat cagtaccttt aagtggagtt acaccactgg aaatggtaag   5340
agatacagaa gcactgctag aaccacctac acctttgcca agccaatggc tgctaactat   5400
cttaagaacc agcctatgta cgtgttccgt aagactgagc tcaagcactc caagaccgag   5460
ctcaacttca aggagtggca aaaggccttt accgatgtga tgggaatgga cgagctttac   5520
aagtaatgta caacacgtgc tacgagattt cgattccgag ctcgaattga cggatcggga   5580
gatctactag aagctttgca aagatggata aagttttaaa cagagaggaa tctttgcagc   5640
taatggacct tctaggtctt gaaaggagtg ggaattggct ccggtgcccg tcagtgggca   5700
gagcgcacat cgcccacagt ccccgagaag ttggggggag gggtcggcaa ttgaaccggt   5760
gcctagagaa ggtggcgcgg ggtaaactgg gaaagtgatg tcgtgtactg gctccgcctt   5820
tttcccgagg gtgggggaga accgtatata agtgcagtag tcgccgtgaa cgttcttttt   5880
cgcaacgggt ttgccgccag aacacaggta agtgccgtgt gtggttcccg cgggcctggc   5940
ctctttacgg gttatggccc ttgcgtgcct tgaattactt ccactggctg cagtacgtga   6000
ttcttgatcc cgagcttcgg gttggaagtg ggtgggagag ttcgaggcct tgcgcttaag   6060
gagccccttc gcctcgtgct tgagttgagg cctggcctgg gcgctggggc cgccgcgtgc   6120
gaatctggtg gcaccttcgc gcctgtctcg ctgctttcga taagtctcta gccatttaaa   6180
atttttgatg acctgctgcg acgctttttt tctggcaaga tagtcttgta aatgcgggcc   6240
aagatctgca cactggtatt tcggtttttg gggccgcggg cggcgacggg gcccgtgcgt   6300
cccagcgcac atgttcggcg aggcggggcc tgcgagcgcg gccaccgaga atcggacggg   6360
ggtagtctca agctggccgg cctgctctgg tgcctggcct cgcgccgccg tgtatcgccc   6420
cgccctgggc ggcaaggctg gcccggtcgg caccagttgc gtgagcggaa agatggccgc   6480
```

-continued

```
ttcccggccc tgctgcaggg agctcaaaat ggaggacgcg gcgctcggga gagcgggcgg   6540
gtgagtcacc cacacaaagg aaaagggcct ttccgtcctc agccgtcgct tcatgtgact   6600
ccacggagta ccgggcgccg tccaggcacc tcgattagtt ctcgagcttt tggagtacgt   6660
cgtctttagg ttggggggag gggttttatg cgatggagtt tccccacact gagtgggtgg   6720
agactgaagt taggccagct tggcacttga tgtaattctc cttggaattt gccctttttg   6780
agtttggatc ttggttcatt ctcaagcctc agacagtggt tcaaagtttt tttcttccat   6840
ttcaggtgtc gtgaccggtc gccaccatgg tgtctaaggg cgaagagctg attaaggaga   6900
acatgcacat gaagctgtac atggagggca ccgtggacaa ccatcacttc aagtgcacat   6960
ccgagggcga aggcaagccc tacgagggca cccagaccat gagaatcaag gtggtcgagg   7020
gcggccctct ccccttcgcc ttcgacatcc tggctactag cttcctctac ggcagcaaga   7080
ccttcatcaa ccacacccag ggcatccccg acttcttcaa gcagtccttc cctgagggct   7140
tcacatggga gagagtcacc acatacgaag acgggggcgt gctgaccgct acccaggaca   7200
ccagcctcca ggacggctgc ctcatctaca acgtcaagat cagaggggtg aacttcacat   7260
ccaacggccc tgtgatgcag aagaaaacac tcggctggga ggccttcacc gagacgctgt   7320
accccgctga cggcggcctg gaaggcagaa acgacatggc cctgaagctc gtgggcggga   7380
gccatctgat cgcaaacgcc aagaccacat atagatccaa gaaacccgct aagaacctca   7440
agatgcctgg cgtctactat gtggactaca gactggaaag aatcaaggag gccaacaacg   7500
agacctacgt cgagcagcac gaggtggcag tggccagata ctgcgacctc cctagcaaac   7560
tggggcacaa gcttaattaa tgtacaaatc aacctctgga ttacaaaatt tgtgaaagat   7620
tgactggtat tcttaactat gttgctcctt ttacgctatg tggatacgct gctttaatgc   7680
ctttgtatca tgctattgct tcccgtatgg ctttcatttt ctcctccttg tataaatcct   7740
ggttgctgtc tctttatgag gagttgtggc ccgttgtcag gcaacgtggc gtggtgtgca   7800
ctgtgtttgc tgacgcaacc cccactggtt ggggcattgc caccacctgt cagctccttt   7860
ccgggacttt cgctttcccc ctccctattg ccacggcgga actcatcgcc gcctgccttg   7920
cccgctgctg gacaggggct cggctgttgg gcactgacaa ttccgtggtg ttgtcgggga   7980
aatcatcgtc ctttccttgg ctgctcgcct atgttgccac ctggattctg cgcgggacgt   8040
ccttctgcta cgtcccttcg gccctcaatc cagcggacct tccttcccgc ggcctgctgc   8100
cggctctgcg gcctcttccg cgtcttcgcc ttcgccctca gacgagtcgg atctcccttt   8160
gggccgcctc cccgctacaa ggcagctgta gatccctttc atagaaggcg gcggtggtac   8220
ctttaagacc aatgacttac aaggcagctg tagatcttag ccacttttta aaagaaaagg   8280
ggggactgga agggctaatt cactcccaac gaagacaaga tctgcttttt gcttgtactg   8340
ggtctctctg gttagaccag atctgagcct gggagctctc tggctaacta gggaacccac   8400
tgcttaagcc tcaataaagc ttgccttgag tgcttcaagt agtgtgtgcc cgtctgttgt   8460
gtgactctgg taactagaga tccctcagac ccttttagtc agtgtggaaa atctctagca   8520
gtagtagttc atgtcatctt attattcagt atttataact tgcaaagaaa tgaatatcag   8580
agagtgagag gaacttgttt attgcagctt ataatggtta caaataaagc aatagcatca   8640
caaatttcac aaataaagca tttttttcac tgcattctag ttgtggtttg tccaaactca   8700
tcaatgtatc ttatcatgtc tggctctagc tatcccgccc ctaactccgc ccatcccgcc   8760
cctaactccg cccagttccg cccattctcc gccccatggc tgactaattt ttttatttta   8820
```

-continued

```
tgcagaggcc gaggccgcct cggcctctga gctattccag aagtagtgag gaggcttttt   8880
tggaggccta ggcttttgcg tcgagacgta cccaattcgc cctatagtga gtcgtattac   8940
gcgcgctcac tggccgtcgt tttacaacgt cgtgactggg aaaaccctgg cgttacccaa   9000
cttaatcgcc ttgcagcaca tccccctttc gccagctggc gtaatagcga agaggcccgc   9060
accgatcgcc cttcccaaca gttgcgcagc ctgaatggcg aatggcgcga cgcgccctgt   9120
agcggcgcat taagcgcggc gggtgtggtg gttacgcgca gcgtgaccgc tacacttgcc   9180
agcgccctag cgcccgctcc tttcgctttc ttcccttcct ttctcgccac gttcgccggc   9240
tttccccgtc aagctctaaa tcgggggctc cctttagggt tccgatttag tgctttacgg   9300
cacctcgacc ccaaaaaact tgattagggt gatggttcac gtagtgggcc atcgccctga   9360
tagacggttt ttcgcccttt gacgttggag tccacgttct ttaatagtgg actcttgttc   9420
caaactggaa caacactcaa ccctatctcg gtctattctt ttgatttata agggattttg   9480
ccgatttcgg cctattggtt aaaaaatgag ctgatttaac aaaaatttaa cgcgaatttt   9540
aacaaaatat taacgtttac aatttcccag gtggcacttt tcggggaaat gtgcgcggaa   9600
cccctatttg tttatttttc taaatacatt caaatatgta tccgctcatg agacaataac   9660
cctgataaat gcttcaataa tattgaaaaa ggaagagtat gagtattcaa catttccgtg   9720
tcgcccttat tccctttttt gcggcatttt gccttcctgt ttttgctcac ccagaaacgc   9780
tggtgaaagt aaaagatgct gaagatcagt tgggtgcacg agtgggttac atcgaactgg   9840
atctcaacag cggtaagatc cttgagagtt ttcgccccga agaacgtttt ccaatgatga   9900
gcacttttaa agttctgcta tgtggcgcgg tattatcccg tattgacgcc gggcaagagc   9960
aactcggtcg ccgcatacac tattctcaga atgacttggt tgagtactca ccagtcacag  10020
aaaagcatct tacggatggc atgacagtaa gagaattatg cagtgctgcc ataaccatga  10080
gtgataacac tgcggccaac ttacttctga caacgatcgg aggaccgaag gagctaaccg  10140
cttttttgca caacatgggg gatcatgtaa ctcgccttga tcgttgggaa ccg         10193
```

<210> SEQ ID NO 26
<211> LENGTH: 9719
<212> TYPE: DNA
<213> ORGANISM: Artificial Sequence
<220> FEATURE:
<223> OTHER INFORMATION: pTLL-SYNHsp70B'1

<400> SEQUENCE: 26

```
ccggagctga atgaagccat accaaacgac gagcgtgaca ccacgatgcc tgtagcaatg     60
gcaacaacgt tgcgcaaact attaactggc gaactactta ctctagcttc ccggcaacaa    120
ttaatagact ggatggaggc ggataaagtt gcaggaccac ttctgcgctc ggcccttccg    180
gctggctggt ttattgctga taaatctgga gccggtgagc gtgggtctcg cggtatcatt    240
gcagcactgg ggccagatgg taagccctcc cgtatcgtag ttatctacac gacggggagt    300
caggcaacta tggatgaacg aaatagacag atcgctgaga taggtgcctc actgattaag    360
cattggtaac tgtcagacca agtttactca tatatacttt agattgattt aaaacttcat    420
ttttaattta aaaggatcta ggtgaagatc ctttttgata atctcatgac caaaatccct    480
taacgtgagt tttcgttcca ctgagcgtca gaccccgtag aaaagatcaa aggatcttct    540
tgagatcctt tttttctgcg cgtaatctgc tgcttgcaaa caaaaaaacc accgctacca    600
gcggtggttt gtttgccgga tcaagagcta ccaactcttt ttccgaaggt aactggcttc    660
agcagagcgc agataccaaa tactgtcctt ctagtgtagc cgtagttagg ccaccacttc    720
```

-continued aagaactctg tagcaccgcc tacatacctc gctctgctaa tcctgttacc agtggctgct 780
gccagtggcg ataagtcgtg tcttaccggg ttggactcaa gacgatagtt accggataag 840
gcgcagcggt cgggctgaac ggggggttcg tgcacacagc ccagcttgga gcgaacgacc 900
tacaccgaac tgagatacct acagcgtgag ctatgagaaa gcgccacgct tcccgaaggg 960
agaaaggcgg acaggtatcc ggtaagcggc agggtcggaa caggagagcg cacgagggag 1020
cttccagggg gaaacgcctg gtatctttat agtcctgtcg ggtttcgcca cctctgactt 1080
gagcgtcgat ttttgtgatg ctcgtcaggg gggcggagcc tatggaaaaa cgccagcaac 1140
gcggcctttt tacggttcct ggccttttgc tggccttttg ctcacatgtt ctttcctgcg 1200
ttatcccctg attctgtgga taaccgtatt accgcctttg agtgagctga taccgctcgc 1260
cgcagccgaa cgaccgagcg cagcgagtca gtgagcgagg aagcggaaga gcgcccaata 1320
cgcaaaccgc ctctccccgc gcgttggccg attcattaat gcagctggca cgacaggttt 1380
cccgactgga aagcgggcag tgagcgcaac gcaattaatg tgagttagct cactcattag 1440
gcaccccagg ctttacactt tatgcttccg gctcgtatgt tgtgtggaat tgtgagcgga 1500
taacaatttc acacaggaaa cagctatgac catgattacg ccaagcgcgc aattaaccct 1560
cactaaaggg aacaaaagct ggagctgcaa gcttggccat tgcatacgtt gtatccatat 1620
cataatatgt acatttatat tggctcatgt ccaacattac cgccatgttg acattgatta 1680
ttgactagtt attaatagta atcaattacg gggtcattag ttcatagccc atatatggag 1740
ttccgcgtta cataacttac ggtaaatggc ccgcctggct gaccgcccaa cgacccccgc 1800
ccattgacgt caataatgac gtatgttccc atagtaacgc caatagggac tttccattga 1860
cgtcaatggg tggagtattt acggtaaact gcccacttgg cagtacatca agtgtatcat 1920
atgccaagta cgccccctat tgacgtcaat gacggtaaat ggcccgcctg gcattatgcc 1980
cagtacatga ccttatggga ctttcctact tggcagtaca tctacgtatt agtcatcgct 2040
attaccatgg tgatgcggtt ttggcagtac atcaatgggc gtggatagcg gtttgactca 2100
cggggatttc caagtctcca ccccattgac gtcaatggga gtttgttttg gcaccaaaat 2160
caacgggact ttccaaaatg tcgtaacaac tccgccccat tgacgcaaat gggcggtagg 2220
cgtgtacggt gggaggtcta tataagcaga gctcgtttag tgaaccgggg tctctctggt 2280
tagaccagat ctgagcctgg gagctctctg gctaactagg gaacccactg cttaagcctc 2340
aataaagctt gccttgagtg cttcaagtag tgtgtgcccg tctgttgtgt gactctggta 2400
actagagatc cctcagaccc ttttagtcag tgtggaaaat ctctagcagt ggcgcccgaa 2460
cagggacttg aaagcgaaag ggaaaccaga ggagctctct cgacgcagga ctcggcttgc 2520
tgaagcgcgc acggcaagag gcgagggggcg gcgactggtg agtacgccaa aaattttgac 2580
tagcggaggc tagaaggaga gagatgggtg cgagagcgtc agtattaagc gggggagaat 2640
tagatcgcga tgggaaaaaa ttcggttaag gccaggggga aagaaaaaat ataaattaaa 2700
acatatagta tgggcaagca gggagctaga acgattcgca gttaatcctg gcctgttaga 2760
aacatcagaa ggctgtagac aaatactggg acagctacaa ccatcccttc agacaggatc 2820
agaagaactt agatcattat ataatacagt agcaaccctc tattgtgtgc atcaaaggat 2880
agagataaaa gacaccaagg aagctttaga caagatagag gaagagcaaa acaaaagtaa 2940
gaccaccgca cagcaagcgg ccgctgatct tcagacctgg aggaggagat atgagggaca 3000
attggagaag tgaattatat aaatataaag tagtaaaaat tgaaccatta ggagtagcac 3060

-continued

```
ccaccaaggc aaagagaaga gtggtgcaga gagaaaaaag agcagtggga ataggagctt   3120
tgttccttgg gttcttggga gcagcaggaa gcactatggg cgcagcctca atgacgctga   3180
cggtacaggc cagacaatta ttgtctggta tagtgcagca gcagaacaat ttgctgaggg   3240
ctattgaggc gcaacagcat ctgttgcaac tcacagtctg gggcatcaag cagctccagg   3300
caagaatcct ggctgtggaa agatacctaa aggatcaaca gctcctgggg atttggggtt   3360
gctctggaaa actcatttgc accactgctg tgccttggaa tgctagttgg agtaataaat   3420
ctctggaaca gattggaatc acacgacctg gatggagtgg gacagagaaa ttaacaatta   3480
cacaagctta atacactcct taattgaaga atcgcaaaac cagcaagaaa agaatgaaca   3540
agaattattg gaattagata aatgggcaag tttgtggaat tggtttaaca taacaaattg   3600
gctgtggtat ataaaattat tcataatgat agtaggaggc ttggtaggtt taagaatagt   3660
tttgctgta ctttctatag tgaatagagt taggcaggga tattcaccat tatcgtttca   3720
gacccacctc ccaaccccga ggggacccga caggcccgaa ggaatagaag aagaaggtgg   3780
agagagagac agagacagat ccattcgatt agtgaacgga tctcgacggt atcgatctcg   3840
acacaaatgg cagtattcat ccacaatttt aaaagaaaag gggggattgg ggggtacagt   3900
gcaggggaaa gaatagtaga cataatagca acagacatac aaactaaaga attacaaaaa   3960
caaattacaa aaattcaaaa ttttcgggtt tattacaggg acagcagaga tccagtttgg   4020
gaattagctt gaccccgatc tgcccgaacc ttctcccggg gtcagcgccg cgccgcgcca   4080
cccggctgag tcagcccggg cgggcgagag gctctcaact gggcgggaag gtgcgggaag   4140
gtgcggaaag gttcgcgaaa gttcgcggcg gcgggggtcg ggtgaggcgc aaaaggataa   4200
aaagccggtg gaagcggagc tgagcagatc cgagccgggc tggctgcaga gaaaccgcag   4260
ggagagcctc actgctgagc gcccctcgac ggcggagcgg cagcagcctc cgtggcctcc   4320
agcatccgac aagaagcttc agccatggtg agcaagggag aggaggataa catggcctct   4380
ctcccagcta cacatgagct tcacatcttt ggatccatca acggtgtgga ctttgacatg   4440
gtgggtcagg gaaccggaaa tccaaatgat ggatatgagg agcttaacct taagtccacc   4500
aagggtgacc tccagttctc ccatggatt cttgtccctc atatcggata tggattccat   4560
cagtaccttc cttaccctga cggtatgtct cctttccagg ccgccatggt tgatggatcc   4620
ggataccaag tccatagaac aatgcagttt gaagatggtg cctcccttac tgttaactac   4680
agatacacct acgagggaag ccacatcaaa ggagaggccc aggtgaaggg aactggtttc   4740
cctgctgacg gtcctgtgat gaccaactct cttaccgctg ctgactggtg caggtctaag   4800
aaaacttacc ctaacgacaa aaccatcatc agtaccttta agtggagtta caccactgga   4860
aatggtaaga gatacagaag cactgctaga accacctaca cctttgccaa gccaatggct   4920
gctaactatc ttaagaacca gcctatgtac gtgttccgta agactgagct caagcactcc   4980
aagaccgagc tcaacttcaa ggagtggcaa aaggccttta ccgatgtgat gggaatggac   5040
gagctttaca agtaatgtac aacacgtgct acgagatttc gattccgagc tcgaattgac   5100
ggatcgggag atctactaga agctttgcaa agatggataa agttttaaac agagaggaat   5160
ctttgcagct aatggacctt ctaggtcttg aaaggagtgg gaattggctc cggtgcccgt   5220
cagtgggcag agcgcacatc gcccacagtc cccgagaagt tggggggagg ggtcggcaat   5280
tgaaccggtg cctagagaag gtggcgcggg gtaaactggg aaagtgatgt cgtgtactgg   5340
ctccgccttt ttcccgaggg tgggggagaa ccgtatataa gtgcagtagt cgccgtgaac   5400
gttctttttc gcaacgggtt tgccgccaga acacaggtaa gtgccgtgtg tggttcccgc   5460
```

gggcctggcc tctttacggg ttatggccct tgcgtgcctt gaattacttc cactggctgc 5520
agtacgtgat tcttgatccc gagcttcggg ttggaagtgg gtgggagagt tcgaggcctt 5580
gcgcttaagg agccccttcg cctcgtgctt gagttgaggc ctggcctggg cgctggggcc 5640
gccgcgtgcg aatctggtgg caccttcgcg cctgtctcgc tgctttcgat aagtctctag 5700
ccatttaaaa tttttgatga cctgctgcga cgcttttttt ctggcaagat agtcttgtaa 5760
atgcgggcca agatctgcac actggtattt cggtttttgg ggccgcgggc ggcgacgggg 5820
cccgtgcgtc ccagcgcaca tgttcggcga ggcggggcct gcgagcgcgg ccaccgagaa 5880
tcggacgggg gtagtctcaa gctggccggc ctgctctggt gcctggcctc gcgccgccgt 5940
gtatcgcccc gccctgggcg gcaaggctgg cccggtcggc accagttgcg tgagcggaaa 6000
gatggccgct tcccggccct gctgcaggga gctcaaaatg gaggacgcgg cgctcgggag 6060
agcgggcggg tgagtcaccc acacaaagga aaagggcctt tccgtcctca gccgtcgctt 6120
catgtgactc cacggagtac cgggcgccgt ccaggcacct cgattagttc tcgagctttt 6180
ggagtacgtc gtctttaggt tggggggagg ggttttatgc gatggagttt ccccacactg 6240
agtgggtgga gactgaagtt aggccagctt ggcacttgat gtaattctcc ttggaatttg 6300
ccctttttga gtttggatct tggttcattc tcaagcctca gacagtggtt caaagttttt 6360
ttcttccatt tcaggtgtcg tgaccggtcg ccaccatggt gtctaagggc gaagagctga 6420
ttaaggagaa catgcacatg aagctgtaca tggagggcac cgtggacaac catcacttca 6480
agtgcacatc cgagggcgaa ggcaagccct acgagggcac ccagaccatg agaatcaagg 6540
tggtcgaggg cggccctctc cccttcgcct tcgacatcct ggctactagc ttcctctacg 6600
gcagcaagac cttcatcaac cacacccagg gcatccccga cttcttcaag cagtccttcc 6660
ctgagggctt cacatgggag agagtcacca catacgaaga cgggggcgtg ctgaccgcta 6720
cccaggacac cagcctccag gacggctgcc tcatctacaa cgtcaagatc agaggggtga 6780
acttcacatc caacggccct gtgatgcaga agaaaacact cggctgggag gccttcaccg 6840
agacgctgta ccccgctgac ggcggcctgg aaggcagaaa cgacatggcc ctgaagctcg 6900
tgggcgggag ccatctgatc gcaaacgcca agaccacata tagatccaag aaacccgcta 6960
agaacctcaa gatgcctggc gtctactatg tggactacag actggaaaga atcaaggagg 7020
ccaacaacga gacctacgtc gagcagcacg aggtggcagt ggccagatac tgcgacctcc 7080
ctagcaaact ggggcacaag cttaattaat gtacaaatca acctctggat tacaaaattt 7140
gtgaaagatt gactggtatt cttaactatg ttgctccttt tacgctatgt ggatacgctg 7200
ctttaatgcc tttgtatcat gctattgctt cccgtatggc tttcattttc tcctccttgt 7260
ataaatcctg gttgctgtct ctttatgagg agttgtggcc cgttgtcagg caacgtggcg 7320
tggtgtgcac tgtgtttgct gacgcaaccc ccactggttg gggcattgcc accacctgtc 7380
agctcctttc cgggactttc gctttccccc tccctattgc cacggcggaa ctcatcgccg 7440
cctgccttgc ccgctgctgg acaggggctc ggctgttggg cactgacaat tccgtggtgt 7500
tgtcggggaa atcatcgtcc tttccttggc tgctcgccta tgttgccacc tggattctgc 7560
gcgggacgtc cttctgctac gtcccttcgg ccctcaatcc agcggacctt ccttcccgcg 7620
gcctgctgcc ggctctgcgg cctcttccgc gtcttcgcct tcgccctcag acgagtcgga 7680
tctccctttg ggccgcctcc ccgctacaag gcagctgtag atccctttca tagaaggcgg 7740
cggtggtacc tttaagacca atgacttaca aggcagctgt agatcttagc cactttttaa 7800

-continued

```
aagaaaaggg gggactggaa gggctaattc actcccaacg aagacaagat ctgctttttg   7860

cttgtactgg gtctctctgg ttagaccaga tctgagcctg ggagctctct ggctaactag   7920

ggaacccact gcttaagcct caataaagct tgccttgagt gcttcaagta gtgtgtgccc   7980

gtctgttgtg tgactctggt aactagagat ccctcagacc cttttagtca gtgtggaaaa   8040

tctctagcag tagtagttca tgtcatctta ttattcagta tttataactt gcaaagaaat   8100

gaatatcaga gagtgagagg aacttgttta ttgcagctta taatggttac aaataaagca   8160

atagcatcac aaatttcaca aataaagcat ttttttcact gcattctagt tgtggtttgt   8220

ccaaactcat caatgtatct tatcatgtct ggctctagct atcccgcccc taactccgcc   8280

catcccgccc ctaactccgc ccagttccgc ccattctccg ccccatggct gactaatttt   8340

ttttatttat gcagaggccg aggccgcctc ggcctctgag ctattccaga agtagtgagg   8400

aggctttttt ggaggcctag gcttttgcgt cgagacgtac ccaattcgcc ctatagtgag   8460

tcgtattacg cgcgctcact ggccgtcgtt ttacaacgtc gtgactggga aaaccctggc   8520

gttacccaac ttaatcgcct tgcagcacat ccccctttcg ccagctggcg taatagcgaa   8580

gaggcccgca ccgatcgccc ttcccaacag ttgcgcagcc tgaatggcga atggcgcgac   8640

gcgccctgta gcggcgcatt aagcgcggcg ggtgtggtgg ttacgcgcag cgtgaccgct   8700

acacttgcca gcgccctagc gcccgctcct ttcgctttct tcccttcctt tctcgccacg   8760

ttcgccggct ttccccgtca agctctaaat cgggggctcc ctttagggtt ccgatttagt   8820

gctttacggc acctcgaccc caaaaaactt gattagggtg atggttcacg tagtgggcca   8880

tcgccctgat agacggtttt tcgccctttg acgttggagt ccacgttctt taatagtgga   8940

ctcttgttcc aaactggaac aacactcaac cctatctcgg tctattcttt tgatttataa   9000

gggattttgc cgatttcggc ctattggtta aaaaatgagc tgatttaaca aaaatttaac   9060

gcgaatttta acaaaatatt aacgtttaca atttcccagg tggcactttt cggggaaatg   9120

tgcgcggaac ccctatttgt ttatttttct aaatacattc aaatatgtat ccgctcatga   9180

gacaataacc ctgataaatg cttcaataat attgaaaaag gaagagtatg agtattcaac   9240

atttccgtgt cgcccttatt cccttttttg cggcattttg ccttcctgtt tttgctcacc   9300

cagaaacgct ggtgaaagta aaagatgctg aagatcagtt gggtgcacga gtgggttaca   9360

tcgaactgga tctcaacagc ggtaagatcc ttgagagttt tcgccccgaa gaacgttttc   9420

caatgatgag cacttttaaa gttctgctat gtggcgcggt attatcccgt attgacgccg   9480

ggcaagagca actcggtcgc cgcatacact attctcagaa tgacttggtt gagtactcac   9540

cagtcacaga aaagcatctt acggatggca tgacagtaag agaattatgc agtgctgcca   9600

taaccatgag tgataacact gcggccaact tacttctgac aacgatcgga ggaccgaagg   9660

agctaaccgc ttttttgcac aacatggggg atcatgtaac tcgccttgat cgttgggaa    9719
```

```
<210> SEQ ID NO 27
<211> LENGTH: 9719
<212> TYPE: DNA
<213> ORGANISM: Artificial Sequence
<220> FEATURE:
<223> OTHER INFORMATION: pTLL-SYNHsp70B'2

<400> SEQUENCE: 27

ccggagctga atgaagccat accaaacgac gagcgtgaca ccacgatgcc tgtagcaatg     60

gcaacaacgt tgcgcaaact attaactggc gaactactta ctctagcttc ccggcaacaa    120

ttaatagact ggatggaggc ggataaagtt gcaggaccac ttctgcgctc ggcccttccg    180
```

-continued

```
gctggctggt ttattgctga taaatctgga gccggtgagc gtgggtctcg cggtatcatt    240
gcagcactgg ggccagatgg taagccctcc cgtatcgtag ttatctacac gacggggagt    300
caggcaacta tggatgaacg aaatagacag atcgctgaga taggtgcctc actgattaag    360
cattggtaac tgtcagacca agtttactca tatatacttt agattgattt aaaacttcat    420
ttttaattta aaaggatcta ggtgaagatc ctttttgata atctcatgac caaaatccct    480
taacgtgagt tttcgttcca ctgagcgtca gaccccgtag aaaagatcaa aggatcttct    540
tgagatcctt tttttctgcg cgtaatctgc tgcttgcaaa caaaaaaacc accgctacca    600
gcggtggttt gtttgccgga tcaagagcta ccaactcttt ttccgaaggt aactggcttc    660
agcagagcgc agataccaaa tactgtcctt ctagtgtagc cgtagttagg ccaccacttc    720
aagaactctg tagcaccgcc tacatacctc gctctgctaa tcctgttacc agtggctgct    780
gccagtggcg ataagtcgtg tcttaccggg ttggactcaa gacgatagtt accggataag    840
gcgcagcggt cgggctgaac ggggggttcg tgcacacagc ccagcttgga gcgaacgacc    900
tacaccgaac tgagatacct acagcgtgag ctatgagaaa gcgccacgct tcccgaaggg    960
agaaaggcgg acaggtatcc ggtaagcggc agggtcggaa caggagagcg cacgagggag   1020
cttccagggg gaaacgcctg gtatctttat agtcctgtcg ggtttcgcca cctctgactt   1080
gagcgtcgat ttttgtgatg ctcgtcaggg gggcggagcc tatggaaaaa cgccagcaac   1140
gcggcctttt tacggttcct ggccttttgc tggccttttg ctcacatgtt ctttcctgcg   1200
ttatcccctg attctgtgga taaccgtatt accgcctttg agtgagctga taccgctcgc   1260
cgcagccgaa cgaccgagcg cagcgagtca gtgagcgagg aagcggaaga gcgcccaata   1320
cgcaaaccgc ctctccccgc gcgttggccg attcattaat gcagctggca cgacaggttt   1380
cccgactgga aagcgggcag tgagcgcaac gcaattaatg tgagttagct cactcattag   1440
gcaccccagg ctttacactt tatgcttccg gctcgtatgt tgtgtggaat tgtgagcgga   1500
taacaatttc acacaggaaa cagctatgac catgattacg ccaagcgcgc aattaaccct   1560
cactaaaggg aacaaaagct ggagctgcaa gcttggccat tgcatacgtt gtatccatat   1620
cataatatgt acatttatat tggctcatgt ccaacattac cgccatgttg acattgatta   1680
ttgactagtt attaatagta atcaattacg gggtcattag ttcatagccc atatatggag   1740
ttccgcgtta cataacttac ggtaaatggc ccgcctggct gaccgcccaa cgacccccgc   1800
ccattgacgt caataatgac gtatgttccc atagtaacgc caatagggac tttccattga   1860
cgtcaatggg tggagtattt acggtaaact gcccacttgg cagtacatca agtgtatcat   1920
atgccaagta cgccccctat tgacgtcaat gacggtaaat ggcccgcctg gcattatgcc   1980
cagtacatga ccttatggga ctttcctact tggcagtaca tctacgtatt agtcatcgct   2040
attaccatgg tgatgcggtt ttggcagtac atcaatgggc gtggatagcg gtttgactca   2100
cggggatttc caagtctcca ccccattgac gtcaatggga gtttgttttg gcaccaaaat   2160
caacgggact ttccaaaatg tcgtaacaac tccgccccat tgacgcaaat gggcggtagg   2220
cgtgtacggt gggaggtcta tataagcaga gctcgtttag tgaaccgggg tctctctggt   2280
tagaccagat ctgagcctgg gagctctctg gctaactagg gaacccactg cttaagcctc   2340
aataaagctt gccttgagtg cttcaagtag tgtgtgcccg tctgttgtgt gactctggta   2400
actagagatc cctcagaccc ttttagtcag tgtggaaaat ctctagcagt ggcgcccgaa   2460
cagggacttg aaagcgaaag ggaaaccaga ggagctctct cgacgcagga ctcggcttgc   2520
```

```
tgaagcgcgc acggcaagag gcgaggggcg gcgactggtg agtacgccaa aaattttgac   2580
tagcggaggc tagaaggaga gagatgggtg cgagagcgtc agtattaagc gggggagaat   2640
tagatcgcga tgggaaaaaa ttcggttaag gccaggggga aagaaaaaat ataaattaaa   2700
acatatagta tgggcaagca gggagctaga acgattcgca gttaatcctg gcctgttaga   2760
aacatcagaa ggctgtagac aaatactggg acagctacaa ccatcccttc agacaggatc   2820
agaagaactt agatcattat ataatacagt agcaaccctc tattgtgtgc atcaaaggat   2880
agagataaaa gacaccaagg aagctttaga caagatagag gaagagcaaa acaaaagtaa   2940
gaccaccgca cagcaagcgg ccgctgatct tcagacctgg aggaggagat atgagggaca   3000
attggagaag tgaattatat aaatataaag tagtaaaaat tgaaccatta ggagtagcac   3060
ccaccaaggc aaagagaaga gtggtgcaga gagaaaaaag agcagtggga ataggagctt   3120
tgttccttgg gttcttggga gcagcaggaa gcactatggg cgcagcctca atgacgctga   3180
cggtacaggc cagacaatta ttgtctggta tagtgcagca gcagaacaat ttgctgaggg   3240
ctattgaggc gcaacagcat ctgttgcaac tcacagtctg gggcatcaag cagctccagg   3300
caagaatcct ggctgtggaa agatacctaa aggatcaaca gctcctgggg atttggggtt   3360
gctctggaaa actcatttgc accactgctg tgccttggaa tgctagttgg agtaataaat   3420
ctctggaaca gattggaatc acacgacctg gatggagtgg gacagagaaa ttaacaatta   3480
cacaagctta atacactcct taattgaaga atcgcaaaac cagcaagaaa agaatgaaca   3540
agaattattg gaattagata aatgggcaag tttgtggaat tggtttaaca taacaaattg   3600
gctgtggtat ataaaattat tcataatgat agtaggaggc ttggtaggtt taagaatagt   3660
tttgctgta ctttctatag tgaatagagt taggcaggga tattcaccat tatcgtttca   3720
gacccacctc ccaaccccga ggggacccga caggcccgaa ggaatagaag aagaaggtgg   3780
agagagagac agagacagat ccattcgatt agtgaacgga tctcgacggt atcgatctcg   3840
acacaaatgg cagtattcat ccacaatttt aaaagaaaag gggggattgg ggggtacagt   3900
gcaggggaaa gaatagtaga cataatagca acagacatac aaactaaaga attacaaaaa   3960
caaattacaa aaattcaaaa ttttcgggtt tattacaggg acagcagaga tccagtttgg   4020
gaattagctt gaccccgatc tgcccgaacc ttctcccggg gtcagcgccg cgccgcgcca   4080
cccggctgca gcagcccggg cgggcgagag gctctcaact gggcgggaag gtgcgggaag   4140
gtgcggaaag gttcgcgaaa gttcgcggcg gcgggggtcg ggtgaggcgc aaaaggataa   4200
aaagccggtg gaagcggagc tgagcagatc cgagccgggc tggctgcaga gaaaccgcag   4260
ggagagcctc actgctgagc gcccctcgac ggcggagcgg cagcagcctc cgtggcctcc   4320
agcatccgac aagaagcttc agccatggtg agcaagggag aggaggataa catggcctct   4380
ctcccagcta cacatgagct tcacatcttt ggatccatca acggtgtgga ctttgacatg   4440
gtgggtcagg gaaccggaaa tccaaatgat ggatatgagg agcttaacct taagtccacc   4500
aagggtgacc tccagttctc ccccatggatt cttgtccctc atatcggata tggattccat   4560
cagtaccttc cttaccctga cggtatgtct cctttccagg ccgccatggt tgatggatcc   4620
ggataccaag tccatagaac aatgcagttt gaagatggtg cctcccttac tgttaactac   4680
agatacacct acgagggaag ccacatcaaa ggagaggccc aggtgaaggg aactggtttc   4740
cctgctgacg gtcctgtgat gaccaactct cttaccgctg ctgactggtg caggtctaag   4800
aaaacttacc ctaacgacaa aaccatcatc agtaccttta agtggagtta caccactgga   4860
aatggtaaga gatacagaag cactgctaga accacctaca cctttgccaa gccaatggct   4920
```

-continued

```
gctaactatc ttaagaacca gcctatgtac gtgttccgta agactgagct caagcactcc   4980
aagaccgagc tcaacttcaa ggagtggcaa aaggccttta ccgatgtgat gggaatggac   5040
gagctttaca agtaatgtac aacacgtgct acgagatttc gattccgagc tcgaattgac   5100
ggatcgggag atctactaga agctttgcaa agatggataa agttttaaac agagaggaat   5160
ctttgcagct aatggacctt ctaggtcttg aaaggagtgg gaattggctc cggtgcccgt   5220
cagtgggcag agcgcacatc gcccacagtc cccgagaagt tggggggagg ggtcggcaat   5280
tgaaccggtg cctagagaag gtggcgcggg gtaaactggg aaagtgatgt cgtgtactgg   5340
ctccgccttt ttcccgaggg tgggggagaa ccgtatataa gtgcagtagt cgccgtgaac   5400
gttctttttc gcaacgggtt tgccgccaga acacaggtaa gtgccgtgtg tggttcccgc   5460
gggcctggcc tctttacggg ttatggccct tgcgtgcctt gaattacttc cactggctgc   5520
agtacgtgat tcttgatccc gagcttcggg ttggaagtgg gtgggagagt tcgaggcctt   5580
gcgcttaagg agccccttcg cctcgtgctt gagttgaggc ctggcctggg cgctggggcc   5640
gccgcgtgcg aatctggtgg caccttcgcg cctgtctcgc tgctttcgat aagtctctag   5700
ccatttaaaa tttttgatga cctgctgcga cgcttttttt ctggcaagat agtcttgtaa   5760
atgcgggcca agatctgcac actggtattt cggtttttgg ggccgcgggc ggcgacgggg   5820
cccgtgcgtc ccagcgcaca tgttcggcga ggcggggcct gcgagcgcgg ccaccgagaa   5880
tcggacgggg gtagtctcaa gctggccggc ctgctctggt gcctggcctc gcgccgccgt   5940
gtatcgcccc gccctgggcg gcaaggctgg cccggtcggc accagttgcg tgagcggaaa   6000
gatggccgct tcccggccct gctgcaggga gctcaaaatg gaggacgcgg cgctcgggag   6060
agcgggcggg tgagtcaccc acacaaagga aaagggcctt tccgtcctca gccgtcgctt   6120
catgtgactc cacggagtac cgggcgccgt ccaggcacct cgattagttc tcgagctttt   6180
ggagtacgtc gtctttaggt tggggggagg ggttttatgc gatggagttt ccccacactg   6240
agtgggtgga gactgaagtt aggccagctt ggcacttgat gtaattctcc ttggaatttg   6300
ccctttttga gtttggatct tggttcattc tcaagcctca gacagtggtt caaagttttt   6360
ttcttccatt tcaggtgtcg tgaccggtcg ccaccatggt gtctaagggc gaagagctga   6420
ttaaggagaa catgcacatg aagctgtaca tggagggcac cgtggacaac catcacttca   6480
agtgcacatc cgagggcgaa ggcaagccct acgagggcac ccagaccatg agaatcaagg   6540
tggtcgaggg cggccctctc cccttcgcct tcgacatcct ggctactagc ttcctctacg   6600
gcagcaagac cttcatcaac cacacccagg gcatccccga cttcttcaag cagtccttcc   6660
ctgagggctt cacatgggag agagtcacca catacgaaga cgggggcgtg ctgaccgcta   6720
cccaggacac cagcctccag gacggctgcc tcatctacaa cgtcaagatc agaggggtga   6780
acttcacatc caacggccct gtgatgcaga agaaaacact cggctgggag gccttcaccg   6840
agacgctgta ccccgctgac ggcggcctgg aaggcagaaa cgacatggcc ctgaagctcg   6900
tgggcgggag ccatctgatc gcaaacgcca agaccacata tagatccaag aaacccgcta   6960
agaacctcaa gatgcctggc gtctactatg tggactacag actggaaaga atcaaggagg   7020
ccaacaacga gacctacgtc gagcagcacg aggtggcagt ggccagatac tgcgacctcc   7080
ctagcaaact ggggcacaag cttaattaat gtacaaatca acctctggat tacaaaattt   7140
gtgaaagatt gactggtatt cttaactatg ttgctccttt tacgctatgt ggatacgctg   7200
ctttaatgcc tttgtatcat gctattgctt cccgtatggc tttcattttc tcctccttgt   7260
```

-continued

```
ataaatcctg gttgctgtct ctttatgagg agttgtggcc cgttgtcagg caacgtggcg   7320
tggtgtgcac tgtgtttgct gacgcaaccc ccactggttg gggcattgcc accacctgtc   7380
agctcctttc cgggactttc gctttccccc tccctattgc cacggcggaa ctcatcgccg   7440
cctgccttgc ccgctgctgg acaggggctc ggctgttggg cactgacaat tccgtggtgt   7500
tgtcggggaa atcatcgtcc tttccttggc tgctcgccta tgttgccacc tggattctgc   7560
gcgggacgtc cttctgctac gtcccttcgg ccctcaatcc agcggacctt ccttcccgcg   7620
gcctgctgcc ggctctgcgg cctcttccgc gtcttcgcct tcgccctcag acgagtcgga   7680
tctccctttg ggccgcctcc ccgctacaag gcagctgtag atccctttca tagaaggcgg   7740
cggtggtacc tttaagacca atgacttaca aggcagctgt agatcttagc cactttttaa   7800
aagaaaaggg gggactggaa gggctaattc actcccaacg aagacaagat ctgctttttg   7860
cttgtactgg gtctctctgg ttagaccaga tctgagcctg ggagctctct ggctaactag   7920
ggaacccact gcttaagcct caataaagct tgccttgagt gcttcaagta gtgtgtgccc   7980
gtctgttgtg tgactctggt aactagagat ccctcagacc cttttagtca gtgtggaaaa   8040
tctctagcag tagtagttca tgtcatctta ttattcagta tttataactt gcaaagaaat   8100
gaatatcaga gagtgagagg aacttgttta ttgcagctta taatggttac aaataaagca   8160
atagcatcac aaatttcaca aataaagcat ttttttcact gcattctagt tgtggtttgt   8220
ccaaactcat caatgtatct tatcatgtct ggctctagct atcccgcccc taactccgcc   8280
catcccgccc ctaactccgc ccagttccgc ccattctccg ccccatggct gactaatttt   8340
ttttatttat gcagaggccg aggccgcctc ggcctctgag ctattccaga agtagtgagg   8400
aggctttttt ggaggcctag gcttttgcgt cgagacgtac ccaattcgcc ctatagtgag   8460
tcgtattacg cgcgctcact ggccgtcgtt ttacaacgtc gtgactggga aaaccctggc   8520
gttacccaac ttaatcgcct tgcagcacat ccccctttcg ccagctggcg taatagcgaa   8580
gaggcccgca ccgatcgccc ttcccaacag ttgcgcagcc tgaatggcga atggcgcgac   8640
gcgccctgta gcggcgcatt aagcgcggcg ggtgtggtgg ttacgcgcag cgtgaccgct   8700
acacttgcca gcgccctagc gcccgctcct ttcgctttct tcccttcctt tctcgccacg   8760
ttcgccggct ttccccgtca agctctaaat cgggggctcc ctttagggtt ccgatttagt   8820
gctttacggc acctcgaccc caaaaaactt gattagggtg atggttcacg tagtgggcca   8880
tcgccctgat agacggtttt tcgccctttg acgttggagt ccacgttctt taatagtgga   8940
ctcttgttcc aaactggaac aacactcaac cctatctcgg tctattcttt tgatttataa   9000
gggattttgc cgatttcggc ctattggtta aaaaatgagc tgatttaaca aaaatttaac   9060
gcgaatttta acaaaatatt aacgtttaca atttcccagg tggcactttt cggggaaatg   9120
tgcgcggaac ccctatttgt ttatttttct aaatacattc aaatatgtat ccgctcatga   9180
gacaataacc ctgataaatg cttcaataat attgaaaaag gaagagtatg agtattcaac   9240
atttccgtgt cgcccttatt cccttttttg cggcattttg ccttcctgtt tttgctcacc   9300
cagaaacgct ggtgaaagta aaagatgctg aagatcagtt gggtgcacga gtgggttaca   9360
tcgaactgga tctcaacagc ggtaagatcc ttgagagttt tcgccccgaa gaacgttttc   9420
caatgatgag cacttttaaa gttctgctat gtggcgcggt attatcccgt attgacgccg   9480
ggcaagagca actcggtcgc cgcatacact attctcagaa tgacttggtt gagtactcac   9540
cagtcacaga aaagcatctt acggatggca tgacagtaag agaattatgc agtgctgcca   9600
taaccatgag tgataacact gcggccaact tacttctgac aacgatcgga ggaccgaagg   9660
```

agctaaccgc ttttttgcac aacatggggg atcatgtaac tcgccttgat cgttgggaa 9719

<210> SEQ ID NO 28
<211> LENGTH: 10024
<212> TYPE: DNA
<213> ORGANISM: Artificial Sequence
<220> FEATURE:
<223> OTHER INFORMATION: pTLL-SYNHsp70B'3

<400> SEQUENCE: 28
ccggagctga atgaagccat accaaacgac gagcgtgaca ccacgatgcc tgtagcaatg 60
gcaacaacgt tgcgcaaact attaactggc gaactactta ctctagcttc ccggcaacaa 120
ttaatagact ggatggaggc ggataaagtt gcaggaccac ttctgcgctc ggcccttccg 180
gctggctggt ttattgctga taaatctgga gccggtgagc gtgggtctcg cggtatcatt 240
gcagcactgg ggccagatgg taagccctcc cgtatcgtag ttatctacac gacggggagt 300
caggcaacta tggatgaacg aaatagacag atcgctgaga taggtgcctc actgattaag 360
cattggtaac tgtcagacca agtttactca tatatacttt agattgattt aaaacttcat 420
ttttaattta aaaggatcta ggtgaagatc ctttttgata atctcatgac caaaatccct 480
taacgtgagt tttcgttcca ctgagcgtca gaccccgtag aaaagatcaa aggatcttct 540
tgagatcctt tttttctgcg cgtaatctgc tgcttgcaaa caaaaaaacc accgctacca 600
gcggtggttt gtttgccgga tcaagagcta ccaactcttt ttccgaaggt aactggcttc 660
agcagagcgc agataccaaa tactgtcctt ctagtgtagc cgtagttagg ccaccacttc 720
aagaactctg tagcaccgcc tacatacctc gctctgctaa tcctgttacc agtggctgct 780
gccagtggcg ataagtcgtg tcttaccggg ttggactcaa gacgatagtt accggataag 840
gcgcagcggt cgggctgaac ggggggttcg tgcacacagc ccagcttgga gcgaacgacc 900
tacaccgaac tgagatacct acagcgtgag ctatgagaaa gcgccacgct tcccgaaggg 960
agaaaggcgg acaggtatcc ggtaagcggc agggtcggaa caggagagcg cacgagggag 1020
cttccagggg gaaacgcctg gtatctttat agtcctgtcg ggtttcgcca cctctgactt 1080
gagcgtcgat ttttgtgatg ctcgtcaggg gggcggagcc tatggaaaaa cgccagcaac 1140
gcggcctttt tacggttcct ggccttttgc tggccttttg ctcacatgtt ctttcctgcg 1200
ttatcccctg attctgtgga taaccgtatt accgcctttg agtgagctga taccgctcgc 1260
cgcagccgaa cgaccgagcg cagcgagtca gtgagcgagg aagcggaaga gcgcccaata 1320
cgcaaaccgc ctctccccgc gcgttggccg attcattaat gcagctggca cgacaggttt 1380
cccgactgga aagcgggcag tgagcgcaac gcaattaatg tgagttagct cactcattag 1440
gcaccccagg ctttacactt tatgcttccg gctcgtatgt tgtgtggaat tgtgagcgga 1500
taacaatttc acacaggaaa cagctatgac catgattacg ccaagcgcgc aattaaccct 1560
cactaaaggg aacaaaagct ggagctgcaa gcttggccat tgcatacgtt gtatccatat 1620
cataatatgt acatttatat tggctcatgt ccaacattac cgccatgttg acattgatta 1680
ttgactagtt attaatagta atcaattacg gggtcattag ttcatagccc atatatggag 1740
ttccgcgtta cataacttac ggtaaatggc ccgcctggct gaccgcccaa cgacccccgc 1800
ccattgacgt caataatgac gtatgttccc atagtaacgc caatagggac tttccattga 1860
cgtcaatggg tggagtattt acggtaaact gcccacttgg cagtacatca agtgtatcat 1920
atgccaagta cgccccctat tgacgtcaat gacggtaaat ggcccgcctg gcattatgcc 1980

-continued

```
cagtacatga ccttatggga ctttcctact tggcagtaca tctacgtatt agtcatcgct   2040
attaccatgg tgatgcggtt ttggcagtac atcaatgggc gtggatagcg gtttgactca   2100
cggggatttc caagtctcca ccccattgac gtcaatggga gtttgttttg gcaccaaaat   2160
caacgggact ttccaaaatg tcgtaacaac tccgccccat tgacgcaaat gggcggtagg   2220
cgtgtacggt gggaggtcta tataagcaga gctcgtttag tgaaccgggg tctctctggt   2280
tagaccagat ctgagcctgg gagctctctg gctaactagg gaacccactg cttaagcctc   2340
aataaagctt gccttgagtg cttcaagtag tgtgtgcccg tctgttgtgt gactctggta   2400
actagagatc cctcagaccc ttttagtcag tgtggaaaat ctctagcagt ggcgcccgaa   2460
cagggacttg aaagcgaaag ggaaaccaga ggagctctct cgacgcagga ctcggcttgc   2520
tgaagcgcgc acggcaagag gcgaggggcg gcgactggtg agtacgccaa aaattttgac   2580
tagcggaggc tagaaggaga gagatgggtg cgagagcgtc agtattaagc gggggagaat   2640
tagatcgcga tgggaaaaaa ttcggttaag gccaggggga aagaaaaaat ataaattaaa   2700
acatatagta tgggcaagca gggagctaga acgattcgca gttaatcctg gcctgttaga   2760
aacatcagaa ggctgtagac aaatactggg acagctacaa ccatcccttc agacaggatc   2820
agaagaactt agatcattat ataatacagt agcaaccctc tattgtgtgc atcaaaggat   2880
agagataaaa gacaccaagg aagctttaga caagatagag gaagagcaaa acaaaagtaa   2940
gaccaccgca cagcaagcgg ccgctgatct tcagacctgg aggaggagat atgagggaca   3000
attggagaag tgaattatat aaatataaag tagtaaaaat tgaaccatta ggagtagcac   3060
ccaccaaggc aaagagaaga gtggtgcaga gagaaaaaag agcagtggga ataggagctt   3120
tgttccttgg gttcttggga gcagcaggaa gcactatggg cgcagcctca atgacgctga   3180
cggtacaggc cagacaatta ttgtctggta tagtgcagca gcagaacaat ttgctgaggg   3240
ctattgaggc gcaacagcat ctgttgcaac tcacagtctg gggcatcaag cagctccagg   3300
caagaatcct ggctgtggaa agatacctaa aggatcaaca gctcctgggg atttggggtt   3360
gctctggaaa actcatttgc accactgctg tgccttggaa tgctagttgg agtaataaat   3420
ctctggaaca gattggaatc acacgacctg gatggagtgg gacagagaaa ttaacaatta   3480
cacaagctta atacactcct taattgaaga atcgcaaaac cagcaagaaa agaatgaaca   3540
agaattattg gaattagata aatgggcaag tttgtggaat tggtttaaca taacaaattg   3600
gctgtggtat ataaaattat tcataatgat agtaggaggc ttggtaggtt taagaatagt   3660
tttgctgta ctttctatag tgaatagagt taggcaggga tattcaccat tatcgtttca    3720
gacccacctc ccaaccccga ggggacccga caggcccgaa ggaatagaag aagaaggtgg   3780
agagagagac agagacagat ccattcgatt agtgaacgga tctcgacggt atcgatctcg   3840
acacaaatgg cagtattcat ccacaatttt aaaagaaaag gggggattgg ggggtacagt   3900
gcaggggaaa gaatagtaga cataatagca acagacatac aaactaaaga attacaaaaa   3960
caaattacaa aaattcaaaa ttttcgggtt tattacaggg acagcagaga tccagtttgg   4020
gaattagctt gaccccgatc tgcccgaacc ttctcccggg gtcagcgccg cgccgcgcca   4080
cccggctgca gcagcccggg cgggcgagag gctctcaact gggcgggaag gtgcgggaag   4140
gtgcggaaag gttcgcgaaa gttcgcggcc ggactagagt ggcgagatcc cccgatctgc   4200
ccgaaccttc tcccggggtc agcgccgcgc cgcgccaccc ggctgcagca gcccgggcgg   4260
gcgagaggct ctcaactggg cgggaaggtg cgggaaggtg cggaaaggtt cgcgaaagtt   4320
cgcggcaatt agcttgaccc cgatctgccc gaaccttctc ccggggtcag cgccgcgccg   4380
```

-continued

```
cgccacccgg ctgcagcagc ccgggcgggc gagaggctct caactgggcg ggaaggtgcg   4440
ggaaggtgcg gaaaggttcg cgaaagttcg cggcggcggg ggtcgggtga ggcgcaaaag   4500
gataaaaagc cggtggaagc ggagctgagc agatccgagc cgggctggct gcagagaaac   4560
cgcagggaga gcctcactgc tgagcgcccc tcgacggcgg agcggcagca gcctccgtgg   4620
cctccagcat ccgacaagaa gcttcagcca tggtgagcaa gggagaggag gataacatgg   4680
cctctctccc agctacacat gagcttcaca tctttggatc catcaacggt gtggactttg   4740
acatggtggg tcagggaacc ggaaatccaa atgatggata tgaggagctt aaccttaagt   4800
ccaccaaggg tgacctccag ttctccccat ggattcttgt ccctcatatc ggatatggat   4860
tccatcagta ccttccttac cctgacggta tgtctccttt ccaggccgcc atggttgatg   4920
gatccggata ccaagtccat agaacaatgc agtttgaaga tggtgcctcc cttactgtta   4980
actacagata cacctacgag ggaagccaca tcaaaggaga ggcccaggtg aagggaactg   5040
gtttccctgc tgacggtcct gtgatgacca actctcttac cgctgctgac tggtgcaggt   5100
ctaagaaaac ttaccctaac gacaaaacca tcatcagtac ctttaagtgg agttacacca   5160
ctggaaatgg taagagatac agaagcactg ctagaaccac ctacaccttt gccaagccaa   5220
tggctgctaa ctatcttaag aaccagccta tgtacgtgtt ccgtaagact gagctcaagc   5280
actccaagac cgagctcaac ttcaaggagt ggcaaaaggc ctttaccgat gtgatgggaa   5340
tggacgagct ttacaagtaa tgtacaacac gtgctacgag atttcgattc cgagctcgaa   5400
ttgacggatc gggagatcta ctagaagctt tgcaaagatg gataaagttt taaacagaga   5460
ggaatctttg cagctaatgg accttctagg tcttgaaagg agtgggaatt ggctccggtg   5520
cccgtcagtg ggcagagcgc acatcgccca cagtccccga gaagttgggg ggaggggtcg   5580
gcaattgaac cggtgcctag agaaggtggc gcggggtaaa ctgggaaagt gatgtcgtgt   5640
actggctccg cctttttccc gagggtgggg gagaaccgta tataagtgca gtagtcgccg   5700
tgaacgttct tttcgcaac gggtttgccg ccagaacaca ggtaagtgcc gtgtgtggtt   5760
cccgcgggcc tggcctcttt acgggttatg gcccttgcgt gccttgaatt acttccactg   5820
gctgcagtac gtgattcttg atcccgagct tcgggttgga agtgggtggg agagttcgag   5880
gccttgcgct taaggagccc cttcgcctcg tgcttgagtt gaggcctggc ctgggcgctg   5940
gggccgccgc gtgcgaatct ggtggcacct tcgcgcctgt ctcgctgctt tcgataagtc   6000
tctagccatt taaaattttt gatgacctgc tgcgacgctt tttttctggc aagatagtct   6060
tgtaaatgcg ggccaagatc tgcacactgg tatttcggtt tttggggccg cgggcggcga   6120
cggggcccgt gcgtcccagc gcacatgttc ggcgaggcgg ggcctgcgag cgcggccacc   6180
gagaatcgga cgggggtagt ctcaagctgg ccggcctgct ctggtgcctg gcctcgcgcc   6240
gccgtgtatc gccccgccct gggcggcaag gctggcccgg tcggcaccag ttgcgtgagc   6300
ggaaagatgg ccgcttcccg gccctgctgc agggagctca aaatggagga cgcggcgctc   6360
gggagagcgg gcgggtgagt cacccacaca aaggaaaagg gcctttccgt cctcagccgt   6420
cgcttcatgt gactccacgg agtaccgggc gccgtccagg cacctcgatt agttctcgag   6480
cttttggagt acgtcgtctt taggttgggg ggaggggttt tatgcgatgg agtttcccca   6540
cactgagtgg gtggagactg aagttaggcc agcttggcac ttgatgtaat tctccttgga   6600
atttgccctt tttgagtttg gatcttggtt cattctcaag cctcagacag tggttcaaag   6660
ttttttttctt ccatttcagg tgtcgtgacc ggtcgccacc atggtgtcta agggcgaaga   6720
```

-continued

```
gctgattaag gagaacatgc acatgaagct gtacatggag ggcaccgtgg acaaccatca   6780
cttcaagtgc acatccgagg gcgaaggcaa gccctacgag ggcacccaga ccatgagaat   6840
caaggtggtc gagggcggcc ctctcccctt cgccttcgac atcctggcta ctagcttcct   6900
ctacggcagc aagaccttca tcaaccacac ccagggcatc cccgacttct tcaagcagtc   6960
cttccctgag ggcttcacat gggagagagt caccacatac gaagacgggg gcgtgctgac   7020
cgctacccag gacaccagcc tccaggacgg ctgcctcatc tacaacgtca agatcagagg   7080
ggtgaacttc acatccaacg gccctgtgat gcagaagaaa acactcggct gggaggcctt   7140
caccgagacg ctgtaccccg ctgacggcgg cctggaaggc agaaacgaca tggccctgaa   7200
gctcgtgggc gggagccatc tgatcgcaaa cgccaagacc acatatagat ccaagaaacc   7260
cgctaagaac ctcaagatgc ctggcgtcta ctatgtggac tacagactgg aaagaatcaa   7320
ggaggccaac aacgagacct acgtcgagca gcacgaggtg gcagtggcca gatactgcga   7380
cctccctagc aaactggggc acaagcttaa ttaatgtaca aatcaacctc tggattacaa   7440
aatttgtgaa agattgactg gtattcttaa ctatgttgct ccttttacgc tatgtggata   7500
cgctgcttta atgcctttgt atcatgctat tgcttcccgt atggctttca ttttctcctc   7560
cttgtataaa tcctggttgc tgtctcttta tgaggagttg tggcccgttg tcaggcaacg   7620
tggcgtggtg tgcactgtgt ttgctgacgc aacccccact ggttggggca ttgccaccac   7680
ctgtcagctc ctttccggga ctttcgcttt ccccctccct attgccacgg cggaactcat   7740
cgccgcctgc cttgcccgct gctggacagg ggctcggctg ttgggcactg acaattccgt   7800
ggtgttgtcg gggaaatcat cgtcctttcc ttggctgctc gcctatgttg ccacctggat   7860
tctgcgcggg acgtccttct gctacgtccc ttcggccctc aatccagcgg accttccttc   7920
ccgcggcctg ctgccggctc tgcggcctct tccgcgtctt cgccttcgcc ctcagacgag   7980
tcggatctcc ctttgggccg cctccccgct acaaggcagc tgtagatccc tttcatagaa   8040
ggcggcggtg gtacctttaa gaccaatgac ttacaaggca gctgtagatc ttagccactt   8100
tttaaaagaa aaggggggac tggaagggct aattcactcc caacgaagac aagatctgct   8160
ttttgcttgt actgggtctc tctggttaga ccagatctga gcctgggagc tctctggcta   8220
actagggaac ccactgctta agcctcaata aagcttgcct tgagtgcttc aagtagtgtg   8280
tgcccgtctg ttgtgtgact ctggtaacta gagatccctc agaccctttt agtcagtgtg   8340
gaaaatctct agcagtagta gttcatgtca tcttattatt cagtatttat aacttgcaaa   8400
gaaatgaata tcagagagtg agaggaactt gtttattgca gcttataatg gttacaaata   8460
aagcaatagc atcacaaatt tcacaaataa agcatttttt tcactgcatt ctagttgtgg   8520
tttgtccaaa ctcatcaatg tatcttatca tgtctggctc tagctatccc gcccctaact   8580
ccgcccatcc cgcccctaac tccgcccagt tccgcccatt ctccgcccca tggctgacta   8640
attttttta tttatgcaga ggccgaggcc gcctcggcct ctgagctatt ccagaagtag   8700
tgaggaggct tttttggagg cctaggcttt tgcgtcgaga cgtacccaat tcgccctata   8760
gtgagtcgta ttacgcgcgc tcactggccg tcgttttaca acgtcgtgac tgggaaaacc   8820
ctggcgttac ccaacttaat cgccttgcag cacatccccc tttcgccagc tggcgtaata   8880
gcgaagaggc ccgcaccgat cgcccttccc aacagttgcg cagcctgaat ggcgaatggc   8940
gcgacgcgcc ctgtagcggc gcattaagcg cggcgggtgt ggtggttacg cgcagcgtga   9000
ccgctacact tgccagcgcc ctagcgcccg ctcctttcgc tttcttccct tcctttctcg   9060
ccacgttcgc cggctttccc cgtcaagctc taaatcgggg gctcccttta gggttccgat   9120
```

```
ttagtgcttt acggcacctc gaccccaaaa aacttgatta gggtgatggt tcacgtagtg   9180

ggccatcgcc ctgatagacg gtttttcgcc ctttgacgtt ggagtccacg ttctttaata   9240

gtggactctt gttccaaact ggaacaacac tcaaccctat ctcggtctat tcttttgatt   9300

tataagggat tttgccgatt tcggcctatt ggttaaaaaa tgagctgatt taacaaaaat   9360

ttaacgcgaa ttttaacaaa atattaacgt ttacaatttc ccaggtggca cttttcgggg   9420

aaatgtgcgc ggaaccccta tttgtttatt tttctaaata cattcaaata tgtatccgct   9480

catgagacaa taaccctgat aaatgcttca ataatattga aaaaggaaga gtatgagtat   9540

tcaacatttc cgtgtcgccc ttattccctt ttttgcggca ttttgccttc ctgtttttgc   9600

tcacccagaa acgctggtga aagtaaaaga tgctgaagat cagttgggtg cacgagtggg   9660

ttacatcgaa ctggatctca acagcggtaa gatccttgag agttttcgcc ccgaagaacg   9720

ttttccaatg atgagcactt ttaaagttct gctatgtggc gcggtattat cccgtattga   9780

cgccgggcaa gagcaactcg gtcgccgcat acactattct cagaatgact tggttgagta   9840

ctcaccagtc acagaaaagc atcttacgga tggcatgaca gtaagagaat tatgcagtgc   9900

tgccataacc atgagtgata acactgcggc caacttactt ctgacaacga tcggaggacc   9960

gaaggagcta accgcttttt tgcacaacat gggggatcat gtaactcgcc ttgatcgttg  10020

ggaa                                                               10024
```

<210> SEQ ID NO 29
<211> LENGTH: 9678
<212> TYPE: DNA
<213> ORGANISM: Artificial Sequence
<220> FEATURE:
<223> OTHER INFORMATION: HSPB-CRE circuit

<400> SEQUENCE: 29

```
ccggagctga atgaagccat accaaacgac gagcgtgaca ccacgatgcc tgtagcaatg     60

gcaacaacgt tgcgcaaact attaactggc gaactactta ctctagcttc ccggcaacaa    120

ttaatagact ggatggaggc ggataaagtt gcaggaccac ttctgcgctc ggcccttccg    180

gctggctggt ttattgctga taaatctgga gccggtgagc gtgggtctcg cggtatcatt    240

gcagcactgg ggccagatgg taagccctcc cgtatcgtag ttatctacac gacggggagt    300

caggcaacta tggatgaacg aaatagacag atcgctgaga taggtgcctc actgattaag    360

cattggtaac tgtcagacca agtttactca tatatacttt agattgattt aaaacttcat    420

ttttaattta aaaggatcta ggtgaagatc ctttttgata atctcatgac caaaatccct    480

taacgtgagt tttcgttcca ctgagcgtca gaccccgtag aaaagatcaa aggatcttct    540

tgagatcctt tttttctgcg cgtaatctgc tgcttgcaaa caaaaaaacc accgctacca    600

gcggtggttt gtttgccgga tcaagagcta ccaactcttt ttccgaaggt aactggcttc    660

agcagagcgc agataccaaa tactgtcctt ctagtgtagc cgtagttagg ccaccacttc    720

aagaactctg tagcaccgcc tacatacctc gctctgctaa tcctgttacc agtggctgct    780

gccagtggcg ataagtcgtg tcttaccggg ttggactcaa gacgatagtt accggataag    840

gcgcagcggt cgggctgaac ggggggttcg tgcacacagc ccagcttgga gcgaacgacc    900

tacaccgaac tgagatacct acagcgtgag ctatgagaaa gcgccacgct tcccgaaggg    960

agaaaggcgg acaggtatcc ggtaagcggc agggtcggaa caggagagcg cacgagggag   1020

cttccagggg gaaacgcctg gtatctttat agtcctgtcg ggtttcgcca cctctgactt   1080
```

-continued gagcgtcgat ttttgtgatg ctcgtcaggg gggcggagcc tatggaaaaa cgccagcaac 1140
gcggcctttt tacggttcct ggccttttgc tggccttttg ctcacatgtt ctttcctgcg 1200
ttatcccctg attctgtgga taaccgtatt accgcctttg agtgagctga taccgctcgc 1260
cgcagccgaa cgaccgagcg cagcgagtca gtgagcgagg aagcggaaga gcgcccaata 1320
cgcaaaccgc ctctccccgc gcgttggccg attcattaat gcagctggca cgacaggttt 1380
cccgactgga aagcgggcag tgagcgcaac gcaattaatg tgagttagct cactcattag 1440
gcaccccagg ctttacactt tatgcttccg gctcgtatgt tgtgtggaat tgtgagcgga 1500
taacaatttc acacaggaaa cagctatgac catgattacg ccaagcgcgc aattaaccct 1560
cactaaaggg aacaaaagct ggagctgcaa gcttggccat tgcatacgtt gtatccatat 1620
cataatatgt acatttatat tggctcatgt ccaacattac cgccatgttg acattgatta 1680
ttgactagtt attaatagta atcaattacg gggtcattag ttcatagccc atatatggag 1740
ttccgcgtta cataacttac ggtaaatggc ccgcctggct gaccgcccaa cgacccccgc 1800
ccattgacgt caataatgac gtatgttccc atagtaacgc caatagggac tttccattga 1860
cgtcaatggg tggagtattt acggtaaact gcccacttgg cagtacatca agtgtatcat 1920
atgccaagta cgccccctat tgacgtcaat gacggtaaat ggcccgcctg gcattatgcc 1980
cagtacatga ccttatggga ctttcctact tggcagtaca tctacgtatt agtcatcgct 2040
attaccatgg tgatgcggtt ttggcagtac atcaatgggc gtggatagcg gtttgactca 2100
cggggatttc caagtctcca ccccattgac gtcaatggga gtttgttttg gcaccaaaat 2160
caacgggact ttccaaaatg tcgtaacaac tccgccccat tgacgcaaat gggcggtagg 2220
cgtgtacggt gggaggtcta tataagcaga gctcgtttag tgaaccgggg tctctctggt 2280
tagaccagat ctgagcctgg gagctctctg gctaactagg gaacccactg cttaagcctc 2340
aataaagctt gccttgagtg cttcaagtag tgtgtgcccg tctgttgtgt gactctggta 2400
actagagatc cctcagaccc ttttagtcag tgtggaaaat ctctagcagt ggcgcccgaa 2460
cagggacctg aaagcgaaag ggaaaccaga ggagctctct cgacgcagga ctcggcttgc 2520
tgaagcgcgc acggcaagag gcgaggggcg gcgactggtg agtacgccaa aaattttgac 2580
tagcggaggc tagaaggaga gagatgggtg cgagagcgtc agtattaagc gggggagaat 2640
tagatcgcga tgggaaaaaa ttcggttaag gccaggggga aagaaaaaat ataaattaaa 2700
acatatagta tgggcaagca gggagctaga acgattcgca gttaatcctg gcctgttaga 2760
aacatcagaa ggctgtagac aaatactggg acagctacaa ccatcccttc agacaggatc 2820
agaagaactt agatcattat ataatacagt agcaaccctc tattgtgtgc atcaaaggat 2880
agagataaaa gacaccaagg aagctttaga caagatagag gaagagcaaa acaaaagtaa 2940
gaccaccgca cagcaagcgg ccgctgatct tcagacctgg aggaggagat atgagggaca 3000
attggagaag tgaattatat aaatataaag tagtaaaaat tgaaccatta ggagtagcac 3060
ccaccaaggc aaagagaaga gtggtgcaga gagaaaaaag agcagtggga ataggagctt 3120
tgttccttgg gttcttggga gcagcaggaa gcactatggg cgcagcctca atgacgctga 3180
cggtacaggc cagacaatta ttgtctggta tagtgcagca gcagaacaat ttgctgaggg 3240
ctattgaggc gcaacagcat ctgttgcaac tcacagtctg gggcatcaag cagctccagg 3300
caagaatcct ggctgtggaa agatacctaa aggatcaaca gctcctgggg atttggggtt 3360
gctctggaaa actcatttgc accactgctg tgccttggaa tgctagttgg agtaataaat 3420
ctctggaaca gattggaatc acacgacctg gatggagtgg gacagagaaa ttaacaatta 3480

-continued cacaagctta atacactcct taattgaaga atcgcaaaac cagcaagaaa agaatgaaca 3540
agaattattg gaattagata aatgggcaag tttgtggaat tggtttaaca taacaaattg 3600
gctgtggtat ataaaattat tcataatgat agtaggaggc ttggtaggtt taagaatagt 3660
ttttgctgta ctttctatag tgaatagagt taggcaggga tattcaccat tatcgtttca 3720
gacccacctc ccaaccccga ggggacccga caggcccgaa ggaatagaag aagaaggtgg 3780
agagagagac agagacagat ccattcgatt agtgaacgga tctcgacggt atcgatctcg 3840
acacaaatgg cagtattcat ccacaatttt aaaagaaaag gggggattgg ggggtacagt 3900
gcaggggaaa gaatagtaga cataatagca acagacatac aaactaaaga attacaaaaa 3960
caaattacaa aaattcaaaa ttttcgggtt tattacaggg acagcagaga tccagtttgg 4020
gaattagctt gaggatcctc cacagccccg gggagacctt gcctctaaag ttgctgcttt 4080
tgcagctctg ccacaaccgc gcgtcctcag agccagccgg gaggagctag aaccttcccc 4140
gcgtttcttt cagcagccct gagtcagagg cgggctggcc ttgcaagtag ccgcccagcc 4200
ttcttcggtc tcacggaccg atccgcccga accttctccc ggggtcagcg ccgcgctgcg 4260
ccgcccggct gactcagccc gggcgggcgg gcgggaggct ctcgactggg cgggaaggtg 4320
cgggaaggtt cgcggcggcg gggtcgggga ggtgcaaaag gatgaaaagc ccgtggacgg 4380
agctgagcag atccggccgg gctggcggca gagaaaccgc agggagagcc tcactgctga 4440
gcgcccctcg acgcgggcgg cagcagcctc cgtggcctcc agcatccgac aagaagcttc 4500
agccatgccc aagaagaaga ggaaggtggc gaatttactg acggtaccag aattccaaaa 4560
tttgcctgca ttaccggtcg atgcaacgag tgatgaggtt cgcaagaacc tgatggacat 4620
gttcagggat cgccaggcgt tttctgagca tacctggaaa atgcttctgt ccgtttgccg 4680
gtcgtgggcg gcatggtgca agttgaataa ccggaaatgg tttcccgcag aacctgaaga 4740
tgttcgcgat tatcttctat atctgcaggt aagtatcaag gttacaagac aggtttaagg 4800
agaccaatag aaactgggct tgtcgagaca gagaagactc ttgcgtttct gataggcacc 4860
tattggtctt actgacatcc actttgcctt tctctccaca ggcgcgcggt ctggcagtaa 4920
aaactatcca gcaacatttg ggccagctaa acatgcttca tcgtcggtcc gggctgccac 4980
gaccaagtga cagcaatgct gtttcactgg ttatgcggcg gatccgaaaa gaaaacgttg 5040
atgccggtga acgtgcaaaa caggctctag cgttcgaacg cactgatttc gaccaggttc 5100
gttcactcat ggaaaatagc gatcgctgcc aggatatacg taatctggca tttctgggga 5160
ttgcttataa caccctgtta cgtatagccg aaattgccag gatcagggtt aaagatatct 5220
cacgtactga cggtgggaga atgttaatcc atattggcag aacgaaaacg ctggttagca 5280
ccgcaggtgt agagaaggca cttagcctgg gggtaactaa actggtcgag cgatggattt 5340
ccgtctctgg tgtagctgat gatccgaata actacctgtt ttgccgggtc agaaaaaatg 5400
gtgttgccgc gccatctgcc accagccagc tatcaactcg cgccctggaa gggatttttg 5460
aagcaactca tcgattgatt tacggcgcta aggatgactc tggtcagaga tacctggcct 5520
ggtctggaca cagtgcccgt gtcggagccg cgcgagatat ggcccgcgct ggagtttcaa 5580
taccggagat catgcaagct ggtggctgga ccaatgtaaa tattgtcatg aactatatcc 5640
gtaacctgga tagtgaaaca ggggcaatgg tgcgcctgct ggaagatggc gattagcgtg 5700
ctacgagatt tcgatcccga gctcgaattg acggatcggg agtaatgtac aacacgtgct 5760
acgtacagaa ttggctccgg tgcccgtcag tgggcagagc gcacatcgcc cacagtcccc 5820

-continued

```
gagaagttgg ggggaggggt cggcaattga accggtgcct agagaaggtg gcgcggggta   5880
aactgggaaa gtgatgtcgt gtactggctc cgcctttttc ccgagggtgg gggagaaccg   5940
tatataagtg cagtagtcgc cgtgaacgtt ctttttcgca acgggtttgc cgccagaaca   6000
caggtaagtg ccgtgtgtgg ttcccgcggg cctggcctct ttacgggtta tggcccttgc   6060
gtgccttgaa ttacttccac tggctgcagt acgtgattct tgatcccgag cttcgggttg   6120
gaagtgggtg ggagagttcg aggccttgcg cttaaggagc cccttcgcct cgtgcttgag   6180
ttgaggcctg gcctgggcgc tggggccgcc gcgtgcgaat ctggtggcac cttcgcgcct   6240
gtctcgctgc tttcgataag tctctagcca tttaaaattt ttgatgacct gctgcgacgc   6300
tttttttctg gcaagatagt cttgtaaatg cgggccaaga tctgcacact ggtatttcgg   6360
tttttggggc cgcgggcggc gacggggccc gtgcgtccca gcgcacatgt tcggcgaggc   6420
ggggcctgcg agcgcggcca ccgagaatcg gacgggggta gtctcaagct ggccggcctg   6480
ctctggtgcc tggcctcgcg ccgccgtgta tcgccccgcc ctgggcggca aggctggccc   6540
ggtcggcacc agttgcgtga gcggaaagat ggccgcttcc cggccctgct gcagggagct   6600
caaaatggag gacgcggcgc tcgggagagc gggcgggtga gtcacccaca caaaggaaaa   6660
gggcctttcc gtcctcagcc gtcgcttcat gtgactccac ggagtaccgg gcgccgtcca   6720
ggcacctcga ttagttctcg agcttttgga gtacgtcgtc tttaggttgg ggggaggggt   6780
tttatgcgat ggagtttccc cacactgagt gggtggagac tgaagttagg ccagcttggc   6840
acttgatgta attctccttg gaatttgccc tttttgagtt tggatcttgg ttcattctca   6900
agcctcagac agtggttcaa agtttttttc ttccatttca ggtgtcgtga ccggtcgcca   6960
ccatggtgtc caagggcgag gaactgttca ccggcgtggt gcccatcctg gtggaactgg   7020
atggcgacgt gaacggccac aagttctctg tgcggggaga gggcgaaggc gacgccacaa   7080
atggcaagct gaccctgaag ttcatctgca ccaccggcaa gctgcccgtg ccttggccta   7140
ccctcgtgac cacactgtct cacggcgtgc agtgcttcgc cagatacccc gaccacatga   7200
agcagcacga tttcttcaag agcgccatgc ccgagggcta cgtgcaggaa cggaccatct   7260
tcttcaagga cgacggcacc tacaagacca gagccgaagt gaagttcgag ggcgacaccc   7320
tcgtgaaccg gatcgagctg aagggcgtgg acttcaaaga ggacggcaac atcctgggcc   7380
acaagctgga gtacaacttc aacagccaca acatctacat catggccgtg aagcagaaaa   7440
acggcatcaa agtgaacttc aagatccggc acaacgtgga agatggcagc gtgcagctgg   7500
ccgaccacta ccagcagaac acccccatcg gagatggccc cgtgctgctg cctgatagcc   7560
actacctgag cacccagagc gtgctgagca aggaccccaa cgagaagcgg gaccacatgg   7620
tgctgctgga atttcggacc gccgctggca tcaccctggg catggatgag ctgtacaagt   7680
gacctttcat agaaggcggc ggtggtacct ttaagaccaa tgacttacaa ggcagctgta   7740
gatcttagcc actttttaaa agaaaagggg ggactggaag ggctaattca ctcccaacga   7800
agacaagatc tgctttttgc ttgtactggg tctctctggt tagaccagat ctgagcctgg   7860
gagctctctg gctaactagg gaacccactg cttaagcctc aataaagctt gccttgagtg   7920
cttcaagtag tgtgtgcccg tctgttgtgt gactctggta actagagatc cctcagaccc   7980
ttttagtcag tgtggaaaat ctctagcagt agtagttcat gtcatcttat tattcagtat   8040
ttataacttg caaagaaatg aatatcagag agtgagagga acttgtttat tgcagcttat   8100
aatggttaca aataaagcaa tagcatcaca aatttcacaa ataaagcatt tttttcactg   8160
cattctagtt gtggtttgtc caaactcatc aatgtatctt atcatgtctg gctctagcta   8220
```

-continued tcccgcccct aactccgccc atcccgcccc taactccgcc cagttccgcc cattctccgc 8280
cccatggctg actaattttt tttatttatg cagaggccga ggccgcctcg gcctctgagc 8340
tattccagaa gtagtgagga ggcttttttg gaggcctagg cttttgcgtc gagacgtacc 8400
caattcgccc tatagtgagt cgtattacgc gcgctcactg gccgtcgttt tacaacgtcg 8460
tgactgggaa aaccctggcg ttacccaact taatcgcctt gcagcacatc cccctttcgc 8520
cagctggcgt aatagcgaag aggcccgcac cgatcgccct tcccaacagt tgcgcagcct 8580
gaatggcgaa tggcgcgacg cgccctgtag cggcgcatta agcgcggcgg gtgtggtggt 8640
tacgcgcagc gtgaccgcta cacttgccag cgccctagcg cccgctcctt tcgctttctt 8700
cccttccttt ctcgccacgt tcgccggctt tccccgtcaa gctctaaatc gggggctccc 8760
tttagggttc cgatttagtg ctttacggca cctcgacccc aaaaaacttg attagggtga 8820
tggttcacgt agtgggccat cgccctgata gacggttttt cgccctttga cgttggagtc 8880
cacgttcttt aatagtggac tcttgttcca aactggaaca acactcaacc ctatctcggt 8940
ctattctttt gatttataag ggattttgcc gatttcggcc tattggttaa aaaatgagct 9000
gatttaacaa aaatttaacg cgaattttaa caaaatatta acgtttacaa tttcccaggt 9060
ggcacttttc ggggaaatgt gcgcggaacc cctatttgtt tatttttcta aatacattca 9120
aatatgtatc cgctcatgag acaataaccc tgataaatgc ttcaataata ttgaaaaagg 9180
aagagtatga gtattcaaca tttccgtgtc gcccttattc ccttttttgc ggcattttgc 9240
cttcctgttt ttgctcaccc agaaacgctg gtgaaagtaa aagatgctga agatcagttg 9300
ggtgcacgag tgggttacat cgaactggat ctcaacagcg gtaagatcct tgagagtttt 9360
cgccccgaag aacgttttcc aatgatgagc acttttaaag ttctgctatg tggcgcggta 9420
ttatcccgta ttgacgccgg gcaagagcaa ctcggtcgcc gcatacacta ttctcagaat 9480
gacttggttg agtactcacc agtcacagaa aagcatctta cggatggcat gacagtaaga 9540
gaattatgca gtgctgccat aaccatgagt gataacactg cggccaactt acttctgaca 9600
acgatcggag gaccgaagga gctaaccgct tttttgcaca acatggggga tcatgtaact 9660
cgccttgatc gttgggaa 9678

<210> SEQ ID NO 30
<211> LENGTH: 9823
<212> TYPE: DNA
<213> ORGANISM: Artificial Sequence
<220> FEATURE:
<223> OTHER INFORMATION: SYNHSPB'3-CRE circuit

<400> SEQUENCE: 30
ccggagctga atgaagccat accaaacgac gagcgtgaca ccacgatgcc tgtagcaatg 60
gcaacaacgt tgcgcaaact attaactggc gaactactta ctctagcttc ccggcaacaa 120
ttaatagact ggatggaggc ggataaagtt gcaggaccac ttctgcgctc ggcccttccg 180
gctggctggt ttattgctga taaatctgga gccggtgagc gtgggtctcg cggtatcatt 240
gcagcactgg ggccagatgg taagccctcc cgtatcgtag ttatctacac gacggggagt 300
caggcaacta tggatgaacg aaatagacag atcgctgaga taggtgcctc actgattaag 360
cattggtaac tgtcagacca agtttactca tatatacttt agattgattt aaaacttcat 420
ttttaattta aaaggatcta ggtgaagatc ctttttgata atctcatgac caaaatccct 480
taacgtgagt tttcgttcca ctgagcgtca gaccccgtag aaaagatcaa aggatcttct 540

-continued

```
tgagatcctt tttttctgcg cgtaatctgc tgcttgcaaa caaaaaaacc accgctacca    600
gcggtggttt gtttgccgga tcaagagcta ccaactcttt ttccgaaggt aactggcttc    660
agcagagcgc agataccaaa tactgtcctt ctagtgtagc cgtagttagg ccaccacttc    720
aagaactctg tagcaccgcc tacatacctc gctctgctaa tcctgttacc agtggctgct    780
gccagtggcg ataagtcgtg tcttaccggg ttggactcaa gacgatagtt accggataag    840
gcgcagcggt cgggctgaac ggggggttcg tgcacacagc ccagcttgga gcgaacgacc    900
tacaccgaac tgagatacct acagcgtgag ctatgagaaa gcgccacgct tcccgaaggg    960
agaaaggcgg acaggtatcc ggtaagcggc agggtcggaa caggagagcg cacgagggag   1020
cttccagggg gaaacgcctg gtatctttat agtcctgtcg ggtttcgcca cctctgactt   1080
gagcgtcgat ttttgtgatg ctcgtcaggg gggcggagcc tatggaaaaa cgccagcaac   1140
gcggcctttt tacggttcct ggccttttgc tggccttttg ctcacatgtt ctttcctgcg   1200
ttatcccctg attctgtgga taaccgtatt accgcctttg agtgagctga taccgctcgc   1260
cgcagccgaa cgaccgagcg cagcgagtca gtgagcgagg aagcggaaga gcgcccaata   1320
cgcaaaccgc ctctccccgc gcgttggccg attcattaat gcagctggca cgacaggttt   1380
cccgactgga aagcgggcag tgagcgcaac gcaattaatg tgagttagct cactcattag   1440
gcaccccagg ctttacactt tatgcttccg gctcgtatgt tgtgtggaat tgtgagcgga   1500
taacaatttc acacaggaaa cagctatgac catgattacg ccaagcgcgc aattaaccct   1560
cactaaaggg aacaaaagct ggagctgcaa gcttggccat tgcatacgtt gtatccatat   1620
cataatatgt acatttatat tggctcatgt ccaacattac cgccatgttg acattgatta   1680
ttgactagtt attaatagta atcaattacg gggtcattag ttcatagccc atatatggag   1740
ttccgcgtta cataacttac ggtaaatggc ccgcctggct gaccgcccaa cgacccccgc   1800
ccattgacgt caataatgac gtatgttccc atagtaacgc caatagggac tttccattga   1860
cgtcaatggg tggagtattt acggtaaact gcccacttgg cagtacatca agtgtatcat   1920
atgccaagta cgccccctat tgacgtcaat gacggtaaat ggcccgcctg gcattatgcc   1980
cagtacatga ccttatggga ctttcctact tggcagtaca tctacgtatt agtcatcgct   2040
attaccatgg tgatgcggtt ttggcagtac atcaatgggc gtggatagcg gtttgactca   2100
cggggatttc caagtctcca ccccattgac gtcaatggga gtttgttttg gcaccaaaat   2160
caacgggact ttccaaaatg tcgtaacaac tccgccccat tgacgcaaat gggcggtagg   2220
cgtgtacggt gggaggtcta tataagcaga gctcgtttag tgaaccgggg tctctctggt   2280
tagaccagat ctgagcctgg gagctctctg gctaactagg gaacccactg cttaagcctc   2340
aataaagctt gccttgagtg cttcaagtag tgtgtgcccg tctgttgtgt gactctggta   2400
actagagatc cctcagaccc ttttagtcag tgtggaaaat ctctagcagt ggcgcccgaa   2460
cagggacttg aaagcgaaag ggaaaccaga ggagctctct cgacgcagga ctcggcttgc   2520
tgaagcgcgc acggcaagag gcgaggggcg gcgactggtg agtacgccaa aaattttgac   2580
tagcggaggc tagaaggaga gagatgggtg cgagagcgtc agtattaagc gggggagaat   2640
tagatcgcga tgggaaaaaa ttcggttaag gccaggggga aagaaaaaat ataaattaaa   2700
acatatagta tgggcaagca gggagctaga acgattcgca gttaatcctg gcctgttaga   2760
aacatcagaa ggctgtagac aaatactggg acagctacaa ccatcccttc agacaggatc   2820
agaagaactt agatcattat ataatacagt agcaaccctc tattgtgtgc atcaaaggat   2880
agagataaaa gacaccaagg aagctttaga caagatagag gaagagcaaa acaaaagtaa   2940
```

-continued

```
gaccaccgca cagcaagcgg ccgctgatct tcagacctgg aggaggagat atgagggaca   3000
attggagaag tgaattatat aaatataaag tagtaaaaat tgaaccatta ggagtagcac   3060
ccaccaaggc aaagagaaga gtggtgcaga gagaaaaaag agcagtggga ataggagctt   3120
tgttccttgg gttcttggga gcagcaggaa gcactatggg cgcagcctca atgacgctga   3180
cggtacaggc cagacaatta ttgtctggta tagtgcagca gcagaacaat ttgctgaggg   3240
ctattgaggc gcaacagcat ctgttgcaac tcacagtctg gggcatcaag cagctccagg   3300
caagaatcct ggctgtggaa agatacctaa aggatcaaca gctcctgggg atttggggtt   3360
gctctggaaa actcatttgc accactgctg tgccttggaa tgctagttgg agtaataaat   3420
ctctggaaca gattggaatc acacgacctg gatggagtgg gacagagaaa ttaacaatta   3480
cacaagctta atacactcct taattgaaga atcgcaaaac cagcaagaaa agaatgaaca   3540
agaattattg gaattagata aatgggcaag tttgtggaat tggtttaaca taacaaattg   3600
gctgtggtat ataaaattat tcataatgat agtaggaggc ttggtaggtt taagaatagt   3660
ttttgctgta ctttctatag tgaatagagt taggcaggga tattcaccat tatcgtttca   3720
gacccacctc ccaaccccga ggggacccga caggcccgaa ggaatagaag aagaaggtgg   3780
agagagagac agagacagat ccattcgatt agtgaacgga tctcgacggt atcgatctcg   3840
acacaaatgg cagtattcat ccacaatttt aaaagaaaag gggggattgg ggggtacagt   3900
gcaggggaaa gaatagtaga cataatagca acagacatac aaactaaaga attacaaaaa   3960
caaattacaa aaattcaaaa ttttcgggtt tattacaggg acagcagaga tccagtttgg   4020
gaattagctt gaccccgatc tgcccgaacc ttctcccggg gtcagcgccg cgccgcgcca   4080
cccggctgca gcagcccggg cgggcgagag gctctcaact gggcgggaag gtgcgggaag   4140
gtgcggaaag gttcgcgaaa gttcgcggcc ggactagagt ggcgagatcc cccgatctgc   4200
ccgaaccttc tcccggggtc agcgccgcgc cgcgccaccc ggctgcagca gcccgggcgg   4260
gcgagaggct ctcaactggg cgggaaggtg cgggaaggtg cggaaaggtt cgcgaaagtt   4320
cgcggcaatt agcttgaccc cgatctgccc gaaccttctc ccggggtcag cgccgcgccg   4380
cgccacccgg ctgcagcagc ccgggcgggc gagaggctct caactgggcg ggaaggtgcg   4440
ggaaggtgcg gaaaggttcg cgaaagttcg cggcggcggg ggtcgggtga ggcgcaaaag   4500
gataaaaagc cggtggaagc ggagctgagc agatccgagc cgggctggct gcagagaaac   4560
cgcagggaga gcctcactgc tgagcgcccc tcgacggcgg agcggcagca gcctccgtgg   4620
cctccagcat ccgacaagaa gcttcagcca tgcccaagaa gaagaggaag gtggcgaatt   4680
tactgacggt accagaattc caaaatttgc ctgcattacc ggtcgatgca acgagtgatg   4740
aggttcgcaa gaacctgatg gacatgttca gggatcgcca ggcgttttct gagcatacct   4800
ggaaaatgct tctgtccgtt tgccggtcgt gggcggcatg gtgcaagttg aataaccgga   4860
aatggtttcc cgcagaacct gaagatgttc gcgattatct tctatatctg caggtaagta   4920
tcaaggttac aagacaggtt taaggagacc aatagaaact gggcttgtcg agacagagaa   4980
gactcttgcg tttctgatag gcacctattg gtcttactga catccacttt gcctttctct   5040
ccacaggcgc gcggtctggc agtaaaaact atccagcaac atttgggcca gctaaacatg   5100
cttcatcgtc ggtccgggct gccacgacca agtgacagca atgctgtttc actggttatg   5160
cggcggatcc gaaaagaaaa cgttgatgcc ggtgaacgtg caaaacaggc tctagcgttc   5220
gaacgcactg atttcgacca ggttcgttca ctcatggaaa atagcgatcg ctgccaggat   5280
```

-continued

```
atacgtaatc tggcatttct ggggattgct tataacaccc tgttacgtat agccgaaatt   5340
gccaggatca gggttaaaga tatctcacgt actgacggtg ggagaatgtt aatccatatt   5400
ggcagaacga aaacgctggt tagcaccgca ggtgtagaga aggcacttag cctgggggta   5460
actaaactgg tcgagcgatg gatttccgtc tctggtgtag ctgatgatcc gaataactac   5520
ctgttttgcc gggtcagaaa aaatggtgtt gccgcgccat ctgccaccag ccagctatca   5580
actcgcgccc tggaagggat ttttgaagca actcatcgat tgatttacgg cgctaaggat   5640
gactctggtc agagatacct ggcctggtct ggacacagtg cccgtgtcgg agccgcgcga   5700
gatatggccc gcgctggagt ttcaataccg gagatcatgc aagctggtgg ctggaccaat   5760
gtaaatattg tcatgaacta tatccgtaac ctggatagtg aaacaggggc aatggtgcgc   5820
ctgctggaag atggcgatta gcgtgctacg agatttcgat cccgagctcg aattgacgga   5880
tcgggagtaa tgtacaacac gtgctacgta cagaattggc tccggtgccc gtcagtgggc   5940
agagcgcaca tcgcccacag tccccgagaa gttgggggga ggggtcggca attgaaccgg   6000
tgcctagaga aggtggcgcg gggtaaactg ggaaagtgat gtcgtgtact ggctccgcct   6060
ttttcccgag ggtgggggag aaccgtatat aagtgcagta gtcgccgtga acgttctttt   6120
tcgcaacggg tttgccgcca gaacacaggt aagtgccgtg tgtggttccc gcgggcctgg   6180
cctctttacg ggttatggcc cttgcgtgcc ttgaattact tccactggct gcagtacgtg   6240
attcttgatc ccgagcttcg ggttggaagt gggtgggaga gttcgaggcc ttgcgcttaa   6300
ggagcccctt cgcctcgtgc ttgagttgag gcctggcctg ggcgctgggg ccgccgcgtg   6360
cgaatctggt ggcaccttcg cgcctgtctc gctgctttcg ataagtctct agccatttaa   6420
aatttttgat gacctgctgc gacgcttttt ttctggcaag atagtcttgt aaatgcgggc   6480
caagatctgc acactggtat ttcggttttt ggggccgcgg gcggcgacgg ggcccgtgcg   6540
tcccagcgca catgttcggc gaggcggggc ctgcgagcgc ggccaccgag aatcggacgg   6600
gggtagtctc aagctggccg gcctgctctg gtgcctggcc tcgcgccgcc gtgtatcgcc   6660
ccgccctggg cggcaaggct ggcccggtcg gcaccagttg cgtgagcgga aagatggccg   6720
cttcccggcc ctgctgcagg gagctcaaaa tggaggacgc ggcgctcggg agagcgggcg   6780
ggtgagtcac ccacacaaag gaaaagggcc tttccgtcct cagccgtcgc ttcatgtgac   6840
tccacggagt accgggcgcc gtccaggcac ctcgattagt tctcgagctt ttggagtacg   6900
tcgtctttag gttgggggga ggggttttat gcgatggagt ttccccacac tgagtgggtg   6960
gagactgaag ttaggccagc ttggcacttg atgtaattct ccttggaatt tgcccttttt   7020
gagtttggat cttggttcat tctcaagcct cagacagtgg ttcaaagttt ttttcttcca   7080
tttcaggtgt cgtgaccggt cgccaccatg gtgtccaagg gcgaggaact gttcaccggc   7140
gtggtgccca tcctggtgga actggatggc gacgtgaacg gccacaagtt ctctgtgcgg   7200
ggagagggcg aaggcgacgc cacaaatggc aagctgaccc tgaagttcat ctgcaccacc   7260
ggcaagctgc ccgtgccttg gcctaccctc gtgaccacac tgtctcacgg cgtgcagtgc   7320
ttcgccagat accccgacca catgaagcag cacgatttct tcaagagcgc catgcccgag   7380
ggctacgtgc aggaacggac catcttcttc aaggacgacg gcacctacaa gaccagagcc   7440
gaagtgaagt tcgagggcga caccctcgtg aaccggatcg agctgaaggg cgtggacttc   7500
aaagaggacg gcaacatcct gggccacaag ctggagtaca acttcaacag ccacaacatc   7560
tacatcatgg ccgtgaagca gaaaaacggc atcaaagtga acttcaagat ccggcacaac   7620
gtggaagatg gcagcgtgca gctggccgac cactaccagc agaacacccc catcggagat   7680
```

-continued

```
ggccccgtgc tgctgcctga tagccactac ctgagcaccc agagcgtgct gagcaaggac   7740
cccaacgaga agcgggacca catggtgctg ctggaatttc ggaccgccgc tggcatcacc   7800
ctgggcatgg atgagctgta caagtgacct ttcatagaag gcggcggtgg tacctttaag   7860
accaatgact tacaaggcag ctgtagatct tagccacttt ttaaaagaaa aggggggact   7920
ggaagggcta attcactccc aacgaagaca agatctgctt tttgcttgta ctgggtctct   7980
ctggttagac cagatctgag cctgggagct ctctggctaa ctagggaacc cactgcttaa   8040
gcctcaataa agcttgcctt gagtgcttca agtagtgtgt gcccgtctgt tgtgtgactc   8100
tggtaactag agatccctca gaccctttta gtcagtgtgg aaaatctcta gcagtagtag   8160
ttcatgtcat cttattattc agtatttata acttgcaaag aaatgaatat cagagagtga   8220
gaggaacttg tttattgcag cttataatgg ttacaaataa agcaatagca tcacaaattt   8280
cacaaataaa gcattttttt cactgcattc tagttgtggt ttgtccaaac tcatcaatgt   8340
atcttatcat gtctggctct agctatcccg cccctaactc cgcccatccc gcccctaact   8400
ccgcccagtt ccgcccattc tccgccccat ggctgactaa ttttttttat ttatgcagag   8460
gccgaggccg cctcggcctc tgagctattc cagaagtagt gaggaggctt ttttggaggc   8520
ctaggctttt gcgtcgagac gtacccaatt cgccctatag tgagtcgtat tacgcgcgct   8580
cactggccgt cgttttacaa cgtcgtgact gggaaaaccc tggcgttacc caacttaatc   8640
gccttgcagc acatccccct ttcgccagct ggcgtaatag cgaagaggcc cgcaccgatc   8700
gcccttccca acagttgcgc agcctgaatg gcgaatggcg cgacgcgccc tgtagcggcg   8760
cattaagcgc ggcgggtgtg gtggttacgc gcagcgtgac cgctacactt gccagcgccc   8820
tagcgcccgc tcctttcgct ttcttccctt cctttctcgc cacgttcgcc ggctttcccc   8880
gtcaagctct aaatcggggg ctccctttag ggttccgatt tagtgcttta cggcacctcg   8940
accccaaaaa acttgattag ggtgatggtt cacgtagtgg gccatcgccc tgatagacgg   9000
tttttcgccc tttgacgttg gagtccacgt tctttaatag tggactcttg ttccaaactg   9060
gaacaacact caaccctatc tcggtctatt cttttgattt ataagggatt ttgccgattt   9120
cggcctattg gttaaaaaat gagctgattt aacaaaaatt taacgcgaat tttaacaaaa   9180
tattaacgtt tacaatttcc caggtggcac ttttcgggga aatgtgcgcg gaacccctat   9240
ttgtttattt ttctaaatac attcaaatat gtatccgctc atgagacaat aaccctgata   9300
aatgcttcaa taatattgaa aaaggaagag tatgagtatt caacatttcc gtgtcgccct   9360
tattcccttt tttgcggcat tttgccttcc tgtttttgct cacccagaaa cgctggtgaa   9420
agtaaaagat gctgaagatc agttgggtgc acgagtgggt tacatcgaac tggatctcaa   9480
cagcggtaag atccttgaga gttttcgccc cgaagaacgt tttccaatga tgagcacttt   9540
taaagttctg ctatgtggcg cggtattatc ccgtattgac gccgggcaag agcaactcgg   9600
tcgccgcata cactattctc agaatgactt ggttgagtac tcaccagtca cagaaaagca   9660
tcttacggat ggcatgacag taagagaatt atgcagtgct gccataacca tgagtgataa   9720
cactgcggcc aacttacttc tgacaacgat cggaggaccg aaggagctaa ccgctttttt   9780
gcacaacatg ggggatcatg taactcgcct tgatcgttgg gaa                     9823
```

<210> SEQ ID NO 31
<211> LENGTH: 9867
<212> TYPE: DNA
<213> ORGANISM: Artificial Sequence
<220> FEATURE:

<223> OTHER INFORMATION: Toggle (mscarlet to CAR)

<400> SEQUENCE: 31

```
ggttcctggc cttttgctgg ccttttgctc acatgttctt tcctgcgtta tcccctgatt      60
ctgtggataa ccgtattacc gcctttgagt gagctgatac cgctcgccgc agccgaacga     120
ccgagcgcag cgagtcagtg agcgaggaag cggaagagcg cccaatacgc aaaccgcctc     180
tccccgcgcg ttggccgatt cattaatgca gctggcacga caggtttccc gactggaaag     240
cgggcagtga gcgcaacgca attaatgtga gttagctcac tcattaggca ccccaggctt     300
tacactttat gcttccggct cgtatgttgt gtggaattgt gagcggataa caatttcaca     360
caggaaacag ctatgaccat gattacgcca agcgcgcaat taaccctcac taaagggaac     420
aaaagctgga gctgcaagct tggccattgc atacgttgta tccatatcat aatatgtaca     480
tttatattgg ctcatgtcca acattaccgc catgttgaca ttgattattg actagttatt     540
aatagtaatc aattacgggg tcattagttc atagcccata tatggagttc cgcgttacat     600
aacttacggt aaatggcccg cctggctgac cgcccaacga cccccgccca ttgacgtcaa     660
taatgacgta tgttcccata gtaacgccaa tagggacttt ccattgacgt caatgggtgg     720
agtatttacg gtaaactgcc cacttggcag tacatcaagt gtatcatatg ccaagtacgc     780
cccctattga cgtcaatgac ggtaaatggc ccgcctggca ttatgcccag tacatgacct     840
tatgggactt tcctacttgg cagtacatct acgtattagt catcgctatt accatggtga     900
tgcggttttg gcagtacatc aatgggcgtg gatagcggtt tgactcacgg ggatttccaa     960
gtctccaccc cattgacgtc aatgggagtt tgttttggca ccaaaatcaa cgggactttc    1020
caaaatgtcg taacaactcc gccccattga cgcaaatggg cggtaggcgt gtacggtggg    1080
aggtctatat aagcagagct cgtttagtga accggggtct ctctggttag accagatctg    1140
agcctgggag ctctctggct aactagggaa cccactgctt aagcctcaat aaagcttgcc    1200
ttgagtgctt caagtagtgt gtgcccgtct gttgtgtgac tctggtaact agagatccct    1260
cagacccttt tagtcagtgt ggaaaatctc tagcagtggc gcccgaacag ggacctgaaa    1320
gcgaaaggga aaccagagga gctctctcga cgcaggactc ggcttgctga agcgcgcacg    1380
gcaagaggcg aggggcggcg actggtgagt acgccaaaaa ttttgactag cggaggctag    1440
aaggagagag atgggtgcga gagcgtcagt attaagcggg ggagaattag atcgcgatgg    1500
gaaaaaattc ggttaaggcc agggggaaag aaaaaatata aattaaaaca tatagtatgg    1560
gcaagcaggg agctagaacg attcgcagtt aatcctggcc tgttagaaac atcagaaggc    1620
tgtagacaaa tactgggaca gctacaacca tcccttcaga caggatcaga agaacttaga    1680
tcattatata atacagtagc aaccctctat tgtgtgcatc aaaggataga gataaaagac    1740
accaaggaag ctttagacaa gatagaggaa gagcaaaaca aaagtaagac caccgcacag    1800
caagcggccg ctgatcttca gacctggagg aggagatatg agggacaatt ggagaagtga    1860
attatataaa tataaagtag taaaaattga accattagga gtagcaccca ccaaggcaaa    1920
gagaagagtg gtgcagagag aaaaaagagc agtgggaata ggagctttgt tccttgggtt    1980
cttgggagca gcaggaagca ctatgggcgc agcctcaatg acgctgacgg tacaggccag    2040
acaattattg tctggtatag tgcagcagca gaacaatttg ctgagggcta ttgaggcgca    2100
acagcatctg ttgcaactca cagtctgggg catcaagcag ctccaggcaa gaatcctggc    2160
tgtggaaaga tacctaaagg atcaacagct cctggggatt tggggttgct ctggaaaact    2220
catttgcacc actgctgtgc cttggaatgc tagttggagt aataaatctc tggaacagat    2280
```

-continued

```
tggaatcaca cgacctggat ggagtgggac agagaaatta acaattacac aagcttaata   2340
cactccttaa ttgaagaatc gcaaaaccag caagaaaaga atgaacaaga attattggaa   2400
ttagataaat gggcaagttt gtggaattgg tttaacataa caaattggct gtggtatata   2460
aaattattca taatgatagt aggaggcttg gtaggtttaa gaatagtttt tgctgtactt   2520
tctatagtga atagagttag gcagggatat tcaccattat cgtttcagac ccacctccca   2580
accccgaggg gacccgacag gcccgaagga atagaagaag aaggtggaga gagagacaga   2640
gacagatcca ttcgattagt gaacggatct cgacggtatc gatctcgaca caaatggcag   2700
tattcatcca caattttaaa agaaaagggg ggattggggg gtacagtgca ggggaaagaa   2760
tagtagacat aatagcaaca gacatacaaa ctaaagaatt acaaaaacaa attacaaaaa   2820
ttcaaaattt tcgggtttat tacagggaca gcagagatcc agtttgggaa ttagcttgaa   2880
agctttgcaa agatggataa agttttaaac agagaggaat ctttgcagct aatggacctt   2940
ctaggtcttg aaaggagtgg gaattggctc cggtgcccgt cagtgggcag agcgcacatc   3000
gcccacagtc cccgagaagt tggggggagg ggtcggcaat tgaaccggtg cctagagaag   3060
gtggcgcggg gtaaactggg aaagtgatgt cgtgtactgg ctccgccttt ttcccgaggg   3120
tgggggagaa ccgtatataa gtgcagtagt cgccgtgaac gttcttttc gcaacgggtt    3180
tgccgccaga acacaggtaa gtgccgtgtg tggttcccgc gggcctggcc tctttacggg   3240
ttatggccct tgcgtgcctt gaattacttc cactggctgc agtacgtgat tcttgatccc   3300
gagcttcggg ttggaagtgg gtgggagagt tcgaggcctt gcgcttaagg agccccttcg   3360
cctcgtgctt gagttgaggc ctggcctggg cgctggggcc gccgcgtgcg aatctggtgg   3420
caccttcgcg cctgtctcgc tgctttcgat aagtctctag ccatttaaaa tttttgatga   3480
cctgctgcga cgcttttttt ctggcaagat agtcttgtaa atgcgggcca agatctgcac   3540
actggtattt cggtttttgg ggccgcgggc ggcgacgggg cccgtgcgtc ccagcgcaca   3600
tgttcggcga ggcggggcct gcgagcgcgg ccaccgagaa tcggacgggg gtagtctcaa   3660
gctggccggc ctgctctggt gcctggcctc gcgccgccgt gtatcgcccc gccctgggcg   3720
gcaaggctgg cccggtcggc accagttgcg tgagcggaaa gatggccgct tcccggccct   3780
gctgcaggga gctcaaaatg gaggacgcgg cgctcgggag agcgggcggg tgagtcaccc   3840
acacaaagga aaagggcctt tccgtcctca gccgtcgctt catgtgactc cacggagtac   3900
cgggcgccgt ccaggcacct cgattagttc tcgagctttt ggagtacgtc gtctttaggt   3960
tggggggagg ggttttatgc gatggagttt ccccacactg agtgggtgga gactgaagtt   4020
aggccagctt ggcacttgat gtaattctcc ttggaatttg ccctttttga gtttggatct   4080
tggttcattc tcaagcctca gacagtggtt caaagttttt ttcttccatt tcaggtgtcg   4140
tgaccggtcg gtaccggatc ctctagagtc gactccggaa taacttcgta taggatactt   4200
tatacgaagt tatgcagaat ggtagctgga ttgtagctgc tattagcaat atgaaacctc   4260
ttaataactt cgtatagcat acattatacg aagttatggc gcgccttatc tagatttagc   4320
caccatggtg agcaagggcg aggcagtgat caaggagttc atgcggttca aggtgcacat   4380
ggagggctcc atgaacggcc acgagttcga gatcgagggc gagggcgagg gccgccccta   4440
cgagggcacc cagaccgcca agctgaaggt gaccaagggt ggccccctgc ccttctcctg   4500
ggacatcctg tcccctcagt tcatgtacgg ctccagggcc ttcatcaagc accccgccga   4560
catccccgac tactataagc agtccttccc cgagggcttc aagtgggagc gcgtgatgaa   4620
```

cttcgaggac ggcggcgccg tgaccgtgac ccaggacacc tccctggagg acggcaccct 4680
gatctacaag gtgaagctcc gcggcaccaa cttccctcct gacggccccg taatgcagaa 4740
gaagacaatg ggctgggaag cgtccaccga gcggttgtac cccgaggacg gcgtgctgaa 4800
gggcgacatt aagatggccc tgcgcctgaa ggacggcggc cgctacctgg cggacttcaa 4860
gaccacctac aaggccaaga agcccgtgca gatgcccggc gcctacaacg tcgaccgcaa 4920
gttggacatc acctcccaca acgaggacta caccgtggtg gaacagtacg aacgctccga 4980
gggccgccac tccaccggcg gcatggacga gctgtataag taattacttg tacagctcgt 5040
ccatgccgag agtgatcccg gcggcggtca cgaactccag caggaccatg tgatctcatc 5100
ttggtggcag agcctgcatg tgcagagcgt cataggtgtc ttttgttgct gtactcagcc 5160
cctggtacag tccgtcgtgg ccttttcctc tccttctttc gcccttcatc ccgatttctg 5220
agtaggcctc agccatcttg tctttctgca gctcattata cagaccttcc tgggggttct 5280
tccgtcttgg tttgccgccc atctcaggat ctctgccccg ccttttgtcc agcacatcgt 5340
attcctcccg tcttcccagg ttcagctcgt tgtacagctg attctgtccc tgctgatagg 5400
ctggggcatc tgcgcttcgg gagaacttca cgcttcgata agcggcgaaa tctctgggag 5460
gggcgtatgg ctggtagtgc tttctggttg ggccaggcct tctaggggtc atgttcatgt 5520
agtcggaatg cccaccgcga gacctcttgc tccgcaccca gaagataatg aaggcgacag 5580
tcaccagcag gctataacag gccagcaccc ctccgaccac gaccagcacc cagaagtaga 5640
tatcacaggc aaagtccagt ccccgagtat gcacagctcc cccggcagca gggcgacagg 5700
cttcagggcg cagtgacagg ggctgacttg cgatagttgg agcaggtgta gggggtctgg 5760
gtgctggagt tgtagtactg ctgacggtga cgctagtgcc ctggccccag tagtccatag 5820
cataactccc gccataataa taatgtttgg cgcagtaata gatggcggtg tcgtcggtct 5880
gcagtgagtt catcttcaga aacacctgtg acttgctatt gtccttaatg atggtcagcc 5940
tgctcttcag ggcggaattg tagtaagttg tctcagatcc ccaaatcacg ccgagccact 6000
ccaggccctt gcgtggaggt tgccgaatcc aacttacccc gtagtcagga agagacactc 6060
cactcactgt acaggttaca ctcagggact gacttggggc taccagcccg gggccacttt 6120
cctgcagctt cacttctgat cctccaccgc cgctgccgcc gccaccagaa cccccgccgc 6180
cagttatttc gagtttagtc ccgcccccga atgtgtaggg caatgtgttg ccttgctgac 6240
agaaatacgt tgcaatgtcc tcctgttcca agttgctaat ggtcagggaa taatctgtac 6300
cggaaccgga gccactgaat cggcttggaa ccccggaatg gagcctagaa gtatgatata 6360
tcaggagttt cacagtacca tcgggcttct gctggtacca attcaggtac ttggaaatgt 6420
cctggctggc ccggcagctg atagtcaccc tgtcccccag gctcgcactg aggctgcttg 6480
tggtctgagt catctgaatg tcagcgtaat ctggaacatc gtatgggtaa ggccgagcgg 6540
cgtgcagcag cagagccaga ggcagcagca gggcggtcac aggcagagcc atggtgaccg 6600
gtagcgctag cataacttcg tataaagtat cctatacgaa gttatttgcc ttaacccaga 6660
aattatcact gttattcttt agaatggtgc aaagaataac ttcgtataat gtatgctata 6720
cgaagttatg aattcgatat caagcttatc gataatcaac ctccaaggca gctgtagatc 6780
ttagccactt tttaaaagaa aaggggggac tggaagggct aattcactcc caacgaagac 6840
aagatctgct tttgcttgt actgggtctc tctggttaga ccagatctga gcctgggagc 6900
tctctggcta actagggaac ccactgctta agcctcaata aagcttgcct tgagtgcttc 6960
aagtagtgtg tgcccgtctg ttgtgtgact ctggtaacta gagatccctc agaccctttt 7020

-continued agtcagtgtg gaaaatctct agcagtagta gttcatgtca tcttattatt cagtatttat 7080
aacttgcaaa gaaatgaata tcagagagtg agaggaactt gtttattgca gcttataatg 7140
gttacaaata aagcaatagc atcacaaatt tcacaaataa agcatttttt tcactgcatt 7200
ctagttgtgg tttgtccaaa ctcatcaatg tatcttatca tgtctggctc tagctatccc 7260
gcccctaact ccgcccatcc cgcccctaac tccgcccagt tccgcccatt ctccgcccca 7320
tggctgacta attttttta tttatgcaga ggccgaggcc gcctcggcct ctgagctatt 7380
ccagaagtag tgaggaggct tttttggagg cctaggcttt tgcgtcgaga cgtacccaat 7440
tcgccctata gtgagtcgta ttacgcgcgc tcactggccg tcgttttaca acgtcgtgac 7500
tgggaaaacc ctggcgttac ccaacttaat cgccttgcag cacatccccc tttcgccagc 7560
tggcgtaata gcgaagaggc ccgcaccgat cgcccttccc aacagttgcg cagcctgaat 7620
ggcgaatggc gcgacgcgcc ctgtagcggc gcattaagcg cggcgggtgt ggtggttacg 7680
cgcagcgtga ccgctacact tgccagcgcc ctagcgcccg ctcctttcgc tttcttccct 7740
tcctttctcg ccacgttcgc cggctttccc cgtcaagctc taaatcgggg gctcccttta 7800
gggttccgat ttagtgcttt acggcacctc gaccccaaaa aacttgatta gggtgatggt 7860
tcacgtagtg ggccatcgcc ctgatagacg gtttttcgcc ctttgacgtt ggagtccacg 7920
ttctttaata gtggactctt gttccaaact ggaacaacac tcaaccctat ctcggtctat 7980
tcttttgatt tataagggat tttgccgatt tcggcctatt ggttaaaaaa tgagctgatt 8040
taacaaaaat ttaacgcgaa ttttaacaaa atattaacgt ttacaatttc ccaggtggca 8100
cttttcgggg aaatgtgcgc ggaaccccta tttgtttatt tttctaaata cattcaaata 8160
tgtatccgct catgagacaa taaccctgat aaatgcttca ataatattga aaaaggaaga 8220
gtatgagtat tcaacatttc cgtgtcgccc ttattccctt ttttgcggca ttttgccttc 8280
ctgtttttgc tcacccagaa acgctggtga aagtaaaaga tgctgaagat cagttgggtg 8340
cacgagtggg ttacatcgaa ctggatctca acagcggtaa gatccttgag agttttcgcc 8400
ccgaagaacg ttttccaatg atgagcactt ttaaagttct gctatgtggc gcggtattat 8460
cccgtattga cgccgggcaa gagcaactcg gtcgccgcat acactattct cagaatgact 8520
tggttgagta ctcaccagtc acagaaaagc atcttacgga tggcatgaca gtaagagaat 8580
tatgcagtgc tgccataacc atgagtgata acactgcggc caacttactt ctgacaacga 8640
tcggaggacc gaaggagcta accgcttttt tgcacaacat gggggatcat gtaactcgcc 8700
ttgatcgttg ggaaccggag ctgaatgaag ccataccaaa cgacgagcgt gacaccacga 8760
tgcctgtagc aatggcaaca acgttgcgca aactattaac tggcgaacta cttactctag 8820
cttcccggca acaattaata gactggatgg aggcggataa agttgcagga ccacttctgc 8880
gctcggccct tccggctggc tggtttattg ctgataaatc tggagccggt gagcgtgggt 8940
ctcgcggtat cattgcagca ctggggccag atggtaagcc ctcccgtatc gtagttatct 9000
acacgacggg gagtcaggca actatggatg aacgaaatag acagatcgct gagataggtg 9060
cctcactgat taagcattgg taactgtcag accaagttta ctcatatata ctttagattg 9120
atttaaaact tcatttttaa tttaaaagga tctaggtgaa gatccttttt gataatctca 9180
tgaccaaaat cccttaacgt gagttttcgt tccactgagc gtcagacccc gtagaaaaga 9240
tcaaaggatc ttcttgagat cctttttttc tgcgcgtaat ctgctgcttg caaacaaaaa 9300
aaccaccgct accagcggtg gtttgtttgc cggatcaaga gctaccaact ctttttccga 9360

-continued

```
aggtaactgg cttcagcaga gcgcagatac caaatactgt ccttctagtg tagccgtagt   9420

taggccacca cttcaagaac tctgtagcac cgcctacata cctcgctctg ctaatcctgt   9480

taccagtggc tgctgccagt ggcgataagt cgtgtcttac cgggttggac tcaagacgat   9540

agttaccgga taaggcgcag cggtcgggct gaacgggggg ttcgtgcaca cagcccagct   9600

tggagcgaac gacctacacc gaactgagat acctacagcg tgagctatga gaaagcgcca   9660

cgcttcccga agggagaaag gcggacaggt atccggtaag cggcagggtc ggaacaggag   9720

agcgcacgag ggagcttcca gggggaaacg cctggtatct ttatagtcct gtcgggtttc   9780

gccacctctg acttgagcgt cgatttttgt gatgctcgtc aggggggcgg agcctatgga   9840

aaaacgccag caacgcggcc tttttac                                       9867
```

<210> SEQ ID NO 32
<211> LENGTH: 10091
<212> TYPE: DNA
<213> ORGANISM: Artificial Sequence
<220> FEATURE:
<223> OTHER INFORMATION: EF1a-aCD19

<400> SEQUENCE: 32

```
ggttcctggc cttttgctgg ccttttgctc acatgttctt tcctgcgtta tcccctgatt     60

ctgtggataa ccgtattacc gcctttgagt gagctgatac cgctcgccgc agccgaacga    120

ccgagcgcag cgagtcagtg agcgaggaag cggaagagcg cccaatacgc aaaccgcctc    180

tccccgcgcg ttggccgatt cattaatgca gctggcacga caggtttccc gactggaaag    240

cgggcagtga gcgcaacgca attaatgtga gttagctcac tcattaggca ccccaggctt    300

tacactttat gcttccggct cgtatgttgt gtggaattgt gagcggataa caatttcaca    360

caggaaacag ctatgaccat gattacgcca agcgcgcaat taaccctcac taaagggaac    420

aaaagctgga gctgcaagct tggccattgc atacgttgta tccatatcat aatatgtaca    480

tttatattgg ctcatgtcca acattaccgc catgttgaca ttgattattg actagttatt    540

aatagtaatc aattacgggg tcattagttc atagcccata tatggagttc cgcgttacat    600

aacttacggt aaatggcccg cctggctgac cgcccaacga cccccgccca ttgacgtcaa    660

taatgacgta tgttcccata gtaacgccaa tagggacttt ccattgacgt caatgggtgg    720

agtatttacg gtaaactgcc cacttggcag tacatcaagt gtatcatatg ccaagtacgc    780

cccctattga cgtcaatgac ggtaaatggc ccgcctggca ttatgcccag tacatgacct    840

tatgggactt tcctacttgg cagtacatct acgtattagt catcgctatt accatggtga    900

tgcggttttg gcagtacatc aatgggcgtg gatagcggtt tgactcacgg ggatttccaa    960

gtctccaccc cattgacgtc aatgggagtt tgttttggca ccaaaatcaa cgggactttc   1020

caaaatgtcg taacaactcc gccccattga cgcaaatggg cggtaggcgt gtacggtggg   1080

aggtctatat aagcagagct cgtttagtga accggggtct ctctggttag accagatctg   1140

agcctgggag ctctctggct aactagggaa cccactgctt aagcctcaat aaagcttgcc   1200

ttgagtgctt caagtagtgt gtgcccgtct gttgtgtgac tctggtaact agagatccct   1260

cagacccttt tagtcagtgt ggaaaatctc tagcagtggc gcccgaacag ggacctgaaa   1320

gcgaaaggga aaccagagga gctctctcga cgcaggactc ggcttgctga agcgcgcacg   1380

gcaagaggcg aggggcggcg actggtgagt acgccaaaaa ttttgactag cggaggctag   1440

aaggagagag atgggtgcga gagcgtcagt attaagcggg ggagaattag atcgcgatgg   1500

gaaaaaattc ggttaaggcc agggggaaag aaaaaatata aattaaaaca tatagtatgg   1560
```

-continued

```
gcaagcaggg agctagaacg attcgcagtt aatcctggcc tgttagaaac atcagaaggc   1620
tgtagacaaa tactgggaca gctacaacca tcccttcaga caggatcaga agaacttaga   1680
tcattatata atacagtagc aaccctctat tgtgtgcatc aaaggataga gataaaagac   1740
accaaggaag ctttagacaa gatagaggaa gagcaaaaca aaagtaagac caccgcacag   1800
caagcggccg ctgatcttca gacctggagg aggagatatg agggacaatt ggagaagtga   1860
attatataaa tataaagtag taaaaattga accattagga gtagcaccca ccaaggcaaa   1920
gagaagagtg gtgcagagag aaaaaagagc agtgggaata ggagctttgt tccttgggtt   1980
cttgggagca gcaggaagca ctatgggcgc agcctcaatg acgctgacgg tacaggccag   2040
acaattattg tctggtatag tgcagcagca gaacaatttg ctgagggcta ttgaggcgca   2100
acagcatctg ttgcaactca cagtctgggg catcaagcag ctccaggcaa gaatcctggc   2160
tgtggaaaga tacctaaagg atcaacagct cctggggatt tggggttgct ctggaaaact   2220
catttgcacc actgctgtgc cttggaatgc tagttggagt aataaatctc tggaacagat   2280
tggaatcaca cgacctggat ggagtgggac agagaaatta acaattacac aagcttaata   2340
cactccttaa ttgaagaatc gcaaaaccag caagaaaaga atgaacaaga attattggaa   2400
ttagataaat gggcaagttt gtggaattgg tttaacataa caaattggct gtggtatata   2460
aaattattca taatgatagt aggaggcttg gtaggtttaa gaatagtttt tgctgtactt   2520
tctatagtga atagagttag gcagggatat tcaccattat cgtttcagac ccacctccca   2580
accccgaggg gacccgacag gcccgaagga atagaagaag aaggtggaga gagagacaga   2640
gacagatcca ttcgattagt gaacggatct cgacggtatc gatctcgaca caaatggcag   2700
tattcatcca caattttaaa agaaaagggg ggattggggg gtacagtgca ggggaaagaa   2760
tagtagacat aatagcaaca gacatacaaa ctaaagaatt acaaaaacaa attacaaaaa   2820
ttcaaaattt tcgggtttat tacagggaca gcagagatcc agtttgggaa ttagcttgaa   2880
agctttgcaa agatggataa agttttaaac agagaggaat ctttgcagct aatggacctt   2940
ctaggtcttg aaaggagtgg gaattggctc cggtgcccgt cagtgggcag agcgcacatc   3000
gcccacagtc cccgagaagt tgggggggagg ggtcggcaat tgaaccggtg cctagagaag   3060
gtggcgcggg gtaaactggg aaagtgatgt cgtgtactgg ctccgccttt ttcccgaggg   3120
tgggggagaa ccgtatataa gtgcagtagt cgccgtgaac gttctttttc gcaacgggtt   3180
tgccgccaga acacaggtaa gtgccgtgtg tggttcccgc gggcctggcc tctttacggg   3240
ttatggccct tgcgtgcctt gaattacttc cactggctgc agtacgtgat tcttgatccc   3300
gagcttcggg ttggaagtgg gtgggagagt tcgaggcctt gcgcttaagg agccccttcg   3360
cctcgtgctt gagttgaggc ctggcctggg cgctggggcc gccgcgtgcg aatctggtgg   3420
caccttcgcg cctgtctcgc tgctttcgat aagtctctag ccatttaaaa tttttgatga   3480
cctgctgcga cgcttttttt ctggcaagat agtcttgtaa atgcgggcca agatctgcac   3540
actggtattt cggtttttgg ggccgcgggc ggcgacgggg cccgtgcgtc ccagcgcaca   3600
tgttcggcga ggcggggcct gcgagcgcgg ccaccgagaa tcggacgggg gtagtctcaa   3660
gctggccggc ctgctctggt gcctggcctc gcgccgccgt gtatcgcccc gccctgggcg   3720
gcaaggctgg cccggtcggc accagttgcg tgagcggaaa gatggccgct tcccggccct   3780
gctgcaggga gctcaaaatg gaggacgcgg cgctcgggag agcgggcggg tgagtcaccc   3840
acacaaagga aaagggcctt tccgtcctca gccgtcgctt catgtgactc cacggagtac   3900
```

-continued

```
cgggcgccgt ccaggcacct cgattagttc tcgagctttt ggagtacgtc gtctttaggt   3960
tggggggagg ggttttatgc gatggagttt ccccacactg agtgggtgga gactgaagtt   4020
aggccagctt ggcacttgat gtaattctcc ttggaatttg ccctttttga gtttggatct   4080
tggttcattc tcaagcctca gacagtggtt caaagttttt ttcttccatt tcaggtgtcg   4140
tgaccggtcg ccaccatggc tctgcctgtg accgccctgc tgctgcctct ggctctgctg   4200
ctgcacgccg ctcggcctta cccatacgat gttccagatt acgctgacat tcagatgact   4260
cagaccacaa gcagcctcag tgcgagcctg gggggacaggg tgactatcag ctgccgggcc   4320
agccaggaca tttccaagta cctgaattgg taccagcaga agcccgatgg tactgtgaaa   4380
ctcctgatat atcatacttc taggctccat tccggggttc caagccgatt cagtggctcc   4440
ggttccggta cagattattc cctgaccatt agcaacttgg aacaggagga cattgcaacg   4500
tatttctgtc agcaaggcaa cacattgccc tacacattcg gggcgggac taaactcgaa   4560
ataactggcg gcgggggttc tggtggcggc ggcagcggcg gtggaggatc agaagtgaag   4620
ctgcaggaaa gtggccccgg gctggtagcc ccaagtcagt ccctgagtgt aacctgtaca   4680
gtgagtggag tgtctcttcc tgactacggg gtaagttgga ttcggcaacc tccacgcaag   4740
ggcctggagt ggctcggcgt gatttgggga tctgagacaa cttactacaa ttccgccctg   4800
aagagcaggc tgaccatcat taaggacaat agcaagtcac aggtgtttct gaagatgaac   4860
tcactgcaga ccgacgacac cgccatctat tactgcgcca aacattatta ttatggcggg   4920
agttatgcta tggactactg gggccagggc actagcgtca ccgtcagcag tactacaact   4980
ccagcaccca gaccccctac acctgctcca actatcgcaa gtcagcccct gtcactgcgc   5040
cctgaagcct gtcgccctgc tgccggggga gctgtgcata ctcggggact ggactttgcc   5100
tgtgatatct acttctgggt gctggtcgtg gtcggagggg tgctggcctg ttatagcctg   5160
ctggtgactg tcgccttcat tatcttctgg gtgcggagca agaggtctcg cggtgggcat   5220
tccgactaca tgaacatgac ccctagaagg cctggcccaa ccagaaagca ctaccagcca   5280
tacgcccctc ccagagattt cgccgcttat cgaagcgtga agttctcccg aagcgcagat   5340
gccccagcct atcagcaggg acagaatcag ctgtacaacg agctgaacct gggaagacgg   5400
gaggaatacg atgtgctgga caaaaggcgg ggcagagatc ctgagatggg cggcaaacca   5460
agacggaaga acccccagga aggtctgtat aatgagctgc agaaagacaa gatggctgag   5520
gcctactcag aaatcgggat gaagggcgaa agaaggagag gaaaaggcca cgacggactg   5580
taccagggc tgagtacagc aacaaaagac acctatgacg ctctgcacat gcaggctctg   5640
ccaccaagat gactgtatat ggtgatggcc cctctccctc cccccccct aacgttactg   5700
gccgaagccg cttggaataa ggccggtgtg cgtttgtcta tatgttattt tccaccatat   5760
tgccgtcttt tggcaatgtg agggcccgga aacctggccc tgtcttcttg acgagcattc   5820
ctaggggtct ttcccctctc gccaaaggaa tgcaaggtct gttgaatgtc gtgaaggaag   5880
cagttcctct ggaagcttct tgaagacaaa caacgtctgt agcgaccctt tgcaggcagc   5940
ggaaccccc acctggcgac aggtgcctct gcggccaaaa gccacgtgta taagatacac   6000
ctgcaaaggc ggcacaaccc cagtgccacg ttgtgagttg gatagttgtg gaaagagtca   6060
aatggctctc ctcaagcgta ttcaacaagg ggctgaagga tgcccagaag gtaccccatt   6120
gtatgggatc tgatctgggg cctcggtgca catgctttac atgtgtttag tcgaggttaa   6180
aaaaacgtct aggccccccg aaccacgggg acgtggtttt cctttgaaaa acacgatgat   6240
aatatggtga gcaagggcga ggcagtgatc aaggagttca tgcggttcaa ggtgcacatg   6300
```

gagggctcca tgaacggcca cgagttcgag atcgagggcg agggcgaggg ccgcccctac 6360
gagggcaccc agaccgccaa gctgaaggtg accaagggtg gccccctgcc cttctcctgg 6420
gacatcctgt cccctcagtt catgtacggc tccagggcct tcatcaagca ccccgccgac 6480
atccccgact actataagca gtccttcccc gagggcttca agtgggagcg cgtgatgaac 6540
ttcgaggacg gcggcgccgt gaccgtgacc caggacacct ccctggagga cggcaccctg 6600
atctacaagg tgaagctccg cggcaccaac ttccctcctg acggccccgt aatgcagaag 6660
aagacaatgg gctgggaagc gtccaccgag cggttgtacc ccgaggacgg cgtgctgaag 6720
ggcgacatta agatggccct gcgcctgaag gacggcggcc gctacctggc ggacttcaag 6780
accacctaca aggccaagaa gcccgtgcag atgcccggcg cctacaacgt cgaccgcaag 6840
ttggacatca cctcccacaa cgaggactac accgtggtgg aacagtacga acgctccgag 6900
ggccgccact ccaccggcgg catggacgag ctgtataagt aacctttcat agaaggcggc 6960
ggtggtacct ttaagaccaa tgacttacaa ggcagctgta gatcttagcc actttttaaa 7020
agaaaagggg ggactggaag ggctaattca ctcccaacga agacaagatc tgctttttgc 7080
ttgtactggg tctctctggt tagaccagat ctgagcctgg gagctctctg gctaactagg 7140
gaacccactg cttaagcctc aataaagctt gccttgagtg cttcaagtag tgtgtgcccg 7200
tctgttgtgt gactctggta actagagatc cctcagaccc ttttagtcag tgtggaaaat 7260
ctctagcagt agtagttcat gtcatcttat tattcagtat ttataacttg caaagaaatg 7320
aatatcagag agtgagagga acttgtttat tgcagcttat aatggttaca aataaagcaa 7380
tagcatcaca aatttcacaa ataaagcatt tttttcactg cattctagtt gtggtttgtc 7440
caaactcatc aatgtatctt atcatgtctg gctctagcta tcccgcccct aactccgccc 7500
atcccgcccc taactccgcc cagttccgcc cattctccgc cccatggctg actaattttt 7560
tttatttatg cagaggccga ggccgcctcg gcctctgagc tattccagaa gtagtgagga 7620
ggcttttttg gaggcctagg cttttgcgtc gagacgtacc caattcgccc tatagtgagt 7680
cgtattacgc gcgctcactg gccgtcgttt tacaacgtcg tgactgggaa aaccctggcg 7740
ttacccaact taatcgcctt gcagcacatc ccccctttcgc cagctggcgt aatagcgaag 7800
aggcccgcac cgatcgccct tcccaacagt tgcgcagcct gaatggcgaa tggcgcgacg 7860
cgccctgtag cggcgcatta agcgcggcgg gtgtggtggt tacgcgcagc gtgaccgcta 7920
cacttgccag cgccctagcg cccgctcctt tcgctttctt cccttccttt ctcgccacgt 7980
tcgccggctt tccccgtcaa gctctaaatc gggggctccc tttagggttc cgatttagtg 8040
ctttacggca cctcgacccc aaaaaacttg attagggtga tggttcacgt agtgggccat 8100
cgccctgata gacggttttt cgccctttga cgttggagtc cacgttcttt aatagtggac 8160
tcttgttcca aactggaaca acactcaacc ctatctcggt ctattctttt gatttataag 8220
ggattttgcc gatttcggcc tattggttaa aaaatgagct gatttaacaa aaatttaacg 8280
cgaattttaa caaaatatta acgtttacaa tttcccaggt ggcacttttc ggggaaatgt 8340
gcgcggaacc cctatttgtt tatttttcta aatacattca aatatgtatc cgctcatgag 8400
acaataaccc tgataaatgc ttcaataata ttgaaaaagg aagagtatga gtattcaaca 8460
tttccgtgtc gcccttattc ccttttttgc ggcattttgc cttcctgttt ttgctcaccc 8520
agaaacgctg gtgaaagtaa aagatgctga agatcagttg ggtgcacgag tgggttacat 8580
cgaactggat ctcaacagcg gtaagatcct tgagagtttt cgccccgaag aacgttttcc 8640

-continued aatgatgagc acttttaaag ttctgctatg tggcgcggta ttatcccgta ttgacgccgg 8700
gcaagagcaa ctcggtcgcc gcatacacta ttctcagaat gacttggttg agtactcacc 8760
agtcacagaa aagcatctta cggatggcat gacagtaaga gaattatgca gtgctgccat 8820
aaccatgagt gataacactg cggccaactt acttctgaca acgatcggag gaccgaagga 8880
gctaaccgct tttttgcaca acatggggga tcatgtaact cgccttgatc gttgggaacc 8940
ggagctgaat gaagccatac caaacgacga gcgtgacacc acgatgcctg tagcaatggc 9000
aacaacgttg cgcaaactat taactggcga actacttact ctagcttccc ggcaacaatt 9060
aatagactgg atggaggcgg ataaagttgc aggaccactt ctgcgctcgg cccttccggc 9120
tggctggttt attgctgata aatctggagc cggtgagcgt gggtctcgcg gtatcattgc 9180
agcactgggg ccagatggta agccctcccg tatcgtagtt atctacacga cggggagtca 9240
ggcaactatg gatgaacgaa atagacagat cgctgagata ggtgcctcac tgattaagca 9300
ttggtaactg tcagaccaag tttactcata tatactttag attgatttaa aacttcattt 9360
ttaatttaaa aggatctagg tgaagatcct ttttgataat ctcatgacca aaatccctta 9420
acgtgagttt tcgttccact gagcgtcaga ccccgtagaa aagatcaaag gatcttcttg 9480
agatcctttt tttctgcgcg taatctgctg cttgcaaaca aaaaaaccac cgctaccagc 9540
ggtggtttgt ttgccggatc aagagctacc aactcttttt ccgaaggtaa ctggcttcag 9600
cagagcgcag ataccaaata ctgtccttct agtgtagccg tagttaggcc accacttcaa 9660
gaactctgta gcaccgccta catacctcgc tctgctaatc ctgttaccag tggctgctgc 9720
cagtggcgat aagtcgtgtc ttaccgggtt ggactcaaga cgatagttac cggataaggc 9780
gcagcggtcg ggctgaacgg ggggttcgtg cacacagccc agcttggagc gaacgaccta 9840
caccgaactg agatacctac agcgtgagct atgagaaagc gccacgcttc ccgaagggag 9900
aaaggcggac aggtatccgg taagcggcag ggtcggaaca ggagagcgca cgagggagct 9960
tccaggggga aacgcctggt atctttatag tcctgtcggg tttcgccacc tctgacttga 10020
gcgtcgattt ttgtgatgct cgtcaggggg gcggagccta tggaaaaacg ccagcaacgc 10080
ggccttttta c 10091

<210> SEQ ID NO 33
<211> LENGTH: 8674
<212> TYPE: DNA
<213> ORGANISM: Artificial Sequence
<220> FEATURE:
<223> OTHER INFORMATION: HSPB-Feednack-IL-21

<400> SEQUENCE: 33
ttgagatcct ttttttctgc gcgtaatctg ctgcttgcaa acaaaaaaac caccgctacc 60
agcggtggtt tgtttgccgg atcaagagct accaactctt tttccgaagg taactggctt 120
cagcagagcg cagataccaa atactgttct tctagtgtag ccgtagttag gccaccactt 180
caagaactct gtagcaccgc ctacatacct cgctctgcta atcctgttac cagtggctgc 240
tgccagtggc gataagtcgt gtcttaccgg gttggactca agacgatagt taccggataa 300
ggcgcagcgg tcgggctgaa cggggggttc gtgcacacag cccagcttgg agcgaacgac 360
ctacaccgaa ctgagatacc tacagcgtga gctatgagaa agcgccacgc ttcccgaagg 420
gagaaaggcg gacaggtatc cggtaagcgg cagggtcgga acaggagagc gcacgaggga 480
gcttccaggg ggaaacgcct ggtatcttta tagtcctgtc gggtttcgcc acctctgact 540
tgagcgtcga tttttgtgat gctcgtcagg ggggcggagc ctatggaaaa acgccagcaa 600

-continued

```
cgcggccttt ttacggttcc tggccttttg ctggcctttt gctcacatgt tctttcctgc    660
gttatcccct gattctgtgg ataaccgtat taccgccttt gagtgagctg ataccgctcg    720
ccgcagccga acgaccgagc gcagcgagtc agtgagcgag gaagcggaag agcgcccaat    780
acgcaaaccg cctctccccg cgcgttggcc gattcattaa tgcagctggc acgacaggtt    840
tcccgactgg aaagcgggca gtgagcgcaa cgcaattaat gtgagttagc tcactcatta    900
ggcaccccag gctttacact ttatgcttcc ggctcgtatg ttgtgtggaa ttgtgagcgg    960
ataacaattt cacacaggaa acagctatga ccatgattac gccaagcgcg caattaaccc   1020
tcactaaagg gaacaaaagc tggagctgca agcttggcca ttgcatacgt tgtatccata   1080
tcataatatg tacatttata ttggctcatg tccaacatta ccgccatgtt gacattgatt   1140
attgactagt tattaatagt aatcaattac ggggtcatta gttcatagcc catatatgga   1200
gttccgcgtt acataactta cggtaaatgg cccgcctggc tgaccgccca acgacccccg   1260
cccattgacg tcaataatga cgtatgttcc catagtaacg ccaataggga ctttccattg   1320
acgtcaatgg gtggagtatt tacggtaaac tgcccacttg gcagtacatc aagtgtatca   1380
tatgccaagt acgcccccta ttgacgtcaa tgacggtaaa tggcccgcct ggcattatgc   1440
ccagtacatg accttatggg actttcctac ttggcagtac atctacgtat tagtcatcgc   1500
tattaccatg gtgatgcggt tttggcagta catcaatggg cgtggatagc ggtttgactc   1560
acggggattt ccaagtctcc accccattga cgtcaatggg agtttgtttt ggcaccaaaa   1620
tcaacgggac tttccaaaat gtcgtaacaa ctccgcccca ttgacgcaaa tgggcggtag   1680
gcgtgtacgg tgggaggtct atataagcag agctcgttta gtgaaccggg gtctctctgg   1740
ttagaccaga tctgagcctg ggagctctct ggctaactag ggaacccact gcttaagcct   1800
caataaagct tgccttgagt gcttcaagta gtgtgtgccc gtctgttgtg tgactctggt   1860
aactagagat ccctcagacc cttttagtca gtgtggaaaa tctctagcag tggcgcccga   1920
acagggactt gaaagcgaaa gggaaaccag aggagctctc tcgacgcagg actcggcttg   1980
ctgaagcgcg cacggcaaga ggcgaggggc ggcgactggt gagtacgcca aaaattttga   2040
ctagcggagg ctagaaggag agagatgggt gcgagagcgt cagtattaag cgggggagaa   2100
ttagatcgcg atgggaaaaa attcggttaa ggccaggggg aaagaaaaaa tataaattaa   2160
aacatatagt atgggcaagc agggagctag aacgattcgc agttaatcct ggcctgttag   2220
aaacatcaga aggctgtaga caaatactgg gacagctaca accatccctt cagacaggat   2280
cagaagaact tagatcatta tataatacag tagcaaccct ctattgtgtg catcaaagga   2340
tagagataaa agacaccaag gaagctttag acaagataga ggaagagcaa aacaaaagta   2400
agaccaccgc acagcaagcg gccgctgatc ttcagacctg gaggaggaga tatgagggac   2460
aattggagaa gtgaattata taaatataaa gtagtaaaaa ttgaaccatt aggagtagca   2520
cccaccaagg caaagagaag agtggtgcag agagaaaaaa gagcagtggg aataggagct   2580
ttgttccttg ggttcttggg agcagcagga agcactatgg gcgcagcctc aatgacgctg   2640
acggtacagg ccagacaatt attgtctggt atagtgcagc agcagaacaa tttgctgagg   2700
gctattgagg cgcaacagca tctgttgcaa ctcacagtct ggggcatcaa gcagctccag   2760
gcaagaatcc tggctgtgga aagataccta aaggatcaac agctcctggg gatttggggt   2820
tgctctggaa aactcatttg caccactgct gtgccttgga atgctagttg gagtaataaa   2880
tctctggaac agatttggaa tcacacgacc tggatggagt gggacagaga aattaacaat   2940
```

-continued

```
tacacaagct taatacactc cttaattgaa gaatcgcaaa accagcaaga aaagaatgaa   3000
caagaattat tggaattaga taaatgggca agtttgtgga attggtttaa cataacaaat   3060
tggctgtggt atataaaatt attcataatg atagtaggag gcttggtagg tttaagaata   3120
gtttttgctg tactttctat agtgaataga gttaggcagg gatattcacc attatcgttt   3180
cagacccacc tcccaacccc gaggggaccc gacaggcccg aaggaataga agaagaaggt   3240
ggagagagag acagagacag atccattcga ttagtgaacg gatctcgacg gtatcgatct   3300
cgacacaaat ggcagtattc atccacaatt ttaaaagaaa aggggggatt ggggggtaca   3360
gtgcagggga aagaatagta gacataatag caacagacat acaaactaaa gaattacaaa   3420
aacaaattac aaaaattcaa aattttcggg tttattacag ggacagcaga gatccagttt   3480
gggacggccc tttcgtcttc actcgagttt actccctatc agtgatagag aacgtatgaa   3540
gagtttactc cctatcagtg atagagaacg tatgcagact ttactcccta tcagtgatag   3600
agaacgtata aggagtttac tccctatcag tgatagagaa cgtatgacca gtttactccc   3660
tatcagtgat agagaacgta tctacagttt actccctatc agtgatagag aacgtatatc   3720
cagtttactc cctatcagtg atagagaacg tatgtcgagg taggcgtgta cggtgggcgc   3780
ctataaaagc agagctcgtt tagtgaaccg tcagatcgcc tggagcaatt ccacaacact   3840
tttgtcttat acttactagg agctcggatc caggaggatc ctccacagcc ccggggagac   3900
cttgcctcta aagttgctgc ttttgcagct ctgccacaac cgcgcgtcct cagagccagc   3960
cgggaggagc tagaaccttc cccgcgtttc tttcagcagc cctgagtcag aggcgggctg   4020
gccttgcaag tagccgccca gccttcttcg gtctcacgga ccgatccgcc cgaaccttct   4080
cccggggtca gcgccgcgct gcgccgcccg gctgactcag cccgggcggg cgggcgggag   4140
gctctcgact gggcgggaag gtgcgggaag gttcgcggcg gcggggtcgg ggaggtgcaa   4200
aaggatgaaa agcccgtgga cggagctgag cagatccggc cgggctggcg gcagagaaac   4260
cgcagggaga gcctcactgc tgagcgcccc tcgacgcggg cggcagcagc ctccgtggcc   4320
tccagcatcc gacaagaagc ttcacggatg tctagactgg acaagagcaa agtcataaac   4380
tctgctctgg aattactcaa tggagtcggt atcgaaggcc tgacgacaag gaaactcgct   4440
caaaagctgg gagttgagca gcctaccctg tactggcacg tgaagaacaa gcgggccctg   4500
ctcgatgccc tgccaatcga gatgctggac aggcatcata cccactcctg cccccctggaa   4560
ggcgagtcat ggcaagactt tctgcggaac aacgccaagt cataccgctg tgctctcctc   4620
tcacatcgcg acggggctaa agtgcatctc ggcacccgcc caacagagaa acagtacgaa   4680
accctggaaa atcagctcgc gttcctgtgt cagcaaggct tctccctgga gaacgcactg   4740
tacgctctgt ccgccgtggg ccactttaca ctgggctgcg tattggagga acaggagcat   4800
caagtagcaa aagaggaaag agagacacct accaccgatt ctatgccccc acttctgaaa   4860
caagcaattg agctgttcga ccggcaggga gccgaacctg ccttcctttt cggcctggaa   4920
ctaatcatat gtggcctgga gaaacagcta aagtgcgaaa gcggcgggcc gaccgacgcc   4980
cttgacgatt ttgacttaga catgctccca gccgatgccc ttgacgactt tgaccttgat   5040
atgctgcctg ctgacgctct tgacgatttt gaccttgaca tgctccccgg gtaagtcccc   5100
ctctccctcc cccccccccta acgttactgg ccgaagccgc ttggaataag gccggtgtgc   5160
gtttgtctat atgttatttt ccaccatatt gccgtctttt ggcaatgtga gggcccggaa   5220
acctggccct gtcttcttga cgagcattcc taggggtctt tcccctctcg ccaaaggaat   5280
gcaaggtctg ttgaatgtcg tgaaggaagc agttcctctg gaagcttctt gaagacaaac   5340
```

```
aacgtctgta gcgacccttt gcaggcagcg gaacccccca cctggcgaca ggtgcctctg   5400
cggccaaaag ccacgtgtat aagatacacc tgcaaaggcg gcacaacccc agtgccacgt   5460
tgtgagttgg atagttgtgg aaagagtcaa atggctctcc tcaagcgtat tcaacaaggg   5520
gctgaaggat gcccagaagg taccccattg tatgggatct gatctggggc ctcggtgcac   5580
atgctttaca tgtgtttagt cgaggttaaa aaaacgtcta ggccccccga accacgggga   5640
cgtggttttc ctttgaaaaa cacgatgata atatggccac aaccatgaga tccagtcctg   5700
gcaacatgga gaggattgtc atctgtctga tggtcatctt cttggggaca ctggtccaca   5760
aatcaagctc ccaaggtcaa gatcgccaca tgattagaat gcgtcaactt atagatattg   5820
ttgatcagct gaaaaattat gtgaatgact tggtccctga atttctgcca gctccagaag   5880
atgtagagac aaactgtgag tggtcagctt tttcctgctt tcagaaggcc caactaaagt   5940
cagcaaatac aggaaacaat gaaaggataa tcaatgtatc aattaaaaag ctgaagagga   6000
aaccaccttc cacaaatgca gggagaagac agaaacacag actaacatgc ccttcatgtg   6060
attcttatga gaaaaaacca cccaaagaat tcctagaaag attcaaatca cttctccaaa   6120
agatgattca tcagcatctg tcctctagaa cacacggaag tgaagattcc taggggcgat   6180
tctataagaa tgtaatacat acaaggccgt acagaattgg ctccggtgcg acttacaagg   6240
cagctgtaga tcttagccac tttttaaaag aaaagggggg actggaaggg ctaattcact   6300
cccaacgaag acaagatctg ctttttgctt gtactgggtc tctctggtta gaccagatct   6360
gagcctggga gctctctggc taactaggga acccactgct taagcctcaa taaagcttgc   6420
cttgagtgct tcaagtagtg tgtgcccgtc tgttgtgtga ctctggtaac tagagatccc   6480
tcagaccctt ttagtcagtg tggaaaatct ctagcagtag tagttcatgt catcttatta   6540
ttcagtattt ataacttgca aagaaatgaa tatcagagag tgagaggaac ttgtttattg   6600
cagcttataa tggttacaaa taaagcaata gcatcacaaa tttcacaaat aaagcatttt   6660
tttcactgca ttctagttgt ggtttgtcca aactcatcaa tgtatcttat catgtctggc   6720
tctagctatc ccgcccctaa ctccgcccat cccgccccat ggctgactaa ttttttttat   6780
ttatgcagag gccgaggccg cctcggcctc tgagctattc cagaagtagt gaggaggctt   6840
ttttggaggc ctagggacgt acccaattcg ccctatagtg agtcgtatta cgcgcgctca   6900
ctggccgtcg ttttacaacg tcgtgactgg gaaaaccctg gcgttaccca acttaatcgc   6960
cttgcagcac atcccccttt cgccagctgg cgtaatagcg aagaggcccg caccgatcgc   7020
ccttcccaac agttgcgcag cctgaatggc gaatgggacg cgccctgtag cggcgcatta   7080
agcgcggcgg gtgtggtggt tacgcgcagc gtgaccgcta cacttgccag cgccctagcg   7140
cccgctcctt tcgctttctt cccttccttt ctcgccacgt tcgccggctt tccccgtcaa   7200
gctctaaatc gggggctccc tttagggttc cgatttagtg ctttacggca cctcgacccc   7260
aaaaaacttg attagggtga tggttcacgt agtgggccat cgccctgata gacggttttt   7320
cgccctttga cgttggagtc cacgttcttt aatagtggac tcttgttcca aactggaaca   7380
acactcaacc ctatctcggt ctattctttt gatttataag ggattttgcc gatttcggcc   7440
tattggttaa aaaatgagct gatttaacaa aaatttaacg cgaattttaa caaaatatta   7500
acgcttacaa tttaggtggc acttttcggg gaaatgtgcg cggaacccct atttgtttat   7560
ttttctaaat acattcaaat atgtatccgc tcatgagaca ataaccctga taaatgcttc   7620
aataatattg aaaaaggaag agtatgagta ttcaacattt ccgtgtcgcc cttattccct   7680
```

```
tttttgcggc attttgcctt cctgtttttg ctcacccaga aacgctggtg aaagtaaaag   7740

atgctgaaga tcagttgggt gcacgagtgg gttacatcga actggatctc aacagcggta   7800

agatccttga gagttttcgc cccgaagaac gttttccaat gatgagcact tttaaagttc   7860

tgctatgtgg cgcggtatta tcccgtattg acgccgggca agagcaactc ggtcgccgca   7920

tacactattc tcagaatgac ttggttgagt actcaccagt cacagaaaag catcttacgg   7980

atggcatgac agtaagagaa ttatgcagtg ctgccataac catgagtgat aacactgcgg   8040

ccaacttact tctgacaacg atcggaggac cgaaggagct aaccgctttt ttgcacaaca   8100

tgggggatca tgtaactcgc cttgatcgtt gggaaccgga gctgaatgaa gccataccaa   8160

acgacgagcg tgacaccacg atgcctgtag caatggcaac aacgttgcgc aaactattaa   8220

ctggcgaact acttactcta gcttcccggc aacaattaat agactggatg gaggcggata   8280

aagttgcagg accacttctg cgctcggccc ttccggctgg ctggtttatt gctgataaat   8340

ctggagccgg tgagcgtggg tctcgcggta tcattgcagc actggggcca gatggtaagc   8400

cctcccgtat cgtagttatc tacacgacgg ggagtcaggc aactatggat gaacgaaata   8460

gacagatcgc tgagataggt gcctcactga ttaagcattg gtaactgtca gaccaagttt   8520

actcatatat actttagatt gatttaaaac ttcattttta atttaaaagg atctaggtga   8580

agatcctttt tgataatctc atgaccaaaa tcccttaacg tgagttttcg ttccactgag   8640

cgtcagaccc cgtagaaaag atcaaaggat cttc                               8674


<210> SEQ ID NO 34
<211> LENGTH: 10020
<212> TYPE: DNA
<213> ORGANISM: Artificial Sequence
<220> FEATURE:
<223> OTHER INFORMATION: Feedback HSPB 50% kozak

<400> SEQUENCE: 34

ttgagatcct ttttttctgc gcgtaatctg ctgcttgcaa acaaaaaaac caccgctacc     60

agcggtggtt tgtttgccgg atcaagagct accaactctt tttccgaagg taactggctt    120

cagcagagcg cagataccaa atactgttct tctagtgtag ccgtagttag gccaccactt    180

caagaactct gtagcaccgc ctacatacct cgctctgcta atcctgttac cagtggctgc    240

tgccagtggc gataagtcgt gtcttaccgg gttggactca agacgatagt taccggataa    300

ggcgcagcgg tcgggctgaa cggggggttc gtgcacacag cccagcttgg agcgaacgac    360

ctacaccgaa ctgagatacc tacagcgtga gctatgagaa agcgccacgc ttcccgaagg    420

gagaaaggcg gacaggtatc cggtaagcgg cagggtcgga acaggagagc gcacgaggga    480

gcttccaggg ggaaacgcct ggtatcttta tagtcctgtc gggtttcgcc acctctgact    540

tgagcgtcga tttttgtgat gctcgtcagg ggggcggagc ctatggaaaa acgccagcaa    600

cgcggccttt ttacggttcc tggccttttg ctggcctttt gctcacatgt tctttcctgc    660

gttatcccct gattctgtgg ataaccgtat taccgccttt gagtgagctg ataccgctcg    720

ccgcagccga acgaccgagc gcagcgagtc agtgagcgag gaagcggaag agcgcccaat    780

acgcaaaccg cctctccccg cgcgttggcc gattcattaa tgcagctggc acgacaggtt    840

tcccgactgg aaagcgggca gtgagcgcaa cgcaattaat gtgagttagc tcactcatta    900

ggcaccccag gctttacact ttatgcttcc ggctcgtatg ttgtgtggaa ttgtgagcgg    960

ataacaattt cacacaggaa acagctatga ccatgattac gccaagcgcg caattaaccc   1020

tcactaaagg gaacaaaagc tggagctgca agcttggcca ttgcatacgt tgtatccata   1080
```

-continued

```
tcataatatg tacatttata ttggctcatg tccaacatta ccgccatgtt gacattgatt   1140

attgactagt tattaatagt aatcaattac ggggtcatta gttcatagcc catatatgga   1200

gttccgcgtt acataactta cggtaaatgg cccgcctggc tgaccgccca acgacccccg   1260

cccattgacg tcaataatga cgtatgttcc catagtaacg ccaataggga ctttccattg   1320

acgtcaatgg gtggagtatt tacggtaaac tgcccacttg gcagtacatc aagtgtatca   1380

tatgccaagt acgcccccta ttgacgtcaa tgacggtaaa tggcccgcct ggcattatgc   1440

ccagtacatg accttatggg actttcctac ttggcagtac atctacgtat tagtcatcgc   1500

tattaccatg gtgatgcggt tttggcagta catcaatggg cgtggatagc ggtttgactc   1560

acggggattt ccaagtctcc accccattga cgtcaatggg agtttgtttt ggcaccaaaa   1620

tcaacgggac tttccaaaat gtcgtaacaa ctccgcccca ttgacgcaaa tgggcggtag   1680

gcgtgtacgg tgggaggtct atataagcag agctcgttta gtgaaccggg gtctctctgg   1740

ttagaccaga tctgagcctg ggagctctct ggctaactag ggaacccact gcttaagcct   1800

caataaagct tgccttgagt gcttcaagta gtgtgtgccc gtctgttgtg tgactctggt   1860

aactagagat ccctcagacc cttttagtca gtgtggaaaa tctctagcag tggcgcccga   1920

acagggactt gaaagcgaaa gggaaaccag aggagctctc tcgacgcagg actcggcttg   1980

ctgaagcgcg cacggcaaga ggcgaggggc ggcgactggt gagtacgcca aaaattttga   2040

ctagcggagg ctagaaggag agagatgggt gcgagagcgt cagtattaag cgggggagaa   2100

ttagatcgcg atgggaaaaa attcggttaa ggccaggggg aaagaaaaaa tataaattaa   2160

aacatatagt atgggcaagc agggagctag aacgattcgc agttaatcct ggcctgttag   2220

aaacatcaga aggctgtaga caaatactgg gacagctaca accatccctt cagacaggat   2280

cagaagaact tagatcatta tataatacag tagcaaccct ctattgtgtg catcaaagga   2340

tagagataaa agacaccaag gaagctttag acaagataga ggaagagcaa aacaaaagta   2400

agaccaccgc acagcaagcg gccgctgatc ttcagacctg gaggaggaga tatgagggac   2460

aattggagaa gtgaattata taaatataaa gtagtaaaaa ttgaaccatt aggagtagca   2520

cccaccaagg caaagagaag agtggtgcag agagaaaaaa gagcagtggg aataggagct   2580

ttgttccttg ggttcttggg agcagcagga agcactatgg gcgcagcctc aatgacgctg   2640

acggtacagg ccagacaatt attgtctggt atagtgcagc agcagaacaa tttgctgagg   2700

gctattgagg cgcaacagca tctgttgcaa ctcacagtct ggggcatcaa gcagctccag   2760

gcaagaatcc tggctgtgga aagataccta aaggatcaac agctcctggg gatttggggt   2820

tgctctggaa aactcatttg caccactgct gtgccttgga atgctagttg gagtaataaa   2880

tctctggaac agatttggaa tcacacgacc tggatggagt gggacagaga aattaacaat   2940

tacacaagct taatacactc cttaattgaa gaatcgcaaa accagcaaga aaagaatgaa   3000

caagaattat tggaattaga taaatgggca agtttgtgga attggtttaa cataacaaat   3060

tggctgtggt atataaaatt attcataatg atagtaggag gcttggtagg tttaagaata   3120

gtttttgctg tactttctat agtgaataga gttaggcagg gatattcacc attatcgttt   3180

cagacccacc tcccaacccc gaggggaccc gacaggcccg aaggaataga agaagaaggt   3240

ggagagagag acagagacag atccattcga ttagtgaacg gatctcgacg gtatcgatct   3300

cgacacaaat ggcagtattc atccacaatt ttaaaagaaa aggggggatt ggggggtaca   3360

gtgcagggga aagaatagta gacataatag caacagacat acaaactaaa gaattacaaa   3420
```

-continued

```
aacaaattac aaaaattcaa aattttcggg tttattacag ggacagcaga gatccagttt   3480
gggacggccc tttcgtcttc actcgagttt actccctatc agtgatagag aacgtatgaa   3540
gagtttactc cctatcagtg atagagaacg tatgcagact ttactcccta tcagtgatag   3600
agaacgtata aggagtttac tccctatcag tgatagagaa cgtatgacca gtttactccc   3660
tatcagtgat agagaacgta tctacagttt actccctatc agtgatagag aacgtatatc   3720
cagtttactc cctatcagtg atagagaacg tatgtcgagg taggcgtgta cggtgggcgc   3780
ctataaaagc agagctcgtt tagtgaaccg tcagatcgcc tggagcaatt ccacaacact   3840
tttgtcttat acttactagg agctcggatc caggaggatc ctccacagcc ccggggagac   3900
cttgcctcta aagttgctgc ttttgcagct ctgccacaac cgcgcgtcct cagagccagc   3960
cgggaggagc tagaaccttc cccgcgtttc tttcagcagc cctgagtcag aggcgggctg   4020
gccttgcaag tagccgccca gccttcttcg gtctcacgga ccgatccgcc cgaaccttct   4080
cccggggtca gcgccgcgct gcgccgcccg gctgactcag cccgggcggg cgggcgggag   4140
gctctcgact gggcgggaag gtgcgggaag gttcgcggcg gcggggtcgg ggaggtgcaa   4200
aaggatgaaa agcccgtgga cggagctgag cagatccggc cgggctggcg gcagagaaac   4260
cgcagggaga gcctcactgc tgagcgcccc tcgacgcggg cggcagcagc ctccgtggcc   4320
tccagcatcc gacaagaagc ttcggatggg ttgagccatg tctagactgg acaagagcaa   4380
agtcataaac tctgctctgg aattactcaa tggagtcggt atcgaaggcc tgacgacaag   4440
gaaactcgct caaaagctgg gagttgagca gcctaccctg tactggcacg tgaagaacaa   4500
gcgggccctg ctcgatgccc tgccaatcga gatgctggac aggcatcata cccactcctg   4560
ccccctggaa ggcgagtcat ggcaagactt tctgcggaac aacgccaagt cataccgctg   4620
tgctctcctc tcacatcgcg acggggctaa agtgcatctc ggcacccgcc caacagagaa   4680
acagtacgaa accctggaaa atcagctcgc gttcctgtgt cagcaaggct tctccctgga   4740
gaacgcactg tacgctctgt ccgccgtggg ccactttaca ctgggctgcg tattggagga   4800
acaggagcat caagtagcaa aagaggaaag agagacacct accaccgatt ctatgccccc   4860
acttctgaaa caagcaattg agctgttcga ccggcaggga gccgaacctg ccttcctttt   4920
cggcctggaa ctaatcatat gtggcctgga gaaacagcta aagtgcgaaa gcggcgggcc   4980
gaccgacgcc cttgacgatt ttgacttaga catgctccca gccgatgccc ttgacgactt   5040
tgaccttgat atgctgcctg ctgacgctct tgacgatttt gaccttgaca tgctccccgg   5100
gtaagtcccc ctctccctcc cccccccccta acgttactgg ccgaagccgc ttggaataag   5160
gccggtgtgc gtttgtctat atgttatttt ccaccatatt gccgtctttt ggcaatgtga   5220
gggcccggaa acctggccct gtcttcttga cgagcattcc taggggtctt tcccctctcg   5280
ccaaaggaat gcaaggtctg ttgaatgtcg tgaaggaagc agttcctctg gaagcttctt   5340
gaagacaaac aacgtctgta gcgacccttt gcaggcagcg gaacccccca cctggcgaca   5400
ggtgcctctg cggccaaaag ccacgtgtat aagatacacc tgcaaaggcg gcacaacccc   5460
agtgccacgt tgtgagttgg atagttgtgg aaagagtcaa atggctctcc tcaagcgtat   5520
tcaacaaggg gctgaaggat gcccagaagg taccccattg tatgggatct gatctggggc   5580
ctcggtgcac atgctttaca tgtgtttagt cgaggttaaa aaaacgtcta ggccccccga   5640
accacgggga cgtggttttc ctttgaaaaa cacgatgata atatggccac aaccatggtg   5700
agcaagggcg aggagctgtt caccggggtg gtgcccatcc tggtcgagct ggacggcgac   5760
gtaaacggcc acaagttcag cgtgtccggc gagggcgagg gcgatgccac ctacggcaag   5820
```

-continued ctgaccctga agttcatctg caccaccggc aagctgcccg tgccctggcc caccctcgtg 5880
accaccctga cctacggcgt gcagtgcttc agccgctacc ccgaccacat gaagcagcac 5940
gacttcttca agtccgccat gcccgaaggc tacgtccagg agcgcaccat cttcttcaag 6000
gacgacggca actacaagac ccgcgccgag gtgaagttcg agggcgacac cctggtgaac 6060
cgcatcgagc tgaagggcat cgacttcaag gaggacggca acatcctggg gcacaagctg 6120
gagtacaact acaacagcca caacgtctat atcatggccg acaagcagaa gaacggcatc 6180
aaggtgaact tcaagatccg ccacaacatc gaggacggca gcgtgcagct cgccgaccac 6240
taccagcaga acacccccat cggcgacggc cccgtgctgc tgcccgacaa ccactacctg 6300
agcacccagt ccgccctgag caaagacccc aacgagaagc gcgatcacat ggtcctgctg 6360
gagttcgtga ccgccgccgg gatcactctc ggcatggacg agctgtacaa gtaatacata 6420
caaggcagct gtagatctta gccaccagaa ttggctccgg tgcccgtcag tgggcagagc 6480
gcacatcgcc cacagtcccc gagaagttgg ggggaggggt cggcaattga accggtgcct 6540
agagaaggtg gcgcggggta aactgggaaa gtgatgtcgt gtactggctc cgcctttttc 6600
ccgagggtgg gggagaaccg tatataagtg cagtagtcgc cgtgaacgtt ctttttcgca 6660
acgggtttgc cgccagaaca caggtgaccg gtcgccacca tgtcgggggc aggtgccacc 6720
ggccgcgcca tggacgggcc gcgcctgctg ctgttgctgc ttctgggggt gtcccttgga 6780
ggtgccaagg aggcatgccc cacaggcctg tacacacaca gcggtgagtg ctgcaaagcc 6840
tgcaacctgg gcgagggtgt ggcccagcct tgtggagcca accagaccgt gtgtgagccc 6900
tgcctggaca gcgtgacgtt ctccgacgtg gtgagcgcga ccgagccgtg caagccgtgc 6960
accgagtgcg tggggctcca gagcatgtcg gcgccatgcg tggaggccga cgacgccgtg 7020
tgccgctgcg cctacggcta ctaccaggat gagacgactg ggcgctgcga ggcgtgccgc 7080
gtgtgcgagg cgggctcggg cctcgtgttc tcctgccagg acaagcagaa caccgtgtgc 7140
gaggagtgcc ccgacggcac gtattccgac gaggccaacc acgtggaccc gtgcctgccc 7200
tgcaccgtgt gcgaggacac cgagcgccag ctccgcgagt gcacacgctg ggccgacgcc 7260
gagtgcgagg agatccctgg ccgttggatt acacggtcca cacccccaga gggctcggac 7320
agcacagccc ccagcaccca ggagcctgag gcacctccag aacaagacct catagccagc 7380
acggtggcag gtgtggtgac cacagtgatg ggcagctccc agcccgtggt gacccgaggc 7440
accaccgaca acctcatccc tgtctattgc tccatcctgg ctgctgtggt tgtgggtctt 7500
gtggcctaca tagccttcaa gaggtggaac agctgacctt tcatagaagg cggcggtggt 7560
acctttaaga ccaatgactt acaaggcagc tgtagatctt agccactttt taaaagaaaa 7620
ggggggactg gaagggctaa ttcactccca acgaagacaa gatctgcttt ttgcttgtac 7680
tgggtctctc tggttagacc agatctgagc ctgggagctc tctggctaac tagggaaccc 7740
actgcttaag cctcaataaa gcttgccttg agtgcttcaa gtagtgtgtg cccgtctgtt 7800
gtgtgactct ggtaactaga gatccctcag acccttttag tcagtgtgga aaatctctag 7860
cagtagtagt tcatgtcatc ttattattca gtatttataa cttgcaaaga aatgaatatc 7920
agagagtgag aggaacttgt ttattgcagc ttataatggt tacaaataaa gcaatagcat 7980
cacaaatttc acaaataaag catttttttc actgcattct agttgtggtt tgtccaaact 8040
catcaatgta tcttatcatg tctggctcta gctatcccgc ccctaactcc gcccatcccg 8100
ccccatggct gactaatttt ttttatttat gcagaggccg aggccgcctc ggcctctgag 8160

```
ctattccaga agtagtgagg aggctttttt ggaggcctag ggacgtaccc aattcgccct   8220

atagtgagtc gtattacgcg cgctcactgg ccgtcgtttt acaacgtcgt gactgggaaa   8280

accctggcgt tacccaactt aatcgccttg cagcacatcc ccctttcgcc agctggcgta   8340

atagcgaaga ggcccgcacc gatcgccctt cccaacagtt gcgcagcctg aatggcgaat   8400

gggacgcgcc ctgtagcggc gcattaagcg cggcgggtgt ggtggttacg cgcagcgtga   8460

ccgctacact tgccagcgcc ctagcgcccg ctcctttcgc tttcttccct tcctttctcg   8520

ccacgttcgc cggctttccc cgtcaagctc taaatcgggg gctcccttta gggttccgat   8580

ttagtgcttt acggcacctc gaccccaaaa aacttgatta gggtgatggt tcacgtagtg   8640

ggccatcgcc ctgatagacg gtttttcgcc ctttgacgtt ggagtccacg ttctttaata   8700

gtggactctt gttccaaact ggaacaacac tcaaccctat ctcggtctat tcttttgatt   8760

tataagggat tttgccgatt tcggcctatt ggttaaaaaa tgagctgatt taacaaaaat   8820

ttaacgcgaa ttttaacaaa atattaacgc ttacaattta ggtggcactt ttcggggaaa   8880

tgtgcgcgga acccctattt gtttattttt ctaaatacat tcaaatatgt atccgctcat   8940

gagacaataa ccctgataaa tgcttcaata atattgaaaa aggaagagta tgagtattca   9000

acatttccgt gtcgccctta ttcccttttt tgcggcattt tgccttcctg tttttgctca   9060

cccagaaacg ctggtgaaag taaaagatgc tgaagatcag ttgggtgcac gagtgggtta   9120

catcgaactg gatctcaaca gcggtaagat ccttgagagt tttcgccccg aagaacgttt   9180

tccaatgatg agcactttta aagttctgct atgtggcgcg gtattatccc gtattgacgc   9240

cgggcaagag caactcggtc gccgcataca ctattctcag aatgacttgg ttgagtactc   9300

accagtcaca gaaaagcatc ttacggatgg catgacagta agagaattat gcagtgctgc   9360

cataaccatg agtgataaca ctgcggccaa cttacttctg acaacgatcg gaggaccgaa   9420

ggagctaacc gcttttttgc acaacatggg ggatcatgta actcgccttg atcgttggga   9480

accggagctg aatgaagcca taccaaacga cgagcgtgac accacgatgc ctgtagcaat   9540

ggcaacaacg ttgcgcaaac tattaactgg cgaactactt actctagctt cccggcaaca   9600

attaatagac tggatggagg cggataaagt tgcaggacca cttctgcgct cggcccttcc   9660

ggctggctgg tttattgctg ataaatctgg agccggtgag cgtgggtctc gcggtatcat   9720

tgcagcactg gggccagatg gtaagccctc ccgtatcgta gttatctaca cgacggggag   9780

tcaggcaact atggatgaac gaaatagaca gatcgctgag ataggtgcct cactgattaa   9840

gcattggtaa ctgtcagacc aagtttactc atatatactt tagattgatt taaaacttca   9900

tttttaattt aaaaggatct aggtgaagat cctttttgat aatctcatga ccaaaatccc   9960

ttaacgtgag ttttcgttcc actgagcgtc agaccccgta gaaaagatca aaggatcttc  10020
```

<210> SEQ ID NO 35
<211> LENGTH: 9362
<212> TYPE: DNA
<213> ORGANISM: Artificial Sequence
<220> FEATURE:
<223> OTHER INFORMATION: Feedforward HSP16F

<400> SEQUENCE: 35

```
tcatgaccaa aatcccttaa cgtgagtttt cgttccactg agcgtcagac cccgtagaaa     60

agatcaaagg atcttcttga gatccttttt ttctgcgcgt aatctgctgc ttgcaaacaa    120

aaaaaccacc gctaccagcg gtggtttgtt tgccggatca agagctacca actctttttc    180

cgaaggtaac tggcttcagc agagcgcaga taccaaatac tgtccttcta gtgtagccgt    240
```

```
agttaggcca ccacttcaag aactctgtag caccgcctac atacctcgct ctgctaatcc    300
tgttaccagt ggctgctgcc agtggcgata agtcgtgtct taccgggttg gactcaagac    360
gatagttacc ggataaggcg cagcggtcgg gctgaacggg gggttcgtgc acacagccca    420
gcttggagcg aacgacctac accgaactga gatacctaca gcgtgagcta tgagaaagcg    480
ccacgcttcc cgaagggaga aaggcggaca ggtatccggt aagcggcagg gtcggaacag    540
gagagcgcac gagggagctt ccagggggaa acgcctggta tctttatagt cctgtcgggt    600
ttcgccacct ctgacttgag cgtcgatttt tgtgatgctc gtcagggggg cggagcctat    660
ggaaaaacgc cagcaacgcg gcctttttac ggttcctggc cttttgctgg ccttttgctc    720
acatgttctt tcctgcgtta tcccctgatt ctgtggataa ccgtattacc gcctttgagt    780
gagctgatac cgctcgccgc agccgaacga ccgagcgcag cgagtcagtg agcgaggaag    840
cggaagagcg cccaatacgc aaaccgcctc tccccgcgcg ttggccgatt cattaatgca    900
gctggcacga caggtttccc gactggaaag cgggcagtga gcgcaacgca attaatgtga    960
gttagctcac tcattaggca ccccaggctt tacactttat gcttccggct cgtatgttgt   1020
gtggaattgt gagcggataa caatttcaca caggaaacag ctatgaccat gattacgcca   1080
agcgcgcaat taaccctcac taaagggaac aaaagctgga gctgcaagct tggccattgc   1140
atacgttgta tccatatcat aatatgtaca tttatattgg ctcatgtcca acattaccgc   1200
catgttgaca ttgattattg actagttatt aatagtaatc aattacgggg tcattagttc   1260
atagcccata tatggagttc cgcgttacat aacttacggt aaatggcccg cctggctgac   1320
cgcccaacga cccccgccca ttgacgtcaa taatgacgta tgttcccata gtaacgccaa   1380
tagggacttt ccattgacgt caatgggtgg agtatttacg gtaaactgcc cacttggcag   1440
tacatcaagt gtatcatatg ccaagtacgc cccctattga cgtcaatgac ggtaaatggc   1500
ccgcctggca ttatgcccag tacatgacct tatgggactt tcctacttgg cagtacatct   1560
acgtattagt catcgctatt accatggtga tgcggttttg gcagtacatc aatgggcgtg   1620
gatagcggtt tgactcacgg ggatttccaa gtctccaccc cattgacgtc aatgggagtt   1680
tgttttggca ccaaaatcaa cgggactttc caaaatgtcg taacaactcc gccccattga   1740
cgcaaatggg cggtaggcgt gtacggtggg aggtctatat aagcagagct cgtttagtga   1800
accggggtct ctctggttag accagatctg agcctgggag ctctctggct aactagggaa   1860
cccactgctt aagcctcaat aaagcttgcc ttgagtgctt caagtagtgt gtgcccgtct   1920
gttgtgtgac tctggtaact agagatccct cagacccttt tagtcagtgt ggaaaatctc   1980
tagcagtggc gcccgaacag ggacttgaaa gcgaaaggga aaccagagga gctctctcga   2040
cgcaggactc ggcttgctga agcgcgcacg gcaagaggcg aggggcggcg actggtgagt   2100
acgccaaaaa ttttgactag cggaggctag aaggagagag atgggtgcga gagcgtcagt   2160
attaagcggg ggagaattag atcgcgatgg gaaaaaattc ggttaaggcc agggggaaag   2220
aaaaaatata aattaaaaca tatagtatgg gcaagcaggg agctagaacg attcgcagtt   2280
aatcctggcc tgttagaaac atcagaaggc tgtagacaaa tactgggaca gctacaacca   2340
tcccttcaga caggatcaga agaacttaga tcattatata atacagtagc aaccctctat   2400
tgtgtgcatc aaaggataga gataaaagac accaaggaag ctttagacaa gatagaggaa   2460
gagcaaaaca aaagtaagac caccgcacag caagcggccg ctgatcttca gacctggagg   2520
aggagatatg agggacaatt ggagaagtga attatataaa tataaagtag taaaaattga   2580
```

-continued

```
accattagga gtagcaccca ccaaggcaaa gagaagagtg gtgcagagag aaaaaagagc   2640
agtgggaata ggagctttgt tccttgggtt cttgggagca gcaggaagca ctatgggcgc   2700
agcctcaatg acgctgacgg tacaggccag acaattattg tctggtatag tgcagcagca   2760
gaacaatttg ctgagggcta ttgaggcgca acagcatctg ttgcaactca cagtctgggg   2820
catcaagcag ctccaggcaa gaatcctggc tgtggaaaga tacctaaagg atcaacagct   2880
cctggggatt tggggttgct ctggaaaact catttgcacc actgctgtgc cttggaatgc   2940
tagttggagt aataaatctc tggaacagat ttggaatcac acgacctgga tggagtggga   3000
cagagaaatt aacaattaca caagcttaat acactcctta attgaagaat cgcaaaacca   3060
gcaagaaaag aatgaacaag aattattgga attagataaa tgggcaagtt tgtggaattg   3120
gtttaacata acaaattggc tgtggtatat aaaattattc ataatgatag taggaggctt   3180
ggtaggttta agaatagttt ttgctgtact ttctatagtg aatagagtta ggcagggata   3240
ttcaccatta tcgtttcaga cccacctccc aaccccgagg ggacccgaca ggcccgaagg   3300
aatagaagaa gaaggtggag agagagacag agacagatcc attcgattag tgaacggatc   3360
tcgacggtat cgatctcgac acaaatggca gtattcatcc acaattttaa aagaaaaggg   3420
gggattgggg ggtacagtgc aggggaaaga atagtagaca taatagcaac agacatacaa   3480
actaaagaat tacaaaaaca aattacaaaa attcaaaatt ttcgggttta ttacagggac   3540
agcgttcacg tcgccatcca gttccaccag gatgggcacc acgccggtga acagttcctc   3600
gcccttggac accatggtgt cttgaagttt agagaatgaa cagtaagcac ttgaacaaag   3660
tgtattggtt tcctctgaac acgattggct tatatacccg tatcctgcag ccgtttagaa   3720
tgttctagaa ggtcctagat gcatctagga ccttctagaa aaaggtggaa atgagtataa   3780
atacagtgac aaaaccgaac caaacaacat tcactctaat tgtgaaatct tcaaactaca   3840
atcgccacca tgtctagact ggacaagagc aaagtcataa actctgctct ggaattactc   3900
aatggagtcg gtatcgaagg cctgacgaca aggaaactcg ctcaaaagct gggagttgag   3960
cagcctaccc tgtactggca cgtgaagaac aagcgggccc tgctcgatgc cctgccaatc   4020
gagatgctgg acaggcatca tacccactcc tgcccccctgg aaggcgagtc atggcaagac   4080
tttctgcgga acaacgccaa gtcataccgc tgtgctctcc tctcacatcg cgacggggct   4140
aaagtgcatc tcggcacccg cccaacagag aaacagtacg aaaccctgga aaatcagctc   4200
gcgttcctgt gtcagcaagg cttctccctg gagaacgcac tgtacgctct gtccgccgtg   4260
ggccacttta cactgggctg cgtattggag gaacaggagc atcaagtagc aaaagaggaa   4320
agagagacac ctaccaccga ttctatgccc ccacttctga aacaagcaat tgagctgttc   4380
gaccggcagg gagccgaacc tgccttcctt ttcggcctgg aactaatcat atgtggcctg   4440
gagaaacagc taaagtgcga aagcggcggg ccgaccgacg cccttgacga ttttgactta   4500
gacatgctcc cagccgatgc ccttgacgac tttgaccttg atatgctgcc tgctgacgct   4560
cttgacgatt ttgaccttga catgctcccc gggtaagtca gattaggccc tggaagtaat   4620
gtacaacacg tgctacggtt tgggaattag cttgacggcc ctttcgtctt cactcgagtt   4680
tactccctat cagtgataga gaacgtatga agagtttact ccctatcagt gatagagaac   4740
gtatgcagac tttactccct atcagtgata gagaacgtat aaggagttta ctccctatca   4800
gtgatagaga acgtatgacc agtttactcc ctatcagtga tagagaacgt atctacagtt   4860
tactccctat cagtgataga gaacgtatat ccagtttact ccctatcagt gatagagaac   4920
gtatgtcgag gtaggcgtgt acggtgggcg cctataaaag cagagctcgt ttagtgaacc   4980
```

-continued

```
gtcagatcgc ctggagcaat tccacaacac ttttgtctta tacttactag gagctcggat   5040
ccagtaccct tcaccatggt gagcaagggc gaggagctgt tcaccggggt ggtgcccatc   5100
ctggtcgagc tggacggcga cgtaaacggc cacaagttca gcgtgtccgg cgagggcgag   5160
ggcgatgcca cctacggcaa gctgaccctg aagttcatct gcaccaccgg caagctgccc   5220
gtgccctggc ccaccctcgt gaccaccctg acctacggcg tgcagtgctt cagccgctac   5280
cccgaccaca tgaagcagca cgacttcttc aagtccgcca tgcccgaagg ctacgtccag   5340
gagcgcacca tcttcttcaa ggacgacggc aactacaaga cccgcgccga ggtgaagttc   5400
gagggcgaca ccctggtgaa ccgcatcgag ctgaagggca tcgacttcaa ggaggacggc   5460
aacatcctgg ggcacaagct ggagtacaac tacaacagcc acaacgtcta tatcatggcc   5520
gacaagcaga agaacggcat caaggtgaac ttcaagatcc gccacaacat cgaggacggc   5580
agcgtgcagc tcgccgacca ctaccagcag aacaccccca tcggcgacgg ccccgtgctg   5640
ctgcccgaca accactacct gagcacccag tccgccctga gcaaagaccc caacgagaag   5700
cgcgatcaca tggtcctgct ggagttcgtg accgccgccg ggatcactct cggcatggac   5760
gagctgtaca agtaatacat acaaggccgt acagaattgg ctccggtgcc cgtcagtggg   5820
cagagcgcac atcgcccaca gtccccgaga agttgggggg aggggtcggc aattgaaccg   5880
gtgcctagag aaggtggcgc ggggtaaact gggaaagtga tgtcgtgtac tggctccgcc   5940
tttttcccga gggtggggga gaaccgtata taagtgcagt agtcgccgtg aacgttcttt   6000
ttcgcaacgg gtttgccgcc agaacacagg tgaccttcac catgtcgggg gcaggtgcca   6060
ccggccgcgc catggacggg ccgcgcctgc tgctgttgct gcttctgggg gtgtcccttg   6120
gaggtgccaa ggaggcatgc cccacaggcc tgtacacaca cagcggtgag tgctgcaaag   6180
cctgcaacct gggcgagggt gtggcccagc cttgtggagc caaccagacc gtgtgtgagc   6240
cctgcctgga cagcgtgacg ttctccgacg tggtgagcgc gaccgagccg tgcaagccgt   6300
gcaccgagtg cgtggggctc cagagcatgt cggcgccatg cgtggaggcc gacgacgccg   6360
tgtgccgctg cgcctacggc tactaccagg atgagacgac tgggcgctgc gaggcgtgcc   6420
gcgtgtgcga ggcgggctcg ggcctcgtgt tctcctgcca ggacaagcag aacaccgtgt   6480
gcgaggagtg ccccgacggc acgtattccg acgaggccaa ccacgtggac ccgtgcctgc   6540
cctgcaccgt gtgcgaggac accgagcgcc agctccgcga gtgcacacgc tgggccgacg   6600
ccgagtgcga ggagatccct ggccgttgga ttacacggtc cacaccccca gagggctcgg   6660
acagcacagc ccccagcacc caggagcctg aggcacctcc agaacaagac ctcatagcca   6720
gcacggtggc aggtgtggtg accacagtga tgggcagctc ccagcccgtg gtgacccgag   6780
gcaccaccga caacctcatc cctgtctatt gctccatcct ggctgctgtg gttgtgggtc   6840
ttgtggccta catagccttc aagaggtgga acagctgacc tttcatagaa ggcggcggtg   6900
gtacctttaa gaccaatgac ttacaaggca gctgtagatc ttagccactt tttaaaagaa   6960
aaggggggac tggaagggct aattcactcc caacgaagac aagatctgct ttttgcttgt   7020
actgggtctc tctggttaga ccagatctga gcctgggagc tctctggcta actagggaac   7080
ccactgctta agcctcaata aagcttgcct tgagtgcttc aagtagtgtg tgcccgtctg   7140
ttgtgtgact ctggtaacta gagatccctc agaccctttt agtcagtgtg gaaaatctct   7200
agcagtagta gttcatgtca tcttattatt cagtatttat aacttgcaaa gaaatgaata   7260
tcagagagtg agaggaactt gtttattgca gcttataatg gttacaaata aagcaatagc   7320
```

-continued

```
atcacaaatt tcacaaataa agcatttttt tcactgcatt ctagttgtgg tttgtccaaa   7380

ctcatcaatg tatcttatca tgtctggctc tagctatccc gcccctaact ccgcccatcc   7440

cgccccatgg ctgactaatt ttttttattt atgcagaggc cgaggccgcc tcggcctctg   7500

agctattcca gaagtagtga ggaggctttt ttggaggcct agggacgtac ccaattcgcc   7560

ctatagtgag tcgtattacg cgcgctcact ggccgtcgtt ttacaacgtc gtgactggga   7620

aaaccctggc gttacccaac ttaatcgcct tgcagcacat ccccctttcg ccagctggcg   7680

taatagcgaa gaggcccgca ccgatcgccc ttcccaacag ttgcgcagcc tgaatggcga   7740

atgggacgcg ccctgtagcg gcgcattaag cgcggcgggt gtggtggtta cgcgcagcgt   7800

gaccgctaca cttgccagcg ccctagcgcc cgctcctttc gctttcttcc cttcctttct   7860

cgccacgttc gccggctttc cccgtcaagc tctaaatcgg gggctccctt tagggttccg   7920

atttagtgct ttacggcacc tcgaccccaa aaaacttgat tagggtgatg gttcacgtag   7980

tgggccatcg ccctgataga cggtttttcg ccctttgacg ttggagtcca cgttctttaa   8040

tagtggactc ttgttccaaa ctggaacaac actcaaccct atctcggtct attcttttga   8100

tttataaggg attttgccga tttcggccta ttggttaaaa aatgagctga tttaacaaaa   8160

atttaacgcg aattttaaca aaatattaac gcttacaatt taggtggcac ttttcgggga   8220

aatgtgcgcg gaacccctat ttgtttattt ttctaaatac attcaaatat gtatccgctc   8280

atgagacaat aaccctgata aatgcttcaa taatattgaa aaaggaagag tatgagtatt   8340

caacatttcc gtgtcgccct tattcccttt tttgcggcat tttgccttcc tgtttttgct   8400

cacccagaaa cgctggtgaa agtaaaagat gctgaagatc agttgggtgc acgagtgggt   8460

tacatcgaac tggatctcaa cagcggtaag atccttgaga gttttcgccc cgaagaacgt   8520

tttccaatga tgagcacttt taaagttctg ctatgtggcg cggtattatc ccgtattgac   8580

gccgggcaag agcaactcgg tcgccgcata cactattctc agaatgactt ggttgagtac   8640

tcaccagtca cagaaaagca tcttacggat ggcatgacag taagagaatt atgcagtgct   8700

gccataacca tgagtgataa cactgcggcc aacttacttc tgacaacgat cggaggaccg   8760

aaggagctaa ccgctttttt gcacaacatg ggggatcatg taactcgcct tgatcgttgg   8820

gaaccggagc tgaatgaagc cataccaaac gacgagcgtg acaccacgat gcctgtagca   8880

atggcaacaa cgttgcgcaa actattaact ggcgaactac ttactctagc ttcccggcaa   8940

caattaatag actggatgga ggcggataaa gttgcaggac cacttctgcg ctcggccctt   9000

ccggctggct ggtttattgc tgataaatct ggagccggtg agcgtgggtc tcgcggtatc   9060

attgcagcac tggggccaga tggtaagccc tcccgtatcg tagttatcta cacgacgggg   9120

agtcaggcaa ctatggatga acgaaataga cagatcgctg agataggtgc ctcactgatt   9180

aagcattggt aactgtcaga ccaagtttac tcatatatac tttagattga tttaaaactt   9240

catttttaat ttaaaaggat ctaggtgaag atcctttttg ataatctcat gaccaaaatc   9300

ccttaacgtg agttttcgtt ccactgagcg tcagaccccg tagaaaagat caaaggatct   9360

tc                                                                  9362
```

```
<210> SEQ ID NO 36
<211> LENGTH: 9489
<212> TYPE: DNA
<213> ORGANISM: Artificial Sequence
<220> FEATURE:
<223> OTHER INFORMATION: Feedforward HSPB 50%

<400> SEQUENCE: 36
```

-continued

```
ttgagatcct tttttctgc gcgtaatctg ctgcttgcaa acaaaaaaac caccgctacc     60
agcggtggtt tgtttgccgg atcaagagct accaactctt tttccgaagg taactggctt    120
cagcagagcg cagataccaa atactgttct tctagtgtag ccgtagttag gccaccactt    180
caagaactct gtagcaccgc ctacatacct cgctctgcta atcctgttac cagtggctgc    240
tgccagtggc gataagtcgt gtcttaccgg gttggactca agacgatagt taccggataa    300
ggcgcagcgg tcgggctgaa cggggggttc gtgcacacag cccagcttgg agcgaacgac    360
ctacaccgaa ctgagatacc tacagcgtga gctatgagaa agcgccacgc ttcccgaagg    420
gagaaaggcg gacaggtatc cggtaagcgg cagggtcgga acaggagagc gcacgaggga    480
gcttccaggg ggaaacgcct ggtatcttta tagtcctgtc gggtttcgcc acctctgact    540
tgagcgtcga tttttgtgat gctcgtcagg ggggcggagc ctatggaaaa acgccagcaa    600
cgcggccttt ttacggttcc tggccttttg ctggcctttt gctcacatgt tctttcctgc    660
gttatcccct gattctgtgg ataaccgtat taccgccttt gagtgagctg ataccgctcg    720
ccgcagccga acgaccgagc gcagcgagtc agtgagcgag gaagcggaag agcgcccaat    780
acgcaaaccg cctctccccg cgcgttggcc gattcattaa tgcagctggc acgacaggtt    840
tcccgactgg aaagcgggca gtgagcgcaa cgcaattaat gtgagttagc tcactcatta    900
ggcaccccag gctttacact ttatgcttcc ggctcgtatg ttgtgtggaa ttgtgagcgg    960
ataacaattt cacacaggaa acagctatga ccatgattac gccaagcgcg caattaaccc   1020
tcactaaagg gaacaaaagc tggagctgca agcttggcca ttgcatacgt tgtatccata   1080
tcataatatg tacatttata ttggctcatg tccaacatta ccgccatgtt gacattgatt   1140
attgactagt tattaatagt aatcaattac ggggtcatta gttcatagcc catatatgga   1200
gttccgcgtt acataactta cggtaaatgg cccgcctggc tgaccgccca acgacccccg   1260
cccattgacg tcaataatga cgtatgttcc catagtaacg ccaataggga ctttccattg   1320
acgtcaatgg gtggagtatt tacggtaaac tgcccacttg gcagtacatc aagtgtatca   1380
tatgccaagt acgcccccta ttgacgtcaa tgacggtaaa tggcccgcct ggcattatgc   1440
ccagtacatg accttatggg actttcctac ttggcagtac atctacgtat tagtcatcgc   1500
tattaccatg gtgatgcggt tttggcagta catcaatggg cgtggatagc ggtttgactc   1560
acggggattt ccaagtctcc accccattga cgtcaatggg agtttgtttt ggcaccaaaa   1620
tcaacgggac tttccaaaat gtcgtaacaa ctccgcccca ttgacgcaaa tgggcggtag   1680
gcgtgtacgg tgggaggtct atataagcag agctcgttta gtgaaccggg gtctctctgg   1740
ttagaccaga tctgagcctg ggagctctct ggctaactag ggaacccact gcttaagcct   1800
caataaagct tgccttgagt gcttcaagta gtgtgtgccc gtctgttgtg tgactctggt   1860
aactagagat ccctcagacc cttttagtca gtgtggaaaa tctctagcag tggcgcccga   1920
acagggactt gaaagcgaaa gggaaaccag aggagctctc tcgacgcagg actcggcttg   1980
ctgaagcgcg cacggcaaga ggcgaggggc ggcgactggt gagtacgcca aaaattttga   2040
ctagcggagg ctagaaggag agagatgggt gcgagagcgt cagtattaag cgggggagaa   2100
ttagatcgcg atgggaaaaa attcggttaa ggccaggggg aaagaaaaaa tataaattaa   2160
aacatatagt atgggcaagc agggagctag aacgattcgc agttaatcct ggcctgttag   2220
aaacatcaga aggctgtaga caaatactgg gacagctaca accatccctt cagacaggat   2280
cagaagaact tagatcatta tataatacag tagcaaccct ctattgtgtg catcaaagga   2340
```

-continued tagagataaa agacaccaag gaagctttag acaagataga ggaagagcaa aacaaaagta 2400
agaccaccgc acagcaagcg gccgctgatc ttcagacctg gaggaggaga tatgagggac 2460
aattggagaa gtgaattata taaatataaa gtagtaaaaa ttgaaccatt aggagtagca 2520
cccaccaagg caaagagaag agtggtgcag agagaaaaaa gagcagtggg aataggagct 2580
ttgttccttg ggttcttggg agcagcagga agcactatgg gcgcagcctc aatgacgctg 2640
acggtacagg ccagacaatt attgtctggt atagtgcagc agcagaacaa tttgctgagg 2700
gctattgagg cgcaacagca tctgttgcaa ctcacagtct ggggcatcaa gcagctccag 2760
gcaagaatcc tggctgtgga aagataccta aaggatcaac agctcctggg gatttggggt 2820
tgctctggaa aactcatttg caccactgct gtgccttgga atgctagttg gagtaataaa 2880
tctctggaac agatttggaa tcacacgacc tggatggagt gggacagaga aattaacaat 2940
tacacaagct taatacactc cttaattgaa gaatcgcaaa accagcaaga aaagaatgaa 3000
caagaattat tggaattaga taaatgggca agtttgtgga attggtttaa cataacaaat 3060
tggctgtggt atataaaatt attcataatg atagtaggag gcttggtagg tttaagaata 3120
gtttttgctg tactttctat agtgaataga gttaggcagg gatattcacc attatcgttt 3180
cagacccacc tcccaacccc gaggggaccc gacaggcccg aaggaataga agaagaaggt 3240
ggagagagag acagagacag atccattcga ttagtgaacg gatctcgacg gtatcgatct 3300
cgacacaaat ggcagtattc atccacaatt ttaaaagaaa aggggggatt ggggggtaca 3360
gtgcagggga aagaatagta gacataatag caacagacat acaaactaaa gaattacaaa 3420
aacaaattac aaaaattcaa aattttcggg tttattacag ggacagcaga gatccagttt 3480
gggaattagc ttgaggatcc tccacagccc cggggagacc ttgcctctaa agttgctgct 3540
tttgcagctc tgccacaacc gcgcgtcctc agagccagcc gggaggagct agaaccttcc 3600
ccgcgtttct ttcagcagcc ctgagtcaga ggcgggctgg ccttgcaagt agccgcccag 3660
ccttcttcgg tctcacggac cgatccgccc gaaccttctc ccggggtcag cgccgcgctg 3720
cgccgcccgg ctgactcagc ccgggcgggc gggcgggagg ctctcgactg ggcgggaagg 3780
tgcgggaagg ttcgcggcgg cggggtcggg gaggtgcaaa aggatgaaaa gcccgtggac 3840
ggagctgagc agatccggcc gggctggcgg cagagaaacc gcagggagag cctcactgct 3900
gagcgcccct cgacgcgggc ggcagcagcc tccgtggcct ccagcatccg acaagaagct 3960
tcggatgggt tgagccatgt ctagactgga caagagcaaa gtcataaact ctgctctgga 4020
attactcaat ggagtcggta tcgaaggcct gacgacaagg aaactcgctc aaaagctggg 4080
agttgagcag cctaccctgt actggcacgt gaagaacaag cgggccctgc tcgatgccct 4140
gccaatcgag atgctggaca ggcatcatac ccactcctgc cccctggaag gcgagtcatg 4200
gcaagacttt ctgcggaaca acgccaagtc ataccgctgt gctctcctct cacatcgcga 4260
cggggctaaa gtgcatctcg gcacccgccc aacagagaaa cagtacgaaa ccctggaaaa 4320
tcagctcgcg ttcctgtgtc agcaaggctt ctccctggag aacgcactgt acgctctgtc 4380
cgccgtgggc cactttacac tgggctgcgt attggaggaa caggagcatc aagtagcaaa 4440
agaggaaaga gagacaccta ccaccgattc tatgccccca cttctgaaac aagcaattga 4500
gctgttcgac cggcagggag ccgaacctgc cttccttttc ggcctggaac taatcatatg 4560
tggcctggag aaacagctaa agtgcgaaag cggcgggccg accgacgccc ttgacgattt 4620
tgacttagac atgctcccag ccgatgccct tgacgacttt gaccttgata tgctgcctgc 4680
tgacgctctt gacgattttg accttgacat gctccccggg taagtcagat taggccctgg 4740
aagtaatgta caacacgtgc tacggtttgg gaattagctt gacggccctt tcgtcttcac 4800
tcgagtttac tccctatcag tgatagagaa cgtatgaaga gtttactccc tatcagtgat 4860
agagaacgta tgcagacttt actccctatc agtgatagag aacgtataag gagtttactc 4920
cctatcagtg atagagaacg tatgaccagt ttactcccta tcagtgatag agaacgtatc 4980
tacagtttac tccctatcag tgatagagaa cgtatatcca gtttactccc tatcagtgat 5040
agagaacgta tgtcgaggta ggcgtgtacg gtgggcgcct ataaaagcag agctcgttta 5100
gtgaaccgtc agatcgcctg gagcaattcc acaacacttt tgtcttatac ttactaggag 5160
ctcggatcca gtacccttca ccatggtgag caagggcgag gagctgttca ccggggtggt 5220
gcccatcctg gtcgagctgg acggcgacgt aaacggccac aagttcagcg tgtccggcga 5280
gggcgagggc gatgccacct acggcaagct gaccctgaag ttcatctgca ccaccggcaa 5340
gctgcccgtg ccctggccca ccctcgtgac caccctgacc tacggcgtgc agtgcttcag 5400
ccgctacccc gaccacatga agcagcacga cttcttcaag tccgccatgc ccgaaggcta 5460
cgtccaggag cgcaccatct tcttcaagga cgacggcaac tacaagaccc gcgccgaggt 5520
gaagttcgag ggcgacaccc tggtgaaccg catcgagctg aagggcatcg acttcaagga 5580
ggacggcaac atcctggggc acaagctgga gtacaactac aacagccaca acgtctatat 5640
catggccgac aagcagaaga acggcatcaa ggtgaacttc aagatccgcc acaacatcga 5700
ggacggcagc gtgcagctcg ccgaccacta ccagcagaac acccccatcg gcgacggccc 5760
cgtgctgctg cccgacaacc actacctgag cacccagtcc gccctgagca aagaccccaa 5820
cgagaagcgc gatcacatgg tcctgctgga gttcgtgacc gccgccggga tcactctcgg 5880
catggacgag ctgtacaagt aatacataca aggccgtaca gaattggctc cggtgcccgt 5940
cagtgggcag agcgcacatc gcccacagtc cccgagaagt tggggggagg ggtcggcaat 6000
tgaaccggtg cctagagaag gtggcgcggg gtaaactggg aaagtgatgt cgtgtactgg 6060
ctccgccttt ttcccgaggg tgggggagaa ccgtatataa gtgcagtagt cgccgtgaac 6120
gttctttttc gcaacgggtt tgccgccaga acacaggtga ccttcaccat gtcgggggca 6180
ggtgccaccg gccgcgccat ggacgggccg cgcctgctgc tgttgctgct tctgggggtg 6240
tcccttggag gtgccaagga ggcatgcccc acaggcctgt acacacacag cggtgagtgc 6300
tgcaaagcct gcaacctggg cgagggtgtg gcccagcctt gtggagccaa ccagaccgtg 6360
tgtgagccct gcctggacag cgtgacgttc tccgacgtgg tgagcgcgac cgagccgtgc 6420
aagccgtgca ccgagtgcgt ggggctccag agcatgtcgg cgccatgcgt ggaggccgac 6480
gacgccgtgt gccgctgcgc ctacggctac taccaggatg agacgactgg gcgctgcgag 6540
gcgtgccgcg tgtgcgaggc gggctcgggc ctcgtgttct cctgccagga caagcagaac 6600
accgtgtgcg aggagtgccc cgacggcacg tattccgacg aggccaacca cgtggacccg 6660
tgcctgccct gcaccgtgtg cgaggacacc gagcgccagc tccgcgagtg cacacgctgg 6720
gccgacgccg agtgcgagga gatccctggc cgttggatta cacggtccac acccccagag 6780
ggctcggaca gcacagcccc cagcacccag gagcctgagg cacctccaga acaagacctc 6840
atagccagca cggtggcagg tgtggtgacc acagtgatgg gcagctccca gcccgtggtg 6900
acccgaggca ccaccgacaa cctcatccct gtctattgct ccatcctggc tgctgtggtt 6960
gtgggtcttg tggcctacat agccttcaag aggtggaaca gctgaccttt catagaaggc 7020
ggcggtggta cctttaagac caatgactta caaggcagct gtagatctta gccacttttt 7080

```
aaaagaaaag gggggactgg aagggctaat tcactcccaa cgaagacaag atctgctttt    7140

tgcttgtact gggtctctct ggttagacca gatctgagcc tgggagctct ctggctaact    7200

agggaaccca ctgcttaagc ctcaataaag cttgccttga gtgcttcaag tagtgtgtgc    7260

ccgtctgttg tgtgactctg gtaactagag atccctcaga ccccttttagt cagtgtggaa    7320

aatctctagc agtagtagtt catgtcatct tattattcag tatttataac ttgcaaagaa    7380

atgaatatca gagagtgaga ggaacttgtt tattgcagct tataatggtt acaaataaag    7440

caatagcatc acaaatttca caaataaagc attttttca ctgcattcta gttgtggttt    7500

gtccaaactc atcaatgtat cttatcatgt ctggctctag ctatcccgcc cctaactccg    7560

cccatcccgc cccatggctg actaatttt ttatttatg cagaggccga ggccgcctcg     7620

gcctctgagc tattccagaa gtagtgagga ggctttttg gaggcctagg acgtaccca    7680

attcgcccta tagtgagtcg tattacgcgc gctcactggc cgtcgtttta caacgtcgtg    7740

actgggaaaa ccctggcgtt acccaactta atcgccttgc agcacatccc cctttcgcca    7800

gctggcgtaa tagcgaagag gcccgcaccg atcgcccttc ccaacagttg cgcagcctga    7860

atggcgaatg ggacgcgccc tgtagcggcg cattaagcgc ggcgggtgtg gtggttacgc    7920

gcagcgtgac cgctacactt gccagcgccc tagcgcccgc tcctttcgct ttcttccctt    7980

cctttctcgc cacgttcgcc ggctttcccc gtcaagctct aaatcgggg ctcccttag     8040

ggttccgatt tagtgcttta cggcacctcg accccaaaa acttgattag ggtgatggtt    8100

cacgtagtgg gccatcgccc tgatagacgg ttttcgccc tttgacgttg gagtccacgt    8160

tctttaatag tggactcttg ttccaaactg gaacaacact caaccctatc tcggtctatt    8220

cttttgattt ataagggatt ttgccgattt cggcctattg gttaaaaaat gagctgattt    8280

aacaaaaatt taacgcgaat tttaacaaaa tattaacgct tacaatttag gtggcacttt    8340

tcggggaaat gtgcgcggaa cccctatttg tttatttttc taaatacatt caaatatgta    8400

tccgctcatg agacaataac cctgataaat gcttcaataa tattgaaaaa ggaagagtat    8460

gagtattcaa catttccgtg tcgcccttat ccctttttt gcggcatttt gccttcctgt    8520

ttttgctcac ccagaaacgc tggtgaaagt aaaagatgct gaagatcagt tgggtgcacg    8580

agtgggttac atcgaactgg atctcaacag cggtaagatc cttgagagtt ttcgccccga    8640

agaacgtttt ccaatgatga gcacttttaa agttctgcta tgtggcgcgg tattatcccg    8700

tattgacgcc gggcaagagc aactcggtcg ccgcatacac tattctcaga atgacttggt    8760

tgagtactca ccagtcacag aaaagcatct tacggatggc atgacagtaa gagaattatg    8820

cagtgctgcc ataaccatga gtgataacac tgcggccaac ttacttctga caacgatcgg    8880

aggaccgaag gagctaaccg cttttttgca acatggggg atcatgtaa ctcgccttga    8940

tcgttgggaa ccggagctga atgaagccat accaaacgac gagcgtgaca ccacgatgcc    9000

tgtagcaatg gcaacaacgt tgcgcaaact attaactggc gaactactta ctctagcttc    9060

ccggcaacaa ttaatagact ggatggaggc ggataaagtt gcaggaccac ttctgcgctc    9120

ggcccttccg gctggctggt ttattgctga taaatctgga gccggtgagc gtgggtctcg    9180

cggtatcatt gcagcactgg ggccagatgg taagccctcc cgtatcgtag ttatctacac    9240

gacggggagt caggcaacta tggatgaacg aaatagacag atcgctgaga taggtgcctc    9300

actgattaag cattggtaac tgtcagacca agtttactca tatatacttt agattgattt    9360

aaaacttcat ttttaattta aaaggatcta ggtgaagatc cttttttgata atctcatgac    9420

caaaatccct taacgtgagt tttcgttcca ctgagcgtca gaccccgtag aaaagatcaa    9480
```

aggatcttc 9489

<210> SEQ ID NO 37
<211> LENGTH: 9501
<212> TYPE: DNA
<213> ORGANISM: Artificial Sequence
<220> FEATURE:
<223> OTHER INFORMATION: Feedforward HSPB with gfp kozak 10%

<400> SEQUENCE: 37
ttgagatcct ttttttctgc gcgtaatctg ctgcttgcaa acaaaaaaac caccgctacc 60
agcggtggtt tgtttgccgg atcaagagct accaactctt tttccgaagg taactggctt 120
cagcagagcg cagataccaa atactgttct tctagtgtag ccgtagttag gccaccactt 180
caagaactct gtagcaccgc ctacatacct cgctctgcta atcctgttac cagtggctgc 240
tgccagtggc gataagtcgt gtcttaccgg gttggactca agacgatagt taccggataa 300
ggcgcagcgg tcgggctgaa cggggggttc gtgcacacag cccagcttgg agcgaacgac 360
ctacaccgaa ctgagatacc tacagcgtga gctatgagaa agcgccacgc ttcccgaagg 420
gagaaaggcg gacaggtatc cggtaagcgg cagggtcgga acaggagagc gcacgaggga 480
gcttccaggg ggaaacgcct ggtatcttta tagtcctgtc gggtttcgcc acctctgact 540
tgagcgtcga tttttgtgat gctcgtcagg ggggcggagc ctatggaaaa acgccagcaa 600
cgcggccttt ttacggttcc tggccttttg ctggcctttt gctcacatgt tctttcctgc 660
gttatcccct gattctgtgg ataaccgtat taccgccttt gagtgagctg ataccgctcg 720
ccgcagccga acgaccgagc gcagcgagtc agtgagcgag gaagcggaag agcgcccaat 780
acgcaaaccg cctctccccg cgcgttggcc gattcattaa tgcagctggc acgacaggtt 840
tcccgactgg aaagcgggca gtgagcgcaa cgcaattaat gtgagttagc tcactcatta 900
ggcaccccag gctttacact ttatgcttcc ggctcgtatg ttgtgtggaa ttgtgagcgg 960
ataacaattt cacacaggaa acagctatga ccatgattac gccaagcgcg caattaaccc 1020
tcactaaagg gaacaaaagc tggagctgca agcttggcca ttgcatacgt tgtatccata 1080
tcataatatg tacatttata ttggctcatg tccaacatta ccgccatgtt gacattgatt 1140
attgactagt tattaatagt aatcaattac ggggtcatta gttcatagcc catatatgga 1200
gttccgcgtt acataactta cggtaaatgg cccgcctggc tgaccgccca acgacccccg 1260
cccattgacg tcaataatga cgtatgttcc catagtaacg ccaataggga ctttccattg 1320
acgtcaatgg gtggagtatt tacggtaaac tgcccacttg gcagtacatc aagtgtatca 1380
tatgccaagt acgcccccta ttgacgtcaa tgacggtaaa tggcccgcct ggcattatgc 1440
ccagtacatg accttatggg actttcctac ttggcagtac atctacgtat tagtcatcgc 1500
tattaccatg gtgatgcggt tttggcagta catcaatggg cgtggatagc ggtttgactc 1560
acggggattt ccaagtctcc accccattga cgtcaatggg agtttgtttt ggcaccaaaa 1620
tcaacgggac tttccaaaat gtcgtaacaa ctccgcccca ttgacgcaaa tgggcggtag 1680
gcgtgtacgg tgggaggtct atataagcag agctcgttta gtgaaccggg gtctctctgg 1740
ttagaccaga tctgagcctg ggagctctct ggctaactag ggaacccact gcttaagcct 1800
caataaagct tgccttgagt gcttcaagta gtgtgtgccc gtctgttgtg tgactctggt 1860
aactagagat ccctcagacc cttttagtca gtgtggaaaa tctctagcag tggcgcccga 1920
acagggactt gaaagcgaaa gggaaaccag aggagctctc tcgacgcagg actcggcttg 1980

-continued

```
ctgaagcgcg cacggcaaga ggcgaggggc ggcgactggt gagtacgcca aaaattttga   2040
ctagcggagg ctagaaggag agagatgggt gcgagagcgt cagtattaag cgggggagaa   2100
ttagatcgcg atgggaaaaa attcggttaa ggccaggggg aaagaaaaaa tataaattaa   2160
aacatatagt atgggcaagc agggagctag aacgattcgc agttaatcct ggcctgttag   2220
aaacatcaga aggctgtaga caaatactgg gacagctaca accatccctt cagacaggat   2280
cagaagaact tagatcatta tataatacag tagcaaccct ctattgtgtg catcaaagga   2340
tagagataaa agacaccaag gaagctttag acaagataga ggaagagcaa aacaaaagta   2400
agaccaccgc acagcaagcg gccgctgatc ttcagacctg gaggaggaga tatgagggac   2460
aattggagaa gtgaattata taaatataaa gtagtaaaaa ttgaaccatt aggagtagca   2520
cccaccaagg caaagagaag agtggtgcag agagaaaaaa gagcagtggg aataggagct   2580
ttgttccttg ggttcttggg agcagcagga agcactatgg gcgcagcctc aatgacgctg   2640
acggtacagg ccagacaatt attgtctggt atagtgcagc agcagaacaa tttgctgagg   2700
gctattgagg cgcaacagca tctgttgcaa ctcacagtct ggggcatcaa gcagctccag   2760
gcaagaatcc tggctgtgga aagataccta aaggatcaac agctcctggg gatttggggt   2820
tgctctggaa aactcatttg caccactgct gtgccttgga atgctagttg gagtaataaa   2880
tctctggaac agatttggaa tcacacgacc tggatggagt gggacagaga aattaacaat   2940
tacacaagct taatacactc cttaattgaa gaatcgcaaa accagcaaga aaagaatgaa   3000
caagaattat tggaattaga taaatgggca agtttgtgga attggtttaa cataacaaat   3060
tggctgtggt atataaaatt attcataatg atagtaggag gcttggtagg tttaagaata   3120
gtttttgctg tactttctat agtgaataga gttaggcagg gatattcacc attatcgttt   3180
cagacccacc tcccaacccc gaggggaccc gacaggcccg aaggaataga agaagaaggt   3240
ggagagagag acagagacag atccattcga ttagtgaacg gatctcgacg gtatcgatct   3300
cgacacaaat ggcagtattc atccacaatt ttaaaagaaa aggggggatt ggggggtaca   3360
gtgcagggga aagaatagta gacataatag caacagacat acaaactaaa gaattacaaa   3420
aacaaattac aaaaattcaa aattttcggg tttattacag ggacagcaga gatccagttt   3480
gggaattagc ttgaggatcc tccacagccc cggggagacc ttgcctctaa agttgctgct   3540
tttgcagctc tgccacaacc gcgcgtcctc agagccagcc gggaggagct agaaccttcc   3600
ccgcgtttct ttcagcagcc ctgagtcaga ggcgggctgg ccttgcaagt agccgcccag   3660
ccttcttcgg tctcacggac cgatccgccc gaaccttctc ccggggtcag cgccgcgctg   3720
cgccgcccgg ctgactcagc ccgggcgggc gggcgggagg ctctcgactg ggcgggaagg   3780
tgcgggaagg ttcgcggcgg cggggtcggg gaggtgcaaa aggatgaaaa gcccgtggac   3840
ggagctgagc agatccggcc gggctggcgg cagagaaacc gcagggagag cctcactgct   3900
gagcgcccct cgacgcgggc ggcagcagcc tccgtggcct ccagcatccg acaagaagct   3960
tcggatgggt tgagccatgt ctagactgga caagagcaaa gtcataaact ctgctctgga   4020
attactcaat ggagtcggta tcgaaggcct gacgacaagg aaactcgctc aaaagctggg   4080
agttgagcag cctaccctgt actggcacgt gaagaacaag cgggccctgc tcgatgccct   4140
gccaatcgag atgctggaca ggcatcatac ccactcctgc cccctggaag gcgagtcatg   4200
gcaagacttt ctgcggaaca acgccaagtc ataccgctgt gctctcctct cacatcgcga   4260
cggggctaaa gtgcatctcg gcacccgccc aacagagaaa cagtacgaaa ccctggaaaa   4320
tcagctcgcg ttcctgtgtc agcaaggctt ctccctggag aacgcactgt acgctctgtc   4380
```

```
cgccgtgggc cactttacac tgggctgcgt attggaggaa caggagcatc aagtagcaaa   4440
agaggaaaga gagacaccta ccaccgattc tatgccccca cttctgaaac aagcaattga   4500
gctgttcgac cggcagggag ccgaacctgc cttccttttc ggcctggaac taatcatatg   4560
tggcctggag aaacagctaa agtgcgaaag cggcgggccg accgacgccc ttgacgattt   4620
tgacttagac atgctcccag ccgatgccct tgacgacttt gaccttgata tgctgcctgc   4680
tgacgctctt gacgattttg accttgacat gctccccggg taagtcagat taggccctgg   4740
aagtaatgta caacacgtgc tacggtttgg gaattagctt gacggccctt tcgtcttcac   4800
tcgagtttac tccctatcag tgatagagaa cgtatgaaga gtttactccc tatcagtgat   4860
agagaacgta tgcagacttt actccctatc agtgatagag aacgtataag gagtttactc   4920
cctatcagtg atagagaacg tatgaccagt ttactcccta tcagtgatag agaacgtatc   4980
tacagtttac tccctatcag tgatagagaa cgtatatcca gtttactccc tatcagtgat   5040
agagaacgta tgtcgaggta ggcgtgtacg gtgggcgcct ataaaagcag agctcgttta   5100
gtgaaccgtc agatcgcctg gagcaattcc acaacacttt tgtcttatac ttactaggag   5160
ctcggatcca gtacccttca ccatgggttg agccatggtg agcaagggcg aggagctgtt   5220
caccggggtg gtgcccatcc tggtcgagct ggacggcgac gtaaacggcc acaagttcag   5280
cgtgtccggc gagggcgagg gcgatgccac ctacggcaag ctgaccctga agttcatctg   5340
caccaccggc aagctgcccg tgccctggcc caccctcgtg accaccctga cctacggcgt   5400
gcagtgcttc agccgctacc ccgaccacat gaagcagcac gacttcttca agtccgccat   5460
gcccgaaggc tacgtccagg agcgcaccat cttcttcaag gacgacggca actacaagac   5520
ccgcgccgag gtgaagttcg agggcgacac cctggtgaac cgcatcgagc tgaagggcat   5580
cgacttcaag gaggacggca acatcctggg gcacaagctg gagtacaact acaacagcca   5640
caacgtctat atcatggccg acaagcagaa gaacggcatc aaggtgaact tcaagatccg   5700
ccacaacatc gaggacggca gcgtgcagct cgccgaccac taccagcaga acacccccat   5760
cggcgacggc cccgtgctgc tgcccgacaa ccactacctg agcacccagt ccgccctgag   5820
caaagacccc aacgagaagc gcgatcacat ggtcctgctg gagttcgtga ccgccgccgg   5880
gatcactctc ggcatggacg agctgtacaa gtaatacata caaggccgta cagaattggc   5940
tccggtgccc gtcagtgggc agagcgcaca tcgcccacag tccccgagaa gttgggggga   6000
ggggtcggca attgaaccgg tgcctagaga aggtggcgcg gggtaaactg ggaaagtgat   6060
gtcgtgtact ggctccgcct ttttcccgag ggtgggggag aaccgtatat aagtgcagta   6120
gtcgccgtga acgttctttt tcgcaacggg tttgccgcca gaacacaggt gaccttcacc   6180
atgtcggggg caggtgccac cggccgcgcc atggacgggc cgcgcctgct gctgttgctg   6240
cttctggggg tgtcccttgg aggtgccaag gaggcatgcc ccacaggcct gtacacacac   6300
agcggtgagt gctgcaaagc ctgcaacctg ggcgagggtg tggcccagcc ttgtggagcc   6360
aaccagaccg tgtgtgagcc ctgcctggac agcgtgacgt tctccgacgt ggtgagcgcg   6420
accgagccgt gcaagccgtg caccgagtgc gtggggctcc agagcatgtc ggcgccatgc   6480
gtggaggccg acgacgccgt gtgccgctgc gcctacggct actaccagga tgagacgact   6540
gggcgctgcg aggcgtgccg cgtgtgcgag gcgggctcgg gcctcgtgtt ctcctgccag   6600
gacaagcaga acaccgtgtg cgaggagtgc cccgacggca cgtattccga cgaggccaac   6660
cacgtggacc cgtgcctgcc ctgcaccgtg tgcgaggaca ccgagcgcca gctccgcgag   6720
```

```
tgcacacgct gggccgacgc cgagtgcgag gagatccctg gccgttggat tacacggtcc   6780
acacccccag agggctcgga cagcacagcc cccagcaccc aggagcctga ggcacctcca   6840
gaacaagacc tcatagccag cacggtggca ggtgtggtga ccacagtgat gggcagctcc   6900
cagcccgtgg tgacccgagg caccaccgac aacctcatcc ctgtctattg ctccatcctg   6960
gctgctgtgg ttgtgggtct tgtggcctac atagccttca agaggtggaa cagctgacct   7020
ttcatagaag gcggcggtgg tacctttaag accaatgact tacaaggcag ctgtagatct   7080
tagccacttt ttaaaagaaa aggggggact ggaagggcta attcactccc aacgaagaca   7140
agatctgctt tttgcttgta ctgggtctct ctggttagac cagatctgag cctgggagct   7200
ctctggctaa ctagggaacc cactgcttaa gcctcaataa agcttgcctt gagtgcttca   7260
agtagtgtgt gcccgtctgt tgtgtgactc tggtaactag agatccctca gaccctttta   7320
gtcagtgtgg aaaatctcta gcagtagtag ttcatgtcat cttattattc agtatttata   7380
acttgcaaag aaatgaatat cagagagtga gaggaacttg tttattgcag cttataatgg   7440
ttacaaataa agcaatagca tcacaaattt cacaaataaa gcattttttt cactgcattc   7500
tagttgtggt ttgtccaaac tcatcaatgt atcttatcat gtctggctct agctatcccg   7560
cccctaactc cgcccatccc gccccatggc tgactaattt tttttattta tgcagaggcc   7620
gaggccgcct cggcctctga gctattccag aagtagtgag gaggcttttt tggaggccta   7680
gggacgtacc caattcgccc tatagtgagt cgtattacgc gcgctcactg gccgtcgttt   7740
tacaacgtcg tgactgggaa aaccctggcg ttacccaact taatcgcctt gcagcacatc   7800
ccccttcgc cagctggcgt aatagcgaag aggcccgcac cgatcgccct tcccaacagt    7860
tgcgcagcct gaatggcgaa tgggacgcgc cctgtagcgg cgcattaagc gcggcgggtg   7920
tggtggttac gcgcagcgtg accgctacac ttgccagcgc cctagcgccc gctcctttcg   7980
ctttcttccc ttcctttctc gccacgttcg ccggctttcc ccgtcaagct ctaaatcggg   8040
ggctcccttt agggttccga tttagtgctt tacggcacct cgaccccaaa aaacttgatt   8100
agggtgatgg ttcacgtagt gggccatcgc cctgatagac ggtttttcgc cctttgacgt   8160
tggagtccac gttctttaat agtggactct tgttccaaac tggaacaaca ctcaacccta   8220
tctcggtcta ttcttttgat ttataaggga ttttgccgat ttcggcctat tggttaaaaa   8280
atgagctgat ttaacaaaaa tttaacgcga attttaacaa aatattaacg cttacaattt   8340
aggtggcact tttcggggaa atgtgcgcgg aacccctatt tgtttatttt tctaaataca   8400
ttcaaatatg tatccgctca tgagacaata accctgataa atgcttcaat aatattgaaa   8460
aaggaagagt atgagtattc aacatttccg tgtcgccctt attccctttt ttgcggcatt   8520
ttgccttcct gtttttgctc acccagaaac gctggtgaaa gtaaaagatg ctgaagatca   8580
gttgggtgca cgagtgggtt acatcgaact ggatctcaac agcggtaaga tccttgagag   8640
ttttcgcccc gaagaacgtt ttccaatgat gagcactttt aaagttctgc tatgtggcgc   8700
ggtattatcc cgtattgacg ccgggcaaga gcaactcggt cgccgcatac actattctca   8760
gaatgacttg gttgagtact caccagtcac agaaaagcat cttacggatg gcatgacagt   8820
aagagaatta tgcagtgctg ccataaccat gagtgataac actgcggcca acttacttct   8880
gacaacgatc ggaggaccga aggagctaac cgcttttttg cacaacatgg gggatcatgt   8940
aactcgcctt gatcgttggg aaccggagct gaatgaagcc ataccaaacg acgagcgtga   9000
caccacgatg cctgtagcaa tggcaacaac gttgcgcaaa ctattaactg gcgaactact   9060
tactctagct tcccggcaac aattaataga ctggatggag gcggataaag ttgcaggacc   9120
```

acttctgcgc tcggcccttc cggctggctg gtttattgct gataaatctg gagccggtga 9180
gcgtgggtct cgcggtatca ttgcagcact ggggccagat ggtaagccct cccgtatcgt 9240
agttatctac acgacgggga gtcaggcaac tatggatgaa cgaaatagac agatcgctga 9300
gataggtgcc tcactgatta agcattggta actgtcagac caagtttact catatatact 9360
ttagattgat ttaaaacttc atttttaatt taaaaggatc taggtgaaga tcctttttga 9420
taatctcatg accaaaatcc cttaacgtga gttttcgttc cactgagcgt cagaccccgt 9480
agaaaagatc aaaggatctt c 9501

<210> SEQ ID NO 38
<211> LENGTH: 9489
<212> TYPE: DNA
<213> ORGANISM: Artificial Sequence
<220> FEATURE:
<223> OTHER INFORMATION: Feedforward HSPB with gfp kozak 75%

<400> SEQUENCE: 38
ttgagatcct ttttttctgc gcgtaatctg ctgcttgcaa acaaaaaaac caccgctacc 60
agcggtggtt tgtttgccgg atcaagagct accaactctt tttccgaagg taactggctt 120
cagcagagcg cagataccaa atactgttct tctagtgtag ccgtagttag gccaccactt 180
caagaactct gtagcaccgc ctacatacct cgctctgcta atcctgttac cagtggctgc 240
tgccagtggc gataagtcgt gtcttaccgg gttggactca agacgatagt taccggataa 300
ggcgcagcgg tcgggctgaa cggggggttc gtgcacacag cccagcttgg agcgaacgac 360
ctacaccgaa ctgagatacc tacagcgtga gctatgagaa agcgccacgc ttcccgaagg 420
gagaaaggcg gacaggtatc cggtaagcgg cagggtcgga acaggagagc gcacgaggga 480
gcttccaggg ggaaacgcct ggtatcttta tagtcctgtc gggtttcgcc acctctgact 540
tgagcgtcga tttttgtgat gctcgtcagg ggggcggagc ctatggaaaa acgccagcaa 600
cgcggccttt ttacggttcc tggccttttg ctggcctttt gctcacatgt tctttcctgc 660
gttatcccct gattctgtgg ataaccgtat taccgccttt gagtgagctg ataccgctcg 720
ccgcagccga acgaccgagc gcagcgagtc agtgagcgag gaagcggaag agcgcccaat 780
acgcaaaccg cctctccccg cgcgttggcc gattcattaa tgcagctggc acgacaggtt 840
tcccgactgg aaagcgggca gtgagcgcaa cgcaattaat gtgagttagc tcactcatta 900
ggcaccccag gctttacact ttatgcttcc ggctcgtatg ttgtgtggaa ttgtgagcgg 960
ataacaattt cacacaggaa acagctatga ccatgattac gccaagcgcg caattaaccc 1020
tcactaaagg gaacaaaagc tggagctgca agcttggcca ttgcatacgt tgtatccata 1080
tcataatatg tacatttata ttggctcatg tccaacatta ccgccatgtt gacattgatt 1140
attgactagt tattaatagt aatcaattac ggggtcatta gttcatagcc catatatgga 1200
gttccgcgtt acataactta cggtaaatgg cccgcctggc tgaccgccca acgacccccg 1260
cccattgacg tcaataatga cgtatgttcc catagtaacg ccaataggga ctttccattg 1320
acgtcaatgg gtggagtatt tacggtaaac tgcccacttg gcagtacatc aagtgtatca 1380
tatgccaagt acgcccccta ttgacgtcaa tgacggtaaa tggcccgcct ggcattatgc 1440
ccagtacatg accttatggg actttcctac ttggcagtac atctacgtat tagtcatcgc 1500
tattaccatg gtgatgcggt tttggcagta catcaatggg cgtggatagc ggtttgactc 1560
acggggattt ccaagtctcc accccattga cgtcaatggg agtttgtttt ggcaccaaaa 1620

-continued

```
tcaacgggac tttccaaaat gtcgtaacaa ctccgcccca ttgacgcaaa tgggcggtag   1680
gcgtgtacgg tgggaggtct atataagcag agctcgttta gtgaaccggg gtctctctgg   1740
ttagaccaga tctgagcctg ggagctctct ggctaactag ggaacccact gcttaagcct   1800
caataaagct tgccttgagt gcttcaagta gtgtgtgccc gtctgttgtg tgactctggt   1860
aactagagat ccctcagacc cttttagtca gtgtggaaaa tctctagcag tggcgcccga   1920
acagggactt gaaagcgaaa gggaaaccag aggagctctc tcgacgcagg actcggcttg   1980
ctgaagcgcg cacggcaaga ggcgaggggc ggcgactggt gagtacgcca aaaattttga   2040
ctagcggagg ctagaaggag agagatgggt gcgagagcgt cagtattaag cgggggagaa   2100
ttagatcgcg atgggaaaaa attcggttaa ggccaggggg aaagaaaaaa tataaattaa   2160
aacatatagt atgggcaagc agggagctag aacgattcgc agttaatcct ggcctgttag   2220
aaacatcaga aggctgtaga caaatactgg gacagctaca accatccctt cagacaggat   2280
cagaagaact tagatcatta tataatacag tagcaaccct ctattgtgtg catcaaagga   2340
tagagataaa agacaccaag gaagctttag acaagataga ggaagagcaa aacaaaagta   2400
agaccaccgc acagcaagcg gccgctgatc ttcagacctg gaggaggaga tatgagggac   2460
aattggagaa gtgaattata taaatataaa gtagtaaaaa ttgaaccatt aggagtagca   2520
cccaccaagg caaagagaag agtggtgcag agagaaaaaa gagcagtggg aataggagct   2580
ttgttccttg ggttcttggg agcagcagga agcactatgg gcgcagcctc aatgacgctg   2640
acggtacagg ccagacaatt attgtctggt atagtgcagc agcagaacaa tttgctgagg   2700
gctattgagg cgcaacagca tctgttgcaa ctcacagtct ggggcatcaa gcagctccag   2760
gcaagaatcc tggctgtgga aagataccta aaggatcaac agctcctggg gatttggggt   2820
tgctctggaa aactcatttg caccactgct gtgccttgga atgctagttg gagtaataaa   2880
tctctggaac agatttggaa tcacacgacc tggatggagt gggacagaga aattaacaat   2940
tacacaagct taatacactc cttaattgaa gaatcgcaaa accagcaaga aaagaatgaa   3000
caagaattat tggaattaga taaatgggca agtttgtgga attggtttaa cataacaaat   3060
tggctgtggt atataaaatt attcataatg atagtaggag gcttggtagg tttaagaata   3120
gtttttgctg tactttctat agtgaataga gttaggcagg gatattcacc attatcgttt   3180
cagacccacc tcccaacccc gaggggaccc gacaggcccg aaggaataga agaagaaggt   3240
ggagagagag acagagacag atccattcga ttagtgaacg gatctcgacg gtatcgatct   3300
cgacacaaat ggcagtattc atccacaatt ttaaaagaaa aggggggatt ggggggtaca   3360
gtgcagggga aagaatagta gacataatag caacagacat acaaactaaa gaattacaaa   3420
aacaaattac aaaaattcaa aattttcggg tttattacag ggacagcaga gatccagttt   3480
gggaattagc ttgaggatcc tccacagccc cggggagacc ttgcctctaa agttgctgct   3540
tttgcagctc tgccacaacc gcgcgtcctc agagccagcc gggaggagct agaaccttcc   3600
ccgcgtttct ttcagcagcc ctgagtcaga ggcgggctgg ccttgcaagt agccgcccag   3660
ccttcttcgg tctcacggac cgatccgccc gaaccttctc ccggggtcag cgccgcgctg   3720
cgccgcccgg ctgactcagc ccgggcgggc gggcgggagg ctctcgactg ggcgggaagg   3780
tgcgggaagg ttcgcggcgg cggggtcggg gaggtgcaaa aggatgaaaa gcccgtggac   3840
ggagctgagc agatccggcc gggctggcgg cagagaaacc gcagggagag cctcactgct   3900
gagcgcccct cgacgcgggc ggcagcagcc tccgtggcct ccagcatccg acaagaagct   3960
tcggatgggt tgagccatgt ctagactgga caagagcaaa gtcataaact ctgctctgga   4020
```

attactcaat ggagtcggta tcgaaggcct gacgacaagg aaactcgctc aaaagctggg 4080
agttgagcag cctaccctgt actggcacgt gaagaacaag cgggccctgc tcgatgccct 4140
gccaatcgag atgctggaca ggcatcatac ccactcctgc cccctggaag gcgagtcatg 4200
gcaagacttt ctgcggaaca acgccaagtc ataccgctgt gctctcctct cacatcgcga 4260
cggggctaaa gtgcatctcg gcacccgccc aacagagaaa cagtacgaaa ccctggaaaa 4320
tcagctcgcg ttcctgtgtc agcaaggctt ctccctggag aacgcactgt acgctctgtc 4380
cgccgtgggc cactttacac tgggctgcgt attggaggaa caggagcatc aagtagcaaa 4440
agaggaaaga gagacaccta ccaccgattc tatgccccca cttctgaaac aagcaattga 4500
gctgttcgac cggcagggag ccgaacctgc cttccttttc ggcctggaac taatcatatg 4560
tggcctggag aaacagctaa agtgcgaaag cggcgggccg accgacgccc ttgacgattt 4620
tgacttagac atgctcccag ccgatgccct tgacgacttt gaccttgata tgctgcctgc 4680
tgacgctctt gacgattttg accttgacat gctccccggg taagtcagat taggccctgg 4740
aagtaatgta caacacgtgc tacggtttgg gaattagctt gacggccctt tcgtcttcac 4800
tcgagtttac tccctatcag tgatagagaa cgtatgaaga gtttactccc tatcagtgat 4860
agagaacgta tgcagacttt actccctatc agtgatagag aacgtataag gagtttactc 4920
cctatcagtg atagagaacg tatgaccagt ttactcccta tcagtgatag agaacgtatc 4980
tacagtttac tccctatcag tgatagagaa cgtatatcca gtttactccc tatcagtgat 5040
agagaacgta tgtcgaggta ggcgtgtacg gtgggcgcct ataaaagcag agctcgttta 5100
gtgaaccgtc agatcgcctg gagcaattcc acaacacttt tgtcttatac ttactaggag 5160
ctcggatcca gtacccttcc ggatggtgag caagggcgag gagctgttca ccggggtggt 5220
gcccatcctg gtcgagctgg acggcgacgt aaacggccac aagttcagcg tgtccggcga 5280
gggcgagggc gatgccacct acggcaagct gaccctgaag ttcatctgca ccaccggcaa 5340
gctgcccgtg ccctggccca ccctcgtgac caccctgacc tacggcgtgc agtgcttcag 5400
ccgctacccc gaccacatga agcagcacga cttcttcaag tccgccatgc ccgaaggcta 5460
cgtccaggag cgcaccatct tcttcaagga cgacggcaac tacaagaccc gcgccgaggt 5520
gaagttcgag ggcgacaccc tggtgaaccg catcgagctg aagggcatcg acttcaagga 5580
ggacggcaac atcctggggc acaagctgga gtacaactac aacagccaca acgtctatat 5640
catggccgac aagcagaaga acggcatcaa ggtgaacttc aagatccgcc acaacatcga 5700
ggacggcagc gtgcagctcg ccgaccacta ccagcagaac acccccatcg gcgacggccc 5760
cgtgctgctg cccgacaacc actacctgag cacccagtcc gccctgagca aagaccccaa 5820
cgagaagcgc gatcacatgg tcctgctgga gttcgtgacc gccgccggga tcactctcgg 5880
catggacgag ctgtacaagt aatacataca aggccgtaca gaattggctc cggtgcccgt 5940
cagtgggcag agcgcacatc gcccacagtc cccgagaagt tggggggagg ggtcggcaat 6000
tgaaccggtg cctagagaag gtggcgcggg gtaaactggg aaagtgatgt cgtgtactgg 6060
ctccgccttt ttcccgaggg tgggggagaa ccgtatataa gtgcagtagt cgccgtgaac 6120
gttctttttc gcaacgggtt tgccgccaga acacaggtga ccttcaccat gtcgggggca 6180
ggtgccaccg gccgcgccat ggacgggccg cgcctgctgc tgttgctgct tctgggggtg 6240
tcccttggag gtgccaagga ggcatgcccc acaggcctgt acacacacag cggtgagtgc 6300
tgcaaagcct gcaacctggg cgagggtgtg gcccagcctt gtggagccaa ccagaccgtg 6360

| | |
|---|---|
| tgtgagccct gcctggacag cgtgacgttc tccgacgtgg tgagcgcgac cgagccgtgc | 6420 |
| aagccgtgca ccgagtgcgt ggggctccag agcatgtcgg cgccatgcgt ggaggccgac | 6480 |
| gacgccgtgt gccgctgcgc ctacggctac taccaggatg agacgactgg gcgctgcgag | 6540 |
| gcgtgccgcg tgtgcgaggc gggctcgggc ctcgtgttct cctgccagga caagcagaac | 6600 |
| accgtgtgcg aggagtgccc cgacggcacg tattccgacg aggccaacca cgtggacccg | 6660 |
| tgcctgccct gcaccgtgtg cgaggacacc gagcgcagc tccgcgagtg cacacgctgg | 6720 |
| gccgacgccg agtgcgagga gatccctggc cgttggatta cacggtccac accccagag | 6780 |
| ggctcggaca gcacagcccc cagcacccag gagcctgagg cacctccaga caagacctc | 6840 |
| atagccagca cggtggcagg tgtggtgacc acagtgatgg gcagctccca gcccgtggtg | 6900 |
| acccgaggca ccaccgacaa cctcatccct gtctattgct ccatcctggc tgctgtggtt | 6960 |
| gtgggtcttg tggcctacat agccttcaag aggtggaaca gctgacctttt catagaaggc | 7020 |
| ggcggtggta cctttaagac caatgactta caaggcagct gtagatctta gccactttt | 7080 |
| aaaagaaaag gggggactgg aagggctaat tcactcccaa cgaagacaag atctgctttt | 7140 |
| tgcttgtact gggtctctct ggttagacca gatctgagcc tgggagctct ctggctaact | 7200 |
| agggaaccca ctgcttaagc ctcaataaag cttgccttga gtgcttcaag tagtgtgtgc | 7260 |
| ccgtctgttg tgtgactctg gtaactagag atccctcaga cccttttagt cagtgtggaa | 7320 |
| aatctctagc agtagtagtt catgtcatct tattattcag tatttataac ttgcaaagaa | 7380 |
| atgaatatca gagagtgaga ggaacttgtt tattgcagct tataatggtt acaaataaag | 7440 |
| caatagcatc acaaatttca caaataaagc atttttttca ctgcattcta gttgtggttt | 7500 |
| gtccaaactc atcaatgtat cttatcatgt ctggctctag ctatcccgcc cctaactccg | 7560 |
| cccatcccgc cccatggctg actaatttt tttatttatg cagaggccga ggccgcctcg | 7620 |
| gcctctgagc tattccagaa gtagtgagga ggcttttttg gaggcctagg acgtaccca | 7680 |
| attcgcccta tagtgagtcg tattacgcgc gctcactggc cgtcgtttta caacgtcgtg | 7740 |
| actgggaaaa ccctggcgtt acccaactta atcgccttgc agcacatccc cctttcgcca | 7800 |
| gctggcgtaa tagcgaagag gcccgcaccg atcgcccttc ccaacagttg cgcagcctga | 7860 |
| atggcgaatg ggacgcgccc tgtagcggcg cattaagcgc ggcgggtgtg gtggttacgc | 7920 |
| gcagcgtgac cgctacactt gccagcgccc tagcgcccgc tcctttcgct ttcttccctt | 7980 |
| cctttctcgc cacgttcgcc ggctttcccc gtcaagctct aaatcggggg ctccctttag | 8040 |
| ggttccgatt tagtgcttta cggcacctcg accccaaaaa acttgattag ggtgatggtt | 8100 |
| cacgtagtgg gccatcgccc tgatagacgg ttttcgccc tttgacgttg gagtccacgt | 8160 |
| tctttaatag tggactcttg ttccaaactg gaacaacact caaccctatc tcggtctatt | 8220 |
| cttttgattt ataagggatt ttgccgattt cggcctattg gttaaaaaat gagctgattt | 8280 |
| aacaaaaatt taacgcgaat tttaacaaaa tattaacgct tacaatttag gtggcacttt | 8340 |
| tcggggaaat gtgcgcggaa cccctatttg tttatttttc taaatacatt caaatatgta | 8400 |
| tccgctcatg agacaataac cctgataaat gcttcaataa tattgaaaaa ggaagagtat | 8460 |
| gagtattcaa catttccgtg tcgcccttat tccctttttt gcggcatttt gccttcctgt | 8520 |
| ttttgctcac ccagaaacgc tggtgaaagt aaaagatgct gaagatcagt tgggtgcacg | 8580 |
| agtgggttac atcgaactgg atctcaacag cggtaagatc cttgagagtt ttcgccccga | 8640 |
| agaacgtttt ccaatgatga gcacttttaa agttctgcta tgtggcgcgg tattatcccg | 8700 |
| tattgacgcc gggcaagagc aactcggtcg ccgcatacac tattctcaga atgacttggt | 8760 |

tgagtactca ccagtcacag aaaagcatct tacggatggc atgacagtaa gagaattatg 8820
cagtgctgcc ataaccatga gtgataacac tgcggccaac ttacttctga caacgatcgg 8880
aggaccgaag gagctaaccg cttttttgca caacatgggg gatcatgtaa ctcgccttga 8940
tcgttgggaa ccggagctga atgaagccat accaaacgac gagcgtgaca ccacgatgcc 9000
tgtagcaatg gcaacaacgt tgcgcaaact attaactggc gaactactta ctctagcttc 9060
ccggcaacaa ttaatagact ggatggaggc ggataaagtt gcaggaccac ttctgcgctc 9120
ggcccttccg gctggctggt ttattgctga taaatctgga gccggtgagc gtgggtctcg 9180
cggtatcatt gcagcactgg ggccagatgg taagccctcc cgtatcgtag ttatctacac 9240
gacggggagt caggcaacta tggatgaacg aaatagacag atcgctgaga taggtgcctc 9300
actgattaag cattggtaac tgtcagacca agtttactca tatatacttt agattgattt 9360
aaaacttcat ttttaattta aaaggatcta ggtgaagatc ctttttgata atctcatgac 9420
caaaatccct taacgtgagt tttcgttcca ctgagcgtca gaccccgtag aaaagatcaa 9480
aggatcttc 9489

<210> SEQ ID NO 39
<211> LENGTH: 9623
<212> TYPE: DNA
<213> ORGANISM: Artificial Sequence
<220> FEATURE:
<223> OTHER INFORMATION: Feedforward HSPB'1

<400> SEQUENCE: 39
ttgagatcct ttttttctgc gcgtaatctg ctgcttgcaa acaaaaaaac caccgctacc 60
agcggtggtt tgtttgccgg atcaagagct accaactctt tttccgaagg taactggctt 120
cagcagagcg cagataccaa atactgttct tctagtgtag ccgtagttag gccaccactt 180
caagaactct gtagcaccgc ctacatacct cgctctgcta atcctgttac cagtggctgc 240
tgccagtggc gataagtcgt gtcttaccgg gttggactca agacgatagt taccggataa 300
ggcgcagcgg tcgggctgaa cggggggttc gtgcacacag cccagcttgg agcgaacgac 360
ctacaccgaa ctgagatacc tacagcgtga gctatgagaa agcgccacgc ttcccgaagg 420
gagaaaggcg gacaggtatc cggtaagcgg cagggtcgga acaggagagc gcacgaggga 480
gcttccaggg ggaaacgcct ggtatcttta tagtcctgtc gggtttcgcc acctctgact 540
tgagcgtcga tttttgtgat gctcgtcagg ggggcggagc ctatggaaaa acgccagcaa 600
cgcggccttt ttacggttcc tggccttttg ctggcctttt gctcacatgt tctttcctgc 660
gttatcccct gattctgtgg ataaccgtat taccgccttt gagtgagctg ataccgctcg 720
ccgcagccga acgaccgagc gcagcgagtc agtgagcgag gaagcggaag agcgcccaat 780
acgcaaaccg cctctccccg cgcgttggcc gattcattaa tgcagctggc acgacaggtt 840
tcccgactgg aaagcgggca gtgagcgcaa cgcaattaat gtgagttagc tcactcatta 900
ggcaccccag gctttacact ttatgcttcc ggctcgtatg ttgtgtggaa ttgtgagcgg 960
ataacaattt cacacaggaa acagctatga ccatgattac gccaagcgcg caattaaccc 1020
tcactaaagg gaacaaaagc tggagctgca agcttggcca ttgcatacgt tgtatccata 1080
tcataatatg tacatttata ttggctcatg tccaacatta ccgccatgtt gacattgatt 1140
attgactagt tattaatagt aatcaattac ggggtcatta gttcatagcc catatatgga 1200
gttccgcgtt acataactta cggtaaatgg cccgcctggc tgaccgccca acgacccccg 1260

-continued

```
cccattgacg tcaataatga cgtatgttcc catagtaacg ccaataggga ctttccattg   1320
acgtcaatgg gtggagtatt tacggtaaac tgcccacttg gcagtacatc aagtgtatca   1380
tatgccaagt acgcccccta ttgacgtcaa tgacggtaaa tggcccgcct ggcattatgc   1440
ccagtacatg accttatggg actttcctac ttggcagtac atctacgtat tagtcatcgc   1500
tattaccatg gtgatgcggt tttggcagta catcaatggg cgtggatagc ggtttgactc   1560
acggggattt ccaagtctcc accccattga cgtcaatggg agtttgtttt ggcaccaaaa   1620
tcaacgggac tttccaaaat gtcgtaacaa ctccgcccca ttgacgcaaa tgggcggtag   1680
gcgtgtacgg tgggaggtct atataagcag agctcgttta gtgaaccggg gtctctctgg   1740
ttagaccaga tctgagcctg ggagctctct ggctaactag ggaacccact gcttaagcct   1800
caataaagct tgccttgagt gcttcaagta gtgtgtgccc gtctgttgtg tgactctggt   1860
aactagagat ccctcagacc cttttagtca gtgtggaaaa tctctagcag tggcgcccga   1920
acagggactt gaaagcgaaa gggaaaccag aggagctctc tcgacgcagg actcggcttg   1980
ctgaagcgcg cacggcaaga ggcgaggggc ggcgactggt gagtacgcca aaaattttga   2040
ctagcggagg ctagaaggag agagatgggt gcgagagcgt cagtattaag cgggggagaa   2100
ttagatcgcg atgggaaaaa attcggttaa ggccaggggg aaagaaaaaa tataaattaa   2160
aacatatagt atgggcaagc agggagctag aacgattcgc agttaatcct ggcctgttag   2220
aaacatcaga aggctgtaga caaatactgg gacagctaca accatccctt cagacaggat   2280
cagaagaact tagatcatta tataatacag tagcaaccct ctattgtgtg catcaaagga   2340
tagagataaa agacaccaag gaagctttag acaagataga ggaagagcaa aacaaaagta   2400
agaccaccgc acagcaagcg gccgctgatc ttcagacctg gaggaggaga tatgagggac   2460
aattggagaa gtgaattata taaatataaa gtagtaaaaa ttgaaccatt aggagtagca   2520
cccaccaagg caaagagaag agtggtgcag agagaaaaaa gagcagtggg aataggagct   2580
ttgttccttg ggttcttggg agcagcagga agcactatgg gcgcagcctc aatgacgctg   2640
acggtacagg ccagacaatt attgtctggt atagtgcagc agcagaacaa tttgctgagg   2700
gctattgagg cgcaacagca tctgttgcaa ctcacagtct ggggcatcaa gcagctccag   2760
gcaagaatcc tggctgtgga aagataccta aaggatcaac agctcctggg gatttggggt   2820
tgctctggaa aactcatttg caccactgct gtgccttgga atgctagttg gagtaataaa   2880
tctctggaac agatttggaa tcacacgacc tggatggagt gggacagaga aattaacaat   2940
tacacaagct taatacactc cttaattgaa gaatcgcaaa accagcaaga aaagaatgaa   3000
caagaattat tggaattaga taaatgggca agtttgtgga attggtttaa cataacaaat   3060
tggctgtggt atataaaatt attcataatg atagtaggag gcttggtagg tttaagaata   3120
gtttttgctg tactttctat agtgaataga gttaggcagg gatattcacc attatcgttt   3180
cagacccacc tcccaacccc gaggggaccc gacaggcccg aaggaataga agaagaaggt   3240
ggagagagag acagagacag atccattcga ttagtgaacg gatctcgacg gtatcgatct   3300
cgacacaaat ggcagtattc atccacaatt ttaaaagaaa aggggggatt ggggggtaca   3360
gtgcagggga aagaatagta gacataatag caacagacat acaaactaaa gaattacaaa   3420
aacaaattac aaaaattcaa aattttcggg tttattacag ggacagcaga gatccagttt   3480
gggaattagc ttgaatcgat aggtaccgag ctcttacgcg tgctagcccc gatgttttct   3540
gagttacttt tgtatcccca cccccctcg actccttctc taggcctcta aagttgctgc   3600
ttttgcagcc tctgccacaa ccgcgcgtcc tcagagccag cccggaggag ctagaacctt   3660
```

```
ccccgcattt ctttcagcag cctgagtcag aggcgggctg gcctggcgta gccgcccagc   3720
ctcgcggctc atgccccgat ctgcccgaac cttctcccgg ggtcagcgcc gcgccgcgcc   3780
acccggctga gtcagcccgg gcgggcgaga ggctctcaac tgggcgggaa ggtgcgggaa   3840
ggtgcggaaa ggttcgcgaa agttcgcggc ggcgggggtc gggtgaggcg caaaaggata   3900
aaaagccggt ggaagcggag ctgagcagat ccgagccggg ctggctgcag agaaaccgca   3960
gggagagcct cactgctgag cgcccctcga cggcggagcg gcagcagcct ccgtggcctc   4020
cagcatccga caagaagctt gaattcgagc tcgccgggga tcctctagtc agctgacgcg   4080
tgctagcgcg gccgcaccac tagtgccacc atgtctagac tggacaagag caaagtcata   4140
aactctgctc tggaattact caatggagtc ggtatcgaag gcctgacgac aaggaaactc   4200
gctcaaaagc tgggagttga gcagcctacc ctgtactggc acgtgaagaa caagcgggcc   4260
ctgctcgatg ccctgccaat cgagatgctg gacaggcatc atacccactc ctgcccccctg   4320
gaaggcgagt catggcaaga ctttctgcgg aacaacgcca agtcataccg ctgtgctctc   4380
ctctcacatc gcgacggggc taaagtgcat ctcggcaccc gcccaacaga gaaacagtac   4440
gaaaccctgg aaaatcagct cgcgttcctg tgtcagcaag gcttctccct ggagaacgca   4500
ctgtacgctc tgtccgccgt gggccacttt acactgggct gcgtattgga ggaacaggag   4560
catcaagtag caaaagagga aagagagaca cctaccaccg attctatgcc cccacttctg   4620
aaacaagcaa ttgagctgtt cgaccggcag ggagccgaac ctgccttcct tttcggcctg   4680
gaactaatca tatgtggcct ggagaaacag ctaaagtgcg aaagcggcgg gccgaccgac   4740
gcccttgacg attttgactt agacatgctc ccagccgatg cccttgacga ctttgacctt   4800
gatatgctgc ctgctgacgc tcttgacgat tttgaccttg acatgctccc cgggtaagtc   4860
agattaggcc ctggaagtaa tgtacaacac gtgctacggt ttgggaatta gcttgacggc   4920
cctttcgtct tcactcgagt ttactcccta tcagtgatag agaacgtatg aagagtttac   4980
tccctatcag tgatagagaa cgtatgcaga ctttactccc tatcagtgat agagaacgta   5040
taaggagttt actccctatc agtgatagag aacgtatgac cagtttactc cctatcagtg   5100
atagagaacg tatctacagt ttactcccta tcagtgatag agaacgtata tccagtttac   5160
tccctatcag tgatagagaa cgtatgtcga ggtaggcgtg tacggtgggc gcctataaaa   5220
gcagagctcg tttagtgaac cgtcagatcg cctggagcaa ttccacaaca cttttgtctt   5280
atacttacta ggagctcgga tccagtaccc ttcaccatgg tgagcaaggg cgaggagctg   5340
ttcaccgggg tggtgcccat cctggtcgag ctggacggcg acgtaaacgg ccacaagttc   5400
agcgtgtccg gcgagggcga gggcgatgcc acctacggca agctgaccct gaagttcatc   5460
tgcaccaccg gcaagctgcc cgtgccctgg cccaccctcg tgaccaccct gacctacggc   5520
gtgcagtgct tcagccgcta ccccgaccac atgaagcagc acgacttctt caagtccgcc   5580
atgcccgaag gctacgtcca ggagcgcacc atcttcttca aggacgacgg caactacaag   5640
acccgcgccg aggtgaagtt cgagggcgac accctggtga accgcatcga gctgaagggc   5700
atcgacttca aggaggacgg caacatcctg gggcacaagc tggagtacaa ctacaacagc   5760
cacaacgtct atatcatggc cgacaagcag aagaacggca tcaaggtgaa cttcaagatc   5820
cgccacaaca tcgaggacgg cagcgtgcag ctcgccgacc actaccagca gaacaccccc   5880
atcggcgacg gccccgtgct gctgcccgac aaccactacc tgagcaccca gtccgccctg   5940
agcaaagacc ccaacgagaa gcgcgatcac atggtcctgc tggagttcgt gaccgccgcc   6000
```

-continued

```
gggatcactc tcggcatgga cgagctgtac aagtaataca tacaaggccg tacagaattg   6060
gctccggtgc ccgtcagtgg gcagagcgca catcgcccac agtccccgag aagttggggg   6120
gaggggtcgg caattgaacc ggtgcctaga gaaggtggcg cggggtaaac tgggaaagtg   6180
atgtcgtgta ctggctccgc ctttttcccg agggtggggg agaaccgtat ataagtgcag   6240
tagtcgccgt gaacgttctt tttcgcaacg ggtttgccgc cagaacacag gtgaccttca   6300
ccatgtcggg ggcaggtgcc accggccgcg ccatggacgg gccgcgcctg ctgctgttgc   6360
tgcttctggg ggtgtccctt ggaggtgcca aggaggcatg ccccacaggc ctgtacacac   6420
acagcggtga gtgctgcaaa gcctgcaacc tgggcgaggg tgtggcccag ccttgtggag   6480
ccaaccagac cgtgtgtgag ccctgcctgg acagcgtgac gttctccgac gtggtgagcg   6540
cgaccgagcc gtgcaagccg tgcaccgagt gcgtggggct ccagagcatg tcggcgccat   6600
gcgtggaggc cgacgacgcc gtgtgccgct gcgcctacgg ctactaccag gatgagacga   6660
ctgggcgctg cgaggcgtgc cgcgtgtgcg aggcgggctc gggcctcgtg ttctcctgcc   6720
aggacaagca gaacaccgtg tgcgaggagt gccccgacgg cacgtattcc gacgaggcca   6780
accacgtgga cccgtgcctg ccctgcaccg tgtgcgagga caccgagcgc cagctccgcg   6840
agtgcacacg ctgggccgac gccgagtgcg aggagatccc tggccgttgg attacacggt   6900
ccacaccccc agagggctcg gacagcacag cccccagcac ccaggagcct gaggcacctc   6960
cagaacaaga cctcatagcc agcacggtgg caggtgtggt gaccacagtg atgggcagct   7020
cccagcccgt ggtgacccga ggcaccaccg acaacctcat ccctgtctat tgctccatcc   7080
tggctgctgt ggttgtgggt cttgtggcct acatagcctt caagaggtgg aacagctgac   7140
ctttcataga aggcggcggt ggtaccttta agaccaatga cttacaaggc agctgtagat   7200
cttagccact ttttaaaaga aaagggggga ctggaagggc taattcactc ccaacgaaga   7260
caagatctgc tttttgcttg tactgggtct ctctggttag accagatctg agcctgggag   7320
ctctctggct aactagggaa cccactgctt aagcctcaat aaagcttgcc ttgagtgctt   7380
caagtagtgt gtgcccgtct gttgtgtgac tctggtaact agagatccct cagacccttt   7440
tagtcagtgt ggaaaatctc tagcagtagt agttcatgtc atcttattat tcagtattta   7500
taacttgcaa agaaatgaat atcagagagt gagaggaact tgtttattgc agcttataat   7560
ggttacaaat aaagcaatag catcacaaat ttcacaaata aagcattttt ttcactgcat   7620
tctagttgtg gtttgtccaa actcatcaat gtatcttatc atgtctggct ctagctatcc   7680
cgcccctaac tccgcccatc ccgcccctaa gctgactaat tttttttatt tatgcagagg   7740
ccgaggccgc ctcggcctct gagctattcc agaagtagtg aggaggcttt tttggaggcc   7800
tagggacgta cccaattcgc cctatagtga gtcgtattac gcgcgctcac tggccgtcgt   7860
tttacaacgt cgtgactggg aaaaccctgg cgttacccaa cttaatcgcc ttgcagcaca   7920
tccccctttc gccagctggc gtaatagcga agaggcccgc accgatcgcc cttcccaaca   7980
gttgcgcagc ctgaatggcg aatgggacgc gccctgtagc ggcgcattaa gcgcggcggg   8040
tgtggtggtt acgcgcagcg tgaccgctac acttgccagc gccctagcgc ccgctccttt   8100
cgctttcttc ccttcctttc tcgccacgtt cgccggcttt ccccgtcaag ctctaaatcg   8160
ggggctccct ttagggttcc gatttagtgc tttacggcac ctcgacccca aaaaacttga   8220
ttagggtgat ggttcacgta gtgggccatc gccctgatag acggtttttc gccctttgac   8280
gttggagtcc acgttcttta atagtggact cttgttccaa actggaacaa cactcaaccc   8340
tatctcggtc tattcttttg atttataagg gattttgccg atttcggcct attggttaaa   8400
```

```
aaatgagctg atttaacaaa aatttaacgc gaattttaac aaaatattaa cgcttacaat   8460

ttaggtggca cttttcgggg aaatgtgcgc ggaaccccta tttgtttatt tttctaaata   8520

cattcaaata tgtatccgct catgagacaa taaccctgat aaatgcttca ataatattga   8580

aaaaggaaga gtatgagtat tcaacatttc cgtgtcgccc ttattccctt ttttgcggca   8640

ttttgccttc ctgtttttgc tcacccagaa acgctggtga aagtaaaaga tgctgaagat   8700

cagttgggtg cacgagtggg ttacatcgaa ctggatctca acagcggtaa gatccttgag   8760

agttttcgcc ccgaagaacg ttttccaatg atgagcactt ttaaagttct gctatgtggc   8820

gcggtattat cccgtattga cgccgggcaa gagcaactcg gtcgccgcat acactattct   8880

cagaatgact tggttgagta ctcaccagtc acagaaaagc atcttacgga tggcatgaca   8940

gtaagagaat tatgcagtgc tgccataacc atgagtgata acactgcggc caacttactt   9000

ctgacaacga tcggaggacc gaaggagcta accgcttttt tgcacaacat gggggatcat   9060

gtaactcgcc ttgatcgttg ggaaccggag ctgaatgaag ccataccaaa cgacgagcgt   9120

gacaccacga tgcctgtagc aatggcaaca acgttgcgca aactattaac tggcgaacta   9180

cttactctag cttcccggca acaattaata gactggatgg aggcggataa agttgcagga   9240

ccacttctgc gctcggccct tccggctggc tggtttattg ctgataaatc tggagccggt   9300

gagcgtgggt ctcgcggtat cattgcagca ctggggccag atggtaagcc ctcccgtatc   9360

gtagttatct acacgacggg gagtcaggca actatggatg aacgaaatag acagatcgct   9420

gagataggtg cctcactgat taagcattgg taactgtcag accaagttta ctcatatata   9480

ctttagattg atttaaaact tcatttttaa tttaaaagga tctaggtgaa gatccttttt   9540

gataatctca tgaccaaaat cccttaacgt gagttttcgt tccactgagc gtcagacccc   9600

gtagaaaaga tcaaaggatc ttc                                          9623
```

```
<210> SEQ ID NO 40
<211> LENGTH: 9624
<212> TYPE: DNA
<213> ORGANISM: Artificial Sequence
<220> FEATURE:
<223> OTHER INFORMATION: Feedforward SYNHSPB'3

<400> SEQUENCE: 40
```

```
ttgagatcct ttttttctgc gcgtaatctg ctgcttgcaa acaaaaaaac caccgctacc     60

agcggtggtt tgtttgccgg atcaagagct accaactctt tttccgaagg taactggctt    120

cagcagagcg cagataccaa atactgttct tctagtgtag ccgtagttag gccaccactt    180

caagaactct gtagcaccgc ctacatacct cgctctgcta atcctgttac cagtggctgc    240

tgccagtggc gataagtcgt gtcttaccgg gttggactca agacgatagt taccggataa    300

ggcgcagcgg tcgggctgaa cggggggttc gtgcacacag cccagcttgg agcgaacgac    360

ctacaccgaa ctgagatacc tacagcgtga gctatgagaa agcgccacgc ttcccgaagg    420

gagaaaggcg gacaggtatc cggtaagcgg cagggtcgga acaggagagc gcacgaggga    480

gcttccaggg ggaaacgcct ggtatcttta tagtcctgtc gggtttcgcc acctctgact    540

tgagcgtcga tttttgtgat gctcgtcagg ggggcggagc ctatggaaaa acgccagcaa    600

cgcggccttt ttacggttcc tggccttttg ctggcctttt gctcacatgt tctttcctgc    660

gttatcccct gattctgtgg ataaccgtat taccgccttt gagtgagctg ataccgctcg    720

ccgcagccga acgaccgagc gcagcgagtc agtgagcgag gaagcggaag agcgcccaat    780
```

acgcaaaccg cctctccccg cgcgttggcc gattcattaa tgcagctggc acgacaggtt 840
tcccgactgg aaagcgggca gtgagcgcaa cgcaattaat gtgagttagc tcactcatta 900
ggcaccccag gctttacact ttatgcttcc ggctcgtatg ttgtgtggaa ttgtgagcgg 960
ataacaattt cacacaggaa acagctatga ccatgattac gccaagcgcg caattaaccc 1020
tcactaaagg gaacaaaagc tggagctgca agcttggcca ttgcatacgt tgtatccata 1080
tcataatatg tacatttata ttggctcatg tccaacatta ccgccatgtt gacattgatt 1140
attgactagt tattaatagt aatcaattac ggggtcatta gttcatagcc catatatgga 1200
gttccgcgtt acataactta cggtaaatgg cccgcctggc tgaccgccca acgacccccg 1260
cccattgacg tcaataatga cgtatgttcc catagtaacg ccaataggga ctttccattg 1320
acgtcaatgg gtggagtatt tacggtaaac tgcccacttg gcagtacatc aagtgtatca 1380
tatgccaagt acgcccccta ttgacgtcaa tgacggtaaa tggcccgcct ggcattatgc 1440
ccagtacatg accttatggg actttcctac ttggcagtac atctacgtat tagtcatcgc 1500
tattaccatg gtgatgcggt tttggcagta catcaatggg cgtggatagc ggtttgactc 1560
acggggattt ccaagtctcc accccattga cgtcaatggg agtttgtttt ggcaccaaaa 1620
tcaacgggac tttccaaaat gtcgtaacaa ctccgcccca ttgacgcaaa tgggcggtag 1680
gcgtgtacgg tgggaggtct atataagcag agctcgttta gtgaaccggg gtctctctgg 1740
ttagaccaga tctgagcctg ggagctctct ggctaactag ggaacccact gcttaagcct 1800
caataaagct tgccttgagt gcttcaagta gtgtgtgccc gtctgttgtg tgactctggt 1860
aactagagat ccctcagacc cttttagtca gtgtggaaaa tctctagcag tggcgcccga 1920
acagggactt gaaagcgaaa gggaaaccag aggagctctc tcgacgcagg actcggcttg 1980
ctgaagcgcg cacggcaaga ggcgaggggc ggcgactggt gagtacgcca aaaattttga 2040
ctagcggagg ctagaaggag agagatgggt gcgagagcgt cagtattaag cgggggagaa 2100
ttagatcgcg atgggaaaaa attcggttaa ggccaggggg aaagaaaaaa tataaattaa 2160
aacatatagt atgggcaagc agggagctag aacgattcgc agttaatcct ggcctgttag 2220
aaacatcaga aggctgtaga caaatactgg gacagctaca accatccctt cagacaggat 2280
cagaagaact tagatcatta tataatacag tagcaaccct ctattgtgtg catcaaagga 2340
tagagataaa agacaccaag gaagctttag acaagataga ggaagagcaa aacaaaagta 2400
agaccaccgc acagcaagcg gccgctgatc ttcagacctg gaggaggaga tatgagggac 2460
aattggagaa gtgaattata taaatataaa gtagtaaaaa ttgaaccatt aggagtagca 2520
cccaccaagg caaagagaag agtggtgcag agagaaaaaa gagcagtggg aataggagct 2580
ttgttccttg ggttcttggg agcagcagga agcactatgg gcgcagcctc aatgacgctg 2640
acggtacagg ccagacaatt attgtctggt atagtgcagc agcagaacaa tttgctgagg 2700
gctattgagg cgcaacagca tctgttgcaa ctcacagtct ggggcatcaa gcagctccag 2760
gcaagaatcc tggctgtgga aagataccta aaggatcaac agctcctggg gatttggggt 2820
tgctctggaa aactcatttg caccactgct gtgccttgga atgctagttg gagtaataaa 2880
tctctggaac agatttggaa tcacacgacc tggatggagt gggacagaga aattaacaat 2940
tacacaagct taatacactc cttaattgaa gaatcgcaaa accagcaaga aaagaatgaa 3000
caagaattat tggaattaga taaatgggca agtttgtgga attggtttaa cataacaaat 3060
tggctgtggt atataaaatt attcataatg atagtaggag gcttggtagg tttaagaata 3120
gtttttgctg tactttctat agtgaataga gttaggcagg gatattcacc attatcgttt 3180

-continued

```
cagacccacc tcccaacccc gaggggaccc gacaggcccg aaggaataga agaagaaggt   3240
ggagagagag acagagacag atccattcga ttagtgaacg gatctcgacg gtatcgatct   3300
cgacacaaat ggcagtattc atccacaatt ttaaaagaaa aggggggatt ggggggtaca   3360
gtgcagggga aagaatagta gacataatag caacagacat acaaactaaa gaattacaaa   3420
aacaaattac aaaaattcaa aattttcggg tttattacag ggacagcaga gatccagttt   3480
gggaattagc ttgaccccga tctgcccgaa ccttctcccg gggtcagcgc cgcgccgcgc   3540
cacccggctg cagcagcccg ggcgggcgag aggctctcaa ctgggcggga aggtgcggga   3600
aggtgcggaa aggttcgcga aagttcgcgg ccggactaga gtggcgagat cccccgatct   3660
gcccgaacct tctcccgggg tcagcgccgc gccgcgccac ccggctgcag cagcccgggc   3720
gggcgagagg ctctcaactg ggcgggaagg tgcgggaagg tgcggaaagg ttcgcgaaag   3780
ttcgcggcaa ttagcttgac cccgatctgc ccgaaccttc tcccggggtc agcgccgcgc   3840
cgcgccaccc ggctgcagca gcccgggcgg gcgagaggct ctcaactggg cgggaaggtg   3900
cgggaaggtg cggaaaggtt cgcgaaagtt cgcggcggcg gggtcgggt gaggcgcaaa    3960
aggataaaaa gccggtggaa gcggagctga gcagatccga gccgggctgg ctgcagagaa   4020
accgcaggga gagcctcact gctgagcgcc cctcgacggc ggagcggcag cagcctccgt   4080
ggcctccagc atccgacaag aagcttcagc catgtctaga ctggacaaga gcaaagtcat   4140
aaactctgct ctggaattac tcaatggagt cggtatcgaa ggcctgacga caaggaaact   4200
cgctcaaaag ctgggagttg agcagcctac cctgtactgg cacgtgaaga acaagcgggc   4260
cctgctcgat gccctgccaa tcgagatgct ggacaggcat catacccact cctgcccccct  4320
ggaaggcgag tcatggcaag actttctgcg gaacaacgcc aagtcatacc gctgtgctct   4380
cctctcacat cgcgacgggg ctaaagtgca tctcggcacc cgcccaacag agaaacagta   4440
cgaaaccctg gaaaatcagc tcgcgttcct gtgtcagcaa ggcttctccc tggagaacgc   4500
actgtacgct ctgtccgccg tgggccactt tacactgggc tgcgtattgg aggaacagga   4560
gcatcaagta gcaaaagagg aaagagagac acctaccacc gattctatgc cccccacttct  4620
gaaacaagca attgagctgt tcgaccggca gggagccgaa cctgccttcc ttttcggcct   4680
ggaactaatc atatgtggcc tggagaaaca gctaaagtgc gaaagcggcg ggccgaccga   4740
cgcccttgac gattttgact tagacatgct cccagccgat gcccttgacg actttgacct   4800
tgatatgctg cctgctgacg ctcttgacga ttttgacctt gacatgctcc ccgggtaagt   4860
cagattaggc cctggaagta atgtacaaca cgtgctacgg tttgggaatt agcttgacgg   4920
ccctttcgtc ttcactcgag tttactccct atcagtgata gagaacgtat gaagagttta   4980
ctccctatca gtgatagaga acgtatgcag actttactcc ctatcagtga tagagaacgt   5040
ataaggagtt tactccctat cagtgataga gaacgtatga ccagtttact ccctatcagt   5100
gatagagaac gtatctacag tttactccct atcagtgata gagaacgtat atccagttta   5160
ctccctatca gtgatagaga acgtatgtcg aggtaggcgt gtacggtggg cgcctataaa   5220
agcagagctc gtttagtgaa ccgtcagatc gcctggagca attccacaac acttttgtct   5280
tatacttact aggagctcgg atccagtacc cttcaccatg gtgagcaagg gcgaggagct   5340
gttcaccggg gtggtgccca tcctggtcga gctggacggc gacgtaaacg gccacaagtt   5400
cagcgtgtcc ggcgagggcg agggcgatgc cacctacggc aagctgaccc tgaagttcat   5460
ctgcaccacc ggcaagctgc ccgtgccctg gcccaccctc gtgaccaccc tgacctacgg   5520
```

-continued

```
cgtgcagtgc ttcagccgct accccgacca catgaagcag cacgacttct tcaagtccgc   5580
catgcccgaa ggctacgtcc aggagcgcac catcttcttc aaggacgacg gcaactacaa   5640
gacccgcgcc gaggtgaagt tcgagggcga caccctggtg aaccgcatcg agctgaaggg   5700
catcgacttc aaggaggacg gcaacatcct ggggcacaag ctggagtaca actacaacag   5760
ccacaacgtc tatatcatgg ccgacaagca gaagaacggc atcaaggtga acttcaagat   5820
ccgccacaac atcgaggacg gcagcgtgca gctcgccgac cactaccagc agaacacccc   5880
catcggcgac ggccccgtgc tgctgcccga caaccactac ctgagcaccc agtccgccct   5940
gagcaaagac cccaacgaga agcgcgatca catggtcctg ctggagttcg tgaccgccgc   6000
cgggatcact ctcggcatgg acgagctgta caagtaatac atacaaggcc gtacagaatt   6060
ggctccggtg cccgtcagtg ggcagagcgc acatcgccca cagtccccga gaagttgggg   6120
ggaggggtcg gcaattgaac cggtgcctag agaaggtggc gcggggtaaa ctgggaaagt   6180
gatgtcgtgt actggctccg cctttttccc gagggtgggg gagaaccgta tataagtgca   6240
gtagtcgccg tgaacgttct ttttcgcaac gggtttgccg ccagaacaca ggtgaccttc   6300
accatgtcgg gggcaggtgc caccggccgc gccatggacg ggccgcgcct gctgctgttg   6360
ctgcttctgg gggtgtccct tggaggtgcc aaggaggcat gccccacagg cctgtacaca   6420
cacagcggtg agtgctgcaa agcctgcaac ctgggcgagg gtgtggccca gccttgtgga   6480
gccaaccaga ccgtgtgtga gccctgcctg gacagcgtga cgttctccga cgtggtgagc   6540
gcgaccgagc cgtgcaagcc gtgcaccgag tgcgtggggc tccagagcat gtcggcgcca   6600
tgcgtggagg ccgacgacgc cgtgtgccgc tgcgcctacg gctactacca ggatgagacg   6660
actgggcgct gcgaggcgtg ccgcgtgtgc gaggcgggct cgggcctcgt gttctcctgc   6720
caggacaagc agaacaccgt gtgcgaggag tgccccgacg gcacgtattc cgacgaggcc   6780
aaccacgtgg acccgtgcct gccctgcacc gtgtgcgagg acaccgagcg ccagctccgc   6840
gagtgcacac gctgggccga cgccgagtgc gaggagatcc ctggccgttg gattacacgg   6900
tccacacccc cagagggctc ggacagcaca gcccccagca cccaggagcc tgaggcacct   6960
ccagaacaag acctcatagc cagcacggtg gcaggtgtgg tgaccacagt gatgggcagc   7020
tcccagcccg tggtgacccg aggcaccacc gacaacctca tccctgtcta ttgctccatc   7080
ctggctgctg tggttgtggg tcttgtggcc tacatagcct tcaagaggtg gaacagctga   7140
cctttcatag aaggcggcgg tggtaccttt aagaccaatg acttacaagg cagctgtaga   7200
tcttagccac tttttaaaag aaaagggggg actggaaggg ctaattcact cccaacgaag   7260
acaagatctg ctttttgctt gtactgggtc tctctggtta gaccagatct gagcctggga   7320
gctctctggc taactaggga acccactgct taagcctcaa taaagcttgc cttgagtgct   7380
tcaagtagtg tgtgcccgtc tgttgtgtga ctctggtaac tagagatccc tcagaccctt   7440
ttagtcagtg tggaaaatct ctagcagtag tagttcatgt catcttatta ttcagtattt   7500
ataacttgca aagaaatgaa tatcagagag tgagaggaac ttgtttattg cagcttataa   7560
tggttacaaa taaagcaata gcatcacaaa tttcacaaat aaagcatttt tttcactgca   7620
ttctagttgt ggtttgtcca aactcatcaa tgtatcttat catgtctggc tctagctatc   7680
ccgcccctaa ctccgcccat cccgccccat ggctgactaa ttttttttat ttatgcagag   7740
gccgaggccg cctcggcctc tgagctattc cagaagtagt gaggaggctt ttttggaggc   7800
ctagggacgt acccaattcg ccctatagtg agtcgtatta cgcgcgctca ctggccgtcg   7860
ttttacaacg tcgtgactgg gaaaaccctg gcgttaccca acttaatcgc cttgcagcac   7920
```

atccccttt cgccagctgg cgtaatagcg aagaggcccg caccgatcgc ccttcccaac 7980
agttgcgcag cctgaatggc gaatgggacg cgccctgtag cggcgcatta agcgcggcgg 8040
gtgtggtggt tacgcgcagc gtgaccgcta cacttgccag cgccctagcg cccgctcctt 8100
tcgctttctt cccttccttt ctcgccacgt tcgccggctt tccccgtcaa gctctaaatc 8160
gggggctccc tttagggttc cgatttagtg ctttacggca cctcgacccc aaaaaacttg 8220
attagggtga tggttcacgt agtgggccat cgccctgata gacggttttt cgccctttga 8280
cgttggagtc cacgttcttt aatagtggac tcttgttcca aactggaaca acactcaacc 8340
ctatctcggt ctattctttt gatttataag ggattttgcc gatttcggcc tattggttaa 8400
aaaatgagct gatttaacaa aaatttaacg cgaattttaa caaaatatta acgcttacaa 8460
tttaggtggc acttttcggg gaaatgtgcg cggaacccct atttgtttat ttttctaaat 8520
acattcaaat atgtatccgc tcatgagaca ataaccctga taaatgcttc aataatattg 8580
aaaaaggaag agtatgagta ttcaacattt ccgtgtcgcc cttattccct tttttgcggc 8640
attttgcctt cctgtttttg ctcacccaga aacgctggtg aaagtaaaag atgctgaaga 8700
tcagttgggt gcacgagtgg gttacatcga actggatctc aacagcggta agatccttga 8760
gagttttcgc cccgaagaac gttttccaat gatgagcact tttaaagttc tgctatgtgg 8820
cgcggtatta tcccgtattg acgccgggca agagcaactc ggtcgccgca tacactattc 8880
tcagaatgac ttggttgagt actcaccagt cacagaaaag catcttacgg atggcatgac 8940
agtaagagaa ttatgcagtg ctgccataac catgagtgat aacactgcgg ccaacttact 9000
tctgacaacg atcggaggac cgaaggagct aaccgctttt ttgcacaaca tgggggatca 9060
tgtaactcgc cttgatcgtt gggaaccgga gctgaatgaa gccataccaa acgacgagcg 9120
tgacaccacg atgcctgtag caatggcaac aacgttgcgc aaactattaa ctggcgaact 9180
acttactcta gcttcccggc aacaattaat agactggatg gaggcggata aagttgcagg 9240
accacttctg cgctcggccc ttccggctgg ctggtttatt gctgataaat ctggagccgg 9300
tgagcgtggg tctcgcggta tcattgcagc actggggcca gatggtaagc cctcccgtat 9360
cgtagttatc tacacgacgg ggagtcaggc aactatggat gaacgaaata gacagatcgc 9420
tgagataggt gcctcactga ttaagcattg gtaactgtca gaccaagttt actcatatat 9480
actttagatt gatttaaaac ttcattttta atttaaaagg atctaggtga agatcctttt 9540
tgataatctc atgaccaaaa tcccttaacg tgagttttcg ttccactgag cgtcagaccc 9600
cgtagaaaag atcaaaggat cttc 9624

<210> SEQ ID NO 41
<211> LENGTH: 10636
<212> TYPE: DNA
<213> ORGANISM: Artificial Sequence
<220> FEATURE:
<223> OTHER INFORMATION: HSPB'1-CAR

<400> SEQUENCE: 41
taccaaacga cgagcgtgac accacgatgc ctgtagcaat ggcaacaacg ttgcgcaaac 60
tattaactgg cgaactactt actctagctt cccggcaaca attaatagac tggatggagg 120
cggataaagt tgcaggacca cttctgcgct cggcccttcc ggctggctgg tttattgctg 180
ataaatctgg agccggtgag cgtgggtctc gcggtatcat tgcagcactg gggccagatg 240
gtaagccctc ccgtatcgta gttatctaca cgacggggag tcaggcaact atggatgaac 300

```
gaaatagaca gatcgctgag ataggtgcct cactgattaa gcattggtaa ctgtcagacc    360
aagtttactc atatatactt tagattgatt taaaacttca tttttaattt aaaaggatct    420
aggtgaagat cctttttgat aatctcatga ccaaaatccc ttaacgtgag ttttcgttcc    480
actgagcgtc agaccccgta gaaaagatca aaggatcttc ttgagatcct ttttttctgc    540
gcgtaatctg ctgcttgcaa acaaaaaaac caccgctacc agcggtggtt tgtttgccgg    600
atcaagagct accaactctt tttccgaagg taactggctt cagcagagcg cagataccaa    660
atactgtcct tctagtgtag ccgtagttag gccaccactt caagaactct gtagcaccgc    720
ctacatacct cgctctgcta atcctgttac cagtggctgc tgccagtggc gataagtcgt    780
gtcttaccgg gttggactca agacgatagt taccggataa ggcgcagcgg tcgggctgaa    840
cggggggttc gtgcacacag cccagcttgg agcgaacgac ctacaccgaa ctgagatacc    900
tacagcgtga gctatgagaa agcgccacgc ttcccgaagg gagaaaggcg gacaggtatc    960
cggtaagcgg cagggtcgga acaggagagc gcacgaggga gcttccaggg ggaaacgcct   1020
ggtatcttta tagtcctgtc gggtttcgcc acctctgact tgagcgtcga tttttgtgat   1080
gctcgtcagg ggggcggagc ctatggaaaa acgccagcaa cgcggccttt ttacggttcc   1140
tggccttttg ctggcctttt gctcacatgt tctttcctgc gttatcccct gattctgtgg   1200
ataaccgtat taccgccttt gagtgagctg ataccgctcg ccgcagccga acgaccgagc   1260
gcagcgagtc agtgagcgag gaagcggaag agcgcccaat acgcaaaccg cctctccccg   1320
cgcgttggcc gattcattaa tgcagctggc acgacaggtt tcccgactgg aaagcgggca   1380
gtgagcgcaa cgcaattaat gtgagttagc tcactcatta ggcaccccag gctttacact   1440
ttatgcttcc ggctcgtatg ttgtgtggaa ttgtgagcgg ataacaattt cacacaggaa   1500
acagctatga ccatgattac gccaagcgcg caattaaccc tcactaaagg gaacaaaagc   1560
tggagctgca agcttggcca ttgcatacgt tgtatccata tcataatatg tacatttata   1620
ttggctcatg tccaacatta ccgccatgtt gacattgatt attgactagt tattaatagt   1680
aatcaattac ggggtcatta gttcatagcc catatatgga gttccgcgtt acataactta   1740
cggtaaatgg cccgcctggc tgaccgccca acgacccccg cccattgacg tcaataatga   1800
cgtatgttcc catagtaacg ccaataggga ctttccattg acgtcaatgg gtggagtatt   1860
tacggtaaac tgcccacttg gcagtacatc aagtgtatca tatgccaagt acgcccccta   1920
ttgacgtcaa tgacggtaaa tggcccgcct ggcattatgc ccagtacatg accttatggg   1980
actttcctac ttggcagtac atctacgtat tagtcatcgc tattaccatg gtgatgcggt   2040
tttggcagta catcaatggg cgtggatagc ggtttgactc acggggattt ccaagtctcc   2100
accccattga cgtcaatggg agtttgtttt ggcaccaaaa tcaacgggac tttccaaaat   2160
gtcgtaacaa ctccgcccca ttgacgcaaa tgggcggtag gcgtgtacgg tgggaggtct   2220
atataagcag agctcgttta gtgaaccggg gtctctctgg ttagaccaga tctgagcctg   2280
ggagctctct ggctaactag ggaacccact gcttaagcct caataaagct tgccttgagt   2340
gcttcaagta gtgtgtgccc gtctgttgtg tgactctggt aactagagat ccctcagacc   2400
cttttagtca gtgtggaaaa tctctagcag tggcgcccga acagggacct gaaagcgaaa   2460
gggaaaccag aggagctctc tcgacgcagg actcggcttg ctgaagcgcg cacggcaaga   2520
ggcgaggggc ggcgactggt gagtacgcca aaaattttga ctagcggagg ctagaaggag   2580
agagatgggt gcgagagcgt cagtattaag cgggggagaa ttagatcgcg atgggaaaaa   2640
attcggttaa ggccaggggg aaagaaaaaa tataaattaa aacatatagt atggcaagc    2700
```

-continued

```
agggagctag aacgattcgc agttaatcct ggcctgttag aaacatcaga aggctgtaga   2760
caaatactgg gacagctaca accatccctt cagacaggat cagaagaact tagatcatta   2820
tataatacag tagcaaccct ctattgtgtg catcaaagga tagagataaa agacaccaag   2880
gaagctttag acaagataga ggaagagcaa aacaaaagta agaccaccgc acagcaagcg   2940
gccgctgatc ttcagacctg gaggaggaga tatgagggac aattggagaa gtgaattata   3000
taaatataaa gtagtaaaaa ttgaaccatt aggagtagca cccaccaagg caaagagaag   3060
agtggtgcag agagaaaaaa gagcagtggg aataggagct ttgttccttg ggttcttggg   3120
agcagcagga agcactatgg gcgcagcctc aatgacgctg acggtacagg ccagacaatt   3180
attgtctggt atagtgcagc agcagaacaa tttgctgagg gctattgagg cgcaacagca   3240
tctgttgcaa ctcacagtct ggggcatcaa gcagctccag gcaagaatcc tggctgtgga   3300
aagataccta aaggatcaac agctcctggg gatttggggt tgctctggaa aactcatttg   3360
caccactgct gtgccttgga atgctagttg gagtaataaa tctctggaac agattggaat   3420
cacacgacct ggatggagtg ggacagagaa attaacaatt acacaagctt aatacactcc   3480
ttaattgaag aatcgcaaaa ccagcaagaa aagaatgaac aagaattatt ggaattagat   3540
aaatgggcaa gtttgtggaa ttggtttaac ataacaaatt ggctgtggta tataaaatta   3600
ttcataatga tagtaggagg cttggtaggt ttaagaatag tttttgctgt actttctata   3660
gtgaatagag ttaggcaggg atattcacca ttatcgtttc agacccacct cccaaccccg   3720
aggggacccg acaggcccga aggaatagaa gaagaaggtg gagagagaga cagagacaga   3780
tccattcgat tagtgaacgg atctcgacgg tatcgatctc gacacaaatg gcagtattca   3840
tccacaattt taaaagaaaa ggggggattg gggggtacag tgcaggggaa agaatagtag   3900
acataatagc aacagacata caaactaaag aattacaaaa acaaattaca aaaattcaaa   3960
attttcgggt ttattacagg gacagcagag atccagtttg ggaattagct tgagcctcta   4020
aagttgctgc ttttgcagcc tctgccacaa ccgcgcgtcc tcagagccag cccggaggag   4080
ctagaacctt ccccgcattt ctttcagcag cctgagtcag aggcgggctg gcctggcgta   4140
gccgcccagc ctcgcggctc atgccccgat ctgcccgaac cttctcccgg ggtcagcgcc   4200
gcgccgcgcc acccggctga gtcagcccgg gcgggcgaga ggctctcaac tgggcgggaa   4260
ggtgcgggaa ggtgcggaaa ggttcgcgaa agttcgcggc ggcgggggtc gggtgaggcg   4320
caaaaggata aaaagccggt ggaagcggag ctgagcagat ccgagccggg ctggctgcag   4380
agaaaccgca gggagagcct cactgctgag cgcccctcga cggcggagcg gcagcagcct   4440
ccgtggcctc cagcatccga caagaagctt gaattcgagc tcgccgggga tcctctagtc   4500
agctgacgcg tgctagcgcg gccgcaccac tagtgccacc atggctctgc ctgtgaccgc   4560
cctgctgctg cctctggctc tgctgctgca cgccgctcgg ccttacccat acgatgttcc   4620
agattacgct gacattcaga tgactcagac cacaagcagc ctcagtgcga gcctggggga   4680
cagggtgact atcagctgcc gggccagcca ggacatttcc aagtacctga attggtacca   4740
gcagaagccc gatggtactg tgaaactcct gatatatcat acttctaggc tccattccgg   4800
ggttccaagc cgattcagtg gctccggttc cggtacagat tattccctga ccattagcaa   4860
cttggaacag gaggacattg caacgtattt ctgtcagcaa ggcaacacat tgccctacac   4920
attcgggggc gggactaaac tcgaaataac tggcggcggg ggttctggtg gcggcggcag   4980
cggcggtgga ggatcagaag tgaagctgca ggaaagtggc cccgggctgg tagccccaag   5040
```

-continued

```
tcagtccctg agtgtaacct gtacagtgag tggagtgtct cttcctgact acggggtaag   5100
ttggattcgg caacctccac gcaagggcct ggagtggctc ggcgtgattt ggggatctga   5160
gacaacttac tacaattccg ccctgaagag caggctgacc atcattaagg acaatagcaa   5220
gtcacaggtg tttctgaaga tgaactcact gcagaccgac gacaccgcca tctattactg   5280
cgccaaacat tattattatg gcgggagtta tgctatggac tactggggcc agggcactag   5340
cgtcaccgtc agcagtacta caactccagc acccagaccc cctacacctg ctccaactat   5400
cgcaagtcag cccctgtcac tgcgccctga agcctgtcgc cctgctgccg gggggagctgt   5460
gcatactcgg ggactggact ttgcctgtga tatctacttc tgggtgctgg tcgtggtcgg   5520
aggggtgctg gcctgttata gcctgctggt gactgtcgcc ttcattatct tctgggtgcg   5580
gagcaagagg tctcgcggtg ggcattccga ctacatgaac atgaccccta gaaggcctgg   5640
cccaaccaga aagcactacc agccatacgc ccctcccaga gatttcgccg cttatcgaag   5700
cgtgaagttc tcccgaagcg cagatgcccc agcctatcag cagggacaga atcagctgta   5760
caacgagctg aacctgggaa gacgggagga atacgatgtg ctggacaaaa ggcggggcag   5820
agatcctgag atgggcggca aaccaagacg gaagaacccc caggaaggtc tgtataatga   5880
gctgcagaaa gacaagatgg ctgaggccta ctcagaaatc gggatgaagg gcgaaagaag   5940
gagaggaaaa ggccacgacg gactgtacca ggggctgagt acagcaacaa aagacaccta   6000
tgacgctctg cacatgcagg ctctgccacc aagatgacaa ggcagctgta gatcttagcc   6060
gatcttagcc accagaattg tacatacaag gccgtacaga attggctccg gtgcccgtca   6120
gtgggcagag cgcacatcgc ccacagtccc cgagaagttg gggggagggg tcggcaattg   6180
aaccggtgcc tagagaaggt ggcgcggggt aaactgggaa agtgatgtcg tgtactggct   6240
ccgccttttt cccgagggtg ggggagaacc gtatataagt gcagtagtcg ccgtgaacgt   6300
tctttttcgc aacgggtttg ccgccagaac acaggtaagt gccgtgtgtg gttcccgcgg   6360
gcctggcctc tttacgggtt atggcccttg cgtgccttga attacttcca ctggctgcag   6420
tacgtgattc ttgatcccga gcttcgggtt ggaagtgggt gggagagttc gaggccttgc   6480
gcttaaggag ccccttcgcc tcgtgcttga gttgaggcct ggcctgggcg ctggggccgc   6540
cgcgtgcgaa tctggtggca ccttcgcgcc tgtctcgctg ctttcgataa gtctctagcc   6600
atttaaaatt tttgatgacc tgctgcgacg ctttttttct ggcaagatag tcttgtaaat   6660
gcgggccaag atctgcacac tggtatttcg gtttttgggg ccgcgggcgg cgacggggcc   6720
cgtgcgtccc agcgcacatg ttcggcgagg cggggcctgc gagcgcggcc accgagaatc   6780
ggacgggggt agtctcaagc tggccggcct gctctggtgc ctggcctcgc gccgccgtgt   6840
atcgccccgc cctgggcggc aaggctggcc cggtcggcac cagttgcgtg agcggaaaga   6900
tggccgcttc ccggccctgc tgcagggagc tcaaaatgga ggacgcggcg ctcgggagag   6960
cgggcgggtg agtcacccac acaaaggaaa agggcctttc cgtcctcagc cgtcgcttca   7020
tgtgactcca cggagtaccg ggcgccgtcc aggcacctcg attagttctc gagcttttgg   7080
agtacgtcgt ctttaggttg gggggagggg ttttatgcga tggagtttcc ccacactgag   7140
tgggtggaga ctgaagttag gccagcttgg cacttgatgt aattctcctt ggaatttgcc   7200
ctttttgagt ttggatcttg gttcattctc aagcctcaga cagtggttca aagttttttt   7260
cttccatttc aggtgtcgtg accggtcgcc accatggtgt ctaagggcga agagctgatt   7320
aaggagaaca tgcacatgaa gctgtacatg gagggcaccg tggacaacca tcacttcaag   7380
tgcacatccg agggcgaagg caagccctac gagggcaccc agaccatgag aatcaaggtg   7440
```

-continued

```
gtcgagggcg gccctctccc cttcgccttc gacatcctgg ctactagctt cctctacggc   7500
agcaagacct tcatcaacca cacccagggc atccccgact tcttcaagca gtccttccct   7560
gagggcttca catgggagag agtcaccaca tacgaagacg gggcgtgct gaccgctacc   7620
caggacacca gcctccagga cggctgcctc atctacaacg tcaagatcag aggggtgaac   7680
ttcacatcca acggccctgt gatgcagaag aaaacactcg gctgggaggc cttcaccgag   7740
acgctgtacc ccgctgacgg cggcctggaa ggcagaaacg acatggccct gaagctcgtg   7800
ggcgggagcc atctgatcgc aaacgccaag accacatata gatccaagaa acccgctaag   7860
aacctcaaga tgcctggcgt ctactatgtg gactacagac tggaaagaat caaggaggcc   7920
aacaacgaga cctacgtcga gcagcacgag gtggcagtgg ccagatactg cgacctccct   7980
agcaaactgg ggcacaagct taattaatgt acaaatcaac ctctggatta caaaatttgt   8040
gaaagattga ctggtattct taactatgtt gctcctttta cgctatgtgg atacgctgct   8100
ttaatgcctt tgtatcatgc tattgcttcc cgtatggctt tcattttctc ctccttgtat   8160
aaatcctggt tgctgtctct ttatgaggag ttgtggcccg ttgtcaggca acgtggcgtg   8220
gtgtgcactg tgtttgctga cgcaaccccc actggttggg gcattgccac cacctgtcag   8280
ctcctttccg ggactttcgc tttccccctc cctattgcca cggcggaact catcgccgcc   8340
tgccttgccc gctgctggac aggggctcgg ctgttgggca ctgacaattc cgtggtgttg   8400
tcggggaaat catcgtcctt tccttggctg ctcgcctatg ttgccacctg gattctgcgc   8460
gggacgtcct tctgctacgt cccttcggcc ctcaatccag cggaccttcc ttcccgcggc   8520
ctgctgccgg ctctgcggcc tcttccgcgt cttcgccttc gccctcagac gagtcggatc   8580
tccctttggg ccgcctcccc gctacaaggc agctgtagat cccttcata gaaggcggcg   8640
gtggtacctt taagaccaat gacttacaag gcagctgtag atcttagcca ctttttaaaa   8700
gaaaaggggg gactggaagg gctaattcac tcccaacgaa gacaagatct gctttttgct   8760
tgtactgggt ctctctggtt agaccagatc tgagcctggg agctctctgg ctaactaggg   8820
aacccactgc ttaagcctca ataaagcttg ccttgagtgc ttcaagtagt gtgtgcccgt   8880
ctgttgtgtg actctggtaa ctagagatcc ctcagaccct tttagtcagt gtggaaaatc   8940
tctagcagta gtagttcatg tcatcttatt attcagtatt tataacttgc aaagaaatga   9000
atatcagaga gtgagaggaa cttgtttatt gcagcttata atggttacaa ataaagcaat   9060
agcatcacaa atttcacaaa taaagcattt ttttcactgc attctagttg tggtttgtcc   9120
aaactcatca atgtatctta tcatgtctgg ctctagctat cccgccccta actccgccca   9180
tcccgcccct aactccgccc agttccgccc attctccgcc ccatggctga ctaatttttt   9240
ttatttatgc agaggccgag gccgcctcgg cctctgagct attccagaag tagtgaggag   9300
gcttttttgg aggcctaggc ttttgcgtcg agacgtaccc aattcgccct atagtgagtc   9360
gtattacgcg cgctcactgg ccgtcgtttt acaacgtcgt gactgggaaa accctggcgt   9420
tacccaactt aatcgccttg cagcacatcc ccctttcgcc agctggcgta atagcgaaga   9480
ggcccgcacc gatcgccctt cccaacagtt gcgcagcctg aatggcgaat ggcgcgacgc   9540
gccctgtagc ggcgcattaa gcgcggcggg tgtggtggtt acgcgcagcg tgaccgctac   9600
acttgccagc gccctagcgc ccgctccttt cgctttcttc ccttcctttc tcgccacgtt   9660
cgccggcttt ccccgtcaag ctctaaatcg ggggctccct ttagggttcc gatttagtgc   9720
tttacggcac ctcgacccca aaaaacttga ttagggtgat ggttcacgta gtgggccatc   9780
```

-continued gccctgatag acggtttttc gccctttgac gttggagtcc acgttcttta atagtggact 9840
cttgttccaa actggaacaa cactcaaccc tatctcggtc tattcttttg atttataagg 9900
gattttgccg atttcggcct attggttaaa aaatgagctg atttaacaaa aatttaacgc 9960
gaattttaac aaaatattaa cgtttacaat ttcccaggtg gcacttttcg gggaaatgtg 10020
cgcggaaccc ctatttgttt atttttctaa atacattcaa atatgtatcc gctcatgaga 10080
caataaccct gataaatgct tcaataatat tgaaaaagga agagtatgag tattcaacat 10140
ttccgtgtcg cccttattcc cttttttgcg gcattttgcc ttcctgtttt tgctcaccca 10200
gaaacgctgg tgaaagtaaa agatgctgaa gatcagttgg gtgcacgagt gggttacatc 10260
gaactggatc tcaacagcgg taagatcctt gagagttttc gccccgaaga acgttttcca 10320
atgatgagca cttttaaagt tctgctatgt ggcgcggtat tatcccgtat tgacgccggg 10380
caagagcaac tcggtcgccg catacactat tctcagaatg acttggttga gtactcacca 10440
gtcacagaaa agcatcttac ggatggcatg acagtaagag aattatgcag tgctgccata 10500
accatgagtg ataacactgc ggccaactta cttctgacaa cgatcggagg accgaaggag 10560
ctaaccgctt ttttgcacaa catgggggat catgtaactc gccttgatcg ttgggaaccg 10620
gagctgaatg aagcca 10636

<210> SEQ ID NO 42
<211> LENGTH: 10581
<212> TYPE: DNA
<213> ORGANISM: Artificial Sequence
<220> FEATURE:
<223> OTHER INFORMATION: HSPB-CAR

<400> SEQUENCE: 42
ccggagctga atgaagccat accaaacgac gagcgtgaca ccacgatgcc tgtagcaatg 60
gcaacaacgt tgcgcaaact attaactggc gaactactta ctctagcttc ccggcaacaa 120
ttaatagact ggatggaggc ggataaagtt gcaggaccac ttctgcgctc ggcccttccg 180
gctggctggt ttattgctga taaatctgga gccggtgagc gtgggtctcg cggtatcatt 240
gcagcactgg ggccagatgg taagccctcc cgtatcgtag ttatctacac gacggggagt 300
caggcaacta tggatgaacg aaatagacag atcgctgaga taggtgcctc actgattaag 360
cattggtaac tgtcagacca agtttactca tatatacttt agattgattt aaaacttcat 420
ttttaattta aaaggatcta ggtgaagatc ctttttgata atctcatgac caaaatccct 480
taacgtgagt tttcgttcca ctgagcgtca gaccccgtag aaaagatcaa aggatcttct 540
tgagatcctt tttttctgcg cgtaatctgc tgcttgcaaa caaaaaaacc accgctacca 600
gcggtggttt gtttgccgga tcaagagcta ccaactcttt ttccgaaggt aactggcttc 660
agcagagcgc agataccaaa tactgtcctt ctagtgtagc cgtagttagg ccaccacttc 720
aagaactctg tagcaccgcc tacatacctc gctctgctaa tcctgttacc agtggctgct 780
gccagtggcg ataagtcgtg tcttaccggg ttggactcaa gacgatagtt accggataag 840
gcgcagcggt cgggctgaac ggggggttcg tgcacacagc ccagcttgga gcgaacgacc 900
tacaccgaac tgagatacct acagcgtgag ctatgagaaa gcgccacgct tcccgaaggg 960
agaaaggcgg acaggtatcc ggtaagcggc agggtcggaa caggagagcg cacgagggag 1020
cttccagggg gaaacgcctg gtatctttat agtcctgtcg ggtttcgcca cctctgactt 1080
gagcgtcgat ttttgtgatg ctcgtcaggg gggcggagcc tatggaaaaa cgccagcaac 1140
gcggcctttt tacggttcct ggccttttgc tggccttttg ctcacatgtt ctttcctgcg 1200

```
ttatcccctg attctgtgga taaccgtatt accgcctttg agtgagctga taccgctcgc   1260
cgcagccgaa cgaccgagcg cagcgagtca gtgagcgagg aagcggaaga gcgcccaata   1320
cgcaaaccgc ctctccccgc gcgttggccg attcattaat gcagctggca cgacaggttt   1380
cccgactgga aagcgggcag tgagcgcaac gcaattaatg tgagttagct cactcattag   1440
gcaccccagg ctttacactt tatgcttccg gctcgtatgt tgtgtggaat tgtgagcgga   1500
taacaatttc acacaggaaa cagctatgac catgattacg ccaagcgcgc aattaaccct   1560
cactaaaggg aacaaaagct ggagctgcaa gcttggccat tgcatacgtt gtatccatat   1620
cataatatgt acatttatat tggctcatgt ccaacattac cgccatgttg acattgatta   1680
ttgactagtt attaatagta atcaattacg gggtcattag ttcatagccc atatatggag   1740
ttccgcgtta cataacttac ggtaaatggc ccgcctggct gaccgcccaa cgacccccgc   1800
ccattgacgt caataatgac gtatgttccc atagtaacgc caatagggac tttccattga   1860
cgtcaatggg tggagtattt acggtaaact gcccacttgg cagtacatca agtgtatcat   1920
atgccaagta cgccccctat tgacgtcaat gacggtaaat ggcccgcctg gcattatgcc   1980
cagtacatga ccttatggga ctttcctact tggcagtaca tctacgtatt agtcatcgct   2040
attaccatgg tgatgcggtt ttggcagtac atcaatgggc gtggatagcg gtttgactca   2100
cggggatttc caagtctcca ccccattgac gtcaatggga gtttgttttg gcaccaaaat   2160
caacgggact ttccaaaatg tcgtaacaac tccgccccat tgacgcaaat gggcggtagg   2220
cgtgtacggt gggaggtcta tataagcaga gctcgtttag tgaaccgggg tctctctggt   2280
tagaccagat ctgagcctgg gagctctctg gctaactagg gaacccactg cttaagcctc   2340
aataaagctt gccttgagtg cttcaagtag tgtgtgcccg tctgttgtgt gactctggta   2400
actagagatc cctcagaccc ttttagtcag tgtggaaaat ctctagcagt ggcgcccgaa   2460
cagggacctg aaagcgaaag ggaaaccaga ggagctctct cgacgcagga ctcggcttgc   2520
tgaagcgcgc acggcaagag gcgaggggcg gcgactggtg agtacgccaa aaattttgac   2580
tagcggaggc tagaaggaga gagatgggtg cgagagcgtc agtattaagc gggggagaat   2640
tagatcgcga tgggaaaaaa ttcggttaag gccaggggga aagaaaaaat ataaattaaa   2700
acatatagta tgggcaagca gggagctaga acgattcgca gttaatcctg gcctgttaga   2760
aacatcagaa ggctgtagac aaatactggg acagctacaa ccatcccttc agacaggatc   2820
agaagaactt agatcattat ataatacagt agcaaccctc tattgtgtgc atcaaaggat   2880
agagataaaa gacaccaagg aagctttaga caagatagag gaagagcaaa acaaaagtaa   2940
gaccaccgca cagcaagcgg ccgctgatct tcagacctgg aggaggagat atgagggaca   3000
attggagaag tgaattatat aaatataaag tagtaaaaat tgaaccatta ggagtagcac   3060
ccaccaaggc aaagagaaga gtggtgcaga gagaaaaaag agcagtggga ataggagctt   3120
tgttccttgg gttcttggga gcagcaggaa gcactatggg cgcagcctca atgacgctga   3180
cggtacaggc cagacaatta ttgtctggta tagtgcagca gcagaacaat ttgctgaggg   3240
ctattgaggc gcaacagcat ctgttgcaac tcacagtctg gggcatcaag cagctccagg   3300
caagaatcct ggctgtggaa agatacctaa aggatcaaca gctcctgggg atttggggtt   3360
gctctggaaa actcatttgc accactgctg tgccttggaa tgctagttgg agtaataaat   3420
ctctggaaca gattggaatc acacgacctg gatggagtgg gacagagaaa ttaacaatta   3480
cacaagctta atacactcct taattgaaga atcgcaaaac cagcaagaaa agaatgaaca   3540
```

agaattattg gaattagata aatgggcaag tttgtggaat tggtttaaca taacaaattg 3600
gctgtggtat ataaaattat tcataatgat agtaggaggc ttggtaggtt taagaatagt 3660
ttttgctgta ctttctatag tgaatagagt taggcaggga tattcaccat tatcgtttca 3720
gacccacctc ccaaccccga ggggacccga caggcccgaa ggaatagaag aagaaggtgg 3780
agagagagac agagacagat ccattcgatt agtgaacgga tctcgacggt atcgatctcg 3840
acacaaatgg cagtattcat ccacaatttt aaaagaaaag gggggattgg ggggtacagt 3900
gcaggggaaa gaatagtaga cataatagca acagacatac aaactaaaga attacaaaaa 3960
caaattacaa aaattcaaaa ttttcgggtt tattacaggg acagcagaga tccagtttgg 4020
gaattagctt gaggatcctc cacagccccg gggagacctt gcctctaaag ttgctgcttt 4080
tgcagctctg ccacaaccgc gcgtcctcag agccagccgg gaggagctag aaccttcccc 4140
gcgtttcttt cagcagccct gagtcagagg cgggctggcc ttgcaagtag ccgcccagcc 4200
ttcttcggtc tcacggaccg atccgcccga accttctccc ggggtcagcg ccgcgctgcg 4260
ccgcccggct gactcagccc gggcgggcgg gcgggaggct ctcgactggg cgggaaggtg 4320
cgggaaggtt cgcggcggcg gggtcgggga ggtgcaaaag gatgaaaagc ccgtggacgg 4380
agctgagcag atccggccgg gctggcggca gagaaaccgc agggagagcc tcactgctga 4440
gcgcccctcg acgcgggcgg cagcagcctc cgtggcctcc agcatccgac aagaagcttc 4500
agccatggct ctgcctgtga ccgccctgct gctgcctctg gctctgctgc tgcacgccgc 4560
tcggccttac ccatacgatg ttccagatta cgctgacatt cagatgactc agaccacaag 4620
cagcctcagt gcgagcctgg gggacagggt gactatcagc tgccgggcca gccaggacat 4680
ttccaagtac ctgaattggt accagcagaa gcccgatggt actgtgaaac tcctgatata 4740
tcatacttct aggctccatt ccggggttcc aagccgattc agtggctccg gttccggtac 4800
agattattcc ctgaccatta gcaacttgga acaggaggac attgcaacgt atttctgtca 4860
gcaaggcaac acattgccct acacattcgg gggcgggact aaactcgaaa taactggcgg 4920
cgggggttct ggtggcggcg gcagcggcgg tggaggatca gaagtgaagc tgcaggaaag 4980
tggccccggg ctggtagccc caagtcagtc cctgagtgta acctgtacag tgagtggagt 5040
gtctcttcct gactacgggg taagttggat tcggcaacct ccacgcaagg gcctggagtg 5100
gctcggcgtg atttggggat ctgagacaac ttactacaat tccgccctga agagcaggct 5160
gaccatcatt aaggacaata gcaagtcaca ggtgtttctg aagatgaact cactgcagac 5220
cgacgacacc gccatctatt actgcgccaa acattattat tatggcggga gttatgctat 5280
ggactactgg ggccagggca ctagcgtcac cgtcagcagt actacaactc cagcacccag 5340 acccccctaca cctgctccaa ctatcgcaag tcagcccctg tcactgcgcc ctgaagcctg 5400
tcgccctgct gccgggggag ctgtgcatac tcggggactg gactttgcct gtgatatcta 5460
cttctgggtg ctggtcgtgg tcggaggggt gctggcctgt tatagcctgc tggtgactgt 5520
cgccttcatt atcttctggg tgcggagcaa gaggtctcgc ggtgggcatt ccgactacat 5580
gaacatgacc cctagaaggc ctggcccaac cagaaagcac taccagccat acgcccctcc 5640
cagagatttc gccgcttatc gaagcgtgaa gttctcccga agcgcagatg ccccagccta 5700
tcagcaggga cagaatcagc tgtacaacga gctgaacctg ggaagacggg aggaatacga 5760
tgtgctggac aaaaggcggg gcagagatcc tgagatgggc ggcaaaccaa gacggaagaa 5820
cccccaggaa ggtctgtata atgagctgca gaaagacaag atggctgagg cctactcaga 5880
aatcgggatg aagggcgaaa gaaggagagg aaaaggccac gacggactgt accaggggct 5940

-continued

```
gagtacagca acaaaagaca cctatgacgc tctgcacatg caggctctgc caccaagatg   6000
acaaggcagc tgtagatctt agccgatctt agccaccaga attgtacata caaggccgta   6060
cagaattggc tccggtgccc gtcagtgggc agagcgcaca tcgcccacag tccccgagaa   6120
gttgggggga ggggtcggca attgaaccgg tgcctagaga aggtggcgcg gggtaaactg   6180
ggaaagtgat gtcgtgtact ggctccgcct ttttcccgag ggtgggggag aaccgtatat   6240
aagtgcagta gtcgccgtga acgttctttt tcgcaacggg tttgccgcca gaacacaggt   6300
aagtgccgtg tgtggttccc gcgggcctgg cctctttacg ggttatggcc cttgcgtgcc   6360
ttgaattact tccactggct gcagtacgtg attcttgatc ccgagcttcg ggttggaagt   6420
gggtgggaga gttcgaggcc ttgcgcttaa ggagcccctt cgcctcgtgc ttgagttgag   6480
gcctggcctg ggcgctgggg ccgccgcgtg cgaatctggt ggcaccttcg cgcctgtctc   6540
gctgctttcg ataagtctct agccatttaa aatttttgat gacctgctgc gacgcttttt   6600
ttctggcaag atagtcttgt aaatgcgggc caagatctgc acactggtat ttcggttttt   6660
ggggccgcgg gcggcgacgg ggcccgtgcg tcccagcgca catgttcggc gaggcggggc   6720
ctgcgagcgc ggccaccgag aatcggacgg gggtagtctc aagctggccg gcctgctctg   6780
gtgcctggcc tcgcgccgcc gtgtatcgcc ccgccctggg cggcaaggct ggcccggtcg   6840
gcaccagttg cgtgagcgga aagatggccg cttcccggcc ctgctgcagg gagctcaaaa   6900
tggaggacgc ggcgctcggg agagcgggcg ggtgagtcac ccacacaaag gaaaagggcc   6960
tttccgtcct cagccgtcgc ttcatgtgac tccacggagt accgggcgcc gtccaggcac   7020
ctcgattagt tctcgagctt ttggagtacg tcgtctttag gttgggggga ggggttttat   7080
gcgatggagt ttccccacac tgagtgggtg gagactgaag ttaggccagc ttggcacttg   7140
atgtaattct ccttggaatt tgcccttttt gagtttggat cttggttcat tctcaagcct   7200
cagacagtgg ttcaaagttt ttttcttcca tttcaggtgt cgtgaccggt cgccaccatg   7260
gtgtctaagg gcgaagagct gattaaggag aacatgcaca tgaagctgta catggagggc   7320
accgtggaca accatcactt caagtgcaca tccgagggcg aaggcaagcc ctacgagggc   7380
acccagacca tgagaatcaa ggtggtcgag ggcggccctc tcccctttcgc cttcgacatc   7440
ctggctacta gcttcctcta cggcagcaag accttcatca accacaccca gggcatcccc   7500
gacttcttca agcagtcctt ccctgagggc ttcacatggg agagagtcac cacatacgaa   7560
gacgggggcg tgctgaccgc taccccaggac accagcctcc aggacggctg cctcatctac   7620
aacgtcaaga tcagaggggt gaacttcaca tccaacggcc ctgtgatgca gaagaaaaca   7680
ctcggctggg aggccttcac cgagacgctg taccccgctg acggcggcct ggaaggcaga   7740
aacgacatgg ccctgaagct cgtgggcggg agccatctga tcgcaaacgc caagaccaca   7800
tatagatcca agaaacccgc taagaacctc aagatgcctg gcgtctacta tgtggactac   7860
agactggaaa gaatcaagga ggccaacaac gagacctacg tcgagcagca cgaggtggca   7920
gtggccagat actgcgacct ccctagcaaa ctggggcaca agcttaatta atgtacaaat   7980
caacctctgg attacaaaat ttgtgaaaga ttgactggta ttcttaacta tgttgctcct   8040
tttacgctat gtggatacgc tgctttaatg cctttgtatc atgctattgc ttcccgtatg   8100
gctttcattt tctcctcctt gtataaatcc tggttgctgt ctctttatga ggagttgtgg   8160
cccgttgtca ggcaacgtgg cgtggtgtgc actgtgtttg ctgacgcaac ccccactggt   8220
tggggcattg ccaccacctg tcagctcctt tccgggactt tcgctttccc cctccctatt   8280
```

-continued

```
gccacggcgg aactcatcgc cgcctgcctt gcccgctgct ggacaggggc tcggctgttg   8340
ggcactgaca attccgtggt gttgtcgggg aaatcatcgt cctttccttg gctgctcgcc   8400
tatgttgcca cctggattct gcgcgggacg tccttctgct acgtcccttc ggccctcaat   8460
ccagcggacc ttccttcccg cggcctgctg ccggctctgc ggcctcttcc gcgtcttcgc   8520
cttcgccctc agacgagtcg gatctccctt tgggccgcct ccccgctaca aggcagctgt   8580
agatcccttt catagaaggc ggcggtggta cctttaagac caatgactta caaggcagct   8640
gtagatctta gccacttttt aaaagaaaag gggggactgg aagggctaat tcactcccaa   8700
cgaagacaag atctgctttt tgcttgtact gggtctctct ggttagacca gatctgagcc   8760
tgggagctct ctggctaact agggaaccca ctgcttaagc ctcaataaag cttgccttga   8820
gtgcttcaag tagtgtgtgc ccgtctgttg tgtgactctg gtaactagag atccctcaga   8880
cccttttagt cagtgtggaa aatctctagc agtagtagtt catgtcatct tattattcag   8940
tatttataac ttgcaaagaa atgaatatca gagagtgaga ggaacttgtt tattgcagct   9000
tataatggtt acaaataaag caatagcatc acaaatttca caaataaagc atttttttca   9060
ctgcattcta gttgtggttt gtccaaactc atcaatgtat cttatcatgt ctggctctag   9120
ctatcccgcc cctaactccg cccatcccgc ccctaactcc gcccagttcc gcccattctc   9180
cgccccatgg ctgactaatt ttttttattt atgcagaggc cgaggccgcc tcggcctctg   9240
agctattcca gaagtagtga ggaggctttt ttggaggcct aggcttttgc gtcgagacgt   9300
acccaattcg ccctatagtg agtcgtatta cgcgcgctca ctggccgtcg ttttacaacg   9360
tcgtgactgg gaaaaccctg gcgttaccca acttaatcgc cttgcagcac atcccccttt   9420
cgccagctgg cgtaatagcg aagaggcccg caccgatcgc ccttcccaac agttgcgcag   9480
cctgaatggc gaatggcgcg acgcgccctg tagcggcgca ttaagcgcgg cgggtgtggt   9540
ggttacgcgc agcgtgaccg ctacacttgc cagcgcccta gcgcccgctc ctttcgcttt   9600
cttcccttcc tttctcgcca cgttcgccgg ctttccccgt caagctctaa atcgggggct   9660
ccctttaggg ttccgattta gtgctttacg gcacctcgac cccaaaaaac ttgattaggg   9720
tgatggttca cgtagtgggc catcgccctg atagacggtt tttcgccctt tgacgttgga   9780
gtccacgttc tttaatagtg gactcttgtt ccaaactgga acaacactca accctatctc   9840
ggtctattct tttgatttat aagggatttt gccgatttcg gcctattggt taaaaaatga   9900
gctgatttaa caaaaattta acgcgaattt taacaaaata ttaacgttta caatttccca   9960
ggtggcactt ttcggggaaa tgtgcgcgga acccctattt gtttattttt ctaaatacat  10020
tcaaatatgt atccgctcat gagacaataa ccctgataaa tgcttcaata atattgaaaa  10080
aggaagagta tgagtattca acatttccgt gtcgccctta ttcccttttt tgcggcattt  10140
tgccttcctg tttttgctca cccagaaacg ctggtgaaag taaaagatgc tgaagatcag  10200
ttgggtgcac gagtgggtta catcgaactg gatctcaaca gcggtaagat ccttgagagt  10260
tttcgccccg aagaacgttt tccaatgatg agcactttta aagttctgct atgtggcgcg  10320
gtattatccc gtattgacgc cgggcaagag caactcggtc gccgcataca ctattctcag  10380
aatgacttgg ttgagtactc accagtcaca gaaaagcatc ttacggatgg catgacagta  10440
agagaattat gcagtgctgc cataaccatg agtgataaca ctgcggccaa cttacttctg  10500
acaacgatcg gaggaccgaa ggagctaacc gcttttttgc acaacatggg ggatcatgta  10560
actcgccttg atcgttggga a                                              10581
```

<210> SEQ ID NO 43
<211> LENGTH: 10726
<212> TYPE: DNA
<213> ORGANISM: Artificial Sequence
<220> FEATURE:
<223> OTHER INFORMATION: SynHSPB'3-CAR

<400> SEQUENCE: 43
ccggagctga atgaagccat accaaacgac gagcgtgaca ccacgatgcc tgtagcaatg 60
gcaacaacgt tgcgcaaact attaactggc gaactactta ctctagcttc ccggcaacaa 120
ttaatagact ggatggaggc ggataaagtt gcaggaccac ttctgcgctc ggcccttccg 180
gctggctggt ttattgctga taaatctgga gccggtgagc gtgggtctcg cggtatcatt 240
gcagcactgg ggccagatgg taagccctcc cgtatcgtag ttatctacac gacggggagt 300
caggcaacta tggatgaacg aaatagacag atcgctgaga taggtgcctc actgattaag 360
cattggtaac tgtcagacca agtttactca tatatacttt agattgattt aaaacttcat 420
ttttaattta aaaggatcta ggtgaagatc ctttttgata atctcatgac caaaatccct 480
taacgtgagt tttcgttcca ctgagcgtca gaccccgtag aaaagatcaa aggatcttct 540
tgagatcctt tttttctgcg cgtaatctgc tgcttgcaaa caaaaaaacc accgctacca 600
gcggtggttt gtttgccgga tcaagagcta ccaactcttt ttccgaaggt aactggcttc 660
agcagagcgc agataccaaa tactgtcctt ctagtgtagc cgtagttagg ccaccacttc 720
aagaactctg tagcaccgcc tacatacctc gctctgctaa tcctgttacc agtggctgct 780
gccagtggcg ataagtcgtg tcttaccggg ttggactcaa gacgatagtt accggataag 840
gcgcagcggt cgggctgaac ggggggttcg tgcacacagc ccagcttgga gcgaacgacc 900
tacaccgaac tgagatacct acagcgtgag ctatgagaaa gcgccacgct tcccgaaggg 960
agaaaggcgg acaggtatcc ggtaagcggc agggtcggaa caggagagcg cacgagggag 1020
cttccagggg gaaacgcctg gtatctttat agtcctgtcg ggtttcgcca cctctgactt 1080
gagcgtcgat ttttgtgatg ctcgtcaggg gggcggagcc tatggaaaaa cgccagcaac 1140
gcggcctttt tacggttcct ggccttttgc tggccttttg ctcacatgtt ctttcctgcg 1200
ttatcccctg attctgtgga taaccgtatt accgcctttg agtgagctga taccgctcgc 1260
cgcagccgaa cgaccgagcg cagcgagtca gtgagcgagg aagcggaaga gcgcccaata 1320
cgcaaaccgc ctctccccgc gcgttggccg attcattaat gcagctggca cgacaggttt 1380
cccgactgga aagcgggcag tgagcgcaac gcaattaatg tgagttagct cactcattag 1440
gcaccccagg ctttacactt tatgcttccg gctcgtatgt tgtgtggaat tgtgagcgga 1500
taacaatttc acacaggaaa cagctatgac catgattacg ccaagcgcgc aattaaccct 1560
cactaaaggg aacaaaagct ggagctgcaa gcttggccat tgcatacgtt gtatccatat 1620
cataatatgt acatttatat tggctcatgt ccaacattac cgccatgttg acattgatta 1680
ttgactagtt attaatagta atcaattacg gggtcattag ttcatagccc atatatggag 1740
ttccgcgtta cataacttac ggtaaatggc ccgcctggct gaccgcccaa cgacccccgc 1800
ccattgacgt caataatgac gtatgttccc atagtaacgc caatagggac tttccattga 1860
cgtcaatggg tggagtattt acggtaaact gcccacttgg cagtacatca agtgtatcat 1920
atgccaagta cgcccccctat tgacgtcaat gacggtaaat ggcccgcctg gcattatgcc 1980
cagtacatga ccttatggga ctttcctact tggcagtaca tctacgtatt agtcatcgct 2040
attaccatgg tgatgcggtt ttggcagtac atcaatgggc gtggatagcg gtttgactca 2100

-continued

```
cggggatttc caagtctcca ccccattgac gtcaatggga gtttgttttg gcaccaaaat   2160
caacgggact ttccaaaatg tcgtaacaac tccgccccat tgacgcaaat gggcggtagg   2220
cgtgtacggt gggaggtcta tataagcaga gctcgtttag tgaaccgggg tctctctggt   2280
tagaccagat ctgagcctgg gagctctctg gctaactagg gaacccactg cttaagcctc   2340
aataaagctt gccttgagtg cttcaagtag tgtgtgcccg tctgttgtgt gactctggta   2400
actagagatc cctcagaccc ttttagtcag tgtggaaaat ctctagcagt ggcgcccgaa   2460
cagggacttg aaagcgaaag ggaaaccaga ggagctctct cgacgcagga ctcggcttgc   2520
tgaagcgcgc acggcaagag gcgaggggcg gcgactggtg agtacgccaa aaattttgac   2580
tagcggaggc tagaaggaga gagatgggtg cgagagcgtc agtattaagc gggggagaat   2640
tagatcgcga tgggaaaaaa ttcggttaag gccaggggga aagaaaaaat ataaattaaa   2700
acatatagta tgggcaagca gggagctaga acgattcgca gttaatcctg gcctgttaga   2760
aacatcagaa ggctgtagac aaatactggg acagctacaa ccatcccttc agacaggatc   2820
agaagaactt agatcattat ataatacagt agcaaccctc tattgtgtgc atcaaaggat   2880
agagataaaa gacaccaagg aagctttaga caagatagag gaagagcaaa acaaaagtaa   2940
gaccaccgca cagcaagcgg ccgctgatct tcagacctgg aggaggagat atgagggaca   3000
attggagaag tgaattatat aaatataaag tagtaaaaat tgaaccatta ggagtagcac   3060
ccaccaaggc aaagagaaga gtggtgcaga gagaaaaaag agcagtggga ataggagctt   3120
tgttccttgg gttcttggga gcagcaggaa gcactatggg cgcagcctca atgacgctga   3180
cggtacaggc cagacaatta ttgtctggta tagtgcagca gcagaacaat ttgctgaggg   3240
ctattgaggc gcaacagcat ctgttgcaac tcacagtctg gggcatcaag cagctccagg   3300
caagaatcct ggctgtggaa agatacctaa aggatcaaca gctcctgggg atttggggtt   3360
gctctggaaa actcatttgc accactgctg tgccttggaa tgctagttgg agtaataaat   3420
ctctggaaca gattggaatc acacgacctg gatggagtgg gacagagaaa ttaacaatta   3480
cacaagctta atacactcct taattgaaga atcgcaaaac cagcaagaaa agaatgaaca   3540
agaattattg gaattagata aatgggcaag tttgtggaat tggtttaaca taacaaattg   3600
gctgtggtat ataaaattat tcataatgat agtaggaggc ttggtaggtt taagaatagt   3660
ttttgctgta ctttctatag tgaatagagt taggcaggga tattcaccat tatcgtttca   3720
gacccacctc ccaaccccga ggggacccga caggcccgaa ggaatagaag aagaaggtgg   3780
agagagagac agagacagat ccattcgatt agtgaacgga tctcgacggt atcgatctcg   3840
acacaaatgg cagtattcat ccacaatttt aaaagaaaag gggggattgg ggggtacagt   3900
gcaggggaaa gaatagtaga cataatagca acagacatac aaactaaaga attacaaaaa   3960
caaattacaa aaattcaaaa ttttcgggtt tattacaggg acagcagaga tccagtttgg   4020
gaattagctt gaccccgatc tgcccgaacc ttctcccggg gtcagcgccg cgccgcgcca   4080
cccggctgca gcagcccggg cgggcgagag gctctcaact gggcgggaag gtgcgggaag   4140
gtgcggaaag gttcgcgaaa gttcgcggcc ggactagagt ggcgagatcc cccgatctgc   4200
ccgaaccttc tcccggggtc agcgccgcgc cgcgccaccc ggctgcagca gcccgggcgg   4260
gcgagaggct ctcaactggg cgggaaggtg cgggaaggtg cggaaaggtt cgcgaaagtt   4320
cgcggcaatt agcttgaccc cgatctgccc gaaccttctc ccggggtcag cgccgcgccg   4380
cgccacccgg ctgcagcagc ccgggcgggc gagaggctct caactgggcg ggaaggtgcg   4440
ggaaggtgcg gaaaggttcg cgaaagttcg cggcggcggg ggtcgggtga ggcgcaaaag   4500
```

-continued

```
gataaaaagc cggtggaagc ggagctgagc agatccgagc cgggctggct gcagagaaac 4560
cgcagggaga gcctcactgc tgagcgcccc tcgacggcgg agcggcagca gcctccgtgg 4620
cctccagcat ccgacaagaa gcttcagcca tggctctgcc tgtgaccgcc ctgctgctgc 4680
ctctggctct gctgctgcac gccgctcggc cttacccata cgatgttcca gattacgctg 4740
acattcagat gactcagacc acaagcagcc tcagtgcgag cctgggggac agggtgacta 4800
tcagctgccg ggccagccag gacatttcca agtacctgaa ttggtaccag cagaagcccg 4860
atggtactgt gaaactcctg atatatcata cttctaggct ccattccggg gttccaagcc 4920
gattcagtgg ctccggttcc ggtacagatt attccctgac cattagcaac ttggaacagg 4980
aggacattgc aacgtatttc tgtcagcaag gcaacacatt gccctacaca ttcgggggcg 5040
ggactaaact cgaaataact ggcggcgggg gttctggtgg cggcggcagc ggcggtggag 5100
gatcagaagt gaagctgcag gaaagtggcc ccgggctggt agccccaagt cagtccctga 5160
gtgtaacctg tacagtgagt ggagtgtctc ttcctgacta cggggtaagt tggattcggc 5220
aacctccacg caagggcctg gagtggctcg gcgtgatttg gggatctgag acaacttact 5280
acaattccgc cctgaagagc aggctgacca tcattaagga caatagcaag tcacaggtgt 5340
ttctgaagat gaactcactg cagaccgacg acaccgccat ctattactgc gccaaacatt 5400
attattatgg cgggagttat gctatggact actggggcca gggcactagc gtcaccgtca 5460
gcagtactac aactccagca cccagacccc ctacacctgc tccaactatc gcaagtcagc 5520
ccctgtcact gcgccctgaa gcctgtcgcc ctgctgccgg gggagctgtg catactcggg 5580
gactggactt tgcctgtgat atctacttct gggtgctggt cgtggtcgga ggggtgctgg 5640
cctgttatag cctgctggtg actgtcgcct tcattatctt ctgggtgcgg agcaagaggt 5700
ctcgcggtgg gcattccgac tacatgaaca tgacccctag aaggcctggc ccaaccagaa 5760
agcactacca gccatacgcc cctcccagag atttcgccgc ttatcgaagc gtgaagttct 5820
cccgaagcgc agatgcccca gcctatcagc agggacagaa tcagctgtac aacgagctga 5880
acctgggaag acgggaggaa tacgatgtgc tggacaaaag gcggggcaga gatcctgaga 5940
tgggcggcaa accaagacgg aagaaccccc aggaaggtct gtataatgag ctgcagaaag 6000
acaagatggc tgaggcctac tcagaaatcg ggatgaaggg cgaaagaagg agaggaaaag 6060
gccacgacgg actgtaccag ggctgagta cagcaacaaa agacacctat gacgctctgc 6120
acatgcaggc tctgccacca agatgacaag gcagctgtag atcttagccg atcttagcca 6180
ccagaattgt acatacaagg ccgtacagaa ttggctccgg tgcccgtcag tgggcagagc 6240
gcacatcgcc cacagtcccc gagaagttgg ggggaggggt cggcaattga accggtgcct 6300
agagaaggtg gcgcggggta aactgggaaa gtgatgtcgt gtactggctc cgcctttttc 6360
ccgagggtgg gggagaaccg tatataagtg cagtagtcgc cgtgaacgtt ctttttcgca 6420
acgggtttgc cgccagaaca caggtaagtg ccgtgtgtgg ttcccgcggg cctggcctct 6480
ttacgggtta tggcccttgc gtgccttgaa ttacttccac tggctgcagt acgtgattct 6540
tgatcccgag cttcgggttg gaagtgggtg ggagagttcg aggccttgcg cttaaggagc 6600
cccttcgcct cgtgcttgag ttgaggcctg gcctgggcgc tggggccgcc gcgtgcgaat 6660
ctggtggcac cttcgcgcct gtctcgctgc tttcgataag tctctagcca tttaaaattt 6720
ttgatgacct gctgcgacgc ttttttctg gcaagatagt cttgtaaatg cgggccaaga 6780
tctgcacact ggtatttcgg tttttggggc cgcgggcggc gacggggccc gtgcgtccca 6840
```

-continued

```
gcgcacatgt tcggcgaggc ggggcctgcg agcgcggcca ccgagaatcg gacgggggta   6900
gtctcaagct ggccggcctg ctctggtgcc tggcctcgcg ccgccgtgta tcgccccgcc   6960
ctgggcggca aggctggccc ggtcggcacc agttgcgtga gcggaaagat ggccgcttcc   7020
cggccctgct gcagggagct caaaatggag gacgcggcgc tcgggagagc gggcgggtga   7080
gtcacccaca caaaggaaaa gggcctttcc gtcctcagcc gtcgcttcat gtgactccac   7140
ggagtaccgg gcgccgtcca ggcacctcga ttagttctcg agcttttgga gtacgtcgtc   7200
tttaggttgg ggggaggggt tttatgcgat ggagtttccc cacactgagt gggtggagac   7260
tgaagttagg ccagcttggc acttgatgta attctccttg gaatttgccc tttttgagtt   7320
tggatcttgg ttcattctca agcctcagac agtggttcaa agtttttttc ttccatttca   7380
ggtgtcgtga ccggtcgcca ccatggtgtc taagggcgaa gagctgatta aggagaacat   7440
gcacatgaag ctgtacatgg agggcaccgt ggacaaccat cacttcaagt gcacatccga   7500
gggcgaaggc aagccctacg agggcaccca gaccatgaga atcaaggtgg tcgagggcgg   7560
ccctctcccc ttcgccttcg acatcctggc tactagcttc ctctacggca gcaagacctt   7620
catcaaccac acccagggca tccccgactt cttcaagcag tccttccctg agggcttcac   7680
atgggagaga gtcaccacat acgaagacgg gggcgtgctg accgctaccc aggacaccag   7740
cctccaggac ggctgcctca tctacaacgt caagatcaga ggggtgaact tcacatccaa   7800
cggccctgtg atgcagaaga aaacactcgg ctgggaggcc ttcaccgaga cgctgtaccc   7860
cgctgacggc ggcctggaag gcagaaacga catggccctg aagctcgtgg gcgggagcca   7920
tctgatcgca aacgccaaga ccacatatag atccaagaaa cccgctaaga acctcaagat   7980
gcctggcgtc tactatgtgg actacagact ggaaagaatc aaggaggcca acaacgagac   8040
ctacgtcgag cagcacgagg tggcagtggc cagatactgc gacctcccta gcaaactggg   8100
gcacaagctt aattaatgta caaatcaacc tctggattac aaaatttgtg aaagattgac   8160
tggtattctt aactatgttg ctccttttac gctatgtgga tacgctgctt taatgccttt   8220
gtatcatgct attgcttccc gtatggcttt cattttctcc tccttgtata aatcctggtt   8280
gctgtctctt tatgaggagt tgtggcccgt tgtcaggcaa cgtggcgtgg tgtgcactgt   8340
gtttgctgac gcaaccccca ctggttgggg cattgccacc acctgtcagc tcctttccgg   8400
gactttcgct ttccccctcc ctattgccac ggcggaactc atcgccgcct gccttgcccg   8460
ctgctggaca ggggctcggc tgttgggcac tgacaattcc gtggtgttgt cggggaaatc   8520
atcgtccttt ccttggctgc tcgcctatgt tgccacctgg attctgcgcg ggacgtcctt   8580
ctgctacgtc ccttcggccc tcaatccagc ggaccttcct tcccgcggcc tgctgccggc   8640
tctgcggcct cttccgcgtc ttcgccttcg ccctcagacg agtcggatct ccctttgggc   8700
cgcctccccg ctacaaggca gctgtagatc cctttcatag aaggcggcgg tggtaccttt   8760
aagaccaatg acttacaagg cagctgtaga tcttagccac tttttaaaag aaaagggggg   8820
actggaaggg ctaattcact cccaacgaag acaagatctg ctttttgctt gtactgggtc   8880
tctctggtta gaccagatct gagcctggga gctctctggc taactaggga acccactgct   8940
taagcctcaa taaagcttgc cttgagtgct tcaagtagtg tgtgcccgtc tgttgtgtga   9000
ctctggtaac tagagatccc tcagaccctt ttagtcagtg tggaaaatct ctagcagtag   9060
tagttcatgt catcttatta ttcagtattt ataacttgca aagaaatgaa tatcagagag   9120
tgagaggaac ttgtttattg cagcttataa tggttacaaa taaagcaata gcatcacaaa   9180
tttcacaaat aaagcatttt tttcactgca ttctagttgt ggtttgtcca aactcatcaa   9240
```

-continued

```
tgtatcttat catgtctggc tctagctatc ccgcccctaa ctccgcccat cccgccccta   9300

actccgccca gttccgccca ttctccgccc catggctgac taattttttt tatttatgca   9360

gaggccgagg ccgcctcggc ctctgagcta ttccagaagt agtgaggagg cttttttgga   9420

ggcctaggct tttgcgtcga gacgtaccca attcgcccta tagtgagtcg tattacgcgc   9480

gctcactggc cgtcgtttta caacgtcgtg actgggaaaa ccctggcgtt acccaactta   9540

atcgccttgc agcacatccc cctttcgcca gctggcgtaa tagcgaagag gcccgcaccg   9600

atcgcccttc ccaacagttg cgcagcctga atggcgaatg gcgcgacgcg ccctgtagcg   9660

gcgcattaag cgcggcgggt gtggtggtta cgcgcagcgt gaccgctaca cttgccagcg   9720

ccctagcgcc cgctcctttc gctttcttcc cttcctttct cgccacgttc gccggctttc   9780

cccgtcaagc tctaaatcgg gggctccctt tagggttccg atttagtgct ttacggcacc   9840

tcgaccccaa aaaacttgat tagggtgatg gttcacgtag tgggccatcg ccctgataga   9900

cggtttttcg ccctttgacg ttggagtcca cgttctttaa tagtggactc ttgttccaaa   9960

ctggaacaac actcaaccct atctcggtct attcttttga tttataaggg attttgccga  10020

tttcggccta ttggttaaaa aatgagctga tttaacaaaa atttaacgcg aattttaaca  10080

aaatattaac gtttacaatt tcccaggtgg cacttttcgg ggaaatgtgc gcggaacccc  10140

tatttgttta tttttctaaa tacattcaaa tatgtatccg ctcatgagac aataaccctg  10200

ataaatgctt caataatatt gaaaaaggaa gagtatgagt attcaacatt tccgtgtcgc  10260

ccttattccc ttttttgcgg cattttgcct tcctgttttt gctcacccag aaacgctggt  10320

gaaagtaaaa gatgctgaag atcagttggg tgcacgagtg ggttacatcg aactggatct  10380

caacagcggt aagatccttg agagttttcg ccccgaagaa cgttttccaa tgatgagcac  10440

ttttaaagtt ctgctatgtg gcgcggtatt atcccgtatt gacgccgggc aagagcaact  10500

cggtcgccgc atacactatt ctcagaatga cttggttgag tactcaccag tcacagaaaa  10560

gcatcttacg gatggcatga cagtaagaga attatgcagt gctgccataa ccatgagtga  10620

taacactgcg gccaacttac ttctgacaac gatcggagga ccgaaggagc taaccgcttt  10680

tttgcacaac atgggggatc atgtaactcg ccttgatcgt tgggaa                10726
```

<210> SEQ ID NO 44
<211> LENGTH: 9968
<212> TYPE: DNA
<213> ORGANISM: Artificial Sequence
<220> FEATURE:
<223> OTHER INFORMATION: HSP nanodeg+GFP oscillator circuit

<400> SEQUENCE: 44

```
ccggagctga atgaagccat accaaacgac gagcgtgaca ccacgatgcc tgtagcaatg     60

gcaacaacgt tgcgcaaact attaactggc gaactactta ctctagcttc ccggcaacaa    120

ttaatagact ggatggaggc ggataaagtt gcaggaccac ttctgcgctc ggcccttccg    180

gctggctggt ttattgctga taaatctgga gccggtgagc gtgggtctcg cggtatcatt    240

gcagcactgg ggccagatgg taagccctcc cgtatcgtag ttatctacac gacggggagt    300

caggcaacta tggatgaacg aaatagacag atcgctgaga taggtgcctc actgattaag    360

cattggtaac tgtcagacca agtttactca tatatacttt agattgattt aaaacttcat    420

ttttaattta aaaggatcta ggtgaagatc ctttttgata atctcatgac caaaatccct    480

taacgtgagt tttcgttcca ctgagcgtca gaccccgtag aaaagatcaa aggatcttct    540
```

-continued

```
tgagatcctt tttttctgcg cgtaatctgc tgcttgcaaa caaaaaaacc accgctacca    600
gcggtggttt gtttgccgga tcaagagcta ccaactcttt ttccgaaggt aactggcttc    660
agcagagcgc agataccaaa tactgtcctt ctagtgtagc cgtagttagg ccaccacttc    720
aagaactctg tagcaccgcc tacatacctc gctctgctaa tcctgttacc agtggctgct    780
gccagtggcg ataagtcgtg tcttaccggg ttggactcaa gacgatagtt accggataag    840
gcgcagcggt cgggctgaac ggggggttcg tgcacacagc ccagcttgga gcgaacgacc    900
tacaccgaac tgagatacct acagcgtgag ctatgagaaa gcgccacgct tcccgaaggg    960
agaaaggcgg acaggtatcc ggtaagcggc agggtcggaa caggagagcg cacgagggag   1020
cttccagggg gaaacgcctg gtatctttat agtcctgtcg ggtttcgcca cctctgactt   1080
gagcgtcgat ttttgtgatg ctcgtcaggg gggcggagcc tatggaaaaa cgccagcaac   1140
gcggcctttt tacggttcct ggccttttgc tggccttttg ctcacatgtt ctttcctgcg   1200
ttatcccctg attctgtgga taaccgtatt accgcctttg agtgagctga taccgctcgc   1260
cgcagccgaa cgaccgagcg cagcgagtca gtgagcgagg aagcggaaga gcgcccaata   1320
cgcaaaccgc ctctccccgc gcgttggccg attcattaat gcagctggca cgacaggttt   1380
cccgactgga aagcgggcag tgagcgcaac gcaattaatg tgagttagct cactcattag   1440
gcaccccagg ctttacactt tatgcttccg gctcgtatgt tgtgtggaat tgtgagcgga   1500
taacaatttc acacaggaaa cagctatgac catgattacg ccaagcgcgc aattaaccct   1560
cactaaaggg aacaaaagct ggagctgcaa gcttggccat tgcatacgtt gtatccatat   1620
cataatatgt acatttatat tggctcatgt ccaacattac cgccatgttg acattgatta   1680
ttgactagtt attaatagta atcaattacg gggtcattag ttcatagccc atatatggag   1740
ttccgcgtta cataacttac ggtaaatggc ccgcctggct gaccgcccaa cgacccccgc   1800
ccattgacgt caataatgac gtatgttccc atagtaacgc caatagggac tttccattga   1860
cgtcaatggg tggagtattt acggtaaact gcccacttgg cagtacatca agtgtatcat   1920
atgccaagta cgccccctat tgacgtcaat gacggtaaat ggcccgcctg gcattatgcc   1980
cagtacatga ccttatggga ctttcctact tggcagtaca tctacgtatt agtcatcgct   2040
attaccatgg tgatgcggtt ttggcagtac atcaatgggc gtggatagcg gtttgactca   2100
cggggatttc caagtctcca ccccattgac gtcaatggga gtttgttttg gcaccaaaat   2160
caacgggact ttccaaaatg tcgtaacaac tccgccccat tgacgcaaat gggcggtagg   2220
cgtgtacggt gggaggtcta tataagcaga gctcgtttag tgaaccgggg tctctctggt   2280
tagaccagat ctgagcctgg gagctctctg gctaactagg gaacccactg cttaagcctc   2340
aataaagctt gccttgagtg cttcaagtag tgtgtgcccg tctgttgtgt gactctggta   2400
actagagatc cctcagaccc ttttagtcag tgtggaaaat ctctagcagt ggcgcccgaa   2460
cagggacttg aaagcgaaag ggaaaccaga ggagctctct cgacgcagga ctcggcttgc   2520
tgaagcgcgc acggcaagag gcgagggcg gcgactggtg agtacgccaa aaattttgac   2580
tagcggaggc tagaaggaga gagatgggtg cgagagcgtc agtattaagc gggggagaat   2640
tagatcgcga tgggaaaaaa ttcggttaag gccaggggga aagaaaaaat ataaattaaa   2700
acatatagta tgggcaagca gggagctaga acgattcgca gttaatcctg gcctgttaga   2760
aacatcagaa ggctgtagac aaatactggg acagctacaa ccatcccttc agacaggatc   2820
agaagaactt agatcattat ataatacagt agcaaccctc tattgtgtgc atcaaaggat   2880
agagataaaa gacaccaagg aagctttaga caagatagag gaagagcaaa acaaaagtaa   2940
```

gaccaccgca cagcaagcgg ccgctgatct tcagacctgg aggaggagat atgagggaca 3000
attggagaag tgaattatat aaatataaag tagtaaaaat tgaaccatta ggagtagcac 3060
ccaccaaggc aaagagaaga gtggtgcaga gagaaaaaag agcagtggga ataggagctt 3120
tgttccttgg gttcttggga gcagcaggaa gcactatggg cgcagcctca atgacgctga 3180
cggtacaggc cagacaatta ttgtctggta tagtgcagca gcagaacaat ttgctgaggg 3240
ctattgaggc gcaacagcat ctgttgcaac tcacagtctg gggcatcaag cagctccagg 3300
caagaatcct ggctgtggaa agatacctaa aggatcaaca gctcctgggg atttggggtt 3360
gctctggaaa actcatttgc accactgctg tgccttggaa tgctagttgg agtaataaat 3420
ctctggaaca gattggaatc acacgacctg gatggagtgg gacagagaaa ttaacaatta 3480
cacaagctta atacactcct taattgaaga atcgcaaaac cagcaagaaa agaatgaaca 3540
agaattattg gaattagata aatgggcaag tttgtggaat tggtttaaca taacaaattg 3600
gctgtggtat ataaaattat tcataatgat agtaggaggc ttggtaggtt taagaatagt 3660
ttttgctgta ctttctatag tgaatagagt taggcaggga tattcaccat tatcgtttca 3720
gacccacctc ccaaccccga ggggacccga caggcccgaa ggaatagaag aagaaggtgg 3780
agagagagac agagacagat ccattcgatt agtgaacgga tctcgacggt atcgatctcg 3840
acacaaatgg cagtattcat ccacaatttt aaaagaaaag gggggattgg ggggtacagt 3900
gcaggggaaa gaatagtaga cataatagca acagacatac aaactaaaga attacaaaaa 3960
caaattacaa aaattcaaaa ttttcgggtt tattacaggg acagcagaga tccagtttgg 4020
gaattagctt gaccccgatc tgcccgaacc ttctcccggg gtcagcgccg cgccgcgcca 4080
cccggctgca gcagcccggg cgggcgagag gctctcaact gggcgggaag gtgcgggaag 4140
gtgcggaaag gttcgcgaaa gttcgcggcc ggactagagt ggcgagatcc cccgatctgc 4200
ccgaaccttc tcccggggtc agcgccgcgc cgcgccaccc ggctgcagca gcccgggcgg 4260
gcgagaggct ctcaactggg cgggaaggtg cgggaaggtg cggaaaggtt cgcgaaagtt 4320
cgcggcaatt agcttgaccc cgatctgccc gaaccttctc ccggggtcag cgccgcgccg 4380
cgccacccgg ctgcagcagc ccgggcgggc gagaggctct caactgggcg ggaaggtgcg 4440
ggaaggtgcg gaaaggttcg cgaaagttcg cggcggcggg ggtcgggtga ggcgcaaaag 4500
gataaaaagc cggtggaagc ggagctgagc agatccgagc cgggctggct gcagagaaac 4560
cgcagggaga gcctcactgc tgagcgcccc tcgacggcgg agcggcagca gcctccgtgg 4620
cctccagcat ccgacaagaa gcttcacgga tgatgaaaat ggagactgac aaaataatgg 4680
acgaaaccaa ctccaatgca caggccttca caaccactat gctgtacgac ccggtgcgca 4740
agaaagactc atcgcccacc taccaaacgg agcgggaact ctgctttcag tacttcaccc 4800
agtggagcga gtcgggccag gtggactttg tggagcacct gctgtcgcgc atgtgccact 4860
atcaacacgg acagatcaat gcctatctca agccgatgct ccagcgggac tttatcacat 4920
tgctgccaat caagggtctg gatcacatcg cagaaaacat tttgtcgtac ttggatgccg 4980
aatcgctcaa atcatccgag ctggtctgca aggaatggct gcgcgtcatt tccgagggca 5040
tgctctggaa gaagctcatc gaacgcaagg tgcgcacaga ttccttgtgg cgcggactgg 5100
ccgagcggcg taattggatg cagtacctct tcaagccaag accgggccag actcaacggc 5160
cacactcatt ccatcgcgag ttgttcccca agataatgaa tgacattgac agcatagaga 5220
acaactggcg gactggccgc cacctcgaga tggatcaagt ccaactggtg gagtctggtg 5280

-continued

```
gcgctttggt gcagccaggt ggctctctgc gtttgtcctg tgccgcttct ggcttcccag   5340
tgaaccgcta ttccatgcgc tggtatcgcc aggctccagg caaagagcgt gagtgggtag   5400
ccggtatgtc cagcgcgggt gatcgtagct cctatgaaga ctccgtgaag ggccgtttca   5460
ccatcagccg tgacgatgcc cgtaacacgg tgtatctgca aatgaacagc ttgaaacctg   5520
aagatacggc cgtgtattac tgtaatgtga acgtgggctt cgagtattgg ggccaaggca   5580
cccaggtcac cgtctccagc taaggctccg gtgcccgtca gtgggcagag cgcacatcgc   5640
ccacagtccc cgagaagttg gggggagggg tcggcaattg aaccggtgcc tagagaaggt   5700
ggcgcggggt aaactgggaa agtgatgtcg tgtactggct ccgccttttt cccgagggtg   5760
ggggagaacc gtatataagt gcagtagtcg ccgtgaacgt tctttttcgc aacgggtttg   5820
ccgccagaac acaggtgacc ggtcgccacc atggctctgc ctgtgaccgc cctgctgctg   5880
cctctggctc tgctgctgca cgccgctcgg ccttacccat acgatgttcc agattacgct   5940
gacattcaga tgactcagac cacaagcagc ctcagtgcga gcctgggggga cagggtgact   6000
atcagctgcc gggccagcca ggacatttcc aagtacctga attggtacca gcagaagccc   6060
gatggtactg tgaaactcct gatatatcat acttctaggc tccattccgg ggttccaagc   6120
cgattcagtg gctccggttc cggtacagat tattccctga ccattagcaa cttggaacag   6180
gaggacattg caacgtattt ctgtcagcaa ggcaacacat tgccctacac attcgggggc   6240
gggactaaac tcgaaataac tggcggcggg ggttctggtg gcggcggcag cggcggtgga   6300
ggatcagaag tgaagctgca ggaaagtggc cccgggctgg tagccccaag tcagtccctg   6360
agtgtaacct gtacagtgag tggagtgtct cttcctgact acggggtaag ttggattcgg   6420
caacctccac gcaagggcct ggagtggctc ggcgtgattt ggggatctga gacaacttac   6480
tacaattccg ccctgaagag caggctgacc atcattaagg acaatagcaa gtcacaggtg   6540
tttctgaaga tgaactcact gcagaccgac gacaccgcca tctattactg cgccaaacat   6600
tattattatg gcgggagtta tgctatggac tactggggcc agggcactag cgtcaccgtc   6660
agcagtacta caactccagc acccagaccc cctacacctg ctccaactat cgcaagtcag   6720
cccctgtcac tgcgccctga agcctgtcgc cctgctgccg gggggagctgt gcatactcgg   6780
ggactggact ttgcctgtga tatctacttc tgggtgctgg tcgtggtcgg aggggtgctg   6840
gcctgttata gcctgctggt gactgtcgcc ttcattatct tctgggtgcg gagcaagagg   6900
tctcgcggtg ggcattccga ctacatgaac atgaccccta gaaggcctgg cccaaccaga   6960
aagcactacc agccatacgc ccctcccaga gatttcgccg cttatcgaag cgtgaagttc   7020
tcccgaagcg cagatgcccc agcctatcag cagggacaga atcagctgta caacgagctg   7080
aacctgggaa gacgggagga atacgatgtg ctggacaaaa ggcggggcag agatcctgag   7140
atgggcggca aaccaagacg gaagaacccc caggaaggtc tgtataatga gctgcagaaa   7200
gacaagatgg ctgaggccta ctcagaaatc gggatgaagg gcgaaagaag gagaggaaaa   7260
ggccacgacg gactgtacca ggggctgagt acagcaacaa aagacaccta tgacgctctg   7320
cacatgcagg ctctgccacc aagaatggtg agcaagggcg aggagctgtt caccggggtg   7380
gtgcccatcc tggtcgagct ggacggcgac gtaaacggcc acaagttcag cgtgtccggc   7440
gagggcgagg gcgatgccac ctacggcaag ctgaccctga agttcatctg caccaccggc   7500
aagctgcccg tgccctggcc caccctcgtg accaccctga cctacggcgt gcagtgcttc   7560
agccgctacc ccgaccacat gaagcagcac gacttcttca agtccgccat gcccgaaggc   7620
tacgtccagg agcgcaccat cttcttcaag gacgacggca actacaagac ccgcgccgag   7680
```

```
gtgaagttcg agggcgacac cctggtgaac cgcatcgagc tgaagggcat cgacttcaag   7740
gaggacggca acatcctggg gcacaagctg gagtacaact acaacagcca caacgtctat   7800
atcatggccg acaagcagaa gaacggcatc aaggtgaact tcaagatccg ccacaacatc   7860
gaggacggca gcgtgcagct cgccgaccac taccagcaga acacccccat cggcgacggc   7920
cccgtgctgc tgcccgacaa ccactacctg agcacccagt ccgccctgag caaagacccc   7980
aacgagaagc gcgatcacat ggtcctgctg gagttcgtga ccgccgccgg gatcactctc   8040
ggcatggacg agctgtacaa gtaatggaag ggctaattca ctcccaacga agacaagatc   8100
tgctttttgc ttgtactggg tctctctggt tagaccagat ctgagcctgg gagctctctg   8160
gctaactagg gaacccactg cttaagcctc aataaagctt gccttgagtg cttcaagtag   8220
tgtgtgcccg tctgttgtgt gactctggta actagagatc cctcagaccc ttttagtcag   8280
tgtggaaaat ctctagcagt agtagttcat gtcatcttat tattcagtat ttataacttg   8340
caaagaaatg aatatcagag agtgagagga acttgtttat tgcagcttat aatggttaca   8400
aataaagcaa tagcatcaca aatttcacaa ataaagcatt tttttcactg cattctagtt   8460
gtggtttgtc caaactcatc aatgtatctt atcatgtctg gctctagcta tcccgcccct   8520
aactccgccc atcccgcccc taactccgcc cagttccgcc cattctccgc cccatggctg   8580
actaattttt tttatttatg cagaggccga ggccgcctcg gcctctgagc tattccagaa   8640
gtagtgagga ggcttttttg gaggcctagg cttttgcgtc gagacgtacc caattcgccc   8700
tatagtgagt cgtattacgc gcgctcactg gccgtcgttt tacaacgtcg tgactgggaa   8760
aaccctggcg ttacccaact taatcgcctt gcagcacatc cccctttcgc cagctggcgt   8820
aatagcgaag aggcccgcac cgatcgccct tcccaacagt tgcgcagcct gaatggcgaa   8880
tggcgcgacg cgccctgtag cggcgcatta agcgcggcgg gtgtggtggt tacgcgcagc   8940
gtgaccgcta cacttgccag cgccctagcg cccgctcctt tcgctttctt cccttccttt   9000
ctcgccacgt tcgccggctt tccccgtcaa gctctaaatc gggggctccc tttagggttc   9060
cgatttagtg ctttacggca cctcgacccc aaaaaacttg attagggtga tggttcacgt   9120
agtgggccat cgccctgata gacggttttt cgccctttga cgttggagtc cacgttcttt   9180
aatagtggac tcttgttcca aactggaaca acactcaacc ctatctcggt ctattctttt   9240
gatttataag ggattttgcc gatttcggcc tattggttaa aaaatgagct gatttaacaa   9300
aaatttaacg cgaattttaa caaaatatta acgtttacaa tttcccaggt ggcacttttc   9360
ggggaaatgt gcgcggaacc cctatttgtt tatttttcta aatacattca aatatgtatc   9420
cgctcatgag acaataaccc tgataaatgc ttcaataata ttgaaaaagg aagagtatga   9480
gtattcaaca tttccgtgtc gcccttattc ccttttttgc ggcattttgc cttcctgttt   9540
ttgctcaccc agaaacgctg gtgaaagtaa aagatgctga agatcagttg ggtgcacgag   9600
tgggttacat cgaactggat ctcaacagcg gtaagatcct tgagagtttt cgccccgaag   9660
aacgttttcc aatgatgagc acttttaaag ttctgctatg tggcgcggta ttatcccgta   9720
ttgacgccgg gcaagagcaa ctcggtcgcc gcatacacta ttctcagaat gacttggttg   9780
agtactcacc agtcacagaa aagcatctta cggatggcat gacagtaaga gaattatgca   9840
gtgctgccat aaccatgagt gataacactg cggccaactt acttctgaca acgatcggag   9900
gaccgaagga gctaaccgct tttttgcaca acatggggga tcatgtaact cgccttgatc   9960
gttgggaa                                                            9968
```

THERMAL CONTROL OF T-CELL IMMUNOTHERAPY THROUGH MOLECULAR AND PHYSICAL ACTUATION

RELATED APPLICATIONS

This application claims the benefit under 35 U.S.C. § 119(e) of U.S. Provisional Patent Application Ser. No. 63/010,525, filed Apr. 15, 2020, the content of this related application is incorporated herein by reference in its entirety for all purposes.

STATEMENT REGARDING FEDERALLY SPONSORED R&D

This invention was made with government support under Grant No. HR0011-14-1-0780 awarded by DARPA. The government has certain rights in the invention.

REFERENCE TO SEQUENCE LISTING

The present application is being filed along with a Sequence Listing in electronic format. The Sequence Listing is provided as a file entitled 30KJ 302427 US, created Apr. 14, 2021, which is 384 kilobytes in size. The information in the electronic format of the Sequence Listing is incorporated herein by reference in its entirety.

BACKGROUND

Field

The present disclosure relates generally to the field of T-cell therapies and more specifically to spatiotemporal control of T-cell activity.

Description of the Related Art

Unlike small molecule and biologic therapies, cells have a natural ability to navigate, persist and proliferate within the body, providing the potential for more targeted and sustained disease treatment. This potential is enhanced by the capacity of cells to probe, process, and respond to their environment and carry out a wide range of sophisticated behaviors, which can be engineered using the tools of synthetic biology. Among the cell types being developed for therapy, T-cells are one of the most promising due to their central roles in cancer, infectious disease and autoimmune disorders, along with their relative ease of isolation, genetic modification and re-engraftment. For example, this potential has been realized in T-cells engineered to express modularly targeted chimeric antigen receptors (CARs), allowing them to specifically eradicate cancers such as lymphomas bearing the CD19 antigen. Unfortunately, it has been challenging to translate these successful results into solid tumors, where CAR T-cells encounter a more immunosuppressive environment and the risk of sometimes fatal on-target off-tumor toxicity due to the presence of tumor-overexpressed epitopes in healthy tissues. Likewise, emerging approaches in which T-cells are used to treat autoimmune disease through local immunosuppression carry the risk of reducing important immune system activity outside the target tissues. Existing strategies seeking to reduce off-target toxicity use additional target recognition elements or chemically triggered kill switches. However, it can be difficult to ensure perfect recognition solely through molecular markers, and premature termination of T-cell therapy using kill-switches turns off their beneficial therapeutic action.

Genetically engineered T-cells are being developed to perform a variety of therapeutic functions. However, no robust mechanisms exist to externally control the activity of T-cells at specific locations within the body. Such spatiotemporal control could help mitigate potential off-target toxicity due to incomplete molecular specificity in applications such as T-cell immunotherapy against solid tumors. Temperature is a versatile external control signal that can be delivered to target tissues in vivo using techniques such as focused ultrasound and magnetic hyperthermia. There is a need for compositions, methods, systems, and kits for mediating thermal actuation of genetic circuits in T-cells at tolerated temperature ranges (e.g., 37-42° C.). There is a need for genetic architectures enabling the tuning of the amplitude and duration of thermal activation. There is a need for compositions, methods, systems, and kits for directing the activity of T-cells after they are deployed inside the body. There is a need for compositions, methods, systems, and kits for spatio-temporal control of T-cell activity.

SUMMARY

Disclosed herein include nucleic acid compositions. In some embodiments, the nucleic acid composition comprises: (a) a first inducible promoter operably linked to a first polynucleotide comprising a payload gene, wherein the first inducible promoter is capable of inducing transcription of the payload gene to generate a payload transcript upon thermal stimulation and/or immune cell stimulation; or (b) the first inducible promoter operably linked to a first polynucleotide comprising a transactivator gene, and a second promoter operably linked to a second polynucleotide comprising a payload gene, wherein the first inducible promoter is capable of inducing transcription of the transactivator gene to generate a transactivator transcript in the presence of thermal stimulation and/or immune cell stimulation, wherein the transactivator transcript is capable of being translated to generate a transactivator; and wherein, in the presence of the transactivator and a transactivator-binding compound, the second promoter is capable of inducing transcription of the payload gene to generate a payload transcript.

Disclosed herein include nucleic acid compositions. In some embodiments, the nucleic acid composition comprises: a first inducible promoter and a second promoter each operably linked to a first polynucleotide comprising a payload gene and to a second polynucleotide comprising a transactivator gene, wherein the first inducible promoter is capable of inducing transcription of the payload gene and the transactivator gene to generate a polycistronic transcript upon thermal stimulation and/or immune cell stimulation, wherein, in the presence of the transactivator and a transactivator-binding compound, the second promoter is capable of inducing transcription of the payload gene and the transactivator gene to generate a polycistronic transcript, and wherein the polycistronic transcript is capable of being translated to generate a transactivator and a payload protein and/or payload RNA agent.

In some embodiments, the second promoter comprises one or more copies of a transactivator recognition sequence the transactivator is capable of binding to induce transcription, and wherein the transactivator is incapable of binding the transactivator recognition sequence in the absence of the transactivator-binding compound. In some embodiments, the one or more copies of a transactivator recognition sequence comprise one or more copies of a tet operator (TetO).

Disclosed herein include nucleic acid compositions. In some embodiments, the nucleic acid composition comprises: (a) a first inducible promoter operably linked to a first polynucleotide comprising a payload gene, wherein the first inducible promoter is capable of inducing transcription of the payload gene to generate a payload transcript upon thermal stimulation and/or immune cell stimulation; or (b) the first inducible promoter operably linked to a first polynucleotide comprising a transactivator gene, and a second promoter operably linked to a second polynucleotide comprising a payload gene, wherein the first inducible promoter is capable of inducing transcription of the transactivator gene to generate a transactivator transcript in the presence of thermal stimulation and/or immune cell stimulation, wherein the second promoter comprises one or more copies of a transactivator recognition sequence the transactivator is capable of binding to induce transcription, and wherein the transactivator is incapable of binding the transactivator recognition sequence in the presence of the transactivator-binding compound, wherein the transactivator transcript is capable of being translated to generate a transactivator; and wherein, in the presence of the transactivator and in the absence of transactivator-binding compound, the second promoter is capable of inducing transcription of the payload gene to generate a payload transcript.

Disclosed herein include nucleic acid compositions. In some embodiments, the nucleic acid composition comprises: a first inducible promoter and a second promoter each operably linked to a first polynucleotide comprising a payload gene and to a second polynucleotide comprising a transactivator gene, wherein the first inducible promoter is capable of inducing transcription of the payload gene and the transactivator gene to generate a polycistronic transcript upon thermal stimulation and/or immune cell stimulation, wherein the second promoter comprises one or more copies of a transactivator recognition sequence the transactivator is capable of binding to induce transcription, and wherein the transactivator is incapable of binding the transactivator recognition sequence in the presence of the transactivator-binding compound, wherein, in the presence of the transactivator and in the absence of a transactivator-binding compound, the second promoter is capable of inducing transcription of the payload gene and the transactivator gene to generate a polycistronic transcript, and wherein the polycistronic transcript is capable of being translated to generate a transactivator and a payload protein and/or payload RNA agent.

In some embodiments, the one or more copies of a transactivator recognition sequence comprise one or more copies of a tet operator (TetO). In some embodiments, the second promoter comprises a tetracycline response element (TRE), and wherein the TRE comprises one or more copies of a tet operator (TetO). In some embodiments, the transactivator comprises reverse tetracycline-controlled transactivator (rtTA). In some embodiments, the transactivator comprises tetracycline-controlled transactivator (tTA). In some embodiments, the transactivator-binding compound comprises tetracycline, doxycycline or a derivative thereof. In some embodiments, the first polynucleotide and the second polynucleotide are operably linked to a tandem gene expression element. In some embodiments, the tandem gene expression element is an internal ribosomal entry site (IRES), foot-and-mouth disease virus 2A peptide (F2A), equine rhinitis A virus 2A peptide (E2A), porcine teschovirus 2A peptide (P2A) or *Thosea asigna* virus 2A peptide (T2A), or any combination thereof. In some embodiments, the payload protein and the transactivator are expressed as separate proteins.

Disclosed herein include nucleic acid compositions. In some embodiments, the nucleic acid composition comprises: a first inducible promoter operably linked to a first polynucleotide comprising a chimeric antigen receptor (CAR) gene, wherein the first inducible promoter is capable of inducing transcription of the CAR gene to generate a CAR transcript upon thermal stimulation and/or immune cell stimulation, wherein the CAR transcript is capable of being translated to generate a CAR, and wherein engagement of the CAR generates immune cell stimulation and thereby induces the first inducible promoter.

Disclosed herein include nucleic acid compositions. In some embodiments, the nucleic acid composition comprises: a first inducible promoter operably linked to a first polynucleotide comprising a recombinase gene, wherein the first inducible promoter is capable of inducing transcription of the recombinase gene to generate a recombinase transcript upon thermal stimulation and/or immune cell stimulation, and wherein the recombinase transcript is capable of being translated to generate a recombinase; a third promoter and a second polynucleotide comprising a payload gene, wherein, in the absence of a recombination event, the third promoter and the second polynucleotide are not operably linked, wherein the recombinase is capable of catalyzing the recombination event, and wherein the third promoter and the second polynucleotide are operably linked after the recombination event such that the second promoter is capable of inducing transcription of the payload gene to generate a payload transcript.

In some embodiments, the recombination event comprises removal of a sequence flanked by recombinase target sites or an inversion of a sequence flanked by recombinase target sites. In some embodiments, the second polynucleotide is flanked by recombinase target sites. In some embodiments, prior to the recombination event, the sequence of the payload gene is inverted relative to the promoter. In some embodiments, the nucleic acid composition comprises: at least one stop cassette situated between the third promoter and the payload gene, wherein the stop cassette comprises one or more stop sequences, and wherein the one or more stop cassettes are flanked by recombinase target sites. In some embodiments, the payload transcript is capable of being translated to generate a payload protein. In some embodiments, the at least one stop cassette is configured to prevent transcription of the payload gene and/or translation of the payload transcript. In some embodiments, the one or more stop sequences comprise a polyadenylation signal, a stop codon, a frame-shifting mutation, or any combination thereof. In some embodiments, the third promoter comprises a ubiquitous promoter. In some embodiments, the ubiquitous promoter is a cytomegalovirus (CMV) immediate early promoter, a CMV promoter, a viral simian virus 40 (SV40) (e.g., early or late), a Moloney murine leukemia virus (MoMLV) LTR promoter, a Rous sarcoma virus (RSV) LTR, an RSV promoter, a herpes simplex virus (HSV) (thymidine kinase) promoter, H5, P7.5, and P11 promoters from vaccinia virus, an elongation factor 1-alpha (EF1a) promoter, early growth response 1 (EGR1), ferritin H (FerH), ferritin L (FerL), Glyceraldehyde 3-phosphate dehydrogenase (GAPDH), eukaryotic translation initiation factor 4A1 (EIF4A1), heat shock 70 kDa protein 5 (HSPA5), heat shock protein 90 kDa beta, member 1 (HSP90B1), heat shock protein 70 kDa (HSP70), β-kinesin (β-KIN), the human ROSA 26 locus, a Ubiquitin C promoter (UBC), a phosphoglycerate kinase-1 (PGK) promoter, 3-phosphoglycerate kinase promoter, a cytomegalovirus enhancer, human β-actin (HBA) promoter, chicken β-actin (CBA) promoter, a CAG promoter, a CBH promoter, or any combination thereof. In some embodiments, the recombinase is Cre, Dre, Flp, KD, B2, B3, λ, HK022, HP1, γ6, ParA, Tn3, Gin, ΦC31, Bxb1, R4, derivatives thereof, or any combination thereof. In some embodiments, the recombinase is a Flp recombinase and the recombinase target sites are FRT sites. In some embodiments, the recombinase is a Cre recombinase and the recombinase target sites are loxP sites.

Disclosed herein include nucleic acid compositions. In some embodiments, the nucleic acid composition comprises: a first inducible promoter operably linked to a first polynucleotide comprising an activity regulator gene, wherein the first inducible promoter is capable of inducing transcription of the activity regulator gene to generate an activity regulator transcript upon thermal stimulation and/or immune cell stimulation, wherein the activity regulator transcript is capable of being translated and/or processed to generate an activity regulator; and wherein the activity regulator is capable of reducing T cell activity.

In some embodiments, the activity regulator comprises a ubiquitin ligase involved in TCR/CAR signal transduction selected from c-CBL, CBL-B, ITCH, R F125, R F128, WWP2, or any combination thereof. In some embodiments, the activity regulator comprises a negative regulatory enzyme selected from SHP1, SHP2, SHTP1, SHTP2, CD45, CSK, CD148, PTPN22, DGKalpha, DGKzeta, DRAK2, HPK1, HPK1, STS1, STS2, SLAT, and any combination thereof. In some embodiments, the activity regulator is a negative regulatory scaffold/adapter protein selected from PAG, LIME, NTAL, LAX31, SIT, GAB2, GRAP, ALX, SLAP, SLAP2, DOK1, DOK2, and any combination thereof. In some embodiments, the activity regulator is a dominant negative version of an activating TCR signaling component selected from ZAP70, LCK, FYN, NCK, VAV1, SLP76, ITK, ADAP, GADS, PLCgammal, LAT, p85, SOS, GRB2, NFAT, p50, p65, API, RAP1, CRKII, C3G, WAVE2, ARP2/3, ABL, ADAP, RIAM, SKAP55, or any combination thereof. In some embodiments, the activity regulator comprises the cytoplasmic tail of a negative co-regulatory receptor selected from CD5, PD1, CTLA4, BTLA, LAG3, B7-H1, B7-1, CD160, TFM3, 2B4, TIGIT, and any combination thereof. In some embodiments, the activity regulator is targeted to the plasma membrane with a targeting sequence derived from LAT, PAG, LCK, FYN, LAX, CD2, CD3, CD4, CD5, CD7, CD8a, PD1, SRC, LYN, or any combination thereof. In some embodiments, the activity regulator reduces or abrogates a pathway and/or a function selected from Ras signaling, PKC signaling, calcium-dependent signaling, NF-kappaB signaling, NFAT signaling, cytokine secretion, T cell survival, T cell proliferation, CTL activity, degranulation, tumor cell killing, differentiation, and any combination thereof.

The nucleic acid composition can comprise: a second promoter operably linked to a second polynucleotide comprising a payload gene, wherein the second promoter is capable of inducing transcription of the payload gene to generate a payload transcript, wherein the payload transcript is capable of being translated to generate a payload protein.

The first inducible promoter can sense T cell activity. In some embodiments, T cell activity comprises one or more of T cell simulation, T cell activation, cytokine secretion, T cell survival, T cell proliferation, CTL activity, T cell degranulation, and T cell differentiation.

Disclosed herein include nucleic acid compositions. In some embodiments, the nucleic acid composition comprises: a first inducible promoter operably linked to a first polynucleotide comprising an oscillator gene, wherein the first inducible promoter is capable of inducing transcription of the oscillator gene to generate an oscillator transcript upon thermal stimulation and/or immune cell stimulation, wherein the oscillator transcript is capable of being translated and/or processed to generate a oscillator; and a second promoter operably linked to a second polynucleotide comprising a payload gene, wherein the second promoter is capable of inducing transcription of the payload gene to generate a payload transcript, wherein the payload transcript is capable of being translated to generate a payload protein, and wherein the oscillator is capable of modulating the concentration, localization, stability, and/or activity of the payload transcript and/or payload protein.

In some embodiments, the concentration, localization, stability, and/or activity of the payload protein is inversely related to the concentration, localization, stability, and/or activity of the oscillator. In some embodiments, the concentration, localization, stability, and/or activity of the oscillator is inversely related to the concentration, localization, stability, and/or activity of the payload protein. In some embodiments, the oscillator gene encodes a siRNA, a shRNA, an antisense RNA oligonucleotide, an antisense miRNA, a trans-splicing RNA, a guide RNA, single-guide RNA, crRNA, a tracrRNA, a trans-splicing RNA, a pre-mRNA, a mRNA, or any combination thereof. In some embodiments, the oscillator comprises a protease. In some embodiments, the payload protein comprises a degron and a cut site the protease is capable of cutting to expose the degron, and wherein the degron of the payload protein being exposed changes the payload protein to a payload protein destabilized state. In some embodiments, the protease comprises tobacco etch virus (TEV) protease, tobacco vein mottling virus (TVMV) protease, hepatitis C virus protease (HCVP), derivatives thereof, or any combination thereof.

In some embodiments, the payload protein comprises a cage polypeptide, wherein the cage polypeptide comprises: (a) a helical bundle, comprising between 2 and 7 alpha-helices, wherein the helical bundle comprises: (i) a structural region; and (ii) a latch region, wherein the latch region comprises a degron located within the latch region, wherein the structural region interacts with the latch region to prevent activity of the degron; and (b) amino acid linkers connecting each alpha helix. In some embodiments, the oscillator comprises a key polypeptide capable of binding to the cage polypeptide structural region, thereby displacing the latch region and activating the degron.

In some embodiments, the oscillator comprises a silencer effector. In some embodiments, the silencer effector comprises a microRNA (miRNA), a precursor microRNA (pre-miRNA), a small interfering RNA (siRNA), a short-hairpin RNA (shRNA), precursors thereof, derivatives thereof, or a combination thereof. In some embodiments, the payload gene comprises a 3' UTR and/or a 5' UTR, and wherein the 3' UTR and/or the 5' UTR of the payload gene comprises one or more silencer effector binding sequences. In some embodiments, said silencer effector is capable of binding the one or more silencer effector binding sequences, thereby reducing the stability of the payload transcript and/or reducing the translation of the payload transcript. In some embodiments, the one or more silencer effector binding sequences comprise miRNA binding sites. In some embodiments, the payload gene comprises about 1 silencer effector binding sequence to about 10 silencer binding sequences. In some embodiments, the one or more silencer effector binding sequences are about 8 nucleotides to about 22 nucleotides in length. In some embodiments, the silencer effector comprises a region of complementarity that is complementary with at least 5 consecutive nucleotides of the one or more silencer effector binding sequences. In some embodiments, the silencer effector comprises at least about 50% complementarity to the one or more silencer effector binding sequences. In some embodiments, immune cell stimulation comprises signal transduction induced by binding of a stimulatory molecule with its cognate ligand on the surface of an immune cell. In some embodiments, the cognate ligand is a CAR or a TCR. In some embodiments, thermal stimulation comprises heating to an activating temperature. In some embodiments, the activating temperature is about 37.5° C., about 38.0° C., about 38.5° C., about 39.0° C., about 39.5° C., about 40.0° C., about 40.5° C., about 41.0° C., about 41.5° C., about 42.0° C., about 42.5° C., about 43.0° C., about 43.5° C., about 44.0° C., about 44.5° C., about 45.0° C., about 45.5° C., or about 46.0° C.

In some embodiments, in the absence of thermal stimulation and/or immune cell stimulation, the payload protein reaches unstimulated steady state payload protein levels in an immune cell. In some embodiments, unstimulated steady state payload protein levels are insufficient to exert a phenotypic effect and/or therapeutic effect on said immune cell. In some embodiments, upon thermal stimulation and/or immune cell stimulation, transcription of the payload gene, transactivator gene, oscillator gene, and/or recombinase gene from the first inducible promoter is increased by at least 1.1-fold. In some embodiments, the steady-state levels of the payload transcript, the steady-state levels of transactivator transcript, the steady-state levels of recombinase transcript, the steady-state levels of oscillator transcript, and/or the steady-state levels of the polycistronic transcript are at least 1.1 higher upon thermal stimulation and/or immune cell stimulation. In some embodiments, upon thermal stimulation and/or immune cell stimulation, the payload protein reaches stimulated steady state payload protein levels in an immune cell. In some embodiments, the payload protein does not return to unstimulated steady state payload protein levels. In some embodiments, stimulated steady state payload protein levels are at least 1.1-fold higher than unstimulated steady state payload protein levels. In some embodiments, increasing transactivator-binding compound concentration increases stimulated steady state payload protein levels. In some embodiments, after a first duration of time, the payload protein returns to unstimulated steady state payload protein levels from stimulated steady state payload protein levels, wherein the first duration of time is about 250 hours, about 200 hours, about 150 hours, about 96 hours, about 48 hours, about 44 hours, about 40 hours, about 35 hours, about 30 hours, about 25 hours, 20 hours, 15 hours, 10 hours, about 8 hours, about 8 hours, 8 hours, about 7 hours, about 6 hours, about 5 hours, about 4 hours, about 3 hours, about 2 hours, about 1 hour, about 30 minutes, about 15 minutes, about 10 minutes, or about 5 minutes. In some embodiments, stimulated steady state payload protein levels can be increased by introducing one or more non-canonical amino acid substitutions into the silencer effector binding sequence, the cut site and/or the degron. In some embodiments, stimulated steady state payload protein levels can be reduced by introducing one or more canonical amino acid substitutions into the silencer effector binding sequence, the cut site and/or the degron.

In some embodiments, in the presence of continuous thermal stimulation and/or immune cell stimulation, steady state payload protein levels oscillate between a lower tuned threshold and an upper tuned threshold of a tuned expression range. In some embodiments, the difference between the lower untuned threshold and the upper untuned threshold of the tuned expression range is greater than about one order of magnitude. In some embodiments, the difference between the lower tuned threshold and the upper tuned threshold of the tuned expression range is less than about one order of magnitude. In some embodiments, the lower tuned threshold and/or the upper tuned threshold of a tuned expression range can be increased by introducing one or more non-canonical amino acid substitutions into the silencer effector binding sequence, the cut site and/or the degron. In some embodiments, the lower tuned threshold and/or the upper tuned threshold of a tuned expression range can be reduced by introducing one or more canonical amino acid substitutions into the silencer effector binding sequence, the cut site and/or the degron.

In some embodiments, the first inducible promoter comprises or is derived from a mammalian heat shock promoter (HSP) or a *C. elegans* HSP. In some embodiments, the mammalian HSP is a human HSP or mouse HSP. In some embodiments, the first inducible promoter comprises a nucleotide sequence that is at least 80%, 85%, 90%, 95%, 98%, 99%, or 100% identical to SEQ ID NOS: 1-14. In some embodiments, the first inducible promoter comprises one or more AP-1 sites. In some embodiments, the first inducible promoter does not comprise an AP-1 site. In some embodiments, the first inducible promoter comprises a bidirectional promoter, optionally a minimal bidirectional promoter. In some embodiments, the first inducible promoter comprises one or more heat shock element (HSE) binding sites (e.g., four HSE binding sites). In some embodiments, the first inducible promoter does not comprise a human transcription factor binding site other than one or more HSE binding sites.

In some embodiments, the nucleic acid composition comprises: a 5' ITR, a 3' ITR, a 5' LTR, a 3' LTR, or any combination thereof. In some embodiments, the nucleic acid composition comprises: a transcript stabilization element. In some embodiments, the transcript stabilization element comprises woodchuck hepatitis post-translational regulatory element (WPRE), bovine growth hormone polyadenylation (bGH-polyA) signal sequence, human growth hormone polyadenylation (hGH-polyA) signal sequence, or any combination thereof. In some embodiments, the payload gene comprises a 5'UTR and/or a 3'UTR. In some embodiments, the transactivator gene comprises a 5'UTR and/or a 3'UTR. In some embodiments, the recombinase gene comprises a 5'UTR and/or a 3'UTR. In some embodiments, the oscillator gene comprises a 5'UTR and/or a 3'UTR. In some embodiments, the 5' UTR comprises a Kozak sequence. In some embodiments, stimulated steady state payload protein levels, unstimulated steady state payload protein levels, the lower tuned threshold, and/or the upper tuned threshold can be tuned by adjusting the presence and/or sequence of the Kozak sequence. In some embodiments, the 5' UTR comprises one or more micro open reading frames. In some embodiments, stimulated steady state payload protein levels, unstimulated steady state payload protein levels, the lower tuned threshold, and/or the upper tuned threshold can be tuned by adjusting the presence and/or sequence of the one or more micro open reading frames.

In some embodiments, the payload gene encodes a payload protein. In some embodiments, stimulated steady state payload protein levels, unstimulated steady state payload protein levels, the lower tuned threshold, and/or the upper tuned threshold can be tuned by adjusting the presence and/or sequence the tandem gene expression element. In some embodiments, the payload gene encodes a payload RNA agent, wherein the payload RNA agent comprises one or more of dsRNA, siRNA, shRNA, pre-miRNA, pri-miRNA, miRNA, stRNA, lncRNA, piRNA, and snoRNA. In some embodiments, the payload gene encodes a siRNA, a shRNA, an antisense RNA oligonucleotide, an antisense miRNA, a trans-splicing RNA, a guide RNA, single-guide RNA, crRNA, a tracrRNA, a trans-splicing RNA, a pre-mRNA, a mRNA, or any combination thereof. In some embodiments, the payload protein comprises a cytokine. In some embodiments, the cytokine is interleukin-1 (IL-1), IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IL-34, IL-35, interleukin-1 (IL-1), IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IL-34, IL-35, granulocyte macrophage colony stimulating factor (GM-CSF), M-CSF, SCF, TSLP, oncostatin M, leukemia-inhibitory factor (LIF), CNTF, Cardiotropin-1, NNT-1/BSF-3, growth hormone, Prolactin, Erythropoietin, Thrombopoietin, Leptin, G-CSF, or receptor or ligand thereof. In some embodiments, the payload protein comprises a member of the TGF-β/BMP family selected from TGF-β1, TGF-β2, TGF-β3, BMP-2, BMP-3a, BMP-3b, BMP-4, BMP-5, BMP-6, BMP-7, BMP-8a, BMP-8b, BMP-9, BMP-10, BMP-11, BMP-15, BMP-16, endometrial bleeding associated factor (EBAF), growth differentiation factor-1 (GDF-1), GDF-2, GDF-3, GDF-5, GDF-6, GDF-7, GDF-8, GDF-9, GDF-12, GDF-14, mullerian inhibiting substance (MIS), activin-1, activin-2, activin-3, activin-4, and activin-5. In some embodiments, the payload protein comprises a member of the TNF family of cytokines selected from TNF-alpha, TNF-beta, LT-beta, CD40 ligand, Fas ligand, CD 27 ligand, CD 30 ligand, and 4-1 BBL. In some embodiments, the payload protein comprises a member of the immunoglobulin superfamily of cytokines selected from B7.1 (CD80) and B7.2 (B70). In some embodiments, the payload protein comprises an interferon. In some embodiments, the interferon is interferon alpha, interferon beta, or interferon gamma. In some embodiments, the payload protein comprises a chemokine. In some embodiments, the chemokine is selected from CCL1, CCL2, CCL3, CCR4, CCL5, CCL7, CCL8/MCP-2, CCL11, CCL13/MCP-4, HCC-1/CCL14, CTAC/CCL17, CCL19, CCL22, CCL23, CCL24, CCL26, CCL27, VEGF, PDGF, lymphotactin (XCL1), Eotaxin, FGF, EGF, IP-10, TRAIL, GCP-2/CXCL6, NAP-2/CXCL7, CXCL8, CXCL10, ITAC/CXCL11, CXCL12, CXCL13, or CXCL15. The payload protein can comprises a interleukin. In some embodiments, the interleukin is selected from IL-10 IL-12, IL-1, IL-6, IL-7, IL-15, IL-2, IL-18 or IL-21. In some embodiments, the payload protein comprises a tumor necrosis factor (TNF). In some embodiments, the TNF is selected from TNF-alpha, TNF-beta, TNF-gamma, CD252, CD154, CD178, CD70, CD153, or 4-1BBL. The payload protein can comprises a factor locally down-regulating the activity of endogenous immune cells. In some embodiments, the payload protein is capable of remodeling a tumor microenvironment and/or reducing immunosuppression at a target site of a subject.

In some embodiments, the payload protein comprises a chimeric antigen receptor (CAR) or T-cell receptor (TCR). In some embodiments, the CAR and/or TCR comprises one or more of an antigen binding domain, a transmembrane domain, and an intracellular signaling domain. In some embodiments, the intracellular signaling domain comprises a primary signaling domain, a costimulatory domain, or both of a primary signaling domain and a costimulatory domain. In some embodiments, the primary signaling domain comprises a functional signaling domain of one or more proteins selected from CD3 zeta, CD3 gamma, CD3 delta, CD3 epsilon, common FcR gamma (FCER1G), FcR beta (Fc Epsilon Rib), CD79a, CD79b, Fcgamma DAP10, and DAP12, or a functional variant thereof. In some embodiments, the costimulatory domain comprises a functional domain of one or more proteins selected from the group consisting of CD27, CD28, 4-1BB (CD137), OX40, CD28-OX40, CD28-4-1BB, CD30, CD40, PD-1, ICOS, lymphocyte function-associated antigen-1 (LFA-1), CD2, CD7, LIGHT, NKG2C, B7-H3, a ligand that specifically binds with CD83, CD5, ICAM-1, GITR, BAFFR, HVEM (LIGHTR), SLAMF7, NKp80 (KLRF1), CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, and NKG2D, or a functional variant thereof. In some embodiments, the antigen binding domain binds a tumor antigen. In some embodiments, the tumor antigen is a solid tumor antigen.

In some embodiments, the tumor antigen is selected from: CD19; CD123; CD22; CD30; CD171; CS-1 (also referred to as CD2 subset 1, CRACC, SLAMF7, CD319, and 19A24); C-type lectin-like molecule-1 (CLL-1 or CLECL1); CD33; epidermal growth factor receptor variant III (EGFRvIII); ganglioside G2 (GD2); ganglioside GD3 (aNeu5Ac(2-8)aNeu5Ac(2-3)bDGalp(1-4)bDGlcp(1-1)Cer); TNF receptor family member B cell maturation (BCMA); Tn antigen ((Tn Ag) or (GalNAcα-Ser/Thr)); prostate-specific membrane antigen (PSMA); Receptor tyrosine kinase-like orphan receptor 1 (ROR1); Fms-Like Tyrosine Kinase 3 (FLT3); Tumor-associated glycoprotein 72 (TAG72); CD38; CD44v6; Carcinoembryonic antigen (CEA); Epithelial cell adhesion molecule (EPCAM); B7H3 (CD276); KIT (CD117); Interleukin-13 receptor subunit alpha-2 (IL-13Ra2 or CD213A2); Mesothelin; Interleukin 11 receptor alpha (IL-11Ra); prostate stem cell antigen (PSCA); Protease Serine 21 (Testisin or PRSS21); vascular endothelial growth factor receptor 2 (VEGFR2); Lewis(Y) antigen; CD24; Platelet-derived growth factor receptor beta (PDGFR-beta); Stage-specific embryonic antigen-4 (SSEA-4); CD20; Folate receptor alpha; Receptor tyrosine-protein kinase ERBB2 (Her2/neu); Mucin 1, cell surface associated (MUC1); epidermal growth factor receptor (EGFR); neural cell adhesion molecule (NCAM); Prostase; prostatic acid phosphatase (PAP); elongation factor 2 mutated (ELF2M); Ephrin B2; fibroblast activation protein alpha (FAP); insulin-like growth factor 1 receptor (IGF-I receptor), carbonic anhydrase IX (CAIX); Proteasome (Prosome, Macropain) Subunit, Beta Type, 9 (LMP2); glycoprotein 100 (gp100); oncogene fusion protein consisting of breakpoint cluster region (BCR) and Abelson murine leukemia viral oncogene homolog 1 (Abl) (bcr-abl); tyrosinase; ephrin type-A receptor 2 (EphA2); Fucosyl GM1; sialyl Lewis adhesion molecule (sLe); ganglioside GM3 (aNeu5Ac(2-3)bDGalp(1-4) bDGlcp(1-1)Cer); transglutaminase 5 (TGS5); high molecular weight-melanoma-associated antigen (HMW-MAA); o-acetyl-GD2 ganglioside (OAcGD2); Folate receptor beta; tumor endothelial marker 1 (TEM1/CD248); tumor endothelial marker 7-related (TEM7R); claudin 6 (CLDN6); thyroid stimulating hormone receptor (TSHR); G protein-coupled receptor class C group 5, member D (GPRC5D); chromosome X open reading frame 61 (CXORF61); CD97; CD179a; anaplastic lymphoma kinase (ALK); Polysialic acid; placenta-specific 1 (PLAC1); hexasaccharide portion of globoH glycoceramide (GloboH); mammary gland differentiation antigen (NY-BR-1); uroplakin 2 (UPK2); Hepatitis A virus cellular receptor 1 (HAVCR1); adrenoceptor beta 3 (ADRB3); pannexin 3 (PANX3); G protein-coupled receptor 20 (GPR20); lymphocyte antigen 6 complex, locus K 9 (LY6K); Olfactory receptor 51E2 (OR51E2); TCR Gamma Alternate Reading Frame Protein (TARP); Wilms tumor protein (WTI); Cancer/testis antigen 1 (NY-ESO-1); Cancer/testis antigen 2 (LAGE-1a); Melanoma-associated antigen 1 (MAGE-A1); ETS translocation-variant gene 6, located on chromosome 12p (ETV6-AML); sperm protein 17 (SPA17); X Antigen Family, Member 1A (XAGE1); angiopoietin-binding cell surface receptor 2 (Tie 2); melanoma cancer testis antigen-1 (MAD-CT-1); melanoma cancer testis antigen-2 (MAD-CT-2); Fos-related antigen 1; tumor protein p53 (p53); p53 mutant; prostein; survivin; telomerase; prostate carcinoma tumor antigen-1 (PCTA-1 or Galectin 8), melanoma antigen recognized by T cells 1 (MelanA or MART1); Rat sarcoma (Ras) mutant; human Telomerase reverse transcriptase (hTERT); sarcoma translocation breakpoints; melanoma inhibitor of apoptosis (ML-IAP); ERG (transmembrane protease, serine 2 (TMPRSS2) ETS fusion gene); N-Acetyl glucosaminyl-transferase V (NA17); paired box protein Pax-3 (PAX3); Androgen receptor; Cyclin B1; v-myc avian myelocytomatosis viral oncogene neuroblastoma derived homolog (MYCN); Ras Homolog Family Member C (RhoC); Tyrosinase-related protein 2 (TRP-2); Cytochrome P450 1B1 (CYP1B1); CCCTC-Binding Factor (Zinc Finger Protein)-Like (BORIS or Brother of the Regulator of Imprinted Sites), Squamous Cell Carcinoma Antigen Recognized By T Cells 3 (SART3); Paired box protein Pax-5 (PAX5); proacrosin binding protein sp32 (OY-TES1); lymphocyte-specific protein tyrosine kinase (LCK); A kinase anchor protein 4 (AKAP-4); synovial sarcoma, X breakpoint 2 (SSX2); Receptor for Advanced Glycation Endproducts (RAGE-1); renal ubiquitous 1 (RU1); renal ubiquitous 2 (RU2); legumain; human papilloma virus E6 (HPV E6); human papilloma virus E7 (HPV E7); intestinal carboxyl esterase; heat shock protein 70-2 mutated (mut hsp70-2); CD79a; CD79b; CD72; Leukocyte-associated immunoglobulin-like receptor 1 (LAIR1); Fc fragment of IgA receptor (FCAR or CD89); Leukocyte immunoglobulin-like receptor subfamily A member 2 (LILRA2); CD300 molecule-like family member f (CD300LF); C-type lectin domain family 12 member A (CLEC12A); bone marrow stromal cell antigen 2 (BST2); EGF-like module-containing mucin-like hormone receptor-like 2 (EMR2); lymphocyte antigen 75 (LY75); Glypican-3 (GPC3); Fc receptor-like 5 (FCRL5); and immunoglobulin lambda-like polypeptide 1 (IGLL1).

In some embodiments, the tumor antigen is CD150, 5T4, ActRIIA, B7, BMCA, CA-125, CCNA1, CD123, CD126, CD138, CD14, CD148, CD15, CD19, CD20, CD200, CD21, CD22, CD23, CD24, CD25, CD26, CD261, CD262, CD30, CD33, CD362, CD37, CD38, CD4, CD40, CD40L, CD44, CD46, CD5, CD52, CD53, CD54, CD56, CD66a-d, CD74, CD8, CD80, CD92, CE7, CS-1, CSPG4, ED-B fibronectin, EGFR, EGFRvIII, EGP-2, EGP-4, EPHa2, ErbB2, ErbB3, ErbB4, FBP, GD2, GD3, HER1-HER2 in combination, HER2-HER3 in combination, HERV-K, HIV-1 envelope glycoprotein gp120, HIV-1 envelope glycoprotein gp41, HLA-DR, HM1.24, HMW-MAA, Her2, Her2/neu, IGF-1R, IL-11Ralpha, IL-13R-alpha2, IL-2, IL-22R-alpha, IL-6, IL-6R, Ia, Ii, L1-CAM, L1-cell adhesion molecule, Lewis Y, L1-CAM, MAGE A3, MAGE-A1, MART-1, MUC1, NKG2C ligands, NKG2D Ligands, NY-ESO-1, OEPHa2, PIGF, PSCA, PSMA, ROR1, T101, TAC, TAG72, TIM-3, TRAIL-R1, TRAIL-R1 (DR4), TRAIL-R2 (DR5), VEGF, VEGFR2, WT-1, a G-protein coupled receptor, alphafetoprotein (AFP), an angiogenesis factor, an exogenous cognate binding molecule (ExoCBM), oncogene product, anti-folate receptor, c-Met, carcinoembryonic antigen (CEA), cyclin (D1), ephrinB2, epithelial tumor antigen, estrogen receptor, fetal acethycholine e receptor, folate binding protein, gp100, hepatitis B surface antigen, kappa chain, kappa light chain, kdr, lambda chain, livin, melanoma-associated antigen, mesothelin, mouse double minute 2 homolog (MDM2), mucin 16 (MUC16), mutated p53, mutated ras, necrosis antigens, oncofetal antigen, ROR2, progesterone receptor, prostate specific antigen, tEGFR, tenascin, β2-Microglobulin, Fc Receptor-like 5 (FcRL5), or molecules expressed by HIV, HCV, HBV, or other pathogens.

In some embodiments, the antigen binding domain comprises an antibody, an antibody fragment, an scFv, a Fv, a Fab, a (Fab')2, a single domain antibody (SDAB), a VH or VL domain, a camelid VHH domain, a Fab, a Fab', a $F(ab')_2$, a Fv, a scFv, a dsFv, a diabody, a triabody, a tetrabody, a multispecific antibody formed from antibody fragments, a single-domain antibody (sdAb), a single chain comprising cantiomplementary scFvs (tandem scFvs) or bispecific tandem scFvs, an Fv construct, a disulfide-linked Fv, a dual variable domain immunoglobulin (DVD-Ig) binding protein or a nanobody, an aptamer, an affibody, an affilin, an affitin, an affimer, an alphabody, an anticalin, an avimer, a DARPin, a Fynomer, a Kunitz domain peptide, a monobody, or any combination thereof. In some embodiments, the antigen binding domain is connected to the transmembrane domain by a hinge region. In some embodiments, the transmembrane domain comprises a transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154, KIRDS2, OX40, CD2, CD27, LFA-1 (CD11a, CD18), ICOS (CD278), 4-1BB (CD137), GITR, CD40, BAFFR, HVEM (LIGHTR), SLAMF7, NKp80 (KLRF1), CD160, CD19, IL2R beta, IL2R gamma, IL7Ra, ITGA1, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), SLAMF6 (NTB-A, Ly108), SLAM (SLAMF1, CD150, IPO-3), BLAME (SLAMF8), SELPLG (CD162), LTBR, PAG/Cbp, NKp44, NKp30, NKp46, NKG2D, and NKG2C, or a functional variant thereof. In some embodiments, the CAR or TCR further comprises a leader peptide. In some embodiments, the TCR further comprises a constant region and/or CDR4.

In some embodiments, the payload protein comprises a degron. In some embodiments, the steady-state levels of the payload protein can be varied by varying the sequence of the degron. In some embodiments, the nucleic acid composition comprises: one or more secondary transgenes, wherein said one or more secondary transgenes encode one or more secondary payload RNA agents and/or one or more secondary payload proteins.

In some embodiments, the nucleic acid composition comprises one or more vectors; optionally at least one of the one or more vectors is a viral vector, a plasmid, a naked DNA vector, a lipid nanoparticle, or any combination thereof. In some embodiments, the viral vector is an AAV vector, a lentivirus vector, a retrovirus vector, an integration-deficient lentivirus (IDLV) vector.

Disclosed herein include compositions. In some embodiments, the composition comprises a nucleic acid composition provided herein. In some embodiments, the composition comprises one or more vectors, a ribonucleoprotein (RNP) complex, a liposome, a nanoparticle, an exosome, a microvesicle, or any combination thereof. In some embodiments, the vector is a viral vector, a plasmid, a naked DNA vector, a lipid nanoparticle, or any combination thereof. In some embodiments, the viral vector is an AAV vector, a lentivirus vector, a retrovirus vector, an integration-deficient lentivirus (IDLV) vector. In some embodiments, the AAV vector comprises single-stranded AAV (ssAAV) vector or a self-complementary AAV (scAAV) vector.

Disclosed herein include thermally actuated immune cells. In some embodiments, the thermally actuated immune cell comprises a nucleic acid composition disclosed herein. In some embodiments, the immune cell is a mammalian cell. In some embodiments, the mammalian cell is a human cell. In some embodiments, the immune cell is derived from blood, cord blood, bone marrow, or iPSC. In some embodiments, the immune cell is a T cell. In some embodiments, the T cell is a primary T cell. In some embodiments, the T cell is an autologous T cell or an allogeneic T cell. In some embodiments, a single thermal stimulus is sufficient to initiate a positive feedback loop of immune cell activation-driven expression of the payload.

Disclosed herein include populations of the thermally actuated immune cells. In some embodiments, the population of the thermally actuated immune cells comprises: a plurality of the thermally actuated immune cells disclosed herein. In some embodiments, the payload comprises a CAR and/or a TCR, wherein in response to continuous engagement of the CAR and/or the TCR for at least about 24 hours, at least about 5 percent of the population of the thermally actuated immune cells have steady state payload protein levels at about the lower tuned threshold and at least about 5 percent of the population of the thermally actuated immune cells have steady state payload protein levels at about the upper tuned threshold. In some embodiments, the payload comprises a CAR and/or a TCR, and wherein in response to continuous engagement of the CAR and/or the TCR for at least about 96 hours, less than about 20 percent of the population of the thermally actuated immune cells exhibit exhaustion. In some embodiments, exhaustion comprises T cell exhaustion. In some embodiments, the payload comprises a CAR and/or a TCR, wherein in response to continuous engagement of the CAR and/or the TCR for 96 hours, at least about 1.1-fold fewer cells of the population of the thermally actuated immune cells exhibit exhaustion as compared to a population of the thermally actuated immune cells which do not comprise the oscillator. In some embodiments, exhaustion comprises T cell exhaustion. In some embodiments, T cell exhaustion comprises expression of one or more T cell exhaustion biomarkers selected from the group comprising a checkpoint inhibitor, PD-1 (Pdcdl), (Havcr2), LAG-3 (Lag3), CTLA-4 (Ctla4), 2B4 (CD244), CD39 (Entpdl), CD 160, eomesodermin (Eomes), T-BET (Tbx21), BATF, BLIMP-1 (Prdml), NFATC1, NR4A2, MAFB, OCT-2 (Pou2f2), Foxpl, retinoic acid receptor alpha (Rara), or any combination thereof. In some embodiments, the payload comprises a CAR and/or a TCR, wherein the payload is not expressed in the absence of thermal stimulus, and wherein engagement of the CAR and/or TCR initiates sustained expression of the payload.

Disclosed herein include methods of generating a thermally actuated immune cell. In some embodiments, the method comprises: introducing a nucleic acid composition disclosed herein or a composition disclosed herein into an immune cell, thereby generating a thermally actuated immune cell. In some embodiments, the introducing step comprises calcium phosphate transfection, DEAE-dextran mediated transfection, cationic lipid-mediated transfection, electroporation, electrical nuclear transport, chemical transduction, electrotransduction, Lipofectamine-mediated transfection, Effectene-mediated transfection, lipid nanoparticle (LNP)-mediated transfection, or any combination thereof.

Disclosed herein include methods of treating a disease or disorder in a subject. In some embodiments, the method comprises: introducing into one or more immune cells a composition comprising a nucleic acid composition disclosed herein or a composition disclosed herein, thereby generating one or more thermally actuated immune cells; and administering to the subject an effective amount of the thermally actuated immune cells.

Disclosed herein include methods of treating a disease or disorder in a subject. In some embodiments, the method comprises: administering to the subject an effective amount of the thermally actuated immune cells disclosed herein.

In some embodiments, the method comprises: applying thermal energy to a target site of the subject sufficient to increase the local temperature of the target site to an activating temperature, thereby inducing the expression of the payload in thermally actuated immune cells at the target site. In some embodiments, the activating temperature is about 37.5° C., about 38.0° C., about 38.5° C., about 39.0° C., about 39.5° C., about 40.0° C., about 40.5° C., about 41.0° C., about 41.5° C., about 42.0° C., about 42.5° C., about 43.0° C., about 43.5° C., about 44.0° C., about 44.5° C., about 45.0° C., about 45.5° C., or about 46.0° C. In some embodiments, applying thermal energy to a target site of the subject comprises the application of one or more of focused ultrasound (FUS), magnetic hyperthermia, microwaves, infrared irradiation, liquid-based heating, and contact heating. In some embodiments, liquid-based heating comprises intraperitoneal chemotherapy (HIPEC). In some embodiments, the period of time between the administering and applying thermal energy is about 48 hours, about 44 hours, about 40 hours, about 35 hours, about 30 hours, about 25 hours, 20 hours, 15 hours, 10 hours, about 8 hours, about 8 hours, 8 hours, about 7 hours, about 6 hours, about 5 hours, about 4 hours, about 3 hours, about 2 hours, about 1 hour, about 30 minutes, about 15 minutes, about 10 minutes, or about 5 minutes. In some embodiments, applying thermal energy to a target site comprises a continuous application of thermal energy to the target site over a second duration of time. In some embodiments, applying thermal energy to a target site comprises applying one or more pulses of thermal energy to the target site over a second duration of time. In some embodiments, the second duration of time is about 48 hours, about 44 hours, about 40 hours, about 35 hours, about 30 hours, about 25 hours, 20 hours, 15 hours, 10 hours, about 8 hours, about 8 hours, 8 hours, about 7 hours, about 6 hours, about 5 hours, about 4 hours, about 3 hours, about 2 hours, about 1 hour, about 30 minutes, about 15 minutes, about 10 minutes, or about 5 minutes. In some embodiments, the one or more pulses have a duty cycle of greater than about 1% and less than about 100%. In some embodiments, the one or more pulses each have a pulse duration of about 1 hour, about 30 minutes, about 15 minutes, about 10 minutes, or about 5 minutes, about 1 minute, about 1 second, or about 1 millisecond. In some embodiments, the method comprises: monitoring the temperature of the target region. In some embodiments, the monitoring is performed by magnetic resonance imaging (MM). In some embodiments, the application of thermal energy to a target site of the subject is guided spatially by magnetic resonance imaging (MRI).

In some embodiments, at least about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100% of the thermally actuated immune cells at the target site express the payload protein after applying thermal energy to the target site. In some embodiments, less than about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, or about 95%, of the thermally actuated immune cells at a site other than the target site express the payload protein. In some embodiments, the ratio of the concentration of payload-expressing thermally actuated immune cells at the subject's target site to the concentration of payload-expressing thermally actuated immune cells in subject's blood, serum, or plasma is at least about 2:1. In some embodiments, the ratio of the concentration of payload protein at the subject's target site to the concentration of payload protein in subject's blood, serum, or plasma is about 2:1 to about 3000:1, about 2:1 to about 2000:1, about 2:1 to about 1000:1, or about 2:1 to about 600:1. In some embodiments, the target site comprises target cells. In some embodiments, the target cells are tumor cells (e.g., solid tumor cells). In some embodiments, the application of thermal energy to a target site of the subject results in the death of at least about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, of the target cells. In some embodiments, non-target cells comprise cells of the subject other than target cells, and wherein the ratio of target cell death to non-target cell death after application of thermal energy is at least about 2:1. In some embodiments, the ratio of target cell death to non-target cell death is at least about 1.1-fold greater as compared to a method comprising immune cells constitutively expressing the payload protein.

In some embodiments, the target site comprises a solid tumor. In some embodiments, the target site comprises a site of disease or disorder or is proximate to a site of a disease or disorder. In some embodiments, the location of the one or more sites of a disease or disorder is predetermined, is determined during the method, or both. In some embodiments, the target site is an immunosuppressive environment. In some embodiments, the target site comprises a tissue. In some embodiments, the tissue is inflamed tissue and/or infected tissue. In some embodiments, the tissue comprises adrenal gland tissue, appendix tissue, bladder tissue, bone, bowel tissue, brain tissue, breast tissue, bronchi, coronal tissue, ear tissue, esophagus tissue, eye tissue, gall bladder tissue, genital tissue, heart tissue, hypothalamus tissue, kidney tissue, large intestine tissue, intestinal tissue, larynx tissue, liver tissue, lung tissue, lymph nodes, mouth tissue, nose tissue, pancreatic tissue, parathyroid gland tissue, pituitary gland tissue, prostate tissue, rectal tissue, salivary gland tissue, skeletal muscle tissue, skin tissue, small intestine tissue, spinal cord, spleen tissue, stomach tissue, thymus gland tissue, trachea tissue, thyroid tissue, ureter tissue, urethra tissue, soft and connective tissue, peritoneal tissue, blood vessel tissue and/or fat tissue. In some embodiments, the tissue comprises: (i) grade I, grade II, grade III or grade IV cancerous tissue; (ii) metastatic cancerous tissue; (iii) mixed grade cancerous tissue; (iv) a sub-grade cancerous tissue; (v) healthy or normal tissue; and/or (vi) cancerous or abnormal tissue.

In some embodiments, the subject is a mammal. In some embodiments, the disease or disorder is an autoimmune disorder. In some embodiments, the disease is associated with expression of a tumor antigen, wherein the disease associated with expression of a tumor antigen is a proliferative disease, a precancerous condition, a cancer, and a non-cancer related indication associated with expression of the tumor antigen. In some embodiments, the disease or disorder is a cancer. In some embodiments, a solid tumor. In some embodiments, the cancer is colon cancer, rectal cancer, renal-cell carcinoma, liver cancer, non-small cell carcinoma of the lung, cancer of the small intestine, cancer of the esophagus, melanoma, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin lymphoma, cancer of the endocrine system, cancer of the thyroid gland, cancer of the parathyroid gland, cancer of the adrenal gland, sarcoma of soft tissue, cancer of the urethra, cancer of the penis, solid tumors of childhood, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers, combinations of said cancers, and metastatic lesions of said cancers. In some embodiments, the cancer is a hematologic cancer chosen from one or more of chronic lymphocytic leukemia (CLL), acute leukemias, acute lymphoid leukemia (ALL), B-cell acute lymphoid leukemia (B-ALL), T-cell acute lymphoid leukemia (T-ALL), chronic myelogenous leukemia (CML), B cell prolymphocytic leukemia, blastic plasmacytoid dendritic cell neoplasm, Burkitt's lymphoma, diffuse large B cell lymphoma, follicular lymphoma, hairy cell leukemia, small cell- or a large cell-follicular lymphoma, malignant lymphoproliferative conditions, MALT lymphoma, mantle cell lymphoma, marginal zone lymphoma, multiple myeloma, myelodysplasia and myelodysplastic syndrome, non-Hodgkin's lymphoma, Hodgkin's lymphoma, plasmablastic lymphoma, plasmacytoid dendritic cell neoplasm, Waldenstrom macroglobulinemia, or pre-leukemia. In some embodiments, the method comprises: administering a transactivator-binding compound to the subject prior to, during, and/or after administration of the thermally actuated immune cells. In some embodiments, the amount of transactivator-binding compound is an amount effective to induce or attenuate a sufficient level of payload expression to treat the subject. In some embodiments, the transactivator-binding compound comprises tetracycline, doxycycline or a derivative thereof.

In some embodiments, the method comprises: administering one or more additional agents to the subject. In some embodiments, the one or more additional agents increases the efficacy of the thermally actuated immune cells. In some embodiments, the one or more additional agents comprise a protein phosphatase inhibitor, a kinase inhibitor, a cytokine, an inhibitor of an immune inhibitory molecule, and/or or an agent that decreases the level or activity of a TREG cell. In some embodiments, the one or more additional agents comprise an immune modulator, an anti-metastatic, a chemotherapeutic, a hormone or a growth factor antagonist, an alkylating agent, a TLR agonist, a cytokine antagonist, a cytokine antagonist, or any combination thereof. In some embodiments, the one or more additional agents comprise an agonistic or antagonistic antibody specific to a checkpoint inhibitor or checkpoint stimulator molecule such as PD1, PD-L1, PD-L2, CD27, CD28, CD40, CD137, OX40, GITR, ICOS, A2AR, B7-H3, B7-H4, BTLA, CTLA4, IDO, KIR, LAG3, PD-1, TIM-3. In some embodiments, the one or more additional agents are selected from alkylating agents (nitrogen mustards, ethylenimine derivatives, alkyl sulfonates, nitrosoureas and triazenes); uracil mustard (Aminouracil Mustard®, Chlorethaminacil®, Demethyldopan®, Desmethyldopan®, Haemanthamine®, Nordopan®, Uracil nitrogen Mustard®, Uracillost®, Uracilmostaza®, Uramustin®, Uramustine®); bendamustine (Treakisym®, Ribomustin®, Treanda®); chlormethine (Mustargen®); cyclophosphamide (Cytoxan®, Neosar®, Clafen®, Endoxan®, Procytox®, Revimmune™); ifosfamide (Mitoxana®); melphalan (Alkeran®); Chlorambucil (Leukeran®); pipobroman (Amedel®, Vercyte®); triethylenemelamine (Hemel®, Hexylen®, Hexastat®); triethylenethiophosphoramine; Temozolomide (Temodar®); thiotepa (Thioplex®); busulfan (Busilvex®, Myleran®); carmustine (BiCNU®); lomustine (CeeNU®); streptozocin (Zanosar®); estramustine (Emcyt®, Estracit®); fotemustine; irofulven; mannosulfan; mitobronitol; nimustine; procarbazine; ranimustine; semustine; triaziquone; treosulfan; and Dacarbazine (DTIC-Dome®); anti-EGFR antibodies (e.g., cetuximab (Erbitux®), panitumumab (Vectibix®), and gefitinib (Iressa®)); anti-Her-2 antibodies (e.g., trastuzumab (Herceptin®) and other antibodies from Genentech); antimetabolites (including, without limitation, folic acid antagonists (also referred to herein as antifolates), pyrimidine analogs, purine analogs and adenosine deaminase inhibitors): methotrexate (Rheumatrex®, Trexall®), 5-fluorouracil (Adrucil®, Efudex®, Fluoroplex®), floxuridine (FUDF®), carmofur, cytarabine (Cytosar-U®, Tarabine PFS), 6-mercaptopurine (Puri-Nethol®)), 6-thioguanine (Thioguanine Tabloid®), fludarabine phosphate (Fludara®), pentostatin (Nipent®), pemetrexed (Alimta®), raltitrexed (Tomudex®), cladribine (Leustatin®), clofarabine (Clofarex®, Clolar®), mercaptopurine (Puri-Nethol®), capecitabine (Xeloda®), nelarabine (Arranon®), azacitidine (Vidaza®), decitabine (Dacogen®), enocitabine (Sunrabin®), sapacitabine, tegafur-uracil, tiazofurine, tioguanine, trofosfamide, and gemcitabine (Gemzar®); vinca alkaloids: vinblastine (Velban®, Velsar®), vincristine (Vincasar®, Oncovin®), vindesine (Eldisine®), vinorelbine (Navelbine®), vinflunine (Javlor®); platinum-based agents: carboplatin (Paraplat®, Paraplatin®), cisplatin (Platinol®), oxaliplatin (Eloxatin®), nedaplatin, satraplatin, and triplatin; anthracyclines: daunorubicin (Cerubidine®, Rubidomycin®), doxorubicin (Adriamycin®), epirubicin (Ellence®), idarubicin (Idamycin®), mitoxantrone (Novantrone®), valrubicin (Valstar®), aclarubicin, amrubicin, liposomal doxorubicin, liposomal daunorubicin, pirarubicin, pixantrone, and zorubicin; topoisomerase inhibitors: topotecan (Hycamtin®), irinotecan (Camptosar®), etoposide (Toposar®, VePesid®), teniposide (Vumon®), lamellarin D, SN-38, camptothecin (e.g., IT-101), belotecan, and rubitecan; taxanes: paclitaxel (Taxol®), docetaxel (Taxotere®), larotaxel, cabazitaxel, ortataxel, and tesetaxel; antibiotics: actinomycin (Cosmegen®), bleomycin (Blenoxane®), hydroxyurea (Droxia®, Hydrea®), mitomycin (Mitozytrex®, Mutamycin®); immunomodulators: lenalidomide (Revlimid®), thalidomide (Thalomid®); immune cell antibodies: alemtuzamab (Campath®), gemtuzumab (Myelotarg®), rituximab (Rituxan®), tositumomab (Bexxar®); interferons (e.g., IFN-alpha (Alferon®, Roferon-A®, Intron®-A) or IFN-gamma (Actimmune®)); interleukins: IL-1, IL-2 (Proleukin®), IL-24, IL-6 (Sigosix®), IL-12; HSP90 inhibitors (e.g., geldanamycin or any of its derivatives). In certain embodiments, the HSP90 inhibitor is selected from geldanamycin, 17-alkylamino-17-desmethoxygeldanamycin ("17-AAG") or 17-(2-dimethylaminoethyl)amino-17-desmethoxygeldanamycin ("17-DMAG"); anti-androgens which include, without limitation nilutamide (Nilandron®) and bicalutamide (Caxodex®); antiestrogens which include, without limitation tamoxifen (Nolvadex®), toremifene (Fareston®), letrozole (Femara®), testolactone (Teslac®), anastrozole (Arimidex®), bicalutamide (Casodex®), exemestane (Aromasin®), flutamide (Eulexin®), fulvestrant (Faslodex®), raloxifene (Evista®, Keoxifene®) and raloxifene hydrochloride; anti-hypercalcaemia agents which include without limitation gallium (III) nitrate hydrate (Ganite®) and pamidronate disodium (Aredia®); apoptosis inducers which include without limitation ethanol, 2-[[3-(2,3-dichlorophenoxy)propyl]amino]-(9Cl), gambogic acid, elesclomol, embelin and arsenic trioxide (Trisenox®); Aurora kinase inhibitors which include without limitation binucleine 2; Bruton's tyrosine kinase inhibitors which include without limitation terreic acid; calcineurin inhibitors which include without limitation cypermethrin, deltamethrin, fenvalerate and tyrphostin 8; CaM kinase II inhibitors which include without limitation 5-Isoquinolinesulfonic acid, 4-[{2S)-2-[(5-isoquinolinylsulfonyl)methylamino]-3-oxo-3-{4-phenyl-1-piperazinyl)propyl]phenyl ester and benzenesulfonamide; CD45 tyrosine phosphatase inhibitors which include without limitation phosphonic acid; CDCl25 phosphatase inhibitors which include without limitation 1,4-naphthalene dione, 2,3-bis[(2-hydroxyethyl)thio]-(9Cl); CHK kinase inhibitors which include without limitation debromohymenialdisine; cyclooxygenase inhibitors which include without limitation 1H-indole-3-acetamide, 1-(4-chlorobenzoyl)-5-methoxy-2-methyl-N-(2-phenylethyl)-(9Cl), 5-alkyl substituted 2-arylaminophenylacetic acid and its derivatives (e.g., celecoxib (Celebrex®), rofecoxib (Vioxx®), etoricoxib (Arcoxia®), lumiracoxib (Prexige®), valdecoxib (Bextra®) or 5-alkyl-2-arylaminophenylacetic acid); cRAF kinase inhibitors which include without limitation 3-(3,5-dibromo-4-hydroxybenzylidene)-5-iodo-1,3-dihydroindol-2-one and benzamide, 3-(dimethylamino)-N-[3-[(4-hydroxybenzoyl)amino]-4-methylphenyl]-(9Cl); cyclin dependent kinase inhibitors which include without limitation olomoucine and its derivatives, purvalanol B, roascovitine (Seliciclib®), indirubin, kenpaullone, purvalanol A and indirubin-3'-monooxime; cysteine protease inhibitors which include without limitation 4-morpholinecarboxamide, N-[(1S)-3-fluoro-2-oxo-1-(2-phenylethyl)propyl]amino]-2-oxo-1-(phenylmethyl)ethyl]-(9Cl); DNA intercalators which include without limitation plicamycin (Mithracin®) and daptomycin (Cubicin®); DNA strand breakers which include without limitation bleomycin (Blenoxane®); E3 ligase inhibitors which include without limitation N-((3,3,3-trifluoro-2-trifluoromethyl)propionyl)sulfanilamide; EGF Pathway Inhibitors which include, without limitation tyrphostin 46, EKB-569, erlotinib (Tarceva®), gefitinib (Iressa®), lapatinib (Tykerb®) and those compounds that are generically and specifically disclosed in WO 97/02266, EP 0 564 409, WO 99/03854, EP 0 520 722, EP 0 566 226, EP 0 787 722, EP 0 837 063, U.S. Pat. No. 5,747,498, WO 98/10767, WO 97/30034, WO 97/49688, WO 97/38983 and WO 96/33980; farnesyltransferase inhibitors which include without limitation ahydroxyfarnesylphosphonic acid, butanoic acid, 2-[(2 S)-2-[[(2S,3S)-2-[[(2R)-2-amino-3-mercaptopropyl] amino]-3-methylpent-yl]oxy]-1-oxo-3-phenylpropyl] amino]-4-(methyl sulfonyl)-1-methyl ethyl ester (2 S)-(9Cl), tipifarnib (Zarnestra®), and manumycin A; Flk-1 kinase inhibitors which include without limitation 2-propenamide, 2-cyano-3-[4-hydroxy-3,5-bis(1-methylethyl)phenyl]-N-(3-phenylpropyl)-(2E-)-(9Cl); glycogen synthase kinase-3 (GSK3) inhibitors which include without limitation indirubin-3'-monooxime; histone deacetylase (HDAC) inhibitors which include without limitation suberoylanilide hydroxamic acid (SAHA), [4-(2-amino-phenylcarbamoyl)-benzyl]carbamic acid pyridine-3-ylmethylester and its derivatives, butyric acid, pyroxamide, trichostatin A, oxamflatin, apicidin, depsipeptide, depudecin, trapoxin, vorinostat (Zolinza®), and compounds disclosed in WO 02/22577; I-kappa B-alpha kinase inhibitors (IKK) which include without limitation 2-propenenitrile, 3-[(4-methylphenyl) sulfonyl]-(2E)-(9Cl); imidazotetrazinones which include without limitation temozolomide (Methazolastone®, Temodar® and its derivatives (e.g., as disclosed generically and specifically in U.S. Pat. No. 5,260,291) and Mitozolomide; insulin tyrosine kinase inhibitors which include without limitation hydroxyl-2-naphthalenylmethylphosphonic acid; c-Jun-N-terminal kinase (JNK) inhibitors which include without limitation pyrazoleanthrone and epigallocatechin gallate; mitogen-activated protein kinase (MAP) inhibitors which include without limitation benzenesulfonamide, N-[2-[[[3-(4-chlorophenyl)-2-propenyl]methyl]amino] methyl]phenyl]-N-(2-hy-droxyethyl)-4-methoxy-(9Cl); MDM2 inhibitors which include without limitation trans-4-iodo, 4'-boranyl-chalcone; MEK inhibitors which include without limitation butanedinitrile, bis[amino[2-aminophenyl)thio]methylene]-(9Cl); MMP inhibitors which include without limitation Actinonin, epigallocatechin gallate, collagen peptidomimetic and non-peptidomimetic inhibitors, tetracycline derivatives marimastat (Marimastat®), prinomastat, incyclinide (Metastat®), shark cartilage extract AE-941 (Neovastat®), Tanomastat, TAA211, MMI270B or AAJ996; mTor inhibitors which include without limitation rapamycin (Rapamune®), and analogs and derivatives thereof, AP23573 (also known as ridaforolimus, deforolimus, or MK-8669), CCI-779 (also known as temsirolimus) (Torisel®) and SDZ-RAD; NGFR tyrosine kinase inhibitors which include without limitation tyrphostin AG 879; p38 MAP kinase inhibitors which include without limitation Phenol, 4-[4-(4-fluorophenyl)-5-(4-pyridinyl)-1H-imidazol-2-yl]-(9Cl), and benzamide, 3-(dimethylamino)-N-[3-[(4-hydroxylbenzoyl)amino]-4-methylphenyl]-(9Cl); p56 tyrosine kinase inhibitors which include without limitation damnacanthal and tyrphostin 46; PDGF pathway inhibitors which include without limitation tyrphostin AG 1296, tyrphostin 9, 1,3-butadiene-1,1,3-tricarbonitrile, 2-amino-4-(1H-indol-5-yl)-(9Cl), imatinib (Gleevec®) and gefitinib (Iressa®) and those compounds generically and specifically disclosed in European Patent No.: 0 564 409 and PCT Publication No.: WO 99/03854; phosphatidylinositol 3-kinase inhibitors which include without limitation wortmannin, and quercetin dihydrate; phosphatase inhibitors which include without limitation cantharidic acid, cantharidin, and L-leucinamide; protein phosphatase inhibitors which include without limitation cantharidic acid, cantharidin, L-P-bromotetramisole oxalate, 2(5H)-furanone, 4-hydroxy-5-(hydroxymethyl)-3-(1-oxohexadecyl)-(5R)-(9Cl) and benzylphosphonic acid; PKC inhibitors which include without limitation 1-H-pyrollo-2,5-dione, 3-[1-3-(dimethylamino)propyl]-1H-indol-3-yl]-4-(1H-indol-3-yl)-(90), Bi sindolylmaleimide IX, Sphinogosine, staurosporine, and Hypericin; PKC delta kinase inhibitors which include without limitation rottlerin; polyamine synthesis inhibitors which include without limitation DMFO; PTP1B inhibitors which include without limitation L-leucinamide; protein tyrosine kinase inhibitors which include, without limitation tyrphostin Ag 216, tyrphostin Ag 1288, tyrphostin Ag 1295, geldanamycin, genistein and 7H-pyrrolo[2,3-d]pyrimidine derivatives as generically and specifically described in PCT Publication No.: WO 03/013541 and U.S. Publication No.: 2008/0139587; SRC family tyrosine kinase inhibitors which include without limitation PP1 and PP2; Syk tyrosine kinase inhibitors which include without limitation piceatannol; Janus (JAK-2 and/or JAK-3) tyrosine kinase inhibitors which include without limitation tyrphostin AG 490 and 2-naphthyl vinyl ketone; retinoids which include without limitation isotretinoin (Accutane®, Amnesteem®, Cistane®, Claravis®, Sotret®) and tretinoin (Aberel®, Aknoten®, Avita®, Renova®, Retin-A®, Retin-A MICRO®, Vesanoid®); RNA polymerase H elongation inhibitors which include without limitation 5,6-dichloro-1-beta-D-ribofuranosylbenzimidazole; serine/Threonine kinase inhibitors which include without limitation 2-aminopurine; sterol biosynthesis inhibitors which include without limitation squalene epoxidase and CYP2D6; VEGF pathway inhibitors, which include without limitation anti-VEGF antibodies, e.g., bevacizumab, and small molecules, e.g., sunitinib (Sutent®), sorafinib (Nexavar®), ZD6474 (also known as vandetanib) (Zactima™), SU6668, CP-547632 and AZD2171 (also known as cediranib) (Recentin™).

In some embodiments, administering comprises aerosol delivery, nasal delivery, vaginal delivery, rectal delivery, buccal delivery, ocular delivery, local delivery, topical delivery, intracisternal delivery, intraperitoneal delivery, oral delivery, intramuscular injection, intravenous injection, subcutaneous injection, intranodal injection, intratumoral injection, intraperitoneal injection, intradermal injection, or any combination thereof.

BRIEF DESCRIPTION OF THE DRAWINGS

(FIG. 2A) Illustration of the screening strategy used to characterize the behaviour of pHSPs. The viral construct used to assay pHSPs is shown, along with the promoters tested. LTR, long terminal repeat. (FIG. 2B) Mean fluorescence intensity 24 hours after a 1-hour incubation at 37° C. or 42° C., as measured via flow cytometry. The fold change between 37° C. and 42° C. is listed above each sample. Where not seen, error bars (±SEM) are smaller than the symbol. N=3 biological replicates for each sample.

(FIG. 4A) Diagram illustrating the thermally trigged feed-forward circuit (top). Fluorescence analysed 24 hours post a 1-hour induction at 37° or 42° C. for cells supplemented with doxycycline (bottom). (FIG. 4B) Diagram illustrating a feed-forward circuit driven by HSPB, <K> indicates varying kozak strength (top). Fluorescence analysed 24 hours post a 1-hour induction at 37° or 42° C. for cells supplemented with doxycycline (bottom). The HSPB data is the same as in FIG. 4A, and is re-shown here to facilitate comparisons. (FIG. 4C) Diagram illustrating the thermally trigged positive feedback circuit (top). Fluorescence analysed 24 hours post a 1-hour induction at 37° or 42° C. for cells supplemented with doxycycline (bottom). (FIG. 4D) Normalized expression monitored over seven days after a 1-hour induction at 42° C. for direct HSPB-driven, feed-forward HSPB and positive-feedback HSPB circuits. Circuits have been modified to replace GFP with a destabilised version of the protein. (FIG. 4E) Illustration of the CRE based thermally triggered permanently stable switch designed to express CAR-CD19 upon induction. (FIG. 4F) Cells were either incubated at 37° C. or thermally stimulated for 1 hour at 42° C. and analysed 24 hours later to determine the number of activated cells. Where not seen, error bars (±SEM) are smaller than the symbol. N=3 biological replicates for each sample.

(FIG. 5A) Diagram illustrating the positive feedback circuit used to express IL-21 (top). Cumulative IL-21 release from 1-hour induction at 37° or 42° C. In one sample, doxycycline was removed after 24 hours (bottom). (FIG. 5B) Illustration of the constructs used to assay the ability of CAR activity to trigger expression of IL-21 in the feedback pHSP circuit (top). Cells were either incubated at 37 C or thermally stimulated for 1 hour at 42° C. with and without bait cells (bottom). Media was collected and frozen at each time point and all samples were analysed simultaneously at the end of collection. Cumulative IL-21 expression was quantified by using an IL-21 ELISA. Where not seen, error bars (±SEM) are smaller than the symbol. N=3 biological replicates for each sample.

(FIG. 6A) Illustration of the constructs used to assay the ability of CAR activity to trigger pHSP. (FIG. 6B) Cells were either incubated at 37° C., thermally stimulated for 1 hour at 42° C., or incubated with $CD19^+$ bait cells. pHSP triggered activity was determined by quantifying GFP expression 24 hours after induction. Where not seen, error bars (±SEM) are smaller than the symbol. N=3 biological replicates for each sample.

(FIG. 7A) Illustration of the viral construct used to assay pHSP (SynHSPB'3)-driven expression of CAR-CD19. Cells were either incubated at 37° C. or thermally stimulated for 1 hour at 42° C. and pHSP-triggered CAR-CD19 expression was quantified by surface staining of an HA tag appended to the CAR 12 hours after induction. N=3 biological replicates. (FIG. 7B) CAR-CD19 expression 6, 12, and 24 hours after 1-hour induction with 37° C. or 42° C. N=3 biological replicates. Negative values in 37° C. samples result from subtraction of signal acquired from wild-type T-cells. Raw data is provided in (FIG. 13). (FIG. 7C) Illustration of the viral construct and assay used to test the ability of pHSP-inducible CAR expression to conditionally kill bait cells. Cells were either incubated at 37° C. or thermally stimulated for 1 hour at 42° C. before being incubated with $CD19^+$ bait cells. (FIG. 7D) Unmodified T-cells and T-cells constitutively expressing CAR-CD19 were used as a negative and positive control respectively. pHSP (SynHSPB'3) triggered killing activity was quantified by counting the % of bait cells alive compared to the negative control for a duration of 13 days. N=3 biological replicates for two T-cell collections from different patients, total N=6. Where not seen, error bars (±SEM) are smaller than the symbol.

(FIG. 11A) Primary T-cells infected with SynHSPB'3 were thermally stimulated for 1 hour at 42° C. CAR expression was assessed 12 hours post stimulation by using and Anti-HA antibody. Cells were gated based on a transfection marker before CAR expression analysis (FIG. 11B) Primary T-cells constitutively expressing CAR-CD19 were used as a positive control. Cells in (FIG. 11B) were not gated with a transfection marker. The left peak represents uninfected cells.

T-cells constitutively expressing CAR-CD19 were used as a control and SynHSPB'3 was used for HSP T-cells. Cells were either incubated at 37° C. or thermally stimulated for 1 hour at 42° C. before being incubated with CD19+ bait cells. T-cell proliferation was quantified by counting the number of T-cells alive and comparing it to day 1 to establish fold change. N=3 biological replicates. Where not seen, error bars (±SEM) are smaller than the symbol.

Figure 13A:
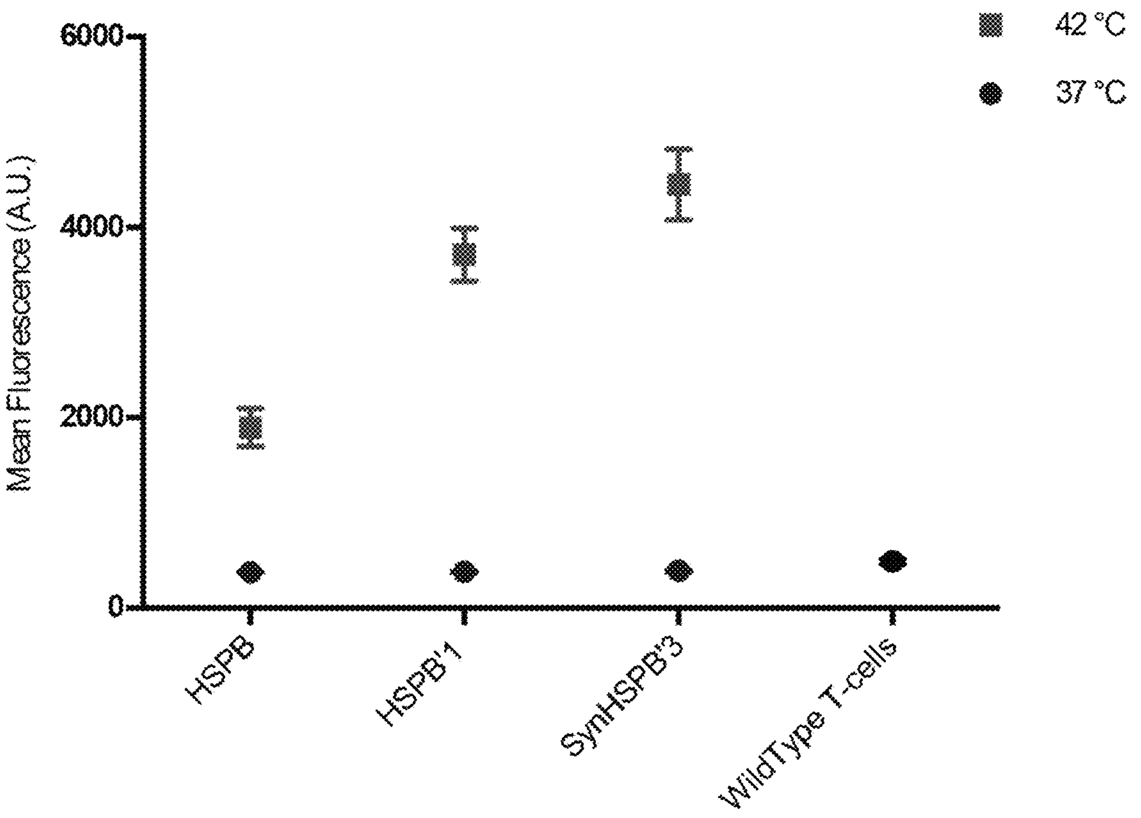
Figure 13B:
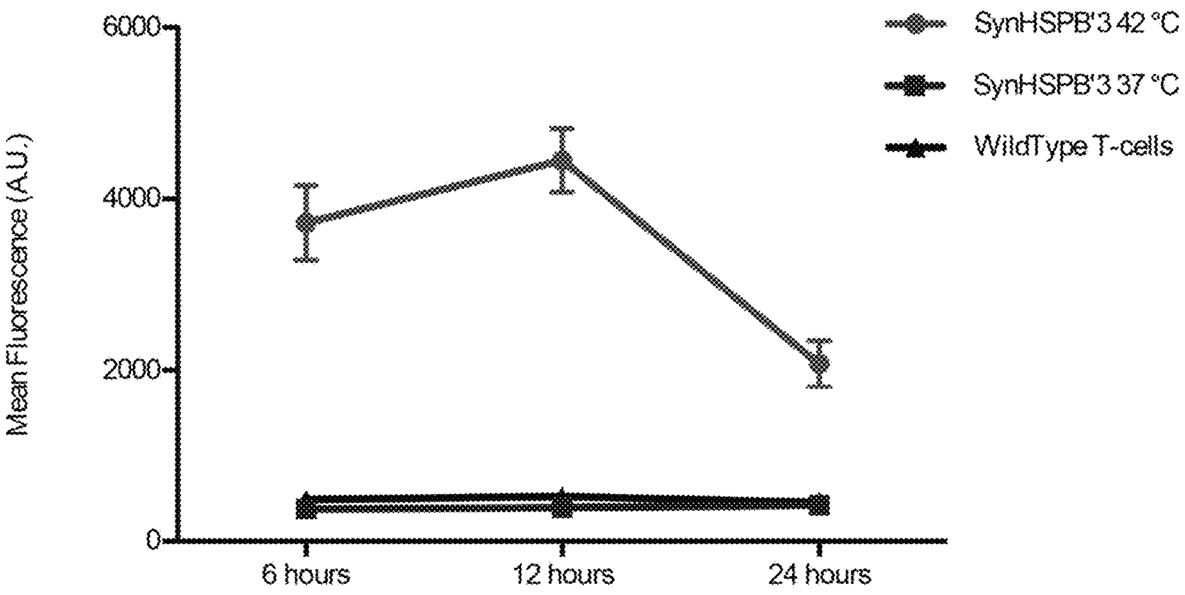

FIGS. 13A-13B depict non-limiting exemplary data related to thermally induced CAR expression. Raw measurements underlying the data shown in FIGS. 7A-7B, including the fluorescence of wild-type T-cells. This background value was subtracted from the experimental cell measurements to generate the plots in FIGS. 7A-7B. (FIG. 13A) Cells were either incubated at 37° C. or thermally stimulated for 1 hour at 42° C. and pHSP-triggered CAR-CD19 expression was quantified by surface staining of an HA tag appended to the CAR 12 hours after induction. N=3 biological replicates. (FIG. 13B) CAR-CD19 expression 6, 12, and 24 hours after 1-hour induction with 37° C. or 42° C. Where not seen, error bars (±SEM) are smaller than the symbol.

Figure 14A:
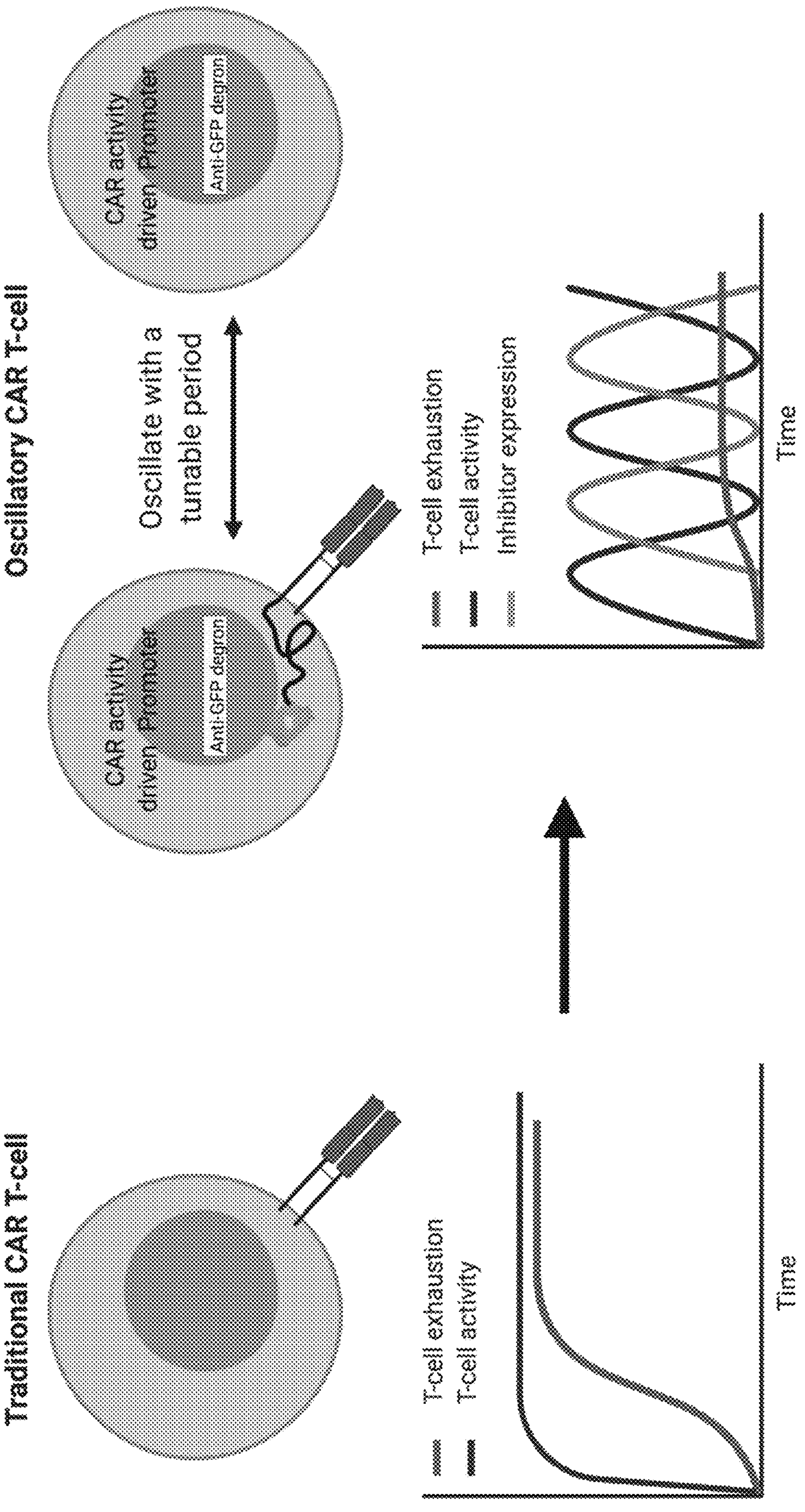
Figure 14B:
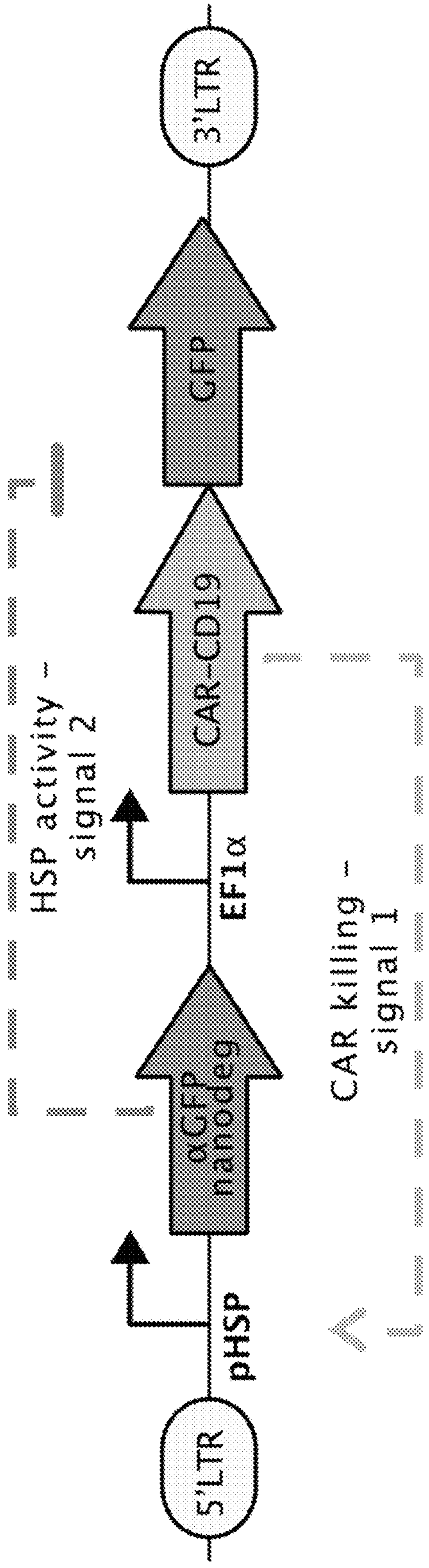
Figure 14C:
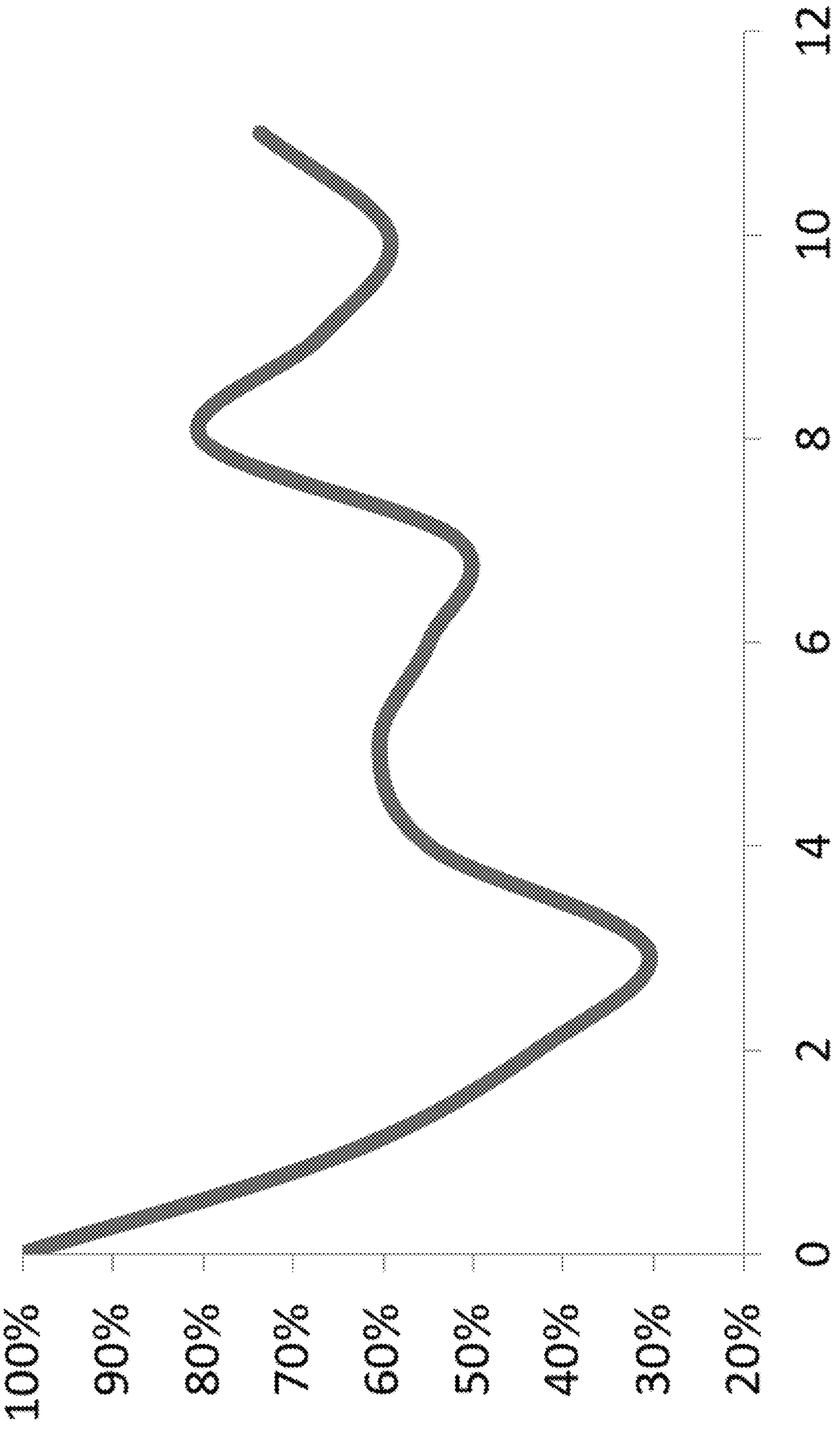

FIGS. 14A-14C depict non-limiting exemplary data and embodiments related to HSP-based feedback circuits that regulate CAR activity to prevent T cell exhaustion. FIG. 14A depicts a non-limiting exemplary traditional CAR T-cell and an exemplary oscillatory CAR T-cell provided herein. FIG. 14B depicts a non-limiting exemplary oscillatory genetic circuit. FIG. 14C depicts exemplary data related to Jurkat cells that were virally infected with the circuit shown in FIG. 14B and then mixed with bait cells at 1:5 Jurkat to bait ratio. Cells were analyzed daily for CAR expression by assaying the intensity of the GFP fused to the CAR. X axis: days, Y axis: % GFP/CAR expression compared to day 0.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein and made part of the disclosure herein.

All patents, published patent applications, other publications, and sequences from GenBank, and other databases referred to herein are incorporated by reference in their entirety with respect to the related technology.

Disclosed herein include nucleic acid compositions. In some embodiments, the nucleic acid composition comprises: (a) a first inducible promoter operably linked to a first polynucleotide comprising a payload gene, wherein the first inducible promoter is capable of inducing transcription of the payload gene to generate a payload transcript upon thermal stimulation and/or immune cell stimulation; or (b) the first inducible promoter operably linked to a first polynucleotide comprising a transactivator gene, and a second promoter operably linked to a second polynucleotide comprising a payload gene, wherein the first inducible promoter is capable of inducing transcription of the transactivator gene to generate a transactivator transcript in the presence of thermal stimulation and/or immune cell stimulation, wherein the transactivator transcript is capable of being translated to generate a transactivator; and wherein, in the presence of the transactivator and a transactivator-binding compound, the second promoter is capable of inducing transcription of the payload gene to generate a payload transcript.

Disclosed herein include nucleic acid compositions. In some embodiments, the nucleic acid composition comprises: a first inducible promoter and a second promoter each operably linked to a first polynucleotide comprising a payload gene and to a second polynucleotide comprising a transactivator gene, wherein the first inducible promoter is capable of inducing transcription of the payload gene and the transactivator gene to generate a polycistronic transcript upon thermal stimulation and/or immune cell stimulation, wherein, in the presence of the transactivator and a transactivator-binding compound, the second promoter is capable of inducing transcription of the payload gene and the transactivator gene to generate a polycistronic transcript, and wherein the polycistronic transcript is capable of being translated to generate a transactivator and a payload protein and/or payload RNA agent.

Disclosed herein include nucleic acid compositions. In some embodiments, the nucleic acid composition comprises: (a) a first inducible promoter operably linked to a first polynucleotide comprising a payload gene, wherein the first inducible promoter is capable of inducing transcription of the payload gene to generate a payload transcript upon thermal stimulation and/or immune cell stimulation; or (b) the first inducible promoter operably linked to a first polynucleotide comprising a transactivator gene, and a second promoter operably linked to a second polynucleotide comprising a payload gene, wherein the first inducible promoter is capable of inducing transcription of the transactivator gene to generate a transactivator transcript in the presence of thermal stimulation and/or immune cell stimulation, wherein the second promoter comprises one or more copies of a transactivator recognition sequence the transactivator is capable of binding to induce transcription, and wherein the transactivator is incapable of binding the transactivator recognition sequence in the presence of the transactivator-binding compound, wherein the transactivator transcript is capable of being translated to generate a transactivator; and wherein, in the presence of the transactivator and in the absence of transactivator-binding compound, the second promoter is capable of inducing transcription of the payload gene to generate a payload transcript.

Disclosed herein include nucleic acid compositions. In some embodiments, the nucleic acid composition comprises: a first inducible promoter and a second promoter each operably linked to a first polynucleotide comprising a payload gene and to a second polynucleotide comprising a transactivator gene, wherein the first inducible promoter is capable of inducing transcription of the payload gene and the transactivator gene to generate a polycistronic transcript upon thermal stimulation and/or immune cell stimulation, wherein the second promoter comprises one or more copies of a transactivator recognition sequence the transactivator is capable of binding to induce transcription, and wherein the transactivator is incapable of binding the transactivator recognition sequence in the presence of the transactivator-binding compound, wherein, in the presence of the transactivator and in the absence of a transactivator-binding compound, the second promoter is capable of inducing transcription of the payload gene and the transactivator gene to generate a polycistronic transcript, and wherein the polycistronic transcript is capable of being translated to generate a transactivator and a payload protein and/or payload RNA agent.

Disclosed herein include nucleic acid compositions. In some embodiments, the nucleic acid composition comprises: a first inducible promoter operably linked to a first polynucleotide comprising a chimeric antigen receptor (CAR) gene, wherein the first inducible promoter is capable of inducing transcription of the CAR gene to generate a CAR transcript upon thermal stimulation and/or immune cell stimulation, wherein the CAR transcript is capable of being translated to generate a CAR, and wherein engagement of the CAR generates immune cell stimulation and thereby induces the first inducible promoter.

Disclosed herein include nucleic acid compositions. In some embodiments, the nucleic acid composition comprises: a first inducible promoter operably linked to a first polynucleotide comprising a recombinase gene, wherein the first inducible promoter is capable of inducing transcription of the recombinase gene to generate a recombinase transcript upon thermal stimulation and/or immune cell stimulation, and wherein the recombinase transcript is capable of being translated to generate a recombinase; a third promoter and a second polynucleotide comprising a payload gene, wherein, in the absence of a recombination event, the third promoter and the second polynucleotide are not operably linked, wherein the recombinase is capable of catalyzing the recombination event, and wherein the third promoter and the second polynucleotide are operably linked after the recombination event such that the second promoter is capable of inducing transcription of the payload gene to generate a payload transcript.

Disclosed herein include nucleic acid compositions. In some embodiments, the nucleic acid composition comprises: a first inducible promoter operably linked to a first polynucleotide comprising an activity regulator gene, wherein the first inducible promoter is capable of inducing transcription of the activity regulator gene to generate an activity regulator transcript upon thermal stimulation and/or immune cell stimulation, wherein the activity regulator transcript is capable of being translated and/or processed to generate an activity regulator; and wherein the activity regulator is capable of reducing T cell activity.

Disclosed herein include nucleic acid compositions. In some embodiments, the nucleic acid composition comprises: a first inducible promoter operably linked to a first polynucleotide comprising an oscillator gene, wherein the first inducible promoter is capable of inducing transcription of the oscillator gene to generate an oscillator transcript upon thermal stimulation and/or immune cell stimulation, wherein the oscillator transcript is capable of being translated and/or processed to generate a oscillator; and a second promoter operably linked to a second polynucleotide comprising a payload gene, wherein the second promoter is capable of inducing transcription of the payload gene to generate a payload transcript, wherein the payload transcript is capable of being translated to generate a payload protein, and wherein the oscillator is capable of modulating the concentration, localization, stability, and/or activity of the payload transcript and/or payload protein.

Disclosed herein include compositions. In some embodiments, the composition comprises a nucleic acid composition provided herein.

Disclosed herein include thermally actuated immune cells. In some embodiments, the thermally actuated immune cell comprises a nucleic acid composition disclosed herein. Disclosed herein include populations of the thermally actuated immune cells. In some embodiments, the population of the thermally actuated immune cells comprises: a plurality of the thermally actuated immune cells disclosed herein.

Disclosed herein include methods of generating a thermally actuated immune cell. In some embodiments, the method comprises: introducing a nucleic acid composition disclosed herein or a composition disclosed herein into an immune cell, thereby generating a thermally actuated immune cell.

Disclosed herein include methods of treating a disease or disorder in a subject. In some embodiments, the method comprises: introducing into one or more immune cells a composition comprising a nucleic acid composition disclosed herein or a composition disclosed herein, thereby generating one or more thermally actuated immune cells; and administering to the subject an effective amount of the thermally actuated immune cells. In some embodiments, the method comprises: administering to the subject an effective amount of the thermally actuated immune cells disclosed herein.

Definitions

Unless defined otherwise, technical and scientific terms used herein have the same meaning as commonly understood by one of ordinary skill in the art to which the present disclosure belongs. See, e.g. Singleton et al., Dictionary of Microbiology and Molecular Biology 2nd ed., J. Wiley & Sons (New York, NY 1994); Sambrook et al., Molecular Cloning, A Laboratory Manual, Cold Spring Harbor Press (Cold Spring Harbor, NY 1989). For purposes of the present disclosure, the following terms are defined below.

As used herein, the terms "nucleic acid" and "polynucleotide" are interchangeable and refer to any nucleic acid, whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sultone linkages, and combinations of such linkages. The terms "nucleic acid" and "polynucleotide" also specifically include nucleic acids composed of bases other than the five biologically occurring bases (adenine, guanine, thymine, cytosine and uracil).

The term "vector" as used herein, can refer to a vehicle for carrying or transferring a nucleic acid. Non-limiting examples of vectors include plasmids and viruses (for example, AAV viruses).

The term "construct," as used herein, refers to a recombinant nucleic acid that has been generated for the purpose of the expression of a specific nucleotide sequence(s), or that is to be used in the construction of other recombinant nucleotide sequences.

As used herein, the term "plasmid" refers to a nucleic acid that can be used to replicate recombinant DNA sequences within a host organism. The sequence can be a double stranded DNA.

The term "element" refers to a separate or distinct part of something, for example, a nucleic acid sequence with a separate function within a longer nucleic acid sequence. The term "regulatory element" and "expression control element" are used interchangeably herein and refer to nucleic acid molecules that can influence the expression of an operably linked coding sequence in a particular host organism. These terms are used broadly to and cover all elements that promote or regulate transcription, including promoters, core elements required for basic interaction of RNA polymerase and transcription factors, upstream elements, enhancers, and response elements (see, e.g., Lewin, "Genes V" (Oxford University Press, Oxford) pages 847-873). Exemplary regulatory elements in prokaryotes include promoters, operator sequences and a ribosome binding sites. Regulatory elements that are used in eukaryotic cells can include, without limitation, transcriptional and translational control sequences, such as promoters, enhancers, splicing signals, polyadenylation signals, terminators, protein degradation signals, internal ribosome-entry element (IRES), 2A sequences, and the like, that provide for and/or regulate expression of a coding sequence and/or production of an encoded polypeptide in a host cell.

As used herein, the term "promoter" is a nucleotide sequence that permits binding of RNA polymerase and directs the transcription of a gene. Typically, a promoter is located in the 5' non-coding region of a gene, proximal to the transcriptional start site of the gene. Sequence elements within promoters that function in the initiation of transcription are often characterized by consensus nucleotide sequences. Examples of promoters include, but are not limited to, promoters from bacteria, yeast, plants, viruses, and mammals (including humans). A promoter can be inducible, repressible, and/or constitutive. Inducible promoters initiate increased levels of transcription from DNA under their control in response to some change in culture conditions, such as a change in temperature.

As used herein, the term "enhancer" refers to a type of regulatory element that can increase the efficiency of transcription, regardless of the distance or orientation of the enhancer relative to the start site of transcription.

As used herein, the term "operably linked" is used to describe the connection between regulatory elements and a gene or its coding region. Typically, gene expression is placed under the control of one or more regulatory elements, for example, without limitation, constitutive or inducible promoters, tissue-specific regulatory elements, and enhancers. A gene or coding region is said to be "operably linked to" or "operatively linked to" or "operably associated with" the regulatory elements, meaning that the gene or coding region is controlled or influenced by the regulatory element. For instance, a promoter is operably linked to a coding sequence if the promoter effects transcription or expression of the coding sequence.

The term "construct," as used herein, refers to a recombinant nucleic acid that has been generated for the purpose of the expression of a specific nucleotide sequence(s), or that is to be used in the construction of other recombinant nucleotide sequences.

As used herein, a "subject" refers to an animal that is the object of treatment, observation or experiment. "Animal" includes cold- and warm-blooded vertebrates and invertebrates such as fish, shellfish, reptiles, and in particular, mammals. "Mammal," as used herein, refers to an individual belonging to the class Mammalia and includes, but not limited to, humans, domestic and farm animals, zoo animals, sports and pet animals. Non-limiting examples of mammals include mice; rats; rabbits; guinea pigs; dogs; cats; sheep; goats; cows; horses; primates, such as monkeys, chimpanzees and apes, and, in particular, humans. In some embodiments, the mammal is a human. However, in some embodiments, the mammal is not a human.

As used herein, the term "treatment" refers to an intervention made in response to a disease, disorder or physiological condition manifested by a patient. The aim of treatment may include, but is not limited to, one or more of the alleviation or prevention of symptoms, slowing or stopping the progression or worsening of a disease, disorder, or condition and the remission of the disease, disorder or condition. The term "treat" and "treatment" includes, for example, therapeutic treatments, prophylactic treatments, and applications in which one reduces the risk that a subject will develop a disorder or other risk factor. Treatment does not require the complete curing of a disorder and encompasses embodiments in which one reduces symptoms or underlying risk factors. In some embodiments, "treatment" refers to both therapeutic treatment and prophylactic or preventative measures. Those in need of treatment include those already affected by a disease or disorder or undesired physiological condition as well as those in which the disease or disorder or undesired physiological condition is to be prevented. As used herein, the term "prevention" refers to any activity that reduces the burden of the individual later expressing those symptoms. This can take place at primary, secondary and/or tertiary prevention levels, wherein: a) primary prevention avoids the development of symptoms/disorder/condition; b) secondary prevention activities are aimed at early stages of the condition/disorder/symptom treatment, thereby increasing opportunities for interventions to prevent progression of the condition/disorder/symptom and emergence of symptoms; and c) tertiary prevention reduces the negative impact of an already established condition/disorder/symptom by, for example, restoring function and/or reducing any condition/disorder/symptom or related complications. The term "prevent" does not require the 100% elimination of the possibility of an event. Rather, it denotes that the likelihood of the occurrence of the event has been reduced in the presence of the compound or method.

As used herein, the term "effective amount" refers to an amount sufficient to effect beneficial or desirable biological and/or clinical results.

"Pharmaceutically acceptable" carriers are ones which are nontoxic to the cell or mammal being exposed thereto at the dosages and concentrations employed. "Pharmaceutically acceptable" carriers can be, but not limited to, organic or inorganic, solid or liquid excipients which is suitable for the selected mode of application such as oral application or injection, and administered in the form of a conventional pharmaceutical preparation, such as solid such as tablets, granules, powders, capsules, and liquid such as solution, emulsion, suspension and the like. Often the physiologically acceptable carrier is an aqueous pH buffered solution such as phosphate buffer or citrate buffer. The physiologically acceptable carrier may also comprise one or more of the following: antioxidants including ascorbic acid, low molecular weight (less than about 10 residues) polypeptides, proteins, such as serum albumin, gelatin, immunoglobulins; hydrophilic polymers such as polyvinylpyrrolidone, amino acids, carbohydrates including glucose, mannose, or dextrins, chelating agents such as EDTA, sugar alcohols such as mannitol or sorbitol, salt-forming counterions such as sodium, and nonionic surfactants such as Tween™, polyethylene glycol (PEG), and Pluronics™. Auxiliary, stabilizer, emulsifier, lubricant, binder, pH adjustor controller, isotonic agent and other conventional additives may also be added to the carriers.

The term "antibody fragment" shall be given its ordinary meaning, and shall also refers to at least one portion of an antibody, that retains the ability to specifically interact with (e.g., by binding, steric hindrance, stabilizing/destabilizing, spatial distribution) an epitope of an antigen. Examples of antibody fragments include, but are not limited to, Fab, Fab', F(ab')2, Fv fragments, scFv antibody fragments, disulfide-linked Fvs (sdFv), a Fd fragment consisting of the VH and CH1 domains, linear antibodies, single domain antibodies such as sdAb (either VL or VH), camelid VHH domains, multi-specific antibodies formed from antibody fragments such as a bivalent fragment comprising two Fab fragments linked by a disulfide bridge at the hinge region, and an isolated CDR or other epitope binding fragments of an antibody. An antigen binding fragment can also be incorporated into single domain antibodies, maxibodies, minibodies, nanobodies, intrabodies, diabodies, triabodies, tetrabodies, v-NAR and bis-scFv (see, e.g., Hollinger and Hudson, Nature Biotechnology 23:1126-1136, 2005). Antigen binding fragments can also be grafted into scaffolds based on polypeptides such as a fibronectin type III (Fn3) (see U.S. Pat. No. 6,703,199, which describes fibronectin polypeptide minibodies).

The term “autologous” shall be given its ordinary meaning, and shall also refer to any material derived from the same individual to whom it is later to be re-introduced into the individual.

The term “allogeneic” shall be given its ordinary meaning, and shall also refer to any material derived from a different animal of the same species as the individual to whom the material is introduced. Two or more individuals are said to be allogeneic to one another when the genes at one or more loci are not identical. In some aspects, allogeneic material from individuals of the same species may be sufficiently unlike genetically to interact antigenically.

The term “stimulation,” shall be given its ordinary meaning, and shall also refer to a primary response induced by binding of a stimulatory molecule (e.g., a TCR/CD3 complex or CAR) with its cognate ligand (or tumor antigen in the case of a CAR) thereby mediating a signal transduction event, such as, but not limited to, signal transduction via the TCR/CD3 complex or signal transduction via the appropriate NK receptor or signaling domains of the CAR. Stimulation can mediate altered expression of certain molecules.

Thermal Control of T-Cell Activation

Genetically engineered T-cells are being developed to perform a variety of therapeutic functions. However, no robust mechanisms exist to externally control the activity of T-cells at specific locations within the body. Such spatiotemporal control could help mitigate potential off-target toxicity due to incomplete molecular specificity in applications such as T-cell immunotherapy against solid tumors. Temperature is a versatile external control signal that can be delivered to target tissues in vivo using techniques such as focused ultrasound and magnetic hyperthermia. As demonstrated herein, heat shock promoters can mediate thermal actuation of genetic circuits in primary human T-cells in the well-tolerated temperature range of 37-42° C. Disclosed herein are genetic architectures enabling the tuning of the amplitude and duration of thermal activation. Provided herein are uses of these circuits to control the expression of payloads (e.g., chimeric antigen receptors and cytokines) and the killing of target cells (e.g., tumor cells). The methods and compositions disclosed herein provide a critical tool to direct the activity of T-cells after they are deployed inside the body.

Provided herein are cellular engineering approaches to regulate the activity of therapeutic T-cells with greater specificity through a combination of molecular and physical actuation. In some embodiments, this approach takes advantage of the ability of technologies such as focused ultrasound (FUS) and magnetic hyperthermia to non-invasively deposit heat at precise locations in deep tissue. By engineering thermal bioswitches that allow T-cells to sense small changes in temperature and use them as inputs for the actuation of genetic circuits, these penetrant forms of energy are enabled to spatially control T-cell activity with the disclosed compositions and methods. In some embodiments, the approach is based on heat shock promoters (pHSP), which have not been tested in primary human T-cells. This is important because the behavior of pHSPs varies greatly between cell types and cellular states. As described herein, a library of pHSPs in primary T-cells was screened and gene circuits were engineered to provide transient and sustained activation of gene expression in T-cells in response to brief thermal stimuli within the well-tolerated temperature range of 37-42° C. The circuits provided herein incorporate feed-forward amplification, positive feedback and/or recombinase-based state switches. Also provided herein are uses of these circuits to control the secretion of a therapeutic cytokine, expression of a CAR, and killing of target tumor cells.

Nucleic Acid Compositions

There are provided, in some embodiments, nucleic acid compositions. A nucleic acid composition can comprise: (a) a first inducible promoter operably linked to a first polynucleotide comprising a payload gene, wherein the first inducible promoter is capable of inducing transcription of the payload gene to generate a payload transcript upon thermal stimulation and/or immune cell stimulation; or (b) the first inducible promoter operably linked to a first polynucleotide comprising a transactivator gene, and a second promoter operably linked to a second polynucleotide comprising a payload gene, wherein the first inducible promoter is capable of inducing transcription of the transactivator gene to generate a transactivator transcript in the presence of thermal stimulation and/or immune cell stimulation, wherein the transactivator transcript is capable of being translated to generate a transactivator; and wherein, in the presence of the transactivator and a transactivator-binding compound, the second promoter is capable of inducing transcription of the payload gene to generate a payload transcript.

There are provided, in some embodiments, nucleic acid compositions. A nucleic acid composition can comprise: a first inducible promoter and a second promoter each operably linked to a first polynucleotide comprising a payload gene and to a second polynucleotide comprising a transactivator gene, wherein the first inducible promoter is capable of inducing transcription of the payload gene and the transactivator gene to generate a polycistronic transcript upon thermal stimulation and/or immune cell stimulation, wherein, in the presence of the transactivator and a transactivator-binding compound, the second promoter is capable of inducing transcription of the payload gene and the transactivator gene to generate a polycistronic transcript, and wherein the polycistronic transcript is capable of being translated to generate a transactivator and a payload protein and/or payload RNA agent.

In some embodiments, the second promoter comprises one or more copies of a transactivator recognition sequence the transactivator is capable of binding to induce transcription, and wherein the transactivator is incapable of binding the transactivator recognition sequence in the absence of the transactivator-binding compound. The one or more copies of a transactivator recognition sequence can comprise one or more copies of a tet operator (TetO).

There are provided, in some embodiments, nucleic acid compositions. A nucleic acid composition can comprise: (a)

a first inducible promoter operably linked to a first polynucleotide comprising a payload gene, wherein the first inducible promoter is capable of inducing transcription of the payload gene to generate a payload transcript upon thermal stimulation and/or immune cell stimulation; or (b) the first inducible promoter operably linked to a first polynucleotide comprising a transactivator gene, and a second promoter operably linked to a second polynucleotide comprising a payload gene, wherein the first inducible promoter is capable of inducing transcription of the transactivator gene to generate a transactivator transcript in the presence of thermal stimulation and/or immune cell stimulation, wherein the second promoter comprises one or more copies of a transactivator recognition sequence the transactivator is capable of binding to induce transcription, and wherein the transactivator is incapable of binding the transactivator recognition sequence in the presence of the transactivator-binding compound, wherein the transactivator transcript is capable of being translated to generate a transactivator; and wherein, in the presence of the transactivator and in the absence of transactivator-binding compound, the second promoter is capable of inducing transcription of the payload gene to generate a payload transcript.

There are provided, in some embodiments, nucleic acid compositions. A nucleic acid composition can comprise: a first inducible promoter and a second promoter each operably linked to a first polynucleotide comprising a payload gene and to a second polynucleotide comprising a transactivator gene, wherein the first inducible promoter is capable of inducing transcription of the payload gene and the transactivator gene to generate a polycistronic transcript upon thermal stimulation and/or immune cell stimulation, wherein the second promoter comprises one or more copies of a transactivator recognition sequence the transactivator is capable of binding to induce transcription, and wherein the transactivator is incapable of binding the transactivator recognition sequence in the presence of the transactivator-binding compound, wherein, in the presence of the transactivator and in the absence of a transactivator-binding compound, the second promoter is capable of inducing transcription of the payload gene and the transactivator gene to generate a polycistronic transcript, and wherein the polycistronic transcript is capable of being translated to generate a transactivator and a payload protein and/or payload RNA agent.

The one or more copies of a transactivator recognition sequence can comprise one or more copies of a tet operator (TetO). The second promoter can comprise a tetracycline response element (TRE). The TRE can comprise one or more copies of a tet operator (TetO). The transactivator can comprise reverse tetracycline-controlled transactivator (rtTA). The transactivator can comprise tetracycline-controlled transactivator (tTA). The transactivator-binding compound can comprise tetracycline, doxycycline or a derivative thereof. The first polynucleotide and the second polynucleotide can be operably linked to a tandem gene expression element. The tandem gene expression element can be an internal ribosomal entry site (IRES), foot-and-mouth disease virus 2A peptide (F2A), equine rhinitis A virus 2A peptide (E2A), porcine teschovirus 2A peptide (P2A) or *Thosea asigna* virus 2A peptide (T2A), or any combination thereof. The payload protein and the transactivator can be expressed as separate proteins. Tetracycline regulated transcriptional element, or tetracycline transactivator (tTA) is a fusion protein that combines the tetracycline repressor protein (tetR) DNA binding domain with the transcriptional activation domain of VP-16, such that when tTA binds to a minimal promoter containing tetR sequences, transcription of the target gene is activated. Tetracycline binding to tTA prevents activation by causing a conformational change in the tetR portion of tTA which blocks binding of tTA to tetR (Hinrichs, W., et al., (1994) Science 264:418-420); gene activation is achieved by removing tetracycline (Gossen, M. & Bujard, H., (1992) Proc. Natl. Acad. Sci. USA 89:5547-5551). Derivatives or analogues of tetracycline may also be used, including, for example, doxycycline (DOX), minocycline, metacycline, sancycline, chloro-tetracycline, demeclocycline, and tigecycline. Alternatives to rtTA-based transactivators are also contemplated herein, such as, for example, gal4-based transactivators and Cas9-based transactivators. In some embodiments, the transactivator comprises a Cas9 polypeptide (e.g., a dCas9 polypeptide or a dCas12 polypeptide) operably linked to a transcriptional activation domain. In some embodiments, the transcriptional activation domain is a VP 16 activation domain, a VP64 activation domain, a p65 activation domain, a MyoDl activation domain, a HSF1 activation domain, a RTA activation domain, a SETT/9 activation domain, a VP64-p65-Rta (VPR) activation domain, a mini VPR activation domain, a yeast GAL4 activation domain, a yeast HAP1 activation domain, a histone acetyltransferase, or any combination thereof. A transactivator recognition sequence can be configured to be recognized by the Cas9 polypeptide. In some embodiments, the second promoter is a TRE3G inducible promoter, a tetracycline-regulated promoter, a steroid-regulated promoter, a metal-regulated promoter, an estrogen receptor-regulated promoter, or a UAS inducible promoter.

There are provided, in some embodiments, nucleic acid compositions. A nucleic acid composition can comprise: a first inducible promoter operably linked to a first polynucleotide comprising a chimeric antigen receptor (CAR) gene, wherein the first inducible promoter is capable of inducing transcription of the CAR gene to generate a CAR transcript upon thermal stimulation and/or immune cell stimulation, wherein the CAR transcript is capable of being translated to generate a CAR, and wherein engagement of the CAR generates immune cell stimulation and thereby induces the first inducible promoter.

There are provided, in some embodiments, nucleic acid compositions. A nucleic acid composition can comprise: a first inducible promoter operably linked to a first polynucleotide comprising a recombinase gene, wherein the first inducible promoter is capable of inducing transcription of the recombinase gene to generate a recombinase transcript upon thermal stimulation and/or immune cell stimulation, and wherein the recombinase transcript is capable of being translated to generate a recombinase; a third promoter and a second polynucleotide comprising a payload gene, wherein, in the absence of a recombination event, the third promoter and the second polynucleotide are not operably linked, wherein the recombinase is capable of catalyzing the recombination event, and wherein the third promoter and the second polynucleotide are operably linked after the recombination event such that the second promoter is capable of inducing transcription of the payload gene to generate a payload transcript.

The recombination event can comprise removal of a sequence flanked by recombinase target sites or an inversion of a sequence flanked by recombinase target sites. The second polynucleotide can be flanked by recombinase target sites. In some embodiments, prior to the recombination event, the sequence of the payload gene is inverted relative to the promoter. In some embodiments, the nucleic acid composition comprises: at least one stop cassette situated between the third promoter and the payload gene, wherein the stop cassette comprises one or more stop sequences, and wherein the one or more stop cassettes are flanked by recombinase target sites. The payload transcript can be capable of being translated to generate a payload protein. The at least one stop cassette can be configured to prevent transcription of the payload gene and/or translation of the payload transcript. The one or more stop sequences can comprise a polyadenylation signal, a stop codon, a frame-shifting mutation, or any combination thereof.

The third promoter can comprise a ubiquitous promoter. The ubiquitous promoter can be a cytomegalovirus (CMV) immediate early promoter, a CMV promoter, a viral simian virus 40 (SV40) (e.g., early or late), a Moloney murine leukemia virus (MoMLV) LTR promoter, a Rous sarcoma virus (RSV) LTR, an RSV promoter, a herpes simplex virus (HSV) (thymidine kinase) promoter, H5, P7.5, and P11 promoters from vaccinia virus, an elongation factor 1-alpha (EF1a) promoter, early growth response 1 (EGR1), ferritin H (FerH), ferritin L (FerL), Glyceraldehyde 3-phosphate dehydrogenase (GAPDH), eukaryotic translation initiation factor 4A1 (EIF4A1), heat shock 70 kDa protein 5 (HSPA5), heat shock protein 90 kDa beta, member 1 (HSP90B1), heat shock protein 70 kDa (HSP70), β-kinesin (β-KIN), the human ROSA 26 locus, a Ubiquitin C promoter (UBC), a phosphoglycerate kinase-1 (PGK) promoter, 3-phosphoglycerate kinase promoter, a cytomegalovirus enhancer, human β-actin (HBA) promoter, chicken β-actin (CBA) promoter, a CAG promoter, a CBH promoter, or any combination thereof.

The recombinase can be Cre, Dre, Flp, KD, B2, B3, λ, HK022, HP1, γ6, ParA, Tn3, Gin, ΦC31, Bxb1, R4, derivatives thereof, or any combination thereof. The recombinase can be a Flp recombinase and the recombinase target sites can be FRT sites. The recombinase can be a Cre recombinase and the recombinase target sites can be loxP sites. As used herein, the term "lox site" refers to a nucleotide sequence at which the product of the ere gene of bacteriophage PI, Cre recombinase, can catalyze a site-specific recombination. A variety of lox sites are known to the art including but not limited to the naturally occurring loxP (the sequence found in the PI genome), loxB, loxL and loxR (these are found in the *E. coli* chromosome) as well as a number of mutant or variant lox sites such as loxP511, lox2272, loxA86, loxA117, loxC2, loxP2, loxP3 and loxP23. The term "frt site" as used herein refers to a nucleotide sequence at which the product of the FLP gene of the yeast 2 pm plasmid, FLP recombinase, can catalyze a site-specific recombination.

The term "recombinase," as used herein, refers to a site-specific enzyme that mediates the recombination of DNA between recombinase recognition sequences (e.g., recombinase target sites), which results in the excision, integration, inversion, or exchange (e.g., translocation) of DNA fragments between the recombinase recognition sequences. Recombinases can be classified into two distinct families: serine recombinases (e.g., resolvases and invertases) and tyrosine recombinases (e.g., integrases). Examples of serine recombinases include, without limitation, Hin, Gin, Tn3, β-six, CinH, ParA, γδ, Bxb1, ϕC31, TP901, TG1, φBT1, R4, φRV1, φFC1, MR11, A118, U153, and gp29. Examples of tyrosine recombinases include, without limitation, Cre, FLP, R, Lambda, HK101, HK022, and pSAM2. The term "recombine" or "recombination," in the context of a nucleic acid modification (e.g., a genomic modification), is used to refer to the process by which two or more nucleic acid molecules, or two or more regions of a single nucleic acid molecule, are modified by the action of a recombinase protein. Recombination can result in, inter alia, the insertion, inversion, excision, or translocation of a nucleic acid sequence, e.g., in or between one or more nucleic acid molecules. As used herein, the term "recombination site sequences" or "recombinase target sites" refers to short polynucleic acid sequences, typically palindromic, that are specifically recognized and acted upon by a DNA recombinase. DNA recombinase/recombination site sequence pairs include, but are not limited to, Cre/loxP, Dre/rox, VCre/VloxP, SCre/SloxP, Vika/vox, λ-int/attP, Flp/FRT, R/RRT, Kw/KwRT, Kd/KdRT, B2/B2RT, and B3/B3RT.

In some embodiments, the nucleic acid composition comprises: one or more secondary transgenes, wherein said one or more secondary transgenes encode one or more secondary payload RNA agents and/or one or more secondary payload proteins. In some embodiments, the nucleic acid composition comprises: a second promoter operably linked to a second polynucleotide comprising a payload gene, wherein the second promoter is capable of inducing transcription of the payload gene to generate a payload transcript, wherein the payload transcript is capable of being translated to generate a payload protein.

The nucleic acid composition can comprise one or more vectors. At least one of the one or more vectors can be a viral vector, a plasmid, a naked DNA vector, a lipid nanoparticle, or any combination thereof. The viral vector can be an AAV vector, a lentivirus vector, a retrovirus vector, an integration-deficient lentivirus (IDLV) vector. In some embodiments, the nucleic acid composition comprises: a 5' ITR, a 3' ITR, a 5' LTR, a 3' LTR, or any combination thereof.

Disclosed herein include compositions. In some embodiments, the composition comprises a nucleic acid composition provided herein. The composition can comprise one or more vectors, a ribonucleoprotein (RNP) complex, a liposome, a nanoparticle, an exosome, a microvesicle, or any combination thereof. The vector can be a viral vector, a plasmid, a naked DNA vector, a lipid nanoparticle, or any combination thereof. The viral vector can be an AAV vector, a lentivirus vector, a retrovirus vector, an integration-deficient lentivirus (IDLV) vector. The AAV vector can comprise single-stranded AAV (ssAAV) vector or a self-complementary AAV (scAAV) vector.

Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity. A retroviral vector may also be, e.g., a gammaretroviral vector. A gammaretroviral vector may include, e.g., a promoter, a packaging signal (ψ), a primer binding site (PBS), one or more (e.g., two) long terminal repeats (LTR), and a transgene of interest, e.g., a gene encoding a CAR. A gammaretroviral vector may lack viral structural gens such as gag, pol, and env. Exemplary gammaretroviral vectors include Murine Leukemia Virus (MLV), Spleen-Focus Forming Virus (SFFV), and Myeloproliferative Sarcoma Virus (MPSV), and vectors derived therefrom. Other gammaretroviral vectors are described, e.g., in Tobias Maetzig et al., "Gammaretroviral Vectors: Biology, Technology and Application" Viruses. 2011 June; 3(6): 677-713.

The term "lentivirus" refers to a genus of the Retroviridae family Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses.

The term "lentiviral vector" refers to a vector derived from at least a portion of a lentivirus genome, including especially a self-inactivating lentiviral vector as provided in Milone et al., Mol. Ther. 17(8): 1453-1464 (2009). Other examples of lentivirus vectors that may be used in the clinic, include but are not limited to, e.g., the LENTIVECTOR® gene delivery technology from Oxford BioMedica, the LENTIMAX™ vector system from Lentigen and the like. Nonclinical types of lentiviral vectors are also available and would be known to one skilled in the art.

Vector technology is well known in the art and is described, for example, in Sambrook et al., 2012, MOLECULAR CLONING: A LABORATORY MANUAL, volumes 1-4, Cold Spring Harbor Press, NY), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

A number of viral based systems have been developed for gene transfer into mammalian cells (e.g., immune cells). For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In one embodiment, lentivirus vectors are used.

The nucleic acid composition can be single-stranded or double-stranded. The nucleic acid composition can contain two or more nucleic acids. The two or more nucleic acids can be in the same form (e.g., a first plasmid and a second plasmid) or different in forms (e.g., a first plasmid and a first viral vector). The nucleic acid composition can comprise a single promoter capable of inducing transcription upon thermal stimulation and/or immune cell stimulation (e.g., a single inducible promoter). The nucleic acid composition can comprise two or more promoters capable of inducing transcription upon thermal stimulation and/or immune cell stimulation (e.g., two or more inducible promoters). The two or more promoters capable of inducing transcription upon thermal stimulation and/or immune cell stimulation can be the same or different (e.g., a nucleic acid composition comprising two HSP promoters differing with respect to at least one nucleotide). The nucleic acid composition can, depending on the needs of the user, be a circuit comprising any configuration of the promoters, inducible promoters, polynucleotides and/or genes contemplated herein. In some embodiments, the first inducible promoter senses T cell activity. T cell activity can comprise one or more of T cell simulation, T cell activation, cytokine secretion, T cell survival, T cell proliferation, CTL activity, T cell degranulation, and T cell differentiation. In some embodiments, the payload comprises a CAR and/or a TCR, wherein the payload is not expressed in the absence of thermal stimulus, and wherein engagement of the CAR and/or TCR initiates sustained expression of the payload.

Payload Expression Levels and Tuning

In some embodiments, in the absence of thermal stimulation and/or immune cell stimulation, the payload protein reaches unstimulated steady state payload protein levels in an immune cell. Unstimulated steady state payload protein levels can be insufficient to exert a phenotypic effect and/or therapeutic effect on said immune cell. In some embodiments, upon thermal stimulation and/or immune cell stimulation, transcription of the payload gene, transactivator gene, oscillator gene, and/or recombinase gene from the first inducible promoter is increased by at least 1.1-fold (e.g., 1.1-fold, 1.3-fold, 1.5-fold, 1.7-fold, 1.9-fold, 2-fold, 3-fold, 4-fold, 5-fold, 6-fold, 7-fold, 8-fold, 9-fold, 10-fold, or a number or a range between any of these values). In some embodiments, increasing transactivator-binding compound concentration increases stimulated steady state payload protein levels.

In some embodiments, the steady-state levels of the payload transcript, the steady-state levels of transactivator transcript, the steady-state levels of recombinase transcript, the steady-state levels of oscillator transcript, and/or the steady-state levels of the polycistronic transcript are at least 1.1-fold (e.g., 1.1-fold, 1.3-fold, 1.5-fold, 1.7-fold, 1.9-fold, 2-fold, 3-fold, 4-fold, 5-fold, 6-fold, 7-fold, 8-fold, 9-fold, 10-fold, or a number or a range between any of these values) higher upon thermal stimulation and/or immune cell stimulation. In some embodiments, upon thermal stimulation and/or immune cell stimulation, the payload protein reaches stimulated steady state payload protein levels in an immune cell. In some embodiments, the payload protein does not return to unstimulated steady state payload protein levels.

Stimulated steady state payload protein levels can be at least 1.1-fold (e.g., 1.1-fold, 1.3-fold, 1.5-fold, 1.7-fold, 1.9-fold, 2-fold, 3-fold, 4-fold, 5-fold, 6-fold, 7-fold, 8-fold, 9-fold, 10-fold, or a number or a range between any of these values) higher than unstimulated steady state payload protein levels.

In some embodiments, after a first duration of time, the payload protein returns to unstimulated steady state payload protein levels from stimulated steady state payload protein levels, wherein the first duration of time is about 250 hours, about 200 hours, about 150 hours, about 96 hours, about 48 hours, about 44 hours, about 40 hours, about 35 hours, about 30 hours, about 25 hours, 20 hours, 15 hours, 10 hours, about 8 hours, about 8 hours, 8 hours, about 7 hours, about 6 hours, about 5 hours, about 4 hours, about 3 hours, about 2 hours, about 1 hour, about 30 minutes, about 15 minutes, about 10 minutes, about 5 minutes, or a number or a range between any two of these values.

In some embodiments, stimulated steady state payload protein levels can be increased by introducing one or more non-canonical amino acid substitutions into the silencer effector binding sequence, the cut site and/or the degron. In some embodiments, stimulated steady state payload protein levels can be reduced by introducing one or more canonical amino acid substitutions into the silencer effector binding sequence, the cut site and/or the degron.

In some embodiments, the nucleic acid composition comprises: a transcript stabilization element. The transcript stabilization element can comprise woodchuck hepatitis post-translational regulatory element (WPRE), bovine growth hormone polyadenylation (bGH-polyA) signal sequence, human growth hormone polyadenylation (hGH-polyA) signal sequence, or any combination thereof. The payload gene can comprise a 5'UTR and/or a 3'UTR. The transactivator gene can comprise a 5'UTR and/or a 3'UTR. The recombinase gene can comprise a 5'UTR and/or a 3'UTR. The oscillator gene can comprise a 5'UTR and/or a 3'UTR. The 5' UTR can comprise a Kozak sequence. In some embodiments, stimulated steady state payload protein levels, unstimulated steady state payload protein levels, the lower tuned threshold, and/or the upper tuned threshold can be tuned by adjusting the presence and/or sequence of the Kozak sequence. The 5' UTR can comprise one or more micro open reading frames. In some embodiments, stimulated steady state payload protein levels, unstimulated steady state payload protein levels, the lower tuned threshold, and/or the upper tuned threshold can be tuned by adjusting the presence and/or sequence of the one or more micro open reading frames.

Inducible Promoters

There are provided, in some embodiments, promoters capable of inducing transcription upon thermal stimulation and/or immune cell stimulation (e.g., inducible promoters). The inducible promoters provided herein can, in some embodiments, sense T cell activity. The first inducible promoter can comprise or can be derived from a mammalian heat shock promoter (HSP) or a *C. elegans* HSP. The mammalian HSP can be a human HSP or mouse HSP. The first inducible promoter can comprise a nucleotide sequence that is at least 80%, 85%, 90%, 95%, 98%, 99%, or 100% identical to SEQ ID NOS: 1-14. The first inducible promoter can comprise one or more AP-1 sites. In some embodiments, the first inducible promoter does not comprise an AP-1 site. The first inducible promoter can comprise a bidirectional promoter and/or a minimal bidirectional promoter. The first inducible promoter can comprise one or more heat shock element (HSE) binding sites (e.g., four HSE binding sites). In some embodiments, the first inducible promoter does not comprise a human transcription factor binding site other than one or more HSE binding sites. In some embodiments, the first inducible promoter comprises one or more of a TATA box, GC-Box, CAAT signal, and AP-1 site. Nucleic acids provided herein can comprise a portion of a promoter, an enhancer, positive or negative cis-acting sequences, inducible or repressible control element, 5' UTR sequences that are upstream of a gene, or any combination thereof. A disclosed promoter (e.g., first inducible promoter, second promoter, third promoter) can comprise 0, 1, 2, 3, 4, 5, 6, 7, 8, 9, 10, 11, 12, 13, 14, 15, 16, 17, 18, 19, or 20 HSE binding sites. The inducible promoter can comprise a promoter sequence shown in Table 1.

A disclosed promoter (e.g., first inducible promoter, second promoter, third promoter) can be derived from the heat shock promoter (HSP) of one or more species selected from: *Arabidopsis thaliana; Aspergillus nidulans; Bombyx mori; Candida albicans; Caenorhabditis elegans; Chlamydomonas rheinhardtii; Cricetulus griseus; Cyanophora paradoxa; Cylindrotheca fusiformis; Danio rerio; Dictyostelium discoideum; Drosophila melanogaster; Drosophila yakuba; Gallus gallus; Homo Sapiens; Leishmania chagasi; Leishmania major; Loligo pealii; Lymantria dispar; Monodelphis domestica; Morone saxatilis; Mus musculus; Nectria haematococca; Neurospora crassa; Nicotiana tabacum; Oryza sativa; Paracentrotus lividus; Plasmodium falciparum; Rattus norvegicus; Saccharomyces cerevisiae; Schizosaccharomyces pombe; Solanum tuberosum; Strongylocentrotus purpuratus; Syncephalastrum racemosum; Tetrahymena thermophila; Trypanosoma brucei; Ustilago maydis; Volvox carteri*; and *Xenopus laevis.*

The length of the promoters provided herein (e.g., first inducible promoter, second promoter, third promoter) can vary. In some embodiments, a disclosed promoter (e.g., first promoter, second promoter, third promoter) is, or is about, 25, 30, 35, 40, 45, 50, 60, 70, 80, 90, 100, 110, 120, 128, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1050, 1100, 1150, 1200, 1250, 1300, 1350, 1400, 1450, 1500, 1550, 1600, 1650, 1700, 1750, 1800, 1850, 1900, 1950, 1100, 1150, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 2200, 2250, 2300, 2350, 2400, 2450, 2500, 2550, 2600, 2650, 2700, 2750, 2800, 2850, 2900, 2950, 3000, or 4000, or a number or a range between any two of these values, nucleotides in length. In some embodiments, a disclosed promoter (e.g., first promoter, second promoter, third promoter) is at least, or is at most, 25, 30, 35, 40, 45, 50, 60, 70, 80, 90, 100, 110, 120, 128, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1050, 1100, 1150, 1200, 1250, 1300, 1350, 1400, 1450, 1500, 1550, 1600, 1650, 1700, 1750, 1800, 1850, 1900, 1950, 1100, 1150, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 2200, 2250, 2300, 2350, 2400, 2450, 2500, 2550, 2600, 2650, 2700, 2750, 2800, 2850, 2900, 2950, 3000, or 4000, nucleotides in length.

In some embodiments, the sequence identity between a disclosed promoter (e.g., first inducible promoter, second promoter, third promoter) and the sequence of any one of SEQ ID NOS: 1-14 can be, or be about, 0.000000001%, 0.00000001%, 0.0000001%, 0.000001%, 0.00001%, 0.0001%, 0.001%, 0.01%, 0.1%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, or a number or a range between any two of these values. In some embodiments, the sequence identity between a disclosed promoter (e.g., first promoter, second promoter, third promoter) and the sequence of any one of SEQ ID NOS: 1-14 can be at least, or at most, 0.000000001%, 0.00000001%, 0.0000001%, 0.000001%, 0.00001%, 0.0001%, 0.001%, 0.01%, 0.1%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%.

A disclosed promoter (e.g., first inducible promoter, second promoter, third promoter) can comprise at least about 20 consecutive nucleotides (e.g., about 20 nt, 25 nt, 30 nt, 35 nt, 40 nt, 45 nt, 50 nt, 60 nt, 70 nt, 80 nt, 90 nt, 100 nt, 110 nt, 120 nt, 128 nt, 130 nt, 140 nt, 150 nt, 160 nt, 170 nt, 180 nt, 190 nt, 200 nt, 210 nt, 220 nt, 230 nt, 240 nt, 250 nt, 260 nt, 270 nt, 280 nt, 290 nt, 300 nt, 310 nt, 320 nt, 330 nt, 340 nt, 350 nt, 360 nt, 370 nt, 380 nt, 390 nt, 400 nt, 410 nt, 420 nt, 430 nt, 440 nt, 450 nt, 460 nt, 470 nt, 480 nt, 490 nt, 500 nt, 510 nt, 520 nt, 530 nt, 540 nt, 550 nt, 560 nt, 570 nt, 580 nt, 590 nt, 600 nt, 610 nt, 620 nt, 630 nt, 640 nt, 650 nt, 660 nt, 670 nt, 680 nt, 690 nt, 700 nt, 710 nt, 720 nt, 730 nt, 740 nt, 750 nt, 760 nt, 770 nt, 780 nt, 790 nt, 800 nt, 810 nt, 820 nt, 830 nt, 840 nt, 850 nt, 860 nt, 870 nt, 880 nt, 890 nt, 900 nt, 910 nt, 920 nt, 930 nt, 940 nt, 950 nt, 960 nt, 970 nt, 980 nt, 990 nt, 1000 nt, or a number or a range between any two of these values) of a sequences described by SEQ ID NOS: 1-14.

Also provided herein are nucleic acids that are at least 80%, 85%, 90%, 95%, 98%, 99%, or 100% identical to SEQ ID NOS: 16-44, or portions thereof. Also provided herein are nucleic acids that comprise at least about 20 consecutive nucleotides (e.g., about 20 nt, 25 nt, 30 nt, 35 nt, 40 nt, 45 nt, 50 nt, 60 nt, 70 nt, 80 nt, 90 nt, 100 nt, 110 nt, 120 nt, 128 nt, 130 nt, 140 nt, 150 nt, 160 nt, 170 nt, 180 nt, 190 nt, 200 nt, 210 nt, 220 nt, 230 nt, 240 nt, 250 nt, 260 nt, 270 nt, 280 nt, 290 nt, 300 nt, 310 nt, 320 nt, 330 nt, 340 nt, 350 nt, 360 nt, 370 nt, 380 nt, 390 nt, 400 nt, 410 nt, 420 nt, 430 nt, 440 nt, 450 nt, 460 nt, 470 nt, 480 nt, 490 nt, 500 nt, 510 nt, 520 nt, 530 nt, 540 nt, 550 nt, 560 nt, 570 nt, 580 nt, 590 nt, 600 nt, 610 nt, 620 nt, 630 nt, 640 nt, 650 nt, 660 nt, 670 nt, 680 nt, 690 nt, 700 nt, 710 nt, 720 nt, 730 nt, 740 nt, 750 nt, 760 nt, 770 nt, 780 nt, 790 nt, 800 nt, 810 nt, 820 nt, 830 nt, 840 nt, 850 nt, 860 nt, 870 nt, 880 nt, 890 nt, 900 nt, 910 nt, 920 nt, 930 nt, 940 nt, 950 nt, 960 nt, 970 nt, 980 nt, 990 nt, 10000 nt, 50000 nt, or a number or a range between any two of these values) of a sequence described by SEQ ID NOS: 16-44.

TABLE 1 pHSP Sequences

| NAME | SEQUENCE | SEQ ID NO: |
|---|---|---|
| HSPB | AATTAGCTTGAggatcctccacagccccggggagaccttgcctctaaagttgctgcttttgcagc<br>tctgccacaaccgcgcgtcctcagagccagccgggaggagctagaaccttccccgcgtactttcagcag<br>ccctgagtcagaggcgggctggccttgcaagtagccgcccagccttcttcggtctcacggaccgatccgc<br>ccgaaccttctcccggggtcagcgccgcgctgcgccgcccggctgactcagcccgggcgggcgggcg<br>ggaggctctcgactgggcgggaaggtgcgggaaggttcgcggcggcggggtcggggaggtgcaaaa<br>ggatgaaaagcccgtggacggagctgagcagatccggccgggctggcggcagagaaaccgcaggga<br>gagcctcactgctgagcgcccctcgacgcgggcggcagcagcctccgtggcctccagcatccgacaag<br>aagcttcagcc | SEQ ID NO: 1 |
| HSPB'1 | AATTAGCTTGAGCCTCTAAAGTTGCTGCTTTTGCAGCCTCTGCC<br>ACAACCGCGCGTCCTCAGAGCCAGCCCGGAGGAGCTAGAACCT<br>TCCCCGCATTTCTTTCAGCAGCCTGAGTCAGAGGCGGGCTGGCC<br>TGGCGTAGCCGCCCAGCCTCGCGGCTCATGCCCCGATCTGCCCG<br>AACCTTCTCCCGGGGTCAGCGCCGCGCCGCGCCACCCGGCTGA<br>GTCAGCCCGGGCGGGCGAGAGGCTCTCAACTGGGCGGGAAGGT<br>GCGGGAAGGTGCGGAAAGGTTCGCGAAAGTTCGCGGCGGCGGG<br>GGTCGGGTGAGGCGCAAAAGGATAAAAAGCCggtggaagcggaGCTG<br>AGCAGATCCGAGCCGGGCTGGCTGCAGAGAAACCGCAGGGAG<br>AGCCTCACTGCTGAGCGCCCCTCGACGGCGGAGCGGCAGCAGC<br>CTCCGTGGCCTCCAGCATCCGACAAGAAGCTTGAATTCGAGCTC<br>GCCGGGGATCCTCTAGTCAGCTGACGCGTGCTAGCGCGGCCGC<br>ACCACTAGTGCCACC | SEQ ID NO: 2 |
| HSPB'2 | AATTAGCTTGAGCCTCTAAAGTTGCTGCTTTTGCAGCCTCTGCC<br>ACAACCGCGCGTCCTCAGAGCCAGCCCGGAGGAGCTAGAACCT<br>TCCCCGCATTTCTTTCAGCAGCCTGAGTCAGAGGCGGGCTGGCC<br>TGGCGTAGCCGCCCAGCCTCGCGGCTCATGCCCCGATCTGCCCG<br>AACCTTCTCCCGGGGTCAGCGCCGCGCCGCGCCACCCGGCTGA<br>GTCAGCCCGGGCGGGCGAGAGGCTCTCAACTGGGCGGGAAGGT<br>GCGGGAAGGTGCGGAAAGGTTCGCGAAAGTTCGCGGCGGCGGG<br>GGTCGGGTGAGGCGCAAAAGGATAAAAAGCCggtggaagcggaGCTG<br>AGCAGATCCGAGCCGGGCTGGCTGCAGAGAAACCGCAGGGAG<br>AGCCTCACTGCTGAGCGCCCCTCGACGGCGGAGCGGCAGCAGC<br>CTCCGTGGCCTCCAGCATCCGACAAGAAGCTTGAATTCGAGCTC<br>GCCGGGGATCCTCTAGTCAGCTGACGCGTGCTAGCGCGGCGCC<br>ACC | SEQ ID NO: 3 |
| HSPB'3 | AATTAGCTTGAGCCTCTAAAGTTGCTGCTTTTGCAGCCTCTGCC<br>ACAACCGCGCGTCCTCAGAGCCAGCCCGGAGGAGCTAGAACCT<br>TCCCCGCATTTCTTTCAGCAGCCTGAGTCAGAGGCGGGCTGGCC<br>TGGCGTAGCCGCCCAGCCTCGCGGCTCATGCCCCGATCTGCCCG<br>AACCTTCTCCCGGGGTCAGCGCCGCGCCGCGCCACCCGGCTGA<br>GTCAGCCCGGGCGGGCGAGAGGCTCTCAACTGGGCGGGAAGGT<br>GCGGGAAGGTGCGGAAAGGTTCGCGAAAGTTCGCGGCGGCGGG<br>GGTCGGGTGAGGCGCAAAAGGATAAAAAGCCggtggaagcggaGCTG<br>AGCAGATCCGAGCCGGGCTGGCTGCAGAGAAACCGCAGGGAG<br>AGCCTCACTGCTGAGCGCCCCTCGACGGCGGAGCGGCAGCAGC<br>CTCCGTGGCCTCCAGCATCCGACAAGAAGCTTcagCC | SEQ ID NO: 4 |

TABLE 1-continued pHSP Sequences

| NAME | SEQUENCE | SEQ ID NO: |
|---|---|---|
| SynHSPB'1 | AATTAGCTTGACCCCGATCTGCCCGAACCTTCTCCCGGGGTCAG<br>CGCCGCGCCGCGCCACCCGGCTGAGTCAGCCCGGGCGGGCGAG<br>AGGCTCTCAACTGGGCGGGAAGGTGCGGGAAGGTGCGGAAAG<br>GTTCGCGAAAGTTCGCGGCGGCGGGGGTCGGGTGAGGCGCAAA<br>AGGATAAAAAGCCggtggaagcggaGCTGAGCAGATCCGAGCCGGGC<br>TGGCTGCAGAGAAACCGCAGGGAGAGCCTCACTGCTGAGCGCC<br>CCTCGACGGCGGAGCGGCAGCAGCCTCCGTGGCCTCCAGCATC<br>CGACAAGAAGCTTcagCC | SEQ ID NO: 5 |
| SynHSPB'2 | AATTAGCTTGACCCCGATCTGCCCGAACCTTCTCCCGGGGTCAG<br>CGCCGCGCCGCGCCACCCGGCTGCAGCAGCCCGGGCGGGCGAG<br>AGGCTCTCAACTGGGCGGGAAGGTGCGGGAAGGTGCGGAAAG<br>GTTCGCGAAAGTTCGCGGCGGCGGGGGTCGGGTGAGGCGCAAA<br>AGGATAAAAAGCCggtggaagcggaGCTGAGCAGATCCGAGCCGGGC<br>TGGCTGCAGAGAAACCGCAGGGAGAGCCTCACTGCTGAGCGCC<br>CCTCGACGGCGGAGCGGCAGCAGCCTCCGTGGCCTCCAGCATC<br>CGACAAGAAGCTTcagCC | SEQ ID NO: 6 |
| SynHSPB'3 | AATTAGCTTGACCCCGATCTGCCCGAACCTTCTCCCGGGGTCAG<br>CGCCGCGCCGCGCCACCCGGCTGCAGCAGCCCGGGCGGGCGAG<br>AGGCTCTCAACTGGGCGGGAAGGTGCGGGAAGGTGCGGAAAG<br>GTTCGCGAAAGTTCGCGGCCGGACTAGAGTGGCGAGATCCCCC<br>GATCTGCCCGAACCTTCTCCCGGGGTCAGCGCCGCGCCGCGCCA<br>CCCGGCTGCAGCAGCCCGGGCGGGCGAGAGGCTCTCAACTGGG<br>CGGGAAGGTGCGGGAAGGTGCGGAAAGGTTCGCGAAAGTTCGC<br>GGCAATTAGCTTGACCCCGATCTGCCCGAACCTTCTCCCGGGGT<br>CAGCGCCGCGCCGCGCCACCCGGCTGCAGCAGCCCGGGCGGGC<br>GAGAGGCTCTCAACTGGGCGGGAAGGTGCGGGAAGGTGCGGA<br>AAGGTTCGCGAAAGTTCGCGGCGGCGGGGGTCGGGTGAGGCGC<br>AAAAGGATAAAAAGCCggtggaagcggaGCTGAGCAGATCCGAGCCG<br>GGCTGGCTGCAGAGAAACCGCAGGGAGAGCCTCACTGCTGAGC<br>GCCCCTCGACGGCGGAGCGGCAGCAGCCTCCGTGGCCTCCAGC<br>ATCCGACAAGAAGCTTcagCC | SEQ ID NO: 7 |
| HSPA/A | AATTAGCTTGAGCCGCCCACTCCCCCTTCCTCTCAGGGTCCCTG<br>TCCCCTCCAGTGAATCCCAGAAGACTCTGGAGAGTTCTGAGCAG<br>GGGGCGGCACTCTGGCCTCTGATTGGTCCAAGGAAGGCTGGGG<br>GGCAGGACGGGAGGCGAAAACCCTGGAATATTCCCGACCTGGC<br>AGCCTCATCGAGCTCGGTGATTGGCTCAGAAGGGAAAAGGCGG<br>GTCTCCGTGACGACTTATAAAAGCCCAGGGGCAAGCGGTCCGG<br>ATAACGGCTAGCCTGAGGAGCTGCTGCGACAGTCCACTACCTTT<br>TTCGAGAGTGACTCCCGTTGTCCCAAGGCTTCCCAGAGCGAACC<br>TGTGCGGCTGCAGGCACCGGCGCGTCGAGTTTCCGGCGTCCGG<br>AAGGACCGAGCTCTTCTCGCGGATCCAGTGTTCCGTTTCCAGCC<br>CCCAATCTCAGAGCGGAGCCGACAGAGAGCAGGGAACCgCC | SEQ ID NO: 8 |
| HSPA/B | AATTAGCTTGActccttcccattaagacggaaaaaacatccgggagagccggtccgtactcag<br>gcagactaggccattaggtgcctcggagaaaggacccaaggctgctccgtccttcacagacacagtcca<br>atcagagtttcccaggcacatcgatgcaccgcctccttcgagaaacaaggtaactttcgggttctggtt<br>gtctccaaagtcatccgaccaatctcgcaccgcccagagcgggcccttcctgtcaattacctactgaag<br>ggcaggcggccagcatcgccatggagaccaacacccttcccaccaccactcccccctactctcagggccc<br>ctgtcccctccagtgaatcccagaagactctggagagttctgagcagagggcggcaccctgccctctga<br>ttggtccaaggaaggctgggggcaggacgggaggcgaaacccctggaatattcccgacctggcagcct<br>catcgagcttggtgattggctcagaaggggaaaggcgggtctccacgacgacttataaaagccgagggg<br>cgcgcggtccggaaaacggccagcctgaggagctgctgcgagggtccgcttcgtctttcgagagtgact<br>cccgcggtcccaaggctaccagagcgaacctgtgcggctgcaggcaccggcgtgttgagtaccggcgtt<br>ccgaaggactgagctcttgtcgcggatcccgtccgccgtaccagcccccagtctcagagcggagcccaca<br>gagcagggcaccggc | SEQ ID NO: 9 |
| HSPm1 | AATTAGCTTGAAAATCAGTCAAACCTAAGAAAATTCTCaaccgcatc<br>aaaccgaggaccaactgggacacagagcttctgccccactccaatcagagccttcccagctcacctggg<br>atctctacgccttcgatccagtttggaaaatttcaagtcgctgagcccctacgagaggagctccaggaa<br>cataccaaactgaggcagccggggtccccccacccccccaccccgcccctcccggcaactttgagcctgt<br>gctgggacagagcctctagttcctaaattagtccatgaggtcagaggcagcactgccattgtaaccgcga<br>ttggagaggatcacgtcaccggacacgccccaggcatctccctgggtctcctaaacttggccggggagaa<br>gttttagcccttaaggttttagcctttaacccccatattcagaactgtgcgagttggcgaaaccccaca<br>aatcacaacaaactgtacacaacaccgaggctagaggtgatctttcttgtccattccacacaggccttag<br>taattgcgtcgccatagcaacagtgtcactagtagcaccagcacgttccccacaccctccccctcaggaa<br>tccgtactctccagtgaaccccagaaacctctggagagttctggacaagggcggaacccacaactccgat<br>tactcaagggaggcggggaagctccaccagacgcgaaactgctggaagattcctggccccaaggcctcct<br>ccggctcgctgattggcccagcggagagtgggcggggccggtgaagactccttaaaggcgcagggcggcg<br>agcacggtcaccagacgctgacagctactcagaaccaaatctggttccatccagagacaagcgaagacaa<br>gagaagcagagcagagcggcgcgttcccgatcctcggccaggaccagccttccccagagcatccctgc<br>cgcgggacgcaaccttcccaggagcatccctgccgcggagcaactaccccggagcatccagcccgga<br>cgcagcCTTCCAGAAGCACGAGCCCACCACTAGTGCCACC | SEQ ID NO: 10 |

TABLE 1-continued pHSP Sequences

| NAME | SEQUENCE | SEQ ID NO: |
|---|---|---|
| HSPm2 | AATTAGCTTGACCTGCAGCCTGAGGCAAAGGGAGTGGCTACAG<br>CCTGGCACGGTCGATTAAGCCCTGCTCTCCGGGTCCTGGGACAC<br>TTTCCTTTTTCCTCTTTTGAGTCACAGGTCCTCCTAACATGAGAA<br>TCAAGTATTTTCACGCTGATTTCCTTATAAAATTGTGAGAACTCC<br>ATAGGCGATGTACCGCCTACTCCTACCTTAACCGTGATGTAAAG<br>ACAGCAAAACAAATGAACTATACTGCAAGATCTCTTCTATTTCC<br>CTATTCAAACCTAAAATGAAGAGGGAGGGGGAGACATGGACAA<br>GCAAGCATTCCACAGGCGCCCCTGCCCAACGCTGTCACTCAAAC<br>CAGGACCCAATCACAGACTTTTTAGCCAAGCCTTATCCCGCCTC<br>TCTTGAGAAACTTTCTGCGTCCGCCATCCTGTAGGAAGGATTTG<br>TACACTTTAAACTCCCTCCCTGGTCTGAGTCCCACACTCTCACC<br>ACCCAGCACCTTCAGGAGCTGACCCTTAACAGCTTCACCCACAG<br>GGACCCCGAAGTTGCGTCGCCTCCGCAACAGTGTCAATAGCAG<br>CACCAGCACTTCCCCACACCCTCCCCCTCAGGAATCCGTACTCT<br>CTAGCGAACCCCAGAAACCTCTGGAGAGTTCTGGACAAGGGCG<br>GAACCCACAACTCCGATTACTCAAGGGAGGCGGGGAAGCTCCA<br>CCAGACGCGAAACTGCTGGAAGATTCCTGGCCCCAAGGCCTCC<br>TCCGGCTCGCTGATTGGCCCAGCGGAGAGTGGGCGGGGCCGGT<br>GAAGACTCCTTAAAGGCGCAGGGCGGCGAGCAGGGCACCAGAC<br>GCTGACAGCTACTCAGAATCAAATCTGGTTCCATCCAGAGACA<br>AGCGAAGACAAGAGAAGCAGAGCGAGCGGCGCGTTCCCGATCC<br>TCGGCCAGGACCAGCCTTCCCCAGAGCATCCACGCCGCGGAGC<br>GCAACCTTCCCAGGAGCATCCCTGCCGCGGAGCGCAACTTTCCC<br>CGGAGCATCCACGCCGCGGAGCGCAGCCTTCCAGAAGCAGAGC<br>GCCACCACTAGTGCCACC | SEQ ID NO: 11 |
| HSPm3 | accagacgctgacagctactcagaaccaaatctggttccatccagagacaagcgaagacaagagaagc<br>agagcgagcggcgcgttcccgatcctcggccaggaccagccttccccagagcatccctgccgcggagc<br>gcaaccttcccaggagcatccctgccgcggagcgcaactttccccggagcatccacgccgcggagcgc<br>agccttccagaagcagagcgcggcgcc | SEQ ID NO: 12 |
| HSP16F | gattgtagTTTgaagatttcacaattagagtgaatgttgtttggttcggttttgtcactgtatttatac<br>tcatttccacctttttCTAGAAGGTCCTAGATGCATCTAGGACCTTCTAGAACATT<br>CTAAacggctgcaggatacgggtatataagccaatcgtgttcagaggaaaccaatacactttgttcaag<br>tgcttactgttcattctctaaacttcaagaCACC | SEQ ID NO: 13 |
| HSPmin | ACATTTCCTGTACAAGTGccCTAGGAGCTCGGATCCAGGAGGCC<br>TAACTGGCCGGTACCTGAGCTCCTGGAAGATTCTAGAACGTTCT<br>GGAAGATTCTAGAACGTTCCTCGAGGATATCAAGATCTGGCCTC<br>GGCGGCCAAGCTTAGACACTAGAGGGTATATAATGGAAGCTCG<br>ACTTCCAGCTTGGCAATCCGGTACTGTTGGTAAAGCgccacc | SEQ ID NO: 14 |

Payloads

In some embodiments, the payload gene encodes a payload protein. The payload protein can comprise a factor locally down-regulating the activity of endogenous immune cells. The payload protein can be capable of remodeling a tumor microenvironment and/or reducing immunosuppression at a target site of a subject. The payload protein can comprise a degron. In some embodiments, the steady-state levels of the payload protein can be varied by varying the sequence of the degron. In some embodiments, the payload comprises a secreted protein. In some embodiments, induction of the first inducible promoter by thermal stimulation and/or immune cell stimulation causes secretion of the payload molecule. In some embodiments, stimulated steady state payload protein levels, unstimulated steady state payload protein levels, the lower tuned threshold, and/or the upper tuned threshold can be tuned by adjusting the presence and/or sequence the tandem gene expression element. In some embodiments, the payload comprises a CAR and/or a TCR, wherein the payload is not expressed in the absence of thermal stimulus, and wherein engagement of the CAR and/or TCR initiates sustained expression of the payload. In some embodiments, the payload comprises a prodrug-converting enzyme (e.g., HSV thymidine kinase (TK), Cytosine Deaminase (CD), Purine nucleoside phosphorylase (PNP), Cytochrome p450 enzymes (CYP), Carboxypeptidases (CP), Caspase-9, Carboxylesterase (CE), Nitroreductase (NTR), Horse radish peroxidase (HRP), Guanine Ribosyltransferase (XGRTP), Glycosidase enzymes, Methionine-α, γ-lyase (MET), Thymidine phosphorylase (TP)).

In some embodiments, the payload gene encodes a payload RNA agent. A payload RNA agent can comprise one or more of dsRNA, siRNA, shRNA, pre-miRNA, pri-miRNA, miRNA, stRNA, lncRNA, piRNA, and snoRNA. In some embodiments, the payload gene encodes a siRNA, a shRNA, an antisense RNA oligonucleotide, an antisense miRNA, a trans-splicing RNA, a guide RNA, single-guide RNA, crRNA, a tracrRNA, a trans-splicing RNA, a pre-mRNA, a mRNA, or any combination thereof.

The payload protein can comprise a cytokine. The cytokine can be interleukin-1 (IL-1), IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IL-34, IL-35, interleukin-1 (IL-1), IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IL-34, IL-35, granulocyte macrophage colony stimulating factor (GM-CSF), M-CSF, SCF, TSLP, oncostatin M, leukemia-inhibitory factor (LIF), CNTF, Cardiotropin-1, NNT-1/BSF-3, growth hormone, Prolactin, Erythropoietin, Thrombopoietin, Leptin, G-CSF, or receptor or ligand thereof.

The payload protein can comprise a member of the TGF-β/BMP family selected from TGF-β1, TGF-β2, TGF-β3, BMP-2, BMP-3a, BMP-3b, BMP-4, BMP-5, BMP-6, BMP-7, BMP-8a, BMP-8b, BMP-9, BMP-10, BMP-11, BMP-15, BMP-16, endometrial bleeding associated factor (EBAF), growth differentiation factor-1 (GDF-1), GDF-2, GDF-3, GDF-5, GDF-6, GDF-7, GDF-8, GDF-9, GDF-12, GDF-14, mullerian inhibiting substance (MIS), activin-1, activin-2, activin-3, activin-4, and activin-5. The payload protein can comprise a member of the TNF family of cytokines selected from TNF-alpha, TNF-beta, LT-beta, CD40 ligand, Fas ligand, CD 27 ligand, CD 30 ligand, and 4-1 BBL. The payload protein can comprise a member of the immunoglobulin superfamily of cytokines selected from B7.1 (CD80) and B7.2 (B70). The payload protein can comprise an interferon. The interferon can be interferon alpha, interferon beta, or interferon gamma. The payload protein can comprise a chemokine. The chemokine can be selected from CCL1, CCL2, CCL3, CCR4, CCL5, CCL7, CCL8/MCP-2, CCL11, CCL13/MCP-4, HCC-1/CCL14, CTAC/CCL17, CCL19, CCL22, CCL23, CCL24, CCL26, CCL27, VEGF, PDGF, lymphotactin (XCL1), Eotaxin, FGF, EGF, IP-10, TRAIL, GCP-2/CXCL6, NAP-2/CXCL7, CXCL8, CXCL10, ITAC/CXCL11, CXCL12, CXCL13, or CXCL15. The payload protein can comprise a interleukin. The interleukin can be IL-10 IL-12, IL-1, IL-6, IL-7, IL-15, IL-2, IL-18 or IL-21. The payload protein can comprise a tumor necrosis factor (TNF). The TNF can be TNF-alpha, TNF-beta, TNF-gamma, CD252, CD154, CD178, CD70, CD153, or 4-1BBL.

The payload protein can comprise a CRE recombinase, GCaMP, a cell therapy component, a knock-down gene therapy component, a cell-surface exposed epitope, or any combination thereof. The payload protein can comprise a chimeric antigen receptor.

The payload protein can comprise a programmable nuclease. In some embodiments, the programmable nuclease is selected from: SpCas9 or a derivative thereof; VRER, VQR, EQR SpCas9; xCas9-3.7; eSpCas9; Cas9-HF1; HypaCas9; evoCas9; HiFi Cas9; ScCas9; StCas9; NmCas9; SaCas9; CjCas9; CasX; Cas9 H940A nickase; Cas12 and derivatives thereof; dcas9-APOBEC1 fusion, BE3, and dcas9-deaminase fusions; dcas9-Krab, dCas9-VP64, dCas9-Tet1, and dcas9-transcriptional regulator fusions; Dcas9-fluorescent protein fusions; Cas13-fluorescent protein fusions; RCas9-fluorescent protein fusions; Cas13-adenosine deaminase fusions. The programmable nuclease can comprise a zinc finger nuclease (ZFN) and/or transcription activator-like effector nuclease (TALEN). The programmable nuclease can comprise *Streptococcus pyogenes* Cas9 (SpCas9), *Staphylococcus aureus* Cas9 (SaCas9), a zinc finger nuclease, TAL effector nuclease, meganuclease, MegaTAL, Tev-m TALEN, MegaTev, homing endonuclease, Cas1, Cas1B, Cas2, Cas3, Cas4, Cas5, Cash, Cas7, Cas8, Cas9, Cas100, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cpf1, C2c1, C2c3, Cas12a, Cas12b, Cas12c, Cas12d, Cas12e, Cas13a, Cas13b, Cas13c, derivatives thereof, or any combination thereof. The nucleic acid composition can comprise a polynucleotide encoding (i) a targeting molecule and/or (ii) a donor nucleic acid. The targeting molecule can be capable of associating with the programmable nuclease. The targeting molecule can comprise single strand DNA or single strand RNA. The targeting molecule can comprise a single guide RNA (sgRNA).

In some embodiments, the payload protein is a therapeutic protein or variant thereof. Non-limiting examples of therapeutic proteins include blood factors, such as β-globin, hemoglobin, tissue plasminogen activator, and coagulation factors; colony stimulating factors (CSF); interleukins, such as IL-1, IL-2, IL-3, IL-4, IL-5, IL-6, IL-7, IL-8, IL-9, etc.; growth factors, such as keratinocyte growth factor (KGF), stem cell factor (SCF), fibroblast growth factor (FGF, such as basic FGF and acidic FGF), hepatocyte growth factor (HGF), insulin-like growth factors (IGFs), bone morphogenetic protein (BMP), epidermal growth factor (EGF), growth differentiation factor-9 (GDF-9), hepatoma derived growth factor (HDGF), myostatin (GDF-8), nerve growth factor (NGF), neurotrophins, platelet-derived growth factor (PDGF), thrombopoietin (TPO), transforming growth factor alpha (TGF-a), transforming growth factor beta (TGF-β), and the like; soluble receptors, such as soluble TNF-receptors, soluble VEGF receptors, soluble interleukin receptors (e.g., soluble IL-1 receptors and soluble type II IL-1 receptors), soluble γ/6 T cell receptors, ligand-binding fragments of a soluble receptor, and the like; enzymes, such as—glucosidase, imiglucarase, β-glucocerebrosidase, and alglucerase; enzyme activators, such as tissue plasminogen activator; chemokines, such as IP-10, monokine induced by interferon-gamma (Mig), Gro/IL-8, RANTES, MIP-1, MIP-I β, MCP-1, PF-4, and the like; angiogenic agents, such as vascular endothelial growth factors (VEGFs, e.g., VEGF121, VEGF165, VEGF-C, VEGF-2), transforming growth factor-beta, basic fibroblast growth factor, glioma-derived growth factor, angiogenin, angiogenin-2; and the like; anti-angiogenic agents, such as a soluble VEGF receptor; protein vaccine; neuroactive peptides, such as nerve growth factor (NGF), bradykinin, cholecystokinin, gastin, secretin, oxytocin, gonadotropin-releasing hormone, beta-endorphin, enkephalin, substance P, somatostatin, prolactin, galanin, growth hormone-releasing hormone, bombesin, dynorphin, warfarin, neurotensin, motilin, thyrotropin, neuropeptide Y, luteinizing hormone, calcitonin, insulin, glucagons, vasopressin, angiotensin II, thyrotropin-releasing hormone, vasoactive intestinal peptide, a sleep peptide, and the like; thrombolytic agents; atrial natriuretic peptide; relaxin; glial fibrillary acidic protein; follicle stimulating hormone (FSH); human alpha-1 antitrypsin; leukemia inhibitory factor (LIF); transforming growth factors (TGFs); tissue factors, luteinizing hormone; macrophage activating factors; tumor necrosis factor (TNF); neutrophil chemotactic factor (NCF); nerve growth factor; tissue inhibitors of metalloproteinases; vasoactive intestinal peptide; angiogenin; angiotropin; fibrin; hirudin; IL-1 receptor antagonists; and the like. Some other non-limiting examples of payload protein include ciliary neurotrophic factor (CNTF); brain-derived neurotrophic factor (BDNF); neurotrophins 3 and 4/5 (NT-3 and 4/5); glial cell derived neurotrophic factor (GDNF); aromatic amino acid decarboxylase (AADC); hemophilia related clotting proteins, such as Factor VIII, Factor IX, Factor X; dystrophin or mini-dystrophin; lysosomal acid lipase; phenylalanine hydroxylase (PAH); glycogen storage disease-related enzymes, such as glucose-6-phosphatase, acid maltase, glycogen debranching enzyme, muscle glycogen phosphorylase, liver glycogen phosphorylase, muscle phosphofructokinase, phosphorylase kinase (e.g., PHKA2), glucose transporter (e.g., GLUT2), aldolase A, β-enolase, and glycogen synthase; lysosomal enzymes (e.g., beta-N-acetylhexosaminidase A); and any variants thereof.

In some embodiments, the payload protein is an active fragment of a protein, such as any of the aforementioned proteins. In some embodiments, the payload protein is a fusion protein comprising some or all of two or more proteins. In some embodiments a fusion protein can comprise all or a portion of any of the aforementioned proteins.

In some embodiments, the payload protein is a multi-subunit protein. For examples, the payload protein can comprise two or more subunits, or two or more independent polypeptide chains. In some embodiments, the payload protein can be an antibody. Examples of antibodies include, but are not limited to, antibodies of various isotypes (for example, IgG1, IgG2, IgG3, IgG4, IgA, IgD, IgE, and IgM); monoclonal antibodies produced by any means known to those skilled in the art, including an antigen-binding fragment of a monoclonal antibody; humanized antibodies; chimeric antibodies; single-chain antibodies; antibody fragments such as Fv, F(ab')2, Fab', Fab, Facb, scFv and the like; provided that the antibody is capable of binding to antigen. In some embodiments, the antibody is a full-length antibody.

In some embodiments, the payload gene encodes a pro-survival protein (e.g., Bcl-2, Bcl-XL, Mcl-1 and A1). In some embodiments, the payload gene encodes a apoptotic factor or apoptosis-related protein such as, for example, AIF, Apaf (e.g., Apaf-1, Apaf-2, and Apaf-3), oder APO-2 (L), APO-3 (L), Apopain, Bad, Bak, Bax, Bcl-2, Bcl-xL, Bcl-xs, bik, CAD, Calpain, Caspase (e.g., Caspase-1, Caspase-2, Caspase-3, Caspase-4, Caspase-5, Caspase-6, Caspase-7, Caspase-8, Caspase-9, Caspase-10, and Caspase-11), ced-3, ced-9, c-Jun, c-Myc, crm A, cytochrom C, CdR1, DcR1, DD, DED, DISC, DNA-PKcs, DR3, DR4, DR5, FADD/MORT-1, FAK, Fas (Fas-ligand CD95/fas (receptor)), FLICE/MACH, FLIP, fodrin, fos, G-Actin, Gas-2, gelsolin, granzyme A/B, ICAD, ICE, JNK, Lamin A/B, MAP, MCL-1, Mdm-2, MEKK-1, MORT-1, NEDD, NF-$_{kappa}$B, NuMa, p53, PAK-2, PARP, perforin, PITSLRE, PKCdelta, pRb, presenilin, prICE, RAIDD, Ras, RIP, sphingomyelinase, thymidinkinase from herpes simplex, TRADD, TRAF2, TRAIL-R1, TRAIL-R2, TRAIL-R3, and/or transglutaminase.

In some embodiments, the payload gene encodes a cellular reprogramming factor capable of converting an at least partially differentiated cell to a less differentiated cell, such as, for example, Oct-3, Oct-4, Sox2, c-Myc, Klf4, Nanog, Lin28, ASCL1, MYT1L, TBX3b, SV40 large T, hTERT, miR-291, miR-294, miR-295, or any combinations thereof. In some embodiments, the payload gene encodes a programming factor that is capable of differentiating a given cell into a desired differentiated state, such as, for example, nerve growth factor (NGF), fibroblast growth factor (FGF), interleukin-6 (IL-6), bone morphogenic protein (BMP), neurogenin3 (Ngn3), pancreatic and duodenal homeobox 1 (Pdx1), Mafa, or any combination thereof.

In some embodiments, the payload gene encodes a human adjuvant protein capable of eliciting an innate immune response, such as, for example, cytokines which induce or enhance an innate immune response, including IL-2, IL-12, IL-15, IL-18, IL-21CCL21, GM-CSF and TNF-alpha; cytokines which are released from macrophages, including IL-1, IL-6, IL-8, IL-12 and TNF-alpha; from components of the complement system including C1q, MBL, C1r, C1s, C2b, Bb, D, MASP-1, MASP-2, C4b, C3b, C5a, C3a, C4a, C5b, C6, C7, C8, C9, CR1, CR2, CR3, CR4, C1qR, C1INH, C4bp, MCP, DAF, H, I, P and CD59; from proteins which are components of the signaling networks of the pattern recognition receptors including TLR and IL-1 R1, whereas the components are ligands of the pattern recognition receptors including IL-1 alpha, IL-1 beta, Beta-defensin, heat shock proteins, such as HSP10, HSP60, HSP65, HSP70, HSP75 and HSP90, gp96, Fibrinogen, TypIII repeat extra domain A of fibronectin; the receptors, including IL-1 RI, TLR1, TLR2, TLR3, TLR4, TLR5, TLR6, TLR7, TLR8, TLR9, TLR10, TLR11; the signal transducers including components of the Small-GTPases signaling (e.g., RhoA, Ras, Rac1, Cdc42), components of the PIP signaling (e.g., PI3K, Src-Kinases), components of the MyD88-dependent signaling (e.g., MyD88, IRAK1, IRAK2), components of the MyD88-independent signaling (TICAM1, TICAM2 etc.); activated transcription factors including NF-κB, c-Fos, c-Jun, c-Myc; and induced target genes including IL-1 alpha, IL-1 beta, Beta-Defensin, IL-6, IFN gamma, IFN alpha and IFN beta; from costimulatory molecules, including CD28 or CD40-ligand or PD1; protein domains, including LAMP; cell surface proteins; or human adjuvant proteins including CD80, CD81, CD86, trif, flt-3 ligand, thymopentin, Gp96 or fibronectin, etc., or any species homolog of any of the above human adjuvant proteins.

As described herein, the nucleotide sequence encoding the payload protein can be modified to improve expression efficiency of the protein. The methods that can be used to improve the transcription and/or translation of a gene herein are not particularly limited. For example, the nucleotide sequence can be modified to better reflect host codon usage to increase gene expression (e.g., protein production) in the host (e.g., a mammal).

The degree of payload gene expression in the immune cell can vary. For example, in some embodiments, the payload gene encodes a payload protein. The amount of the payload protein expressed in the subject (e.g., the serum of the subject) can vary. For example, in some embodiments the protein can be expressed in the serum of the subject in the amount of at least about 9 μg/ml, at least about 10 μg/ml, at least about 50 μg/ml, at least about 100 μg/ml, at least about 200 μg/ml, at least about 300 μg/ml, at least about 400 μg/ml, at least about 500 μg/ml, at least about 600 μg/ml, at least about 700 μg/ml, at least about 800 μg/ml, at least about 900 μg/ml, or at least about 1000 μg/ml. In some embodiments, the payload protein is expressed in the serum of the subject in the amount of about 9 μg/ml, about 10 μg/ml, about 50 μg/ml, about 100 μg/ml, about 200 μg/ml, about 300 μg/ml, about 400 μg/ml, about 500 μg/ml, about 600 μg/ml, about 700 μg/ml, about 800 μg/ml, about 900 μg/ml, about 1000 μg/ml, about 1500 μg/ml, about 2000 μg/ml, about 2500 μg/ml, or a range between any two of these values. A skilled artisan will understand that the expression level in which a payload protein is needed for the method to be effective can vary depending on non-limiting factors such as the particular payload protein and the subject receiving the treatment, and an effective amount of the protein can be readily determined by a skilled artisan using conventional methods known in the art without undue experimentation.

A payload protein encoded by a payload gene can be of various lengths. For example, the payload protein can be at least about 200 amino acids, at least about 250 amino acids, at least about 300 amino acids, at least about 350 amino acids, at least about 400 amino acids, at least about 450 amino acids, at least about 500 amino acids, at least about 550 amino acids, at least about 600 amino acids, at least about 650 amino acids, at least about 700 amino acids, at least about 750 amino acids, at least about 800 amino acids, or longer in length. In some embodiments, the payload protein is at least about 480 amino acids in length. In some embodiments, the payload protein is at least about 500 amino acids in length. In some embodiments, the payload protein is about 750 amino acids in length.

The payload genes can have different lengths in different implementations. The number of payload genes can be different in different embodiments. In some embodiments, the number of payload genes in a nucleic acid composition can be, or can be about, 1, 2, 3, 4, 5, 6, 7, 8, 9, 10, 11, 12, 13, 14, 15, 16, 17, 18, 19, 20, 21, 22, 23, 24, 25, or a number or a range between any two of these values. In some embodiments, the number of payload genes in a nucleic acid composition can be at least, or can be at most, 1, 2, 3, 4, 5, 6, 7, 8, 9, 10, 11, 12, 13, 14, 15, 16, 17, 18, 19, 20, 21, 22, 23, 24, 25. In some embodiments, a payload genes is, or is about, 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 110, 120, 128, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1100, 1200, 1300, 1400, 1500, 1600, 1700, 1800, 1900, 2000, 2100, 2200, 2300, 2400, 2500, 2600, 2700, 2800, 2900, 3000, 3250, 3500, 3750, 4000, 4250, 4500, 4750, 5000, 5500, 6000, 6500, 7000, 7500, 8000, 8500, 9000, 9500, 10000, or a number or a range between any two of these values, nucleotides in length. In some embodiments, a payload gene is at least, or is at most, 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 110, 120, 128, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1100, 1200, 1300, 1400, 1500, 1600, 1700, 1800, 1900, 2000, 2100, 2200, 2300, 2400, 2500, 2600, 2700, 2800, 2900, 3000, 3250, 3500, 3750, 4000, 4250, 4500, 4750, 5000, 5500, 6000, 6500, 7000, 7500, 8000, 8500, 9000, 9500, or 10000 nucleotides in length.

The payload can be an inducer of cell death. The payload can be induce cell death by a non-endogenous cell death pathway (e.g., a bacterial pore-forming toxin). In some embodiments, the payload can be a pro-survival protein. In some embodiments, the payload is a modulator of the immune system. The payload protein can comprise a CRE recombinase, GCaMP, a cell therapy component, a knock-down gene therapy component, a cell-surface exposed epitope, or any combination thereof.

Chimeric Antigen Receptors and Engineered T Cell Receptors

The payload protein can comprise a chimeric antigen receptor (CAR) or T-cell receptor (TCR). In some embodiments, the CAR comprises a T-cell receptor (TCR) antigen binding domain. The term "Chimeric Antigen Receptor" or alternatively a "CAR" refers to a set of polypeptides, typically two in the simplest embodiments, which when in an immune effector cell, provides the cell with specificity for a target cell, typically a cancer cell, and with intracellular signal generation. The terms "CAR" and "CAR molecule" are used interchangeably. In some embodiments, a CAR comprises at least an extracellular antigen binding domain, a transmembrane domain and a cytoplasmic signaling domain (also referred to herein as "an intracellular signaling domain") comprising a functional signaling domain derived from a stimulatory molecule and/or costimulatory molecule as defined below. In some embodiments, the set of polypeptides are in the same polypeptide chain (e.g., comprise a chimeric fusion protein). In some aspects, the set of polypeptides are contiguous with each other. In some embodiments, the set of polypeptides are not contiguous with each other, e.g., are in different polypeptide chains. In some embodiments, the set of polypeptides include a dimerization switch that, upon the presence of a dimerization molecule, can couple the polypeptides to one another, e.g., can couple an antigen binding domain to an intracellular signaling domain. In some embodiments, the stimulatory molecule is the zeta chain associated with the T cell receptor complex. In some embodiments, the cytoplasmic signaling domain further comprises one or more functional signaling domains derived from at least one costimulatory molecule as defined below. In some embodiments, the costimulatory molecule is chosen from the costimulatory molecules described herein, e.g., 4-1BB (i.e., CD137), CD27 and/or CD28. In some embodiments, the CAR comprises a chimeric fusion protein comprising an extracellular antigen binding domain, a transmembrane domain and an intracellular signaling domain comprising a functional signaling domain derived from a stimulatory molecule. In some embodiments, the CAR comprises a chimeric fusion protein comprising an extracellular antigen binding domain, a transmembrane domain and an intracellular signaling domain comprising a functional signaling domain derived from a costimulatory molecule and a functional signaling domain derived from a stimulatory molecule. In some embodiments, the CAR comprises a chimeric fusion protein comprising an extracellular antigen binding domain, a transmembrane domain and an intracellular signaling domain comprising two functional signaling domains derived from one or more costimulatory molecule (s) and a functional signaling domain derived from a stimulatory molecule. In some embodiments, the CAR comprises a chimeric fusion protein comprising an extracellular antigen binding domain, a transmembrane domain and an intracellular signaling domain comprising at least two functional signaling domains derived from one or more costimulatory molecule(s) and a functional signaling domain derived from a stimulatory molecule. In some embodiments the CAR comprises an optional leader sequence at the amino-terminus (N-ter) of the CAR fusion protein. In some embodiments, the CAR further comprises a leader sequence at the N-terminus of the extracellular antigen binding domain, wherein the leader sequence is optionally cleaved from the antigen binding domain (e.g., a scFv) during cellular processing and localization of the CAR to the cellular membrane.

The CAR and/or TCR can comprise one or more of an antigen binding domain, a transmembrane domain, and an intracellular signaling domain. The CAR or TCR further can comprise a leader peptide. The TCR further can comprise a constant region and/or CDR4. The term "signaling domain" refers to the functional portion of a protein which acts by transmitting information within the cell to regulate cellular activity via defined signaling pathways by generating second messengers or functioning as effectors by responding to such messengers. An "intracellular signaling domain," as the term is used herein, refers to an intracellular portion of a molecule. The intracellular signaling domain generates a signal that promotes an immune effector function of the CAR containing cell, e.g., a CART cell. Examples of immune effector function, e.g., in a CART cell, include cytolytic activity and helper activity, including the secretion of cytokines. In an embodiment, the intracellular signaling domain can comprise a primary intracellular signaling domain. Exemplary primary intracellular signaling domains include those derived from the molecules responsible for primary stimulation, or antigen dependent simulation. In an embodiment, the intracellular signaling domain can comprise a costimulatory intracellular domain. Exemplary costimulatory intracellular signaling domains include those derived from molecules responsible for costimulatory signals, or antigen independent stimulation. For example, in the case of a CART, a primary intracellular signaling domain can comprise a cytoplasmic sequence of a T cell receptor, and a costimulatory intracellular signaling domain can comprise cytoplasmic sequence from co-receptor or costimulatory molecule. A primary intracellular signaling domain can comprise a signaling motif which is known as an immunoreceptor tyrosine-based activation motif or ITAM. Examples of ITAM containing primary cytoplasmic signaling sequences include, but are not limited to, those derived from CD3 zeta, common FcR gamma (FCER1G), Fc gamma RIIa, FcR beta (Fc Epsilon Rib), CD3 gamma, CD3 delta, CD3 epsilon, CD79a, CD79b, DAP10, and DAP12.

The intracellular signaling domain can comprise a primary signaling domain, a costimulatory domain, or both of a primary signaling domain and a costimulatory domain. The cytoplasmic domain or region of the CAR includes an intracellular signaling domain. An intracellular signaling domain is generally responsible for activation of at least one of the normal effector functions of the immune cell in which the CAR has been introduced. The term "effector function" refers to a specialized function of a cell. Effector function of a T cell, for example, may be cytolytic activity or helper activity including the secretion of cytokines. Thus the term "intracellular signaling domain" refers to the portion of a protein which transduces the effector function signal and directs the cell to perform a specialized function. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

The term a "costimulatory molecule" refers to a cognate binding partner on a T cell that specifically binds with a costimulatory ligand, thereby mediating a costimulatory response by the T cell, such as, but not limited to, proliferation. Costimulatory molecules are cell surface molecules other than antigen receptors or their ligands that are contribute to an efficient immune response. Costimulatory molecules include, but are not limited to an MEW class I molecule, BTLA and a Toll ligand receptor, as well as OX40, CD27, CD28, CD5, ICAM-1, LFA-1 (CD11a/CD18), ICOS (CD278), and 4-1BB (CD137). Further examples of such costimulatory molecules include CD5, ICAM-1, GITR, BAFFR, HVEM (LIGHTR), SLAMF7, NKp80 (KLRF1), NKp44, NKp30, NKp46, CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, and a ligand that specifically binds with CD83. A costimulatory intracellular signaling domain can be the intracellular portion of a costimulatory molecule. A costimulatory molecule can be represented in the following protein families: TNF receptor proteins, Immunoglobulin-like proteins, cytokine receptors, integrins, signaling lymphocytic activation molecules (SLAM proteins), and activating NK cell receptors. The intracellular signaling domain can comprise the entire intracellular portion, or the entire native intracellular signaling domain, of the molecule from which it is derived, or a functional fragment or derivative thereof.

Examples of intracellular signaling domains for use in the CAR disclosed herein include the cytoplasmic sequences of the T cell receptor (TCR) and co-receptors that act in concert to initiate signal transduction following antigen receptor engagement, as well as any derivative or variant of these sequences and any recombinant sequence that has the same functional capability. It is known that signals generated through the TCR alone are insufficient for full activation of the T cell and that a secondary and/or costimulatory signal is also required. Thus, T cell activation can be said to be mediated by two distinct classes of cytoplasmic signaling sequences: those that initiate antigen-dependent primary activation through the TCR (primary intracellular signaling domains) and those that act in an antigen-independent manner to provide a secondary or costimulatory signal (secondary cytoplasmic domain, e.g., a costimulatory domain). A primary signaling domain regulates primary activation of the TCR complex either in a stimulatory way, or in an inhibitory way. Primary intracellular signaling domains that act in a stimulatory manner may contain signaling motifs which are known as immunoreceptor tyrosine-based activation motifs or ITAMs. The primary signaling domain can comprise a functional signaling domain of one or more proteins selected from CD3 zeta, CD3 gamma, CD3 delta, CD3 epsilon, common FcR gamma (FCER1G), FcR beta (Fc Epsilon Rib), CD79a, CD79b, Fcgamma RIIa, DAP10, and DAP12, or a functional variant thereof.

In some embodiments, the intracellular signaling domain is designed to comprise two or more, e.g., 2, 3, 4, 5, or more, costimulatory signaling domains. In an embodiment, the two or more, e.g., 2, 3, 4, 5, or more, costimulatory signaling domains, are separated by a linker molecule, e.g., a linker molecule described herein. In one embodiment, the intracellular signaling domain comprises two costimulatory signaling domains. In some embodiments, the linker molecule is a glycine residue. In some embodiments, the linker is an alanine residue. The costimulatory domain can comprise a functional domain of one or more proteins selected from CD27, CD28, 4-1BB (CD137), OX40, CD28-OX40, CD28-4-1BB, CD30, CD40, PD-1, ICOS, lymphocyte function-associated antigen-1 (LFA-1), CD2, CD7, LIGHT, NKG2C, B7-H3, a ligand that specifically binds with CD83, CD5, ICAM-1, GITR, BAFFR, HVEM (LIGHTR), SLAMF7, NKp80 (KLRF1), CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, and NKG2D, or a functional variant thereof.

The portion of the CAR comprising an antibody or antibody fragment thereof may exist in a variety of forms where the antigen binding domain is expressed as part of a contiguous polypeptide chain including, for example, a single domain antibody fragment (sdAb), a single chain antibody (scFv), a humanized antibody, or bispecific antibody (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426). The antigen binding domain of a CAR composition disclosed herein can comprises an antibody fragment. In some embodiments, the CAR comprises an antibody fragment that comprises a scFv.

In some embodiments, the CAR comprises a target-specific binding element otherwise referred to as an antigen binding domain. The choice of moiety depends upon the type and number of ligands that define the surface of a target cell. For example, the antigen binding domain may be chosen to recognize a ligand that acts as a cell surface marker on target cells associated with a particular disease state. Thus, examples of cell surface markers that may act as ligands for the antigen binding domain in a CAR include those associated with viral, bacterial and parasitic infections, autoimmune disease and cancer cells.

In some embodiments, the CAR-mediated T-cell response can be directed to an antigen of interest by way of engineering an antigen binding domain that specifically binds a desired antigen into the CAR. In some embodiments, the portion of the CAR comprising the antigen binding domain comprises an antigen binding domain that targets a tumor antigen, e.g., a tumor antigen described herein. The antigen binding domain can be any domain that binds to the antigen including but not limited to a monoclonal antibody, a polyclonal antibody, a recombinant antibody, a human antibody, a humanized antibody, and a functional fragment thereof, including but not limited to a single-domain antibody such as a heavy chain variable domain (VH), a light chain variable domain (VL) and a variable domain (VHH) of camelid derived nanobody, and to an alternative scaffold known in the art to function as antigen binding domain, such as a recombinant fibronectin domain, a T cell receptor (TCR), or a fragment there of, e.g., single chain TCR, and the like. In some instances, it is beneficial for the antigen binding domain to be derived from the same species in which the CAR will ultimately be used in. For example, for use in humans, it may be beneficial for the antigen binding domain of the CAR to comprise human or humanized residues for the antigen binding domain of an antibody or antibody fragment. In some embodiments, the antigen binding domain comprises a humanized antibody or an antibody fragment. The non-human antibody can be humanized, where specific sequences or regions of the antibody are modified to increase similarity to an antibody naturally produced in a human or fragment thereof. In some embodiments, the antigen binding domain is humanized.

The antigen binding domain can comprise an antibody, an antibody fragment, an scFv, a Fv, a Fab, a (Fab')2, a single domain antibody (SDAB), a VH or VL domain, a camelid VHH domain, a Fab, a Fab', a $F(ab')_2$, a Fv, a scFv, a dsFv, a diabody, a triabody, a tetrabody, a multispecific antibody formed from antibody fragments, a single-domain antibody (sdAb), a single chain comprising cantiomplementary scFvs (tandem scFvs) or bispecific tandem scFvs, an Fv construct, a disulfide-linked Fv, a dual variable domain immunoglobulin (DVD-Ig) binding protein or a nanobody, an aptamer, an affibody, an affilin, an affitin, an affimer, an alphabody, an anticalin, an avimer, a DARPin, a Fynomer, a Kunitz domain peptide, a monobody, or any combination thereof.

In some embodiments, the antigen binding domain is a T cell receptor ("TCR"), or a fragment thereof, for example, a single chain TCR (scTCR). Methods to make such TCRs are known in the art. See, e.g., Willemsen R A et al, Gene Therapy 7: 1369-1377 (2000); Zhang T et al, Cancer Gene Ther 11: 487-496 (2004); Aggen et al, Gene Ther. 19(4): 365-74 (2012) (references are incorporated herein by its entirety). For example, scTCR can be engineered that contains the Vα and Vβ genes from a T cell clone linked by a linker (e.g., a flexible peptide). This approach is very useful to cancer associated target that itself is intracellar, however, a fragment of such antigen (peptide) is presented on the surface of the cancer cells by MHC.

In some embodiments, the antigen binding domain is a multispecific antibody molecule. In some embodiments, the multispecific antibody molecule is a bispecific antibody molecule. A bispecific antibody has specificity for no more than two antigens. A bispecific antibody molecule is characterized by a first immunoglobulin variable domain sequence which has binding specificity for a first epitope and a second immunoglobulin variable domain sequence that has binding specificity for a second epitope. In an embodiment the first and second epitopes are on the same antigen, e.g., the same protein (or subunit of a multimeric protein). In an embodiment the first and second epitopes overlap. In an embodiment the first and second epitopes do not overlap. In an embodiment the first and second epitopes are on different antigens, e.g., different proteins (or different subunits of a multimeric protein). In an embodiment a bispecific antibody molecule comprises a heavy chain variable domain sequence and a light chain variable domain sequence which have binding specificity for a first epitope and a heavy chain variable domain sequence and a light chain variable domain sequence which have binding specificity for a second epitope. In an embodiment a bispecific antibody molecule comprises a half antibody having binding specificity for a first epitope and a half antibody having binding specificity for a second epitope. In an embodiment a bispecific antibody molecule comprises a half antibody, or fragment thereof, having binding specificity for a first epitope and a half antibody, or fragment thereof, having binding specificity for a second epitope. In an embodiment a bispecific antibody molecule comprises a scFv, or fragment thereof, have binding specificity for a first epitope and a scFv, or fragment thereof, have binding specificity for a second epitope.

The antigen binding domain can be configured to bind to a tumor antigen. The terms "cancer associated antigen" or "tumor antigen" interchangeably refers to a molecule (typically a protein, carbohydrate or lipid) that is expressed on the surface of a cancer cell, either entirely or as a fragment (e.g., MHC/peptide), and which is useful for the preferential targeting of a pharmacological agent to the cancer cell. In some embodiments, a tumor antigen is a marker expressed by both normal cells and cancer cells, e.g., a lineage marker, e.g., CD19 on B cells. In some embodiments, a tumor antigen is a cell surface molecule that is overexpressed in a cancer cell in comparison to a normal cell, for instance, 1-fold over expression, 2-fold overexpression, 3-fold overexpression or more in comparison to a normal cell. In some embodiments, a tumor antigen is a cell surface molecule that is inappropriately synthesized in the cancer cell, for instance, a molecule that contains deletions, additions or mutations in comparison to the molecule expressed on a normal cell. In some embodiments, a tumor antigen will be expressed exclusively on the cell surface of a cancer cell, entirely or as a fragment (e.g., MHC/peptide), and not synthesized or expressed on the surface of a normal cell. In some embodiments, the CARs includes CARs comprising an antigen binding domain (e.g., antibody or antibody fragment) that binds to a MHC presented peptide. Normally, peptides derived from endogenous proteins fill the pockets of Major histocompatibility complex (MHC) class I molecules, and are recognized by T cell receptors (TCRs) on CD8+T lymphocytes. The MHC class I complexes are constitutively expressed by all nucleated cells. In cancer, virus-specific and/or tumor-specific peptide/MHC complexes represent a unique class of cell surface targets for immunotherapy. TCR-like antibodies targeting peptides derived from viral or tumor antigens in the context of human leukocyte antigen (HLA)-A1 or HLA-A2 have been described (see, e.g., Sastry et al., J Virol. 2011 85(5):1935-1942; Sergeeva et al., Blood, 2011 117(16):4262-4272; Verma et al., J Immunol 2010 184(4):2156-2165; Willemsen et al., Gene Ther 2001 8(21):1601-1608; Dao et al., Sci Transl Med 2013 5(176):176ra33; Tassev et al., Cancer Gene Ther 2012 19(2):84-100). For example, TCR-like antibody can be identified from screening a library, such as a human scFv phage displayed library.

The tumor antigen can be a solid tumor antigen. The tumor antigen can be: CD19; CD123; CD22; CD30; CD171; CS-1 (also referred to as CD2 subset 1, CRACC, SLAMF7, CD319, and 19A24); C-type lectin-like molecule-1 (CLL-1 or CLECL1); CD33; epidermal growth factor receptor variant III (EGFRvIII); ganglioside G2 (GD2); ganglioside GD3 (aNeu5Ac(2-8)aNeu5Ac(2-3)bDGalp(1-4)bDGlcp(1-1) Cer); TNF receptor family member B cell maturation (BCMA); Tn antigen ((Tn Ag) or (GalNAcα-Ser/Thr)); prostate-specific membrane antigen (PSMA); Receptor tyrosine kinase-like orphan receptor 1 (ROR1); Fms-Like Tyrosine Kinase 3 (FLT3); Tumor-associated glycoprotein 72 (TAG72); CD38; CD44v6; Carcinoembryonic antigen (CEA); Epithelial cell adhesion molecule (EPCAM); B7H3 (CD276); KIT (CD117); Interleukin-13 receptor subunit alpha-2 (IL-13Ra2 or CD213A2); Mesothelin; Interleukin 11 receptor alpha (IL-11Ra); prostate stem cell antigen (PSCA); Protease Serine 21 (Testisin or PRSS21); vascular endothelial growth factor receptor 2 (VEGFR2); Lewis(Y) antigen; CD24; Platelet-derived growth factor receptor beta (PDGFR-beta); Stage-specific embryonic antigen-4 (SSEA-4); CD20; Folate receptor alpha; Receptor tyrosine-protein kinase ERBB2 (Her2/neu); Mucin 1, cell surface associated (MUC1); epidermal growth factor receptor (EGFR); neural cell adhesion molecule (NCAM); Prostase; prostatic acid phosphatase (PAP); elongation factor 2 mutated (ELF2M); Ephrin B2; fibroblast activation protein alpha (FAP); insulin-like growth factor 1 receptor (IGF-I receptor), carbonic anhydrase IX (CAIX); Proteasome (Prosome, Macropain) Subunit, Beta Type, 9 (LMP2); glycoprotein 100 (gp100); oncogene fusion protein consisting of breakpoint cluster region (BCR) and Abelson murine leukemia viral oncogene homolog 1 (Abl) (bcr-abl); tyrosinase; ephrin type-A receptor 2 (EphA2); Fucosyl GM1; sialyl Lewis adhesion molecule (sLe); ganglioside GM3 (aNeu5Ac(2-3)bDGalp(1-4) bDGlcp(1-1)Cer); transglutaminase 5 (TGS5); high molecular weight-melanoma-associated antigen (HMW-MAA); o-acetyl-GD2 ganglioside (OAcGD2); Folate receptor beta; tumor endothelial marker 1 (TEM1/CD248); tumor endothelial marker 7-related (TEM7R); claudin 6 (CLDN6); thyroid stimulating hormone receptor (TSHR); G protein-coupled receptor class C group 5, member D (GPRC5D); chromosome X open reading frame 61 (CXORF61); CD97; CD179a; anaplastic lymphoma kinase (ALK); Polysialic acid; placenta-specific 1 (PLAC1); hexasaccharide portion of globoH glycoceramide (GloboH); mammary gland differentiation antigen (NY-BR-1); uroplakin 2 (UPK2); Hepatitis A virus cellular receptor 1 (HAVCR1); adrenoceptor beta 3 (ADRB3); pannexin 3 (PANX3); G protein-coupled receptor 20 (GPR20); lymphocyte antigen 6 complex, locus K 9 (LY6K); Olfactory receptor 51E2 (OR51E2); TCR Gamma Alternate Reading Frame Protein (TARP); Wilms tumor protein (WT1); Cancer/testis antigen 1 (NY-ESO-1); Cancer/testis antigen 2 (LAGE-1a); Melanoma-associated antigen 1 (MAGE-A1); ETS translocation-variant gene 6, located on chromosome 12p (ETV6-AML); sperm protein 17 (SPA17); X Antigen Family, Member 1A (XAGE1); angiopoietin-binding cell surface receptor 2 (Tie 2); melanoma cancer testis antigen-1 (MAD-CT-1); melanoma cancer testis antigen-2 (MAD-CT-2); Fos-related antigen 1; tumor protein p53 (p53); p53 mutant; prostein; survivin; telomerase; prostate carcinoma tumor antigen-1 (PCTA-1 or Galectin 8), melanoma antigen recognized by T cells 1 (MelanA or MART1); Rat sarcoma (Ras) mutant; human Telomerase reverse transcriptase (hTERT); sarcoma translocation breakpoints; melanoma inhibitor of apoptosis (ML-IAP); ERG (transmembrane protease, serine 2 (TMPRSS2) ETS fusion gene); N-Acetyl glucosaminyl-transferase V (NA17); paired box protein Pax-3 (PAX3); Androgen receptor; Cyclin B1; v-myc avian myelocytomatosis viral oncogene neuroblastoma derived homolog (MYCN); Ras Homolog Family Member C (RhoC); Tyrosinase-related protein 2 (TRP-2); Cytochrome P450 1B1 (CYP1B1); CCCTC-Binding Factor (Zinc Finger Protein)-Like (BORIS or Brother of the Regulator of Imprinted Sites), Squamous Cell Carcinoma Antigen Recognized By T Cells 3 (SART3); Paired box protein Pax-5 (PAX5); proacrosin binding protein sp32 (OY-TES1); lymphocyte-specific protein tyrosine kinase (LCK); A kinase anchor protein 4 (AKAP-4); synovial sarcoma, X breakpoint 2 (SSX2); Receptor for Advanced Glycation Endproducts (RAGE-1); renal ubiquitous 1 (RU1); renal ubiquitous 2 (RU2); legumain; human papilloma virus E6 (HPV E6); human papilloma virus E7 (HPV E7); intestinal carboxyl esterase; heat shock protein 70-2 mutated (mut hsp70-2); CD79a; CD79b; CD72; Leukocyte-associated immunoglobulin-like receptor 1 (LAIR1); Fc fragment of IgA receptor (FCAR or CD89); Leukocyte immunoglobulin-like receptor subfamily A member 2 (LILRA2); CD300 molecule-like family member f (CD300LF); C-type lectin domain family 12 member A (CLEC12A); bone marrow stromal cell antigen 2 (BST2); EGF-like module-containing mucin-like hormone receptor-like 2 (EMR2); lymphocyte antigen 75 (LY75); Glypican-3 (GPC3); Fc receptor-like 5 (FCRL5); and immunoglobulin lambda-like polypeptide 1 (IGLL1).

The tumor antigen can be CD150, 5T4, ActRIIA, B7, BMCA, CA-125, CCNA1, CD123, CD126, CD138, CD14, CD148, CD15, CD19, CD20, CD200, CD21, CD22, CD23, CD24, CD25, CD26, CD261, CD262, CD30, CD33, CD362, CD37, CD38, CD4, CD40, CD40L, CD44, CD46, CD5, CD52, CD53, CD54, CD56, CD66a-d, CD74, CD8, CD80, CD92, CE7, CS-1, CSPG4, ED-B fibronectin, EGFR, EGFRvIII, EGP-2, EGP-4, EPHa2, ErbB2, ErbB3, ErbB4, FBP, GD2, GD3, HER1-HER2 in combination, HER2-HER3 in combination, HERV-K, HIV-1 envelope glycoprotein gp120, HIV-1 envelope glycoprotein gp41, HLA-DR, HM1.24, HMW-MAA, Her2, Her2/neu, IGF-1R, IL-11Ralpha, IL-13R-alpha2, IL-2, IL-22R-alpha, IL-6, IL-6R, Ia, Ii, L1-CAM, L1-cell adhesion molecule, Lewis Y, L1-CAM, MAGE A3, MAGE-A1, MART-1, MUC1, NKG2C ligands, NKG2D Ligands, NY-ESO-1, OEPHa2, PIGF, PSCA, PSMA, ROR1, T101, TAC, TAG72, TIM-3, TRAIL-R1, TRAIL-R1 (DR4), TRAIL-R2 (DR5), VEGF, VEGFR2, WT-1, a G-protein coupled receptor, alphafetoprotein (AFP), an angiogenesis factor, an exogenous cognate binding molecule (ExoCBM), oncogene product, anti-folate receptor, c-Met, carcinoembryonic antigen (CEA), cyclin (D1), ephrinB2, epithelial tumor antigen, estrogen receptor, fetal acethycholine e receptor, folate binding protein, gp100, hepatitis B surface antigen, kappa chain, kappa light chain, kdr, lambda chain, livin, melanoma-associated antigen, mesothelin, mouse double minute 2 homolog (MDM2), mucin 16 (MUC16), mutated p53, mutated ras, necrosis antigens, oncofetal antigen, ROR2, progesterone receptor, prostate specific antigen, tEGFR, tenascin, β2-Microglobulin, Fc Receptor-like 5 (FcRL5), or molecules expressed by HIV, HCV, HBV, or other pathogens.

The antigen binding domain can be connected to the transmembrane domain by a hinge region. In some instances, the transmembrane domain can be attached to the extracellular region of the CAR, e.g., the antigen binding domain of the CAR, via a hinge, e.g., a hinge from a human protein. For example, in one embodiment, the hinge can be a human Ig (immunoglobulin) hinge (e.g., an IgG4 hinge, an IgD hinge), a GS linker (e.g., a GS linker described herein), a KIR2DS2 hinge or a CD8a hinge.

With respect to the transmembrane domain, in various embodiments, a CAR can be designed to comprise a transmembrane domain that is attached to the extracellular domain of the CAR. A transmembrane domain can include one or more additional amino acids adjacent to the transmembrane region, e.g., one or more amino acid associated with the extracellular region of the protein from which the transmembrane was derived (e.g., 1, 2, 3, 4, 5, 6, 7, 8, 9, 10 up to 15 amino acids of the extracellular region) and/or one or more additional amino acids associated with the intracellular region of the protein from which the transmembrane protein is derived (e.g., 1, 2, 3, 4, 5, 6, 7, 8, 9, 10 up to 15 amino acids of the intracellular region). In some embodiments, the transmembrane domain is one that is associated with one of the other domains of the CAR e.g., in one embodiment, the transmembrane domain may be from the same protein that the signaling domain, costimulatory domain or the hinge domain is derived from. In some embodiments, the transmembrane domain is not derived from the same protein that any other domain of the CAR is derived from. In some instances, the transmembrane domain can be selected or modified by amino acid substitution to avoid binding of such domains to the transmembrane domains of the same or different surface membrane proteins, e.g., to minimize interactions with other members of the receptor complex. In some embodiments, the transmembrane domain is capable of homodimerization with another CAR on the cell surface of a CAR-expressing cell. In some embodiments, the amino acid sequence of the transmembrane domain may be modified or substituted so as to minimize interactions with the binding domains of the native binding partner present in the same CAR-expressing cell.

The transmembrane domain can comprise a transmembrane domain of a protein selected from the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154, KIRDS2, OX40, CD2, CD27, LFA-1 (CD11a, CD18), ICOS (CD278), 4-1BB (CD137), GITR, CD40, BAFFR, HVEM (LIGHTR), SLAMF7, NKp80 (KLRF1), CD160, CD19, IL2R beta, IL2R gamma, IL7Ra, ITGA1, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), SLAMF6 (NTB-A, Ly108), SLAM (SLAMF1, CD150, IPO-3), BLAME (SLAMF8), SELPLG (CD162), LTBR, PAG/Cbp, NKp44, NKp30, NKp46, NKG2D, and NKG2C, or a functional variant thereof. The transmembrane domain may be derived either from a natural or from a recombinant source. Where the source is natural, the domain may be derived from any membrane-bound or transmembrane protein. In some embodiments the transmembrane domain is capable of signaling to the intracellular domain(s) whenever the CAR has bound to a target.

T Cell Activity Sensors and Oscillator Circuits

While the current generations of CAR-T cell therapies have shown high response rates in B cell malignancies, their efficacy in solid tumors remains modest at best. One of the primary factors implicated in their poor performance is T cell "exhaustion" in which CAR-T cells have reduced effector function. Many research groups have focused on studying this phenomenon to generate new therapeutic leads for solid tumor therapy. In methods and compositions provided herein, T cell exhaustion can be reversed through transient inactivation of CAR-T cells. There are provided, in some embodiments, cell-autonomous genetic controllers that utilize HSP promoters to circumvent T cell exhaustion by periodically resting T cells. Disclosed herein are activity-regulated feedback circuits, based on HSP promoters as sensors of T cell activity (as described herein), that autonomously down regulates the expression of CAR to rest T cells following events of high CAR activity.

There are provided, in some embodiments of the methods and compositions disclosed herein, activity-driven oscillators preventing T cell exhaustion. In some embodiments, a central component the disclosed activity-driven oscillators is a new class of HSP-based transcriptional sensors which are described herein. In some embodiments, T cells use HSP-based promoters to sense their activity and down-regulate CAR expression after a period of stimulation, allowing the T cells to rest. In some embodiments, rested cells will express CAR again in an oscillatory pattern. In some embodiments, therapeutic T cells will oscillate asynchronously allowing some T cells to rest while the remaining cells engage with the tumor, resulting in sustained therapy while avoiding excessive activity in any given T cell. To regulate CAR expression, the activity of HSP-based sensors can be connected to the expression of proteins, such as the anti-GFP nanobody and LOCKR, which target and degrade engineered CARs. In some embodiments, to increase the length of the rest period, feed-forward control elements are included in the circuit. In some embodiments, to decrease the rest period, the N-end rule is used to control the CAR half-life. FIGS. 14A-14C depict non-limiting exemplary data and embodiments related to HSP-based feedback circuits that regulate CAR activity to prevent T cell exhaustion.

"Exhaustion" or "unresponsiveness" refers to a state of a cell where the cell does not perform its usual function or activity in response to normal input signals, and includes refractivity of immune cells to stimulation, such as stimulation via an activating receptor or a cytokine. Such a function or activity includes, but is not limited to, proliferation or cell division, entrance into the cell cycle, cytokine production, cytotoxicity, trafficking, phagocytotic activity, or any combination thereof. Normal input signals can include, but are not limited to, stimulation via a receptor (e.g., T cell receptor, B cell receptor, co-stimulatory receptor, and the like).

Exhausted immune cells can have a reduction of at least 10%, 15%, 20%, 25%, 30%, 35%, 40%, 45%, 50%, 55%, 60%, 65%, 70%, 75%, 80%, 85%, 90%, 95%, 99% or more in cytotoxic activity, cytokine production, proliferation, trafficking, phagocytotic activity, or any combination thereof, relative to a corresponding control immune cell of the same type. In one embodiment, a cell that is exhausted is a CD8+ T cell (e.g., an effector CD8+ T cell that is antigen-specific). CD8 cells normally proliferate (e.g., clonally expand) in response to T cell receptor and/or co-stimulatory receptor stimulation, as well as in response to cytokines such as IL-2. Thus, an exhausted CD8 T cell is one which does not proliferate and/or produce cytokines in response to normal input signals. It is well known that the exhaustion of effector functions can be delineated according to several stages, which eventually lead to terminal or full exhaustion and, ultimately, deletion (Yi et al. (2010) Immunol. 129:474-481; Wherry and Ahmed (2004) J. Virol. 78:5535-5545). In the first stage, functional T cells enter a "partial exhaustion I" phase characterized by the loss of a subset of effector functions, including loss of IL-2 production, reduced TNFa production, and reduced capacity for proliferation and/or ex vivo lysis ability. In the second stage, partially exhausted T cells enter a "partial exhaustion II" phase when both IL-2 and TNFa production ceases following antigenic stimulation and IFNy production is reduced. "Full exhaustion" or "terminal exhaustion" occurs when CD8+ T cells lose all effector functions, including the lack of production of IL-2, TNFa, and IFNy and loss of ex vivo lytic ability and proliferative potential, following antigenic stimulation. A fully exhausted CD8+ T cell is one which does not proliferate, does not lyse target cells (cytotoxicity), and/or does not produce appropriate cytokines, such as IL-2, TNFa, or IFNy, in response to normal input signals. Such lack of effector functions can occur when the antigen load is high and/or CD4 help is low. This hierarchical loss of function is also associated with the expression of co-inhibitor immune receptors, such as PD-1, 'HM-3, LAG-3, and the like (Day et al. (2006) Nature 443:350-4; Trauttnann et al. (2006) Nat. Med 12: 1198-202; and Urbani et al. (2006) J. Virol. 80: 1398-1403). Other molecular markers distinguish the hierarchical stages of immune cell exhaustion, such as high eomesodermin (EOMES) and low TBET expression as a marker of terminally exhausted T cells (Paley et al. (2012) Science 338: 1220-1225). Additional markers of exhausted T cells, such as the reduction of Bcl-b and the increased production of BLIMP-1 (Pdrml). T cell exhaustion can comprise expression of one or more T cell exhaustion biomarkers selected from the group comprising a checkpoint inhibitor, PD-1 (Pdcdl), TIIM-3 (Havcr2), LAG-3 (Lag3), CTLA-4 (Ctla4), 2B4 (CD244), CD39 (Entpdl), CD 160, eomesodermin (Eomes), T-BET (Tbx21), BATF, BLIMP-1 (Prdml), NFATC1, NR4A2, MAFB, OCT-2 (Pou2f2), Foxpl, retinoic acid receptor alpha (Rara), or any combination thereof.

There are provided, in some embodiments, nucleic acid compositions. A nucleic acid composition can comprise: a first inducible promoter operably linked to a first polynucleotide comprising an oscillator gene, wherein the first inducible promoter is capable of inducing transcription of the oscillator gene to generate an oscillator transcript upon thermal stimulation and/or immune cell stimulation, wherein the oscillator transcript is capable of being translated and/or processed to generate a oscillator; and a second promoter operably linked to a second polynucleotide comprising a payload gene, wherein the second promoter is capable of inducing transcription of the payload gene to generate a payload transcript, wherein the payload transcript is capable of being translated to generate a payload protein, and wherein the oscillator is capable of modulating the concentration, localization, stability, and/or activity of the payload transcript and/or payload protein.

The concentration, localization, stability, and/or activity of the payload protein can be inversely related to the concentration, localization, stability, and/or activity of the oscillator. The concentration, localization, stability, and/or activity of the oscillator can be inversely related to the concentration, localization, stability, and/or activity of the payload protein. In some embodiments, the oscillator gene encodes a siRNA, a shRNA, an antisense RNA oligonucleotide, an antisense miRNA, a trans-splicing RNA, a guide RNA, single-guide RNA, crRNA, a tracrRNA, a trans-splicing RNA, a pre-mRNA, a mRNA, or any combination thereof.

The oscillator can comprise a protease. In some embodiments, the payload protein comprises a degron and a cut site the protease is capable of cutting to expose the degron, and wherein the degron of the payload protein being exposed changes the payload protein to a payload protein destabilized state. The protease can comprise tobacco etch virus (TEV) protease, tobacco vein mottling virus (TVMV) protease, hepatitis C virus protease (HCVP), derivatives thereof, or any combination thereof.

The oscillator can be configured to bind the payload protein and reduce the concentration, localization, stability, and/or activity of the payload protein. The oscillator and/or payload protein can be configured such that the oscillator binds to the payload protein. The oscillator can comprise one or more elements (e.g., a degron) which can reduce the concentration, localization, stability, and/or activity of a binding partner. For example, the oscillator can comprise an anti-GFP nanobody fused to the AID degron, and the payload protein can comprise GFP.

The payload protein can comprise a cage polypeptide. A cage polypeptide can comprise: (a) a helical bundle, comprising between 2 and 7 alpha-helices, wherein the helical bundle comprises: (i) a structural region; and (ii) a latch region, wherein the latch region comprises a degron located within the latch region, wherein the structural region interacts with the latch region to prevent activity of the degron; and (b) amino acid linkers connecting each alpha helix. The oscillator can comprise a key polypeptide capable of binding to the cage polypeptide structural region, thereby displacing the latch region and activating the degron.

In some embodiments, the genetic circuits provided herein (e.g., oscillator genetic circuits) comprise Degron LOCKRs. The disclosure provides non-naturally occurring cage polypeptides, comprising: (a) a helical bundle, comprising between 2 and 7 alpha-helices, wherein the helical bundle comprises: (i) a structural region; and (ii) a latch region, wherein the latch region comprises a degron, wherein the structural region interacts with the latch region to prevent activity of the degron; and (b) amino acid linkers connecting each alpha helix. The non-naturally occurring cage polypeptides of this embodiment (which may also be referred to here as the "lock") can be used, for example, as a component of the oscillator genetic circuits disclosed in detail herein. The combined use of the cage and key polypeptides is described in more detail herein in the examples that follow, and is referred to as a LOCKR switch. LOCKR stands for Latching Orthogonal Cage-Key pRotiens; each LOCKR design consists of a cage polypeptide and a key polypeptide, which are two separate polypeptide chains. As used herein, a "degron" shall be given its ordinary meaning, and shall also refer to a single amino acid or peptide capable of targeting the cage polypeptide and any functional polypeptide domain fused for degradation. For example, degrons may target polypeptides for degradation through targeting to the proteasome (including ubiquitin-dependent degrons (ubiquitin protein is enzymatically attached to a protein, which marks it for degradation/targeting to proteasome), and ubiquitin-independent degrons (a degron that targets a protein to the proteasome without ubiquitin), targeting to lysosomes, or recruitment of protease enzymes. In some embodiments of the methods and compositions provided herein, when a key polypeptide is expressed and activates the cage polypeptide by interacting with the structural region, the degron targets the cage polypeptide, and any functional polypeptide domains and/or additional bioactive domain fused to the cage polypeptide, for degradation. In this way, a functional polypeptide domain of interest fused to the cage polypeptide having a degron can be conditionally degraded in a titratable manner via expression of the key. This is sometimes referred to herein as degronLOCKR. Degron LOCKRs including the cage polypeptides and key polypeptides, as well as methods of using, have been previously disclosed, for example, in PCT Application Publication No. WO2020/146260, the content of which is hereby expressly incorporated by reference in its entirety.

The oscillator can comprise a silencer effector. The silencer effector can comprise a microRNA (miRNA), a precursor microRNA (pre-miRNA), a small interfering RNA (siRNA), a short-hairpin RNA (shRNA), precursors thereof, derivatives thereof, or a combination thereof. In some embodiments, the payload gene comprises a 3' UTR and/or a 5' UTR, and wherein the 3' UTR and/or the 5' UTR of the payload gene comprises one or more silencer effector binding sequences. The silencer effector can be capable of binding the one or more silencer effector binding sequences, thereby reducing the stability of the payload transcript and/or reducing the translation of the payload transcript. The one or more silencer effector binding sequences can comprise miRNA binding sites. The payload gene can comprise about 1 silencer effector binding sequence to about 10 silencer binding sequences. The one or more silencer effector binding sequences can be about 8 nucleotides to about 22 nucleotides in length. The silencer effector can comprise a region of complementarity that is complementary with at least 5 consecutive nucleotides of the one or more silencer effector binding sequences. The silencer effector can comprise at least about 50% complementarity to the one or more silencer effector binding sequences.

In some embodiments, in the presence of continuous thermal stimulation and/or immune cell stimulation, steady state payload protein levels oscillate between a lower tuned threshold and an upper tuned threshold of a tuned expression range. The difference between the lower untuned threshold and the upper untuned threshold of the tuned expression range can be greater than about one order of magnitude. The difference between the lower tuned threshold and the upper tuned threshold of the tuned expression range can be less than about one order of magnitude.

In some embodiments, the lower tuned threshold and/or the upper tuned threshold of a tuned expression range can be increased by introducing one or more non-canonical amino acid substitutions into the silencer effector binding sequence, the cut site and/or the degron. In some embodiments, the lower tuned threshold and/or the upper tuned threshold of a tuned expression range can be reduced by introducing one or more canonical amino acid substitutions into the silencer effector binding sequence, the cut site and/or the degron.

In some embodiments, the payload comprises a CAR and/or a TCR, wherein in response to continuous engagement of the CAR and/or the TCR for at least about 24 hours, at least about 5 percent of the population of the thermally actuated immune cells have steady state payload protein levels at about the lower tuned threshold and at least about 5 percent (e.g., 5%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 200%, 300%, 400%, 500%, 600%, 700%, 800%, 900%, 1000%, or a number or a range between any two of these values) of the population of the thermally actuated immune cells have steady state payload protein levels at about the upper tuned threshold.

The payload can comprises a CAR and/or a TCR, and wherein in response to continuous engagement of the CAR and/or the TCR for at least about 96 hours, less than about 20 percent (e.g., 0%, 0.000000001%, 0.00000001%, 0.0000001%, 0.000001%, 0.00001%, 0.0001%, 0.001%, 0.01%, 0.1%, 1%, 2%, 3%, 4%, 5%, 6%, 7%, 8%, 9%, 10%, 11%, 12%, 13%, 14%, 15%, 16%, 17%, 18%, 19%, 20%, or a number or a range between any two of these values) of the population of the thermally actuated immune cells exhibit exhaustion (e.g., T cell exhaustion). In some embodiments, the payload comprises a CAR and/or a TCR, wherein in response to continuous engagement of the CAR and/or the TCR for 96 hours, at least about 1.1-fold (e.g., 1.1-fold, 1.3-fold, 1.5-fold, 1.7-fold, 1.9-fold, 2-fold, 3-fold, 4-fold, 5-fold, 6-fold, 7-fold, 8-fold, 9-fold, 10-fold, or a number or a range between any of these values) fewer cells of the population of the thermally actuated immune cells exhibit exhaustion (e.g., T cell exhaustion) as compared to a population of the thermally actuated immune cells which do not comprise the oscillator.

There are provided, in some embodiments, nucleic acid compositions. A nucleic acid composition can comprise: a first inducible promoter operably linked to a first polynucleotide comprising an activity regulator gene, wherein the first inducible promoter is capable of inducing transcription of the activity regulator gene to generate an activity regulator transcript upon thermal stimulation and/or immune cell stimulation, wherein the activity regulator transcript is capable of being translated and/or processed to generate an activity regulator; and wherein the activity regulator is capable of reducing T cell activity. The activity regulator can comprise a ubiquitin ligase involved in TCR/CAR signal transduction selected from c-CBL, CBL-B, ITCH, R F125, R F128, WWP2, or any combination thereof. The activity regulator can comprise a negative regulatory enzyme selected from SHP1, SHP2, SHTP1, SHTP2, CD45, CSK, CD148, PTPN22, DGKalpha, DGKzeta, DRAK2, HPK1, HPK1, STS1, STS2, SLAT, or any combination thereof. The activity regulator can be a negative regulatory scaffold/adapter protein selected from PAG, LIME, NTAL, LAX31, SIT, GAB2, GRAP, ALX, SLAP, SLAP2, DOK1, DOK2, or any combination thereof. The activity regulator can be a dominant negative version of an activating TCR signaling component selected from ZAP70, LCK, FYN, NCK, VAV1, SLP76, ITK, ADAP, GADS, PLCgammal, LAT, p85, SOS, GRB2, NFAT, p50, p65, API, RAP1, CRKII, C3G, WAVE2, ARP2/3, ABL, ADAP, RIAM, SKAP55, or any combination thereof. The activity regulator can comprise the cytoplasmic tail of a negative co-regulatory receptor selected from CD5, PD1, CTLA4, BTLA, LAG3, B7-H1, B7-1, CD160, TFM3, 2B4, TIGIT, or any combination thereof. The activity regulator can be targeted to the plasma membrane with a targeting sequence derived from LAT, PAG, LCK, FYN, LAX, CD2, CD3, CD4, CD5, CD7, CD8a, PD1, SRC, LYN, or any combination thereof. In some embodiments, the activity regulator reduces or abrogates a pathway and/or a function selected from Ras signaling, PKC signaling, calcium-dependent signaling, NF-kappaB signaling, NFAT signaling, cytokine secretion, T cell survival, T cell proliferation, CTL activity, degranulation, tumor cell killing, differentiation, or any combination thereof. The activity regulator can comprise a silencer effector. The silencer effector can comprise a microRNA (miRNA), a precursor microRNA (pre-miRNA), a small interfering RNA (siRNA), a short-hairpin RNA (shRNA), precursors thereof, derivatives thereof, or a combination thereof. In some embodiments, the silencer effector can be capable of reducing the expression of protein associated with T cell activity. The activity regulator can be a synthetic protein. For example, the activity regulator can be a protease (e.g., cleaving the CAR) or nanobody (e.g., binds and degrades the CAR), thereby lowering CAR/TCR activity. In some embodiments, the activity regulator comprises a synthetic protein described herein (e.g. a protease, a nanobody, a cage polypeptide) configured to bind and degrade a protein other than a TCR/CAR that promotes T cell activity.

Engineered Immune Cells

Disclosed herein include thermally actuated immune cells. In some embodiments, the thermally actuated immune cell comprises a nucleic acid composition disclosed herein. The immune cell can be a mammalian cell (e.g., a human cell). The immune cell can be derived from blood, cord blood, bone marrow, or iPSC. The immune cell can be a T cell. The T cell can be a primary T cell. The T cell can be an autologous T cell or an allogeneic T cell. A single thermal stimulus can be sufficient to initiate a positive feedback loop of immune cell activation-driven expression of the payload.

Disclosed herein include populations of the thermally actuated immune cells. In some embodiments, the population of the thermally actuated immune cells comprises: a plurality of the thermally actuated immune cells disclosed herein. Thermally actuated immune cells disclosed herein can be actuated (e.g., induction of expression from an inducible promoter) by T cell activity (e.g., immune cell stimulation) and/or thermal stimulation.

Disclosed herein include methods of generating a thermally actuated immune cell. In some embodiments, the method comprises: introducing a nucleic acid composition disclosed herein or a composition disclosed herein into an immune cell, thereby generating a thermally actuated immune cell. The introducing step can comprise calcium phosphate transfection, DEAE-dextran mediated transfection, cationic lipid-mediated transfection, electroporation, electrical nuclear transport, chemical transduction, electrotransduction, Lipofectamine-mediated transfection, Effectene-mediated transfection, lipid nanoparticle (LNP)-mediated transfection, or any combination thereof.

In embodiments described herein, the immune effector cell can be an allogeneic immune effector cell, e.g., T cell or NK cell. For example, the cell can be an allogeneic T cell, e.g., an allogeneic T cell lacking expression of a functional T cell receptor (TCR) and/or human leukocyte antigen (HLA), e.g., HLA class I and/or HLA class II. A T cell lacking a functional TCR can be, e.g., engineered such that it does not express any functional TCR on its surface, engineered such that it does not express one or more subunits that comprise a functional TCR or engineered such that it produces very little functional TCR on its surface. Alternatively, the T cell can express a substantially impaired TCR, e.g., by expression of mutated or truncated forms of one or more of the subunits of the TCR. The term "substantially impaired TCR" means that this TCR will not elicit an adverse immune reaction in a host. Modified T cells that lack expression of a functional TCR and/or HLA can be obtained by any suitable means, including a knock out or knock down of one or more subunit of TCR or HLA. For example, the T cell can include a knock down of TCR and/or HLA using siRNA, shRNA, clustered regularly interspaced short palindromic repeats (CRISPR) transcription-activator like effector nuclease (TALEN), or zinc finger endonuclease (ZFN).

In some embodiments, the T cells are obtained from a donor subject. In some embodiments, the donor subject is human patient afflicted with a cancer or a tumor. In other embodiments, the donor subject is a human patient not afflicted with a cancer or a tumor.

The immune cells can be obtained through any source known in the art. For example, T cells can be differentiated in vitro from a hematopoietic stem cell population, or T cells can be obtained from a subject. T cells can be obtained from, e.g., peripheral blood mononuclear cells, bone marrow, lymph node tissue, cord blood, thymus tissue, tissue from a site of infection, ascites, pleural effusion, spleen tissue, and tumors. In addition, the T cells can be derived from one or more T cell lines available in the art. T cells can also be obtained from a unit of blood collected from a subject using any number of techniques known to the skilled artisan, such as FICOLL™ separation and/or apheresis. The cells collected by apheresis can be washed to remove the plasma fraction, and placed in an appropriate buffer or media for subsequent processing. In some embodiments, the cells are washed with PBS. As will be appreciated, a washing step can be used, such as by using a semiautomated flowthrough centrifuge, e.g., the Cobe™ 2991 cell processor, the Baxter CytoMate™, or the like. In some embodiments, the washed cells are resuspended in one or more biocompatible buffers, or other saline solution with or without buffer. In some embodiments, the undesired components of the apheresis sample are removed. Additional methods of isolating T cells for a T cell therapy are disclosed in U.S. Patent Publication No. 2013/0287748, which is herein incorporated by references in its entirety.

In some embodiments, T cells are isolated from PBMCs by lysing the red blood cells and depleting the monocytes, e.g., by using centrifugation through a PERCOLL™ gradient. In some embodiments, a specific subpopulation of T cells, such as $CD4^+$, $CD8^+$, $CD28^+$, $CD45RA^+$, and $CD45RO^+$ T cells is further isolated by positive or negative selection techniques known in the art. For example, enrichment of a T cell population by negative selection can be accomplished with a combination of antibodies directed to surface markers unique to the negatively selected cells. In some embodiments, cell sorting and/or selection via negative magnetic immunoadherence or flow cytometry that uses a cocktail of monoclonal antibodies directed to cell surface markers present on the cells negatively selected can be used. For example, to enrich for $CD4^+$ cells by negative selection, a monoclonal antibody cocktail typically includes antibodies to CD8, CD11b, CD14, CD16, CD20, and HLA-DR. In some embodiments, flow cytometry and cell sorting are used to isolate cell populations of interest for use.

In some embodiments, the immune cells, e.g., T cells, are genetically modified following isolation using known methods, or the immune cells are activated and expanded (or differentiated in the case of progenitors) in vitro prior to being genetically modified. In another embodiment, the immune cells, e.g., T cells, are genetically modified with the chimeric antigen receptors described herein (e.g., transduced with a viral vector comprising one or more nucleotide sequences encoding a CAR) and then are activated and/or expanded in vitro. Methods for activating and expanding T cells are known in the art and are described, e.g., in U.S. Pat. Nos. 6,905,874; 6,867,041; and 6,797,514; and PCT Publication No. WO 2012/079000, the contents of which are hereby incorporated by reference in their entirety. Generally, such methods include contacting PBMC or isolated T cells with a stimulatory agent and costimulatory agent, such as anti-CD3 and anti-CD28 antibodies, generally attached to a bead or other surface, in a culture medium with appropriate cytokines, such as IL-2. Anti-CD3 and anti-CD28 antibodies attached to the same bead serve as a "surrogate" antigen presenting cell (APC). One example is the Dynaheads® system, a CD3/CD2S activator/stimulator system for physiological activation of human 'I' cells. In other embodiments, the T cells are activated and stimulated to proliferate with feeder cells and appropriate antibodies and cytokines using methods such as those described in U.S. Pat. Nos. 6,040,177 and 5,827,642 and PCT Publication No. WO 2012/129514, the contents of which are hereby incorporated by reference in their entirety.

Physical methods for introducing a polynucleotide into an immune cell include calcium phosphate precipitation, lipofection, particle bombardment, microinjection, electroporation, and the like. Methods for producing cells comprising vectors and/or exogenous nucleic acids are well-known in the art. See, for example, Sambrook et al., 2012, MOLECULAR CLONING: A LABORATORY MANUAL, volumes 1-4, Cold Spring Harbor Press, NY). A preferred method for the introduction of a polynucleotide into an immune cell is calcium phosphate transfection Chemical means for introducing a polynucleotide into an immune cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle). Other methods of state-of-the-art targeted delivery of nucleic acids are available, such as delivery of polynucleotides with targeted nanoparticles or other suitable submicron sized delivery system.

In the case where a non-viral delivery system is utilized, an exemplary delivery vehicle is a liposome. The use of lipid formulations is contemplated for the introduction of the nucleic acids into an immune cell (in vitro, ex vivo or in vivo). In some embodiments, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution.

Nucleic acids described herein can be introduced into immune cells using any of a number of different methods, for instance, commercially available methods which include, but are not limited to, electroporation (Amaxa Nucleofector-II (Amaxa Biosystems, Cologne, Germany)), (ECM 830 (BTX) (Harvard Instruments, Boston, Mass.) or the Gene Pulser II (BioRad, Denver, Colo.), Multiporator (Eppendort, Hamburg Germany), cationic liposome mediated transfection using lipofection, polymer encapsulation, peptide mediated transfection, or biolistic particle delivery systems such as "gene guns" (see, for example, Nishikawa, et al. Hum Gene Ther., 12(8):861-70 (2001).

In some embodiments, non-viral methods can be used to deliver a nucleic acid described herein into an immune cell. In some embodiments, the non-viral method includes the use of a transposon (also called a transposable element). In some embodiments, a transposon is a piece of DNA that can insert itself at a location in a genome, for example, a piece of DNA that is capable of self-replicating and inserting its copy into a genome, or a piece of DNA that can be spliced out of a longer nucleic acid and inserted into another place in a genome. For example, a transposon comprises a DNA sequence made up of inverted repeats flanking genes for transposition. Exemplary methods of nucleic acid delivery using a transposon include a Sleeping Beauty transposon system (SBTS) and a piggyBac (PB) transposon system. In some embodiments, thermally actuated immune cells described herein are generated by using a combination of gene insertion using the SBTS and genetic editing using a nuclease (e.g., Zinc finger nucleases (ZFNs), Transcription Activator-Like Effector Nucleases (TALENs), the CRISPR/Cas system, or engineered meganuclease re-engineered homing endonucleases). In some embodiments, use of a non-viral method of delivery permits reprogramming of cells, e.g., T cells, and direct infusion of the thermally actuated immune cells described herein into a subject. Advantages of non-viral vectors include but are not limited to the ease and relatively low cost of producing sufficient amounts required to meet a patient population, stability during storage, and lack of immunogenicity.

Methods of Treating a Disease or Disorder

Disclosed herein include methods of treating a disease or disorder in a subject. In some embodiments, the method comprises: introducing into one or more immune cells a composition comprising a nucleic acid composition disclosed herein or a composition disclosed herein, thereby generating one or more thermally actuated immune cells; and administering to the subject an effective amount of the thermally actuated immune cells.

Disclosed herein include methods of treating a disease or disorder in a subject. In some embodiments, the method comprises: administering to the subject an effective amount of the thermally actuated immune cells disclosed herein.

The subject can be a mammal. The disease can be associated with expression of a tumor antigen, wherein the disease associated with expression of a tumor antigen is selected from a proliferative disease, a precancerous condition, a cancer, and a non-cancer related indication associated with expression of the tumor antigen. The disease or disorder can be a cancer (e.g., a solid tumor). The cancer can be colon cancer, rectal cancer, renal-cell carcinoma, liver cancer, non-small cell carcinoma of the lung, cancer of the small intestine, cancer of the esophagus, melanoma, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin lymphoma, cancer of the endocrine system, cancer of the thyroid gland, cancer of the parathyroid gland, cancer of the adrenal gland, sarcoma of soft tissue, cancer of the urethra, cancer of the penis, solid tumors of childhood, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers, combinations of said cancers, and metastatic lesions of said cancers.

The cancer can be a hematologic cancer, for example chronic lymphocytic leukemia (CLL), acute leukemias, acute lymphoid leukemia (ALL), B-cell acute lymphoid leukemia (B-ALL), T-cell acute lymphoid leukemia (T-ALL), chronic myelogenous leukemia (CIVIL), B cell prolymphocytic leukemia, blastic plasmacytoid dendritic cell neoplasm, Burkitt's lymphoma, diffuse large B cell lymphoma, follicular lymphoma, hairy cell leukemia, small cell- or a large cell-follicular lymphoma, malignant lymphoproliferative conditions, MALT lymphoma, mantle cell lymphoma, marginal zone lymphoma, multiple myeloma, myelodysplasia and myelodysplastic syndrome, non-Hodgkin's lymphoma, Hodgkin's lymphoma, plasmablastic lymphoma, plasmacytoid dendritic cell neoplasm, Waldenstrom macroglobulinemia, or pre-leukemia.

The disease or disorder can be an autoimmune disorder. An "autoimmune disease" refers to a disease arising from an inappropriate immune response of the body of a subject against substances and tissues normally present in the body. In other words, the immune system mistakes some part of the body as a pathogen and attacks its own cells. This may be restricted to certain organs (e.g., in autoimmune thyroiditis) or involve a particular tissue in different places (e.g., Goodpasture's disease which may affect the basement membrane in both the lung and kidney). The treatment of autoimmune diseases is typically with immunosuppression, e.g., medications which decrease the immune response. Exemplary autoimmune diseases include, but are not limited to, glomerulonephritis, Goodpasture's syndrome, necrotizing vasculitis, lymphadenitis, peri-arteritis nodosa, systemic lupus erythematosis, rheumatoid arthritis, psoriatic arthritis, systemic lupus erythematosis, psoriasis, ulcerative colitis, systemic sclerosis, dermatomyositis/polymyositis, anti-phospholipid antibody syndrome, scleroderma, pemphigus vulgaris, ANCA-associated vasculitis (e.g., Wegener's granulomatosis, microscopic polyangiitis), uveitis, Sjogren's syndrome, Crohn's disease, Reiter's syndrome, ankylosing spondylitis, Lyme disease, Guillain-Barre syndrome, Hashimoto's thyroiditis, and cardiomyopathy.

The method can comprise: administering a transactivator-binding compound to the subject prior to, during, and/or after administration of the thermally actuated immune cells. The amount of transactivator-binding compound can be an amount effective to induce or attenuate a sufficient level of payload expression to treat the subject. In some embodiments, the transactivator-binding compound comprises tetracycline, doxycycline or a derivative thereof.

Administering can comprise aerosol delivery, nasal delivery, vaginal delivery, rectal delivery, buccal delivery, ocular delivery, local delivery, topical delivery, intracisternal delivery, intraperitoneal delivery, oral delivery, intramuscular injection, intravenous injection, subcutaneous injection, intranodal injection, intratumoral injection, intraperitoneal injection, intradermal injection, or any combination thereof. The thermally actuated immune cells can be administered at a therapeutically effective amount. For example, a therapeutically effective amount of the thermally actuated immune cells can be at least about $10^4$ cells, at least about $10^5$ cells, at least about $10^6$ cells, at least about $10^7$ cells, at least about $10^8$ cells, at least about $10^9$, or at least about $10^{10}$. In another embodiment, the therapeutically effective amount of the thermally actuated immune cells is about $10^4$ cells, about $10^5$ cells, about $10^6$ cells, about $10^7$ cells, or about $10^8$ cells. In one particular embodiment, the therapeutically effective amount of the thermally actuated immune cells is about $2\times10^6$ cells/kg, about $3\times10^6$ cells/kg, about $4\times10^6$ cells/kg, about $5\times10^6$ cells/kg, about $6\times10^6$ cells/kg, about $7\times10^6$ cells/kg, about $8\times10^6$ cells/kg, about $9\times10^6$ cells/kg, about $1\times10^7$ cells/kg, about $2\times10^7$ cells/kg, about $3\times10^7$ cells/kg, about $4\times10^7$ cells/kg, about $5\times10^7$ cells/kg, about $6\times10^7$ cells/kg, about $7\times10^7$ cells/kg, about $8\times10^7$ cells/kg, or about $9\times10^7$ cells/kg.

The thermally actuated immune cells described herein may be included in a composition for therapy. In some embodiments, the composition comprises a population of thermally actuated immune cells. The composition may include a pharmaceutical composition and further include a pharmaceutically acceptable carrier. A therapeutically effective amount of the pharmaceutical composition comprising the thermally actuated immune cells may be administered. The thermally actuated immune cells may be administered either alone, or as a pharmaceutical composition in combination with diluents and/or with other components such as IL-2 or other cytokines or cell populations. Ex vivo procedures are well known in the art. Briefly, cells are isolated from a mammal (e.g., a human) and genetically modified (i.e., transduced or transfected in vitro) with a nucleic acid composition (e.g., a vector) disclosed herein or a composition disclosed herein, thereby generating one or more thermally actuated immune cells. The thermally actuated immune cells can be administered to a mammalian recipient to provide a therapeutic benefit. The mammalian recipient may be a human and the thermally actuated immune cells can be autologous with respect to the recipient. Alternatively, the thermally actuated immune cells can be allogeneic, syngeneic or xenogeneic with respect to the recipient.

Applying Thermal Energy

The method can comprise: applying thermal energy to a target site of the subject sufficient to increase the local temperature of the target site to an activating temperature, thereby inducing the expression of the payload in thermally actuated immune cells at the target site. The activating temperature can be about 37.5° C., about 38.0° C., about 38.5° C., about 39.0° C., about 39.5° C., about 40.0° C., about 40.5° C., about 41.0° C., about 41.5° C., about 42.0° C., about 42.5° C., about 43.0° C., about 43.5° C., about 44.0° C., about 44.5° C., about 45.0° C., about 45.5° C., or about 46.0° C., or a number or a range between any two of these values.

Applying thermal energy to a target site of the subject can comprise the application of one or more of focused ultrasound (FUS), magnetic hyperthermia, microwaves, infrared irradiation, liquid-based heating, and contact heating. Liquid-based heating can comprise intraperitoneal chemotherapy (HIPEC). The term "applying ultrasound" shall be given its ordinary meaning, and shall also refer to sending ultrasound-range acoustic energy to a target. The sound energy produced by the piezoelectric transducer can be focused by beamforming, through transducer shape, lensing, or use of control pulses. The soundwave formed is transmitted to the body, then partially reflected or scattered by structures within a body; larger structures typically reflecting, and smaller structures typically scattering. The return sound energy reflected/scattered to the transducer vibrates the transducer and turns the return sound energy into electrical signals to be analyzed for imaging. The frequency and pressure of the input sound energy can be controlled and are selected based on the needs of the particular imaging/delivery task The period of time between the administering and applying thermal energy can be about 48 hours, about 44 hours, about 40 hours, about 35 hours, about 30 hours, about 25 hours, 20 hours, 15 hours, 10 hours, about 8 hours, about 8 hours, 8 hours, about 7 hours, about 6 hours, about 5 hours, about 4 hours, about 3 hours, about 2 hours, about 1 hour, about 30 minutes, about 15 minutes, about 10 minutes, about 5 minutes, or a number or a range between any two of these values.

Applying thermal energy to a target site can comprise a continuous application of thermal energy to the target site over a second duration of time. Applying thermal energy to a target site can comprise applying one or more pulses of thermal energy to the target site over a second duration of time. The second duration of time can be about 48 hours, about 44 hours, about 40 hours, about 35 hours, about 30 hours, about 25 hours, 20 hours, 15 hours, 10 hours, about 8 hours, about 8 hours, 8 hours, about 7 hours, about 6 hours, about 5 hours, about 4 hours, about 3 hours, about 2 hours, about 1 hour, about 30 minutes, about 15 minutes, about 10 minutes, about 5 minutes, or a number or a range between any two of these values.

The one or more pulses can have a duty cycle of greater than about 1% and less than about 100%. The one or more pulses have a duty cycle of about 0.000000001%, 0.00000001%, 0.0000001%, 0.000001%, 0.00001%, 0.0001%, 0.001%, 0.01%, 0.1%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, or a number or a range between any two of these values.

The one or more pulses each can have a pulse duration of about 1 hour, about 30 minutes, about 15 minutes, about 10 minutes, or about 5 minutes, about 1 minute, about 1 second, about 1 millisecond, or a number or a range between any two of these values.

In some embodiments, the method comprises: monitoring the temperature of the target region. The monitoring can be performed by magnetic resonance imaging (MM). The application of thermal energy to a target site of the subject can be guided spatially by magnetic resonance imaging (MM).

Target Sites

The target site can comprise a solid tumor. The target site can comprise a site of disease or disorder or can be proximate to a site of a disease or disorder. The location of the one or more sites of a disease or disorder can be predetermined, can be determined during the method, or both. The target site can be an immunosuppressive environment. The target site can comprise a tissue. The tissue can be inflamed tissue and/or infected tissue. The tissue can comprise adrenal gland tissue, appendix tissue, bladder tissue, bone, bowel tissue, brain tissue, breast tissue, bronchi, coronal tissue, ear tissue, esophagus tissue, eye tissue, gall bladder tissue, genital tissue, heart tissue, hypothalamus tissue, kidney tissue, large intestine tissue, intestinal tissue, larynx tissue, liver tissue, lung tissue, lymph nodes, mouth tissue, nose tissue, pancreatic tissue, parathyroid gland tissue, pituitary gland tissue, prostate tissue, rectal tissue, salivary gland tissue, skeletal muscle tissue, skin tissue, small intestine tissue, spinal cord, spleen tissue, stomach tissue, thymus gland tissue, trachea tissue, thyroid tissue, ureter tissue, urethra tissue, soft and connective tissue, peritoneal tissue, blood vessel tissue and/or fat tissue. The tissue can comprise: (i) grade I, grade II, grade III or grade IV cancerous tissue; (ii) metastatic cancerous tissue; (iii) mixed grade cancerous tissue; (iv) a sub-grade cancerous tissue; (v) healthy or normal tissue; and/or (vi) cancerous or abnormal tissue. In some embodiments, at least about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, or a number or a range between any two of these values, of the thermally actuated immune cells at the target site express the payload protein after applying thermal energy to the target site. In some embodiments, less than about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or a number or a range between any two of these values, of the thermally actuated immune cells at a site other than the target site express the payload protein.

The ratio of the concentration of payload-expressing thermally actuated immune cells at the subject's target site to the concentration of payload-expressing thermally actuated immune cells in subject's blood, serum, or plasma can be vary. In some embodiments, the ratio of the concentration of payload-expressing thermally actuated immune cells at the subject's target site to the concentration of payload-expressing thermally actuated immune cells in subject's blood, serum, or plasma can be, or be about, 1:1, 1.1:1, 1.2:1, 1.3:1, 1.4:1, 1.5:1, 1.6:1, 1.7:1, 1.8:1, 1.9:1, 2:1, 2.5:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1, 40:1, 41:1, 42:1, 43:1, 44:1, 45:1, 46:1, 47:1, 48:1, 49:1, 50:1, 51:1, 52:1, 53:1, 54:1, 55:1, 56:1, 57:1, 58:1, 59:1, 60:1, 61:1, 62:1, 63:1, 64:1, 65:1, 66:1, 67:1, 68:1, 69:1, 70:1, 71:1, 72:1, 73:1, 74:1, 75:1, 76:1, 77:1, 78:1, 79:1, 80:1, 81:1, 82:1, 83:1, 84:1, 85:1, 86:1, 87:1, 88:1, 89:1, 90:1, 91:1, 92:1, 93:1, 94:1, 95:1, 96:1, 97:1, 98:1, 99:1, 100:1, 200:1, 300:1, 400:1, 500:1, 600:1, 700:1, 800:1, 900:1, 1000:1, 2000:1, 3000:1, 4000:1, 5000:1, 6000:1, 7000:1, 8000:1, 9000:1, 10000:1, or a number or a range between any two of the values. In some embodiments, the ratio of the concentration of payload-expressing thermally actuated immune cells at the subject's target site to the concentration of payload-expressing thermally actuated immune cells in subject's blood, serum, or plasma can be at least, or be at most, 1:1, 1.1:1, 1.2:1, 1.3:1, 1.4:1, 1.5:1, 1.6:1, 1.7:1, 1.8:1, 1.9:1, 2:1, 2.5:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1, 40:1, 41:1, 42:1, 43:1, 44:1, 45:1, 46:1, 47:1, 48:1, 49:1, 50:1, 51:1, 52:1, 53:1, 54:1, 55:1, 56:1, 57:1, 58:1, 59:1, 60:1, 61:1, 62:1, 63:1, 64:1, 65:1, 66:1, 67:1, 68:1, 69:1, 70:1, 71:1, 72:1, 73:1, 74:1, 75:1, 76:1, 77:1, 78:1, 79:1, 80:1, 81:1, 82:1, 83:1, 84:1, 85:1, 86:1, 87:1, 88:1, 89:1, 90:1, 91:1, 92:1, 93:1, 94:1, 95:1, 96:1, 97:1, 98:1, 99:1, 100:1, 200:1, 300:1, 400:1, 500:1, 600:1, 700:1, 800:1, 900:1, 1000:1, 2000:1, 3000:1, 4000:1, 5000:1, 6000:1, 7000:1, 8000:1, 9000:1, or 10000:1.

The ratio of the concentration of payload protein at the subject's target site to the concentration of payload protein in subject's blood, serum, or plasma can be vary. In some embodiments, the ratio of the concentration of payload protein at the subject's target site to the concentration of payload protein in subject's blood, serum, or plasma can be, or be about, 1:1, 1.1:1, 1.2:1, 1.3:1, 1.4:1, 1.5:1, 1.6:1, 1.7:1, 1.8:1, 1.9:1, 2:1, 2.5:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1, 40:1, 41:1, 42:1, 43:1, 44:1, 45:1, 46:1, 47:1, 48:1, 49:1, 50:1, 51:1, 52:1, 53:1, 54:1, 55:1, 56:1, 57:1, 58:1, 59:1, 60:1, 61:1, 62:1, 63:1, 64:1, 65:1, 66:1, 67:1, 68:1, 69:1, 70:1, 71:1, 72:1, 73:1, 74:1, 75:1, 76:1, 77:1, 78:1, 79:1, 80:1, 81:1, 82:1, 83:1, 84:1, 85:1, 86:1, 87:1, 88:1, 89:1, 90:1, 91:1, 92:1, 93:1, 94:1, 95:1, 96:1, 97:1, 98:1, 99:1, 100:1, 200:1, 300:1, 400:1, 500:1, 600:1, 700:1, 800:1, 900:1, 1000:1, 2000:1, 3000:1, 4000:1, 5000:1, 6000:1, 7000:1, 8000:1, 9000:1, 10000:1, or a number or a range between any two of the values. In some embodiments, the ratio of the concentration of payload protein at the subject's target site to the concentration of payload protein in subject's blood, serum, or plasma can be at least, or be at most, 1:1, 1.1:1, 1.2:1, 1.3:1, 1.4:1, 1.5:1, 1.6:1, 1.7:1, 1.8:1, 1.9:1, 2:1, 2.5:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1, 40:1, 41:1, 42:1, 43:1, 44:1, 45:1, 46:1, 47:1, 48:1, 49:1, 50:1, 51:1, 52:1, 53:1, 54:1, 55:1, 56:1, 57:1, 58:1, 59:1, 60:1, 61:1, 62:1, 63:1, 64:1, 65:1, 66:1, 67:1, 68:1, 69:1, 70:1, 71:1, 72:1, 73:1, 74:1, 75:1, 76:1, 77:1, 78:1, 79:1, 80:1, 81:1, 82:1, 83:1, 84:1, 85:1, 86:1, 87:1, 88:1, 89:1, 90:1, 91:1, 92:1, 93:1, 94:1, 95:1, 96:1, 97:1, 98:1, 99:1, 100:1, 200:1, 300:1, 400:1, 500:1, 600:1, 700:1, 800:1, 900:1, 1000:1, 2000:1, 3000:1, 4000:1, 5000:1, 6000:1, 7000:1, 8000:1, 9000:1, or 10000:1.

The target site can comprise target cells. The target cells can be tumor cells (e.g., solid tumor cells). In some embodiments, the application of thermal energy to a target site of the subject results in the death of at least about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, or a number or a range between any two of these values, of the target cells. Non-target cells can comprise cells of the subject other than target cells. The ratio of target cell death to non-target cell death after application of thermal energy can be at least about 2:1 In some embodiments, the ratio of target cell death to non-target cell death after application of thermal energy can be, or be about, 1:1, 1.1:1, 1.2:1, 1.3:1, 1.4:1, 1.5:1, 1.6:1, 1.7:1, 1.8:1, 1.9:1, 2:1, 2.5:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1, 40:1, 41:1, 42:1, 43:1, 44:1, 45:1, 46:1, 47:1, 48:1, 49:1, 50:1, 51:1, 52:1, 53:1, 54:1, 55:1, 56:1, 57:1, 58:1, 59:1, 60:1, 61:1, 62:1, 63:1, 64:1, 65:1, 66:1, 67:1, 68:1, 69:1, 70:1, 71:1, 72:1, 73:1, 74:1, 75:1, 76:1, 77:1, 78:1, 79:1, 80:1, 81:1, 82:1, 83:1, 84:1, 85:1, 86:1, 87:1, 88:1, 89:1, 90:1, 91:1, 92:1, 93:1, 94:1, 95:1, 96:1, 97:1, 98:1, 99:1, 100:1, 200:1, 300:1, 400:1, 500:1, 600:1, 700:1, 800:1, 900:1, 1000:1, 2000:1, 3000:1, 4000:1, 5000:1, 6000:1, 7000:1, 8000:1, 9000:1, 10000:1, or a number or a range between any two of the values. In some embodiments, the ratio of target cell death to non-target cell death after application of thermal energy can be at least, or be at most, 1:1, 1.1:1, 1.2:1, 1.3:1, 1.4:1, 1.5:1, 1.6:1, 1.7:1, 1.8:1, 1.9:1, 2:1, 2.5:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1, 40:1, 41:1, 42:1, 43:1, 44:1, 45:1, 46:1, 47:1, 48:1, 49:1, 50:1, 51:1, 52:1, 53:1, 54:1, 55:1, 56:1, 57:1, 58:1, 59:1, 60:1, 61:1, 62:1, 63:1, 64:1, 65:1, 66:1, 67:1, 68:1, 69:1, 70:1, 71:1, 72:1, 73:1, 74:1, 75:1, 76:1, 77:1, 78:1, 79:1, 80:1, 81:1, 82:1, 83:1, 84:1, 85:1, 86:1, 87:1, 88:1, 89:1, 90:1, 91:1, 92:1, 93:1, 94:1, 95:1, 96:1, 97:1, 98:1, 99:1, 100:1, 200:1, 300:1, 400:1, 500:1, 600:1, 700:1, 800:1, 900:1, 1000:1, 2000:1, 3000:1, 4000:1, 5000:1, 6000:1, 7000:1, 8000:1, 9000:1, or 10000:1. The ratio of target cell death to non-target cell death can be at least about 1.1-fold (e.g., 1.1-fold, 1.3-fold, 1.5-fold, 1.7-fold, 1.9-fold, 2-fold, 3-fold, 4-fold, 5-fold, 6-fold, 7-fold, 8-fold, 9-fold, 10-fold, or a number or a range between any of these values) greater as compared to a method comprising immune cells constitutively expressing the payload protein.

Additional Agents

In some embodiments, the method comprises administering one or more additional agents to the subject. In some embodiments, the one or more additional agents increases the efficacy of the thermally actuated immune cells. The one or more additional agents can comprise a protein phosphatase inhibitor, a kinase inhibitor, a cytokine, an inhibitor of an immune inhibitory molecule, and/or or an agent that decreases the level or activity of a TREG cell. The one or more additional agents can comprise an immune modulator, an anti-metastatic, a chemotherapeutic, a hormone or a growth factor antagonist, an alkylating agent, a TLR agonist, a cytokine antagonist, a cytokine antagonist, or any combination thereof. The one or more additional agents can comprise an agonistic or antagonistic antibody specific to a checkpoint inhibitor or checkpoint stimulator molecule such as PD1, PD-L1, PD-L2, CD27, CD28, CD40, CD137, OX40, GITR, ICO S, A2AR, B7-H3, B7-H4, BTLA, CTLA4, IDO, KIR, LAG3, PD-1, TIM-3.

The one or more additional agents can be alkylating agents (nitrogen mustards, ethylenimine derivatives, alkyl sulfonates, nitrosoureas and triazenes); uracil mustard (Aminouracil Mustard®, Chlorethaminacil®, Demethyldopan®, Desmethyldopan®, Haemanthamine®, Nordopan®, Uracil nitrogen Mustard®, Uracillost®, Uracilmostaza®, Uramustin®, Uramustine®); bendamustine (Treakisym®, Ribomustin®, Treanda®); chlormethine (Mustargen®); cyclophosphamide (Cytoxan®, Neosar®, Clafen®, Endoxan®, Procytox®, Revimmune™); ifosfamide (Mitoxana®); melphalan (Alkeran®); Chlorambucil (Leukeran®); pipobroman (Amedel®, Vercyte®); triethylenemelamine (Hemel®, Hexylen®, Hexastat®); triethylenethiophosphoramine; Temozolomide (Temodar®); thiotepa (Thioplex®); busulfan (Busilvex®, Myleran®); carmustine (BiCNU®); lomustine (CeeNU®); streptozocin (Zanosar®); estramustine (Emcyt®, Estracit®); fotemustine; irofulven; mannosulfan;

mitobronitol; nimustine; procarbazine; ranimustine; semustine; triaziquone; treosulfan; and Dacarbazine (DTIC-Dome®); anti-EGFR antibodies (e.g., cetuximab (Erbitux®), panitumumab (Vectibix®), and gefitinib (Iressa®)); anti-Her-2 antibodies (e.g., trastuzumab (Herceptin®) and other antibodies from Genentech); antimetabolites (including, without limitation, folic acid antagonists (also referred to herein as antifolates), pyrimidine analogs, purine analogs and adenosine deaminase inhibitors): methotrexate (Rheumatrex®, Trexall®), 5-fluorouracil (Adrucil®, Efudex®, Fluoroplex®), floxuridine (FUDF®), carmofur, cytarabine (Cytosar-U®, Tarabine PFS), 6-mercaptopurine (Puri-Nethol®)), 6-thioguanine (Thioguanine Tabloid®), fludarabine phosphate (Fludara®), pentostatin (Nipent®), pemetrexed (Alimta®), raltitrexed (Tomudex®), cladribine (Leustatin®), clofarabine (Clofarex®, Clolar®), mercaptopurine (Puri-Nethol®), capecitabine (Xeloda®), nelarabine (Arranon®), azacitidine (Vidaza®), decitabine (Dacogen®), enocitabine (Sunrabin®), sapacitabine, tegafur-uracil, tiazofurine, tioguanine, trofosfamide, and gemcitabine (Gemzar®); vinca alkaloids: vinblastine (Velban®, Velsar®), vincristine (Vincasar®, Oncovin®), vindesine (Eldisine®), vinorelbine (Navelbine®), vinflunine (Javlor®); platinum-based agents: carboplatin (Paraplat®, Paraplatin®), cisplatin (Platinol®), oxaliplatin (Eloxatin®), nedaplatin, satraplatin, and triplatin; anthracyclines: daunorubicin (Cerubidine®, Rubidomycin®), doxorubicin (Adriamycin®), epirubicin (Ellence®), idarubicin (Idamycin®), mitoxantrone (Novantrone®), valrubicin (Valstar®), aclarubicin, amrubicin, liposomal doxorubicin, liposomal daunorubicin, pirarubicin, pixantrone, and zorubicin; topoisomerase inhibitors: topotecan (Hycamtin®), irinotecan (Camptosar®), etoposide (Toposar®, VePesid®), teniposide (Vumon®), lamellarin D, SN-38, camptothecin (e.g., IT-101), belotecan, and rubitecan; taxanes: paclitaxel (Taxol®), docetaxel (Taxotere®), larotaxel, cabazitaxel, ortataxel, and tesetaxel; antibiotics: actinomycin (Cosmegen®), bleomycin (Blenoxane®), hydroxyurea (Droxia®, Hydrea®), mitomycin (Mitozytrex®, Mutamycin®); immunomodulators: lenalidomide (Revlimid®), thalidomide (Thalomid®); immune cell antibodies: alemtuzamab (Campath®), gemtuzumab (Myelotarg®), rituximab (Rituxan®), tositumomab (Bexxar®); interferons (e.g., IFN-alpha (Alferon®, Roferon-A®, Intron®-A) or IFN-gamma (Actimmune®)); interleukins: IL-1, IL-2 (Proleukin®), IL-24, IL-6 (Sigosix®), IL-12; HSP90 inhibitors (e.g., geldanamycin or any of its derivatives). In some embodiments, the HSP90 inhibitor is selected from geldanamycin, 17-alkylamino-17-desmethoxygeldanamycin ("17-AAG") or 17-(2-dimethylaminoethyl)amino-17-desmethoxygeldanamycin ("17-DMAG"); anti-androgens which include, without limitation nilutamide (Nilandron®) and bicalutamide (Caxodex®); antiestrogens which include, without limitation tamoxifen (Nolvadex®), toremifene (Fareston®), letrozole (Femara®), testolactone (Teslac®), anastrozole (Arimidex®), bicalutamide (Casodex®), exemestane (Aromasin®), flutamide (Eulexin®), fulvestrant (Faslodex®), raloxifene (Evista®, Keoxifene®) and raloxifene hydrochloride; anti-hypercalcaemia agents which include without limitation gallium (III) nitrate hydrate (Ganite®) and pamidronate disodium (Aredia®); apoptosis inducers which include without limitation ethanol, 2-[[3-(2,3-dichlorophenoxy)propyl]amino]-(9Cl), gambogic acid, elesclomol, embelin and arsenic trioxide (Trisenox®); Aurora kinase inhibitors which include without limitation binucleine 2; Bruton's tyrosine kinase inhibitors which include without limitation terreic acid; calcineurin inhibitors which include without limitation cypermethrin, deltamethrin, fenvalerate and tyrphostin 8; CaM kinase II inhibitors which include without limitation 5-Isoquinolinesulfonic acid, 4-[{2S)-2-[(5-isoquinolinyl sulfonyl)methylamino]-3-oxo-3-{4-phenyl-1-piperazinyl) propyl]phenyl ester and benzenesulfonamide; CD45 tyrosine phosphatase inhibitors which include without limitation phosphonic acid; CDC125 phosphatase inhibitors which include without limitation 1,4-naphthalene dione, 2,3-bis [(2-hydroxyethyl)thio]-(9Cl); CHK kinase inhibitors which include without limitation debromohymenialdisine; cyclooxygenase inhibitors which include without limitation 1H-indole-3-acetamide, 1-(4-chlorobenzoyl)-5-methoxy-2-methyl-N-(2-phenylethyl)-(9Cl), 5-alkyl substituted 2-arylaminophenylacetic acid and its derivatives (e.g., celecoxib (Celebrex®), rofecoxib (Vioxx®), etoricoxib (Arcoxia®), lumiracoxib (Prexige®), valdecoxib (Bextra®) or 5-alkyl-2-arylaminophenylacetic acid); cRAF kinase inhibitors which include without limitation 3-(3,5-dibromo-4-hydroxybenzylidene)-5-iodo-1,3-dihydroindol-2-one and benzamide, 3-(dimethylamino)-N-[3-[(4-hydroxybenzoyl) amino]-4-methylphenyl]-(9Cl); cyclin dependent kinase inhibitors which include without limitation olomoucine and its derivatives, purvalanol B, roascovitine (Seliciclib®), indirubin, kenpaullone, purvalanol A and indirubin-3'-monooxime; cysteine protease inhibitors which include without limitation 4-morpholinecarboxamide, N-[(1S)-3-fluoro-2-oxo-1-(2-phenylethyl)propyl]amino]-2-oxo-1-(phenylmethyl)ethyl]-(9Cl); DNA intercalators which include without limitation plicamycin (Mithracin®) and daptomycin (Cubicin®); DNA strand breakers which include without limitation bleomycin (Blenoxane®); E3 ligase inhibitors which include without limitation N-((3,3,3-trifluoro-2-trifluoromethyl)propionyl)sulfanilamide; EGF Pathway Inhibitors which include, without limitation tyrphostin 46, EKB-569, erlotinib (Tarceva®), gefitinib (Iressa®), lapatinib (Tykerb®) and those compounds that are generically and specifically disclosed in WO 97/02266, EP 0 564 409, WO 99/03854, EP 0 520 722, EP 0 566 226, EP 0 787 722, EP 0 837 063, U.S. Pat. No. 5,747,498, WO 98/10767, WO 97/30034, WO 97/49688, WO 97/38983 and WO 96/33980; farnesyltransferase inhibitors which include without limitation ahydroxyfarnesylphosphonic acid, butanoic acid, 2-[(2S)-2-[[(2S,3S)-2-[[(2R)-2-amino-3-mercaptopropyl] amino]-3-methylpent-yl]oxy]-1-oxo-3-phenylpropyl] amino]-4-(methylsulfonyl)-1-methylethylester (2S)-(9Cl), tipifarnib (Zarnestra®), and manumycin A; Flk-1 kinase inhibitors which include without limitation 2-propenamide, 2-cyano-3-[4-hydroxy-3,5-bis(1-methylethyl)phenyl]-N-(3-phenylpropyl)-(2E-)-(9Cl); glycogen synthase kinase-3 (GSK3) inhibitors which include without limitation indirubin-3'-monooxime; histone deacetylase (HDAC) inhibitors which include without limitation suberoylanilide hydroxamic acid (SAHA), [4-(2-amino-phenylcarbamoyl)-benzyl]carbamic acid pyridine-3-ylmethylester and its derivatives, butyric acid, pyroxamide, trichostatin A, oxamflatin, apicidin, depsipeptide, depudecin, trapoxin, vorinostat (Zolinza®), and compounds disclosed in WO 02/22577; I-kappa B-alpha kinase inhibitors (IKK) which include without limitation 2-propenenitrile, 3-[(4-methylphenyl) sulfonyl]-(2E)-(9Cl); imidazotetrazinones which include without limitation temozolomide (Methazolastone®, Temodar® and its derivatives (e.g., as disclosed generically and specifically in U.S. Pat. No. 5,260,291) and Mitozolomide; insulin tyrosine kinase inhibitors which include without limitation hydroxyl-2-naphthalenylmethylphosphonic acid; c-Jun-N-terminal kinase (JNK) inhibitors which include without limitation pyrazoleanthrone and epigallocatechin gallate; mitogen-activated protein kinase (MAP) inhibitors which include without limitation benzenesulfonamide, N-[2-[[[3-(4-chlorophenyl)-2-propenyl]methyl]amino] methyl]phenyl]-N-(2-hy-droxyethyl)-4-methoxy-(9Cl); MDM2 inhibitors which include without limitation trans-4-iodo, 4'-boranyl-chalcone; MEK inhibitors which include without limitation butanedinitrile, bis[amino[2-aminophenyl)thio]methylene]-(9Cl); MMP inhibitors which include without limitation Actinonin, epigallocatechin gallate, collagen peptidomimetic and non-peptidomimetic inhibitors, tetracycline derivatives marimastat (Marimastat®), prinomastat, incyclinide (Metastat®), shark cartilage extract AE-941 (Neovastat®), Tanomastat, TAA211, MMI270B or AAJ996; mTor inhibitors which include without limitation rapamycin (Rapamune®), and analogs and derivatives thereof, AP23573 (also known as ridaforolimus, deforolimus, or MK-8669), CCI-779 (also known as temsirolimus) (Torisel®) and SDZ-RAD; NGFR tyrosine kinase inhibitors which include without limitation tyrphostin AG 879; p38 MAP kinase inhibitors which include without limitation Phenol, 4-[4-(4-fluorophenyl)-5-(4-pyridinyl)-1H-imidazol-2-yl]-(9Cl), and benzamide, 3-(dimethylamino)-N-[3-[(4-hydroxylbenzoyl)amino]-4-methylphenyl]-(9Cl); p56 tyrosine kinase inhibitors which include without limitation damnacanthal and tyrphostin 46; PDGF pathway inhibitors which include without limitation tyrphostin AG 1296, tyrphostin 9, 1,3-butadiene-1,1,3-tricarbonitrile, 2-amino-4-(1H-indol-5-yl)-(9Cl), imatinib (Gleevec®) and gefitinib (Iressa®) and those compounds generically and specifically disclosed in European Patent No.: 0 564 409 and PCT Publication No.: WO 99/03854; phosphatidylinositol 3-kinase inhibitors which include without limitation wortmannin, and quercetin dihydrate; phosphatase inhibitors which include without limitation cantharidic acid, cantharidin, and L-leucinamide; protein phosphatase inhibitors which include without limitation cantharidic acid, cantharidin, L-P-bromotetramisole oxalate, 2(5H)-furanone, 4-hydroxy-5-(hydroxymethyl)-3-(1-oxohexadecyl)-(5R)-(9Cl) and benzylphosphonic acid; PKC inhibitors which include without limitation 1-H-pyrollo-2,5-dione, 3-[1-3-(dimethylamino)propyl]-1H-indol-3-yl]-4-(1H-indol-3-yl)-(90), Bi sindolylmaleimide IX, Sphinogosine, staurosporine, and Hypericin; PKC delta kinase inhibitors which include without limitation rottlerin; polyamine synthesis inhibitors which include without limitation DMFO; PTP1B inhibitors which include without limitation L-leucinamide; protein tyrosine kinase inhibitors which include, without limitation tyrphostin Ag 216, tyrphostin Ag 1288, tyrphostin Ag 1295, geldanamycin, genistein and 7H-pyrrolo[2,3-d]pyrimidine derivatives as generically and specifically described in PCT Publication No.: WO 03/013541 and U.S. Publication No.: 2008/0139587; SRC family tyrosine kinase inhibitors which include without limitation PP1 and PP2; Syk tyrosine kinase inhibitors which include without limitation piceatannol; Janus (JAK-2 and/or JAK-3) tyrosine kinase inhibitors which include without limitation tyrphostin AG 490 and 2-naphthyl vinyl ketone; retinoids which include without limitation isotretinoin (Accutane®, Amnesteem®, Cistane®, Claravis®, Sotret®) and tretinoin (Aberel®, Aknoten®, Avita®, Renova®, Retin-A®, Retin-A MICRO®, Vesanoid®); RNA polymerase H elongation inhibitors which include without limitation 5, 6-dichloro-1-beta-D-ribofuranosylbenzimidazole; serine/Threonine kinase inhibitors which include without limitation 2-aminopurine; sterol biosynthesis inhibitors which include without limitation squalene epoxidase and CYP2D6; VEGF pathway inhibitors, which include without limitation anti-VEGF antibodies, e.g., bevacizumab, and small molecules, e.g., sunitinib (Sutent®), sorafinib (Nexavar®), ZD6474 (also known as vandetanib) (Zactima™), SU6668, CP-547632 and AZD2171 (also known as cediranib) (Recentin™).

EXAMPLES

Some aspects of the embodiments discussed above are disclosed in further detail in the following examples, which are not in any way intended to limit the scope of the present disclosure.

Example 1

Thermal Control of Engineered T-Cells

Materials and Methods

Plasmid Construction and Molecular Biology

All plasmids were designed using SnapGene (GSL Biotech) and assembled via reagents from New England Biolabs for KLD mutagenesis (E05545) or Gibson Assembly (E2621L). After assembly, constructs were transformed into NEB Turbo (C2984I) and NEB Stable (C30401) *E. coli* for growth and plasmid preparation. The CAR-CD19 gene containing the CD28 and CD3z signaling domain was a kind gift from the Laboratory of David Baltimore (Caltech). Integrated DNA Technologies synthesized other genes, the pHSP, and all PCR primers. Kozak used in FIG. 4C: CGG-ATG for 75% and ACCATGGGTTGAGCC-ATG (SEQ ID NO: 15) for 10%. The original kozak was ACC-ATG.

Cell Lines

Raji cells (CCL-86) were obtained from ATCC and cultured in RPMI 1640 media (Thermo Fisher Scientific) with 1x Penicillin/Streptomycin (Corning). 1000 ng/ml of doxycycline was used for induction of the Tet promoter. $GFP^+$ Raji cells were constructed via viral infection of a GFP driven by the EF1a promoter. Lentivirus was prepared using a third-generation viral vector and helper plasmids (gifts of D. Baltimore). Virus was packaged in HEK293T cells grown in 10 cm dishes. After 3 days of transfection, viral particles were concentrated via Ultracentrifugation. Infection was performed by following the "RetroNectin" (T100B Takara Bio) reagent protocol. Experiments were performed at least two weeks after infection.

Primary T-Cells

T-cells were isolated with the EasySep Human T-cell isolation Kit (STEMCELL Technologies 17951) from frozen human peripheral blood mononuclear cells obtained from healthy donors. T-cells were stimulated with CD3/CD28 Dynabeads (Thermo Fisher Scientific 11132D) at 1:1 cell:bead ratio for 1 day before viral transduction. Dynabeads were removed on day seven and the cells were allowed to rest until day fourteen before proceeding with experiments. This delay was designed to avoid any activation interference with HSP activity. T-cells were cultured in RPMI supplemented with 50 U/ml IL-2 (Miltenyi Biotech 130-097-744) and 1 ng/ml IL-15 (Miltenyi Biotech 130-095-762) every other day. T-cells were enriched by LNGFR magnetic bead based sorting (Miltenyi Biotech 130-091-330) when appropriate.

Thermal Regulation Assay

Thermal stimulation of T-cells was performed in a Bio-Rad C1000 thermocycler. T-cells at 1-2 million/ml were supplemented with doxycycline, if needed, and mixed well before transferring 50 μl into a sterile PCR tube. The temperature and duration of stimulation was varied based on the experimental procedure. Upon completion of thermal stimulation, cells were moved back into a mammalian incubator and supplemented 1:1 with fresh media containing cytokines and in some cases doxycycline. Cells were typically incubated for 24 hours unless stated otherwise before assaying with a flow cytometer (MACSQuant VYB). Dead cells were typically excluded via FSC/SSC gating for routine assays. In FIG. 3, a LIVE/DEAD viability/cytotoxicity kit (Thermo Fisher L3224) was used for a more accurate quantification of cell state. Live cells were further gated via a transfection marker to isolate virally infected cells for further analysis. The change in mean fluorescence of the cell population was used to characterize the fold change of pHSP constructs. To account for cellular auto-fluorescence, the mean fluorescence signal from non-transduced T-cells was collected in each experiment and subtracted from the mean fluorescence of experimental T-cells. Anti-HA antibodies (Miltenyi Biotech 130-120-722) were used to stain for CAR expression and V450 Mouse Anti-human CD271 was used to stain LNGFR (BD biosciences 562123). IL-21 expression was measured using a human IL-21 DuoSet ELISA (R&D systems DY8879-05).

T-Cell Bait Assay

Raji and $GFP^+$ Raji cells were used as bait cells for CAR-CD19 T-cells. Bait assays were initiated by mixing T-cells with bait cells at a 3:1 ratio. This ratio was established to avoid excessive bait cell growth before T-cell engagement. To assess T-cell killing of bait cells $GFP^+$ Raji were used and the count of $GFP^+$ cells was tracked over time.

Results

Evaluating Candidate pHSPs in Primary T-Cells

Figure 1:
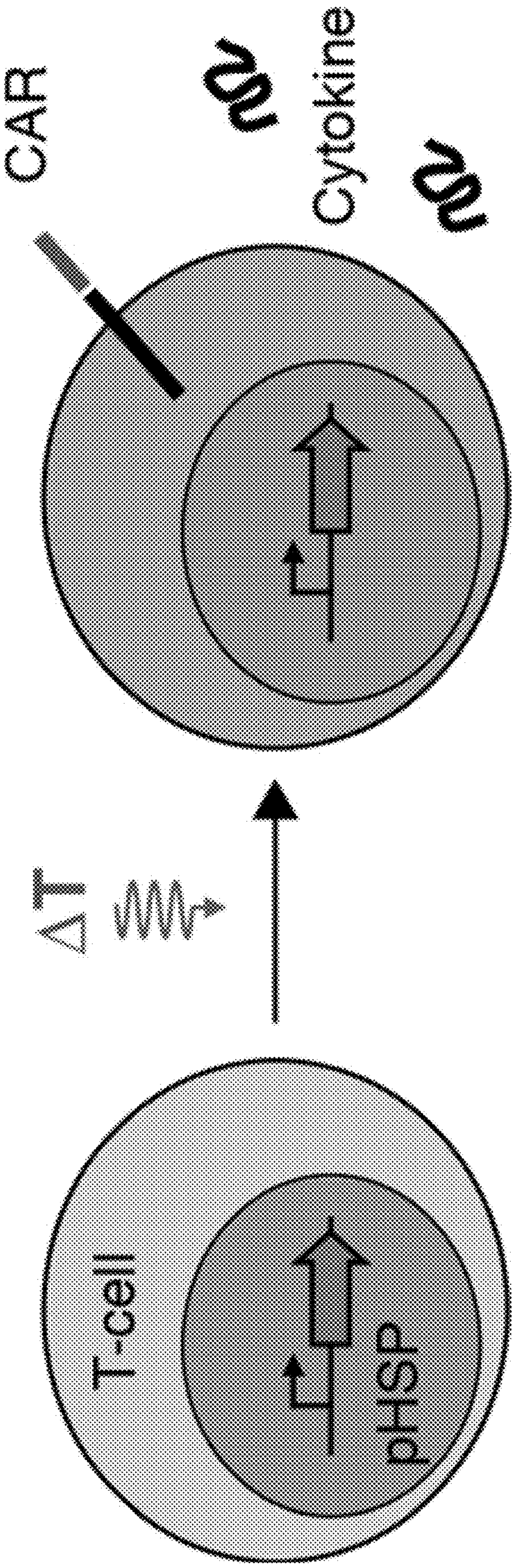
FIG. 1 depicts a non-limiting exemplary embodiment of the genetic circuits and engineered T-cells provided herein.
Figure 2A:
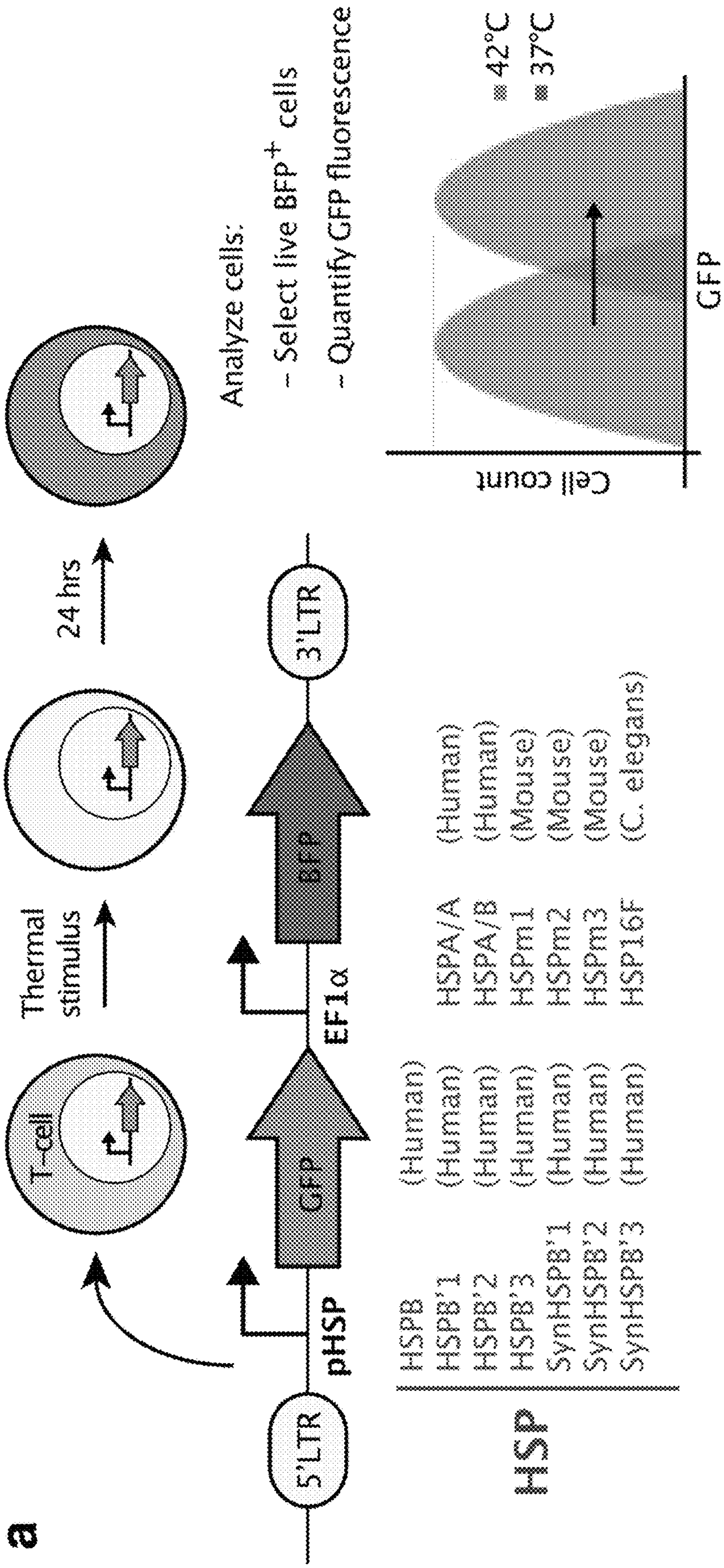
FIGS. 2A-2B depict non-limiting exemplary data and embodiments related to candidate pHSPs in primary T-cells.

To enable thermal control of T-cell activity, there is a need for a pHSP with robust switching behavior in primary human T-cells. Given the variability in pHSP responses between cell types, the activity of 13 different pHSPs in response to a 1-hour incubation at 42° C. was systematically evaluated. This thermal stimulus was chosen based on its tolerability by most tissues, and the convenience of relatively short treatment durations in potential clinical scenarios. The panel of pHSPs included nine human, three mouse, and one *C. elegans* promoters (Table 1). The human promoters included four naturally occurring sequences (HSPB, HSPB'2, HSP A/A, HSP A/B), two modifications of HSPB'2 generated by varying the 5' UTR (HSPB'1, HSPB'3), and three rational modifications of HSPB'2 (SynHSPB'1, SynHSPB'2, SynHSPB'3) inspired by a previously developed sensor of cellular stress. Truncating HSPB'2 and leaving 192 base pairs resulted in SynHSPB'1NO. To lower potential baseline activity, the AP-1 binding site in SynHSPB'1 was mutated leading to SynHSPB'2. Duplicating SynHSPB'2 four times to increase the number of heat shock elements (HSE) resulted in SynHSPB'3. The three mouse-derived pHSPs were naturally occurring promoters. HSP16, derived from *C. elegans*, was rationally modified to form a minimal bidirectional promoter encompassing four HSE binding sites. HSP16 excludes other transcription factor binding sites that typically exist in human promoters. Each pHSP was incorporated into a standardized lentiviral construct in which the pHSP drives the expression of a green fluorescent protein (GFP), with a constitutively expressed blue fluorescent protein (BFP) serving as a marker of transduction (FIG. 2A).

Figure 2B:
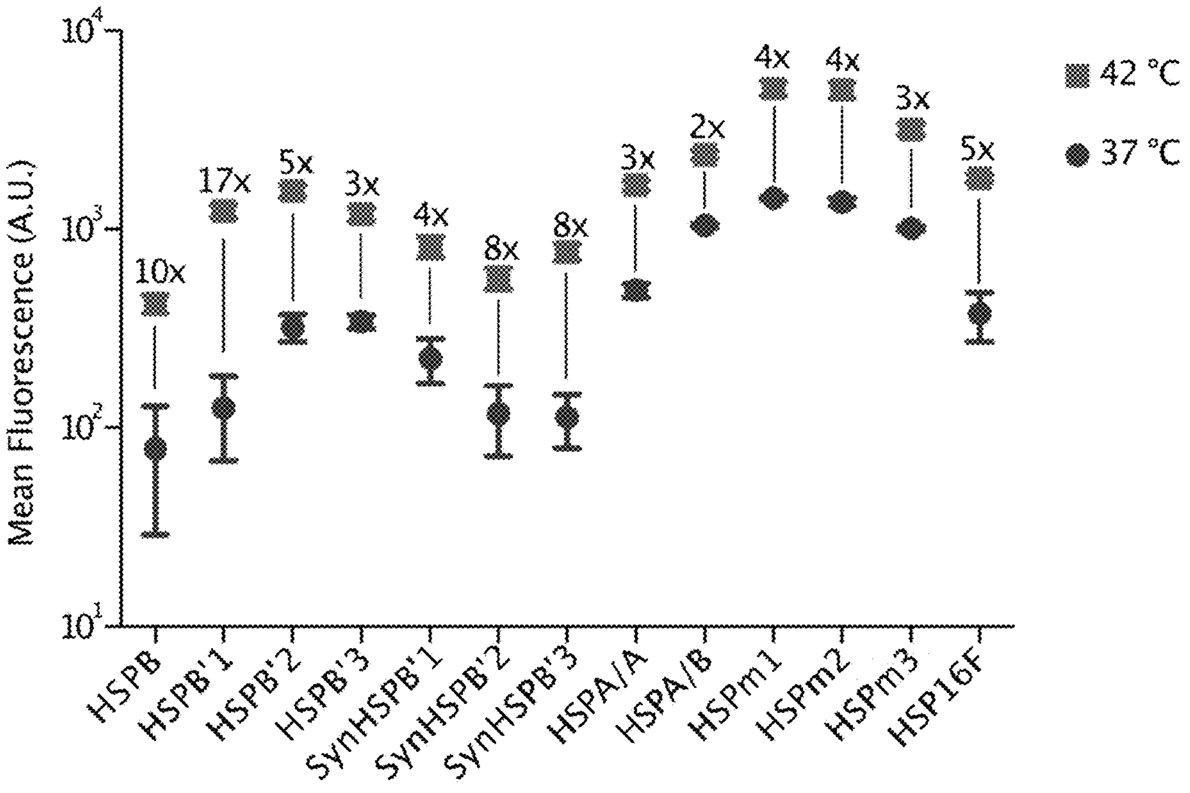
Figure 8:
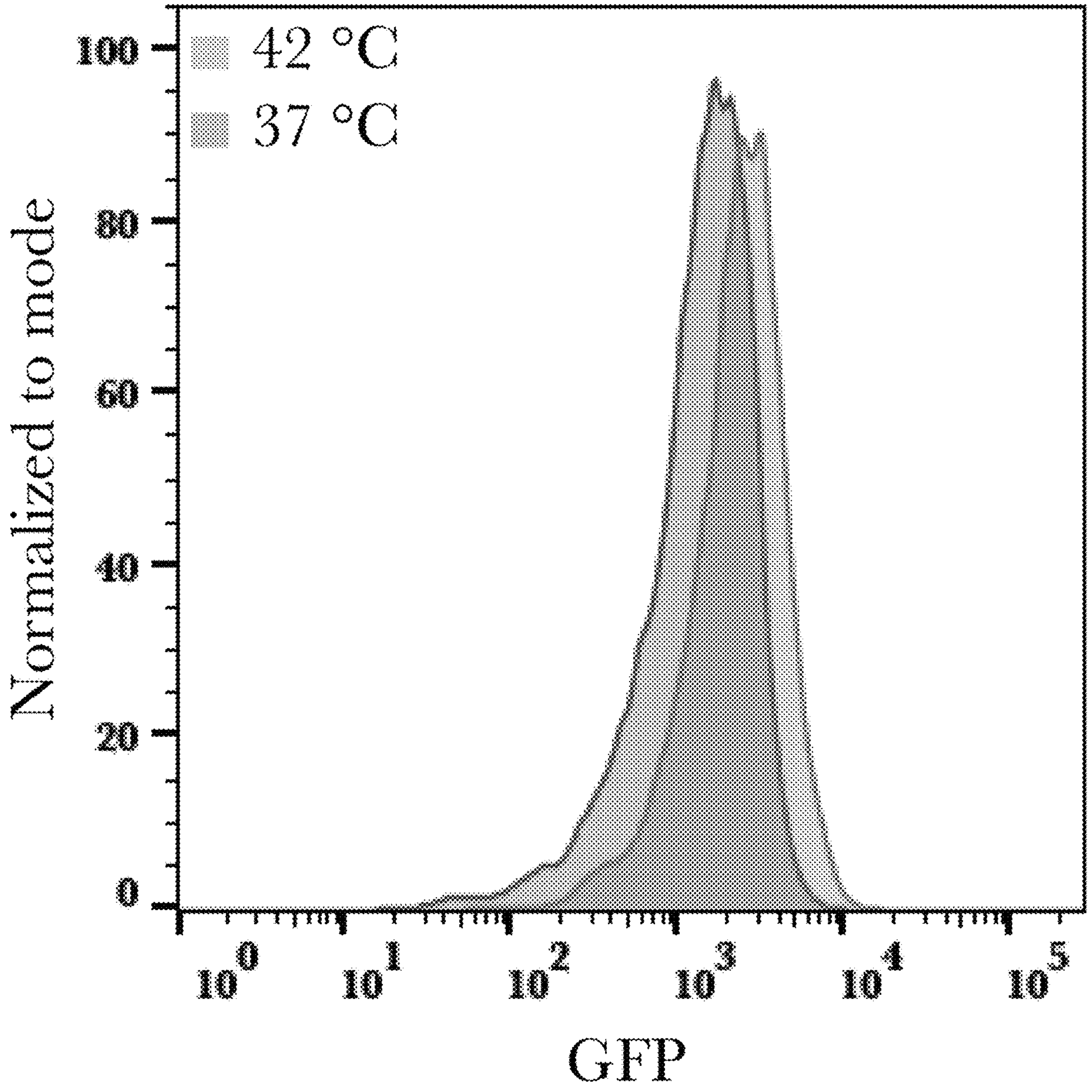
FIG. 8 depicts non-limiting exemplary data related to thermally induced shift in gene expression. T-cells were transfected with the HSPB'1 promoter viral vector from FIG. 2. The histogram represents the green fluorescence intensity of infected cells 24 hours after a 1-hour incubation at 37° C. or 42° C., as measured via flow cytometry. Thermal induction led to a uniform increase in gene expression across the cell population.

Once stimulated, all of the promoters displayed a uniform level of activation across the cell population allowing use of mean fluorescence as a metric of fold induction (FIG. 8). Of the 13 promoters, HSPB had the lowest baseline expression at 37° C. (FIG. 2B), an important property for minimizing activity in the absence of the thermal trigger. HSPB'1 showed the largest fold-change in gene expression, reflecting a combination of relatively low baseline expression and strong promoter activity when stimulated. Among the rationally engineered HSPB'2 variants, SYNHSPB'3 had a lower baseline than the natural promoter, albeit with lower maximum expression on activation. The rest of the human and mouse-derived promoters exhibited high baseline activity, resulting in their elimination from further experiments. Finally, the *C. elegans* minimal promoter exhibited acceptable performance and was included in further testing to investigate whether its minimal composition would be advantageous for specific activation in response to temperature. Based on these factors, HSPB, HSPB'1, SynHSPB'3 and HSP16 were chosen as the starting points for further circuit engineering.

Thermal Parameters for pHSP Activation

Figure 3A:
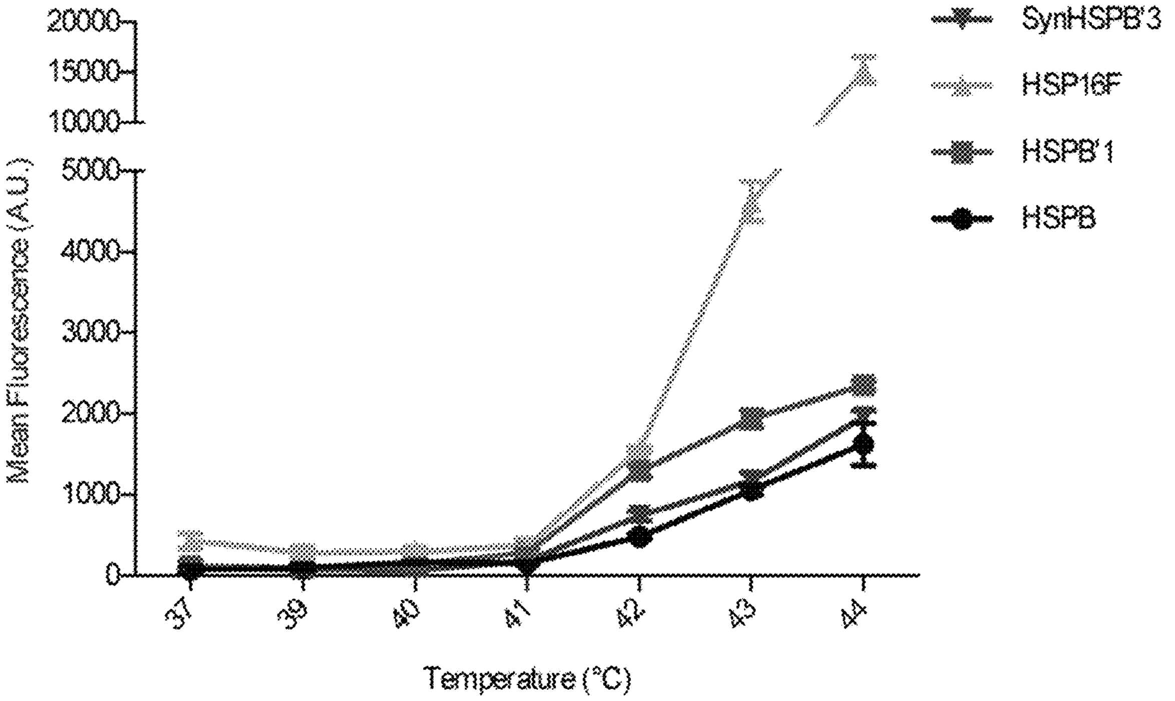
FIGS. 3A-3F depict non-limiting exemplary data and embodiments related to thermal parameters for pHSP activation in primary human T-cells. GFP expression from constructs driven by the HSPB, HSPB'1, SynHSPB'3 and HSP16F promoters (FIG. 3A, FIG. 3C, FIG. 3E) and T-cell viability (FIG. 3B, FIG. 3D, FIG. 3F) as a function of (FIG. 3A, FIG. 3B) induction temperature for a continuous 1 hour stimulus, (FIG. 3C, FIG. 3D) pulse duration of stimuli delivered with a 50% duty cycle alternating between 37° C. and 42° C. for a fixed thermal exposure of 1 hour, and (FIG. 3E, FIG. 3F) induction duration for continuous heating at 42° C. Where not seen, error bars (±SEM) are smaller than the symbol. N=3 biological replicates for each sample.
Figure 3B:
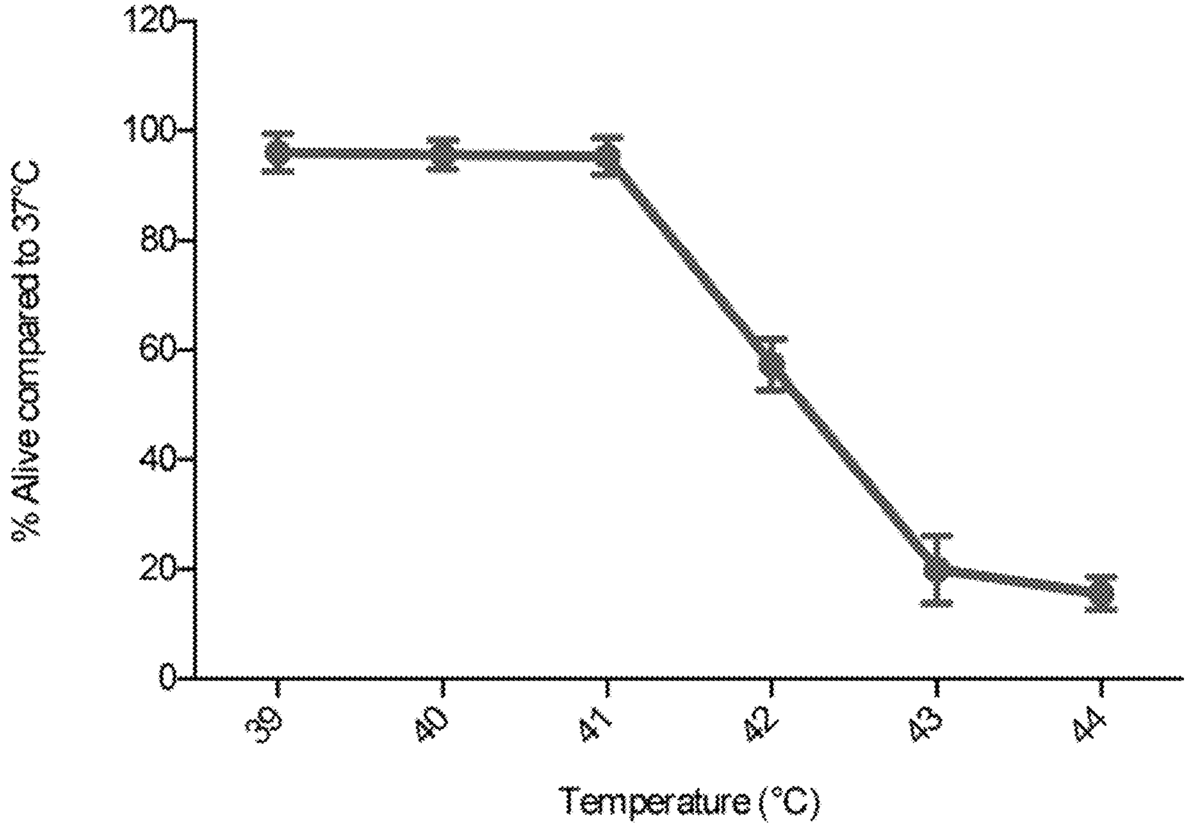
Figure 3C:
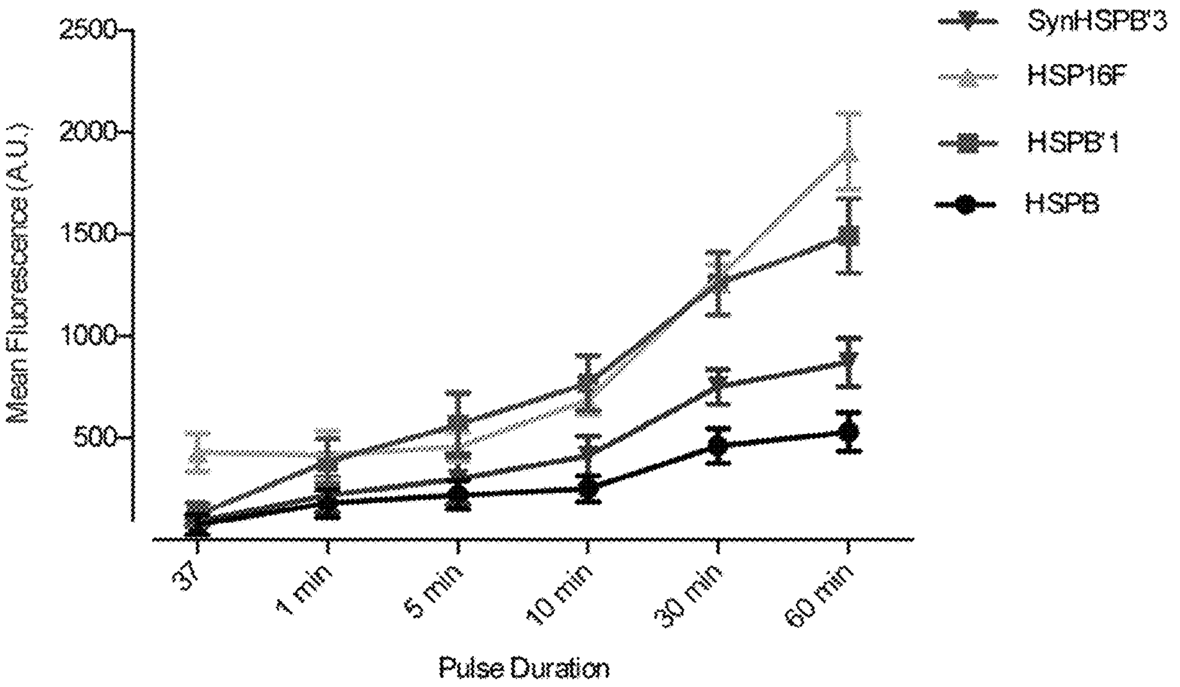
Figure 3D:
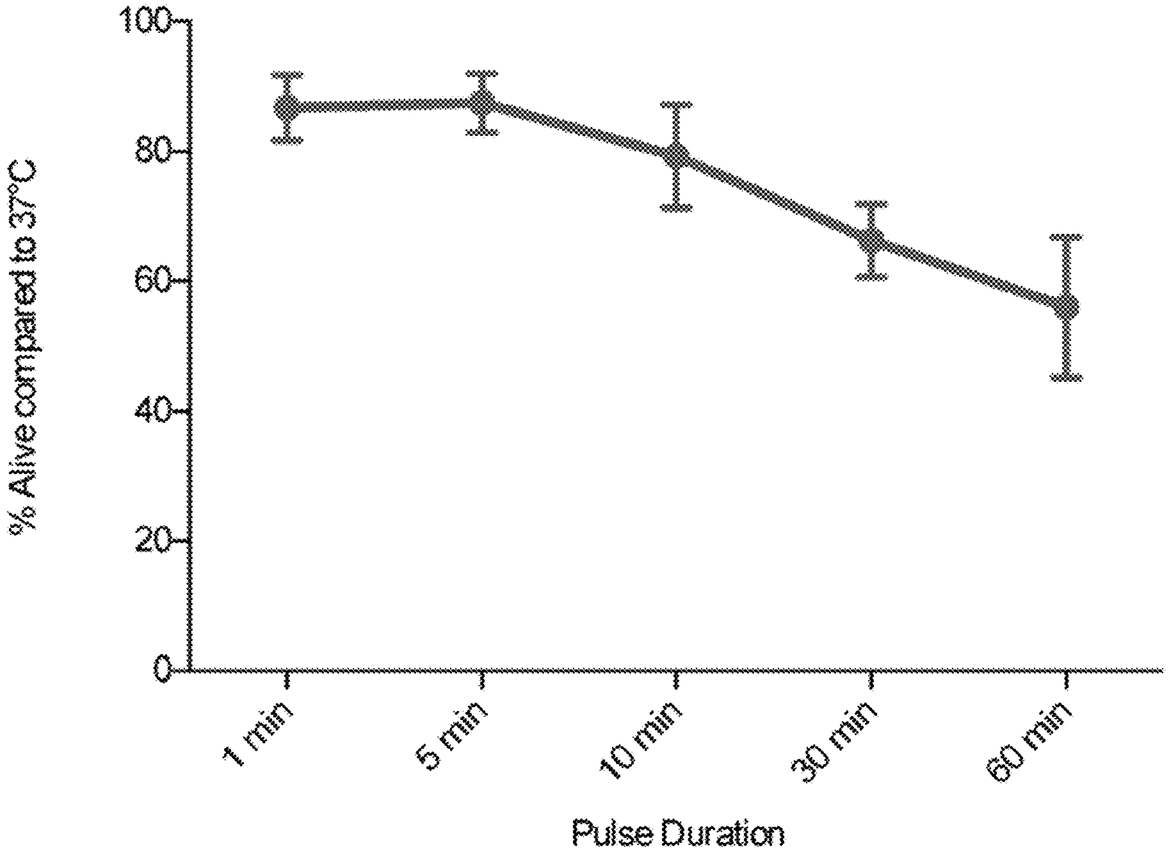
Figure 3E:
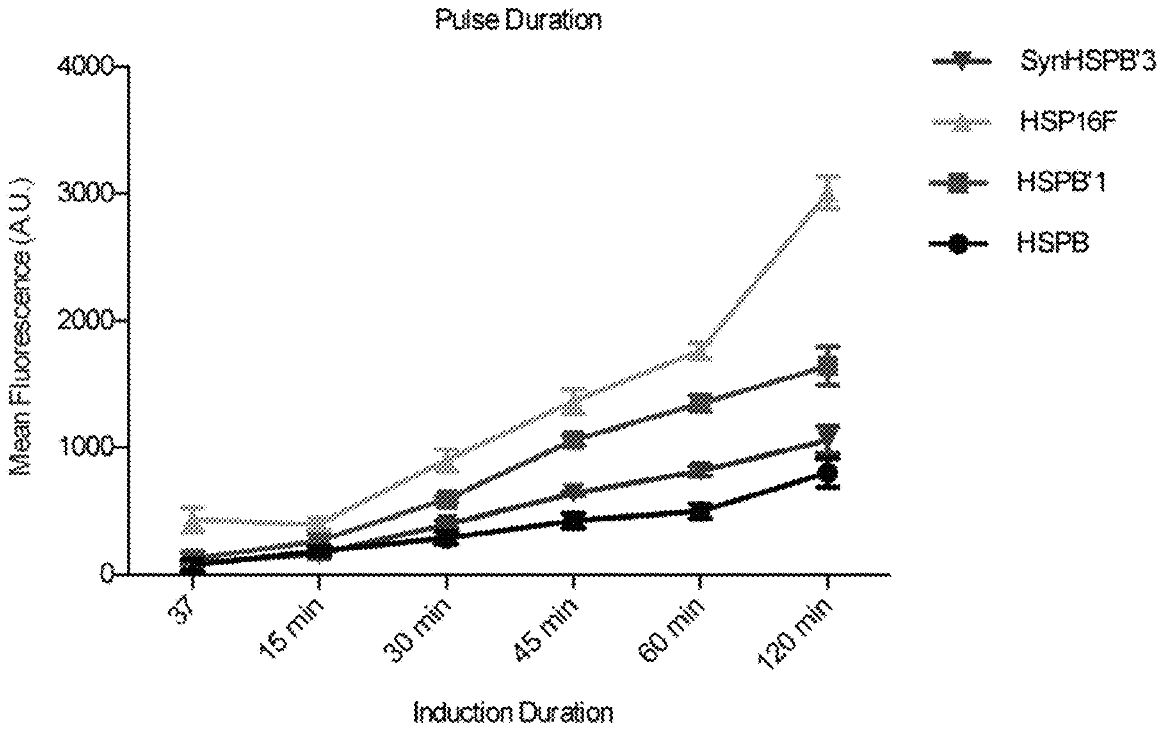
Figure 3F:
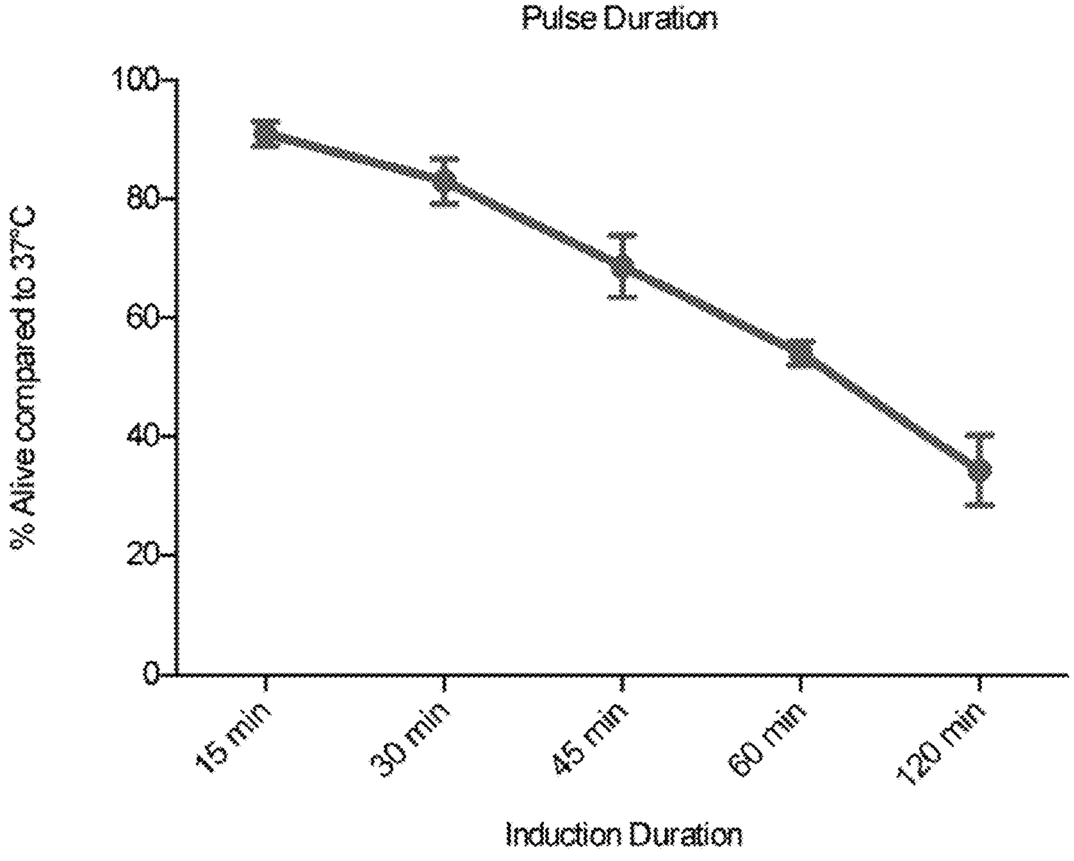

After identifying four candidate pHSPs, their response to a range of induction parameters was tested. To search for temperatures that provide rapid induction with minimal thermal burden to the cells, pHSP-transduced T-cells were incubated at temperatures ranging from 37° C. to 44° C. for 1 hour. All four promoters exhibited a significant increase in activity starting at 42° C. (FIG. 3A). Increasing the induction temperature beyond this point resulted in a significant enhancement of transcriptional activity, but compromised cell viability (FIG. 3B). To optimize induction with minimal cell damage, 42° C. was chosen for further experiments. Unlike the gradual increase in gene expression observed with the mammalian promoters above 42° C., HSP16 exhibited a large jump between this temperature and 43° C., which is employed in various circuit engineering applications disclosed herein.

To reduce the effect of thermal exposure on cell viability, a pulsatile heating scheme with a 50% duty cycle was tested. In this scheme, cells underwent repeated cycles of heating to 42° C. for a fixed duration and an equal amount of time at 37° C., adding up to a total of one hour at 42° C. over a two-hour treatment period. The stimulation period was varied between one minute and continuous heating for 60 min. This experiment revealed a trade-off between promoter activity (FIG. 3C) and cell viability (FIG. 3D), with shorter pulses reducing the former while increasing the latter. For the purposes of T-cell therapy, in which cells can expand after activation, a 40% decrease in cell viability was determined to be a suitable trade-off for improved activation, therefore a continuous heating paradigm was selected. This paradigm also simplifies the application of heating during therapy. Continuous stimulation durations ranging from 15 to 120 minutes was also investigated. Shorter induction enhanced viability (FIG. 3E) at the expense of lower gene expression (FIG. 3F), with a one-hour stimulation providing a reasonable balance. The optimal stimulation scheme can vary depending on the promoter used, circuit design, targeted tissue, and therapeutic dose required. A one-hour continuous stimulus at 42° C. was chosen as the heating paradigm for subsequent experiments to maximize of the likelihood of getting a meaningful response despite the possibility of damage to the cells.

Genetic Circuits for Amplified and Sustained Thermal Activation

Figure 4A:
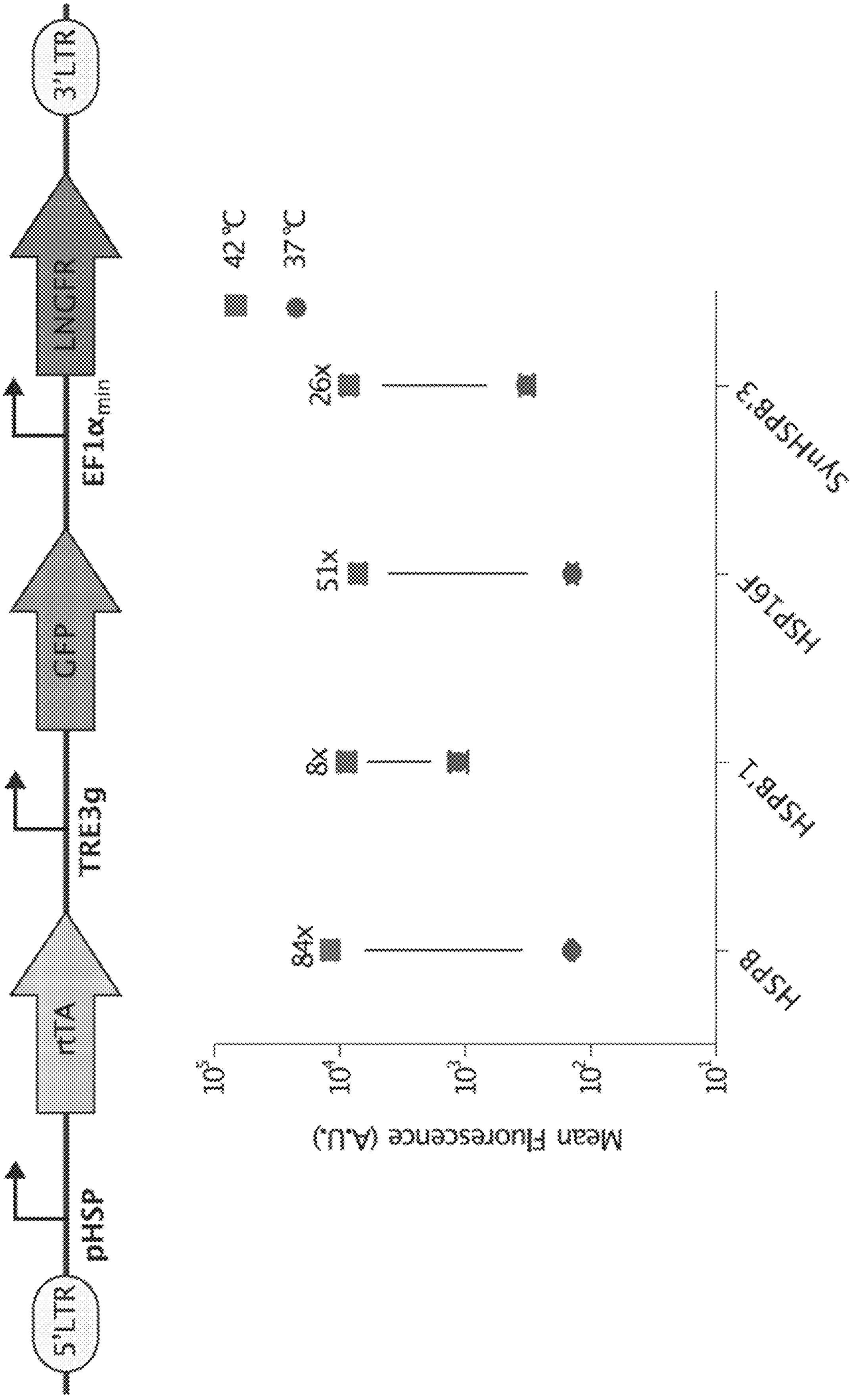
FIGS. 4A-4F depict non-limiting exemplary data and embodiments related to genetic circuits for amplified and sustained thermal activation.
Figure 4B:
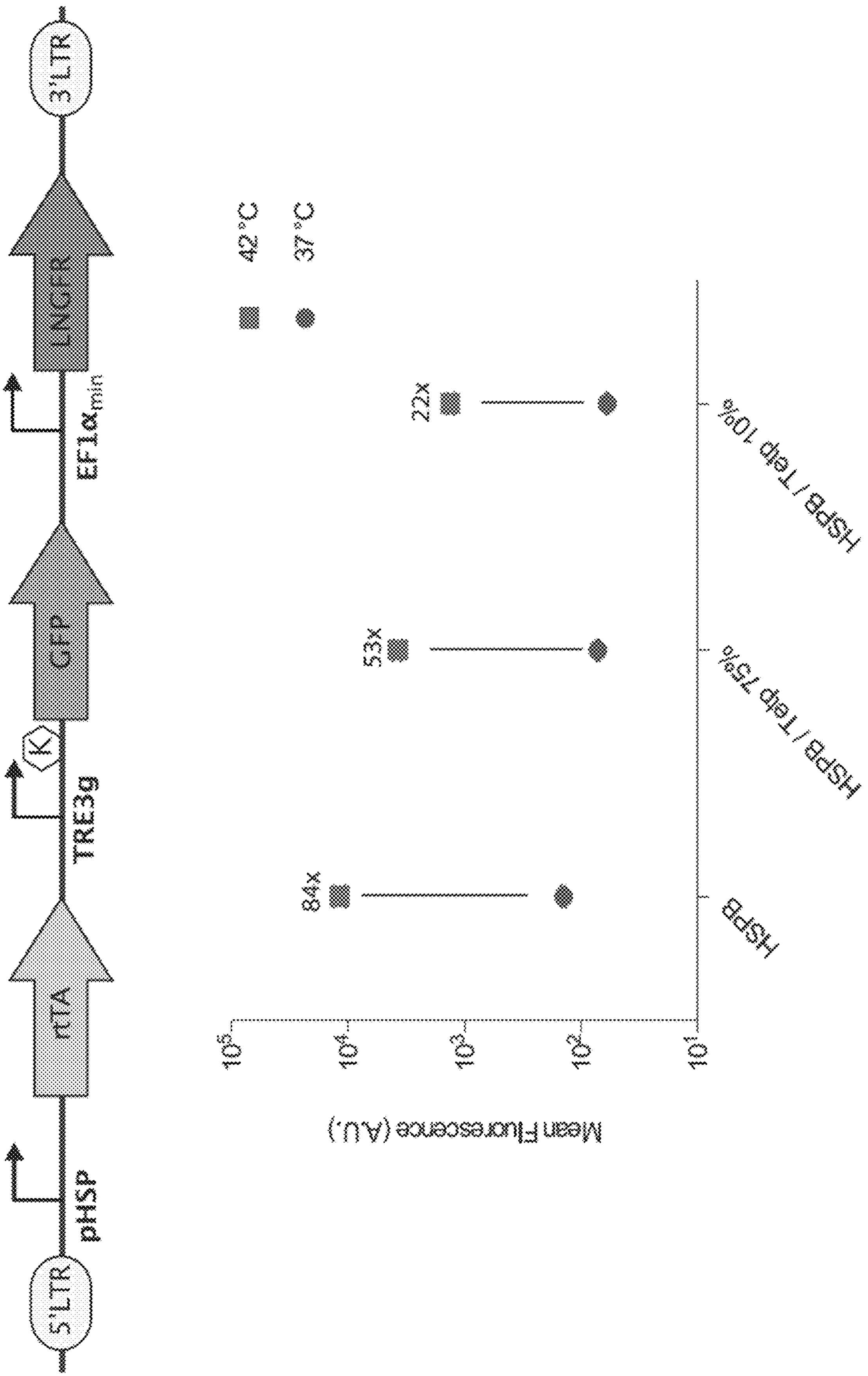
Figure 9:
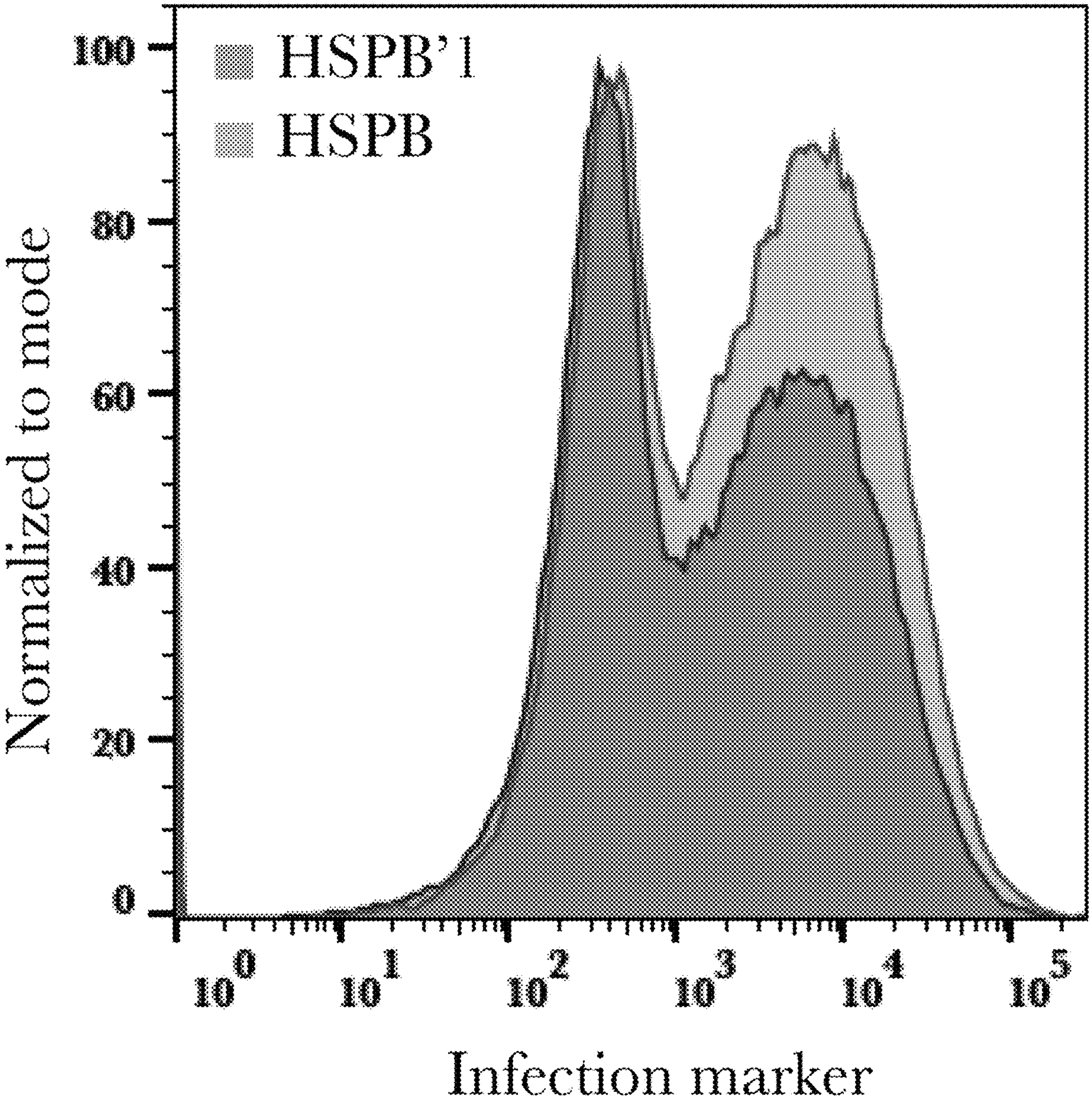
FIG. 9 depicts non-limiting exemplary data related to expression of a transduction marker to control for variability in infection. Constructs in our experiments carried an infection marker that was used to assess any differences in viral integration efficiency. In this example, T-cells were infected with the HSPB and HSPB'1 feed-forward circuits from FIG. 4A. Both constructs had similar expression levels of the infection marker and comparable transduction efficiency HSPB (63%) and HSPB'1 (54%).

In some embodiments, on their own, pHSPs drove a relatively small amount of transient protein expression upon induction. To enable the use of pHSPs in T-cell therapy applications it is useful to amplify the output of pHSP-driven circuits. This would enable cells to, for example, release a relatively large therapeutic bolus after a single thermal stimulus. To achieve this goal, a feed-forward amplification circuit in which the pHSP drives an rtTA transactivator was implemented, which produces stronger transcriptional activation tunable with doxycycline. In addition, LNGFR was constitutively expressed to identify virally transfected cells (FIG. 4A). Amplification circuits incorporating HSPB, HSPB'1, SynHSPB'3 and HSP16 all exhibited a substantial increase in their fold-induction, while only modestly elevating baseline expression. HSPB showed the best performance, suggesting that in the context of feed-forward amplification driving the maximum expression level, a promoter with lower leakage (FIG. 2B) is preferable. The expression of a constitutive transduction marker was similar across constructs (e.g. FIG. 9), indicating that infection levels did not affect their relative performance. To further tune the performance of the HSPB amplifier circuit, constructs were designed with reduced translation of the GFP by varying the Kozak sequence or inserting a micro open reading frame upstream (FIG. 4B). These modifications enabled the tuning of both the baseline expression and the maximal activation level.

Figure 4C:
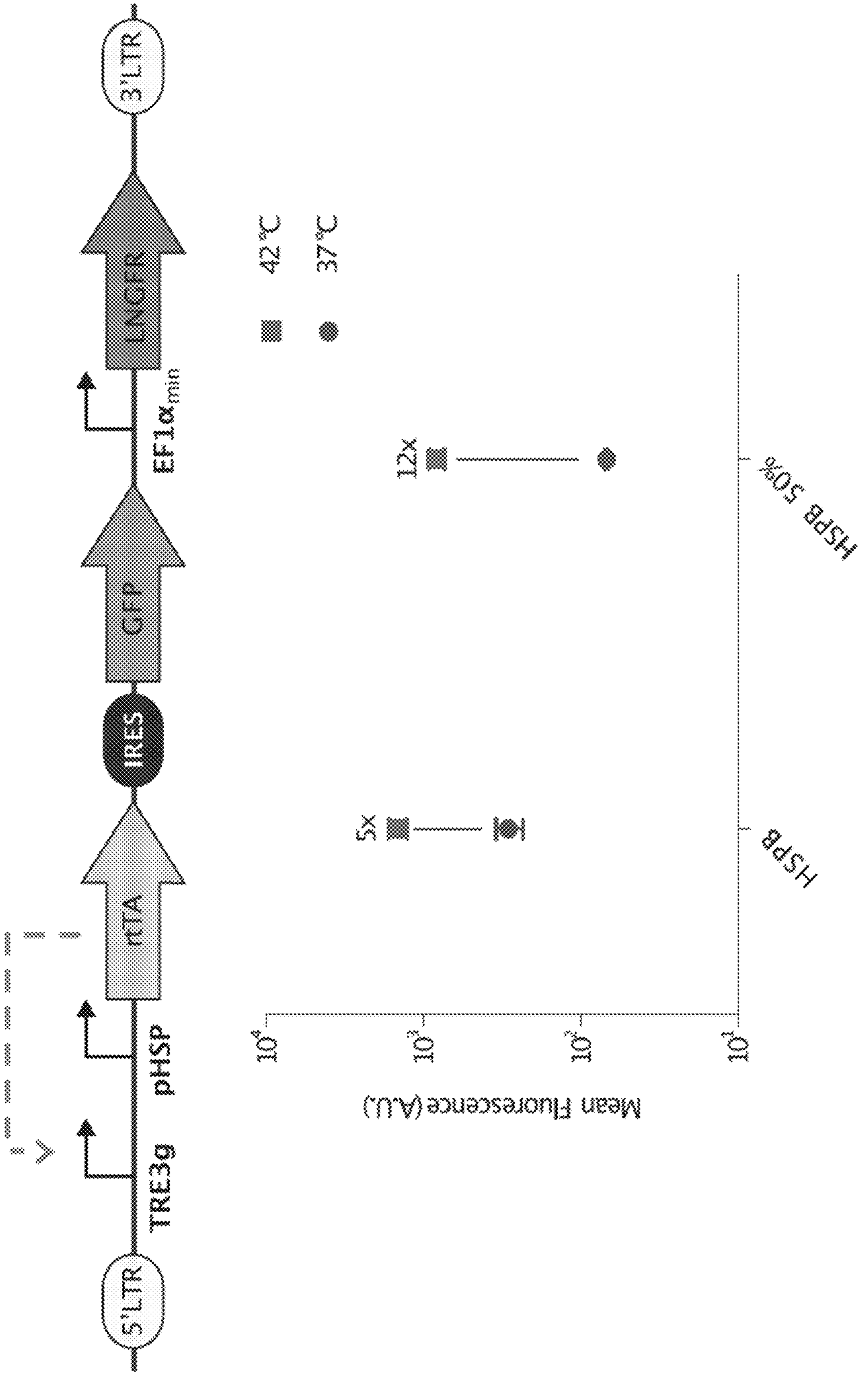
Figure 4D:
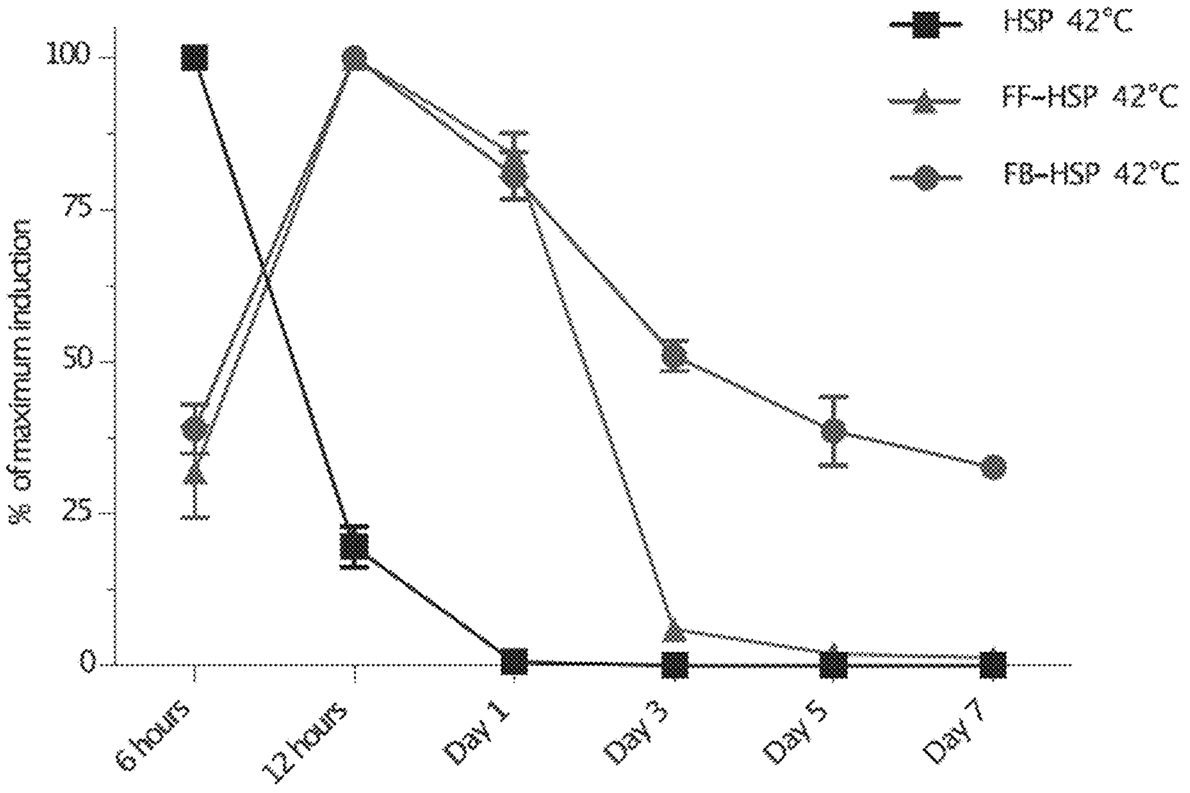

In some therapeutic scenarios, it is critical to prolong the therapeutic action of T-cells following a thermal induction treatment. This would eliminate the need to apply repeated stimuli to maintain treatment efficacy. To develop this capability a positive feedback amplifier circuit was established by rearranging the elements of the feed-forward amplifier such that rtTA could drive its own expression in the presence of doxycycline (FIG. 4C). The HSPB feedback circuit maintained its thermal induction level, and baseline activity was reduced by tuning the Kozak sequence upstream of rtTA. In some embodiments, the output of the positive feedback circuit is lower than that of the feed-forward amplifier when GFP payload is placed after an IRES element. In some embodiments such "low but steady" activity is desirable; in other embodiments, a "high and steady" mode can be achieved by exchanging the IRES for a 2A element. In some embodiments, the IRES element can be replaced with a 2A element. The dynamic expression profiles of the direct, feed-forward, and feedback HSPB circuits are compared in FIG. 4D, demonstrating prolonged expression with positive feedback.

Figure 4E:
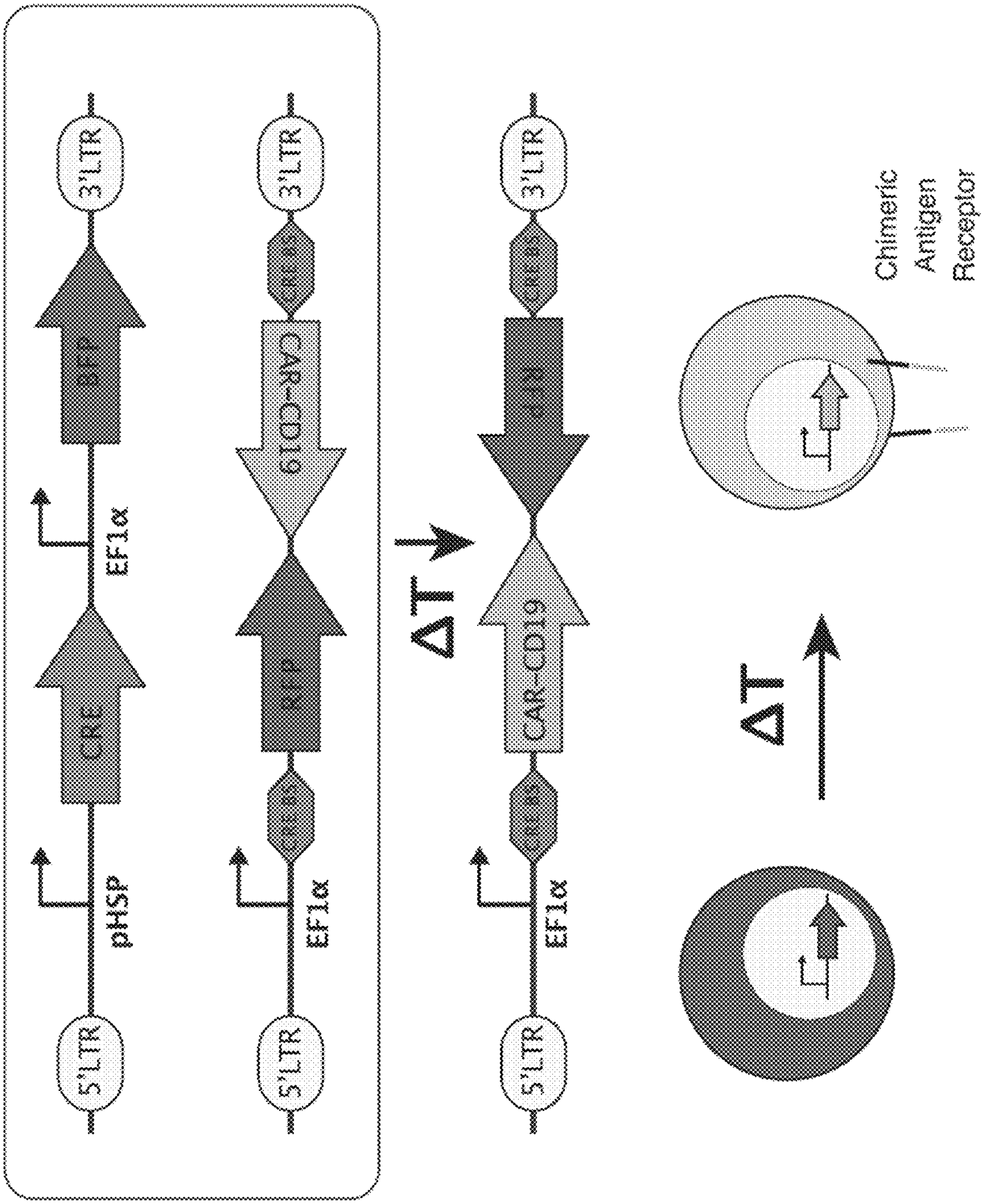
Figure 4F:
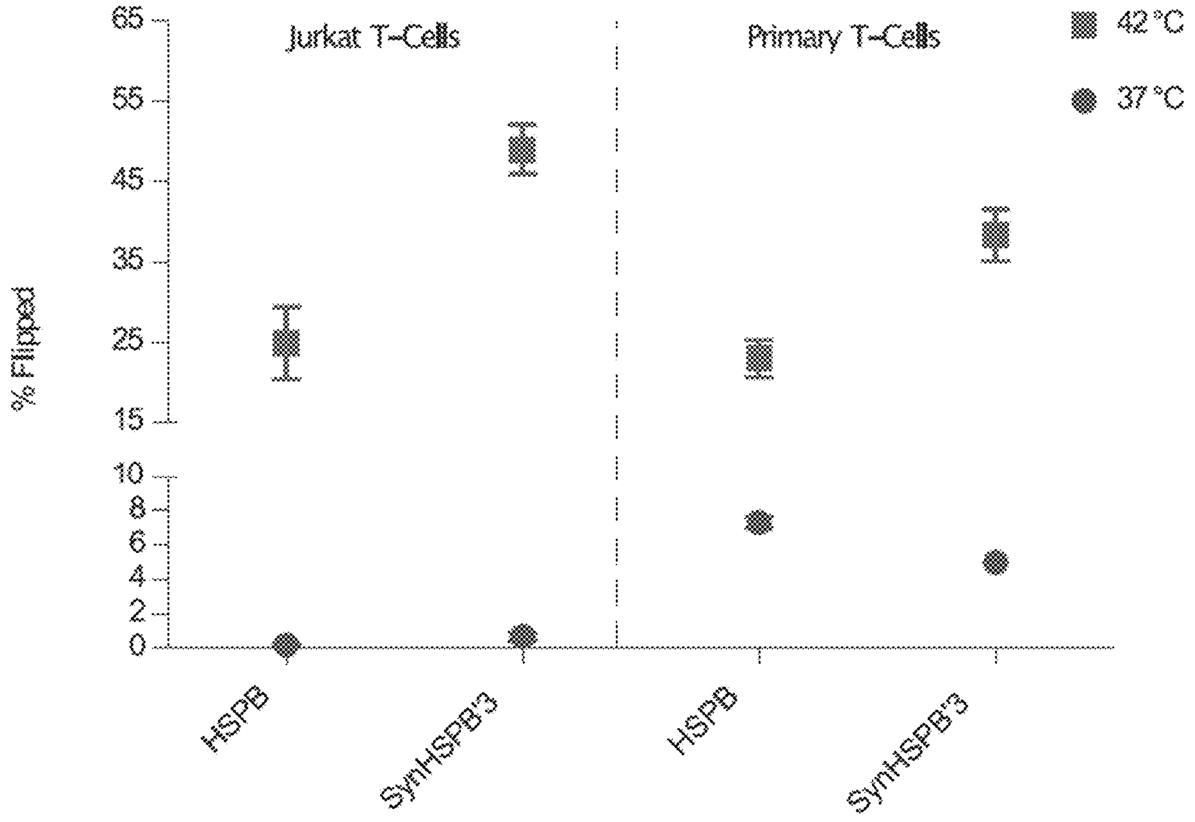

The positive feedback circuit sustained expression for several days. In some embodiments, circuits can eventually turn off amid dilution or fluctuating expression of the transactivator. To establish a permanent thermal switch, gene circuits were tested in which the expression of CRE recombinase was placed under the control of candidate pHSPs (FIG. 4E). In these circuits, the pHSP-driven expression of CRE permanently toggles the circuit from expressing RFP to expressing anti-CD19 CAR by recombining the target vector. In a Jurkat T-cell line, these circuits demonstrated robust activation and minimal leakage (FIG. 4F). In some embodiments of the compositions and methods disclosed herein, when tested in primary T-cells, higher levels of background activation are observed (FIG. 4F). Without being bound by any particular theory, this may arise from the fact that immune stimulation is used to maintain primary T-cells in culture and our finding, discussed below, that pHSPs show significant background activity in stimulated primary T-cells. Taken together, these results show that in primary T-cells, feed-forward and feed-back amplification provide robust methods for thermal control of gene expression.

Temperature-Activated Cytokine Release

Figure 5A:
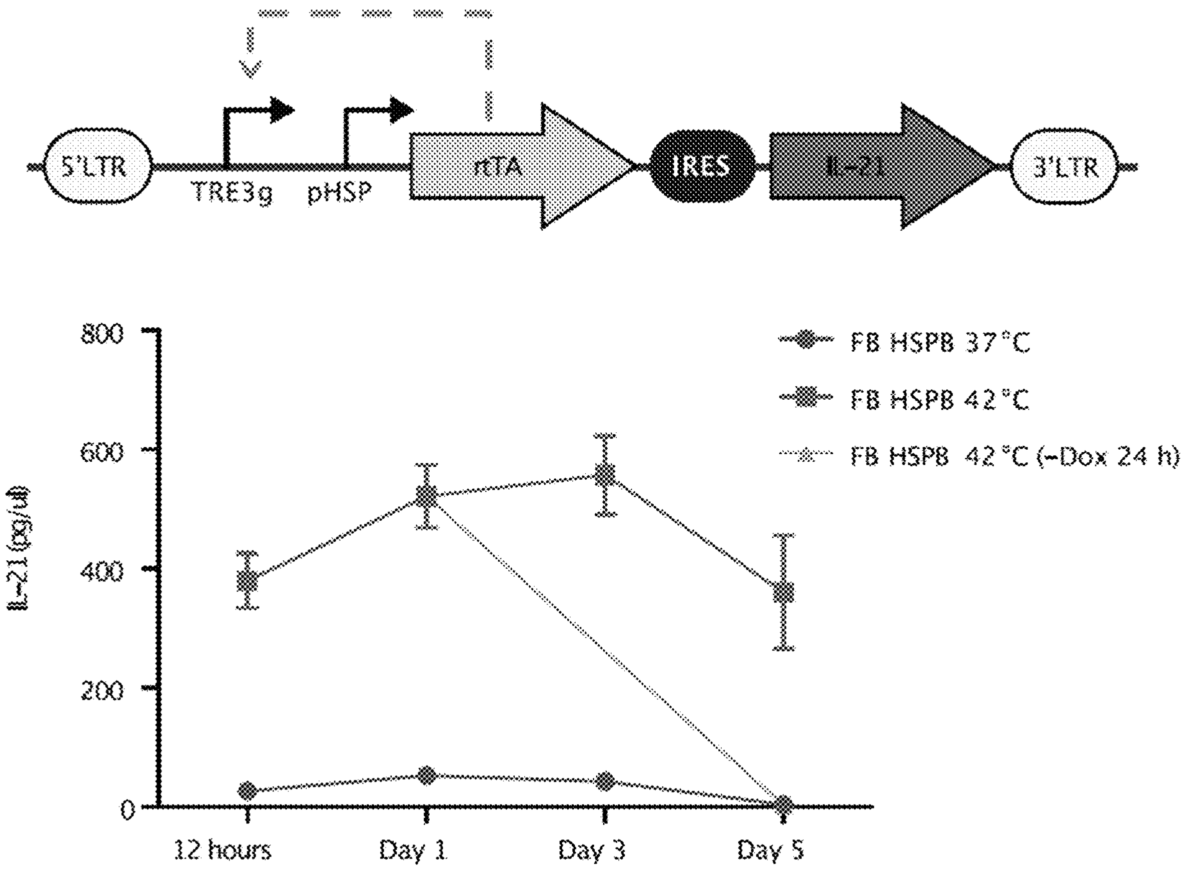
FIGS. 5A-5B depict non-limiting exemplary data and embodiments related to temperature activated cytokine release.

To demonstrate the ability of the positive feedback circuit to sustain a therapeutically relevant function after thermal induction, the output of the positive feedback circuit was connected to the production of a cytokine. The local delivery of cytokines from engineered T-cells would be useful in cancer immunotherapy by allowing T-cells to secrete immune-stimulatory factors to remodel the tumor microenvironment and reduce immunosuppression. It would also be useful in treatments of autoimmune disease by allowing T-cells to secrete factors locally down-regulating the activity of endogenous immune cells. As a model cytokine, IL-21 was selected, which has potential utility in cancer immunotherapy due to its ability to stimulate NK cells and $CD8^+$ T-cells. Human IL-21 was incorporated in place of GFP in the positive feedback circuit (FIG. 5A). Without thermal induction, primary T-cells transduced with this circuit produced minimal IL-21. Once stimulated, the cells rapidly secreted IL-21, reaching a near-maximal level by 12 hours, and sustained activity for at least 5 days (FIG. 5A). The dependence of continued circuit function on doxycycline provides an additional layer of control, allowing the termination of therapy production at a desired time by removing doxycycline. To demonstrate this capability, doxycycline was removed 24 hours after cell induction, resulting in the abrogation of cytokine production by day five. The ability to chemically terminate the activity of the positive feedback circuit enhances its safety profile in potential therapeutic applications.

Figure 5B:
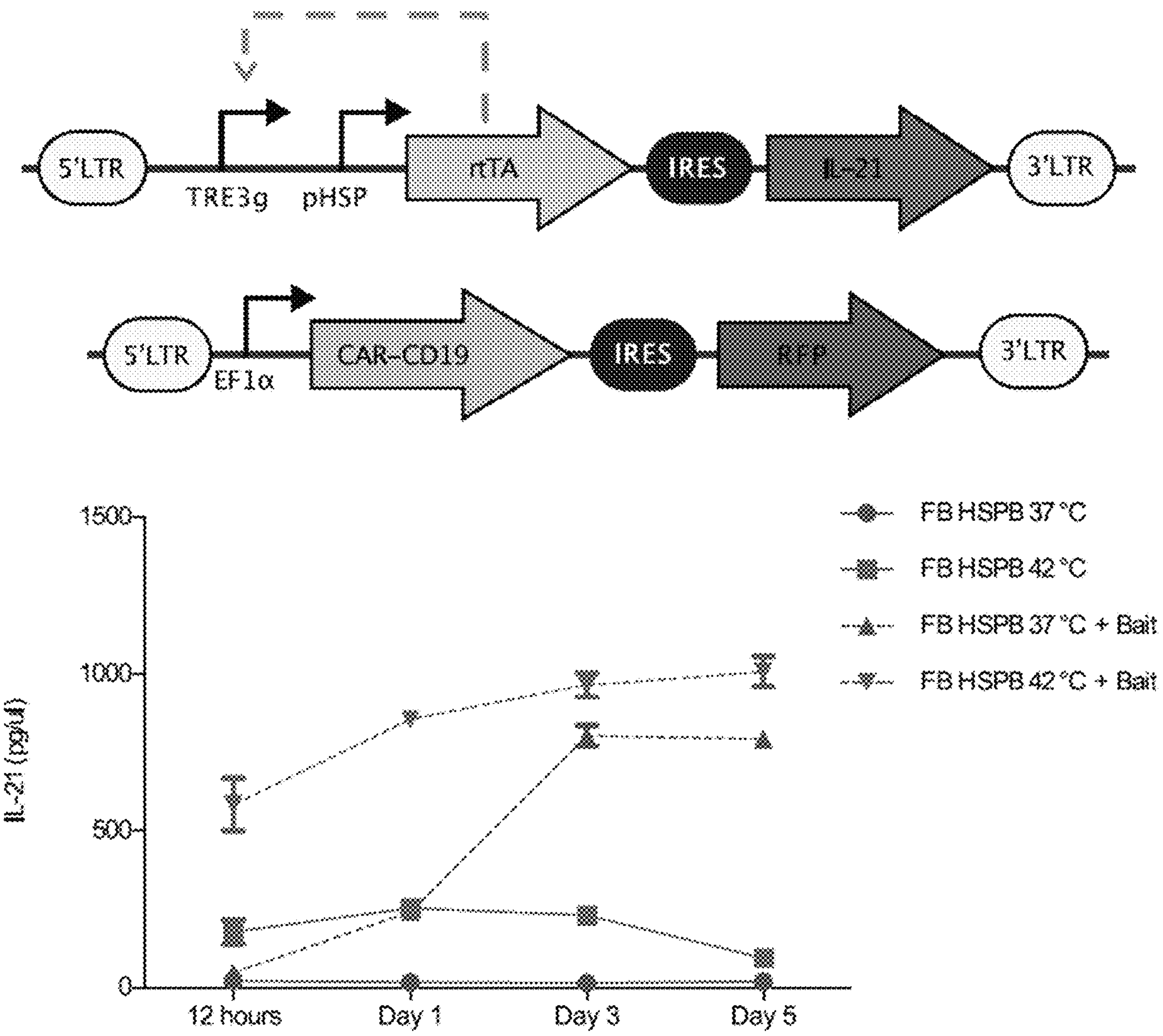

In some scenarios, it would be useful for cytokine release to be triggered from a T-cell constitutively expressing a CAR, allowing the cytokine to locally boost immune activation during CAR-directed killing. To test this possibility, primary T-cells were co-transduced with the positive IL-21 circuit and a constitutively expressed anti-CD19 CAR (FIG. 5B). In the absence of target Raji bait cells expressing CD19, IL-21 release was well-controlled by thermal induction (FIG. 5B). However, co-incubation with bait cells resulted in the activation of IL-21 release after 3 days in co-culture even in the absence of a thermal treatment (FIG. 5B). These results suggested that HSP activity may be driven by T-cell stimulation, as evidenced by IL-21 release. However, since certain subsets of T-cells have been shown to release endogenous IL-21 when stimulated, we set out to directly test the induction of pHSP upon T-cell stimulation using a non-cytokine output, as discussed below.

Dependence of pHSP-Driven Circuits on T-Cell Activation

Figure 6A:
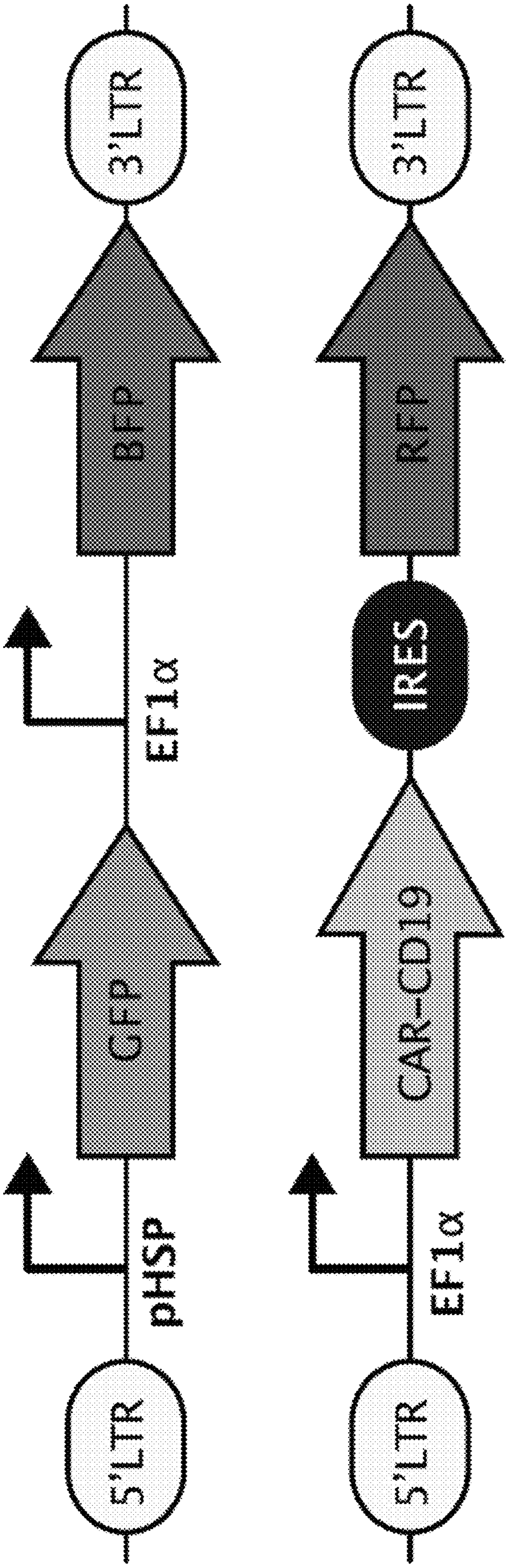
FIGS. 6A-6B depict non-limiting exemplary data and embodiments related to dependence of pHSP-driven circuits on T-cell activation.
Figure 6B:
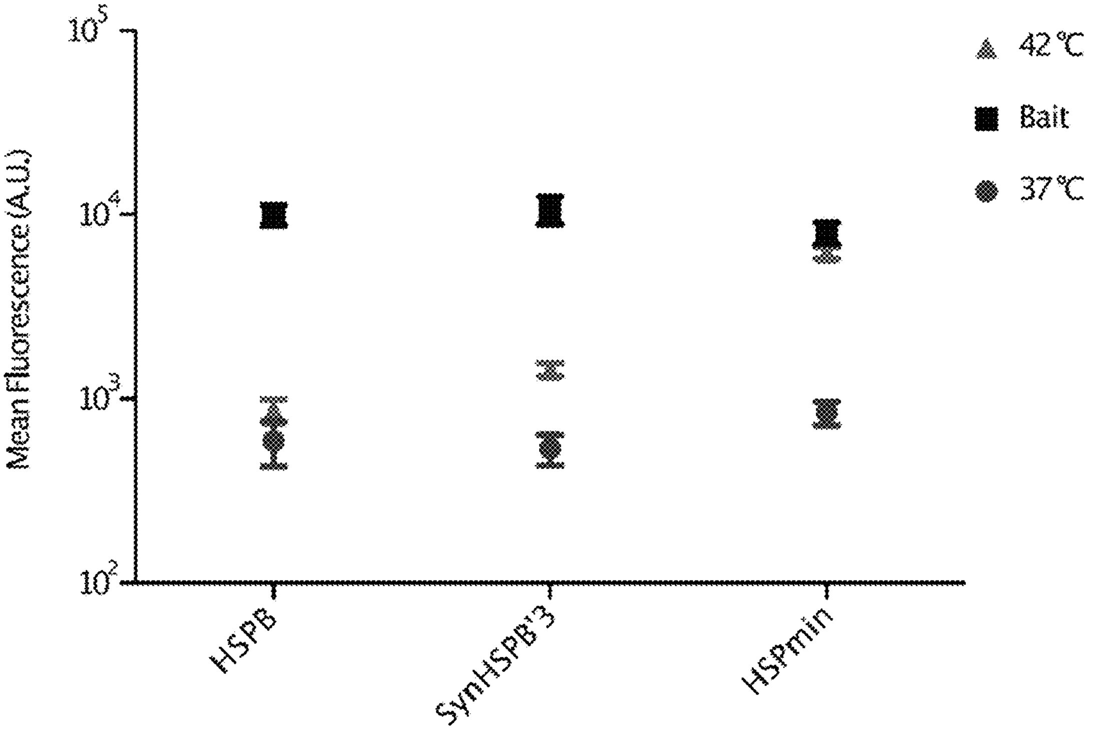

To directly examine the possibility that pHSPs are turned on in response to CAR-driven T-cell activation, the expression of pHSP-driven GFP in constitutively CAR-expressing T-cells was tested (FIG. 6A) upon exposure to a thermal stimulus or bait cells. Both thermal stimulation and CAR engagement were found to lead to pHSP-driven gene expression (FIG. 6B). This response occurred in cells expressing circuits based on HSPB, SynHSPB'3 and HSPmin promoters. Because SynHSPB'3 lacks the AP-1 site present in wild-type pHSPs such as HSPB, and HSPmin is composed of only HSE binding sites driving a minimal promoter, these results suggest that pHSP induction takes place via an HSF1-mediated mechanism. This unexpected finding suggests that, in some embodiments, activated T-cells experience cellular stress—for example due-to rapid proliferation—potentially resulting in an increased number of misfolded proteins, leading to HSP upregulation. This provides an important insight for the design of thermally inducible immunotherapies.

Auto-Sustained Thermally Induced CAR Expression and Tumor Cell Killing

The finding that CAR engagement drives pHSP activity suggested that a simple, auto-sustained gene circuit could drive CAR-mediated killing in response to the combination of a thermal stimulus and the presence of target cells. In particular, it was hypothesized that placing CAR expression under the control of a pHSP (FIG. 7A) would result in T-cells with no initial CAR expression or activity, even in the presence of target cells. Upon thermal induction, CAR would become transiently expressed. If the CAR target is present in the vicinity of T-cells, these cells would become activated, driving sustained expression of additional CAR from the pHSP and target cell killing.

Figure 7A:
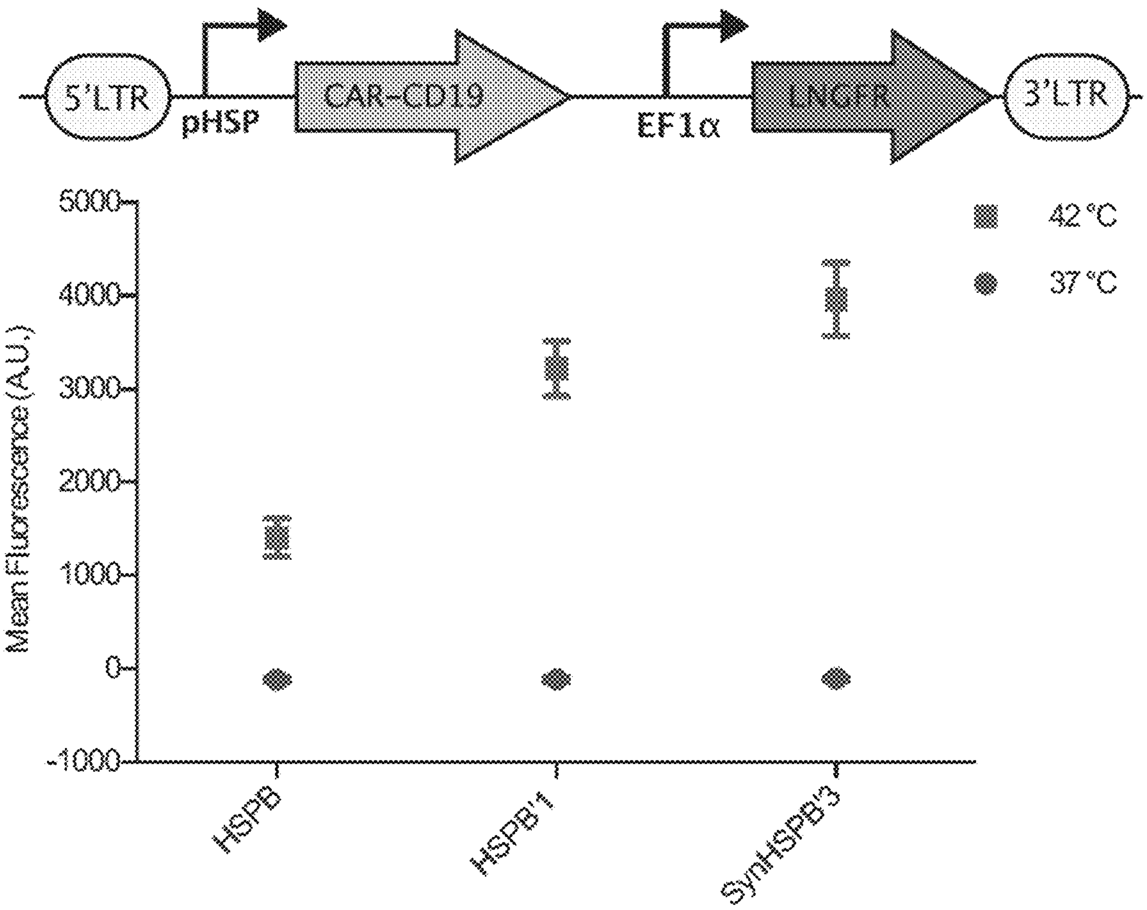
FIGS. 7A-7D depict non-limiting exemplary data and embodiments related to auto-sustained thermally induced CAR expression and tumor cell killing.
Figure 7B:
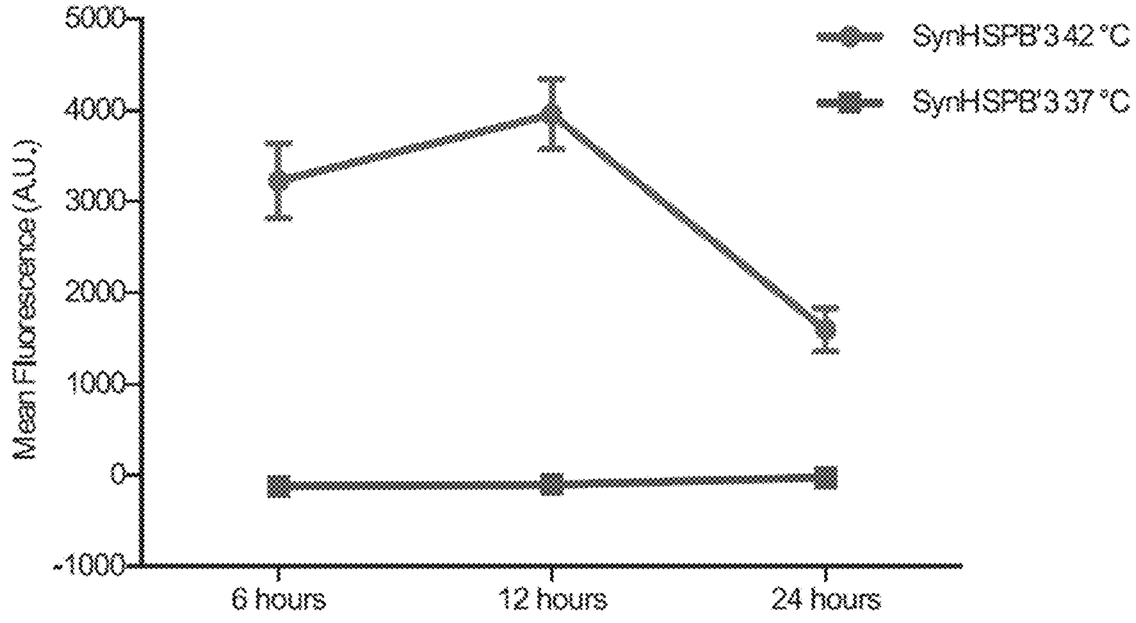
Figure 7C:
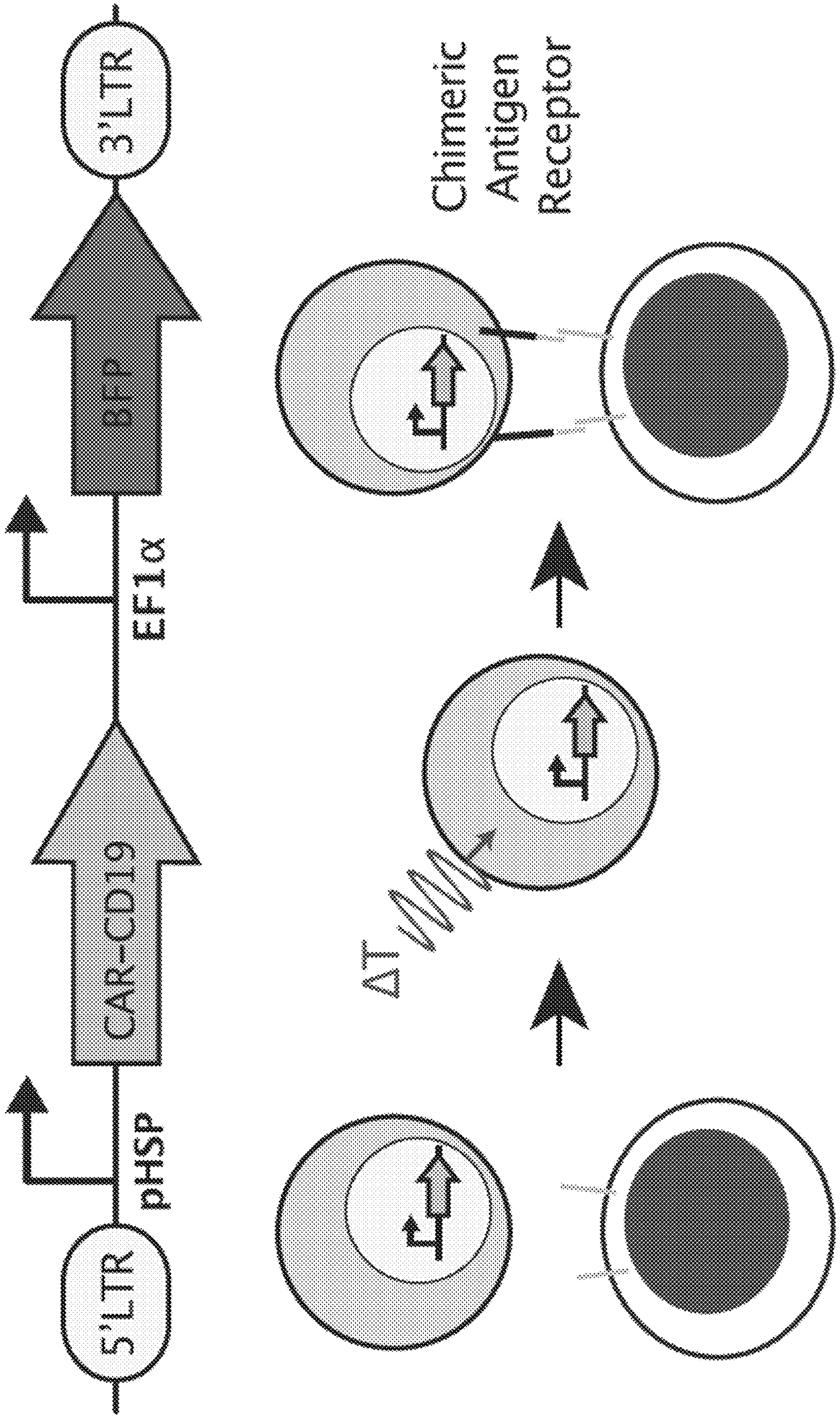
Figure 7D:
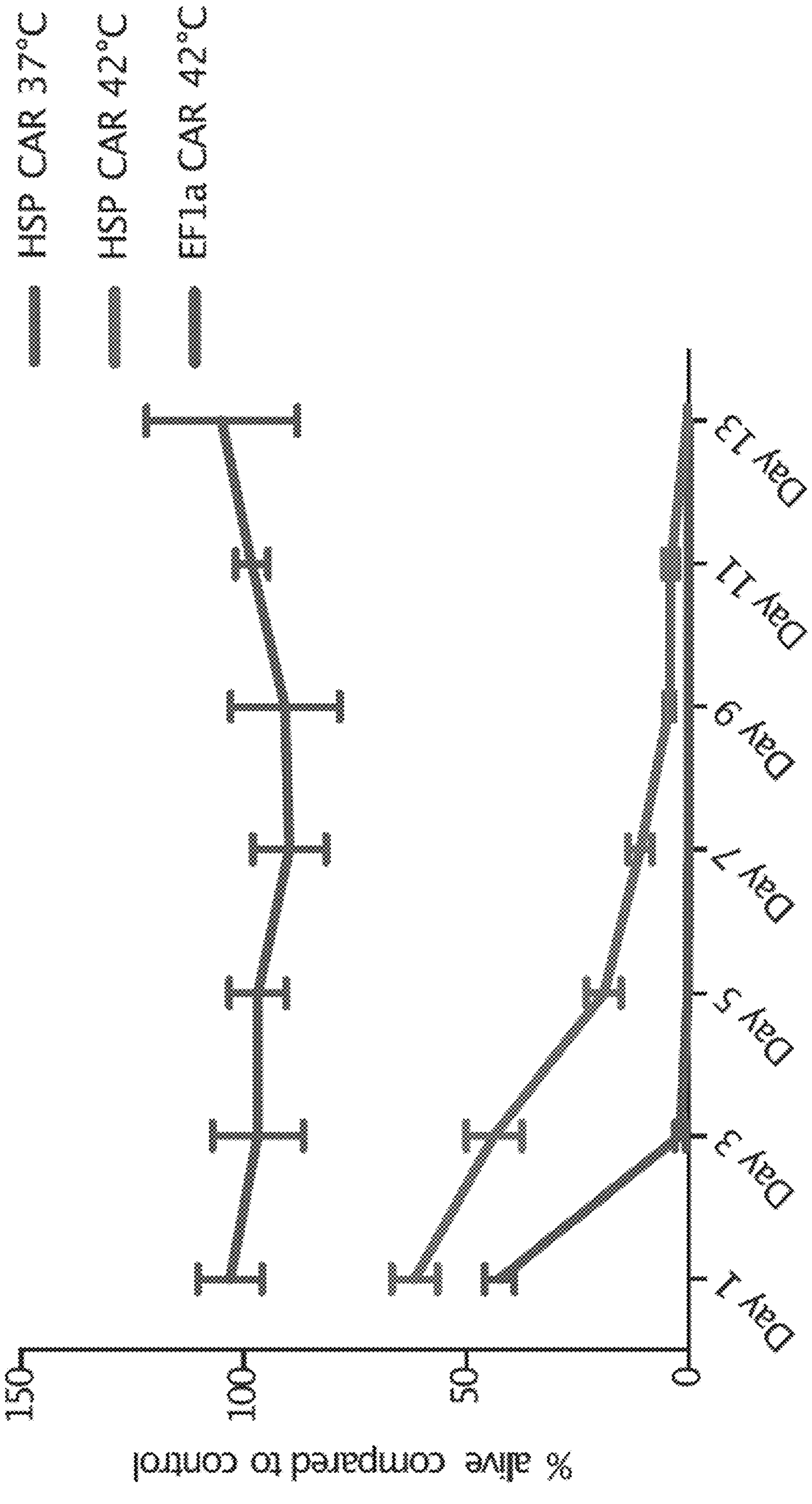
Figure 10:
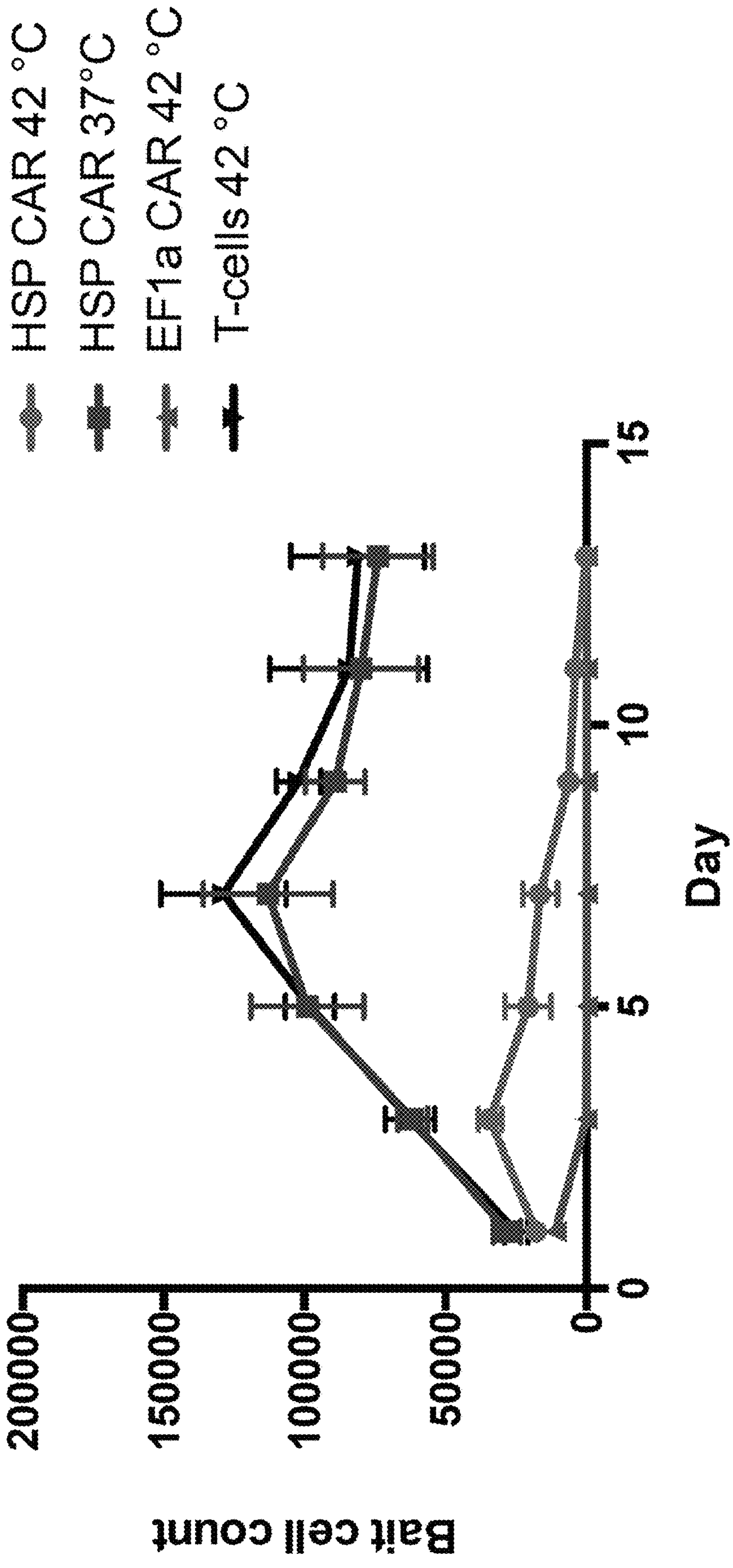
FIG. 10 depicts non-limiting exemplary data related to bait cell count for the HSP CAR killing experiment. Primary T-cells were either incubated at 37° C. or thermally stimulated for 1 hour at 42° C. before being incubated with CD19+ bait cells. Unmodified T-cells and T-cells constitutively expressing CAR-CD19 were used as a negative and positive control, respectively. HSP (SynHSPB'3) triggered killing activity was quantified by counting the number of bait cells alive over 13 days. N=3 biological replicates. Where not seen, error bars (±SEM) are smaller than the symbol.
Figure 11A:
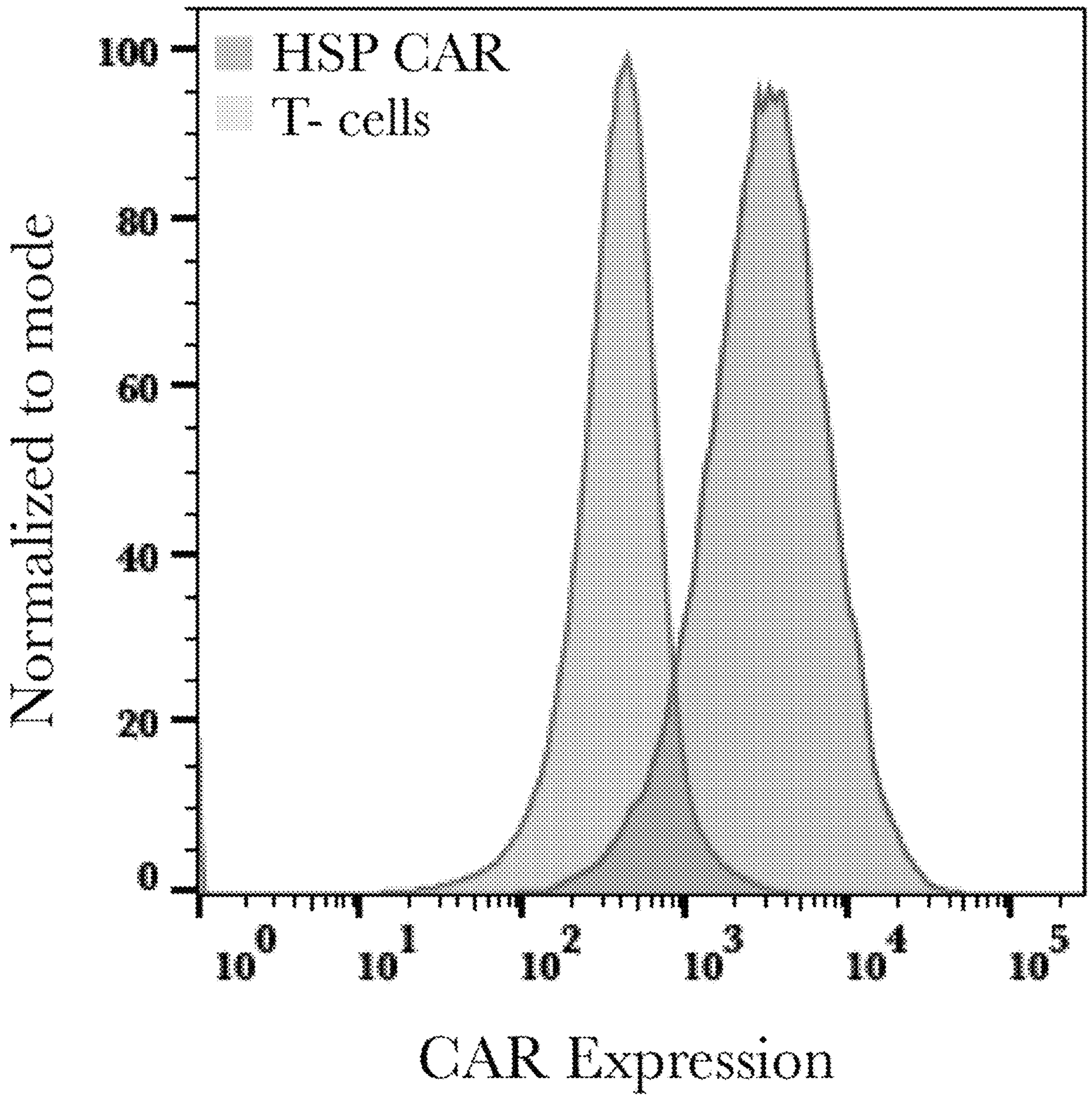
FIGS. 11A-11B depict non-limiting exemplary data related to CAR expression from constitutive and induced constructs.
Figure 11B:
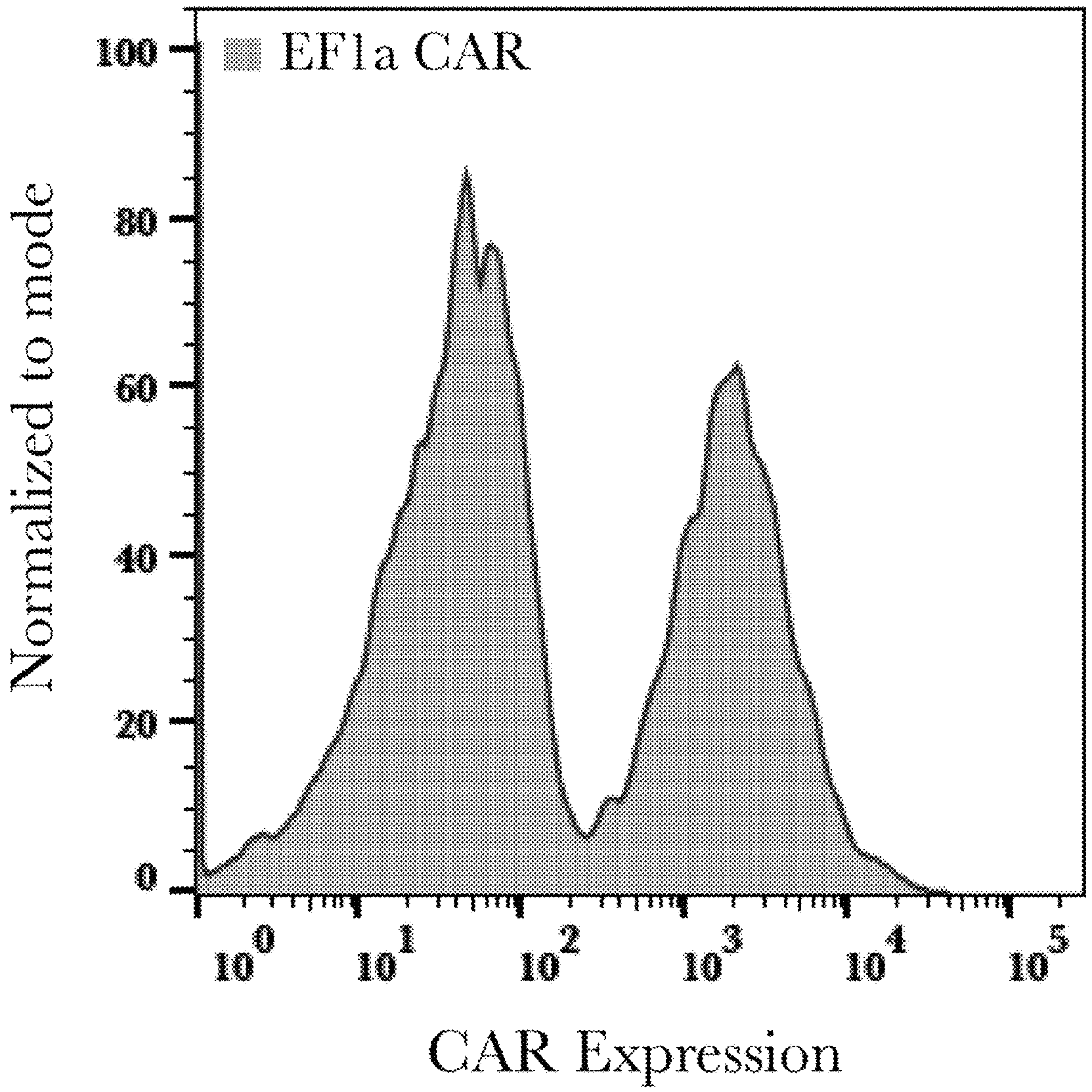
Figure 12:
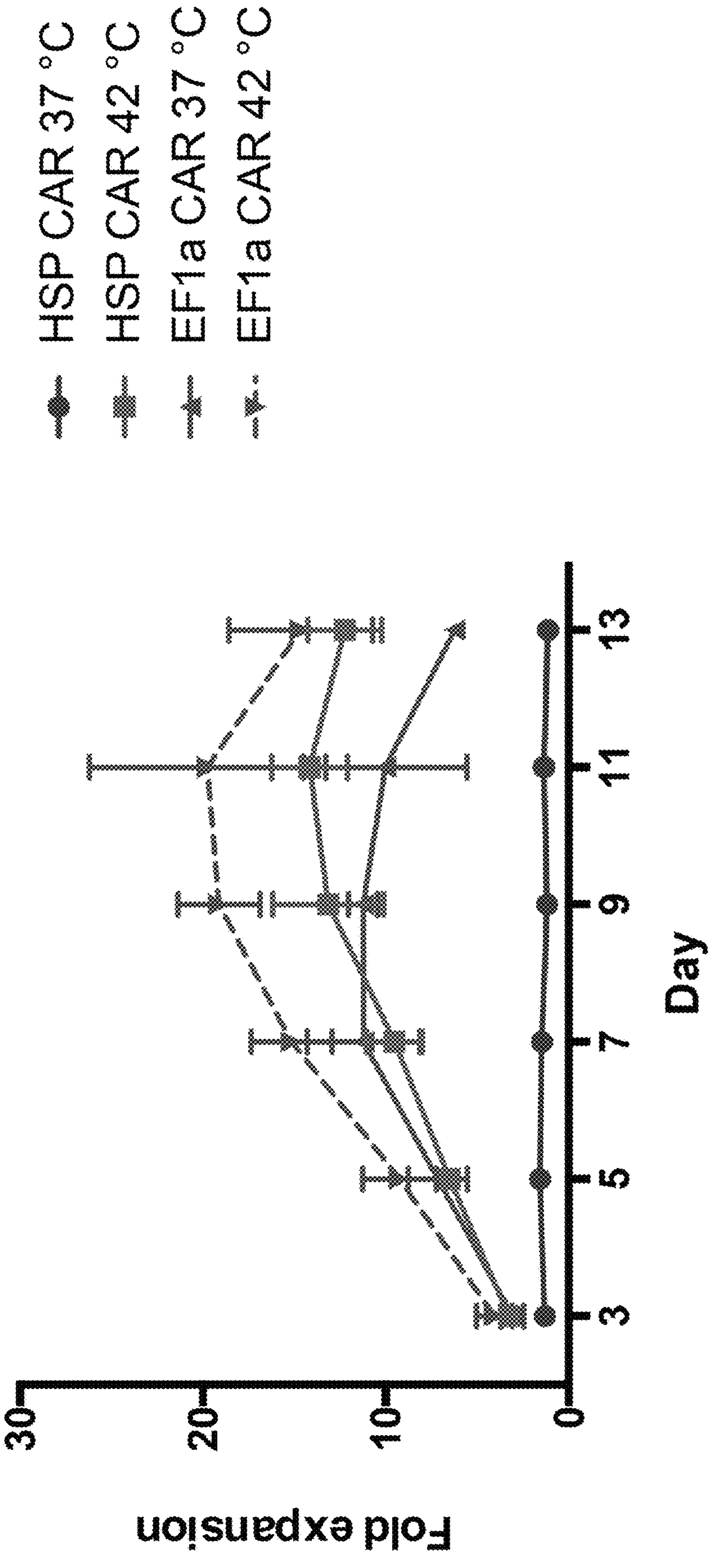
FIG. 12 depicts non-limiting exemplary data related to assessing the proliferative capacity of stimulated T-cells.

As predicted, this pHSP-CAR circuit showed no baseline CAR expression in primary T-cells, but began to express CAR when thermally stimulated (FIG. 7A). CAR expression was greatly reduced after 24 hours in the absence of target engagement (FIG. 7B). When cultured with $CD19^+$ bait cells (FIG. 7C), thermally activated pHSP-CAR T-cells eliminated the bait cells after 9 days in co-culture (FIG. 7D, FIG. 10). This killing was as complete as with positive control T-cells carrying a constitutively expressed CAR driven by the EF1$\alpha$ promoter, albeit over a longer time span. Without being bound by any particular theory, this difference may be due to the maximum level of pHSP-driven CAR expression being lower than the level observed with a constitutive EF1$\alpha$ promoter (FIG. 11). When pHSP-CAR T-cells and bait cells were co-incubated without thermal stimulation, no apparent killing took place. While the initial thermal stimulus results in some cell death, T-cells maintain their proliferative capacity and rapidly make up for the initial loss in T-cells (FIG. 12). These results suggest that a thermal stimulus can kick-start a positive feedback loop of activation-driven expression of CAR from pHSP, leading to effective bait cell elimination. This activation paradigm could help with mitigating off-target toxicity since CAR expression will be abrogated once T-cells leave the tumor site.

Discussion

The results shown in this Example demonstrate that engineered bioswitch circuits using pHSP can provide control of T-cell therapy with mild hyperthermia. While it has been previously shown that light-switchable proteins could also confer spatiotemporal control over T-cell activity, light has poor penetration into tissues, limiting the utility of such tools. On the other hand, temperature can be elevated at arbitrary depth and with high spatial precision using non-invasive methods such as FUS or magnetic hyperthermia.

Our study showed that temperatures in the well-tolerated range of 37-42° C. can provide control over T-cell function, including the synthesis and release of a cytokine and the CAR-mediated killing of cancer cells in vitro, with minimal baseline activity. In some embodiments of the methods provided herein, thermal tissue damage is not a major concern in tumor therapy (where it can be synergistic). In some embodiments of the methods provided herein, the FUS treatment duration is substantially less than the 1 hour heat pulse used in this study.

Disclosed herein are compositions and methods employing the surprising non-thermal pHSP induction by the T-cell receptor pathway to generate sustained killing circuits.

Example 2

Oscillatory Circuits

While the current generations of CAR-T cell therapies have shown high response rates in B cell malignancies, their efficacy in solid tumors remains modest at best. One of the primary factors implicated in their poor performance is T cell "exhaustion" in which CAR-T cells have reduced effector function. Many research groups have focused on studying this phenomenon to generate new therapeutic leads for solid tumor therapy. In methods and compositions provided herein, T cell exhaustion can be reversed through transient inactivation of CAR-T cells. There are provided, in some embodiments, cell-autonomous genetic controllers that utilize HSP promoters to circumvent T cell exhaustion by periodically resting T cells. Disclosed herein are activity-regulated feedback circuits, based on HSP promoters as sensors of T cell activity (as described herein), that autonomously down regulates the expression of CAR to rest T cells following events of high CAR activity.

There are provided, in some embodiments of the methods and compositions disclosed herein, activity-driven oscillators preventing T cell exhaustion. In some embodiments, a central component the disclosed activity-driven oscillators is a new class of HSP-based transcriptional sensors which are described herein. In some embodiments, T cells use HSP-based promoters to sense their activity and down-regulate CAR expression after a period of stimulation, allowing the T cells to rest. In some embodiments, rested cells will express CAR again in an oscillatory pattern. In some embodiments, therapeutic T cells will oscillate asynchronously allowing some T cells to rest while the remaining cells engage with the tumor, resulting in sustained therapy while avoiding excessive activity in any given T cell. To regulate CAR expression, the activity of HSP-based sensors can be connected to the expression of proteins, such as the anti-GFP nanobody and LOCKR, which target and degrade engineered CARs. In some embodiments, to increase the length of the rest period, feed-forward control elements are included in the circuit. In some embodiments, to decrease the rest period, the N-end rule is used to control the CAR half-life. FIGS. 14A-14C depict non-limiting exemplary data and embodiments related to HSP-based feedback circuits that regulate CAR activity to prevent T cell exhaustion. FIG. 14A depicts a non-limiting exemplary traditional CAR T-cell and an exemplary oscillatory CAR T-cell provided herein. FIG. 14B depicts a non-limiting exemplary oscillatory genetic circuit. FIG. 14C depicts exemplary data related to Jurkat cells that were virally infected with the circuit shown in FIG. 14B and then mixed with bait cells at 1:5 Jurkat to bait ratio. Cells were analyzed daily for CAR expression by assaying the intensity of the GFP fused to the CAR. X axis: days, Y axis: % GFP/CAR expression compared to day 0.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. As used in this specification and the appended claims, the singular forms "a," "an," and "the" include plural references unless the context clearly dictates otherwise. Any reference to "or" herein is intended to encompass "and/or" unless otherwise stated.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A nucleic acid composition, comprising:

(a) a first inducible promoter comprising a nucleic acid sequence selected from the group consisting of SEQ ID NOs: 1-14 operably linked to a first polynucleotide comprising a payload gene that encodes a chimeric antigen receptor (CAR), a T-cell receptor (TCR), or a cytokine, wherein the first inducible promoter is capable of inducing transcription of the payload gene to generate a payload transcript upon thermal stimulation and/or immune cell stimulation; or (b) a first inducible promoter comprising a nucleic acid sequence selected from the group consisting of SEQ ID NOs: 1-14 operably linked to a first polynucleotide comprising a transactivator gene, and a second promoter operably linked to a second polynucleotide comprising a payload gene that encodes a chimeric antigen receptor (CAR), a T-cell receptor (TCR), or a cytokine, wherein the first inducible promoter is capable of inducing transcription of the transactivator gene to generate a transactivator transcript in the presence of thermal stimulation and/or immune cell stimulation, wherein the transactivator transcript is capable of being translated to generate a transactivator; and wherein, in the presence of the transactivator and a transactivator-binding compound, the second promoter is capable of inducing transcription of the payload gene to generate a payload transcript.

2. A nucleic acid composition, comprising:

a first inducible promoter comprising a nucleic acid sequence selected from the group consisting of SEQ ID NOs: 1-14 and a second promoter each operably linked to a first polynucleotide comprising a payload gene that encodes a chimeric antigen receptor (CAR), a T-cell receptor (TCR), or a cytokine and to a second polynucleotide comprising a transactivator gene, wherein the first inducible promoter is capable of inducing transcription of the payload gene and the transactivator gene to generate a polycistronic transcript upon thermal stimulation and/or immune cell stimulation, wherein, in the presence of the transactivator and a transactivator-binding compound, the second promoter is capable of inducing transcription of the payload gene and the transactivator gene to generate a polycistronic transcript, and wherein the polycistronic transcript is capable of being translated to generate a transactivator and a CAR, a TCR, or a cytokine.

3. The nucleic acid composition of claim 1, wherein the second promoter comprises a tetracycline response element (TRE), and wherein the TRE comprises one or more copies of a tet operator (TetO).

4. The nucleic acid composition of claim 1, wherein the transactivator comprises reverse tetracycline-controlled transactivator (rtTA).

5. The nucleic acid composition of claim 1, wherein the transactivator comprises tetracycline-controlled transactivator (tTA).

6. The nucleic acid composition of claim 1, wherein the transactivator-binding compound comprises tetracycline, doxycycline or a derivative thereof.

7. The nucleic acid composition of claim 1, wherein the first polynucleotide and the second polynucleotide are operably linked to a tandem gene expression element, optionally wherein the tandem gene expression element is an internal ribosomal entry site (IRES), foot-and-mouth disease virus 2A peptide (F2A), equine rhinitis A virus 2A peptide (E2A), porcine teschovirus 2A peptide (P2A) or Thosea asigna virus 2A peptide (T2A), or any combination thereof.

8. The nucleic acid composition of claim 1, wherein the CAR, TCR, or cytokine and the transactivator are expressed as separate proteins.

9. The nucleic acid composition of claim 1, wherein the payload transcript is capable of being translated to generate a payload protein, wherein the payload protein is a CAR, a TCR, or a cytokine.

10. The nucleic acid composition of claim 9, comprising at least one stop cassette comprising one or more stop sequences, wherein the at least one stop cassette is configured to prevent transcription of the payload gene and/or translation of the payload transcript, optionally wherein the one or more stop sequences comprises a polyadenylation signal, a stop codon, a frame-shifting mutation, or any combination thereof.

11. The nucleic acid composition of claim 1, wherein immune cell stimulation comprises signal transduction induced by binding of a stimulatory molecule with its cognate ligand on the surface of an immune cell, optionally wherein the cognate ligand is a CAR or a TCR.

12. The nucleic acid composition of claim 1, wherein, in the absence of thermal stimulation and/or immune cell stimulation, the CAR, TCR, or cytokine reaches unstimulated steady state levels in an immune cell, optionally wherein unstimulated steady state levels are insufficient to exert a phenotypic effect and/or therapeutic effect on said immune cell.

13. The nucleic acid composition of claim 1, wherein upon thermal stimulation and/or immune cell stimulation, transcription of the payload gene, and/or transactivator gene from the first inducible promoter is increased by at least 1.1-fold.

14. The nucleic acid composition of claim 1, wherein, upon thermal stimulation and/or immune cell stimulation, the CAR, TCR, or cytokine reaches stimulated steady state levels in an immune cell, optionally wherein the CAR, TCR, or cytokine does not return to unstimulated steady state levels.

15. The nucleic acid composition of claim 14, wherein:

(a) stimulated steady state CAR, TCR, or cytokine levels can be increased by introducing one or more non-canonical amino acid substitutions into a silencer effector binding sequence, cut site, and/or degron; and/or (b) stimulated steady state CAR, TCR, or cytokine levels can be reduced by introducing one or more canonical amino acid substitutions into a silencer effector binding sequence, cut site, and/or degron.

16. The nucleic acid composition of claim 1, wherein, in the presence of continuous thermal stimulation and/or immune cell stimulation, steady state CAR, TCR, or cytokine levels oscillate between a lower tuned threshold and an upper tuned threshold of a tuned expression range.

17. The nucleic acid composition of claim 1, wherein the CAR, TCR, or cytokine is capable of remodeling a tumor microenvironment and/or reducing immunosuppression at a target site of a subject.

18. The nucleic acid composition of claim 1, wherein the CAR or TCR comprises a leader peptide, and wherein the TCR comprises a constant region and/or CDR4.

* * * * *